(12) United States Patent
Van Zandt et al.

(10) Patent No.: US 9,040,703 B2
(45) Date of Patent: May 26, 2015

(54) INHIBITORS OF ARGINASE AND THEIR THERAPEUTIC APPLICATIONS

(75) Inventors: Michael Van Zandt, Branford, CT (US);
Adam Golebiowski, Branford, CT (US);
Min Koo Ji, Branford, CT (US); Darren Whitehouse, Branford, CT (US); Todd Ryder, Branford, CT (US); Paul Beckett, Branford, CT (US)

(73) Assignee: Mars, Incorporated, McLean, VA (US)

( * ) Notice: Subject to any disclaimer, the term of this patent is extended or adjusted under 35 U.S.C. 154(b) by 491 days.

(21) Appl. No.: 13/090,714

(22) Filed: Apr. 20, 2011

(65) Prior Publication Data

US 2012/0083469 A1 Apr. 5, 2012

Related U.S. Application Data

(60) Provisional application No. 61/326,892, filed on Apr. 22, 2010, provisional application No. 61/413,202, filed on Nov. 12, 2010.

(51) Int. Cl.
| | | |
|---|---|---|
| *C07F 5/02* | (2006.01) | |
| *A61K 31/69* | (2006.01) | |
| *A61P 9/00* | (2006.01) | |
| *A61P 1/00* | (2006.01) | |
| *A61P 37/00* | (2006.01) | |
| *A61P 31/00* | (2006.01) | |
| *A61P 11/00* | (2006.01) | |
| *A61P 9/12* | (2006.01) | |
| *A61P 9/10* | (2006.01) | |
| *A61P 19/02* | (2006.01) | |
| *A61P 21/04* | (2006.01) | |
| *A61P 25/00* | (2006.01) | |
| *A61P 31/18* | (2006.01) | |
| *A61P 1/04* | (2006.01) | |
| *A61P 17/06* | (2006.01) | |
| *A61P 29/00* | (2006.01) | |
| *A61P 17/02* | (2006.01) | |
| *A61P 15/00* | (2006.01) | |
| *C12N 9/99* | (2006.01) | |

(52) U.S. Cl.
CPC .................... *C07F 5/025* (2013.01)

(58) Field of Classification Search
USPC ........... 514/64; 546/13; 548/405, 952; 562/7; 544/58.1, 229; 540/541; 435/184
See application file for complete search history.

(56) References Cited

U.S. PATENT DOCUMENTS

2010/0189644 A1 * 7/2010 Christianson et al. ....... 424/1.65

FOREIGN PATENT DOCUMENTS

| WO | WO-99/19295 | 4/1999 |
| WO | WO-2010/085797 A2 | 7/2010 |
| WO | WO-2011133653 A1 | 10/2011 |

OTHER PUBLICATIONS

International Search Report & Written Opinion in PCT/US2011/033223 dated Jul. 14, 2011.
International Application Serial No. PCT/US2011/033223, International Preliminary Report on Patentability mailed Nov. 1, 2012, 7 pgs.
Mexican Application Serial No. MX/a/2012/012082, Office Action mailed May 14, 2014, 2 pgs.
New Zealand Application Serial No. 603364, First Examiner Report mailed Jun. 13, 2013, 2 pgs.

* cited by examiner

*Primary Examiner* — Kendra D Carter
*Assistant Examiner* — Jason A Deck
(74) *Attorney, Agent, or Firm* — Foley Hoag LLP; David P. Halstead

(57) ABSTRACT

Compounds according to Formula I and Formula II are potent inhibitors of Arginase I and II activity:

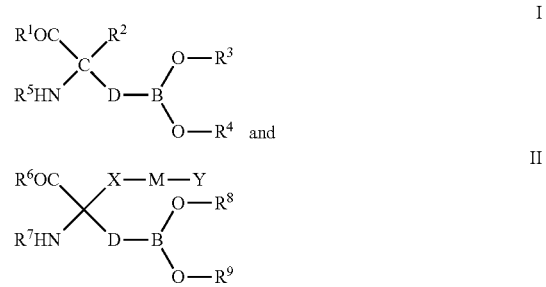

where $R^1$, $R^2$, $R^3$, $R^4$, $R^5$, $R^6$, $R^7$, $R^8$, $R^9$, D, M, X, and Y are defined as set forth in the specification. The invention also provides pharmaceutical compositions of the compounds and methods of their use for treating or preventing a disease or a condition associated with arginase activity.

2 Claims, No Drawings

INHIBITORS OF ARGINASE AND THEIR THERAPEUTIC APPLICATIONS

The present application claims the benefit of priority of U.S. Provisional Applications No. 61/326,892, which was filed on Apr. 22, 2010, and No. 61/413,202, which was filed on Nov. 12, 2010, the entire disclosures which are incorporated by reference as if fully set forth herein.

BACKGROUND OF THE INVENTION

The present invention relates generally to inhibitors of arginase and their use for the treatment of pathological states. Two isoforms of arginase have been identified to date. arginase I (ARG I), that is expressed in the cytosole and arginase II (ARG II), that is expressed in mitochondria. The arginase enzymes together with the nitric oxide synthase (NOS) enzymes play an important role in regulating the levels of nitric oxide in cells and in the development of pathophysiological disease states.

The arginases are implicated in various pathological states. These include without limitation erectile dysfunction, pulmonary hypertension, hypertension, atherosclerosis, renal disease, asthma, T-cell dysfunction, ischemia reperfusion injury, neurodegenerative diseases, wound healing, and fibrotic diseases. Although the mechanism of action of arginase enzymes in these disease states is still a subject of ongoing research, several studies imply that the arginase enzymes are often upregulated during pathological disease states.

For example, it is postulated that upregulation of arginase activity results in reduced levels of arginine which in turn reduces the level of nitric oxide (NO) a physiologically important signaling molecule that is required for cell division, arterial vasodilation, regulation of blood flow and for controlling muscular and neurological signal transduction.

In addition to its role in regulating nitric oxide (NO) levels, arginase also affects production of critical polyamines such as putrescine, spermidine and spermine. As arginase catabolizes L-arginine it produces ornithine. Ornithine is subsequently converted to putrescine, spermidine and spermine via ornithine decarboxylase, spermidine synthase and spermine synthase respectively. Thus, the arginase enzymes control physiological signaling events by controlling the intracellular levels of polyamine signal transducers. See Wang, J-Y; and Casero, Jr., R. A., Ed; Humana Press, Totowa, N.J., 2006. Ornithine also provides an alternative biosynthetic pathway to proline and thereby supports collagen production (Smith, R. J.; Phang, J. M., The importance of ornithine as a precursor for proline in mammalian cells. J. Cell. Physiol. 1979, 98, 475-482. Albina, J. E.; Abate, J. A.; Mastrofrancesco, B. Role of ornithine as a proline precursor in healing wounds. J. Surg. Res. 1993, 55, 97-102.)

Given the role of arginase in various pathological states, the present invention provides Formula I and Formula II compounds as inhibitors of arginase activity, as well as methodologies for using the inventive compounds as therapeutics.

SUMMARY OF THE INVENTION

The present invention provides certain boron-containing compounds according to Formulae I and II as described herein that are inhibitors of arginase activity. The invention also provides methods for using the inventive compounds in treatment. In one embodiment, therefore, inventive compounds and their pharmaceutically acceptable formulations are provided as therapeutic agents capable of inhibiting arginase activity. Compounds and pharmaceutical formulations in accordance with this invention are useful for treating a number of diseases and conditions, including but not limited to pulmonary hypertension, erectile dysfunction (ED), hypertension, atherosclerosis, renal disease, asthma, T-cell dysfunction, ischemia reperfusion injury, neurodegenerative diseases, wound healing, and fibrotic diseases.

In one embodiment, the present invention provides compounds that conform to Formula I and to stereoisomers, tautomers, prodrugs, and pharmaceutically acceptable salts or esters thereof:

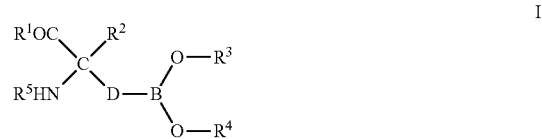

I

In Formula I, $R^1$ is selected from the group consisting of —OH, $OR^a$, and $NR^bR^c$. Substituent $R^a$ is selected from the group consisting of hydrogen, straight or branched chain $(C_1$-$C_6)$alkyl, $(C_3$-$C_{14})$aryl, $(C_3$-$C_{14})$heterocyclo alkyl-$(C_1$-$C_6)$alkylene-, $(C_3$-$C_{14})$hetero aryl-$(C_1$-$C_6)$alkylene-, and $(C_3$-$C_{14})$aryl$(C_1$-$C_6)$alkylene-. Substituents $R^b$ and $R^c$ are each independently selected from the group consisting of H, —OH, straight or branched $(C_1$-$C_6)$alkyl, —S(O)$_2$—$(C_1$-$C_6)$alkyl, $(C_3$-$C_{14})$aryl-S(O)$_2$—, $(C_3$-$C_{14})$heterocycloalkyl-$(C_1$-$C_6)$alkylene-, and $(C_3$-$C_{14})$heteroaryl-$(C_1$-$C_6)$alkylene-.

Substituent $R^2$ in Formula I is selected from the group consisting of straight or branched $(C_1$-$C_6)$alkyl, straight or branched $(C_2$-$C_6)$alkenyl, straight or branched $(C_2$-$C_6)$alkynyl, $(C_3$-$C_{14})$aryl, $(C_3$-$C_{14})$-cycloalkyl, $(C_3$-$C_{14})$aryl$(C_1$-$C_6)$alkylene-, $(C_3$-$C_{14})$heteroaryl-$(C_1$-$C_6)$alkylene-, $(C_3$-$C_{14})$hetero aryl, $(C_3$-$C_{14})$heterocyclo alkyl, $(C_3$-$C_{14})$heterocycloalkyl-$(C_1$-$C_6)$alkylene-, $(C_3$-$C_{14})$heteroaryl-$(C_3$-$C_6)$heterocycloalkylene-, $(C_3$-$C_{14})$aryl-$(C_3$-$C_{14})$heterocycloalkylene-, $(C_3$-$C_{14})$-aryl-$(C_1$-$C_6)$alkyl-$(C_3$-$C_{14})$heterocycloalkylene-, $(C_3$-$C_{14})$heteroaryl-$(C_1$-$C_6)$alkyl-$(C_3$-$C_{14})$heterocycloalkylene-, $(C_3$-$C_{14})$heterocycloalkyl-$(C_1$-$C_6)$alkyl-$(C_3$-$C_{14})$heterocycloalkylene-, and —$(CH_2)_m$—$(X)_u$—$(CH_2)_n$—$(Y)_v$—$R^f$.

When $R^2$ is —$(CH_2)_m$—$(X)_u$—$(CH_2)_n$—$(Y)_v$—$R^f$, u and v are each independently 0 or 1 such that u+v≥1. Subscripts m and n are each independently 0, 1, 2, 3, 4, 5, or 6, wherein m+n≥1.

Variables X and Y are independently selected from the group consisting of —NH—, —O— and —S—

Substituent $R^f$ is selected from the group consisting of H, hydroxyl, straight or branched $(C_1$-$C_6)$alkyl and $(C_3$-$C_{14})$aryl.

Substituents $R^3$ and $R^4$ are each independently hydrogen or straight or branched $(C_1$-$C_6)$alkyl.

Alternatively, $R^3$ and $R^4$ together with the boron atom to which they are bound form a 5- or 6-membered ring that is fully or partially saturated, and that optionally contains 1-3 additional heteroatom ring members selected from O, S, and N.

Also contemplated are compounds wherein the boronic acid moiety in Formula I is esterified with a sugar. Compounds of this class are useful as prodrugs.

Substituent $R^5$ is selected from the group consisting of H, straight or branched $(C_1$-$C_6)$ alkyl, and $(C_1$-$C_6)$alkyl-C(O)—.

In formula I, D is selected from the group consisting of straight or branched $(C_1$-$C_6)$alkylene, straight or branched $(C_2$-$C_8)$alkenylene, $(C_3$-$C_{14})$arylene, straight or branched $(C_2$-$C_8)$alkynylene, and $(C_3$-$C_{14})$cycloalkylene. In some embodiments, one or more —CH$_2$-groups in D are optionally and independently replaced with a moiety selected from group the consisting of —O—, —NR'—, —S—, —SO—, —SO$_2$—, and —CR'R"— wherein R' and R" are each independently selected from the group consisting of H, (C$_1$-C$_8$) alkyl, and (C$_3$-C$_6$)aryl. In other embodiments, any two adjacent —CH$_2$— groups optionally represent two members of a (C$_3$-C$_{14}$)-cycloalkylenyl group.

Any alkyl, alkylene, alkenyl, alkenylene, alkynyl, or alkynylene in Formula I is optionally substituted with one or more members selected from the group consisting of halogen, oxo, —COOH, —CN, —NO$_2$, —OH, —NR$^d$R$^e$, —NR$^g$S(O)$_2$R$^h$, (C$_1$-C$_6$)alkoxy, and (C$_3$-C$_{14}$)aryloxy.

Substituents R$^d$, R$^e$, R$^g$, and R$^h$ are independently selected from the group consisting of H, straight or branched (C$_1$-C$_6$) alkyl, optionally substituted (C$_3$-C$_{14}$)aryl(C$_1$-C$_6$)alkylene-, (C$_1$-C$_6$)alkoxy, optionally substituted (C$_3$-C$_{14}$)aryl, (C$_1$-C$_6$) hydroxyalkyl, (C$_1$-C$_6$)aminoalkyl, H$_2$N(C$_1$-C$_6$)alkylene-, optionally substituted (C$_3$-C$_6$)cycloalkyl, optionally substituted (C$_3$-C$_{14}$)heterocycloalkyl, optionally substituted (C$_3$-C$_{14}$)heteroaryl, optionally substituted (C$_3$-C$_{14}$)aryl-(C$_1$-C$_6$) alkylene-, NR'R"C(O)—, and (C$_3$-C$_6$)aryl-(C$_3$-C$_{14}$)-cycloalkylene-, and R' and R" can each independently be selected from the group consisting of H, (C$_1$-C$_8$)alkyl, and (C$_3$-C$_6$)aryl.

Any aryl, heteroaryl, cycloalkyl, or heterocycloalkyl is optionally substituted with one or more members selected from the group consisting of halogen, —OH, oxo, —COOH, (C$_3$-C$_{14}$)aryl(C$_1$-C$_6$)alkylene-, —CN, —NO$_2$, —NH$_2$, (C$_1$-C$_6$)alkyl-S—, (C$_3$-C$_{14}$)cyclo alkyl, (C$_3$-C$_{14}$)heterocycloalkyl, (C$_3$-C$_{14}$)aryl, (C$_3$-C$_{14}$)hetero aryl, —C(O)NH—(C$_1$-C$_6$)alkyl, —NHC(O)—(C$_1$-C$_6$)alkyl, (C$_1$-C$_6$)alkyl, (C$_2$-C$_8$)alkenyl, (C$_2$-C$_8$)alkynyl, (C$_1$-C$_6$)alkoxy, (C$_1$-C$_6$) haloalkyl, and (C$_1$-C$_6$)hydroxyalkyl.

It should be understood that, notwithstanding the description of Formula I given herein, Formula I does not include 2-amino-4-borono-2-methylbutanoic acid.

The present invention also provides compounds that conform to Formula II, to stereoisomers, tautomers, prodrugs, and pharmaceutically acceptable salts or esters thereof, and to their pharmaceutically acceptable formulations as therapeutics for treating various disease states associated with an imbalance of the arginase enzymes.

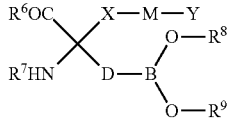

II

In Formula II, R$^6$ is selected from the group consisting of OR$^a$, and NR$^b$R$^c$.

Substituent R$^a$ is selected from the group consisting of hydrogen, straight or branched chain (C$_1$-C$_6$)alkyl, (C$_3$-C$_8$) cycloalkyl, (C$_3$-C$_{14}$)aryl, (C$_3$-C$_{14}$)heterocycloalkyl-(C$_1$-C$_6$) alkylene-, (C$_3$-C$_{14}$)heteroaryl-(C$_1$-C$_6$)alkylene-, and (C$_3$-C$_{14}$)aryl(C$_1$-C$_6$)alkylene-, while substituent groups R$^b$ and R$^c$ are each independently selected from the group consisting of H, —OH, straight or branched (C$_1$-C$_6$)alkyl, —S(O)$_2$—(C$_1$-C$_6$)alkyl, (C$_3$-C$_{14}$)aryl-S(O)$_2$—, (C$_3$-C$_{14}$)heterocycloalkyl-(C$_1$-C$_6$)alkylene-, and (C$_3$-C$_{14}$)heteroaryl-(C$_1$-C$_6$) alkylene-.

Substituent R$^7$ is selected from the group consisting of H, straight or branched (C$_1$-C$_6$) alkyl, (C$_3$-C$_{14}$)aryl(C$_1$-C$_6$)alkylene-, (C$_3$-C$_{14}$)heteroaryl-(C$_1$-C$_6$)alkylene-, (C$_3$-C$_{14}$)heterocycloalkyl-(C$_1$-C$_6$)alkylene- and (C$_1$-C$_6$)alkyl-C(O)—.

Variable X in Formula II is selected from the group consisting of a (C$_3$-C$_{14}$)-cycloalkylene and (C$_3$-C$_{14}$)heterocycloalkylene and variable M is selected from the group consisting of a bond, (C$_1$-C$_6$)alkylene-, —O—, —C(O)—, —C(S)—, —C(O)NH—, —C(S)NH—, —S—, —S(O)—, —S(O)$_2$—, —NR'—, and —C═NR$^{11}$—.

Variable Y in Formula II is selected from the group consisting of H, (C$_1$-C$_{14}$)alkyl, —NR'R", hydroxy(C$_1$-C$_6$)alkylene, (C$_3$-C$_{14}$)-cycloalkyl, (C$_3$-C$_{14}$)-cycloalkyl-(C$_1$-C$_6$)alkylene, (C$_3$-C$_{14}$)aryl, (C$_3$-C$_{14}$)aryl-(C$_1$-C$_6$)alkylene, (C$_3$-C$_{14}$) heterocycloalkyl, (C$_3$-C$_{14}$)heterocycloalkyl-(C$_1$-C$_6$) alkylene, (C$_3$-C$_{14}$)heteroaryl, (C$_3$-C$_{14}$)heteroaryl-(C$_1$-C$_6$) alkylene, (C$_3$-C$_{14}$)heteroaryl-(C$_3$-C$_6$)heterocycloalkylene-, (C$_3$-C$_{14}$)aryl-(C$_3$-C$_{14}$)heterocycloalkylene-, (C$_3$-C$_{14}$)-aryl-(C$_1$-C$_6$)alkyl-(C$_3$-C$_{14}$)heterocycloalkylene-, (C$_3$-C$_{14}$)heteroaryl-(C$_1$-C$_6$)alkyl-(C$_3$-C$_{14}$)heterocycloalkylene-, and (C$_3$-C$_{14}$)heterocycloalkyl-(C$_1$-C$_6$)alkyl-(C$_3$-C$_{14}$) heterocycloalkylene-.

In one embodiment X is a (C$_3$-C$_{14}$)-cycloalkylene, M is a bond and Y is —NH$_2$. In other aspects of the present invention, X is a (C$_3$-C$_{14}$)heterocycloalkylene and Y is selected from the group consisting of (C$_3$-C$_{14}$)-cycloalkyl, (C$_3$-C$_{14}$) aryl, (C$_3$-C$_{14}$)aryl-(C$_1$-C$_6$)alkylene, (C$_3$-C$_{14}$)heteroaryl and (C$_3$-C$_{14}$)heteroaryl-(C$_1$-C$_6$)alkylene. For example, Y can be a (C$_3$-C$_{14}$)heteroaryl, a (C$_3$-C$_{14}$)aryl, a (C$_3$-C$_{14}$)cycloalkyl, or a (C$_3$-C$_{14}$) aryl-(C$_1$-C$_6$)alkylene.

Substituent groups R$^8$ and R$^9$ are independently selected from hydrogen, straight or branched (C$_1$-C$_6$)alkyl, (C$_3$-C$_8$) cycloalkyl, (C$_3$-C$_{14}$)aryl, and C(O)—R'. Alternatively, R$^8$ and R$^9$ together with the boron atom to which they are bound form a 5- or 6-membered ring that is fully or partially saturated, and that optionally contains 1-3 additional heteroatom ring members selected from O, S, and N. In an embodiment of the invention, R$^8$ and R$^9$ together with the boron atom to which they are bound are linked to form a 5-membered dioxaborolane or a 6-membered dioxaborinane ring which is optionally fused with a cycloalkyl, heterocyclic or aromatic ring.

In Formula II, D is selected from the group consisting of straight or branched (C$_3$-C$_5$)alkylene, straight or branched (C$_2$-C$_8$)alkenylene, straight or branched (C$_2$-C$_8$)alkynylene, (C$_3$-C$_{14}$)arylene, and (C$_3$-C$_{14}$)cycloalkylene. In one embodiment one or more —CH$_2$— groups in D are optionally and independently replaced with a moiety selected from the group consisting of O, NR', S, SO, SO$_2$, and CR'R". No two adjacent —CH$_2$— groups in D, however, are simultaneously O, NR', S, SO, or SO$_2$.

For certain Formula II compounds, any two adjacent —CH$_2$— groups in D optionally represent two members of a (C$_3$-C$_{14}$)-cycloalkylenyl group. In other embodiments, D conforms to one of formulae -L$^1$-L$^2$-CH$_2$—CH$_2$—, —CH$_2$-L$^1$-L$^2$-CH$_2$—, —CH$_2$—CH$_2$-L$^1$-L$^2$-, -L$^1$-CH$_2$—CH$_2$-L$^2$-, -L$^1$-CH$_2$-L$^2$-CH$_2$—, or —CH$_2$-L$^1$-CH$_2$-L$^2$-. The variables L$^1$ and L$^2$ are independently selected from the group consisting of O, NR', S, SO, SO$_2$, and CR'R", wherein R' and R" are as defined below. In embodiments where -L$^1$ and -L$^2$ are adjacent to each other, however, L$^1$ and L$^2$ are not simultaneously O, NR', S, SO or a SO$_2$ group.

Substituents R' and R" in Formula II are independently selected from the group consisting of H, (C$_1$-C$_8$)alkyl, —C(O)—(C$_1$-C$_8$)alkylene, optionally substituted (C$_3$-C$_6$) aryl, optionally substituted (C$_3$-C$_{14}$)aryl(C$_1$-C$_6$)alkylene-, optionally substituted (C$_1$-C$_6$)aminoalkyl, optionally substituted (C$_3$-C$_6$)cycloalkyl, optionally substituted (C$_3$-C$_{14}$)heterocycloalkyl, optionally substituted (C$_3$-C$_{14}$)heteroaryl.

Moreover, any alkyl, alkylene, aryl, heteroaryl, cycloalkyl, or heterocycloalkyl substituent as defined herein is optionally substituted with one or more members selected from the group consisting of halogen, oxo, —COOH, —CN, —NO$_2$, —OH, —NR$^d$R$^e$, —NR$^g$S(O)$_2$R$^h$, (C$_1$-C$_6$)alkyl, —(C$_6$)haloalkyl, —(C$_6$)haloalkoxy, —(C$_6$)alkoxy, (C$_3$-C$_{14}$)aryl, (C$_3$-C$_{14}$)heteroaryl, (C$_3$-C$_{14}$)heterocyclo alkyl, (C$_3$-C$_{14}$)heteroaryl-(C$_1$-C$_6$)alkylene and (C$_3$-C$_{14}$)aryloxy.

Each of R$^d$, R$^e$, R$^g$, and R$^h$ are independently selected from the group consisting of H, straight or branched (C$_1$-C$_6$)alkyl, optionally substituted (C$_3$-C$_{14}$)aryl(C$_1$-C$_6$)alkylene-, optionally substituted (C$_3$-C$_{14}$)aryl, (C$_1$-C$_6$)hydroxyalkyl, (C$_1$-C$_6$) aminoalkyl, H$_2$N(C$_1$-C$_6$)alkylene-, optionally substituted (C$_3$-C$_6$)cycloalkyl, optionally substituted (C$_3$-C$_{14}$)heterocycloalkyl, optionally substituted (C$_3$-C$_{14}$)heteroaryl, optionally substituted (C$_3$-C$_{14}$)aryl-(C$_1$-C$_6$)alkylene- and NR'R"C(O)—.

The present invention also provides a pharmaceutically acceptable salt, stereoisomer, tautomer, or prodrug of Formula II compounds.

Compounds in accordance with Formula I or II and their pharmaceutical formulations are useful for treating a number of diseases and conditions, including but not limited to pulmonary hypertension, erectile dysfunction (ED), hypertension, atherosclerosis, renal disease, asthma, T-cell dysfunction, ischemia reperfusion injury, neurodegenerative diseases, wound healing, and fibrotic diseases.

In one embodiment, the present invention provides a pharmaceutical composition that comprises a therapeutically effective amount of at least one of the compounds of Formula I or Formula II, and a pharmaceutically acceptable carrier.

The invention provides in one embodiment a method for inhibiting arginase I, arginase II, or a combination thereof in a cell comprising contacting the cell with at least one compound according to Formula I or Formula II. Pursuant to another embodiment, the invention provides a method for treating or preventing a disease or a condition associated with expression or activity of arginase I, arginase II, or a combination thereof in a subject, comprising administering to the subject a therapeutically effective amount of at least one compound of Formula I or Formula II.

Pursuant to one embodiment, as noted above, the invention provides a compound of Formula I or Formula II for the treatment or prevention of a disease or condition associated with expression or activity of arginase I, arginase II, or a combination thereof in a subject. The invention also provides, in another embodiment, the use of a compound of Formula I or Formula II for the same purpose. Alternatively, another embodiment provides for the use of Formula I or Formula II compounds in the manufacture of a medicament for treatment or prevention of a disease or condition associated with expression or activity of arginase I, arginase II, or a combination of both enzymes in cells.

DETAILED DESCRIPTION

The compounds as described herein are small molecule inhibitors of arginase that conform to Formula I or II. As will be apparent from the description hereinbelow, some Formula II compounds also are Formula I compounds. The compounds and their pharmaceutical compositions are useful in treating or preventing diseases or conditions that are associated with the expression or activity of arginase.

Definitions

"Alkyl" refers to straight, branched chain, or cyclic hydrocarbyl groups including from 1 to about 20 carbon atoms. For instance, an alkyl can have from 1 to 10 carbon atoms or 1 to 5 carbon atoms. Exemplary alkyl includes straight chain alkyl groups such as methyl, ethyl, propyl, butyl, pentyl, hexyl, heptyl, octyl, nonyl, decyl, undecyl, dodecyl, and the like, and also includes branched chain isomers of straight chain alkyl groups, for example without limitation, —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, —CH(CH$_3$)CH(CH$_3$)CH(CH$_3$)$_2$, and the like. Thus, alkyl groups include primary alkyl groups, secondary alkyl groups, and tertiary alkyl groups.

The phrase "substituted alkyl" refers to alkyl substituted at 1 or more, e.g., 1, 2, 3, 4, 5, or even 6 positions, which substituents are attached at any available atom to produce a stable compound, with substitution as described herein. "Optionally substituted alkyl" refers to alkyl or substituted alkyl.

Each of the terms "halogen," "halide," and "halo" refers to —F, —Cl, —Br, or —I.

The terms "alkylene" and "substituted alkylene" refer to divalent alkyl and divalent substituted alkyl, respectively. Examples of alkylene include without limitation, ethylene (—CH$_2$—CH$_2$—). "Optionally substituted alkylene" refers to alkylene or substituted alkylene.

"Alkene" refers to straight, branched chain, or cyclic hydrocarbyl groups including from 2 to about 20 carbon atoms having one or more carbon to carbon double bonds, such as 1 to 3, 1 to 2, or at least one carbon to carbon double bond. "Substituted alkene" refers to alkene substituted at 1 or more, e.g., 1, 2, 3, 4, 5, or even 6 positions, which substituents are attached at any available atom to produce a stable compound, with substitution as described herein. "Optionally substituted alkene" refers to alkene or substituted alkene.

The term "alkenylene" refers to divalent alkene. Examples of alkenylene include without limitation, ethenylene (—CH═CH—) and all stereoisomeric and conformational isomeric forms thereof. "Substituted alkenylene" refers to divalent substituted alkene. "Optionally substituted alkenylene" refers to alkenylene or substituted alkenylene.

"Alkyne or "alkynyl" refers to a straight or branched chain unsaturated hydrocarbon having the indicated number of carbon atoms and at least one triple bond. Examples of a (C$_2$-C$_8$)alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne. An alkynyl group can be unsubstituted or optionally substituted with one or more substituents as described herein below.

The term "alkynylene" refers to divalent alkyne. Examples of alkynylene include without limitation, ethynylene, propynylene. "Substituted alkynylene" refers to divalent substituted alkyne.

The term "alkoxy" refers to an —O-alkyl group having the indicated number of carbon atoms. For example, a (C$_1$-C$_6$) alkoxy group includes —O-methyl (methoxy), —O-ethyl (ethoxy), —O-propyl (propoxy), —O-isopropyl (isopropoxy), —O-butyl (butoxy), —O-sec-butyl (sec-butoxy), —O-tert-butyl (tert-butoxy), —O-pentyl (pentoxy), —O-isopentyl (isopentoxy), —O-neopentyl (neopentoxy), —O-hexyl (hexyloxy), —O-isohexyl (isohexyloxy), and —O-neohexyl (neohexyloxy).

The term "aryl," alone or in combination refers to an aromatic monocyclic or bicyclic ring system such as phenyl or naphthyl. "Aryl" also includes aromatic ring systems that are optionally fused with a cycloalkyl ring as herein defined.

A "substituted aryl" is an aryl that is independently substituted with one or more substituents attached at any available atom to produce a stable compound, wherein the substituents are as described herein. "Optionally substituted aryl" refers to aryl or substituted aryl.

"Arylene" denotes divalent aryl, and "substituted arylene" refers to divalent substituted aryl. "Optionally substituted arylene" refers to arylene or substituted arylene.

The term "heteroatom" refers to N, O, and S. Inventive compounds that contain N or S atoms can be optionally oxidized to the corresponding N-oxide, sulfoxide or sulfone compounds.

"Heteroaryl," alone or in combination with any other moiety described herein, refers to a monocyclic aromatic ring structure containing 5 or 6 ring atoms, or a bicyclic aromatic group having 8 to 10 atoms, containing one or more, such as 1 to 4, 1 to 3, or 1 to 2, heteroatoms independently selected from the group consisting of O, S, and N. Heteroaryl is also intended to include oxidized S or N, such as sulfinyl, sulfonyl and N-oxide of a tertiary ring nitrogen. A carbon or heteroatom is the point of attachment of the heteroaryl ring structure such that a stable compound is produced. Examples of heteroaryl groups include, but are not limited to, pyridinyl, pyridazinyl, pyrazinyl, quinoxalyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, and indolyl. "Heteroaryl" also contemplates fused ring systems wherein the heteroaryl is fused to an aryl or cycloalkyl ring as defined herein.

A "substituted heteroaryl" is a heteroaryl that is independently substituted, unless indicated otherwise, with one or more, e.g., 1, 2, 3, 4 or 5, attached at any available atom to produce a stable compound, wherein the substituents are as described herein. "Optionally substituted heteroaryl" refers to heteroaryl or substituted heteroaryl.

"Heteroarylene" refers to divalent heteroaryl, and "substituted heteroarylene" refers to divalent substituted heteroaryl. "Optionally substituted heteroarylene" refers to heteroarylene or substituted heteroarylene.

"Heterocycloalkyl" means a saturated or unsaturated non-aromatic monocyclic, bicyclic, tricyclic or polycyclic ring system that has from 5 to 14 atoms in which from 1 to 3 carbon atoms in the ring are replaced by heteroatoms of O, S or N. A heterocycloalkyl is optionally fused with benzo or heteroaryl of 5-6 ring members, and includes oxidized S or N, such as sulfinyl, sulfonyl and N-oxide of a tertiary ring nitrogen. The point of attachment of the heterocycloalkyl ring is at a carbon or heteroatom such that a stable ring is retained. Examples of heterocycloalkyl groups include without limitation morpholino, tetrahydrofuranyl, dihydropyridinyl, piperidinyl, pyrrolidinyl, piperazinyl, dihydrobenzofuryl, and dihydroindolyl.

"Optionally substituted heterocycloalkyl" denotes heterocycloalkyl that is substituted with 1 to 3 substituents, e.g., 1, 2 or 3 substituents, attached at any available atom to produce a stable compound, wherein the substituents are as described herein.

"Heteroalkyl" means a saturated alkyl group having from 1 to about 20 carbon atoms, 1 to 10 carbon atoms, 1 to 6 carbon atoms, or 1 to 3 carbon atoms, in which from 1 to 3 carbon atoms are replaced by heteroatoms of O, S or N. Heteroalkyl is also intended to include oxidized S or N, such as sulfinyl, sulfonyl and N-oxide of a tertiary ring nitrogen. The point of attachment of the heteroalkyl substituent is at an atom such that a stable compound is formed. Examples of heteroalkyl groups include, but are not limited to, N-alkylaminoalkyl (e.g., $CH_3NHCH_2$—), N,N-dialkylaminoalkyl (e.g., $(CH_3)_2NCH_2$—), and the like.

"Heteroalkylene" refers to divalent heteroalkyl. The term "optionally substituted heteroalkylene" refers to heteroalkylene that is substituted with 1 to 3 substituents, e.g., 1, 2 or 3 substituents, attached at any available atom to produce a stable compound, wherein the substituents are as described herein.

"Heteroalkene" means a unsaturated alkyl group having from 1 to about 20 carbon atoms, 1 to 10 carbon atoms, 1 to 6 carbon atoms, or 1 to 3 carbon atoms, in which from 1 to 3 carbon atoms are replaced by heteroatoms of O, S or N, and having 1 to 3, 1 to 2, or at least one carbon to carbon double bond or carbon to heteroatom double bond.

"Heteroalkenylene" refers to divalent heteroalkene. The term "optionally substituted heteroalkenylene" refers to heteroalkenylene that is substituted with 1 to 3 substituents, e.g., 1, 2 or 3 substituents, attached at any available atom to produce a stable compound, wherein the substituents are as described herein.

The term "cycloalkyl" refer to monocyclic, bicyclic, tricyclic, or polycyclic, 3- to 14-membered ring systems, which are either saturated, unsaturated or aromatic. The cycloalkyl group may be attached via any atom. Cycloalkyl also contemplates fused rings wherein the cycloalkyl is fused to an aryl or hetroaryl ring as defined above. Representative examples of cycloalkyl include, but are not limited to cyclopropyl, cyclobutyl, cyclopentyl, and cyclohexyl. A cycloalkyl group can be unsubstituted or optionally substituted with one or more substituents as described herein below.

The term "cycloalkenyl" refers to a monocyclic, bicyclic, tricyclic, or polycyclic, 3- to 14-membered ring system, which is unsaturated. The cycloalkenyl group may be attached via any atom. Representative examples of cycloalkenyl include, but are not limited to, cyclopropenyl, cyclobutenyl, cyclopentenyl and cyclohexenyl.

The term "cycloalkylene" refers to divalent cycloalkyl. The term "optionally substituted cycloalkylene" refers to cycloalkylene that is substituted with 1 to 3 substituents, e.g., 1, 2 or 3 substituents, attached at any available atom to produce a stable compound, wherein the substituents are as described herein.

The term 'nitrile or cyano" can be used interchangeably and refer to a —CN group which is bound to a carbon atom of a heteroaryl ring, aryl ring and a heterocycloalkyl ring.

The term "oxo" refers to a =O atom attached to a saturated or unsaturated ($C_3$-$C_8$) cyclic or a ($C_1$-$C_8$) acyclic moiety. The =O atom can be attached to a carbon, sulfur, and nitrogen atom that is part of the cyclic or acyclic moiety.

The term "amine or amino" refers to an —$NR^dR^e$ group wherein $R^d$ and $R^e$ each independently refer to a hydrogen, ($C_1$-$C_8$)alkyl, aryl, heteroaryl, heterocycloalkyl, ($C_1$-$C_8$)haloalkyl, and ($C_1$-$C_6$)hydroxyalkyl group.

The term "amide" refers to a —NR'R"C(O)— group wherein R' and R" each independently refer to a hydrogen, ($C_1$-$C_8$)alkyl, or ($C_3$-$C_6$)aryl.

The term "carboxamido" refers to a —C(O)NR'R" group wherein R' and R" each independently refer to a hydrogen, ($C_1$-$C_8$)alkyl, or ($C_3$-$C_6$)aryl.

The term "aryloxy" refers to an —O-aryl group having the indicated number of carbon atoms. Examples of aryloxy groups include, but are not limited to, phenoxy, napthoxy and cyclopropeneoxy.

The term "haloalkoxy," refers to an —O—($C_1$-$C_6$)alkyl group wherein one or more hydrogen atoms in the $C_1$-$C_8$ alkyl group is replaced with a halogen atom, which can be the same or different. Examples of haloalkyl groups include, but are not limited to, difluoromethoxy, trifluoromethoxy, 2,2,2-trifluoroethoxy, 4-chlorobutoxy, 3-bromopropyloxy, pentachloroethoxy, and 1,1,1-trifluoro-2-bromo-2-chloroethoxy.

The term "hydroxyalkyl," refers to an alkyl group having the indicated number of carbon atoms wherein one or more of the alkyl group's hydrogen atoms is replaced with an —OH group. Examples of hydroxyalkyl groups include, but are not limited to, —CH$_2$OH, —CH$_2$CH$_2$OH, —CH$_2$CH$_2$CH$_2$OH, —CH$_2$CH$_2$CH$_2$CH$_2$OH, —CH$_2$CH$_2$CH$_2$CH$_2$CH$_2$OH, —CH$_2$CH$_2$CH$_2$CH$_2$CH$_2$CH$_2$OH, and branched versions thereof.

The term "alkylsulfonyl" refers to a (C$_1$-C$_6$)alkyl group wherein one or more hydrogen atoms in the C$_1$-C$_6$ alkyl group is replaced with a —S(O)$_a$ group. Subscript "a" can either be 1 or 2, so as to give an alkyl sulfoxide (sulfinyl group), or an alkyl sulfone respectively. Examples of alkylsulfonyl groups include, but are not limited to dimethylsulfoxide, ethylmethyl sulfoxide, and methylvinylsulfone.

The term "haloalkyl," refers to an (C$_1$-C$_6$)alkyl group wherein one or more hydrogen atoms in the C$_1$-C$_6$ alkyl group is replaced with a halogen atom, which can be the same or different. Examples of haloalkyl groups include, but are not limited to, difluoromethyl, trifluoromethyl, 2,2,2-trifluoroethyl, 4-chlorobutyl, 3-bromopropylyl, pentachloroethyl, and 1,1,1-trifluoro-2-bromo-2-chloroethyl.

The term "aminoalkyl," refers to an (C$_1$-C$_6$)alkyl group wherein one or more hydrogen atoms in the C$_1$-C$_6$ alkyl group is replaced with a —NR$^d$R$^e$ group, where R$^d$ and R$^e$ can be the same or different, for example, R$^d$ and R$^e$ each independently refer to a hydrogen, (C$_1$-C$_8$)alkyl, aryl, heteroaryl, heterocycloalkyl, (C$_1$-C$_8$)haloalkyl, and (C$_1$-C$_6$)hydroxyalkyl group. Examples of aminoalkyl groups include, but are not limited to, aminomethyl, aminoethyl, 4-aminobutyl and 3-aminobutylyl.

The term "thioalkyl" or "alkylthio" refers to a (C$_1$-C$_6$)alkyl group wherein one or more hydrogen atoms in the C$_1$-C$_6$ alkyl group is replaced with a —SR$^j$ group, wherein R$^j$ is selected from the group consisting of hydrogen, (C$_1$-C$_6$)alkyl and (C$_3$-C$_{14}$)aryl.

"Amino (C$_1$-C$_6$)alkylene" refers to a divalent alkylene wherein one or more hydrogen atoms in the C$_1$-C$_6$ alkylene group is replaced with a —NR$^d$R$^e$ group. Examples of amino (C$_1$-C$_6$)alkylene include, but are not limited to, aminomethylene, aminoethylene, 4-aminobutylene and 3-aminobutylylene.

The term "sulfonamide" refers to an —NR$^g$S(O)$_2$R$^h$ group where R$^g$ and R$^h$ are each independently refer to a hydrogen, (C$_1$-C$_8$)alkyl, aryl, heteroaryl, heterocycloalkyl, (C$_1$-C$_8$)haloalkyl, and (C$_1$-C$_6$)hydroxyalkyl group.

A "hydroxyl" or "hydroxy" refers to an —OH group.

The term "(C$_3$-C$_{14}$)aryl-(C$_1$-C$_6$)alkylene" refers to a divalent alkylene wherein one or more hydrogen atoms in the C$_1$-C$_6$ alkylene group is replaced by a (C$_3$-C$_{14}$)aryl group. Examples of (C$_3$-C$_{14}$)aryl-(C$_1$-C$_6$)alkylene groups include without limitation 1-phenylbutylene, phenyl-2-butylene, 1-phenyl-2-methylpropylene, phenylmethylene, phenylpropylene, and naphthylethylene.

The term "(C$_3$-C$_{14}$)heteroaryl-(C$_1$-C$_6$)alkylene" refers to a divalent alkylene wherein one or more hydrogen atoms in the C$_1$-C$_6$ alkylene group is replaced a (C$_3$-C$_{14}$)heteroaryl group. Examples of (C$_3$-C$_{14}$)heteroaryl-(C$_1$-C$_6$)alkylene groups include without limitation 1-pyridylbutylene, quinolinyl-2-butylene and 1-pyridyl-2-methylpropylene.

The term "(C$_3$-C$_{14}$)heterocycloalkyl-(C$_1$-C$_6$)alkylene" refers to a divalent alkylene wherein one or more hydrogen atoms in the C$_1$-C$_6$ alkylene group is replaced by a (C$_3$-C$_{14}$)heterocycloalkyl group. Examples of (C$_3$-C$_{14}$)heterocycloalkyl-(C$_1$-C$_6$)alkylene groups include without limitation 1-morpholinopropylene, azetidinyl-2-butylene and 1-tetrahydrofuranyl-2-methylpropylene.

The term "(C$_3$-C$_{14}$)heteroaryl-(C$_1$-C$_{14}$)heterocycloalkylene" refers to a divalent heterocycloalkylene wherein one or more hydrogen atoms in the C$_1$-C$_6$ heterocycloalkylene group is replaced by a (C$_3$-C$_{14}$)heteroaryl group. Examples of (C$_3$-C$_{14}$)heteroaryl-(C$_1$-C$_6$)heterocycloalkylene groups include without limitation pyridylazetidinylene and 4-quinolino-1-piperazinylene.

The term "(C$_3$-C$_{14}$)aryl-(C$_1$-C$_{14}$)heterocycloalkylene" refers to a divalent heterocycloalkylene wherein one or more hydrogen atoms in the C$_1$-C$_{14}$ heterocycloalkylene group is replaced by a (C$_3$-C$_{14}$)aryl group. Examples of (C$_3$-C$_{14}$)aryl-(C$_1$-C$_{14}$)heterocycloalkylene groups include without limitation 1-naphthyl-piperazinylene, phenylazetidinylene, and phenylpiperidinylene.

The term "(C$_3$-C$_{14}$)aryl-(C$_1$-C$_6$)alkyl-(C$_1$-C$_{14}$)heterocycloalkylene" refers to a divalent heterocycloalkylene wherein one or more hydrogen atoms in the C$_1$-C$_{14}$ heterocycloalkylene group is replaced by a (C$_1$-C$_6$) alkyl group that is further substituted by replacing one or more hydrogen atoms of the (C$_1$-C$_6$) alkyl group with a (C$_3$-C$_{14}$)aryl group.

The term "(C$_3$-C$_{14}$)heteroaryl-(C$_1$-C$_6$)alkyl-(C$_1$-C$_{14}$)heterocycloalkylene" refers to a divalent heterocycloalkylene wherein one or more hydrogen atoms in the C$_1$-C$_{14}$ heterocycloalkylene group is replaced by a (C$_1$-C$_6$) alkyl group that is further substituted by replacing one or more hydrogen atoms of the (C$_1$-C$_6$) alkyl group with a (C$_3$-C$_{14}$)heteroaryl group.

The term "(C$_3$-C$_{14}$)heterocycloalkyl-(C$_1$-C$_6$)alkyl-(C$_1$-C$_{14}$)heterocycloalkylene" refers to a divalent heterocycloalkylene wherein one or more hydrogen atoms in the C$_1$-C$_{14}$ heterocycloalkylene group is replaced by a (C$_1$-C$_6$) alkyl group that is further substituted by replacing one or more hydrogen atoms of the (C$_1$-C$_6$) alkyl group with a (C$_3$-C$_{14}$)heterocycloalkyl group.

The term "(C$_3$-C$_{14}$)aryl-(C$_1$-C$_{14}$)cycloalkylene" refers to a divalent cycloalkylene that is monocyclic, bicyclic or polycyclic and wherein one or more hydrogen atoms in the (C$_1$-C$_{14}$)cycloalkylene group is replaced by a (C$_3$-C$_{14}$)aryl group. Examples of (C$_3$-C$_{14}$)aryl-(C$_1$-C$_{14}$)cycloalkylene groups include without limitation phenylcyclobutylene, phenyl-cyclopropylene and 3-phenyl-2-methylbutylene-1-one.

The substituent —CO$_2$H, may be replaced with bioisosteric replacements such as:

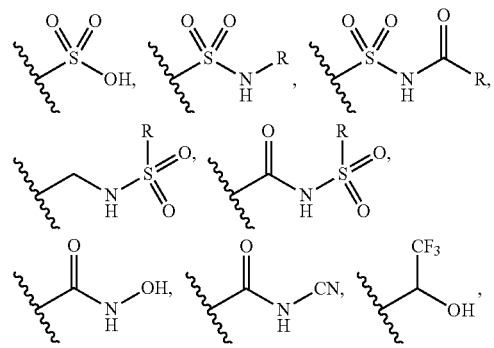

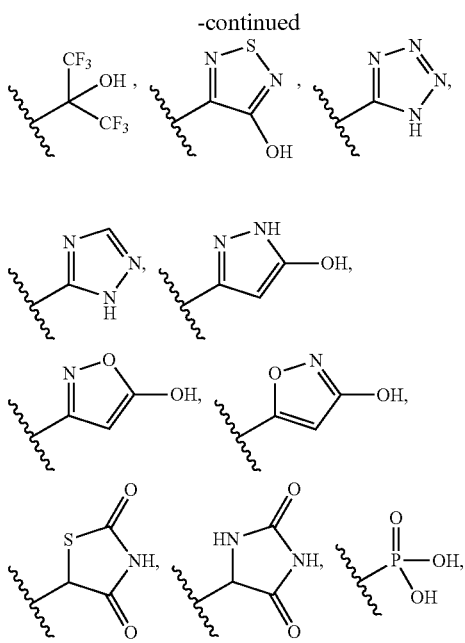

and the like, wherein R has the same definition as R' and R'' as defined herein. See, e.g., THE PRACTICE OF MEDICINAL CHEMISTRY (Academic Press: New York, 1996), at page 203.

The compound of the invention can exist in various isomeric forms, including configurational, geometric, and conformational isomers, including, for example, cis- or trans-conformations. Compounds of the present invention may also exist in one or more tautomeric forms, including both single tautomers and mixtures of tautomers. The term "isomer" is intended to encompass all isomeric forms of a compound of this invention, including tautomeric forms of the compound.

The compounds of the present invention may also exist in open-chain or cyclized forms. In some cases one or more of the cyclized forms may result in loss of water. The specific composition of the open-chain and cyclized forms may be dependent on how the compound is isolated, stored or administered. For example the compound may exist primarily in an open-chained form under acidic conditions but cyclize under neutral conditions. All forms are included in the invention.

Some compounds described here can have asymmetric centers and therefore exist in different enantiomeric and diastereomeric forms. A compound of the invention can be in the form of an optical isomer or a diastereomer. Accordingly, the invention encompasses compounds of the invention and their uses as described herein in the form of their optical isomers, diastereoisomers and mixtures thereof, including a racemic mixture. Optical isomers of the compounds of the invention can be obtained by known techniques such as asymmetric synthesis, chiral chromatography, simulated moving bed technology or via chemical separation of stereoisomers through the employment of optically active resolving agents.

Unless otherwise indicated, "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

If there is a discrepancy between a depicted structure and a name given to that structure, then the depicted structure controls. Additionally, if the stereochemistry of a structure or a portion of a structure is not indicated with, for example, bold or dashed lines, the structure or portion of the structure is to be interpreted as encompassing all stereoisomers of it. In some cases, however, where more than one chiral center exists, the structures and names may be represented as single enantiomers to help describe the relative stereochemistry. Those skilled in the art of organic synthesis will know if the compounds are prepared as single enantiomers from the methods used to prepare them.

A "pharmaceutically acceptable salt" is a pharmaceutically acceptable, organic or inorganic acid or base salt of a compound of the invention. Representative pharmaceutically acceptable salts include, e.g., alkali metal salts, alkali earth salts, ammonium salts, water-soluble and water-insoluble salts, such as the acetate, amsonate (4,4-diaminostilbene-2, 2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts. A pharmaceutically acceptable salt can have more than one charged atom in its structure. In this instance the pharmaceutically acceptable salt can have multiple counterions. Thus, a pharmaceutically acceptable salt can have one or more charged atoms and/or one or more counterions.

The terms "treat", "treating" and "treatment" refer to the amelioration or eradication of a disease or symptoms associated with a disease. In certain embodiments, such terms refer to minimizing the spread or worsening of the disease resulting from the administration of one or more prophylactic or therapeutic agents to a patient with such a disease.

The terms "prevent," "preventing," and "prevention" refer to the prevention of the onset, recurrence, or spread of the disease in a patient resulting from the administration of a prophylactic or therapeutic agent.

The term "effective amount" refers to an amount of a compound of the invention, such as a Formula I or Formula II compound, or other active ingredient sufficient to provide a therapeutic or prophylactic benefit in the treatment or prevention of a disease or to delay or minimize symptoms associated with a disease. Further, a therapeutically effective amount with respect to a compound of the invention means that amount of therapeutic agent alone, or in combination with other therapies, that provides a therapeutic benefit in the treatment or prevention of a disease. Used in connection with a compound of the invention, the term can encompass an amount that improves overall therapy, reduces or avoids symptoms or causes of disease, or enhances the therapeutic efficacy of or synergies with another therapeutic agent.

The terms "modulate", "modulation" and the like refer to the ability of a Formula I or Formula II compound to increase or decrease the function, or activity of, for example, Arginase I or Arginase II. "Modulation", in its various forms, is intended to encompass inhibition, antagonism, partial antagonism, activation, agonism and/or partial agonism of the activity associated with arginase. Arginase inhibitors are compounds that, e.g., bind to, partially or totally block stimulation, decrease, prevent, delay activation, inactivate, desensitize, or down regulate signal transduction. The ability of a compound to modulate arginase activity can be demonstrated in an enzymatic assay or a cell-based assay.

A "patient" includes an animal, such as a human, cow, horse, sheep, lamb, pig, chicken, turkey, quail, cat, dog, mouse, rat, rabbit or guinea pig. The animal can be a mammal such as a non-primate and a primate (e.g., monkey and human). In one embodiment, a patient is a human, such as a human infant, child, adolescent or adult.

The term "prodrug" refers to a precursor of a drug that is a compound which upon administration to a patient, must undergo chemical conversion by metabolic processes before becoming an active pharmacological agent. Exemplary prodrugs of compounds in accordance with Formula I and II are esters, pinenes, dioxaborolanes, and amides.

Formula I Compounds

As described above, the present invention relates to compounds according to Formula I.

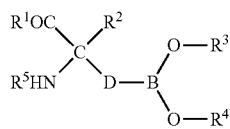

For Formula I compounds, D is selected from the group consisting of straight or branched $(C_1-C_6)$alkylene, straight or branched $(C_2-C_8)$alkenylene, straight or branched $(C_2-C_8)$alkynylene, $(C_3-C_{14})$arylene, and $(C_3-C_{14})$cycloalkylene. In some embodiments, one or more —$CH_2$— groups in D are optionally and independently replaced with a moiety selected from group the consisting of —O—, —NR'—, —S—, —SO—, —$SO_2$—, and —CR'R"—. For instance, D can be a four atom linker having the formula -$L^1$-$CH_2$—$CH_2$—, —$CH_2$-$L^1$-$L^2$-$CH_2$—, —$CH_2$—$CH_2$-$L^1$-$L^2$-, -$L^1$-$CH_2$—$CH_2$-$L^2$-, -$L^1$-$CH_2$-$L^2$-$CH_2$—, or -$L^1$-$CH_2$—$CH_2$-$L^2$-. The variables $L^1$ and $L^2$ are independently selected from the group consisting of O, NR', S, SO, $SO_2$, and CR'R", wherein R' and R" are as defined above.

In other embodiments, D contains a $(C_3-C_{14})$-cycloalkylenyl ring, two ring members of which are two adjacent —$CH_2$— groups in D, each having a hydrogen atom removed. A specific example of D is n-butylene wherein the second and third carbon atoms are part of a cyclopropyl group, as shown in the moiety

Variable D is advantageously a three to five atom linker. A particularly advantageous embodiment provides for D as a four atom linker as described herein.

In one embodiment, for example, the invention provides Formula I compounds in which D is butylene, $R^1$ is —OH, each of $R^3$, $R^4$ and $R^5$ are hydrogen and $R^2$ is selected from the group consisting of $(C_1-C_6)$alkyl, $(C_3-C_{14})$aryl, $(C_3-C_{14})$heteroaryl, $(C_3-C_{14})$heterocycloalkyl, $(C_3-C_{14})$heteroaryl-$(C_1-C_6)$alkylene-, $(C_3-C_{14})$heterocycloalkyl-$(C_1-C_6)$alkylene-, $(C_3-C_{14})$aryl-$(C_1-C_6)$alkylene- and —$(CH_2)_n$—$(X)_u$—$(CH_2)_m$—$(Y)_v$—$R^f$.

In another embodiment, $R^2$ is —$(CH_2)_n$—$(X)_u$—$(CH_2)_m$—$(Y)_v$—$R^f$. X and Y are each independently —NH, subscripts m and n are 1 and 2 respectively and u and v are both 1.

Alternatively, $R^2$ can be an alkyl group that is optionally substituted by hydroxyl or —$NR^dR^e$, where each of $R^d$ and $R^e$ are independently selected from the group consisting of H, straight or branched $(C_1-C_6)$alkyl, $(C_1-C_6)$aminoalkyl, optionally substituted $(C_3-C_{14})$aryl$(C_1-C_6)$alkylene-, optionally substituted $(C_3-C_{14})$aryl, and optionally substituted $(C_3-C_6)$ cycloalkyl. For example, when $R^2$ is an aminoalkyl, each of $R^d$ and $R^e$ can be a $(C_1-C_6)$aminoalkyl.

In another embodiment, $R^2$ can be a $(C_3-C_{14})$heterocycloalkyl-$(C_1-C_6)$alkylene-, for example, a $(C_3-C_6)$heterocycloalkyl-$(C_1-C_2)$alkylene-. Suitable $(C_3-C_6)$heterocycloalkyls include azetidinyl, pyrrolidinyl, piperidinyl, piperazinyl, morpholinyl, tetrahydro-2H-pyran, and thiomorpholinyl. The $(C_3-C_6)$heterocycloalkyl can optionally be substituted with one or more members selected from the group consisting of —$(C_1-C_6)$alkoxy, —$(C_1-C_6)$alkyl, and —OH. In one embodiment, the $(C_3-C_6)$heterocycloalkyl can be piperidinyl or pyrrolidinyl and the —$(C_1-C_6)$alkylene- can be methylene or ethylene.

For Formula I compounds, when $R^2$ is $(C_3-C_{14})$heteroaryl-$(C_1-C_6)$alkylene-, $R^2$ can be a $(C_3-C_6)$heteroaryl-$(C_1-C_6)$alkylene-group. Exemplary $(C_3-C_6)$heteroaryl groups without limitation include pyridinyl, benzimidazolyl, benzothiazol, imidazole, 1,2,3-triazole, 1,2,4-triazole, tetrazole, pyrimidine, imidazo[1,2-a]pyridine, oxazole, isoxazole, and furan. In an embodiment of the invention, the —$(C_1-C_6)$alkylene- can be methylene, or ethylene.

In some embodiments, $R^3$ and $R^4$ together with the boron atom to which they are bound form a 5- or 6-membered ring that is fully or partially saturated, and that optionally contains 1-3 additional heteroatom ring members selected from O, S, and N. The ring is optionally substituted with one or more substituents as defined herein for R' and R".

Cyclic structures of this type are useful as prodrug forms of the inventive compounds by virtue of $R^3$ and $R^4$ forming a cyclic ester from diols. A useful diol in this regard is pinacol, and another diol is pinanediol. Other diols include but are not limited to neopentylglycol, 1,2-ethanediol, 1,2-propoanediol, 1,3-propanediol, 2,3-butanediol, 1,2-diisopropylethanediol and 5,6-decanediol.

Also contemplated are compounds wherein the boronic acid moiety in Formula I is esterified with a sugar. Compounds of this class are also useful as prodrugs. Suitable sugars include without limitation monosaccharides and disaccharides, for example, sugars selected from the group consisting of glucose, mannitol and sorbitol.

In other embodiments, $R^2$ is a $(C_3-C_{14})$-cycloalkyl, optionally substituted by 1-3 substituents as defined hereinabove. Exemplary cycloalkyl groups are cyclohexyl and cyclopentyl. Alternatively, $R^2$ is a $(C_3-C_{14})$heterocycloalkyl, such as five- or six-membered heterocycloalkyl. Examples of Formula I compounds of these embodiments include those in the following table, wherein R' is defined as above, R has the same meaning as R', and W is a heteroatom as defined above:

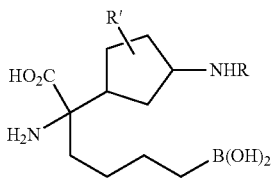

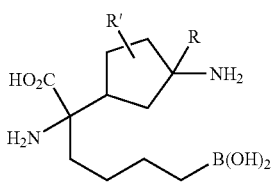

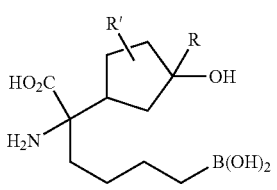

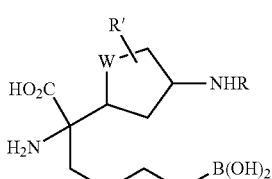

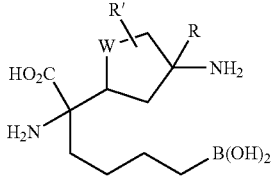

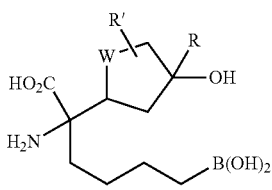

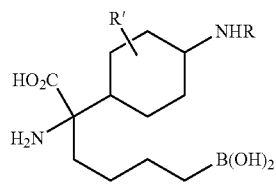

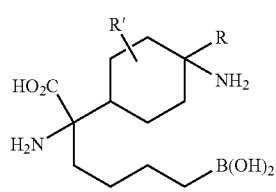

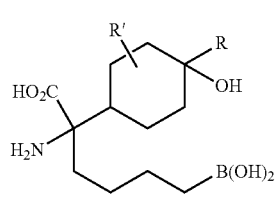

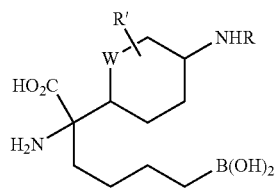

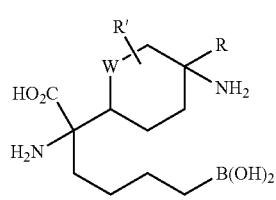

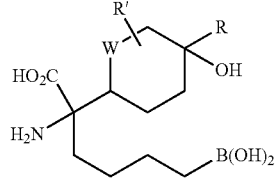

It should be understood that 2-amino-4-borono-2-methylbutanoic acid is excluded from Formula I.

Exemplary Formula I compounds include without limitation compounds mentioned in Table 1 below. While some exemplary compounds are depicted with stereochemistry, it should be understood that the invention includes all possible stereoisomers, such as diastereomers, of the compounds.

TABLE 1

| Ex. | Structure | Name |
|---|---|---|
| 1 | 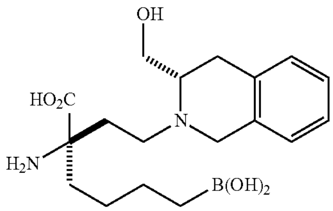 | (R)-2-amino-6-borono-2-(2-((S)-3-(hydroxymethyl)-3,4-dihydroisoquinolin-2(1H)-yl)ethyl)hexanoic acid |
| 2 | 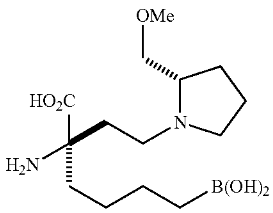 | (R)-2-amino-6-borono-2-(2-((S)-2-(methoxymethyl)pyrrolidin-1-yl)ethyl)hexanoic acid |
| 3 | 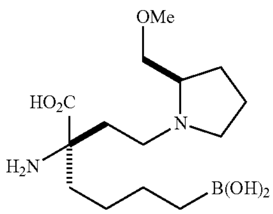 | (R)-2-amino-6-borono-2-(2-((R)-2-(methoxymethyl)pyrrolidin-1-yl)ethyl)hexanoic acid |
| 4 | 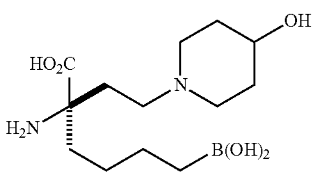 | (R)-2-amino-6-borono-2-(2-(4-hydroxypiperidin-1-yl)ethyl)hexanoic acid |
| 5 | 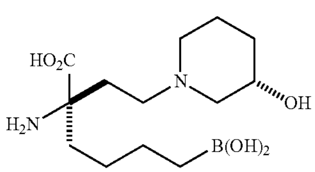 | (R)-2-amino-6-borono-2-(2-((S)-3-hydroxypiperidin-1-yl)ethyl)hexanoic acid |
| 6 | 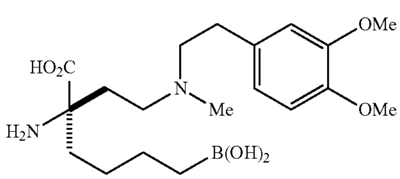 | (R)-2-amino-6-borono-2-(2-((3,4-dimethoxyphenethyl)(methyl)amino)ethyl)hexanoic acid |
| 7 | 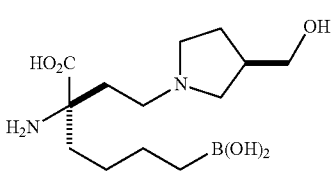 | (R)-2-amino-6-borono-2-(2-((R)-3-(hydroxymethyl)pyrrolidin-1-yl)ethyl)hexanoic acid |
| 8 | 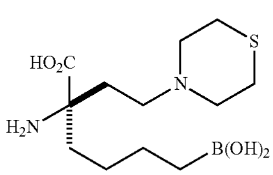 | (R)-2-amino-6-borono-2-(2-thiomorpholinoethyl)hexanoic acid |

TABLE 1-continued

| Ex. | Structure | Name |
|---|---|---|
| 9 | 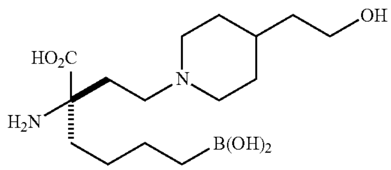 | (R)-2-amino-6-borono-2-(2-(4-(2-hydroxyethyl)piperidin-1-yl)ethyl)hexanoic acid |
| 10 | 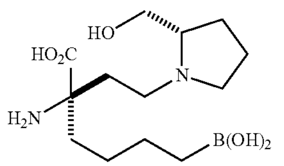 | (R)-2-amino-6-borono-2-(2-((S)-2-(hydroxymethyl)pyrrolidin-1-yl)ethyl)hexanoic acid |
| 11 | 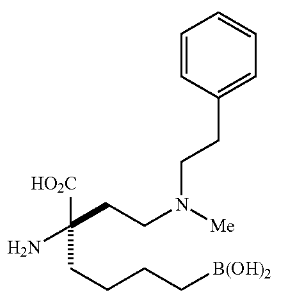 | (R)-2-amino-6-borono-2-(2-(methyl(phenethyl)amino)ethyl)hexanoic acid |
| 12 | 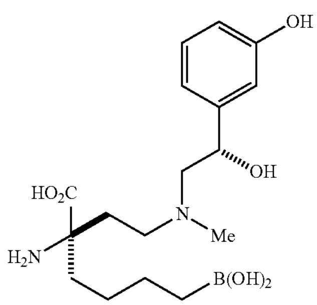 | (R)-2-amino-6-borono-2-(2-(((S)-2-hydroxy-2-(3-hydroxyphenyl)ethyl)(methyl)amino)ethyl)hexanoic acid |
| 13 | 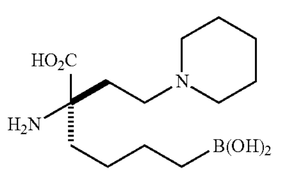 | (R)-2-amino-6-borono-2-(2-(piperidin-1-yl)ethyl)hexanoic acid |
| 14 | 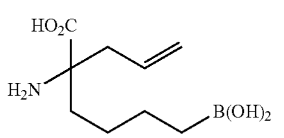 | 2-allyl-2-amino-6-boronohexanoic acid |
| 15 | 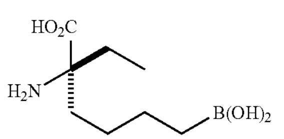 | (S)-2-amino-6-borono-2-ethylhexanoic acid |
| 16 | 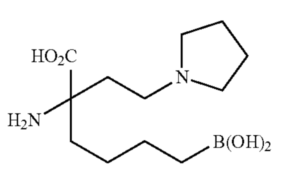 [SMILES: NC(CCCCB(O)O)(CCN1CCCC1)C(=O)O] | 2-amino-6-borono-2-(2-(pyrrolidin-1-yl)ethyl)hexanoic acid |

TABLE 1-continued

| Ex. | Structure | Name |
|---|---|---|
| 17 | 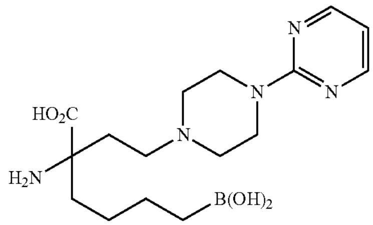 [SMILES: NC(CCCCB(O)O)(CCN1CCN(c2ncccn2)CC1)C(=O)O] | 2-amino-6-borono-2-(2-(4-(pyrimidin-2-yl)piperazin-1-yl)ethyl)hexanoic acid |
| 18 | 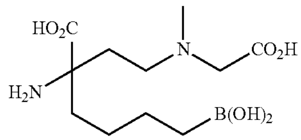 [SMILES: CN(CCC(N)(CCCCB(O)O)C(=O)O)CC(=O)O] | 2-amino-6-borono-2-(2-((carboxymethyl)(methyl)amino)ethyl)hexanoic acid |
| 19 | 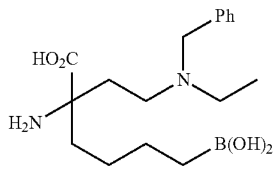 [SMILES: CCN(CCC(N)(CCCCB(O)O)C(=O)O)Cc1ccccc1] | 2-amino-2-(2-(benzyl)ethyl)amino)ethyl)-6-boronohexanoic acid |
| 20 | 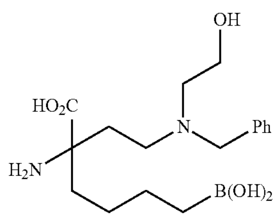 [SMILES: NC(CCCCB(O)O)(CCN(CCO)Cc1ccccc1)C(=O)O] | 2-amino-2-(2-benzyl(2-hydroxyethyl)amino)ethyl)-6-boronohexanoic acid |
| 21 | 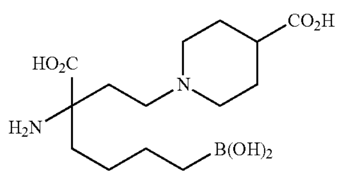 [SMILES: NC(CCCCB(O)O)(CCN1CCC(C(=O)O)CC1)C(=O)O] | 1-(3-amino-7-borono-3-carboxyheptyl)piperidine-4-carboxylic acid |
| 22 | 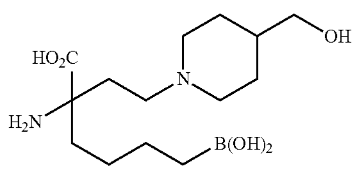 [SMILES: NC(CCCCB(O)O)(CCN1CCC(CO)CC1)C(=O)O] | 2-amino-6-borono-2-(2-(4-(hydroxymethyl)piperidin-1-yl)ethyl)hexanoic acid |
| 23 | 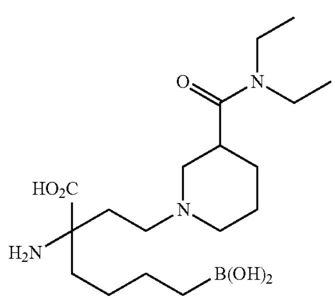 [SMILES: CCN(CC)C(=O)C1CCCN(CCC(N)(CCCCB(O)O)C(=O)O)C1] | 2-amino-6-borono-2-(2-(3-(diethylcarbamoyl)piperidin-1-yl)ethyl)hexanoic acid |
| 24 | 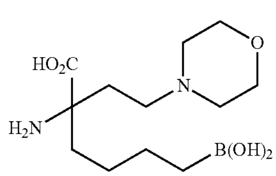 [SMILES: NC(CCCCB(O)O)(CCN1CCOCC1)C(=O)O] | 2-amino-6-borono-2-(2-morpholinoethyl)hexanoic acid |

TABLE 1-continued

| Ex. | Structure | Name |
|---|---|---|
| 25 | 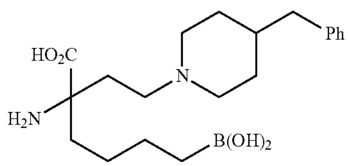 [SMILES: NC(CCCCB(O)O)(CCN1CCC(Cc2ccccc2)CC1)C(=O)O] | 2-amino-2-(2-(4-benzylpiperidin-1-yl)ethyl)-6-boronohexanoic acid |
| 26 | 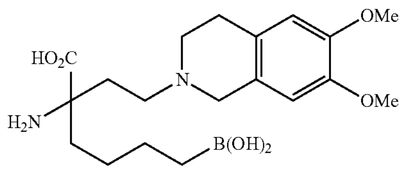 [SMILES: COc1cc2c(cc1OC)CN(CCC(N)(CCCCB(O)O)C(=O)O)CC2] | 2-amino-6-borono-2-(2-(6,7-dimethoxy-3,4-dihydroisoquinolin-2(1H)-yl)ethyl)hexanoic acid |
| 27 | 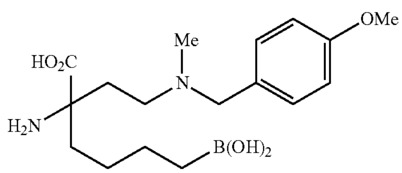 [SMILES: COc1ccc(CN(C)CCC(N)(CCCCB(O)O)C(=O)O)cc1] | 2-amino-6-borono-2-(2-((4-methoxybenzyl)(methyl)amino)ethyl)hexanoic acid |
| 28 | 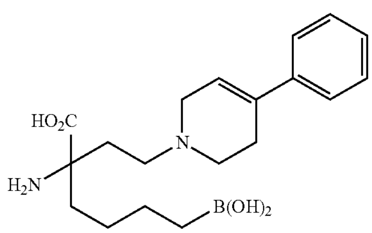 [SMILES: NC(CCCCB(O)O)(CCN1CC=C(c2ccccc2)CC1)C(=O)O] | 2-amino-6-borono-2-(2-(4-phenyl-5,6-dihydropyridin-1(2H)-yl)ethyl)hexanoic acid |
| 29 | 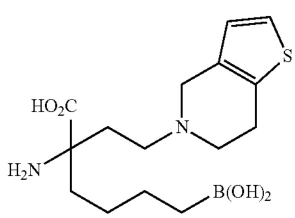 [SMILES: NC(CCCCB(O)O)(CCN1CCc2sccc2C1)C(=O)O] | 2-amino-6-borono-2-(2-(6,7-dihydrothieno[3,2-c]pyridin-5(4H)-yl)ethyl)hexanoic acid |
| 30 | 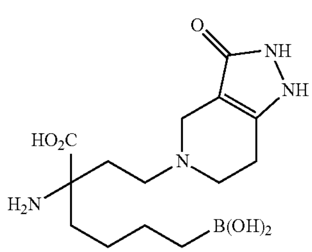 [SMILES: NC(CCCCB(O)O)(CCN1CCc2[nH][nH]c(=O)c2C1)C(=O)O] | 2-amino-6-borono-2-(2-(3-oxo-2,3,6,7-tetrahydro-1H-pyrazolo[4,3-c]pyridin-5(4H)-yl)ethyl)hexanoic acid |
| 31 | 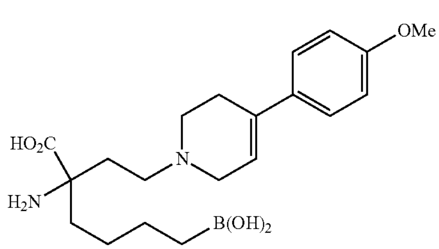 [SMILES: COc1ccc(C2=CCN(CCC(N)(CCCCB(O)O)C(=O)O)CC2)cc1] | 2-amino-6-borono-2-(2-(4-(4-methoxyphenyl)-5,6-dihydropyridin-1(2H)-yl)ethyl)hexanoic acid |

TABLE 1-continued

| Ex. | Structure | Name |
|---|---|---|
| 32 | 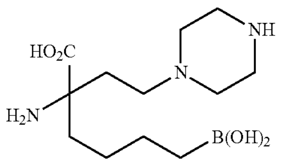 [SMILES: NC(CCCCB(O)O)(CCN1CCNCC1)C(=O)O] | 2-amino-6-borono-2-(2-(piperazin-1-yl)ethyl)hexanoic acid |
| 33 | 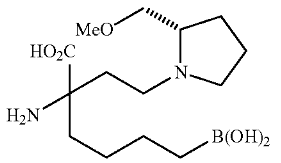 [SMILES: COC[C@@H]1CCCN1CCC(N)(CCCCB(O)O)C(=O)O] | 2-amino-6-borono-2-(2-((S)-2-(methoxymethyl)pyrrolidin-1-yl)ethyl)hexanoic acid |
| 34 | 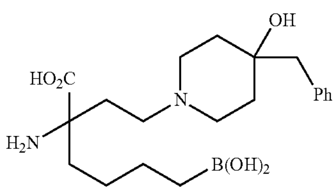 [SMILES: NC(CCCCB(O)O)(CCN1CCC(O)(Cc2ccccc2)CC1)C(=O)O] | 2-amino-2-(2-(4-benzyl-4-hydroxypiperidin-1-yl)ethyl)-6-boronohexanoic acid |
| 35 | 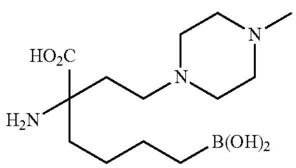 [SMILES: CN1CCN(CCC(N)(CCCCB(O)O)C(=O)O)CC1] | 2-amino-6-borono-2-(2-(4-methylpiperazin-1-yl)ethyl)hexanoic acid |
| 36 | 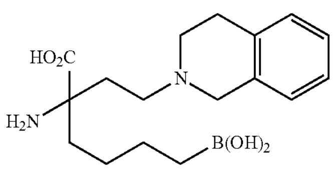 [SMILES: NC(CCCCB(O)O)(CCN1CCc2ccccc2C1)C(=O)O] | 2-amino-6-borono-2-(2-(3,4-dihydroisoquinolin-2(1H)-yl)ethyl)hexanoic acid |
| 37 | 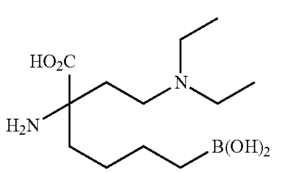 [SMILES: CCN(CC)CCC(N)(CCCCB(O)O)C(=O)O] | 2-amino-6-borono-2-(2-(diethylamino)ethyl)hexanoic acid |
| 38 | 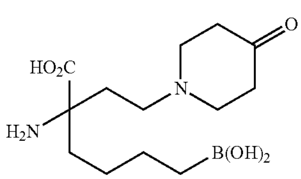 [SMILES: NC(CCCCB(O)O)(CCN1CCC(=O)CC1)C(=O)O] | 2-amino-6-borono-2-(2-(4-oxopiperidin-1-yl)ethyl)hexanoic acid |
| 39 | 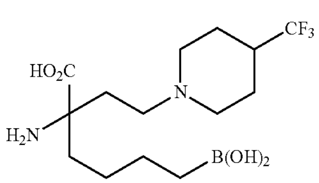 [SMILES: NC(CCCCB(O)O)(CCN1CCC(C(F)(F)F)CC1)C(=O)O] | 2-amino-6-borono-2-(2-(4-(trifluoromethyl)piperidin-1-yl)ethyl)hexanoic acid |

TABLE 1-continued

| Ex. | Structure | Name |
|---|---|---|
| 40 | 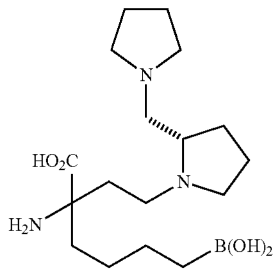 [SMILES: NC(CCCCB(O)O)(CCN1CCC[C@H]1CN1CCCC1)C(=O)O] | 2-amino-6-borono-2-(2-((S)-2-(pyrrolidin-1-ylmethyl)pyrrolidin-1-yl)ethyl)hexanoic acid |
| 41 | 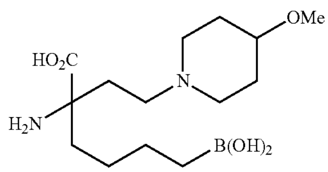 [SMILES: COC1CCN(CCC(N)(CCCCB(O)O)C(=O)O)CC1] | 2-amino-6-borono-2-(2-(4-methoxypiperidin-1-yl)ethyl)hexanoic acid |
| 42 | 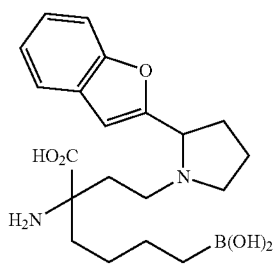 [SMILES: NC(CCCCB(O)O)(CCN1CCCC1c1cc2ccccc2o1)C(=O)O] | 2-amino-2-(2-(2-(benzofuran-2-yl)pyrrolidin-1-yl)ethyl)-6-boronohexanoic acid |
| 43 | 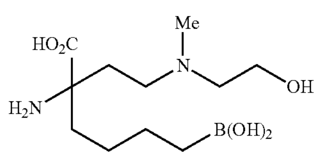 [SMILES: CN(CCO)CCC(N)(CCCCB(O)O)C(=O)O] | 2-amino-6-borono-2-(2-((2-hydroxyethyl)(methyl)amino)ethyl)hexanoic acid |
| 44 | 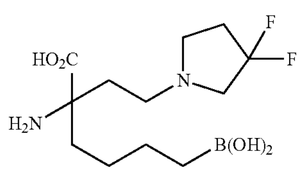 [SMILES: NC(CCCCB(O)O)(CCN1CCC(F)(F)C1)C(=O)O] | 2-amino-6-borono-2-(2-(3,3-difluoropyrrolidin-1-yl)ethyl)hexanoic acid |
| 45 | 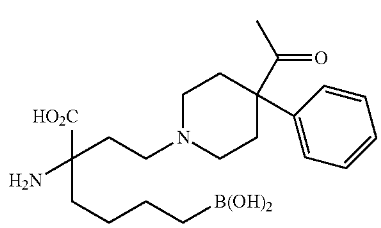 [SMILES: CC(=O)C1(c2ccccc2)CCN(CCC(N)(CCCCB(O)O)C(=O)O)CC1] | 2-(2-(4-acetyl-4-phenylpiperidin-1-yl)ethyl)-2-amino-6-boronohexanoic acid |
| 46 | 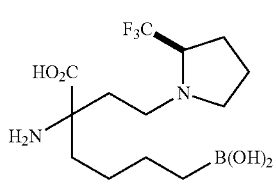 [SMILES: NC(CCCCB(O)O)(CCN1CCC[C@@H]1C(F)(F)F)C(=O)O] | 2-amino-6-borono-2-(2-((R)-2-(trifluoromethyl)pyrrolidin-1-yl)ethyl)hexanoic acid |

TABLE 1-continued

| Ex. | Structure | Name |
|---|---|---|
| 47 | 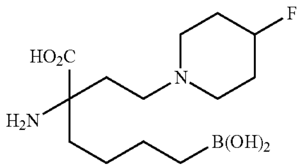 [SMILES: NC(CCCCB(O)O)(CCN1CCC(F)CC1)C(=O)O] | 2-amino-6-borono-2-(2-(4-fluoropiperidin-1-yl)ethyl)hexanoic acid |
| 48 | 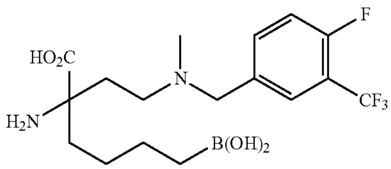 [SMILES: CN(CCC(N)(CCCCB(O)O)C(=O)O)Cc1ccc(F)c(C(F)(F)F)c1] | 2-amino-6-borono-2-(2-((4-fluoro-3-(trifluoromethyl)benzyl)(methyl)amino)ethyl)hexanoic acid |
| 49 | 3 HCl | 2-amino-6-borono-2-(2-(3-methyl-1,3-diazepan-1-yl)ethyl)hexanoic acid |
| 50 | 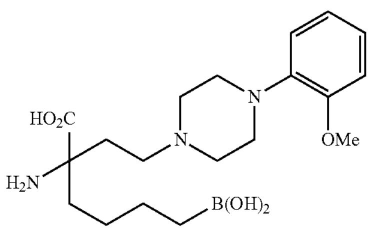 [SMILES: COc1ccccc1N1CCN(CCC(N)(CCCCB(O)O)C(=O)O)CC1] | 2-amino-6-borono-2-(2-(4-(2-methoxyphenyl)piperazin-1-yl)ethyl)hexanoic acid |
| 51 | 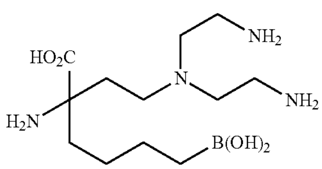 [SMILES: NCCN(CCN)CCC(N)(CCCCB(O)O)C(=O)O] | 2-amino-2-(2-(bis(2-aminoethyl)amino)ethyl)-6-boronohexanoic acid |
| 52 | 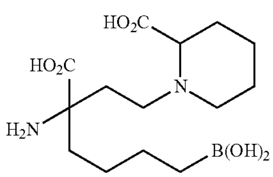 [SMILES: NC(CCCCB(O)O)(CCN1CCCCC1C(=O)O)C(=O)O] | 1-(3-amino-7-borono-3-carboxyheptyl)piperidine-2-carboxylic acid |
| 53 | 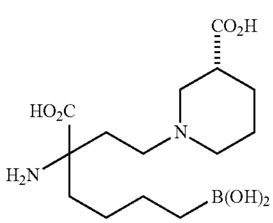 [SMILES: NC(CCCCB(O)O)(CCN1CCC[C@@H](C(=O)O)C1)C(=O)O] | (3R)-1-(3-amino-7-borono-3-carboxyheptyl)piperidine-3-carboxylic acid |
| 54 | 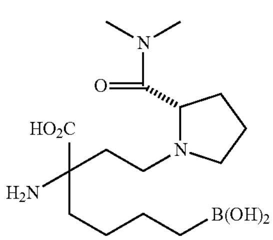 [SMILES: CN(C)C(=O)[C@@H]1CCCN1CCC(N)(CCCCB(O)O)C(=O)O] | 2-amino-6-borono-2-(2-((S)-2-(dimethylcarbamoyl)pyrrolidin-1-yl)ethyl)hexanoic acid |

TABLE 1-continued

| Ex. | Structure | Name |
|---|---|---|
| 55 | 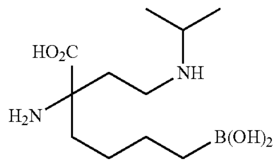 [SMILES: CC(C)NCCC(N)(CCCCB(O)O)C(=O)O] | 2-amino-6-borono-2-(2-(isopropylamino)ethyl)hexanoic acid |
| 56 | 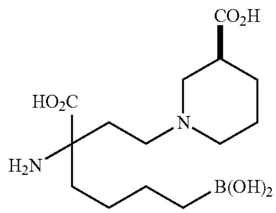 [SMILES: NC(CCCCB(O)O)(CCN1CCC[C@H](C(=O)O)C1)C(=O)O] | (3S)-1-(3-amino-7-borono-3-carboxyheptyl)piperidine-3-carboxylic acid |
| 57 | 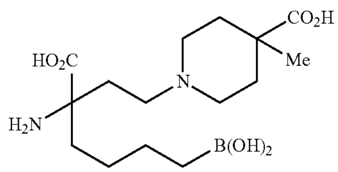 [SMILES: CC1(C(=O)O)CCN(CCC(N)(CCCCB(O)O)C(=O)O)CC1] | 1-(3-amino-7-borono-3-carboxyheptyl)-4-methylpiperidine-4-carboxylic acid |
| 58 | 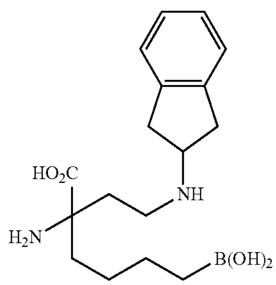 [SMILES: NC(CCCCB(O)O)(CCNC1Cc2ccccc2C1)C(=O)O] | 2-amino-6-borono-2-(2-(2,3-dihydro-1H-inden-2-ylamino)ethyl)hexanoic acid |
| 59 | 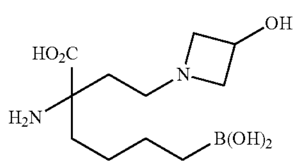 [SMILES: NC(CCCCB(O)O)(CCN1CC(O)C1)C(=O)O] | 2-amino-6-borono-2-(2-(3-hydroxyazetidin-1-yl)ethyl)hexanoic acid |
| 60 | 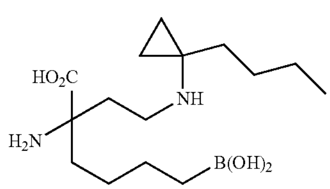 [SMILES: CCCCC1(NCCC(N)(CCCCB(O)O)C(=O)O)CC1] | 2-amino-6-borono-2-(2-(1-butylcyclopropylamino)ethyl)hexanoic acid |
| 61 | 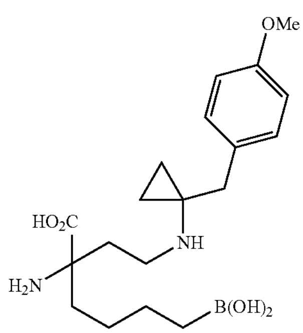 [SMILES: COc1ccc(CC2(NCCC(N)(CCCCB(O)O)C(=O)O)CC2)cc1] | 2-amino-6-borono-2-(2-(1-(4-methoxybenzyl)cyclopropylamino)ethyl)hexanoic acid |

TABLE 1-continued

| Ex. | Structure | Name |
|---|---|---|
| 62 | 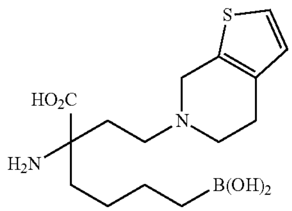 [SMILES: NC(CCCCB(O)O)(CCN1CCc2ccsc2C1)C(=O)O] | 2-amino-6-borono-2-(2-(4,5-dihydrothieno[2,3-c]pyridin-6(7H)-yl)ethyl)hexanoic acid |
| 63 | 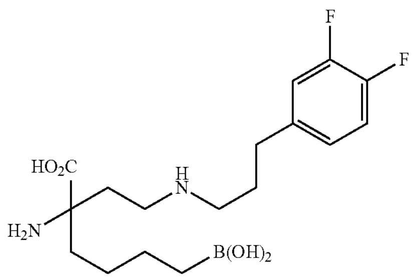 [SMILES: NC(CCCCB(O)O)(CCNCCCc1ccc(F)c(F)c1)C(=O)O] | 2-amino-6-borono-2-(2-(3-(3,4-difluorophenyl)propylamino)ethyl)hexanoic acid |
| 64 | 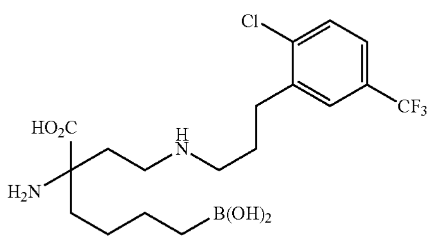 [SMILES: NC(CCCCB(O)O)(CCNCCCc1cc(C(F)(F)F)ccc1Cl)C(=O)O] | 2-amino-6-borono-2-(2-(3-(2-chloro-5-(trifluoromethyl)phenyl)propylamino)ethyl)hexanoic acid |
| 65 | 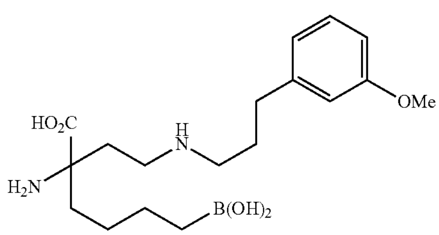 [SMILES: COc1cccc(CCCNCCC(N)(CCCCB(O)O)C(=O)O)c1] | 2-amino-6-borono-2-(2-(3-(3-methoxyphenyl)propylamino)ethyl)hexanoic acid |
| 66 | 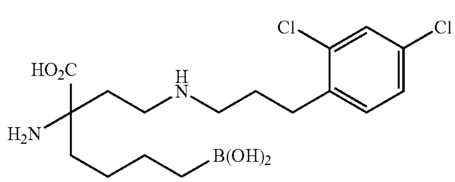 [SMILES: NC(CCCCB(O)O)(CCNCCCc1ccc(Cl)cc1Cl)C(=O)O] | 2-amino-6-borono-2-(2-(3-(2,4-dichlorophenyl)propylamino)ethyl)hexanoic acid |
| 67 | 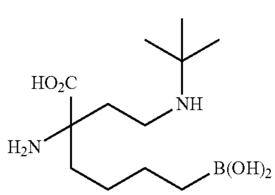 [SMILES: CC(C)(C)NCCC(N)(CCCCB(O)O)C(=O)O] | 2-amino-6-borono-2-(2-(tert-butylamino)ethyl)hexanoic acid |
| 68 | 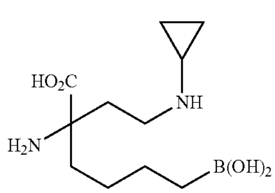 [SMILES: NC(CCCCB(O)O)(CCNC1CC1)C(=O)O] | 2-amino-6-borono-2-(2-(cyclopropylamino)ethyl)hexanoic acid |

TABLE 1-continued

| Ex. | Structure | Name |
|---|---|---|
| 69 | 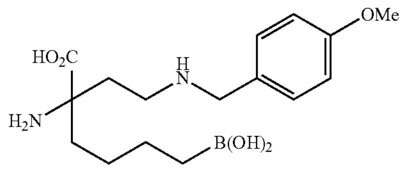 [SMILES: COc1ccc(CNCCC(N)(CCCCB(O)O)C(=O)O)cc1] | 2-amino-6-borono-2-(2-(4-methoxybenzylamino)ethyl)hexanoic acid |
| 70 | 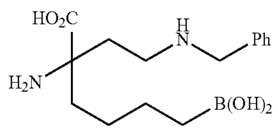 [SMILES: NC(CCCCB(O)O)(CCNCc1ccccc1)C(=O)O] | 2-amino-2-(2-(benzylamino)ethyl)-6-boronohexanoic acid |
| 71 | 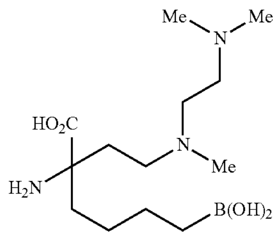 [SMILES: CN(C)CCN(C)CCC(N)(CCCCB(O)O)C(=O)O] | 2-amino-6-borono-2-(2-((2-(dimethylamino)ethyl)(methyl)amino)ethyl)hexanoic acid |
| 72 | 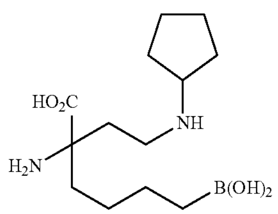 [SMILES: NC(CCCCB(O)O)(CCNC1CCCC1)C(=O)O] | 2-amino-6-borono-2-(2-(cyclopentylamino)ethyl)hexanoic acid |
| 73 | 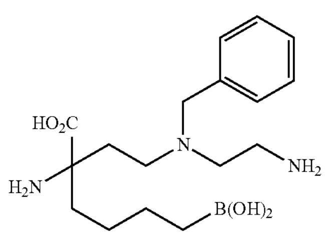 [SMILES: NCCN(CCC(N)(CCCCB(O)O)C(=O)O)Cc1ccccc1] | 2-amino-2-(2-((2-aminoethyl)(benzyl)amino)ethyl)-6-boronohexanoic acid |
| 74 | 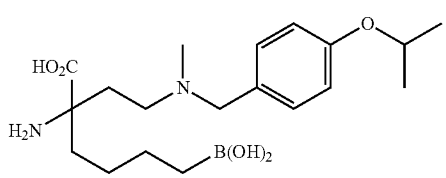 [SMILES: CC(C)Oc1ccc(CN(C)CCC(N)(CCCCB(O)O)C(=O)O)cc1] | 2-amino-6-borono-2-(2-((4-isopropoxybenzyl)(methyl)amino)ethyl)hexanoic acid |
| 75 | 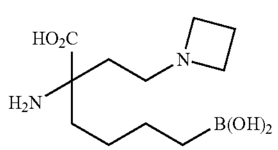 [SMILES: NC(CCCCB(O)O)(CCN1CCC1)C(=O)O] | 2-amino-2-(2-(azetidin-1-yl)ethyl)-6-boronohexanoic acid |
| 76 | 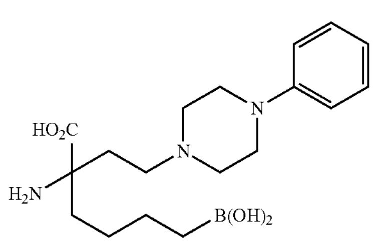 [SMILES: NC(CCCCB(O)O)(CCN1CCN(c2ccccc2)CC1)C(=O)O] | 2-amino-6-borono-2-(2-(4-phenylpiperazin-1-yl)ethyl)hexanoic acid |

TABLE 1-continued

| Ex. | Structure | Name |
|---|---|---|
| 77 | 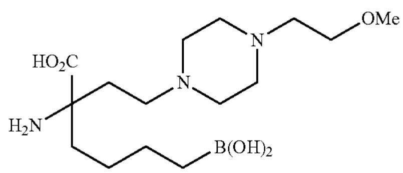 [SMILES: COCCN1CCN(CCC(N)(CCCCB(O)O)C(=O)O)CC1] | 2-amino-6-borono-2-(2-(4-(2-methoxyethyl)piperazin-1-yl)ethyl)hexanoic acid |
| 78 | 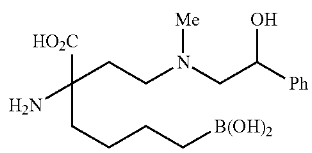 [SMILES: CN(CCC(N)(CCCCB(O)O)C(=O)O)CC(O)c1ccccc1] | 2-amino-6-borono-2-(2-((2-hydroxy-2-phenylethyl)(methyl)amino)ethyl)hexanoic acid |
| 79 | 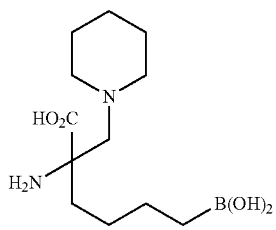 [SMILES: NC(CCCCB(O)O)(CN1CCCCC1)C(=O)O] | 2-amino-6-borono-2-(piperidin-1-ylmethyl)hexanoic acid |
| 80 | 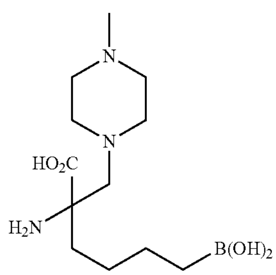 [SMILES: CN1CCN(CC(N)(CCCCB(O)O)C(=O)O)CC1] | 2-amino-6-borono-2-((4-methylpiperazin-1-yl)methyl)hexanoic acid |
| 81 | 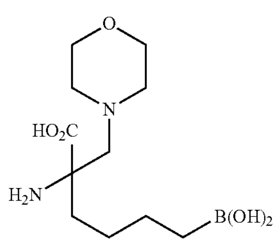 [SMILES: NC(CCCCB(O)O)(CN1CCOCC1)C(=O)O] | 2-amino-6-borono-2-(morpholinomethyl)hexanoic acid |
| 82 | 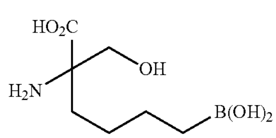 [SMILES: NC(CO)(CCCCB(O)O)C(=O)O] | 2-amino-6-borono-2-(hydroxymethyl)hexanoic acid |
| 83 | 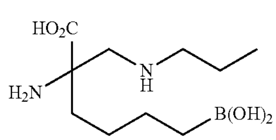 [SMILES: CCCNCC(N)(CCCCB(O)O)C(=O)O] | 2-amino-6-borono-2-((propylamino)methyl)hexanoic acid |
| 84 | 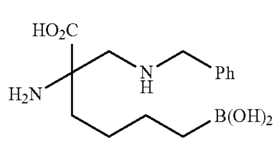 [SMILES: NC(CCCCB(O)O)(CNCc1ccccc1)C(=O)O] | 2-amino-2-((benzylamino)methyl)-6-boronohexanoic acid |

TABLE 1-continued

| Ex. | Structure | Name |
|---|---|---|
| 85 | 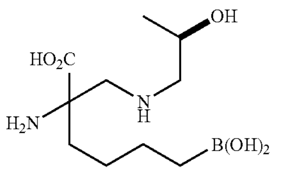 [SMILES: C[C@@H](O)CNCC(N)(CCCCB(O)O)C(=O)O] | 2-amino-6-borono-2-(((R)-2-hydroxypropylamino)methyl)hexanoic acid |
| 86 | 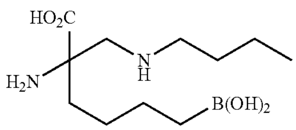 [SMILES: CCCCNCC(N)(CCCCB(O)O)C(=O)O] | 2-amino-6-borono-2-((butylamino)methyl)hexanoic acid |
| 87 | 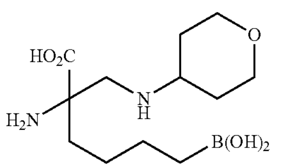 [SMILES: NC(CCCCB(O)O)(CNC1CCOCC1)C(=O)O] | 2-amino-6-borono-2-((tetrahydro-2H-pyran-4-ylamino)methyl)hexanoic acid |
| 88 | 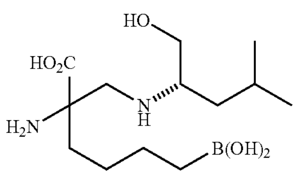 | 2-amino-6-borono-2-(((S)-1-hydroxy-4-methylpentan-2-ylamino)methyl)hexanoic acid |
| 89 | 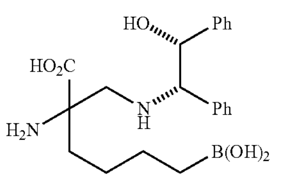 | 2-amino-6-borono-2-(((1S,2R)-2-hydroxy-1,2-diphenylethylamino)methyl)hexanoic acid |
| 90 | 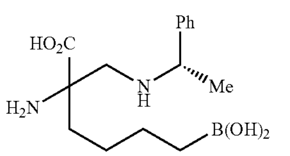 [SMILES: C[C@H](NCC(N)(CCCCB(O)O)C(=O)O)c1ccccc1] | 2-amino-6-borono-2-(((S)-1-phenylethylamino)methyl)hexanoic acid |
| 91 | 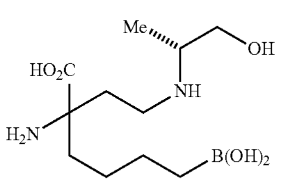 [SMILES: C[C@H](CO)NCCC(N)(CCCCB(O)O)C(=O)O] | 2-amino-6-borono-2-(2-((R)-1-hydroxypropan-2-ylamino)ethyl)hexanoic acid |
| 92 | 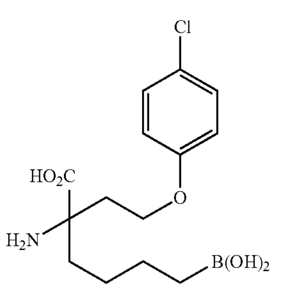 [SMILES: NC(CCCCB(O)O)(CCOc1ccc(Cl)cc1)C(=O)O] | 2-amino-6-borono-2-(2-(4-chlorophenoxy)ethyl)hexanoic acid |

TABLE 1-continued

| Ex. | Structure | Name |
|---|---|---|
| 93 | 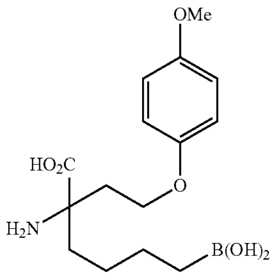 [SMILES: COc1ccc(OCCC(N)(CCCCB(O)O)C(=O)O)cc1] | 2-amino-6-borono-2-(2-(4-methoxyphenoxy)ethyl)hexanoic acid |
| 94 | 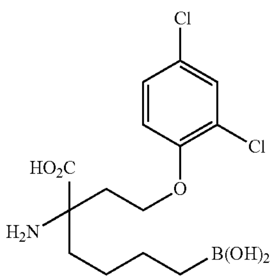 [SMILES: NC(CCCCB(O)O)(CCOc1ccc(Cl)cc1Cl)C(=O)O] | 2-amino-6-borono-2-(2-(2,4-dichlorophenoxy)ethyl)hexanoic acid |
| 95 | 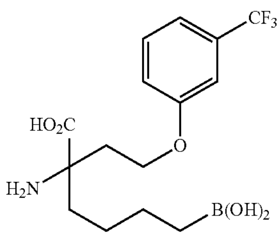 [SMILES: NC(CCCCB(O)O)(CCOc1cccc(C(F)(F)F)c1)C(=O)O] | 2-amino-6-borono-2-(2-(3-(trifluoromethyl)phenoxy)ethyl)hexanoic acid |
| 96 | 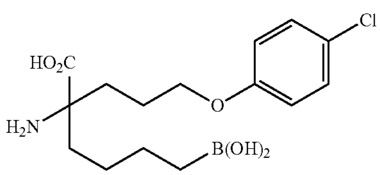 [SMILES: NC(CCCCB(O)O)(CCCOc1ccc(Cl)cc1)C(=O)O] | 2-amino-6-borono-2-(3-(4-chlorophenoxy)propyl)hexanoic acid |
| 97 | 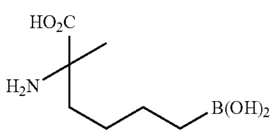 | 2-amino-6-borono-2-methylhexanoic acid |
| 98 | 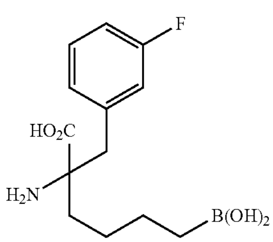 [SMILES: NC(CCCCB(O)O)(Cc1cccc(F)c1)C(=O)O] | 2-amino-6-borono-2-(3-fluorobenzyl)hexanoic acid |
| 99 | 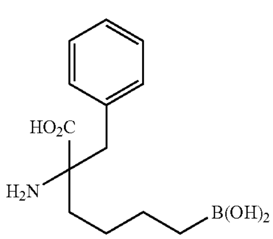 [SMILES: NC(CCCCB(O)O)(Cc1ccccc1)C(=O)O] | 2-amino-2-benzyl-6-boronohexanoic acid |

TABLE 1-continued

| Ex. | Structure | Name |
|---|---|---|
| 100 | 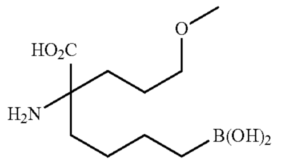 [SMILES: COCCCC(N)(CCCCB(O)O)C(=O)O] | 2-amino-6-borono-2-(3-methoxypropyl)hexanoic acid |
| 101 | 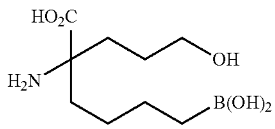 [SMILES: NC(CCCO)(CCCCB(O)O)C(=O)O] | 2-amino-6-borono-2-(3-hydroxypropyl)hexanoic acid |
| 102 | 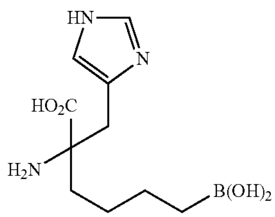 [SMILES: NC(CCCCB(O)O)(Cc1c[nH]cn1)C(=O)O] | 2-((1H-imidazol-4-yl)methyl)-2-amino-6-boronohexanoic acid |
| 103 | 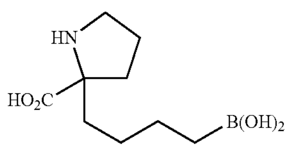 [SMILES: O=C(O)C1(CCCCB(O)O)CCCN1] | 2-(4-boronobutyl)pyrrolidine-2-carboxylic acid |
| 104 | 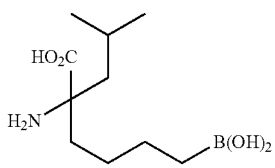 [SMILES: CC(C)CC(N)(CCCCB(O)O)C(=O)O] | 2-amino-6-borono-2-isobutylhexanoic acid |
| 105 | 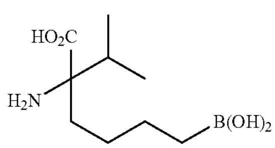 | 2-amino-6-borono-2-isopropylhexanoic acid |
| 106 | 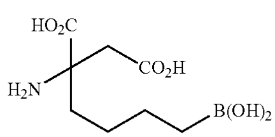 | 2-amino-2-(4-boronobutyl)succinic acid |
| 107 | 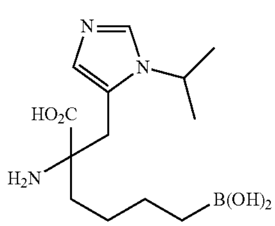 [SMILES: CC(C)n1cncc1CC(N)(CCCCB(O)O)C(=O)O] | 2-amino-6-borono-2-((1-isopropyl-1H-imidazol-5-yl)methyl)hexanoic acid |
| 108 | 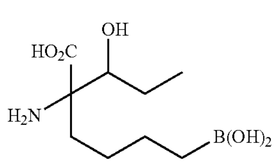 [SMILES: CCC(O)C(N)(CCCCB(O)O)C(=O)O] | 2-amino-6-borono-2-(1-hydroxypropyl)hexanoic acid |

TABLE 1-continued

| Ex. | Structure | Name |
|---|---|---|
| 109 | 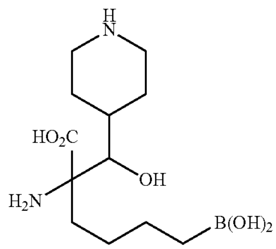 [SMILES: NC(CCCCB(O)O)(C(=O)O)C(O)C1CCNCC1] | 2-amino-6-borono-2-(hydroxy(piperidin-4-yl)methyl)hexanoic acid |
| 110 | 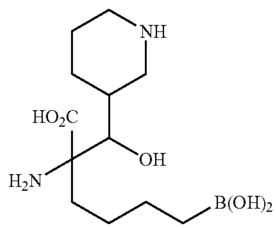 [SMILES: NC(CCCCB(O)O)(C(=O)O)C(O)C1CCCNC1] | 2-amino-6-borono-2-(hydroxy(piperidin-3-yl)methyl)hexanoic acid |
| 111 | 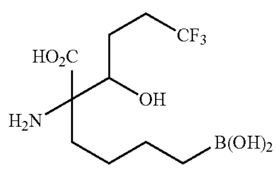 [SMILES: NC(CCCCB(O)O)(C(=O)O)C(O)CCC(F)(F)F] | 2-amino-2-(4-boronobutyl)-6,6,6-trifluoro-3-hydroxyhexanoic acid |
| 112 | 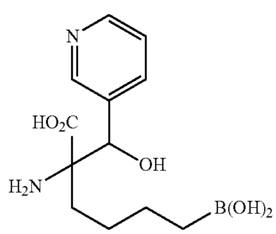 [SMILES: NC(CCCCB(O)O)(C(=O)O)C(O)c1cccnc1] | 2-amino-6-borono-2-(hydroxy(pyridin-3-yl)methyl)hexanoic acid |
| 113 | 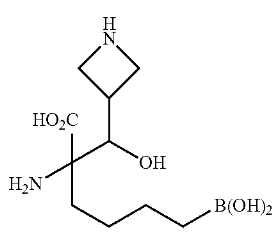 [SMILES: NC(CCCCB(O)O)(C(=O)O)C(O)C1CNC1] | 2-amino-2-(azetidin-3-yl(hydroxy)methyl)-6-boronohexanoic acid |
| 114 | 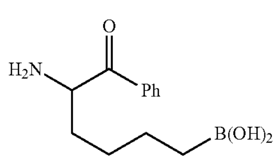 [SMILES: NC(CCCCB(O)O)C(=O)c1ccccc1] | 5-amino-6-oxo-6-phenylhexylboronic acid |
| 115 | 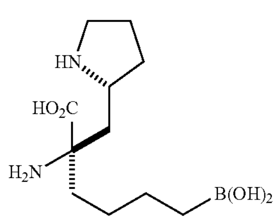 | (R)-2-amino-6-borono-2-((R)-pyrrolidin-2-ylmethyl)hexanoic acid |

TABLE 1-continued

| Ex. | Structure | Name |
|---|---|---|
| 116 | 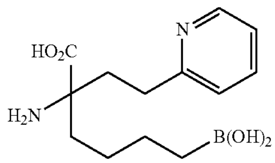 [SMILES: NC(CCCCB(O)O)(CCc1ccccn1)C(=O)O] | 2-amino-6-borono-2-(2-(pyridin-2-yl)ethyl)hexanoic acid |
| 117 | 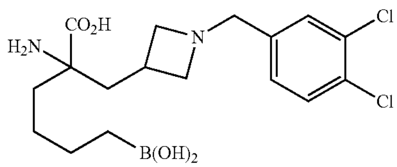 [SMILES: NC(CCCCB(O)O)(CC1CN(Cc2ccc(Cl)c(Cl)c2)C1)C(=O)O] | 2-amino-6-borono-2-((1-(3,4-dichlorobenzyl)azetidin-3-yl)methyl)hexanoic acid |
| 118 | 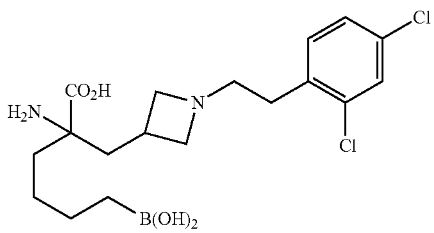 [SMILES: NC(CCCCB(O)O)(CC1CN(CCc2ccc(Cl)cc2Cl)C1)C(=O)O] | 2-amino-6-borono-2-((1-(2,4-dichlorophenethyl)azetidin-3-yl)methyl)hexanoic acid |
| 119 | 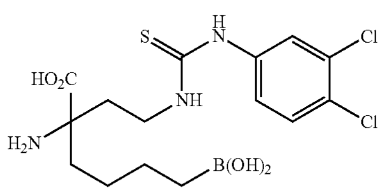 [SMILES: NC(CCCCB(O)O)(CCNC(=S)Nc1ccc(Cl)c(Cl)c1)C(=O)O] | 2-amino-6-borono-2-(2-(3-(3,4-dichlorophenyl)thioureido)ethyl)hexanoic acid |
| 120 | 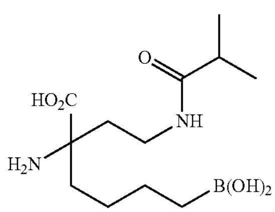 [SMILES: CC(C)C(=O)NCCC(N)(CCCCB(O)O)C(=O)O] | 2-amino-6-borono-2-(2-isobutyramidoethyl)hexanoic acid |
| 121 | 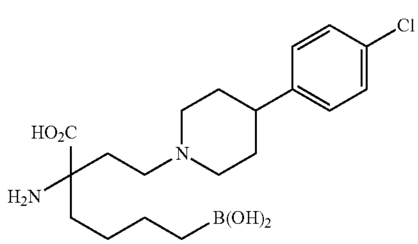 [SMILES: NC(CCCCB(O)O)(CCN1CCC(c2ccc(Cl)cc2)CC1)C(=O)O] | 2-amino-6-borono-2-(2-(4-(4-chlorophenyl)piperidin-1-yl)ethyl)hexanoic acid |
| 122 | 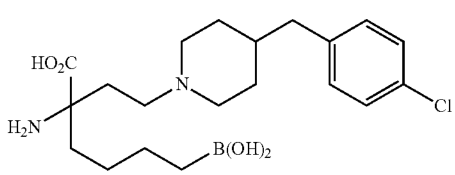 [SMILES: NC(CCCCB(O)O)(CCN1CCC(Cc2ccc(Cl)cc2)CC1)C(=O)O] | 2-amino-6-borono-2-(2-(4-(4-chlorobenzyl)piperidin-1-yl)ethyl)hexanoic acid |

TABLE 1-continued

| Ex. | Structure | Name |
|---|---|---|
| 123 | 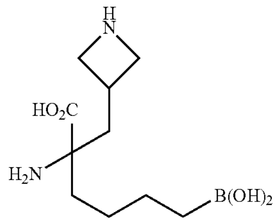 [SMILES: NC(CCCCB(O)O)(CC1CNC1)C(=O)O] | 2-amino-2-(azetidin-3-ylmethyl)-6-boronohexanoic acid |
| 124 | 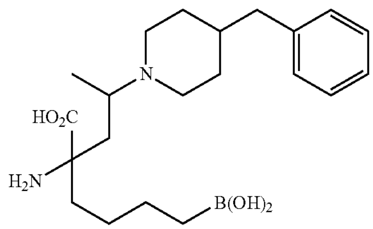 [SMILES: CC(CC(N)(CCCCB(O)O)C(=O)O)N1CCC(Cc2ccccc2)CC1] | 2-amino-2-(2-(4-benzylpiperidin-1-yl)propyl)-6-boronohexanoic acid |
| 125 | 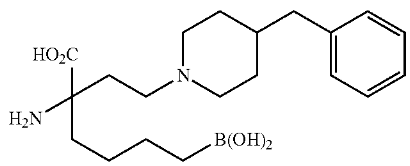 [SMILES: NC(CCCCB(O)O)(CCN1CCC(Cc2ccccc2)CC1)C(=O)O] | 2-amino-2-(2-(4-benzylpiperidin-1-yl)ethyl)-6-boronohexanoic acid |
| 126 | 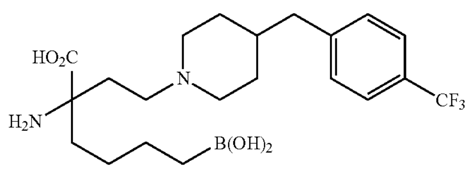 [SMILES: NC(CCCCB(O)O)(CCN1CCC(Cc2ccc(C(F)(F)F)cc2)CC1)C(=O)O] | 2-amino-6-borono-2-(2-(4-(4-(trifluoromethyl)benzyl)piperidin-1-yl)ethyl)hexanoic acid |
| 127 | 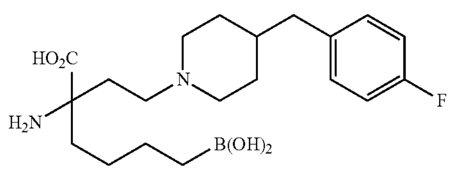 [SMILES: NC(CCCCB(O)O)(CCN1CCC(Cc2ccc(F)cc2)CC1)C(=O)O] | 2-amino-6-borono-2-(2-(4-(4-fluorobenzyl)piperidin-1-yl)ethyl)hexanoic acid |
| 128 | 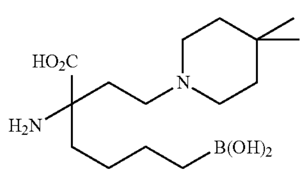 [SMILES: CC1(C)CCN(CCC(N)(CCCCB(O)O)C(=O)O)CC1] | 2-amino-6-borono-2-(2-(4,4-dimethylpiperidin-1-yl)ethyl)hexanoic acid |
| 129 | 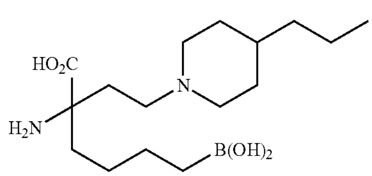 [SMILES: CCCC1CCN(CCC(N)(CCCCB(O)O)C(=O)O)CC1] | 2-amino-6-borono-2-(2-(4-propylpiperidin-1-yl)ethyl)hexanoic acid |
| 130 | 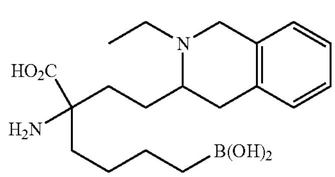 [SMILES: CCN1Cc2ccccc2CC1CCC(N)(CCCCB(O)O)C(=O)O] | 2-amino-6-borono-2-(2-(2-ethyl-1,2,3,4-tetrahydroisoquinolin-3-yl)ethyl)hexanoic acid |

TABLE 1-continued

| Ex. | Structure | Name |
|---|---|---|
| 131 | 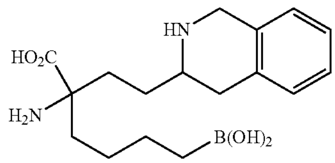 [SMILES: NC(CCCCB(O)O)(CCC1Cc2ccccc2CN1)C(=O)O] | 2-amino-6-borono-2-(2-(1,2,3,4-tetrahydroisoquinolin-3-yl)ethyl)hexanoic acid |
| 132 | 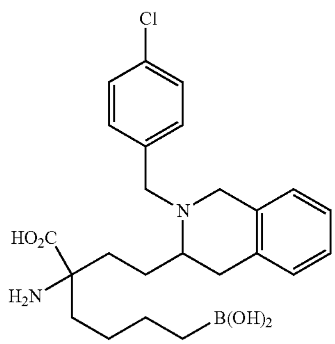 [SMILES: NC(CCCCB(O)O)(CCC1Cc2ccccc2CN1Cc1ccc(Cl)cc1)C(=O)O] | 2-amino-6-borono-2-(2-(2-(4-chlorobenzyl)-1,2,3,4-tetrahydroisoquinolin-3-yl)ethyl)hexanoic acid |
| 133 | 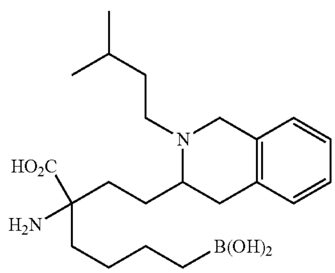 [SMILES: CC(C)CCN1Cc2ccccc2CC1CCC(N)(CCCCB(O)O)C(=O)O] | 2-amino-6-borono-2-(2-(2-isopentyl-1,2,3,4-tetrahydroisoquinolin-3-yl)ethyl)hexanoic acid |
| 134 | 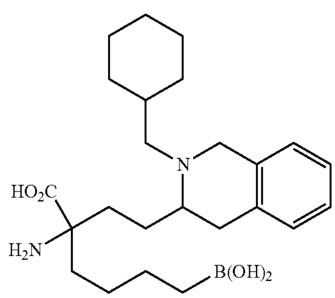 [SMILES: NC(CCCCB(O)O)(CCC1Cc2ccccc2CN1CC1CCCCC1)C(=O)O] | 2-amino-6-borono-2-(2-(2-(cyclohexylmethyl)-1,2,3,4-tetrahydroisoquinolin-3-yl)ethyl)hexanoic acid |
| 135 | 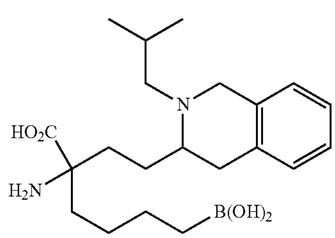 [SMILES: CC(C)CN1Cc2ccccc2CC1CCC(N)(CCCCB(O)O)C(=O)O] | 2-amino-6-borono-2-(2-(2-isobutyl-1,2,3,4-tetrahydroisoquinolin-3-yl)ethyl)hexanoic acid |
| 136 | 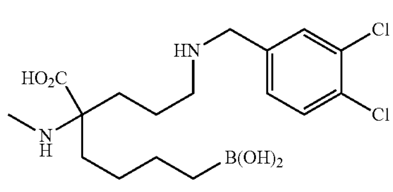 [SMILES: CNC(CCCCB(O)O)(CCCNCc1ccc(Cl)c(Cl)c1)C(=O)O] | 6-borono-2-(3-(3,4-dichlorobenzylamino)propyl)-2-(methylamino)hexanoic acid |

TABLE 1-continued

| Ex. | Structure | Name |
|---|---|---|
| 137 | 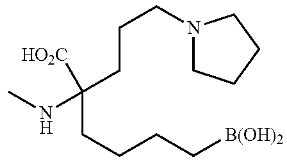 [SMILES: CNC(CCCCB(O)O)(CCCN1CCCC1)C(=O)O] | 6-borono-2-(methylamino)-2-(3-(pyrrolidin-1-yl)propyl)hexanoic acid |
| 138 | 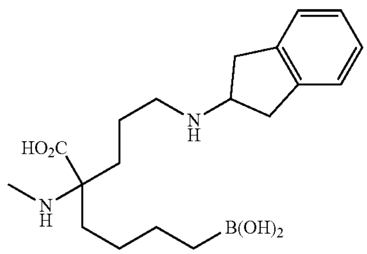 [SMILES: CNC(CCCCB(O)O)(CCCNC1Cc2ccccc2C1)C(=O)O] | 6-borono-2-(3-(2,3-dihydro-1H-inden-2-ylamino)propyl)-2-(methylamino)hexanoic acid |
| 139 | 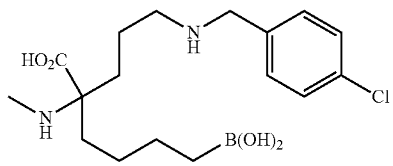 [SMILES: CNC(CCCCB(O)O)(CCCNCc1ccc(Cl)cc1)C(=O)O] | 6-borono-2-(3-(4-chlorobenzylamino)propyl)-2-(methylamino)hexanoic acid |
| 140 | 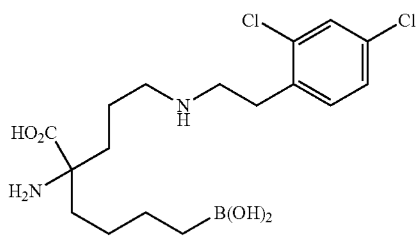 [SMILES: NC(CCCCB(O)O)(CCCNCCc1ccc(Cl)cc1Cl)C(=O)O] | 2-amino-6-borono-2-(3-(2,4-dichlorophenethylamino)propyl)hexanoic acid |
| 141 | 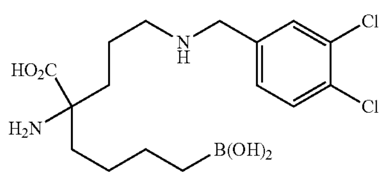 [SMILES: NC(CCCCB(O)O)(CCCNCc1ccc(Cl)c(Cl)c1)C(=O)O] | 2-amino-6-borono-2-(3-(3,4-dichlorobenzylamino)propyl)hexanoic acid |
| 142 | 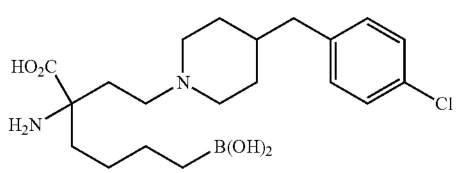 [SMILES: NC(CCCCB(O)O)(CCN1CCC(Cc2ccc(Cl)cc2)CC1)C(=O)O] | 2-amino-6-borono-2-(2-(4-(4-chlorobenzyl)piperidin-1-yl)ethyl)hexanoic acid |
| 143 | 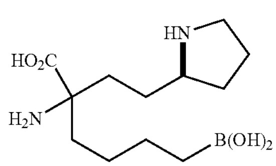 | 2-amino-6-borono-2-(2-((S)-pyrrolidin-2-yl)ethyl)hexanoic acid |
| 144 | 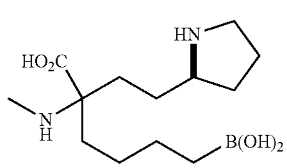 | 6-borono-2-(methylamino)-2-(2-((S)-pyrrolidin-2-yl)ethyl)hexanoic acid |

TABLE 1-continued

| Ex. | Structure | Name |
|---|---|---|
| 145 | 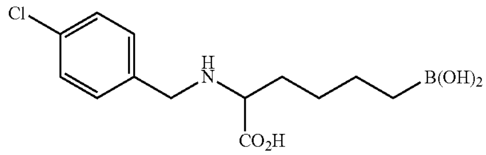 [SMILES: O=C(O)C(CCCCB(O)O)NCc1ccc(Cl)cc1] | 6-borono-2-(4-chlorobenzylamino)hexanoic acid |
| 146 | 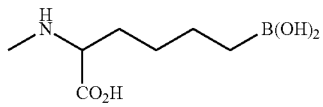 | 6-borono-2-(methylamino)hexanoic acid |
| 147 | 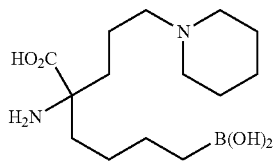 [SMILES: NC(CCCCB(O)O)(CCCN1CCCCC1)C(=O)O] | 2-amino-6-borono-2-(3-(piperidin-1-yl)propyl)hexanoic acid |
| 148 | 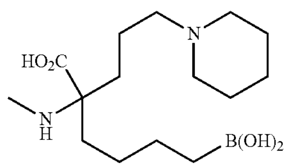 [SMILES: CNC(CCCCB(O)O)(CCCN1CCCCC1)C(=O)O] | 6-borono-2-(methylamino)-2-(3-(piperidin-1-yl)propyl)hexanoic acid |
| 149 | 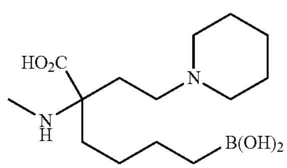 [SMILES: CNC(CCCCB(O)O)(CCN1CCCCC1)C(=O)O] | 6-borono-2-(methylamino)-2-(2-(piperidin-1-yl)ethyl)hexanoic acid |

Formula II Compounds

The present invention also relates to compounds according to Formula II.

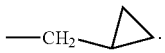
II

For compounds that conform to Formula II, D is selected from the group consisting of straight or branched ($C_3$-$C_5$) alkylene, straight or branched ($C_2$-$C_8$)alkenylene, straight or branched ($C_2$-$C_8$)alkynylene, ($C_3$-$C_{14}$)arylene, and ($C_3$-$C_{14}$) cycloalkylene. In one embodiment one or more —$CH_2$— groups in D are optionally and independently replaced with a moiety selected from the group consisting of O, NR', S, SO, $SO_2$, and CR'R". However, no two adjacent —$CH_2$— groups in D are simultaneously replaced by O, NR', S, SO, or $SO_2$.

According to one embodiment, D conforms to formula -$L^1$-$L^2$-$CH_2$—$CH_2$—, —$CH_2$-$L^1$-$L^2$-$CH_2$—, —$CH_2$—$CH_2$-$L^1$-$L^2$-, -$L^1$-$CH_2$-$L^2$-, -$L^1$-$CH_2$-$L^2$-$CH_2$—, or —$CH_2$-$L^1$-$CH_2$-$L^2$-. While variables $L^1$ and $L^2$ are each independently selected from the group consisting of O, NR', S, SO, $SO_2$, and CR'R", when -$L^1$ and -$L^2$ are adjacent to each other $L^1$ and $L^2$ are not simultaneously O, NR', S, SO or a $SO_2$ group.

For certain Formula II compounds, any two adjacent —$CH_2$— groups in D optionally represent two members of a ($C_3$-$C_{14}$)-cycloalkylenyl group. Thus, for instance, when D is propylene the $C_2$ and $C_3$ atom can each omit a hydrogen atom so as to couple a —$CH_2$— group to form a cyclopropyl ring as illustrated by the following moiety

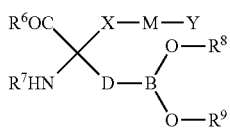

Variable D is advantageously a three to five atom linker. A particularly advantageous embodiment provides for D as a four atom linker as described herein.

For formula II compounds, substituent X is selected from the group consisting of ($C_3$-$C_{14}$)-cycloalkylene and a ($C_3$-$C_{14}$)heterocycloalkylene. Variable M is selected from the group consisting of a bond, ($C_1$-$C_6$)alkylene-, —O—, —C(O)—, —C(S)—, —C(O)NH—, —C(S)NH—, —S—, —S(O)—, —S(O)$_2$—, —NR'—, and —C=$NR^{11}$—.

Substituent Y in Formula II is selected from the group consisting of H, ($C_1$-$C_{14}$)alkyl, —NR'R", hydroxy($C_1$-$C_6$) alkylene, ($C_3$-$C_{14}$)-cycloalkyl, ($C_3$-$C_{14}$)-cycloalkyl-($C_1$-$C_6$) alkylene, ($C_3$-$C_{14}$)aryl, ($C_3$-$C_{14}$)aryl-($C_1$-$C_6$)alkylene, ($C_3$-$C_{14}$)heterocycloalkyl, ($C_3$-$C_{14}$)heterocycloalkyl-($C_1$-$C_6$) alkylene, ($C_3$-$C_{14}$)heteroaryl, ($C_3$-$C_{14}$)heteroaryl-($C_1$-$C_6$) alkylene, ($C_3$-$C_{14}$)heteroaryl-($C_3$-$C_6$)heterocycloalkylene-, ($C_3$-$C_{14}$)aryl-($C_3$-$C_{14}$)heterocycloalkylene-, ($C_3$-$C_{14}$)-aryl-($C_1$-$C_6$)alkyl-($C_3$-$C_{14}$)heterocycloalkylene-, ($C_3$-$C_{14}$)heteroaryl-($C_1$-$C_6$)alkyl-($C_3$-$C_{14}$)heterocycloalkylene-, and ($C_3$-$C_{14}$)heterocycloalkyl-($C_1$-$C_6$)alkyl-($C_3$-$C_{14}$) heterocycloalkylene-.

For certain Formula II compounds, D is butylene, X is a $(C_3-C_{14})$heterocycloalkylene, M is selected from the group consisting of a bond, $(C_1-C_6)$alkylene-, —O—, —C(O)—, —C(S)—, —C(O)NH—, —C(S)NH—, —S—, —S(O)—, —S(O)$_2$—, —NR'—, and —C=NR$^{11}$— and Y is selected from the group consisting of $(C_3-C_{14})$heteroaryl, $(C_3-C_{14})$cycloalkyl, $(C_3-C_{14})$aryl, $(C_3-C_{14})$aryl-$(C_1-C_6)$alkylene and $(C_3-C_{14})$heteroaryl-$(C_1-C_6)$alkylene. According to another embodiment, however, M is selected from the group consisting of —C(O)—, —C(S)—, —C(O)NH—, —C(S)NH—, —S(O)$_2$— and —NR'—.

For certain Formula II compounds when M is —NR'—, substituent R' can be a methylene group or an ethylene group. Alternatively, R' is —C(O)—$(C_1-C_8)$alkylene, such as —C(O)-methylene.

Exemplary Formula II compounds include without limitation those illustrated in Table 1-A below. While some exemplary compounds are depicted with stereochemistry, it should be understood that the invention includes all possible stereoisomers, such as diastereomers, of the compounds.

TABLE 1-A

| Ex. | Structure | Name |
|---|---|---|
| 1-A | 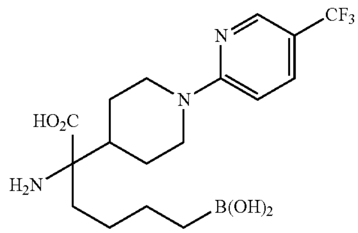 [SMILES: NC(CCCCB(O)O)(C(=O)O)C1CCN(c2ccc(C(F)(F)F)cn2)CC1] | 2-amino-6-borono-2-(1-(5-(trifluoromethyl)pyridin-2-yl)piperidin-4-yl)hexanoic acid |
| 2-A | 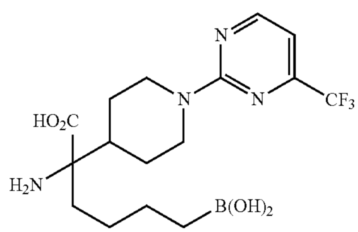 [SMILES: NC(CCCCB(O)O)(C(=O)O)C1CCN(c2nccc(C(F)(F)F)n2)CC1] | 2-amino-6-borono-2-(1-(4-(trifluoromethyl)pyrimidin-2-yl)piperidin-4-yl)hexanoic acid |
| 3-A | 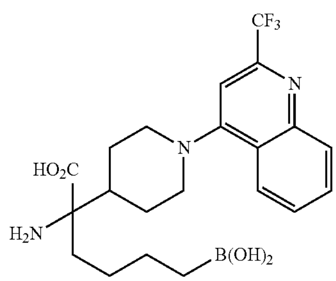 [SMILES: NC(CCCCB(O)O)(C(=O)O)C1CCN(c2cc(C(F)(F)F)nc3ccccc23)CC1] | 2-amino-6-borono-2-(1-(2-(trifluoromethyl)quinolin-4-yl)piperidin-4-yl)hexanoic acid |
| 4-A | 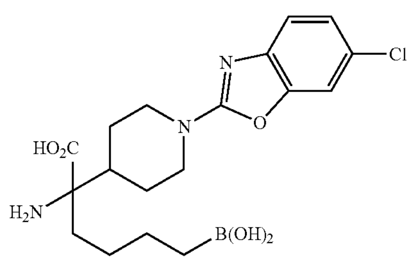 [SMILES: NC(CCCCB(O)O)(C(=O)O)C1CCN(c2nc3ccc(Cl)cc3o2)CC1] | 2-amino-6-borono-2-(1-(6-chlorobenzo[d]oxazol-2-yl)piperidin-4-yl)hexanoic acid |
| 5-A | 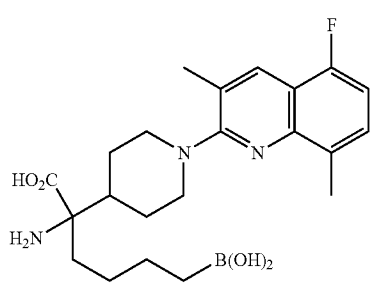 [SMILES: Cc1cc2c(F)ccc(C)c2nc1N1CCC(C(N)(CCCCB(O)O)C(=O)O)CC1] | 2-amino-6-borono-2-(1-(5-fluoro-3,8-dimethylquinolin-2-yl)piperidin-4-yl)hexanoic acid |

TABLE 1-A-continued

| Ex. | Structure | Name |
|---|---|---|
| 6-A | 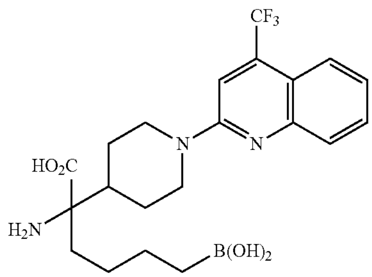 [SMILES: NC(CCCCB(O)O)(C(=O)O)C1CCN(c2cc(C(F)(F)F)c3ccccc3n2)CC1] | 2-amino-6-borono-2-(1-(4-(trifluoromethyl)quinolin-2-yl)piperidin-4-yl)hexanoic acid |
| 7-A | 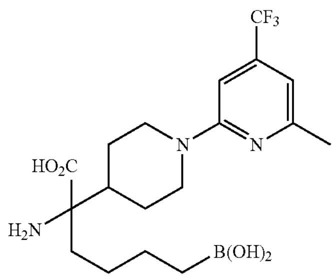 [SMILES: Cc1cc(C(F)(F)F)cc(N2CCC(C(N)(CCCCB(O)O)C(=O)O)CC2)n1] | 2-amino-6-borono-2-(1-(6-methyl-4-(trifluoromethyl)pyridin-2-yl)piperidin-4-yl)hexanoic acid |
| 8-A | 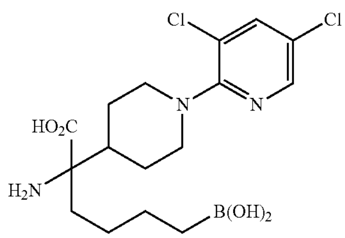 [SMILES: NC(CCCCB(O)O)(C(=O)O)C1CCN(c2ncc(Cl)cc2Cl)CC1] | 2-amino-6-borono-2-(1-(3,5-dichloropyridin-2-yl)piperidin-4-yl)hexanoic acid |
| 9-A | 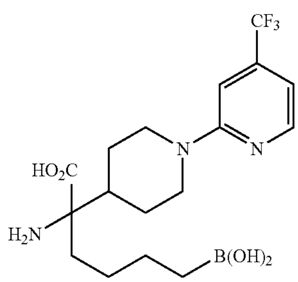 [SMILES: NC(CCCCB(O)O)(C(=O)O)C1CCN(c2cc(C(F)(F)F)ccn2)CC1] | 2-amino-6-borono-2-(1-(4-(trifluoromethyl)pyridin-2-yl)piperidin-4-yl)hexanoic acid |
| 10-A | 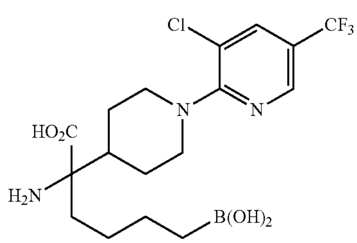 [SMILES: NC(CCCCB(O)O)(C(=O)O)C1CCN(c2ncc(C(F)(F)F)cc2Cl)CC1] | 2-amino-6-borono-2-(1-(3-chloro-5-(trifluoromethyl)pyridin-2-yl)piperidin-4-yl)hexanoic acid |
| 11-A | 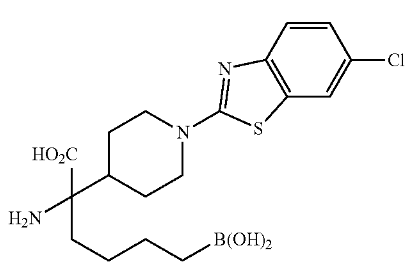 | 2-amino-6-borono-2-(1-(6-chlorobenzo[d]thiazol-2-yl)piperidin-4-yl)hexanoic acid |

TABLE 1-A-continued

| Ex. | Structure | Name |
|---|---|---|
| 12-A | 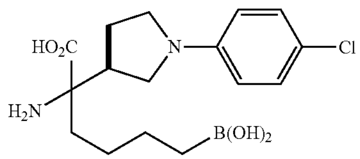 | 2-amino-6-borono-2-((S)-1-(4-chlorophenyl)pyrrolidin-3-yl)hexanoic acid |
| 13-A | 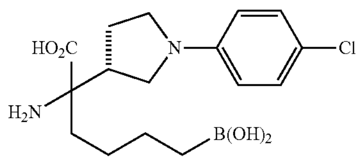 | 2-amino-6-borono-2-((R)-1-(4-chlorophenyl)pyrrolidin-3-yl)hexanoic acid |
| 14-A | 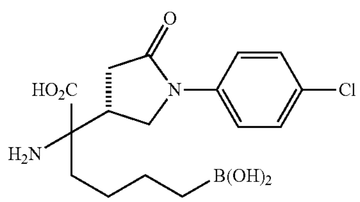 | 2-amino-6-borono-2-((R)-1-(4-chlorophenyl)-5-oxopyrrolidin-3-yl)hexanoic acid |
| 15-A | 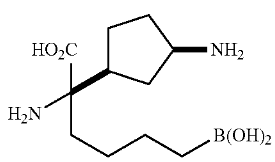 | (R)-2-amino-2-((1S,3R)-3-aminocyclopentyl)-6-boronohexanoic acid |
| 16-A | 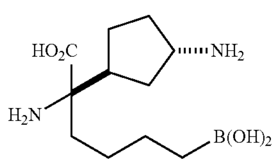 | (R)-2-amino-2-((1S,3S)-3-aminocyclopentyl)-6-boronohexanoic acid |
| 17-A | 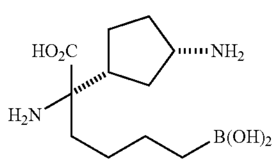 [SMILES: N[C@H]1CC[C@@H](C(N)(CCCCB(O)O)C(=O)O)C1] | (S)-2-amino-2-((1R,3S)-3-aminocyclopentyl)-6-boronohexanoic acid |
| 18-A | 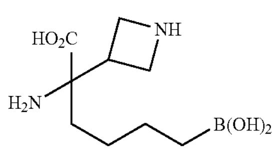 [SMILES: NC(CCCCB(O)O)(C(=O)O)C1CNC1] | 2-amino-2-(azetidin-3-yl)-6-boronohexanoic acid |
| 19-A | 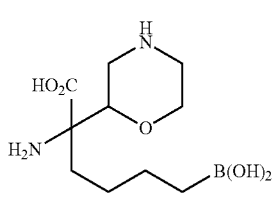 [SMILES: NC(CCCCB(O)O)(C(=O)O)C1CNCCO1] | 2-amino-6-borono-2-(morpholin-2-yl)hexanoic acid |
| 20-A | 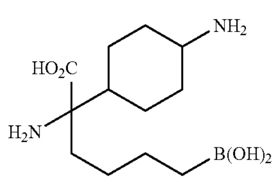 [SMILES: NC1CCC(C(N)(CCCCB(O)O)C(=O)O)CC1] | 2-amino-2-(4-aminocyclohexyl)-6-boronohexanoic acid |

TABLE 1-A-continued

| Ex. | Structure | Name |
|---|---|---|
| 21-A | 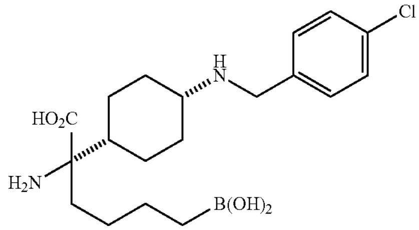 | (S)-2-amino-6-borono-2-((1s,4R)-4-(4-chlorobenzylamino)cyclohexyl)hexanoic acid |
| 22-A | 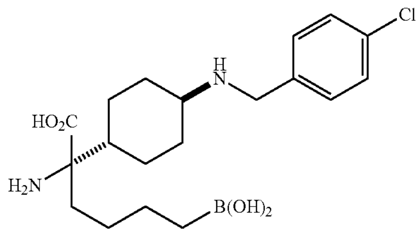 | (S)-2-amino-6-borono-2-((1r,4S)-4-(4-chlorobenzylamino)cyclohexyl)hexanoic acid |
| 23-A | 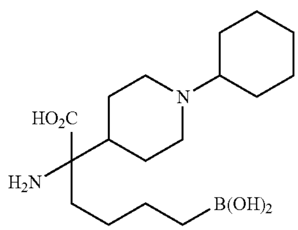 [SMILES: NC(CCCCB(O)O)(C(=O)O)C1CCN(C2CCCCC2)CC1] | 2-amino-6-borono-2-(1-cyclohexylpiperidin-4-yl)hexanoic acid |
| 24-A | 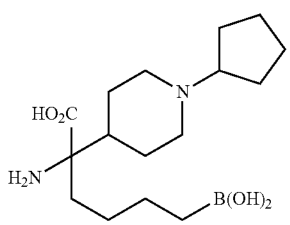 [SMILES: NC(CCCCB(O)O)(C(=O)O)C1CCN(C2CCCC2)CC1] | 2-amino-6-borono-2-(1-cyclopentylpiperidin-4-yl)hexanoic acid |
| 25-A | 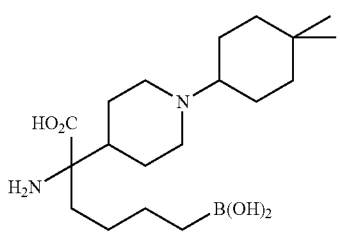 [SMILES: CC1(C)CCC(N2CCC(C(N)(CCCCB(O)O)C(=O)O)CC2)CC1] | 2-amino-6-borono-2-(1-(4,4-dimethylcyclohexyl)piperidin-4-yl)hexanoic acid |
| 26-A | 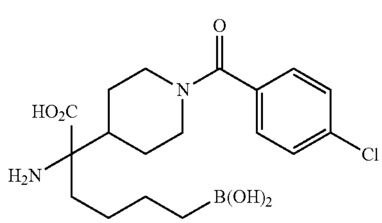 [SMILES: NC(CCCCB(O)O)(C(=O)O)C1CCN(C(=O)c2ccc(Cl)cc2)CC1] | 2-amino-6-borono-2-(1-(4-chlorobenzoyl)piperidin-4-yl)hexanoic acid |
| 27-A | 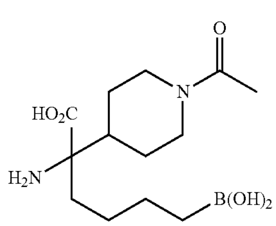 [SMILES: CC(=O)N1CCC(C(N)(CCCCB(O)O)C(=O)O)CC1] | 2-(1-acetylpiperidin-4-yl)-2-amino-6-boronohexanoic acid |

TABLE 1-A-continued

| Ex. | Structure | Name |
|---|---|---|
| 28-A | 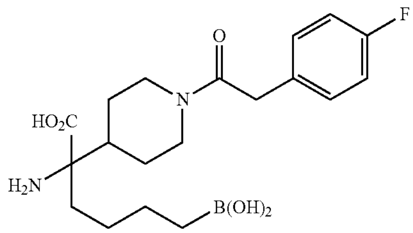 [SMILES: NC(CCCCB(O)O)(C(=O)O)C1CCN(C(=O)Cc2ccc(F)cc2)CC1] | 2-amino-6-borono-2-(1-(2-(4-fluorophenyl)acetyl)piperidin-4-yl)hexanoic acid |
| 29-A | 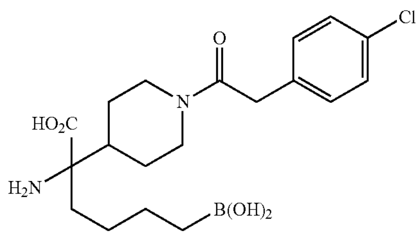 [SMILES: NC(CCCCB(O)O)(C(=O)O)C1CCN(C(=O)Cc2ccc(Cl)cc2)CC1] | 2-amino-6-borono-2-(1-(2-(4-chlorophenyl)acetyl)piperidin-4-yl)hexanoic acid |
| 30-A | 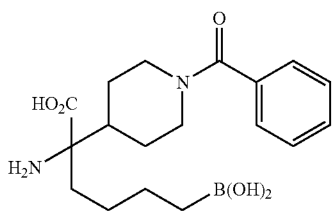 [SMILES: NC(CCCCB(O)O)(C(=O)O)C1CCN(C(=O)c2ccccc2)CC1] | 2-amino-2-(1-benzoylpiperidin-4-yl)-6-boronohexanoic acid |
| 31-A | 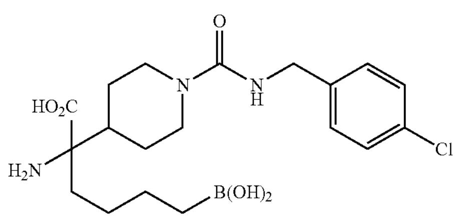 | 2-amino-6-borono-2-(1-(4-chlorobenzylcarbamoyl)piperidin-4-yl)hexanoic acid |
| 32-A | 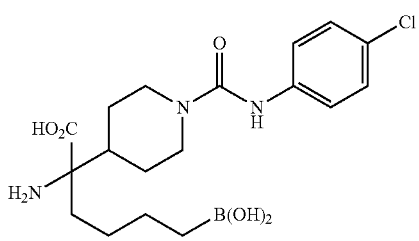 [SMILES: NC(CCCCB(O)O)(C(=O)O)C1CCN(C(=O)Nc2ccc(Cl)cc2)CC1] | 2-amino-6-borono-2-(1-(4-chlorophenylcarbamoyl)piperidin-4-yl)hexanoic acid |
| 33-A | 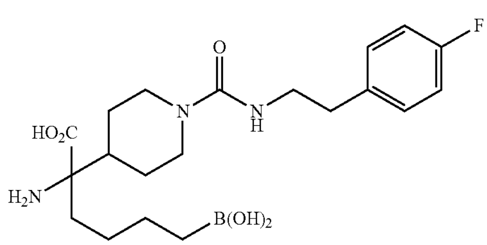 [SMILES: NC(CCCCB(O)O)(C(=O)O)C1CCN(C(=O)NCCc2ccc(F)cc2)CC1] | 2-amino-6-borono-2-(1-(4-fluorophenethylcarbamoyl)piperidin-4-yl)hexanoic acid |

TABLE 1-A-continued

| Ex. | Structure | Name |
|---|---|---|
| 34-A | 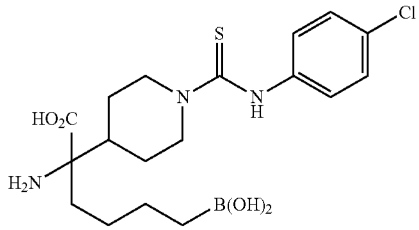 | 2-amino-6-borono-2-(1-(4-chlorophenylcarbamothioyl)piperidin-4-yl)hexanoic acid |
| 35-A | 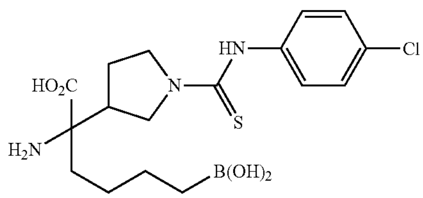 | 2-amino-6-borono-2-(1-(4-chlorophenylcarbamothioyl)pyrrolidin-3-yl)hexanoic acid |
| 36-A | 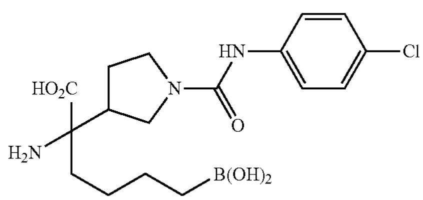 [SMILES: NC(CCCCB(O)O)(C(=O)O)C1CCN(C(=S)Nc2ccc(Cl)cc2)C1] | 2-amino-6-borono-2-(1-(4-chlorophenylcarbamoyl)pyrrolidin-3-yl)hexanoic acid |
| 37-A | 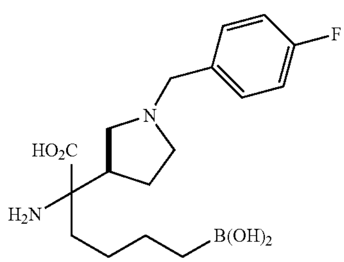 | 2-amino-6-borono-2-((R)-1-(4-fluorobenzyl)pyrrolidin-3-yl)hexanoic acid |
| 38-A | 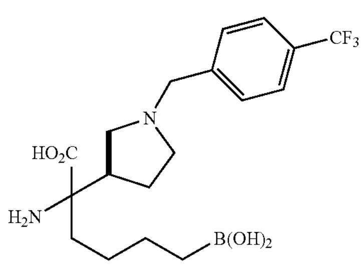 | 2-amino-6-borono-2-((R)-1-(4-(trifluoromethyl)benzyl)pyrrolidin-3-yl)hexanoic acid |
| 39-A | 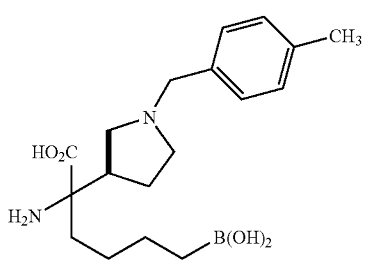 | 2-amino-6-borono-2-((R)-1-(4-methylbenzyl)pyrrolidin-3-yl)hexanoic acid |

TABLE 1-A-continued

| Ex. | Structure | Name |
|---|---|---|
| 40-A | 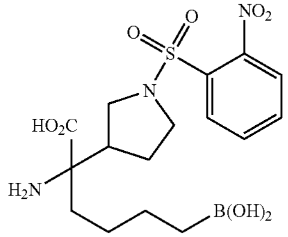 [SMILES: NC(CCCCB(O)O)(C(=O)O)C1CCN(S(=O)(=O)c2ccccc2[N+](=O)[O-])C1] | 2-amino-6-borono-2-(1-(2-nitrophenylsulfonyl)pyrrolidin-3-yl)hexanoic acid |
| 41-A | 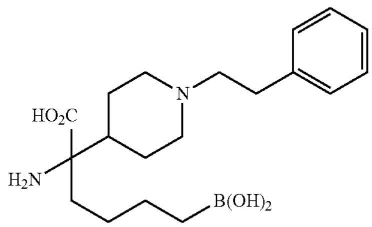 [SMILES: NC(CCCCB(O)O)(C(=O)O)C1CCN(CCc2ccccc2)CC1] | 2-amino-6-borono-2-(1-phenethylpiperidin-4-yl)hexanoic acid |
| 42-A | 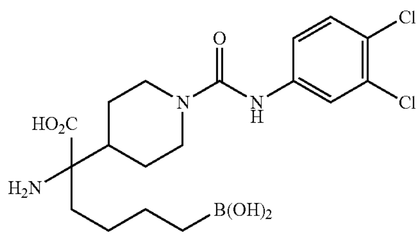 [SMILES: NC(CCCCB(O)O)(C(=O)O)C1CCN(C(=O)Nc2ccc(Cl)c(Cl)c2)CC1] | 2-amino-6-borono-2-(1-(3,4-dichlorophenylcarbamoyl)piperidin-4-yl)hexanoic acid |
| 43-A | 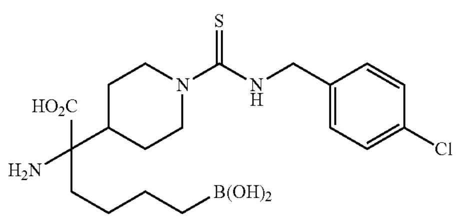 | 2-amino-6-borono-2-(1-(4-chlorobenzylcarbamothioyl)piperidin-4-yl)hexanoic acid |
| 44-A | 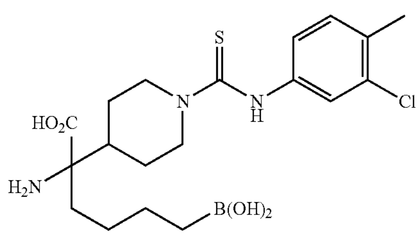 [SMILES: Cc1ccc(NC(=S)N2CCC(C(N)(CCCCB(O)O)C(=O)O)CC2)cc1Cl] | 2-amino-6-borono-2-(1-(3-chloro-4-methylphenylcarbamothioyl)piperidin-4-yl)hexanoic acid |
| 45-A | 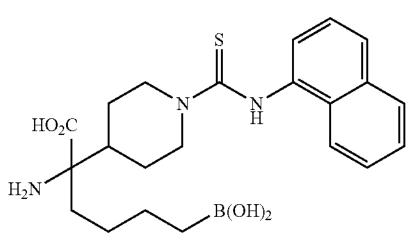 [SMILES: NC(CCCCB(O)O)(C(=O)O)C1CCN(C(=S)Nc2cccc3ccccc23)CC1] | 2-amino-6-borono-2-(1-(naphthalen-1-ylcarbamothioyl)piperidin-4-yl)hexanoic acid |
| 46-A | 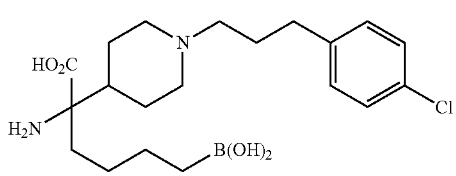 [SMILES: NC(CCCCB(O)O)(C(=O)O)C1CCN(CCCc2ccc(Cl)cc2)CC1] | 2-amino-6-borono-2-(1-(3-(4-chlorophenyl)propyl)piperidin-4-yl)hexanoic acid |

TABLE 1-A-continued

| Ex. | Structure | Name |
|---|---|---|
| 47-A | 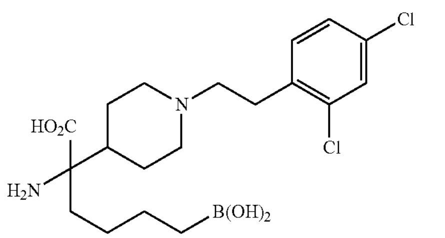 [SMILES: NC(CCCCB(O)O)(C(=O)O)C1CCN(CCc2ccc(Cl)cc2Cl)CC1] | 2-amino-6-borono-2-(1-(2,4-dichlorophenethyl)piperidin-4-yl)hexanoic acid |
| 48-A | 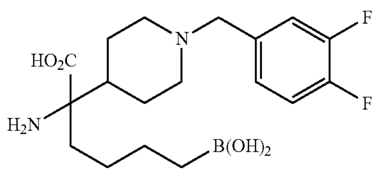 [SMILES: NC(CCCCB(O)O)(C(=O)O)C1CCN(Cc2ccc(F)c(F)c2)CC1] | 2-amino-6-borono-2-(1-(3,4-difluorobenzyl)piperidin-4-yl)hexanoic acid |
| 49-A | 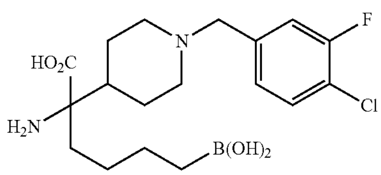 [SMILES: NC(CCCCB(O)O)(C(=O)O)C1CCN(Cc2ccc(Cl)c(F)c2)CC1] | 2-amino-6-borono-2-(1-(4-chloro-3-fluorobenzyl)piperidin-4-yl)hexanoic acid |
| 50-A | 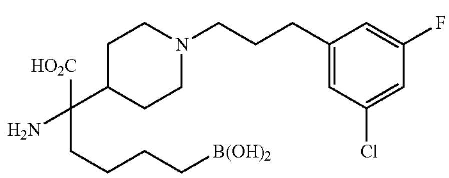 [SMILES: NC(CCCCB(O)O)(C(=O)O)C1CCN(CCCc2cc(F)cc(Cl)c2)CC1] | 2-amino-6-borono-2-(1-(3-(3-chloro-5-fluorophenyl)propyl)piperidin-4-yl)hexanoic acid |
| 51-A | 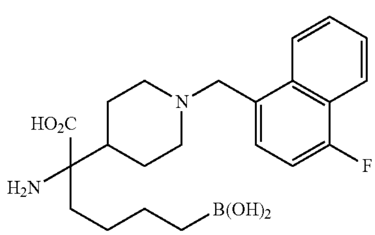 [SMILES: NC(CCCCB(O)O)(C(=O)O)C1CCN(Cc2ccc(F)c3ccccc23)CC1] | 2-amino-6-borono-2-(1-((4-fluoronaphthalen-1-yl)methyl)piperidin-4-yl)hexanoic acid |
| 52-A | 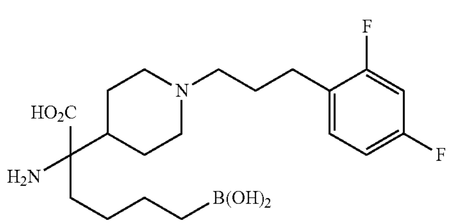 [SMILES: NC(CCCCB(O)O)(C(=O)O)C1CCN(CCCc2ccc(F)cc2F)CC1] | 2-amino-6-borono-2-(1-(3-(2,4-difluorophenyl)propyl)piperidin-4-yl)hexanoic acid |
| 53-A | 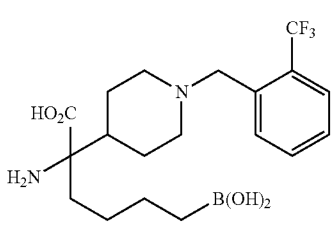 [SMILES: NC(CCCCB(O)O)(C(=O)O)C1CCN(Cc2ccccc2C(F)(F)F)CC1] | 2-amino-6-borono-2-(1-(2-(trifluoromethyl)benzyl)piperidin-4-yl)hexanoic acid |

TABLE 1-A-continued

| Ex. | Structure | Name |
|---|---|---|
| 54-A | 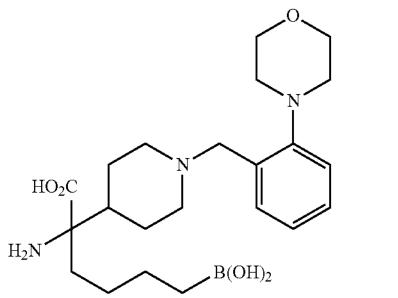 [SMILES: NC(CCCCB(O)O)(C(=O)O)C1CCN(Cc2ccccc2N2CCOCC2)CC1] | 2-amino-6-borono-2-(1-(2-morpholinobenzyl)piperidin-4-yl)hexanoic acid |
| 55-A | 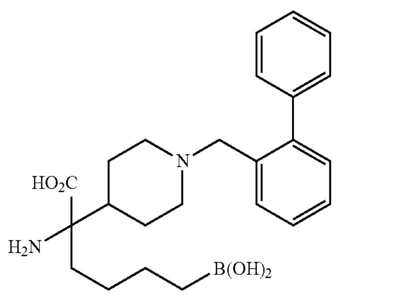 [SMILES: NC(CCCCB(O)O)(C(=O)O)C1CCN(Cc2ccccc2-c2ccccc2)CC1] | 2-amino-2-(1-(biphenyl-2-ylmethyl)piperidin-4-yl)-6-boronohexanoic acid |
| 56-A | 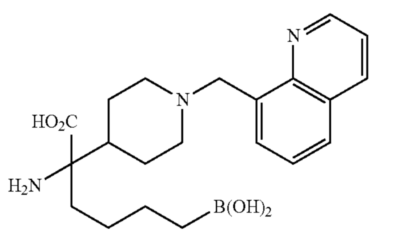 [SMILES: NC(CCCCB(O)O)(C(=O)O)C1CCN(Cc2cccc3cccnc23)CC1] | 2-amino-6-borono-2-(1-(quinolin-8-ylmethyl)piperidin-4-yl)hexanoic acid |
| 57-A | 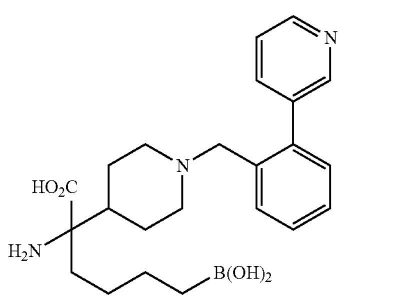 [SMILES: NC(CCCCB(O)O)(C(=O)O)C1CCN(Cc2ccccc2-c2cccnc2)CC1] | 2-amino-6-borono-2-(1-(2-(pyridin-3-yl)benzyl)piperidin-4-yl)hexanoic acid |
| 58-A | 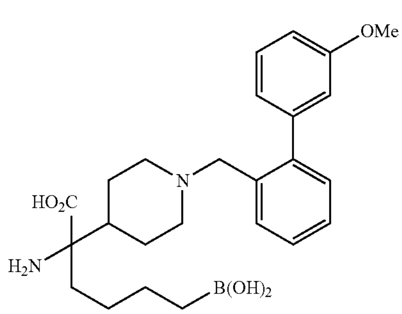 [SMILES: COc1cccc(-c2ccccc2CN2CCC(C(N)(CCCCB(O)O)C(=O)O)CC2)c1] | 2-amino-6-borono-2-(1-((3'-methoxybiphenyl-2-yl)methyl)piperidin-4-yl)hexanoic acid |

TABLE 1-A-continued

| Ex. | Structure | Name |
|---|---|---|
| 59-A | 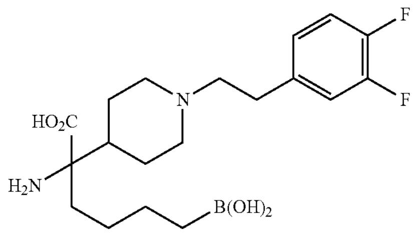 [SMILES: NC(CCCCB(O)O)(C(=O)O)C1CCN(CCc2ccc(F)c(F)c2)CC1] | 2-amino-6-borono-2-(1-(3,4-difluorophenethyl)piperidin-4-yl)hexanoic acid |
| 60-A | 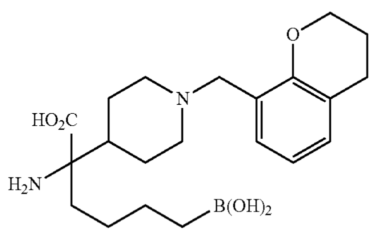 [SMILES: NC(CCCCB(O)O)(C(=O)O)C1CCN(Cc2cccc3c2OCCC3)CC1] | 2-amino-6-borono-2-(1-(chroman-8-ylmethyl)piperidin-4-yl)hexanoic acid |
| 61-A | 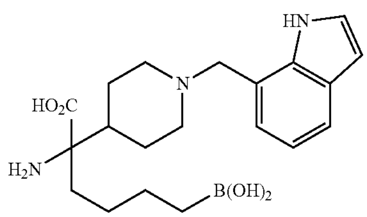 [SMILES: NC(CCCCB(O)O)(C(=O)O)C1CCN(Cc2cccc3cc[nH]c23)CC1] | 2-(1-((1H-indol-7-yl)methyl)piperidin-4-yl)-2-amino-6-boronohexanoic acid |
| 62-A | 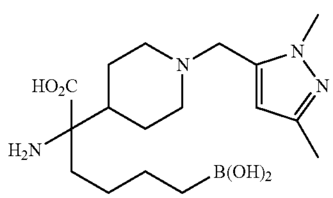 [SMILES: Cc1cc(CN2CCC(C(N)(CCCCB(O)O)C(=O)O)CC2)n(C)n1] | 2-amino-6-borono-2-(1-((1,3-dimethyl-1H-pyrazol-5-yl)methyl)piperidin-4-yl)hexanoic acid |
| 63-A | 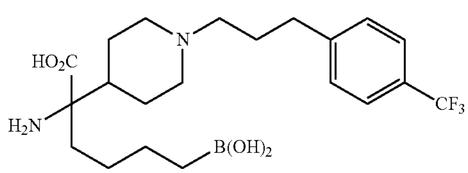 [SMILES: NC(CCCCB(O)O)(C(=O)O)C1CCN(CCCc2ccc(C(F)(F)F)cc2)CC1] | 2-amino-6-borono-2-(1-(3-(4-(trifluoromethyl)phenyl)propyl)piperidin-4-yl)hexanoic acid |
| 64-A | 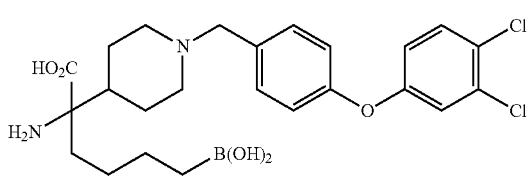 [SMILES: NC(CCCCB(O)O)(C(=O)O)C1CCN(Cc2ccc(Oc3ccc(Cl)c(Cl)c3)cc2)CC1] | 2-amino-6-borono-2-(1-(4-(3,4-dichlorophenoxy)benzyl)piperidin-4-yl)hexanoic acid |
| 65-A | 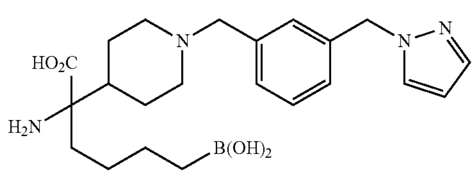 [SMILES: NC(CCCCB(O)O)(C(=O)O)C1CCN(Cc2cccc(Cn3cccn3)c2)CC1] | 2-(1-(3-((1H-pyrazol-1-yl)methyl)benzyl)piperidin-4-yl)-2-amino-6-boronohexanoic acid |
| 66-A | 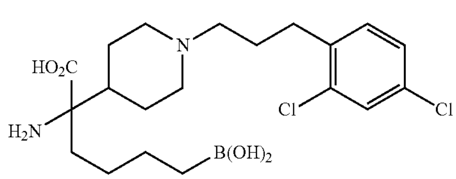 [SMILES: NC(CCCCB(O)O)(C(=O)O)C1CCN(CCCc2ccc(Cl)cc2Cl)CC1] | 2-amino-6-borono-2-(1-(3-(2,4-dichlorophenyl)propyl)piperidin-4-yl)hexanoic acid |

TABLE 1-A-continued

| Ex. | Structure | Name |
|---|---|---|
| 67-A | 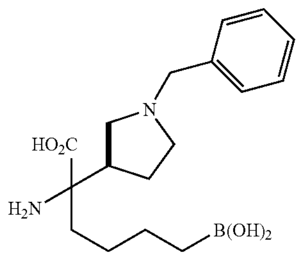 | 2-amino-2-((R)-1-benzylpyrrolidin-3-yl)-6-boronohexanoic acid |
| 68-A | 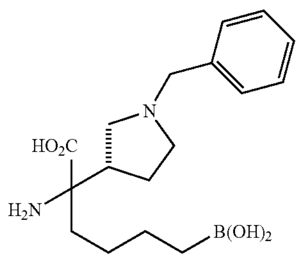 | 2-amino-2-((S)-1-benzylpyrrolidin-3-yl)-6-boronohexanoic acid |
| 69-A | 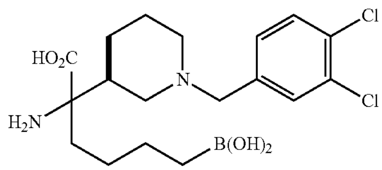 | 2-amino-6-borono-2-((S)-1-(3,4-dichlorobenzyl)piperidin-3-yl)hexanoic acid |
| 70-A | 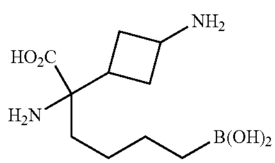 [SMILES: NC1CC(C(N)(CCCCB(O)O)C(=O)O)C1] | 2-amino-2-(3-aminocyclobutyl)-6-boronohexanoic acid |
| 71-A | 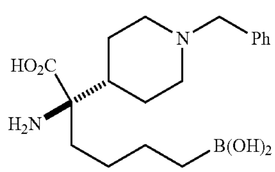 | (R)-2-amino-2-(1-benzylpiperidin-4-yl)-6-boronohexanoic acid |
| 72-A | 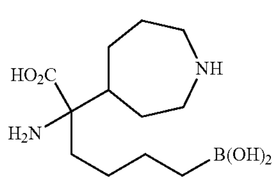 [SMILES: NC(CCCCB(O)O)(C(=O)O)C1CCCNCC1] | 2-amino-2-(azepan-4-yl)-6-boronohexanoic acid |
| 73-A | 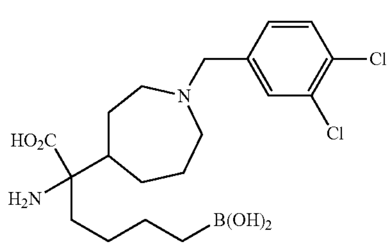 [SMILES: NC(CCCCB(O)O)(C(=O)O)C1CCCN(Cc2ccc(Cl)c(Cl)c2)CC1] | 2-amino-6-borono-2-(1-(3,4-dichlorobenzyl)azepan-4-yl)hexanoic acid |

TABLE 1-A-continued

| Ex. | Structure | Name |
|---|---|---|
| 74-A | 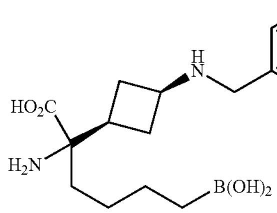 | cis-2-amino-2-(3-(benzylamino)cyclobutyl)-6-boronohexanoic acid |
| 75-A | 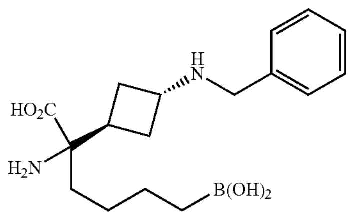 [SMILES: NC(CCCCB(O)O)(C(=O)O)[C@H]1C[C@H](NCc2ccccc2)C1] | trans-2-amino-2-(3-(benzylamino)cyclobutyl)-6-boronohexanoic acid |
| 76-A | 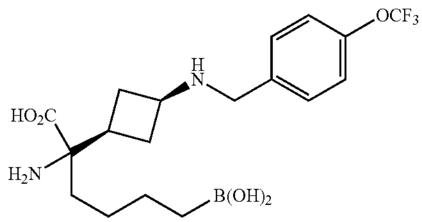 [SMILES: NC(CCCCB(O)O)(C(=O)O)[C@H]1C[C@@H](NCc2ccc(OC(F)(F)F)cc2)C1] | Cis-2-amino-6-borono-2-(3-(4-(trifluoromethoxy)benzylamino)cyclobutyl)hexanoic acid |
| 77-A | 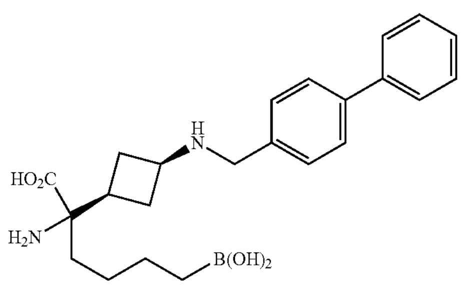 [SMILES: NC(CCCCB(O)O)(C(=O)O)[C@H]1C[C@@H](NCc2ccc(-c3ccccc3)cc2)C1] | Cis 2-amino-2-(3-(biphenyl-4-ylmethylamino)cyclobutyl)-6-boronohexanoic acid |
| 78-A | 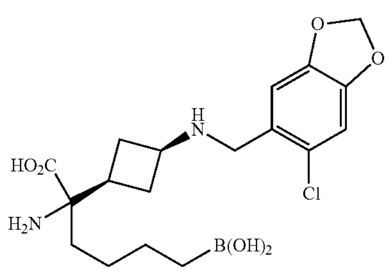 [SMILES: NC(CCCCB(O)O)(C(=O)O)[C@H]1C[C@@H](NCc2cc3c(cc2Cl)OCO3)C1] | Cis-2-amino-6-borono-2-(3-((6-chlorobenzo[d][1,3]dioxol-5-yl)methylamino)cyclobutyl)hexanoic acid |
| 79-A | 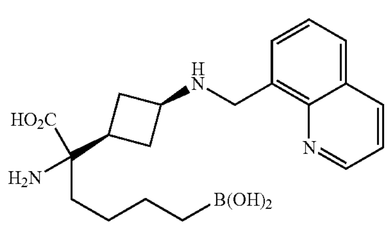 | Cis-2-amino-6-borono-2-(3-(quinolin-8-ylmethylamino)cyclobutyl)hexanoic acid |

TABLE 1-A-continued

| Ex. | Structure | Name |
|---|---|---|
| 80-A | 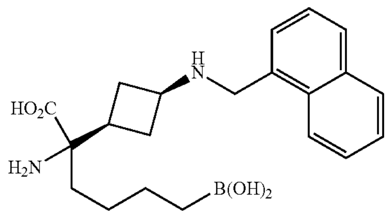 [SMILES: NC(CCCCB(O)O)(C(=O)O)[C@H]1C[C@@H](NCc2cccc3ccccc23)C1] | Cis-2-amino-6-borono-2-(3-(naphthalen-1-ylmethylamino)cyclobutyl)hexanoic acid |
| 81-A | 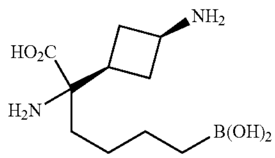 [SMILES: NC(CCCCB(O)O)(C(=O)O)[C@H]1C[C@@H](N)C1] | Cis-2-amino-2-(3-aminocyclobutyl)-6-boronohexanoic acid |
| 82-A | 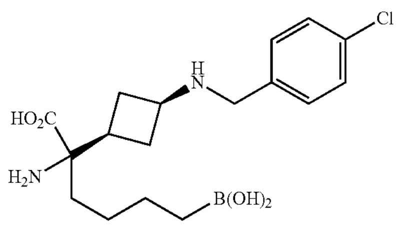 [SMILES: NC(CCCCB(O)O)(C(=O)O)[C@H]1C[C@@H](NCc2ccc(Cl)cc2)C1] | Cis-2-amino-6-borono-2-(3-(4-chlorobenzylamino)cyclobutyl)hexanoic acid |
| 83-A | 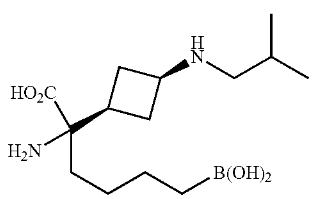 [SMILES: CC(C)CN[C@H]1C[C@@H](C(N)(CCCCB(O)O)C(=O)O)C1] | Cis-2-amino-6-borono-2-(3-(isobutylamino)cyclobutyl)hexanoic acid |
| 84-A | 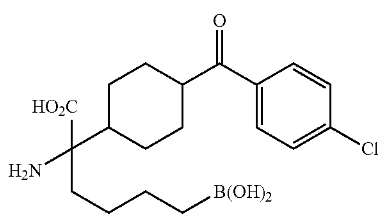 [SMILES: NC(CCCCB(O)O)(C(=O)O)C1CCC(C(=O)c2ccc(Cl)cc2)CC1] | 2-amino-6-borono-2-(4-(4-chlorobenzoyl)cyclohexyl)hexanoic acid |
| 85-A | 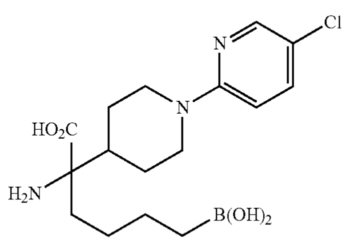 [SMILES: NC(CCCCB(O)O)(C(=O)O)C1CCN(c2ccc(Cl)cn2)CC1] | 2-amino-6-borono-2-(1-(5-chloropyridin-2-yl)piperidin-4-yl)hexanoic acid |
| 86-A | 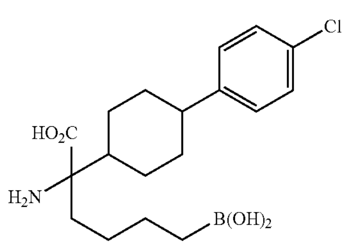 [SMILES: NC(CCCCB(O)O)(C(=O)O)C1CCC(c2ccc(Cl)cc2)CC1] | 2-amino-6-borono-2-(4-(4-chlorophenyl)cyclohexyl)hexanoic acid |

TABLE 1-A-continued

| Ex. | Structure | Name |
|---|---|---|
| 87-A | 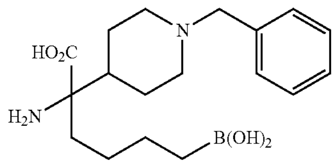 [SMILES: NC(CCCCB(O)O)(C(=O)O)C1CCN(Cc2ccccc2)CC1] | 2-amino-2-(1-benzylpiperidin-4-yl)-6-boronohexanoic acid |
| 88-A | 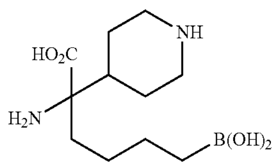 [SMILES: NC(CCCCB(O)O)(C(=O)O)C1CCNCC1] | 2-amino-6-borono-2-(piperidin-4-yl)hexanoic acid |
| 89-A | 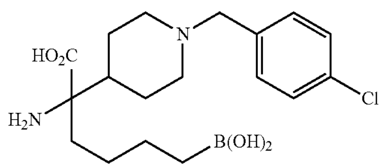 [SMILES: NC(CCCCB(O)O)(C(=O)O)C1CCN(Cc2ccc(Cl)cc2)CC1] | 2-amino-6-borono-2-(1-(4-chlorobenzyl)piperidin-4-yl)hexanoic acid |
| 90-A | 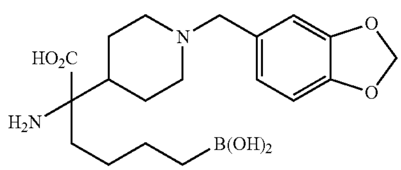 [SMILES: NC(CCCCB(O)O)(C(=O)O)C1CCN(Cc2ccc3c(c2)OCO3)CC1] | 2-amino-2-(1-(benzo[d][1,3]dioxol-5-ylmethyl)piperidin-4-yl)-6-boronohexanoic acid |
| 91-A | 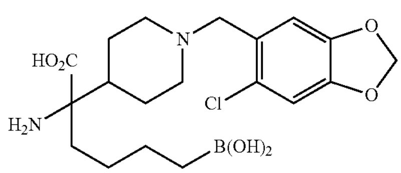 [SMILES: NC(CCCCB(O)O)(C(=O)O)C1CCN(Cc2cc3c(cc2Cl)OCO3)CC1] | 2-amino-6-borono-2-(1-((6-chlorobenzo[d][1,3]dioxol-5-yl)methyl)piperidin-4-yl)hexanoic acid |
| 92-A | 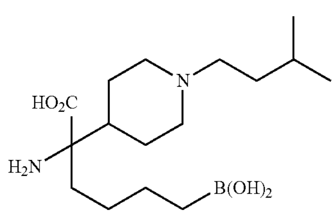 [SMILES: CC(C)CCN1CCC(C(N)(CCCCB(O)O)C(=O)O)CC1] | 2-amino-6-borono-2-(1-isopentylpiperidin-4-yl)hexanoic acid |
| 93-A | 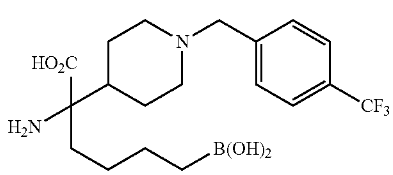 [SMILES: NC(CCCCB(O)O)(C(=O)O)C1CCN(Cc2ccc(C(F)(F)F)cc2)CC1] | 2-amino-6-borono-2-(1-(4-(trifluoromethyl)benzyl)piperidin-4-yl)hexanoic acid |
| 94-A | 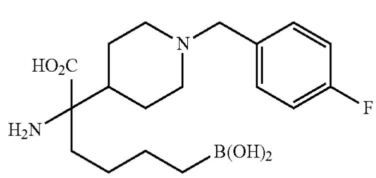 [SMILES: NC(CCCCB(O)O)(C(=O)O)C1CCN(Cc2ccc(F)cc2)CC1] | 2-amino-6-borono-2-(1-(4-fluorobenzyl)piperidin-4-yl)hexanoic acid |
| 95-A | 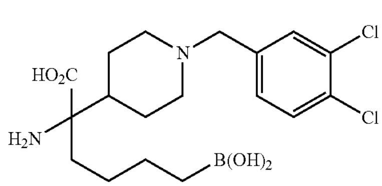 [SMILES: NC(CCCCB(O)O)(C(=O)O)C1CCN(Cc2ccc(Cl)c(Cl)c2)CC1] | 2-amino-6-borono-2-(1-(3,4-dichlorobenzyl)piperidin-4-yl)hexanoic acid |

TABLE 1-A-continued

| Ex. | Structure | Name |
|---|---|---|
| 96-A | 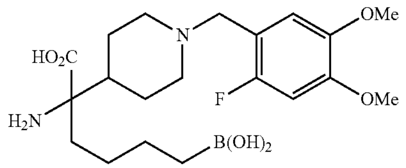 [SMILES: COc1cc(F)c(CN2CCC(C(N)(CCCCB(O)O)C(=O)O)CC2)cc1OC] | 2-amino-6-borono-2-(1-(2-fluoro-4,5-dimethoxybenzyl)piperidin-4-yl)hexanoic acid |
| 97-A | 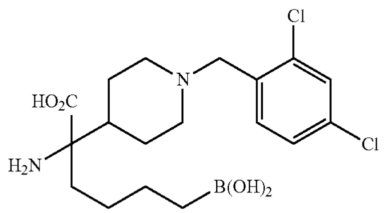 [SMILES: NC(CCCCB(O)O)(C(=O)O)C1CCN(Cc2ccc(Cl)cc2Cl)CC1] | 2-amino-6-borono-2-(1-(2,4-dichlorobenzyl)piperidin-4-yl)hexanoic acid |
| 98-A | 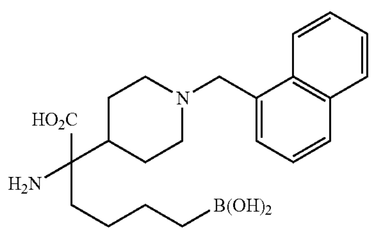 [SMILES: NC(CCCCB(O)O)(C(=O)O)C1CCN(Cc2cccc3ccccc23)CC1] | 2-amino-6-borono-2-(1-(naphthalen-1-ylmethyl)piperidin-4-yl)hexanoic acid |
| 99-A | 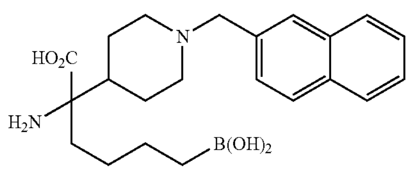 [SMILES: NC(CCCCB(O)O)(C(=O)O)C1CCN(Cc2ccc3ccccc3c2)CC1] | 2-amino-6-borono-2-(1-(naphthalen-2-ylmethyl)piperidin-4-yl)hexanoic acid |
| 100-A | 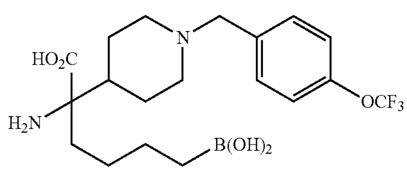 [SMILES: NC(CCCCB(O)O)(C(=O)O)C1CCN(Cc2ccc(OC(F)(F)F)cc2)CC1] | 2-amino-6-borono-2-(1-(4-(trifluoromethoxy)benzyl)piperidin-4-yl)hexanoic acid |
| 101-A | 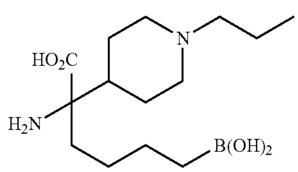 [SMILES: CCCN1CCC(C(N)(CCCCB(O)O)C(=O)O)CC1] | 2-amino-6-borono-2-(1-propylpiperidin-4-yl)hexanoic acid |
| 102-A | 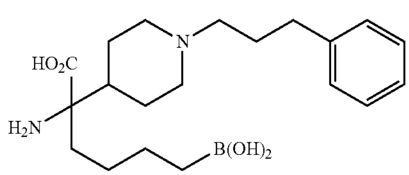 [SMILES: NC(CCCCB(O)O)(C(=O)O)C1CCN(CCCc2ccccc2)CC1] | 2-amino-6-borono-2-(1-(3-phenylpropyl)piperidin-4-yl)hexanoic acid |
| 103-A | 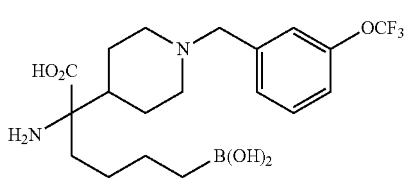 [SMILES: NC(CCCCB(O)O)(C(=O)O)C1CCN(Cc2cccc(OC(F)(F)F)c2)CC1] | 2-amino-6-borono-2-(1-(3-(trifluoromethoxy)benzyl)piperidin-4-yl)hexanoic acid |

TABLE 1-A-continued

| Ex. | Structure | Name |
|---|---|---|
| 104-A | 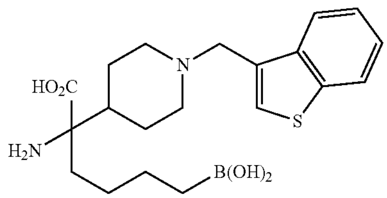 [SMILES: NC(CCCCB(O)O)(C(=O)O)C1CCN(Cc2csc3ccccc23)CC1] | 2-amino-2-(1-(benzo[b]thiophen-3-ylmethyl)piperidin-4-yl)-6-boronohexanoic acid |
| 105-A | 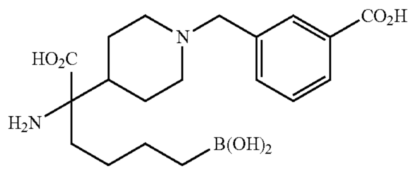 [SMILES: NC(CCCCB(O)O)(C(=O)O)C1CCN(Cc2cccc(C(=O)O)c2)CC1] | 3-((4-(1-amino-5-borono-1-carboxypentyl)piperidin-1-yl)methyl)benzoic acid |
| 106-A | 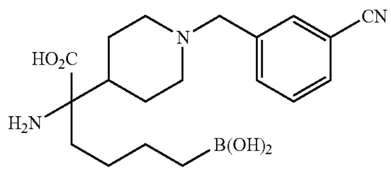 [SMILES: N#Cc1cccc(CN2CCC(C(N)(CCCCB(O)O)C(=O)O)CC2)c1] | 2-amino-6-borono-2-(1-(3-cyanobenzyl)piperidin-4-yl)hexanoic acid |

Pharmaceutical Compositions and Dosages

The present invention is directed in part to pharmaceutical formulations of Formula I or Formula II compounds and the use of the inventive formulations to treat disease conditions associated with an imbalance of arginase activity or the improper function of the arginase enzymes. In one aspect, the present invention provides combination therapy in which a patient or subject in need of therapy is administered a formulation of a Formula I or Formula II compound in combination with one or more other compounds having similar or different biological activities.

According to one aspect of the combination therapy routine, a therapeutically effective dose of a Formula I or Formula II compound may be administered separately to a patient or subject in need thereof from a therapeutically effective dose of the combination drug. The person of skill in the art will recognize that the two doses may be administered within hours or days of each other or the two doses may be administered together.

Exemplary disease conditions for which combination therapy in accordance with the present invention may be administered include any of the conditions more specifically described hereinbelow. These include without limitation heart disease, hypertension, sexual disorders, gastric disorders, autoimmune disorders, parasitic infections, pulmonary disorders, smooth muscle relaxation disorders and hemolytic disorders.

Suitable compounds that may be used in combination with a Formula I or a Formula II compound include without limitation:
Erectile Dysfunction: sildenafil, vardenafil, tadalafil and alprostadil.
Pulmonary Hypertension/Hypertension: epoprostenol, iloprost, bosentan, amlodipine, diltiazem, nifedipine, ambrisentan and warfarin.
Asthma: fluticasone, budesonide, mometasone, flunisolide, beclomethasone, montelukast, zafirlukast, zileuton, salmeterol, formoterol, theophylline, albuterol, levalbuterol, pirbuterol, ipratropium, prednisone, methylprednisolone, omalizumab, corticosteroid and cromolyn.
Artherosclerosis: atorvastatin, lovastatin, simvastatin, pravastatin, fluvastatin, rosuvastatin, gemfibrozil, fenofibrate, nicotinic acid, clopidogrel.

The invention also provides a pharmaceutical composition comprising one or more compounds according to Formula I or Formula II or pharmaceutically acceptable salts, solvates, stereoisomers, tautomers, or prodrugs, in admixture with a pharmaceutically acceptable carrier. In some embodiments, the composition further contains, in accordance with accepted practices of pharmaceutical compounding, one or more additional therapeutic agents, pharmaceutically acceptable excipients, diluents, adjuvants, stabilizers, emulsifiers, preservatives, colorants, buffers, or flavor imparting agents.

In one embodiment, the pharmaceutical composition comprises a compound selected from those illustrated in Table 1 or Table 1-A, or a pharmaceutically acceptable salt, solvate, stereoisomer, tautomer, or prodrug thereof, and a pharmaceutically acceptable carrier.

Suitable oral compositions in accordance with the invention include without limitation tablets, troches, lozenges, aqueous or oily suspensions, dispersible powders or granules, emulsion, hard or soft capsules, syrups or elixirs.

Encompassed within the scope of the invention are pharmaceutical compositions suitable for single unit dosages that comprise a compound of the invention, its pharmaceutically acceptable stereoisomer, prodrug, salt, solvate, hydrate, or tautomer and a pharmaceutically acceptable carrier.

Inventive compositions suitable for oral use may be prepared according to any method known to the art for the manufacture of pharmaceutical compositions. For instance, liquid formulations of the inventive compounds can contain one or more agents selected from the group consisting of sweetening agents, flavoring agents, coloring agents and preserving agents in order to provide pharmaceutically elegant and palatable preparations of the arginase inhibitor.

For tablet compositions of Formula I or Formula II compounds, the active ingredient in admixture with non-toxic pharmaceutically acceptable excipients is used for the manufacture of tablets. Examples of such excipients include without limitation inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known coating techniques to delay disintegration and absorption in the gastrointestinal tract and thereby to provide a sustained therapeutic action over a desired time period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

For aqueous suspensions the inventive compound is admixed with excipients suitable for maintaining a stable suspension. Examples of such excipients include without limitation are sodium carboxymethylcellulose, methylcellulose, hydropropylmethylcellulose, sodium alginate, polyvinylpyrrolidone, gum tragacanth and gum acacia.

Oral suspensions can also contain dispersing or wetting agents, such as naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol.

Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water can provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth naturally-occurring phosphatides, for example soy bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable, an aqueous suspension or an oleaginous suspension. This suspension may be formulated according to the known art using those suitable dispersing or wetting agents and suspending agents which have been mentioned above. The sterile injectable preparation may also be sterile injectable solution or suspension in a non-toxic, parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds that conform to Formula I or Formula II may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Examples of such materials are cocoa butter and polyethylene glycols.

Compositions for parenteral administrations are administered in a sterile medium. Depending on the vehicle used and the concentration of the drug in the formulation, the parenteral formulation can either be a suspension or a solution containing dissolved drug. Adjuvants such as local anesthetics, preservatives and buffering agents can also be added to parenteral compositions.

Synthesis of Compounds

Compounds of the invention are prepared using any number of the general methodologies described hereinbelow and can be adapted to the synthesis of compounds not specifically described. The choice of an appropriate synthetic methodology is guided by the choice of the Formula I or Formula II compound desired and the nature of functional groups present in the intermediate and final product. Thus, selective protection/deprotection protocols may be necessary during synthesis depending on the specific functional groups desired and protecting groups being used. A description of such protecting groups and how to introduce and remove them is found in: *Protective Groups in Organic Synthesis*, Third Edition, T. W. Green and P. G. M. Wuts, John Wiley and Sons, New York, 1999. Illustrative of the general synthetic methodologies used to make Formula I or Formula II compounds are those set forth below.

I. Synthesis of Formula I Compounds

Formula I compounds where D-B(OR$^3$)(OR$^4$) is —CH$_2$-L$_1$-L$_2$-CH$_2$—B(OH)$_2$ and R$_2$ is a substituted alkyl group, can be conveniently prepared using a glycine benzophenone imine ester as illustrated in Scheme A set forth below. In this method the starting amino acid imine A-1 can be purchased or prepared by reacting benzophenone imine with the desired amino acid ester (O'Donnell, M. J., *Aldrichimica Acta*, 2001, 34, 3-15). Alkylation of A-1 in Scheme A with electrophile A-2 using typical alkylation conditions such as lithium bis(trimethylsilyl)amide, LDA or sodium hydride in a polar aprotic solvent such as THF provides the monoalkylated product A-3. Similar reaction conditions can be used to introduce the second substituent to provide intermediate A-4. Subsequent hydrolysis provides the target compound A-5 (Scheme A).

In some instances it may be preferable or necessary to build one or both amino acid substituents in a multi-step process. An example of this is provided in Scheme A where allyl bromide is used in the second alkylation step giving intermediate A-6 under alkylating conditions described above. Following removal of the benzophenone and subsequent protection of the amine, the terminal olefin is oxidized to give aldehyde intermediate A-8.

The highly versatile aldehyde group can be utilized to prepare a wide variety of target compounds. One convenient use is in reductive amination reactions as shown in Scheme A. Here, treatment with the desired amine and a reducing agent like sodium cyanoborohydride gives amine intermediate A-9, which after hydrolysis, provides the target compounds A-10. Depending on the specific functional group desired, certain protecting groups may be required.

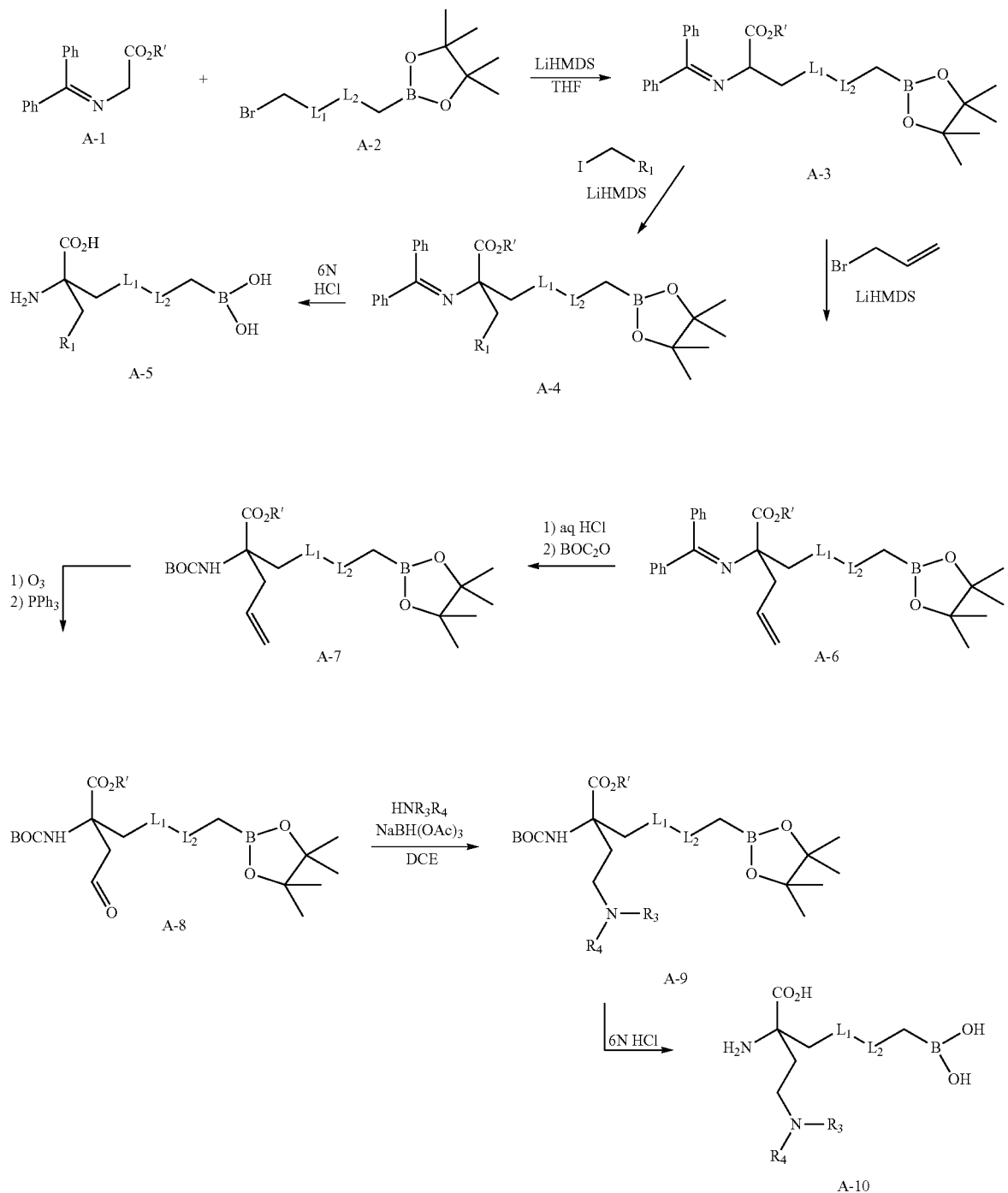

Alternatively, in the case where a protected boronic acid electrophile is not available or is incompatible with synthetic protocol, Formula I compounds can be synthesized by replacing electrophile A-2 with a terminal olefin followed by the introduction of boron in a later step following alkylation using hydroboration chemistry.

For enantioselective synthesis of Formula I compounds, a variety of different synthetic approaches may be used. Accordingly, in one embodiment an optically pure ketone is used in place of the achiral benzophenone. See, for example, Tabcheh, et al. *Tetrahedron* 1991, 47, 4611-4618 and Belokon et al. *Angew Chem, Int Ed* 2001, 40, 1948-1951.

Alternatively, asymmetric induction can be achieved in the second alkylation reaction by using a chiral catalyst. See, for example, Ooi, et al. *Tet Lett.* 2004, 45, 1675-1678; Ohshima et al. *J. Am. Chem. Soc.* 2009, 125, 11206-11207; and, Belokon et al. *Tetrahedron* 2001, 57, 2491-2498.

In yet another embodiment, enantioselectivity can be introduced by the use of an optically pure oxazinone to synthesize Formula I compounds (Dastlik, K. A.; Sundermeier, U., Johns, D. M.; Chen, Y.; Williams, R. M. *Synlett* 2005, 4, 693-696). This approach is illustrated in Scheme B.

obtained by decomposition of the di-substituted oxazinone followed by removal of the protecting groups. Thus, cleaving the oxazinone heterocycle via hydrogenation or using an alkali metal/ammonia reduction followed by treatment of intermediate B-8 with aqueous acid provides the target disubstituted amino acid B-9.

If a butaneboronic acid is desired as one of the substituents in the final product electrophile, B-2 or B-3 can be used as an alkylating agent. B-2 can be easily prepared from B-1 by treatment with pinacol in THF. If iodo-intermediate B-3 is desired, it can be prepared from the corresponding bromide via treatment with sodium iodide in acetone.

Alternatively, synthesis entails modification of one or both substituents after the alkylation steps. This may be required when the desired functionality in the final product is not compatible with the alkylation reaction conditions or if the desired substituent is not conveniently introduced as an electrophile due to limited reactivity. An example is illustrated in Scheme C, wherein allyl iodide is used as an efficient alkylating agent then further modified after cleavage of the oxazinone ring system. In this example, the allyl intermediate C-1 is treated with lithium in ammonia to remove the oxazinone

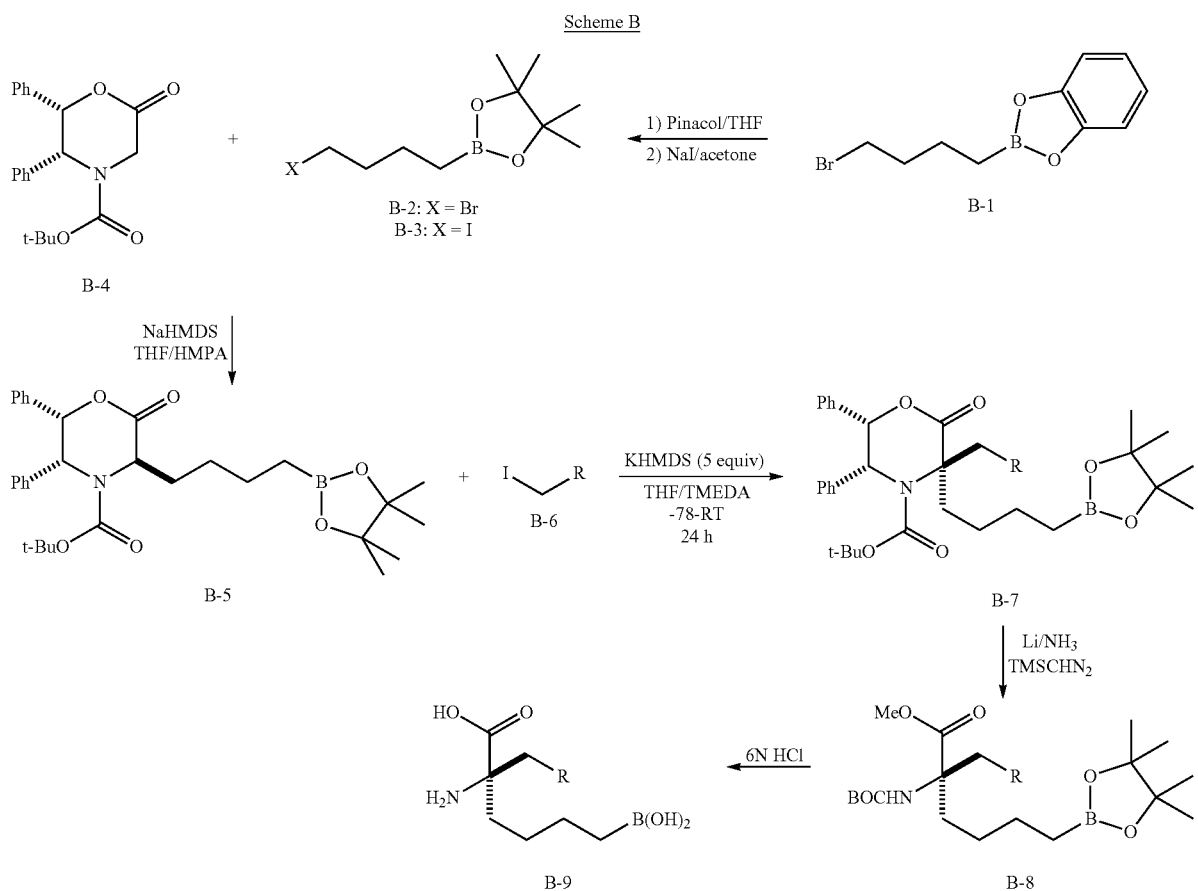

Here, the optically active oxazinone B-4 is used to stereoselectively direct sequential alkylations to form intermediate B-7. These alkylations can be carried out under reaction conditions that are specific for the electrophile being used (e.g. B-2, B-3, and B-6). Alternative approaches to synthesize B-5 and B-7 include the aldol reaction that involves the coupling of an aldehyde with the oxazinone followed by reduction of the resulting double bond. The inventive compounds are ring. The resulting acid can be protected as ester C-3 and subsequently treated with ozone to give the corresponding aldehyde.

The aldehyde (C-4) is a very flexible functional group and can be used in many types of reactions to make a wide variety of different analogs. As an example, it can be used in reductive amination reactions to prepare compounds with amine substituents R1 and R2 as in intermediate C-5. The final target compounds (C-6) can be obtained after deprotection of the ester, amino and boronic acid moieties.

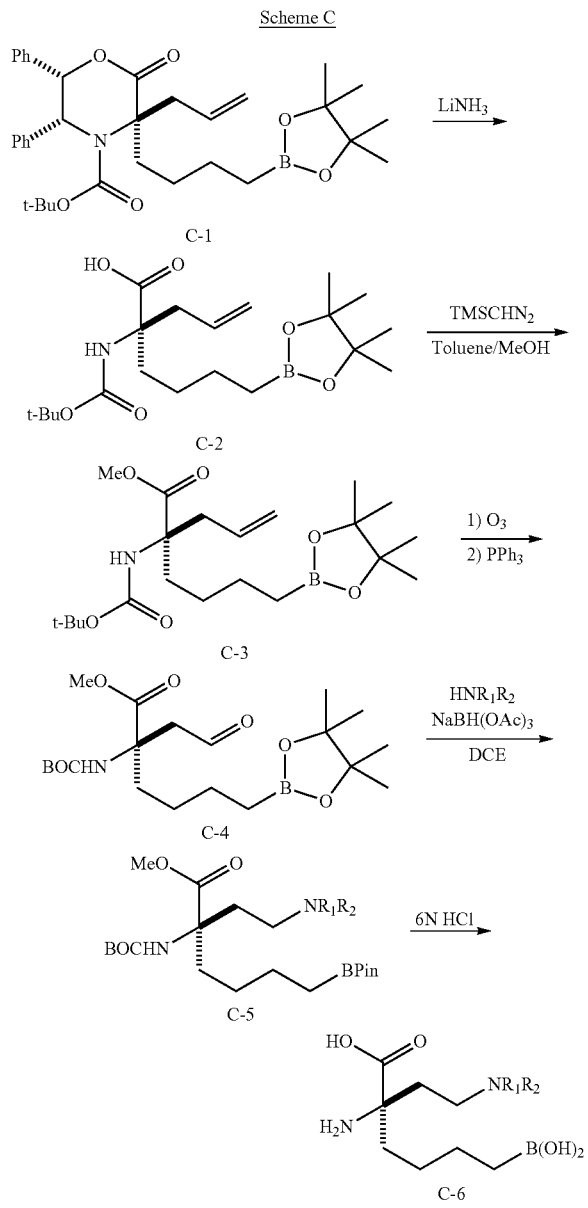

Scheme C

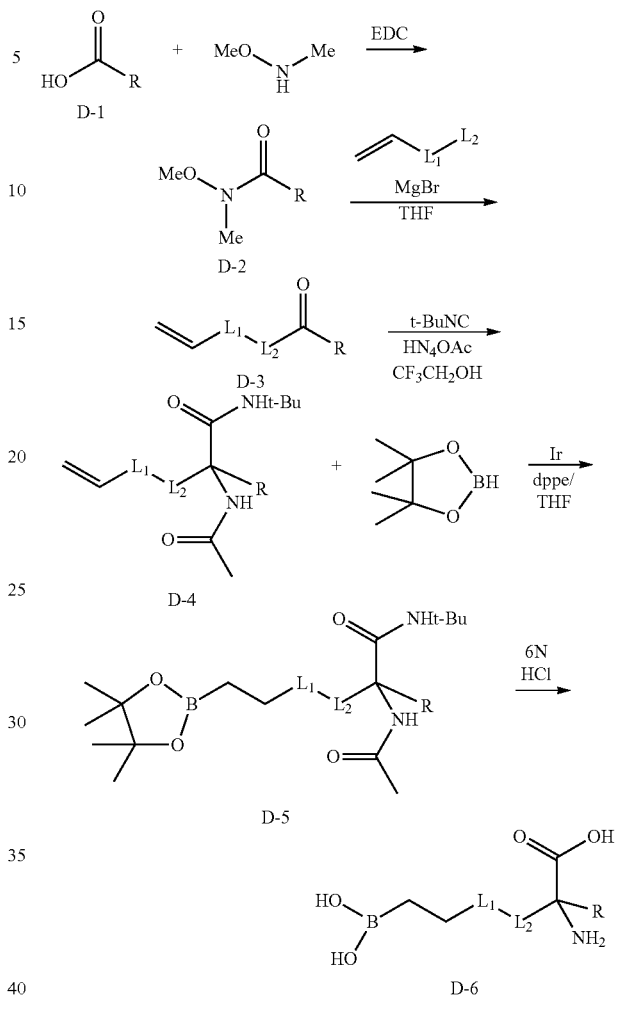

Scheme D

In another embodiment, syntheses of some Formula I compounds employ the Ugi reaction (Doemling, A., *Chem. Rev.* 2006, 106, 17-89. This method is illustrated in Scheme D. In the Ugi reaction a ketone or aldehyde (D-3) is treated with an isocyanate such as tert-butyl isocyanate and an amine source like ammonium acetate to give directly the amino acid derivative with the carboxylic acid and amine protected as a tert-butylamide and acetamide respectively. In this reaction different isocyanates and amine sources can be used depending on the desired amine and carboxylic acid protecting groups desired. If optically active products are desired chiral optically pure isocyanates and/or amine sources can be used. The reactions using these reagents may be enantioselective, or at least provide diastereomeric mixtures of products that can be easily separated.

The synthesis of key intermediate D-3 can be completed using a wide variety of methods. One very convenient method utilizes carboxylic acid D-1. In this method the carboxylic acid is activated and coupled with methoxymethylamine to form Weinreb amide D-2. This can be completed using a wide variety of coupling regents such as EDC, DCC or PyBOP, or directly from the acid chloride of D-1. The Weinreb amide can be converted to the desired ketone by reacting it with the appropriate Grignard reagent to give intermediate D-3.

After the Ugi reaction is complete, the terminal olefin can be treated with a borane source such as pinacolborane to introduce the boronic acid moiety. Final deprotection of intermediate D-5 gives target compound D-6.

Many examples with an aminomethylene substituent in the α-position can be conveniently prepared using the method illustrated in Scheme E. Here an aminomalonate starting material such as E-1, where the amine is protected as a benzyl carbamate (Cbz) and the acids are protected as esters, is used to generate disubstituted amino acid derivative E-2 via alkylation with 4-bromobutene. Selective hydrolysis of the diester with potassium hydroxide in ethanol gives acid ester E-3. Selective reduction of the carboxylic acid using a chloroformate and sodium borohydride gives alcohol E-4 which can be protected using dimethoxypropane and an organic acid such as toluenesulfonic acid. Hydrboration of E-5 with pinacolborane gives E-6, which after deprotection provides alcohol E-7. Oxidation of the alcohol provides the intermediate aldehyde E-8, which after reductive amination and final deprotection gives the target compound E-11.

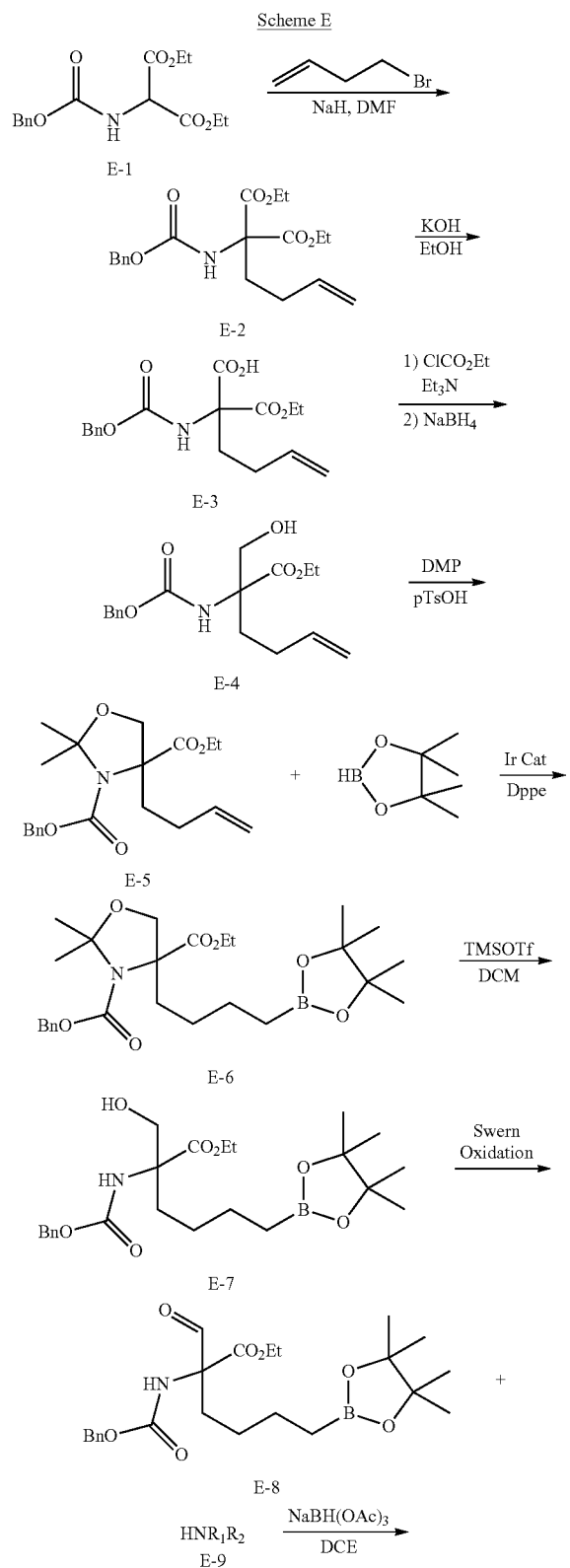

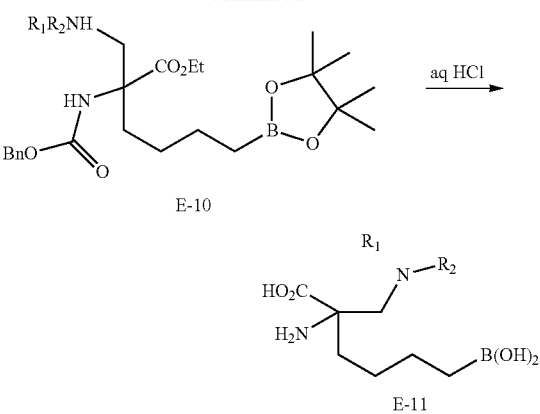

As an alternative to the method in Scheme E where the benzyl carbamate is used as the amine protecting group, the corresponding t-butyl carbamate (Boc) protected amino malonate derivative can also be used. Here, as illustrated in Scheme F, diethyl 2-(tert-butoxycarbonylamino)malonate F-1 is alkylated with 4-bromobutene to give the disubstituted malonate intermediate F-2. Selective hydrolysis of the diester using basic conditions such as potassium hydroxide in ethanol gives mono acid F-3. Reduction of the carboxylic acid using ethyl chloroformate and sodium borohydride gives the primary alcohol which can be conveniently protected as an acetate using standard conditions such as acetic anhydride and DMAP. If desired, many alternative protecting groups can be used. This group is simply introduced to facilitate the subsequent hydroboration reaction that provides intermediate F-6. Once the hydroboration reaction is complete, the acetate can be removed and the resulting alcohol (F-7) can be oxidized to the corresponding aldehyde (F-8) and used in reductive amination reactions with amine F-9 to give protected products F-10. Deprotection using aqueous acid then gives the desired products F-11. In addition to reductive amination reactions, intermediate aldehyde F-8 can be used in a wide variety of reactions to produce desired substituents. The use of aldehydes to form heterocycles or other products is well known to those skilled in the art of organic synthesis.

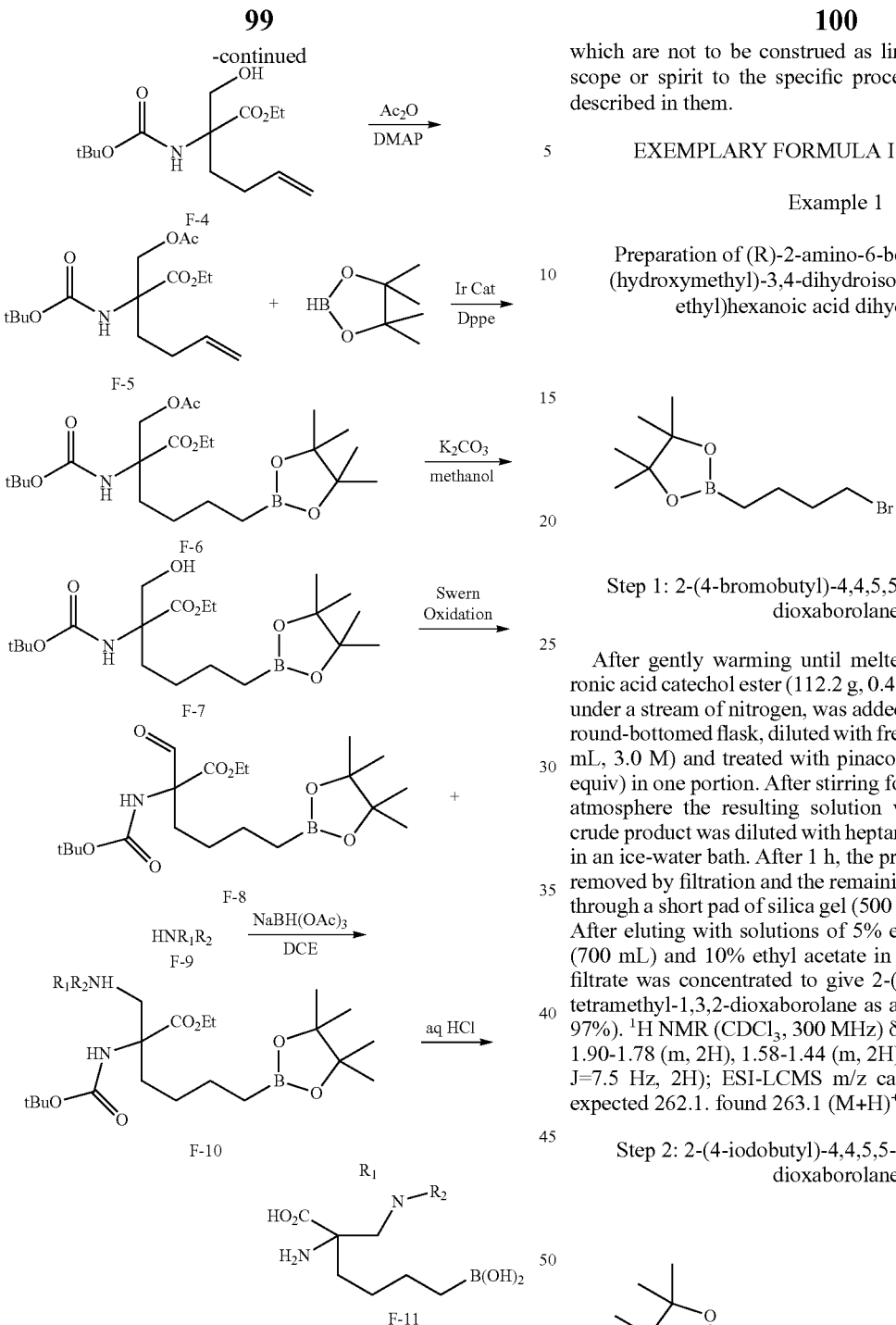

which are not to be construed as limiting the invention in scope or spirit to the specific procedures and compounds described in them.

EXEMPLARY FORMULA I COMPOUNDS

Example 1

Preparation of (R)-2-amino-6-borono-2-(2-((S)-3-(hydroxymethyl)-3,4-dihydroisoquinolin-2(1H)-yl)ethyl)hexanoic acid dihydrochloride Step 1: 2-(4-bromobutyl)-4,4,5,5-tetramethyl-1,3,2-dioxaborolane After gently warming until melted, 4-bromo-1-butylboronic acid catechol ester (112.2 g, 0.44 mol, 1.0 equiv), while under a stream of nitrogen, was added to a 3-necked 500 mL round-bottomed flask, diluted with freshly distilled THF (150 mL, 3.0 M) and treated with pinacol (104.0 g, 0.88 mol, 2 equiv) in one portion. After stirring for 16 h under a nitrogen atmosphere the resulting solution was concentrated. The crude product was diluted with heptane (500 mL) and cooled in an ice-water bath. After 1 h, the precipitated catechol was removed by filtration and the remaining solution was filtered through a short pad of silica gel (500 g) wetted with heptane. After eluting with solutions of 5% ethyl acetate in heptane (700 mL) and 10% ethyl acetate in heptane (700 mL), the filtrate was concentrated to give 2-(4-bromobutyl)-4,4,5,5-tetramethyl-1,3,2-dioxaborolane as a colorless oil (112.7 g, 97%). $^1$H NMR (CDCl$_3$, 300 MHz) δ 3.38 (t, J=6.6 Hz, 2H), 1.90-1.78 (m, 2H), 1.58-1.44 (m, 2H), 1.26 (s, 12H), 0.78 (t, J=7.5 Hz, 2H); ESI-LCMS m/z calcd for $C_{10}H_{20}BBrO_2$: expected 262.1. found 263.1 (M+H)$^+$.

Step 2: 2-(4-iodobutyl)-4,4,5,5-tetramethyl-1,3,2-dioxaborolane

While under a nitrogen atmosphere, a solution of 2-(4-bromobutyl)-4,4,5,5-tetramethyl-1,3,2-dioxaborolane (46.2 g, 0.176 mol, 1.0 equiv) and sodium iodide (52.8 g, 0.35 mol, 2 equiv) in acetone (176 mL, 1.0 M) was heated to 50° C. for 4 h. After cooling to room temperature the solution was concentrated under reduced pressure. The resulting residue was diluted with heptane (200 mL) and filtered through a short pad of silica gel (300 g) wetted with heptane. After eluting with a solution of 10% ethyl acetate in heptane (500 mL) the filtrate was concentrated to give 2-(4-iodobutyl)-4,4,5,5-tetramethyl-1,3,2-dioxaborolane as a colorless oil (53.5

Those having skill in the art will recognize that the starting materials and reaction conditions may be varied, the sequence of the reactions altered, and additional steps employed to produce compounds encompassed by the present invention, as demonstrated by the following examples. In some cases, protection of certain reactive functionalities may be necessary to achieve some of the above transformations. In general, the need for such protecting groups as well as the conditions necessary to attach and remove such groups will be apparent to those skilled in the art of organic synthesis.

The preparation of Formula I compounds of the present invention is illustrated further by the following examples, g, 98%). $^1$H NMR (CDCl$_3$, 300 MHz) δ 3.18 (t, J=7.2 Hz, 2H), 1.90-1.78 (m, 2H), 1.58-1.44 (m, 2H), 1.24 (s, 12H), 0.79 (t, J=7.5 Hz, 2H); ESI-LCMS m/z calcd for $C_{10}H_{20}BIO_2$: expected 310.1. found 311.1 (M+H)$^+$.

Step 3: (3R,5R,6S)-tert-butyl 2-oxo-5,6-diphenyl-3-(4-(4,4,5,5-tetramethyl-1,3,2-dioxaborolan-2-yl)butyl)morpholine-4-carboxylate

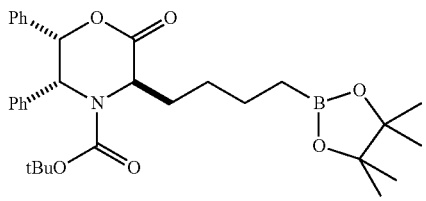 [SMILES: CC(C)(C)OC(=O)N1[C@H](CCCCB2OC(C)(C)C(C)(C)O2)C(=O)O[C@@H](c2ccccc2)[C@H]1c1ccccc1]

A solution of (2S,3R)-tert-butyl 6-oxo-2,3-diphenylmorpholine-4-carboxylate (4.69 g, 13.27 mmol) and 2-(4-iodobutyl)-4,4,5,5-tetramethyl-1,3,2-dioxaborolane (d 1.38, 5.96 mL, 8.23 g, 26.5 mmol, 2 equiv) in THF (66 mL, 0.2 M) and HMPA (6.6 mL) was cooled to −78° C. and treated with sodium bis(trimethylsilyl)amide (14.6 mL, 1.0 M, 1.1 equiv) drop wise over 5 min and stirred for 1 h. After warming to room temperature and stirring for an additional 2 h, the solution was cooled to 0° C. and quenched with 0.5 NHC (2-3 equiv). The resulting solution was diluted with heptane and washed successively with water and saturated aqueous NaCl, dried over MgSO$_4$, filtered and concentrated. Purification by MPLC (1-60% ethyl acetate in heptane over 6 CV) gave (3R,5R,6S)-tert-butyl 2-oxo-5,6-diphenyl-3-(4-(4,4,5,5-tetramethyl-1,3,2-dioxaborolan-2-yl)butyl)morpholine-4-carboxylate as a white solid (6.66 g, 94%); ESI-LCMS m/z calcd for $C_{31}H_{42}BNO_2$: expected 535.3. found 536.4 (M+H)$^+$.

Step 4: (3R,5R,6S)-tert-butyl 3-allyl-2-oxo-5,6-diphenyl-3-(4-(4,4,5,5-tetramethyl-1,3,2-dioxaborolan-2-yl)butyl)morpholine-4-carboxylate

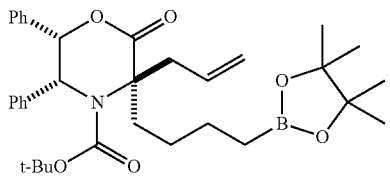 [SMILES: C=CC[C@]1(CCCCB2OC(C)(C)C(C)(C)O2)C(=O)O[C@@H](c2ccccc2)[C@@H](c2ccccc2)N1C(=O)OC(C)(C)C]

A solution of (3R,5R,6S)-tert-butyl 2-oxo-5,6-diphenyl-3-(4-(4,4,5,5-tetramethyl-1,3,2-dioxaborolan-2-yl)butyl)morpholine-4-carboxylate (5.00 g, 9.34 mmol) and TMEDA (10 mL, 65 mmol, 7 equiv) in THF (51 mL, 0.2 M) was cooled to −78° C. and treated with allyl iodide (17 mL, 187 mmol, 20 equiv) and potassium bis(trimethylsilyl)amide (47 mL, 0.9 M in THF, 46.7 mmol, 5 equiv) drop wise and stirred for 30 min. Once the addition was complete, the cooling bath was removed and the mixture was stirred over night. Once complete by TLC, the reaction mixture was quenched with 0.5N HCl (5-10 equiv), diluted with heptane and washed successively with water and saturated aqueous NaCl, dried over MgSO$_4$, filtered and concentrated. Purification by MPLC (1-60% ethyl acetate in heptane over 6 CV) gave (3R,5R,6S)-tert-butyl 3-allyl-2-oxo-5,6-diphenyl-3-(4-(4,4,5,5-tetramethyl-1,3,2-dioxaborolan-2-yl)butyl)morpholine-4-carboxylate as colorless oil (5.2 g, 96%). R$_f$ 0.55 (30% ethyl acetate in heptane); $^1$H NMR (CDCl$_3$, 300 MHz) δ 7.39-7.14 (m, 10H), 7.10 (dd, J$_1$=5.4 Hz, J$_2$=1.8 Hz, 1H), 6.08 (d, J=5.4 Hz, 1H), 5.95-5.80 (m, 1H), 5.27-5.17 (m, 2H), 3.30-3.15 (m, 1H), 2.89-2.76 (m, 1H), 2.20-2.07 (m, 2H), 1.54 (s, 9H), 1.35-1.21 (m, 4H), 1.78 (s, 12H), 0.46 (t, J=8.4 Hz, 2H); ESI-LCMS m/z calcd for $C_{34}H_{46}BNO_6$: expected 575.3. found 574.3 (M+H)$^+$.

Step 5: (R)-methyl 2-allyl-2-(tert-butoxycarbonylamino)-6-(4,4,5,5-tetramethyl-1,3,2-dioxaborolan-2-yl)hexanoate

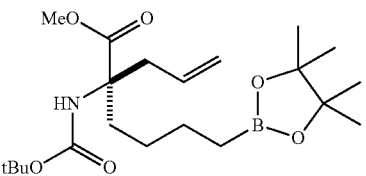 [SMILES: C=CC[C@@](CCCCB1OC(C)(C)C(C)(C)O1)(NC(=O)OC(C)(C)C)C(=O)OC]

A three-necked RBF equipped with nitrogen inlet tube and dry ice condenser was charged with (3R,5R,6S)-tert-butyl 3-allyl-2-oxo-5,6-diphenyl-3-(4-(4,4,5,5-tetramethyl-1,3,2-dioxaborolan-2-yl)butyl)morpholine-4-carboxylate (4.60 g, 8.00 mmol) and THF (10 mL). After cooling the condenser to −78° C. and the flask to −45° C. (CO$_2$ (s), CH$_3$CN), ammonia (80 mL) was condensed into the flask. Once complete, lithium metal (0.55 g, 80 mmol, small pieces) was carefully added over 10 min. After stirring an additional 40 min, the reaction mixture was carefully quenched with NH$_4$Cl (s) until the solution became clear. The bath was removed and the ammonia was allowed to evaporate over night. The resulting residue was diluted with ethyl acetate and washed successively with 0.5N HCl and saturated aqueous NaCl, dried over MgSO$_4$, filtered and concentrated. The crude product was dissolved in 50% methanol in toluene (80 mL, 0.1 M) and treated with TMSCHN$_2$ (2.0 M in hexanes) until the pale yellow color persisted. With TLC indicating the reaction complete, the excess TMSCHN$_2$ was quenched with acetic acid until the solution became clear. The solution was concentrated, diluted with ethyl acetate and washed successively with saturated aqueous NaHCO$_3$ and saturated aqueous NaCl, dried over MgSO$_4$, filtered and concentrated. Purification by MPLC (1-60% ethyl acetate in heptane over 6 CV) gave (R)-methyl 2-allyl-2-(tert-butoxycarbonylamino)-6-(4,4,5,5-tetramethyl-1,3,2-dioxaborolan-2-yl)hexanoate as colorless oil (1.9 g, 58%). R$_f$ 0.46 (30% ethyl acetate in heptane); $^1$H NMR (CDCl$_3$, 300 MHz) δ 5.70-5.52 (m, 1H), 5.49-5.36 (m, 1H), 5.05 (dd, J$_1$=13.8 Hz, J$_2$=1.2 Hz, 1H), 3.73 (s, 3H), 3.09-2.96 (m, 1H), 2.50 (dd, J$_1$=13.8 Hz, J$_2$=7.8 Hz, 1H), 2.29-2.10 (m, 1H), 1.78-1.65 (m, 1H), 1.43 (s, 9H), 1.42-1.26 (m, 4H), 1.23 (s, 12H), 0.74 (t, J=7.5 Hz, 2H); ESI-LCMS m/z calcd for $C_{21}H_{38}BNO_6$: expected 411.3. found 412.3 (M+H)$^+$.

Step 6: (R)-methyl 2-(tert-butoxycarbonylamino)-2-(2-oxoethyl)-6-(4,4,5,5-tetramethyl-1,3,2-dioxaborolan-2-yl)hexanoate

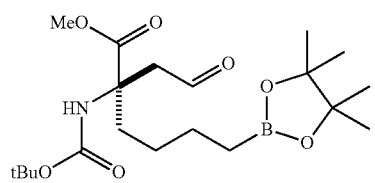 [SMILES: COC(=O)[C@](CC=O)(CCCCB1OC(C)(C)C(C)(C)O1)NC(=O)OC(C)(C)C]

A solution of (R)-methyl 2-allyl-2-(tert-butoxycarbonylamino)-6-(4,4,5,5-tetramethyl-1,3,2-dioxaborolan-2-yl)hexanoate (1.90 g, 4.62 mmol) in dichloromethane (90 mL, 0.05 M) was cooled to −78° C. and treated with ozone until a pale blue-gray color appeared. After TLC indicated the absence of starting material, the ozone inlet tube was replaced with nitrogen and nitrogen was bubbled through the solution for 20 min to remove any excess ozone. Triphenylphosphine (3.6 g, 13.8 mmol, 3 equiv) was added in one portion, the cooling bath was removed and the mixture was stirred for 4 h. The solution was concentrated and purified by MPLC (1-50% ethyl acetate in heptane over 6 CV) and gave (R)-methyl 2-(tert-butoxycarbonylamino)-2-(2-oxoethyl)-6-(4,4,5,5-tetramethyl-1,3,2-dioxaborolan-2-yl)hexanoate as a colorless oil (1.28 g, 67%). $R_f$ 0.55 (30% ethyl acetate in heptane); $^1$H NMR (CDCl$_3$, 300 MHz) δ 9.66 (s, 1H), 5.62 (br s, 1H), 3.75 (s, 3H), 3.60 (br d, J=17.4 Hz, 1H), 2.95 (d, J=17.4 Hz, 1H), 2.30-2.15 (m, 1H), 1.70-1.54 (m, 1H), 1.40 (s, 9H), 1.39-1.24 (m, 4H), 0.74 (t, J=7.8 Hz, 2H); ESI-LCMS m/z calcd for $C_{20}H_{36}BNO_7$: expected 413.3. found 414.3 (M+H)$^+$.

Step 7: (R)-methyl 2-(tert-butoxycarbonylamino)-2-(2-((S)-3-(hydroxymethyl)-3,4-dihydroisoquinolin-2(1H)-yl)ethyl)-6-(4,4,5,5-tetramethyl-1,3,2-dioxaborolan-2-yl)hexanoate

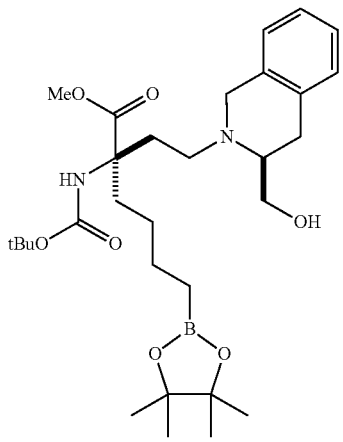 [SMILES: COC(=O)[C@@](CCCCB1OC(C)(C)C(C)(C)O1)(CCN1Cc2ccccc2C[C@H]1CO)NC(=O)OC(C)(C)C]

A solution of (R)-methyl 2-(tert-butoxycarbonylamino)-2-(2-oxoethyl)-6-(4,4,5,5-tetramethyl-1,3,2-dioxaborolan-2-yl)hexanoate (0.148 g, 0.358 mmol, 1.0 equiv.) and (S)-(1,2,3,4-tetrahydroisoquinolin-3-yl)methanol (0.088 g, 0.54 mmol, 1.5 equiv.) in 1,2-dichloroethane (0.34 mL, 0.5 M) was treated with sodium triacetoxyborohydride (0.19 g, 0.90 mmol, 2.5 equiv) in one portion. After stirring for 1.5 h, the reaction mixture was quenched with saturated aqueous NaHCO$_3$ (1 mL) and stirred for an additional 5 min. The resulting mixture was added to a separatory funnel, diluted with saturated aqueous NaCl (5 mL) and extracted with dichloromethane (2×10 mL). The organic layer was dried over MgSO$_4$, filtered and concentration under reduced pressure. Purification by flash column chromatography eluting with 5% methanol in chloroform gave (R)-methyl 2-(tert-butoxycarbonylamino)-2-(2-((S)-3-(hydroxymethyl)-3,4-dihydroisoquinolin-2(1H)-yl)ethyl)-6-(4,4,5,5-tetramethyl-1,3,2-dioxaborolan-2-yl)hexanoate as a pale yellow oil (0.187 g, 93%). $R_f$ 0.52 (10% methanol in dichloromethane); $^1$H NMR (CDCl$_3$, 300 MHz) δ 7.15-7.08 (m, 2H), 7.07-6.98 (m, 2H), 5.90 (s, 1H), 3.78 (d, J=16.2 Hz, 1H), 3.70 (s, 3H), 3.60-3.47 (m, 2H), 3.04-2.93 (m, 1H), 2.92-2.82 (m, 1H), 2.71-2.60 (m, 1H), 2.56-2.38 (m, 2H), 2.37-2.23 (m, 1H), 2.21-2.10 (m, 1H), 1.77-1.63 (m, 1H), 1.42 (s, 9H), 1.43-1.26 (m, 3H), 1.23 (s, 12H), 1.22-1.16 (m, 1H), 0.99-0.82 (m, 2H), 0.74 (t, J=7.5 Hz, 2H); ESI-LCMS m/z calcd for $C_{30}H_{49}BN_2O_7$: expected 560.4. found 561.4 (M+H)$^+$.

Step 8: (R)-2-amino-6-borono-2-(2-((S)-3-(hydroxymethyl)-3,4-dihydroisoquinolin-2(1H)-yl)ethyl)hexanoic acid dihydrochloride

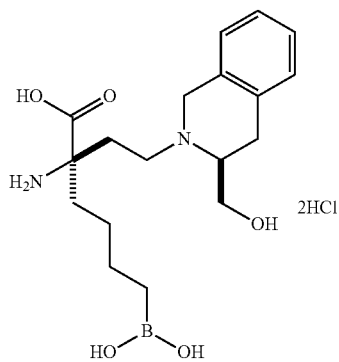

(1)

A solution of (R)-methyl 2-(tert-butoxycarbonylamino)-2-(2-((S)-3-(hydroxymethyl)-3,4-dihydroisoquinolin-2(1H)-yl)ethyl)-6-(4,4,5,5-tetramethyl-1,3,2-dioxaborolan-2-yl)hexanoate (0.187 g, 0.334 mmol) in 6 N HCl (5 mL) was heated to a gentle reflux for 16 h. After cooling to room temperature, the reaction mixture was transferred to a separatory funnel, diluted with deionized water (5 mL) and washed with dichloromethane (3×5 mL). The aqueous layer was frozen in liquid nitrogen and lyophilized to give (R)-2-amino-6-borono-2-(2-((S)-3-(hydroxymethyl)-3,4-dihydroisoquinolin-2(1H)-yl)ethyl)hexanoic acid dihydrochloride as an off-white foam (0.122 g, 89%). $^1$H NMR (D$_2$O, 300 MHz) δ 7.26-7.08 (m, 4H), 3.89-375 (m, 1H), 3.78-3.65 (m, 1H), 3.61-3.50 (m, 1H), 3.41-3.18 (m, 1H), 3.10-3.00 (m, 1H), 2.99-2.75 (m, 2H), 2.35-2.20 (m, 2H), 1.84-1.60 (m, 2H), 1.31-1.16 (m, 2H), 1.15-1.00 (m, 2H), 0.66-0.50 (m, 2H); ESI-LCMS m/z calcd for $C_{18}H_{29}BN_2O_5$: expected 364.2. found 365.2 (M+H)$^+$.

Example 2

Preparation of (R)-2-amino-6-borono-2-(2-((S)-2-(methoxymethyl)pyrrolidin-1-yl)ethyl)hexanoic acid dihydrochloride

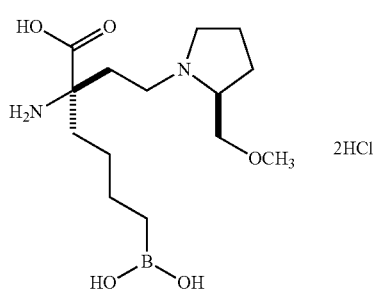

(2)

(R)-2-Amino-6-borono-2-(2-((S)-2-(methoxymethyl)pyrrolidin-1-yl)ethyl)hexanoic acid dihydrochloride is prepared in a manner analogous to that set forth in Example 1, except (S)-2-(methoxymethyl)pyrrolidine is used as the amine in step 7. $^1$H NMR (D$_2$O, 300 MHz) δ 3.68-3.50 (m, 3H), 3.50-3.39 (m, 1H), 3.38-3.10 (m, 2H), 3.24 (s, 3H), 3.10-2.96 (m, 1H), 2.22-2.10 (m, 2H), 2.10-2.01 (m, 1H), 2.01-1.89 (m, 1H), 1.88-1.62 (m, 4H), 1.35-1.16 (m, 3H), 1.16-1.00 (m, 1H), 0.63 (t, J=7.8 Hz, 2H); ESI-LCMS m/z calcd for C$_{14}$H$_{29}$BN$_2$O$_5$: expected 316.2. found 317.2 (M+H)$^+$.

Example 3

Preparation of (R)-2-amino-6-borono-2-(2-((R)-2-(methoxymethyl)pyrrolidin-1-yl)ethyl)hexanoic acid dihydrochloride

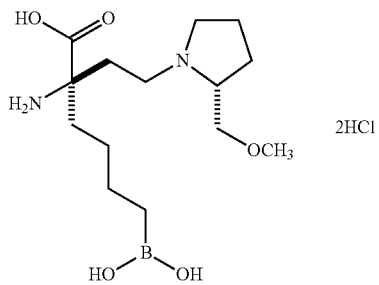

(3)

(R)-2-Amino-6-borono-2-(2-((R)-2-(methoxymethyl)pyrrolidin-1-yl)ethyl)hexanoic acid dihydrochloride is prepared in a manner analogous to that set forth in Example 1, except (R)-2-(methoxymethyl)pyrrolidine is used as the amine in step 7. $^1$H NMR (D$_2$O, 300 MHz) δ 3.67-3.35 (m, 4H), 3.23 (s, 3H), 3.08-2.91 (m, 3H), 2.25-1.55 (m, 8H), 1.36-1.16 (m, 3H), 1.16-1.00 (m, 1H), 0.63 (br s, 2H); ESI-LCMS m/z calcd for C$_{14}$H$_{29}$BN$_2$O$_5$: expected 316.2. found 317.2 (M+H)$^+$.

Example 4

Preparation of (R)-2-amino-6-borono-2-(2-(4-hydroxypiperidin-1-yl)ethyl)hexanoic acid dihydrochloride

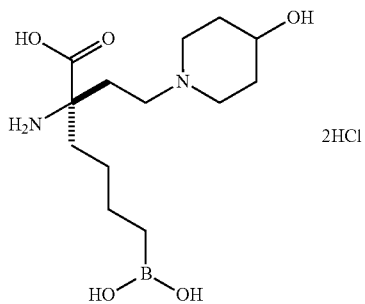

(4)

(R)-2-Amino-6-borono-2-(2-(4-hydroxypiperidin-1-yl)ethyl)hexanoic acid dihydrochloride is prepared in a manner analogous to that set forth in Example 1, except piperidin-4-ol is used as the amine in step 7. $^1$H NMR (D$_2$O, 300 MHz) δ 4.05-3.96 (m, 1H), 3.82-3.68 (m, 1H), 3.51-3.49 (m, 1H), 3.33-3.05 (m, 2H), 3.05-2.81 (m, 2H), 2.17-1.98 (m, 3H), 1.87-1.44 (m, 5H), 1.30-1.15 (m, 3H), 1.12-0.99 (m, 1H), 0.62 (t, J=7.8 Hz, 2H); ESI-LCMS m/z calcd for C$_{13}$H$_{27}$BN$_2$O$_5$: 302.2. found 303.2 (M+H)$^+$.

Example 5

Preparation of (R)-2-amino-6-borono-2-(2-((S)-3-hydroxypiperidin-1-yl)ethyl)hexanoic acid dihydrochloride

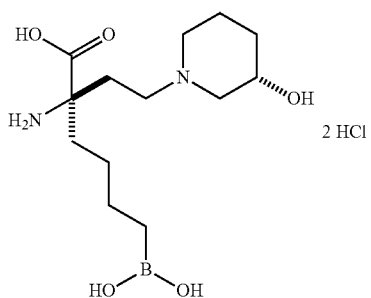

(5)

(R)-2-Amino-6-borono-2-(2-((S)-3-hydroxypiperidin-1-yl)ethyl)hexanoic acid dihydrochloride is prepared in a manner analogous to that set forth in Example 1, except (S)-piperidin-3-ol is used as the amine in step 7. $^1$H NMR (D$_2$O, 300 MHz) δ 4.16-4.04 (m, 1H), 3.48-3.12 (m, 4H), 3.07-2.90 (m, 1H), 2.88-2.70 (m, 1H), 2.25-2.00 (m, 2H), 2.00-1.80 (m, 1H), 1.80-1.45 (m, 5H), 1.32-1.14 (m, 3H), 1.14-1.00 (m, 1H), 0.63 (t, J=7.8 Hz, 2H); ESI-LCMS m/z calcd for C$_{13}$H$_{27}$BN$_2$O$_5$: 302.2. found 303.2 (M+H)$^+$.

Example 6

Preparation of (R)-2-amino-6-borono-2-(2-((3,4-dimethoxyphenethyl)(methyl)amino)ethyl)hexanoic acid dihydrochloride

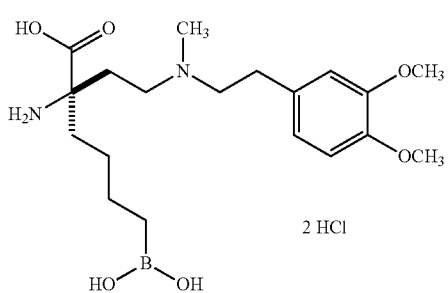

(6)

(R)-2-Amino-6-borono-2-(2-((3,4-dimethoxyphenethyl)(methyl)amino)ethyl) hexanoic acid dihydrochloride is prepared in a manner analogous to that set forth in Example 1, except 2-(3,4-dimethoxyphenyl)-N-methylethanamine is used as the amine in step 7. $^1$H NMR (D$_2$O, 300 MHz) δ 6.83-6.59 (m, 3H), 3.68 (s, 3H), 3.66 (s, 3H), 3.40-2.99 (m, 4H), 2.97-2.79 (m, 2H), 2.75 (s, 3H), 2.20-2.01 (m, 2H), 1.81-1.47 (m, 2H), 1.33-1.08 (3H), 1.07-0.96 (m, 1H), 0.61 (t, J=6.9 Hz, 2H); ESI-LCMS m/z calcd for $C_{19}H_{33}BN_2O_6$: 396.2. found 397.2 (M+H)$^+$.

Example 7

Preparation of (R)-2-amino-6-borono-2-(2-((R)-3-(hydroxymethyl)pyrrolidin-1-yl)ethyl)hexanoic acid dihydrochloride

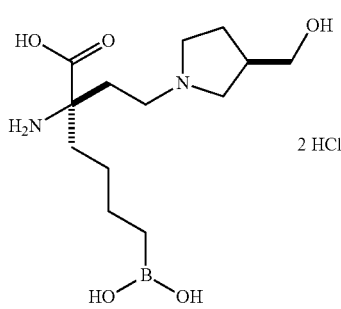

(7)

(R)-2-Amino-6-borono-2-(2-((R)-3-(hydroxymethyl)pyrrolidin-1-yl)ethyl)hexanoic acid dihydrochloride is prepared in a manner analogous to that set forth in Example 1, except (R)-pyrrolidin-3-ylmethanol is used as the amine in step 7. $^1$H NMR (D$_2$O, 300 MHz) δ 3.70-3.18 (m, 5H), 3.16-2.88 (m, 3H), 2.11-1.85 (m, 3H), 1.82-1.51 (3H), 1.30-1.14 m, 3H), 1.11-0.99 (m, 1H), 0.62 (t, J=7.8 Hz, 2H); ESI-LCMS m/z calcd for $C_{13}H_{27}BN_2O_5$: 302.2. found 303.3 (M+1)$^+$.

Example 8

Preparation of (R)-2-amino-6-borono-2-(2-thiomorpholinoethyl)hexanoic acid dihydrochloride

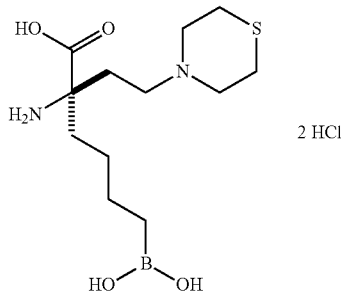

(8)

(R)-2-Amino-6-borono-2-(2-thiomorpholinoethyl)hexanoic acid dihydrochloride is prepared in a manner analogous to that set forth in Example 1, except thiomorpholine is used as the amine in step 7. $^1$H NMR (D$_2$O, 300 MHz) δ 3.61-3.57 (m, 2H), 3.30-3.17 (m, 1H), 3.16-2.99 (m, 3H), 2.98-2.80 (m, 2H), 2.73-2.60 (m, 2H), 2.29-2.14 (m, 2H), 1.90-1.61 (m, 2H), 1.30-1.15 (m, 3H), 1.12-0.95 (m, 1H), 0.78 (t, J=7.2 Hz, 2H); ESI-LCMS m/z calcd for $C_{12}H_{25}BN_2O_4S$: 304.2. found 305.2 (M+1)$^+$.

Example 9

Preparation of (R)-2-amino-6-borono-2-(2-(4-(2-hydroxyethyl)piperidin-1-yl)ethyl)hexanoic acid dihydrochloride

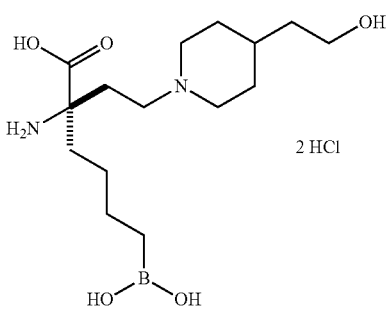

(9)

(R)-2-Amino-6-borono-2-(2-(4-(2-hydroxyethyl)piperidin-1-yl)ethyl)hexanoic acid dihydrochloride is prepared in a manner analogous to that set forth in Example 1, except 2-(piperidin-4-yl)ethanol is used as the amine in step 7. $^1$H NMR (D$_2$O, 300 MHz) δ 3.51-3.30 (m, 3H), 3.30-3.02 (m, 2H), 3.01-2.89 (m, 1H), 2.88-2.60 (m, 2H), 2.20-1.95 (m, 2H), 1.90-1.63 (m, 6H), 1.64-1.40 (m, 1H), 1.40-1.28 (m, 2H), 1.28-1.10 (m, 3H), 1.11-0.93 (m, 1H), 0.61 (t, J=7.5 Hz, 2H); ESI-LCMS m/z calcd for $C_{15}H_{31}BN_2O_5$: 330.2. found 331.3 (M+1)$^+$.

Example 10

Preparation of (R)-2-amino-6-borono-2-(2-((S)-2-(hydroxymethyl)pyrrolidin-1-yl)ethyl)hexanoic acid

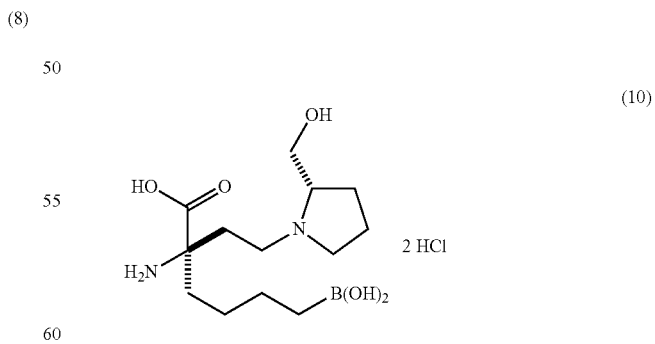

(10)

(R)-2-Amino-6-borono-2-(2-((S)-2-(hydroxymethyl)pyrrolidin-1-yl)ethyl)hexanoic acid is prepared in a manner analogous to that set forth in Example 1, except (S)-pyrrolidin-2-ylmethanol is used as the amine in step 7. $^1$H NMR (D$_2$O, 400 MHz) δ 3.85-3.75 (m, 1H), 3.72-3.63 (m, 1H), 3.60-3.45 (m, 2H), 3.34-3.12 (m, 2H), 3.10-3.00 (m, 1H), 2.22-2.07 (m, 3H), 2.10-1.75 (m, 5H), 1.87 (s, 3H), 1.45-1.30 (m, 3H), 1.28-1.10 (m, 1H), 0.72 (t, J=7.5 Hz, 2H). ESI⁺ MS: obsd m/z 267.1 (M−36+H)⁺.

Example 11

Preparation of (R)-2-amino-6-borono-2-(2-(methyl (phenethyl)amino)ethyl) hexanoic acid dihydrochloride

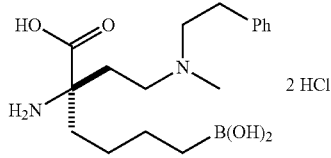

(11)

(R)-2-Amino-6-borono-2-(2-(methyl(phenethyl)amino) ethyl)hexanoic acid dihydrochloride is prepared in a manner analogous to that set forth in Example 1, except N-methyl-2-phenylethanamine is used as the amine in step 7. ¹H NMR (D₂O, 400 MHz) δ 7.45-7.38 (m, 2H), 7.37-7.31 (m, 3H), 3.51-3.36 (m, 3H), 3.25-3.13 (m, 1H), 3.09 (t, J=7.8 Hz, 2H), 2.92 (s, 3H), 2.26-2.16 (m, 2H), 1.88-1.70 (m, 2H), 1.45-1.33 (m, 2H), 1.26-1.12 (m, 2H), 0.78 (t, J=7.6 Hz, 2H). ESI⁺ MS: obsd m/z 319.1 (M−18+H)⁺, 301.1 (M−36+H)⁺.

Example 12

Preparation of (R)-2-amino-6-borono-2-(2-(((S)-2-hydroxy-2-(3-hydroxyphenyl)ethyl)(methyl)amino) ethyl)hexanoic acid dihydrochloride

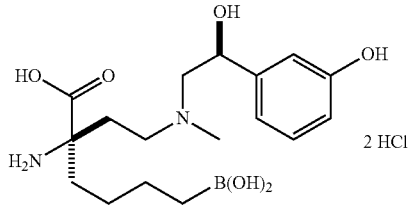

(12)

(R)-2-Amino-6-borono-2-(2-(((S)-2-hydroxy-2-(3-hydroxyphenyl)ethyl)(methyl)amino)ethyl)hexanoic acid is prepared in a manner analogous to that set forth in Example 1, except (S)-3-(1-hydroxy-2-(methylamino)ethyl)phenol is used as the amine in step 7. ¹H NMR (D₂O, 400 MHz) δ 7.33 (t, J=7.8 Hz, 1H), 7.02-6.86 (m, 3H), 5.14-5.08 (m, 1H), 3.52-3.23 (m, 3H), 2.97 (s, 3H), 2.40-2.28 (m, 1H), 2.27-2.15 (m, 1H), 1.87-1.70 (m, 2H), 1.46-1.32 (m, 3H), 1.30-1.15 (m, 2H), 0.78 (t, J=7.6 Hz, 2H). ESI⁺ MS: obsd m/z 333.1 (M−36+H)⁺, 315.1 (M−54+H)⁺.

Example 13

Preparation of (R)-2-Amino-6-borono-2-[2-piperidin-1-yl)-ethyl]-hexanoic acid dihydrochloride

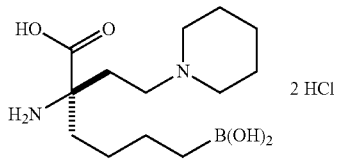

(13)

(R)-2-Amino-6-borono-2-[2-piperidin-1-yl)-ethyl]-hexanoic acid dihydrochloride is prepared in a manner analogous to that set forth in Example 1, except piperidinyl is used as the amine in step 7. The final step is as follows: a solution of (R)-2-tert-butoxycarbonylamino-2-(2-piperidin-1-yl-ethyl)-6-(4,4,5,5-tetramethyl-[1,3,2]-dioxa-borolan-2-yl)-hexanoic acid methyl ester (182 mg) in 6 N hydrochloric acid (5 mL) was stirred at 95° C. overnight. After cooling to room temperature, the reaction mixture was transferred to a separatory funnel, diluted with deionized water (5 mL) and washed with dichloromethane (3×). The aqueous layer was frozen in liquid nitrogen and lyophilized to give (R)-2-amino-6-borono-2-[2-piperidin-1-yl)-ethyl]-hexanoic acid dihydrochloride as a colorless foam (72 mg, 53%); ¹H NMR (D₂O, 300 MHz) δ 3.34 (d, J=11.5 Hz, 2H), 3.14 (m, 1H), 2.97 (m, 1H), 2.77 (t, J=12 Hz, 2H), 2.19 (t, J=8.5 Hz, 2H), 1.76 (m, 4H), 1.55 (m, 3H), 1.23 (m, 4H), 1.06 (m, 1H) and 0.59 (t, J=7.5 Hz, 2H).

Example 14

Preparation of (R)-2-amino-2-[4-borono-butyl)]-pent-4-enoic acid hydrochloride

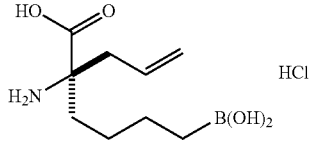

(14)

(R)-2-amino-2-[4-borono-butyl)]-pent-4-enoic acid hydrochloride is prepared in a manner analogous to that set forth in Example 1, except step 6 and 7 are not done. The final step is as follows: a solution of (R)-2-tert-butoxycarbonylamino-2-[4-(4,4,5,5-tetramethyl-[1,3,2]-dioxa-borolan-2-yl)-butyl]-pent-4-enoic acid (85 mg) in 6 N hydrochloric acid (4 mL) was stirred at 65° C. overnight. After cooling to room temperature, the reaction mixture was transferred to a separatory funnel, diluted with deionized water (5 mL) and washed with dichloromethane (3×). The aqueous layer was frozen in liquid nitrogen and lyophilized to give (R)-2-amino-2-[4-borono-butyl)]-pent-4-enoic acid hydrochloride as a colorless foam (48 mg, 89%); ¹H NMR (D₂O, 300 MHz) δ 5.60 (m, 1H), 5.16 (m, 2H), 2.60 (m, 1H), 2.45 (m, 1H), 1.78

(m, 2H), 1.26 (m, 3H), 1.09 (m, 1H) and 0.63 (t, J=7.5 Hz, 2H); ESI-LCMS m/z calcd for $C_9H_{18}BNO_4$: 215.1. found 216.1 (M+1)$^+$.

Example 15

Preparation of (S)-2-amino-6-borono-2-ethylhexanoic acid hydrochloride

Step 1: (3S,5R,6S)-tert-butyl 3-ethyl-2-oxo-5,6-diphenyl-3-(4-(4,4,5,5-tetramethyl-1,3,2-dioxaborolan-2-yl)butyl)morpholine-4-carboxylate

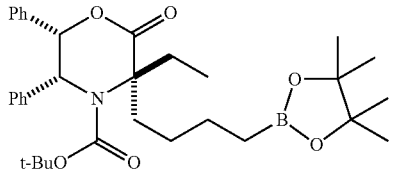

A solution of (3R,5R,6S)-tert-butyl 2-oxo-5,6-diphenyl-3-(4-(4,4,5,5-tetramethyl-1,3,2-dioxaborolan-2-yl)butyl)morpholine-4-carboxylate (1.00 g, 1.87 mmol) and TMEDA (2 mL, 13 mmol, 7 equiv) in 1,2-dimethoxyethane (9.4 mL, 0.2 M) was cooled to −78° C. and treated with ethyl iodide (3 mL, 37 mmol, 20 equiv) and potassium bis(trimethylsilyl)amide (9.4 mL, 0.9 M in THF, 9.4 mmol, 5 equiv) drop wise. After stirring for an additional 30 min at −78° C., the cooling bath was removed and the mixture was stirred over night. The reaction was incomplete by TLC and therefore was recooled to −78° C. and treated with additional potassium bis(trimethylsilyl)amide (9.4 mL, 0.9 M in THF, 9.4 mmol, 5 equiv) and ethyl iodide (3 mL, 37 mmol, 20 equiv). After the additions were complete, the bath was removed and the solution was stirred overnight. Once complete by TLC, the reaction mixture was quenched with 0.5N HCl (5-10 equiv), diluted with heptane and washed successively with water and saturated aqueous NaCl, dried over MgSO$_4$, filtered and concentrated. Purification by MPLC (1-60% ethyl acetate in heptane over 6 CV) gave (3S,5R,6S)-tert-butyl 3-ethyl-2-oxo-5,6-diphenyl-3-(4-(4,4,5,5-tetramethyl-1,3,2-dioxaborolan-2-yl)butyl) morpholine-4-carboxylate as colorless oil (0.68 g, 65%). R$_f$ 0.40 (30% ethyl acetate in heptane); $^1$H NMR (CDCl$_3$, 300 MHz) δ 7.31-7.15 (m, 10H), 7.08 (d, J=2.4 Hz, 1H), 6.02 (d, J=2.4 Hz, 1H), 2.35-2.22 (m, 2H), 2.22-2.07 (m, 2H), 1.47 (s, 9H), 1.26-1.21 (m, 4H), 1.15 (s, 12H), 1.00 (t, J=7.5 Hz, 3H), 0.85 (t, J=6.8 Hz, 2H); ESI-LCMS m/z calcd for $C_{33}H_{46}BNO_6$: 563.3. found 564.3 (M+1)$^+$.

Step 2: (S)-methyl 2-(tert-butoxycarbonylamino)-2-ethyl-6-(4,4,5,5-tetramethyl-1,3,2-dioxaborolan-2-yl)hexanoate

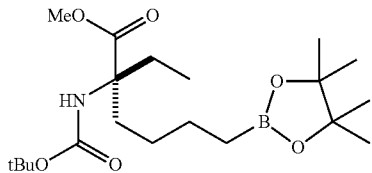

A three-necked round-bottomed flask equipped with nitrogen inlet tube and dry ice condenser was charged with (3S, 5R,6S)-tert-butyl 3-ethyl-2-oxo-5,6-diphenyl-3-(4-(4,4,5,5-tetramethyl-1,3,2-dioxaborolan-2-yl)butyl)morpholine-4-carboxylate (0.57 g, 1.01 mmol) and THF (1 mL). After cooling the condenser to −78° C. and the flask to −45° C. (CO$_2$ (s), CH$_3$CN), ammonia (50 mL) was condensed into the flask. Once complete, lithium metal (0.07 g, 10 mmol, small pieces) was carefully added over 10 min. After stirring an additional 1 h, the reaction mixture was carefully quenched with NH$_4$Cl (s) until the solution became clear. The bath was removed and the ammonia was allowed to evaporate over night. The resulting residue was diluted with ethyl acetate and washed successively with 0.5N HCl and saturated aqueous NaCl, dried over MgSO$_4$, filtered and concentrated. The crude product was dissolved in 50% methanol in toluene (50 mL, 0.1 M) and treated with TMSCHN$_2$ (2.0 M in hexanes) until the pale yellow color persisted. With TLC indicating the reaction complete, the excess TMSCHN$_2$ was quenched with acetic acid until the solution became clear. The solution was concentrated, diluted with ethyl acetate and washed successively with saturated aqueous NaHCO$_3$ and saturated aqueous NaCl, dried over MgSO$_4$, filtered and concentrated. Purification by MPLC (1-60% ethyl acetate in heptane over 4 CV) gave (S)-methyl 2-(tert-butoxycarbonylamino)-2-ethyl-6-(4, 4,5,5-tetramethyl-1,3,2-dioxaborolan-2-yl)hexanoate as colorless oil (0.283 g, 71%). R$_f$ 0.88 (30% ethyl acetate in heptane); ESI-LCMS m/z calcd for $C_{20}H_{38}BNO_6$: 399.3. found 400.3 (M+1)$^+$.

Step 3: (S)-2-amino-6-borono-2-ethylhexanoic acid hydrochloride

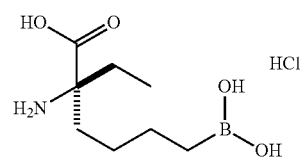

(15)

A solution of (S)-methyl 2-(tert-butoxycarbonylamino)-2-ethyl-6-(4,4,5,5-tetramethyl-1,3,2-dioxaborolan-2-yl)hexanoate (0.283 g, 0.709 mmol) in 6 N HCl (5 mL) was heated to a gentle reflux for 16 h. After cooling to room temperature, the reaction mixture was transferred to a separatory funnel, diluted with deionized water (5 mL) and washed with dichloromethane (3×10 mL). The aqueous layer was concentrated to give an off-white solid that was dissolved in deionized water (3 mL) and passed through a C-18 Isolute SPE column (20 g) eluted with 10% methanol in deionized water (200 mL). The fractions containing product were concentrated under reduced pressure, redissolved in deionized water (5 mL), frozen in liquid nitrogen and lyophilized to give (S)-2-amino-6-borono-2-ethylhexanoic acid hydrochloride as an white foam (0.096 g, 67%). $^1$H NMR (D$_2$O, 300 MHz) δ☐ (m, 4H), 1.31-1.17 (m, 3H), 1.13-0.97 (m, 1H), 0.794 (t, J=7.6

Hz, 3H), 0.63 (t, J=7.8 Hz, 2H); ESI-LCMS m/z calcd for C$_8$H$_{18}$BNO$_4$: 203.1. found 204.1 (M+1)$^+$.

Example 16

Preparation of (R/S)-2-Amino-6-borono-2-[2-pyrrolidin-1-yl)-ethyl]-hexanoic acid hydrochloride Step 1: ethyl 2-(diphenylmethyleneamino)-6-(4,4,5,5-tetramethyl-1,3,2-dioxaborolan-2-yl)hexanoate

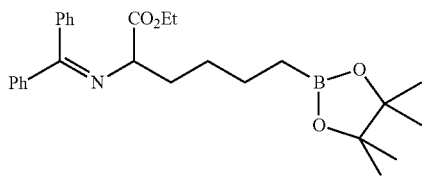 [SMILES: CCOC(=O)C(CCCCB1OC(C)(C)C(C)(C)O1)N=C(c1ccccc1)c1ccccc1]

A solution of N-(diphenylmethylene)glycine ethyl ester (8.24 g, 30.8 mmol) and 2-(4-bromobutyl)-4,4,5,5-tetramethyl-1,3,2-dioxaborolane (8.92 g, 33.9 mmol) in freshly distilled THF (77 mL, 0.4 M) was cooled to −78° C. and treated with lithium bis(trimethylsilyl)amide (32.3 mL, 1.0 M in THF). Once the addition was complete, the reaction was warmed to 50° C. and heated for 8 h. After being complete by TLC, the reaction mixture was cooled to 0° C., diluted with ethyl acetate and washed successively with saturated aqueous NaHCO$_3$ and saturated aqueous NaCl, dried over MgSO$_4$, filtered and concentrated. Rapid purification by MPLC (1-15% ethyl acetate in heptane with 0.5% triethylamine over 6 CV) gave ethyl 2-(diphenylmethyleneamino)-6-(4,4,5,5-tetramethyl-1,3,2-dioxaborolan-2-yl)hexanoate as a colorless oil (8.9 g, 64%). R$_f$ 0.40 (30% ethyl acetate in heptane).

Step 2: ethyl 2-allyl-2-(diphenylmethyleneamino)-6-(4,4,5,5-tetramethyl-1,3,2-dioxaborolan-2-yl)hexanoate

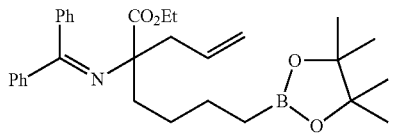 [SMILES: C=CCC(CCCCB1OC(C)(C)C(C)(C)O1)(N=C(c1ccccc1)c1ccccc1)C(=O)OCC]

A solution of ethyl 2-(diphenylmethyleneamino)-6-(4,4,5,5-tetramethyl-1,3,2-dioxaborolan-2-yl)hexanoate (2.79 g, 6.21 mmol) in freshly distilled (THF 15 mL, 0.4 M) was cooled to −78° C. and treated with lithium bis(trimethylsilyl)amide (6.8 mL, 1.0 M in THF). After stirring for 10 min allyl bromide (2.25 g, 18.6 mmol) was added the reaction was warmed to room temperature and stirred for 16 h. After being complete by TLC, the reaction mixture was cooled to 0° C., diluted with ethyl acetate and washed successively with saturated aqueous NaHCO$_3$ and saturated aqueous NaCl, dried over MgSO$_4$, filtered and concentrated. Purification by MPLC (1-20% ethyl acetate in heptane with 0.5% triethylamine over 6 CV) gave ethyl 2-allyl-2-(diphenylmethyleneamino)-6-(4,4,5,5-tetramethyl-1,3,2-dioxaborolan-2-yl)hexanoate as a colorless oil (1.81 g, 59%). R$_f$ 0.52 (30% ethyl acetate in heptane); $^1$H NMR (CDCl$_3$, 300 MHz) δ 7.58-7.53 (m, 2H), 7.39-7.22 (m, 6H), 7.16-7.12 (m, 2H), 5.89-5.74 (m, 1H), 5.07 (dd, J$_1$=15.3 Hz, J$_2$=2.1 Hz, 1H), 5.05 (dd, J$_1$=8.7 Hz, J$_2$=2.1 Hz, 1H), 3.70 (q, J=7.5 Hz, 1H$_{diasterotopic}$), 3.69 (q, J=7.2 Hz, 1H$_{diasterotopic}$), 2.70 (dd, J$_1$=7.2 Hz, J$_2$=1.2 Hz, 2H), 1.92-1.83 (m, 2H), 1.44-1.35 (m, 2H), 1.35-1.23 (m, 2H), 1.19 (s, 12H), 1.10 (t, J=7.2 Hz, 3H), 0.78 (t, J=6.6 Hz, 2H).

Step 3: ethyl 2-allyl-2-amino-6-(4,4,5,5-tetramethyl-1,3,2-dioxaborolan-2-yl)hexanoate

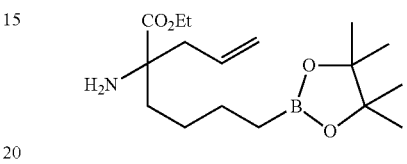

A solution of ethyl 2-allyl-2-(diphenylmethyleneamino)-6-(4,4,5,5-tetramethyl-1,3,2-dioxaborolan-2-yl)hexanoate (0.32 g, 0.65 mmol) in diethyl ether (3.4 mL, 0.2 M) was treated with 1N HCl (3 mL). After stirring 16 h, the layers were separated and the aqueous phase was diluted with saturated aqueous K$_2$CO$_3$ and extracted with chloroform to give ethyl 2-allyl-2-amino-6-(4,4,5,5-tetramethyl-1,3,2-dioxaborolan-2-yl)hexanoate as a colorless oil (0.20 g, 94%). R$_f$ 0.62 (10% methanol in dichloromethane); $^1$H NMR (CDCl$_3$, 300 MHz) δ 5.76-5.60 (m, 1H), 5.18-5.07 (m, 2H), 4.15 (q, J=7.2 Hz, 2H), 2.54 (ddt, J$_1$=13.5 Hz, J$_2$=6.3 Hz, J$_3$=1.2 Hz, 1H), 2.23 (dd, J$_1$=13.5 Hz, J$_2$=8.7 Hz, 1H), 1.8-1.68 (m, 2H), 1.70-1.60 (m, 1H), 1.60-1.46 (m, 2H), 1.46-1.32 (m, 3H), 1.24 (s, 12H), 1.20-1.06 (m, 1H), 0.766 (t, J=7.8 Hz, 2H); ESI-LCMS m/z calcd for C$_{17}$H$_{32}$BNO$_4$: 325.2. found 326.2 (M+H)$^+$.

Step 4: ethyl 2-allyl-2-amino-6-(4,4,5,5-tetramethyl-1,3,2-dioxaborolan-2-yl)hexanoate

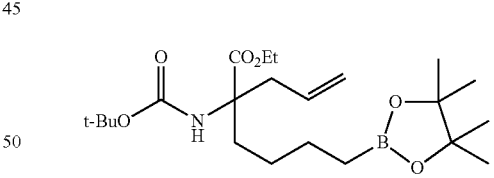

A solution of ethyl 2-allyl-2-amino-6-(4,4,5,5-tetramethyl-1,3,2-dioxaborolan-2-yl)hexanoate (0.0897 g, 0.276 mmol) in ethyl acetate (0.6 mL, 0.5 M) and saturated aqueous NaHCO$_3$ (0.6 mL) was treated with di-tert-butyl carbonate (0.090 g, 0.414 mmol) and stirred at room temperature. After 16 h, the layers were separated and the aqueous layer was extracted with ethyl acetate. The combined organic layers were washed with saturated aqueous NaCl, dried over MgSO$_4$, filtered and concentrated. Purification by MPLC (0-20% ethyl acetate in heptane over 6 CV) gave ethyl 2-allyl-2-(tert-butoxycarbonylamino)-6-(4,4,5,5-tetramethyl-1,3,2-dioxaborolan-2-yl)hexanoate as a colorless oil (0.096 g, 82%). $R_f$ 0.53 (30% ethyl acetate in heptane); ESI-LCMS m/z calcd for $C_{22}H_{40}BNO_6$: 425.3. found 426.3 (M+H)$^+$.

Step 5: 2-tert-Butoxycarbonylamino-2-(2-oxo-ethyl)-6-(4,4,5,5-tetramethyl-[1,3,2]-dioxaborolan-2-yl)-hexanoic acid ethyl ester

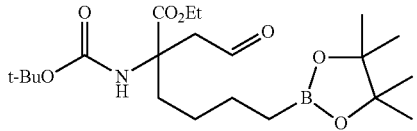 [SMILES: CCOC(=O)C(CC=O)(CCCCB1OC(C)(C)C(C)(C)O1)NC(=O)OC(C)(C)C]

A solution of Ethyl-2-allyl-2-(tert-butoxycarbonylamino)-6-(4,4,5,5-tetramethyl-1,3,2-dioxaborolan-2-yl)hexanoate (650 mg, 1.53 mmol) in dichloromethane (30 mL,) was cooled to −78° C. and treated with ozone until a pale blue-gray color appeared. After TLC indicated the absence of starting material, the ozone inlet tube was replaced with nitrogen and nitrogen was bubbled through the solution for 20 min to remove any excess ozone. Triphenylphosphine (1.20 g, 4.59 mmol, 3 equiv) was added in one portion, the cooling bath was removed and the mixture was stirred for 4 h. The solution was concentrated and purified by MPLC (0-40% ethyl acetate in heptane) gave the title compound as a colorless oil (608 mg, 93%). $R_f$ 0.25 (30% ethyl acetate in heptane); $^1$H NMR (CDCl$_3$, 300 MHz): δ 9.64 (s, CHO, 1H), 5.60 (br, s, NH, 1H), 4.19 (q, J=7.5 Hz, 2H), 3.56 (d, J=17 Hz, 1H), 2.93 (d, J=17.5 Hz, 1H), 2.20 (m, 1H), 1.62 (m, 1H), 1.38 (s, 9H), 1.28-1.43 (m, 4H), 1.23 (t, J=7 Hz, 3H), 1.21 (s, 12H) and 0.72 (t, J=7.5 Hz, 2H).

Step 6: 2-tert-Butoxycarbonylamino-2-(2-pyrrolidin-yl-ethyl)-6-(4,4,5,5-tetramethyl-[1,3,2]-dioxaborolan-2-yl)-hexanoic acid ethyl ester

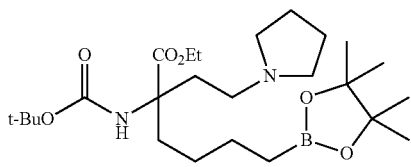 [SMILES: CCOC(=O)C(CCCCB1OC(C)(C)C(C)(C)O1)(CCN1CCCC1)NC(=O)OC(C)(C)C]

A solution of 2-tert-Butoxycarbonylamino-2-(2-oxo-ethyl)-6-(4,4,5,5-tetramethyl-[1,3,2]-dioxaborolan-2-yl)-hexanoic acid ethyl ester (100 mg, 0.23 mmol, 1.0 equiv.) and pyrrolidine (21 mg, 0.29 mmol, 1.2 equiv.) in 1,2-dichloroethane (0.5 mL) was treated with sodium triacetoxyborohydride (125 mg, 0.59 mmol) in one portion. After stirring at room temperature overnight, the reaction mixture was quenched with saturated aqueous NaHCO$_3$ (1 mL) and stirred for an additional 5 min. The resulting mixture was added to a separatory funnel, diluted with saturated aqueous NaCl (5 mL) and extracted with dichloromethane (2×10 mL). The organic layer was dried over MgSO$_4$, filtered and concentration under reduced pressure. Purification by flash column chromatography eluting with 5% methanol in chloroform to give 2-tert-butoxycarbonylamino-2-(2-pyrrolidin-yl-ethyl)-6-(4,4,5,5-tetramethyl-[1,3,2]-dioxaborolan-2-yl)-hexanoic acid ethyl ester as a pale yellow oil (92 mg, 83%). $R_f$ 0.32 (10% methanol in dichloromethane); $^1$H NMR (CDCl$_3$, 300 MHz) δ 5.67 (br, s, NH, 1H), 4.19 (m, 2H), 2.46-2.82 (m, 6H), 2.18 (m, 2H), 1.88 (m, 3H), 1.76 (m, 2H), 1.42 (s, 9H), 1.26-1.41 (m, 3H), 1.28 (t, J=7.0 Hz, 3H), 1.22 (s, 12H), 1.06 (m, 1H) and 0.73 (t, J=7.5 Hz, 2H).

Step 7: 2-Amino-6-borono-2-[2-pyrrolidin-1-yl)-ethyl]-hexanoic acid dihydrochloride

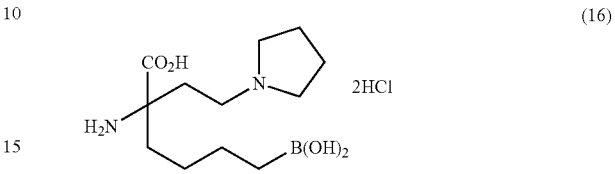

(16)

A solution of (R)-2-tert-butoxycarbonylamino-2-(2-pyrrolidin-1-yl-ethyl)-6-(4,4,5,5-tetramethyl-[1,3,2]-dioxa-borolan-2-yl)-hexanoic acid ethyl ester (98 mg) in 6 N hydrochloric acid (5 mL) was stirred at 95° C. overnight. After cooling to room temperature, the reaction mixture was transferred to a separatory funnel, diluted with deionized water (5 mL) and washed with dichloromethane (3×). The aqueous layer was frozen in liquid nitrogen and lyophilized to give 2-amino-6-borono-2-[2-pyrrolidin-1-yl)-ethyl]-hexanoic acid dihydrochloride, as a colorless foam (36 mg, 53%); $^1$H NMR (D$_2$O, 300 MHz) δ 3.47 (m, 2H), 3.24 (m, 1H), 3.07 (m, 1H), 2.88 m, 2H), 2.12 (t, J=8 Hz, 2H), 1.94 (m, 2H), 1.60-1.82 (m, 4H), 1.20 (m, 3H), 1.04 (m, 1H) and 0.59 (t, J=7 Hz, 2H); MS (+CI): m/z for $C_{12}H_{25}BN_2O_4$: expected 272.2. found 273.2 (M+H)$^+$.

Example 17

Preparation of 2-Amino-6-borono-2-[2-(4-pyrimidin-2-yl-piperazin-1-yl)ethyl]-hexanoic acid trihydrochloride

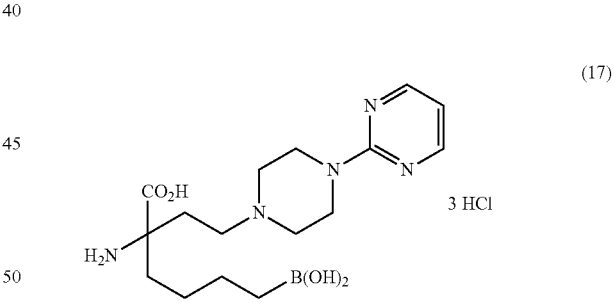

(17)

2-Amino-6-borono-2-[2-(4-pyrimidin-2-yl-piperazin-1-yl)ethyl]-hexanoic acid trihydrochloride is prepared in a manner analogous to that set forth in Example 16, except 1-2-(1-piperidinyl)pyrimidine is used as the amine in step 6. The final step is as follows: a solution of (R/S)-2-tert-butoxycarbonylamino-2-[2-(4-pyrimidin-2-yl-piperazin-1-yl)-ethyl]-6-(4,4,5,5-tetramethyl-[1,3,2]-dioxa-borolan-2-yl)-hexanoic acid ethyl ester (126 mg) in 6 N hydrochloric acid (6 mL) was stirred at 95° C. overnight. After cooling to room temperature, the reaction mixture was transferred to a separatory funnel, diluted with deionized water (5 mL) and washed with dichloromethane (3×). The aqueous layer was frozen in liquid nitrogen and lyophilized to give the title compound as a white solid (80 mg, 83%); $^1$H NMR (D$_2$O, 300 MHz) δ 8.47 (d, J=5.5 Hz, 2H), 6.96 (t, J=5.5 Hz, 1H), 3.48-3.76 (m, 4H), 3.14-3.40 (m, 6H), 2.29 (t, J=8 Hz, 2H), 1.81 (m, 2H), 1.28 (m, 3H), 1.11 (m, 1H) and 0.62 (t, J=7.5 Hz, 2H).

Example 18

Preparation of 2-amino-6-borono-2-(2-((carboxymethyl)(methyl)amino)ethyl)hexanoic acid dihydrochloride

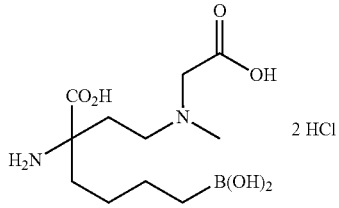

(18)

2 HCl

2-Amino-6-borono-2-(2-((carboxymethyl)(methyl)amino)ethyl)hexanoic acid dihydrochloride is prepared in a manner analogous to that set forth in Example 16, except 2-(methylamino)acetic acid is used as the amine in step 6. The final step is as follows: a solution of (R/S)-2-tert-butoxycarbonylamino-2-[2-(2-ethoxycarbonylmethyl-methyl-amino)-ethyl]-6-(4,4,5,5-tetramethyl-[1,3,2]-dioxa-borolan-2-yl)-hexanoic acid ethyl ester (138 mg) in 6 N hydrochloric acid (6 mL) was stirred at 95° C. overnight. After cooling to room temperature, the reaction mixture was transferred to a separatory funnel, diluted with deionized water (5 mL) and washed with dichloromethane (3×). The aqueous layer was frozen in liquid nitrogen and lyophilized to give the title compound as a colorless foam (72 mg, 76%); $^1$H NMR (D$_2$O, 300 MHz) δ 3.94 (s, 2H), 3.37 (m, 1H), 3.20 (m, 1H), 2.83 (s, 3H), 2.24 (t, J=8 Hz, 2H), 1.66-1.88 (m, 2H), 1.27 (m, 3H), 1.11 (m, 1H) and 0.63 (t, J=7.5 Hz, 2H).

Example 19

Preparation of (R/S)-2-Amino-2-[2-(benzyl-ethyl-amino)-ethyl]-6-borono-hexanoic acid dihydrochloride

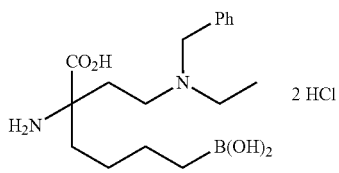

(19)

2 HCl

2-Amino-2-[2-(benzyl-ethyl-amino)-ethyl]-6-borono-hexanoic acid dihydrochloride is prepared in a manner analogous to that set forth in Example 16, except ethylbenzylamine is used as the amine in step 6. The final step is as follows: a solution of (R/S)-2-[2-(benzyl-ethyl-amino)-ethyl]-2-tert-butoxycarbonylamino-6-(4,4,5,5-tetramethyl-[1,3,2]-dioxa-borolan-2-yl)-hexanoic acid ethyl ester (104 mg) in 6 N hydrochloric acid (6 mL) was stirred at 95° C. overnight. After cooling to room temperature, the reaction mixture was transferred to a separatory funnel, diluted with deionized water (5 mL) and washed with dichloromethane (3×). The aqueous layer was frozen in liquid nitrogen and lyophilized to give the title compound as a colorless foam (41 mg); $^1$H NMR (D$_2$O, 300 MHz) δ 7.36 (s, 5H), 4.31 (m, 1H), 4.11 (m, 1H), 2.96-3.29 (m, 4H), 2.10 (m, 2H), 1.68 (m, 1H), 1.43 (t, J=8 Hz, 1H), 1.21 (t, J=6.5 Hz, 3H), 0.89-1.20 (m, 4H), and 0.59 (m, 2H); MS (+CI): m/z for C$_{17}$H$_{29}$BN$_2$O$_4$: expected 336.2. found 337.2 (M+H)$^+$, 319 (M+H–H$_2$O)$^+$.

Example 20

Preparation of 2-Amino-2-{2-[benzyl-(2-hydroxyethyl)-amino]-ethyl}-6-borono-hexanoic acid dihydrochloride

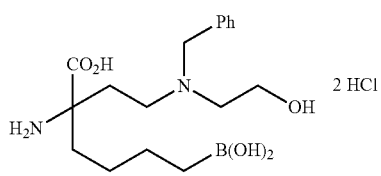

(20)

2 HCl

2-Amino-2-{2-[benzyl-(2-hydroxyethyl)-amino]-ethyl}-6-borono-hexanoic acid dihydrochloride is prepared in a manner analogous to that set forth in Example 16, except 2-(benzylamino)ethanol is used as the amine in step 6. The final step is as follows: a solution of 2-{2-[benzyl-(2-hydroxyethyl)-amino]-ethyl}-2-tert-butoxycarbonylamino-6-(4,4,5,5-tetramethyl-[1,3,2]-dioxa-borolan-2-yl)-hexanoic acid ethyl ester (111 mg) in 6 N hydrochloric acid (6 mL) was stirred at 95° C. overnight. After cooling to room temperature, the reaction mixture was transferred to a separatory funnel, diluted with deionized water (5 mL) and washed with dichloromethane (3×). The aqueous layer was frozen in liquid nitrogen and lyophilized to give the title compound as a colorless foam (48 mg); $^1$H NMR (D$_2$O, 300 MHz) δ 7.35 (s, 5H), 4.11-4.25 (m, 2H), 3.76 (s, 2H), 3.06-3.34 (m, 4H), 2.18 (m, 2H), 1.76 (m, 1H), 1.43 (m, 1H), 1.18 (m, 4H) and 0.56 (m, 2H); MS (+CI): m/z for C$_{17}$H$_{29}$BN$_2$O$_5$: expected 352.2. found 371.2 (M+H+H$_2$O)$^+$353.2 (M+H)$^+$, 335.2 (M+H—H$_2$O)$^+$.

Example 21

Preparation of (R/S)-1-[(3-Amino-7-borono-3-carboxy)-heptyl)-piperidine-4-carboxylic acid dihydrochloride

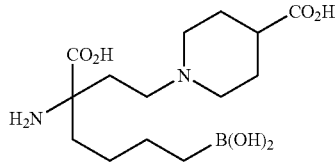

(21)

1-[(3-Amino-7-borono-3-carboxy)-heptyl)-piperidine-4-carboxylic acid dihydrochloride is prepared in a manner analogous to that set forth in Example 16, except ethyl piperidine-4-carboxylate is used as the amine in step 6. The final step is as follows: a solution of 2-tert-butoxycarbonylamino- 2-[2-(4-methylcarbamoyl-piperidin-1-yl)-ethyl]-6-(4,4,5,5-tetramethyl-[1,3,2]-dioxa-borolan-2-yl)-hexanoic acid ethyl ester (106 mg) in 6 N hydrochloric acid (6 mL) was stirred at 95° C. overnight. After cooling to room temperature, the reaction mixture was transferred to a separatory funnel, diluted with deionized water (5 mL) and washed with dichloromethane (3×). The aqueous layer was frozen in liquid nitrogen and lyophilized to give the title compound as a colorless foam (34 mg); $^1$H NMR (D$_2$O, 300 MHz) δ 3.50 (m, 1H), 3.22 (m, 1H), 2.84-3.08 (m, 3H), 2.58 (tt, J$_1$=12 Hz, J$_2$=3.5 Hz, 1H), 2.14 (m, 4H), 1.75 (m, 5H), 1.26 (m, 3H), 1.10 (m, 1H) and 0.64 (t, J=7.5 Hz, 2H).

Example 22

Preparation of 2-Amino-6-borono-2-[2-(4-hyrdoxymethylpiperidin-1-yl)-ethyl]-hexanoic acid dihydrochloride

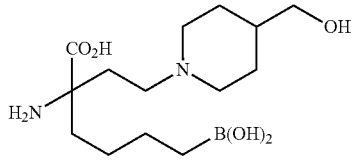

(22)

(2-Amino-6-borono-2-[2-(4-hyrdoxymethylpiperidin-1-yl)-ethyl]-hexanoic acid dihydrochloride is prepared in a manner analogous to that set forth in Example 16, except piperidin-4-ylmethanol is used as the amine in step 6. The final step is as follows: a solution of (R)-2-tert-butoxycarbonylamino-2-[2-(4-hydroxymethyl-piperidin-1-yl)-ethyl]-6-(4,4,5,5-tetramethyl-[1,3,2]-dioxa-borolan-2-yl)-hexanoic acid ethyl ester (78 mg) in 6 N hydrochloric acid (5 mL) was stirred at 95° C. overnight. After cooling to room temperature, the reaction mixture was transferred to a separatory funnel, diluted with deionized water (5 mL) and washed with dichloromethane (3×). The aqueous layer was frozen in liquid nitrogen and lyophilized to give the title compound as a colorless foam (20 mg, 53%); $^1$H NMR (D$_2$O, 300 MHz) δ 3.48 (m, 2H), 3.33 (d, J=6 Hz, 2H), 3.21 (m, 1H), 3.04 (m, 1H), 2.86 (m, 2H), 2.19 (2H, t, J=8.5 Hz), 1.86 (m, 2H), 1.60-1.78 (m, 3H), 1.20-1.36 (m, 5H), 1.09 (m, 1H) and 0.64 (t, J=7.5 Hz, 2H,); MS (+CI): m/z for C$_{12}$H$_{25}$BN$_2$O$_4$: expected 272.2. found 273.2 (M+H)$^+$.

Example 23

Preparation of 2-Amino-6-borono-2-[2-(3-diethyl-carbamoyl-piperidin-1-yl)-ethyl]-hexanoic acid dihydrochloride

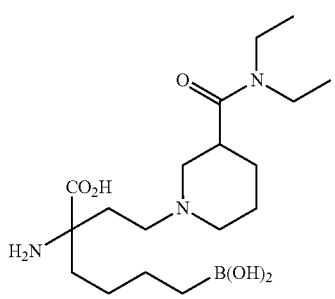

(23)

2-Amino-6-borono-2-[2-(3-diethylcarbamoyl-piperidin-1-yl)-ethyl]-hexanoic acid dihydrochloride is prepared in a manner analogous to that set forth in Example 16, except N,N-diethylpiperidine-3-carboxamide is used as the amine in step 6. The final step is as follows: a solution of (2R/S, 3"R/S)-2-tert-butoxycarbonylamino-2-[2-(3-diethylcarbamoyl-piperidin-1-yl)-ethyl]-6-(4,4,5,5-tetramethyl-[1,3,2]-dioxa-borolan-2-yl)-hexanoic acid ethyl ester (128 mg) in 6 N hydrochloric acid (5 mL) was stirred at 95° C. overnight. After cooling to room temperature, the reaction mixture was transferred to a separatory funnel, diluted with deionized water (5 mL) and washed with dichloromethane (3×). The aqueous layer was frozen in liquid nitrogen and lyophilized to give a diastereomeric mixture of the title compounds as a colorless foam (54 mg); $^1$H NMR (D$_2$O, 300 MHz) δ 3.46 (m, 2H), 3.26 (m, 4H), 3.10 (m, 2H), 2.94 (m, 4H), 2.20 (m, 2H), 1.62-1.92 (6H, m), 1.28 (m, 2H), 1.10 (t, J=7.0 Hz, 3H), 1.06 (m, 1H), 0.93 (t, J=7.0 Hz, 3H) and 0.64 (t, J=7.5 Hz, 2H); MS (+CI): m/z for C$_{18}$H$_{36}$BN$_3$O$_5$: expected 385.3. found 386.2 (M+H)$^+$, 368.2 (M+H–H$_2$O)$^+$.

Example 24

Preparation of 2-Amino-6-borono-2-(2-morpholin-4-yl)-ethyl)-hexanoic acid dihydrochloride

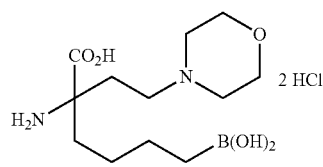

(24)

2-Amino-6-borono-2-(2-morpholin-4-yl)-ethyl)-hexanoic acid dihydrochloride is prepared in a manner analogous to that set forth in Example 16, except morpholine is used as the amine in step 6. The final step is as follows: a solution of (R)-2-tert-butoxycarbonylamino-2-(2-morpholin-4-yl-ethyl)-6-(4,4,5,5-tetramethyl-[1,3,2]-dioxa-borolan-2-yl)-hexanoic acid ethyl ester (102 mg) in 6 N hydrochloric acid (5 mL) was stirred at 95° C. overnight. After cooling to room temperature, the reaction mixture was transferred to a separatory funnel, diluted with deionized water (5 mL) and washed with dichloromethane (3×). The aqueous layer was frozen in liquid nitrogen and lyophilized to give the title compound as a colorless foam (61 mg); $^1$H NMR (D$_2$O, 300 MHz) δ 3.96 (d, J=12.5 Hz, 2H), 3.66 (t, J=12.5 Hz, 2H), 3.40 (m, 2H), 3.10 (m, 4H), 2.20 (m, 2H), 1.64-1.82 (m, 2H), 1.26 (m, 3H), 1.08 (m, 1H) and 0.62 (t, J=7.0 Hz, 2H); MS (+CI): m/z for C$_{12}$H$_{25}$BN$_2$O$_5$: expected 288.2. found 289.2 (M+H)$^+$.

Example 25

Preparation of 2-Amino-2-[2-(4-benzylpiperidin-1-yl)ethyl]-6-borono-hexanoic acid dihydrochloride

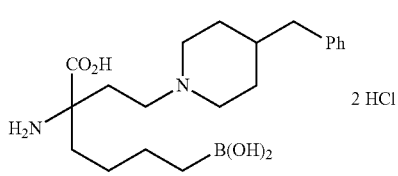

(25)

2-Amino-2-[2-(4-benzylpiperidin-1-yl)ethyl]-6-borono-hexanoic acid dihydrochloride is prepared in a manner analogous to that set forth in Example 16, except 4-benzylpiperidine is used as the amine in step 6. The final step is as follows: a solution of 2-[2-(4-benzylpiperidin-1-yl)ethyl]-2-tert-butoxycarbonylamino-6-(4,4,5,5-tetramethyl-[1,3,2]-dioxaborolan-2-yl)-hexanoic acid ethyl ester (95 mg) in 6 N hydrochloric acid (5 mL) was stirred at 95° C. overnight. After cooling to room temperature, the reaction mixture was transferred to a separatory funnel, diluted with deionized water (5 mL) and washed with dichloromethane (3×). The aqueous layer was frozen in liquid nitrogen and lyophilized to give the title compound as a colorless foam (42 mg); $^1$H NMR (D$_2$O, 300 MHz) δ 7.24 (m, 2H), 7.13 (m, 3H), 3.42 (m, 2H), 3.18 (m, 1H), 3.00 (m, 1H), 2.78 (m, 2H), 2.44 (d, J=7.0 Hz, 2H), 2.16 (t, J=7.0 Hz, 2H), 1.76 (m, 5H), 1.24 (m, 5H), 1.09 (m, 1H) and 0.61 (t, J=7.0 Hz, 2H); MS (+CI): m/z for C$_{20}$H$_{33}$BN$_2$O$_4$: expected 376.3. found 377.2 (M+H)$^+$, 359.2 (M+H–H$_2$O)$^+$.

Example 26

Preparation of 2-Amino-6-borono-2-[2-(6,7-dimethoxy-3,4-dihydro-1H-isoquinolin-2-yl)ethyl]-hexanoic acid dihydrochloride

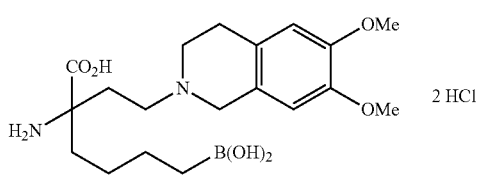

(26)

2-Amino-6-borono-2-[2-(6,7-dimethoxy-3,4-dihydro-1H-isoquinolin-2-yl)ethyl]-hexanoic acid dihydrochloride is prepared in a manner analogous to that set forth in Example 16, except 6,7-dimethoxy-1,2,3,4-tetrahydroisoquinoline is used as the amine in step 6. The final step is as follows: a solution of 2-tert-butoxycarbonylamino-2-[2-(6,7-dimethoxy-3,4-dihydro-1H-isoquinolin-2-yl)ethyl]-6-(4,4,5,5-tetramethyl-[1,3,2]-dioxa-borolan-2-yl)-hexanoic acid ethyl ester (108 mg) in 6 N hydrochloric acid (5 mL) was stirred at 95° C. overnight. After cooling to room temperature, the reaction mixture was transferred to a separatory funnel, diluted with deionized water (5 mL) and washed with dichloromethane (3×). The aqueous layer was frozen in liquid nitrogen and lyophilized to give the title compound as a colorless foam (66 mg); $^1$H NMR (D$_2$O, 300 MHz) δ 6.75 (s, 1H), 6.66 (s, 1H), 4.39 (d, J=15 Hz, 1H), 4.14 (d, J=15 Hz, 1H), 3.67 (s, 3H), 3.66 (s, 3H), 3.18-3.46 (m, 4H), 2.97 (m, 2H), 2.31 (t, J=8 Hz, 2H), 1.82 (m, 2H), 1.27 (m, 3H), 1.12 (m, 1H) and 0.64 (m, 2H); MS (+CI): m/z for C$_{19}$H$_{31}$BN$_2$O$_6$: expected 394.2. found 395.5 (M+H)$^+$, 377.4 (M+H–H$_2$O)$^+$, 359.4 (M+H–2H$_2$O)$^+$.

Example 27

Preparation of 2-amino-6-borono-2-(2-((4-methoxybenzyl)(methyl)amino)ethyl)hexanoic acid dihydrochloride

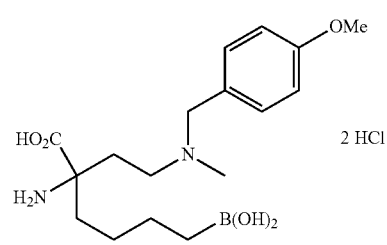

(27)

2-Amino-6-borono-2-(2-((4-methoxybenzyl)(methyl)amino)ethyl)hexanoic acid dihydrochloride is prepared in a manner analogous to that set forth in Example 16, except 1-(4-methoxyphenyl)-N-methylmethanamine is used as the amine in step 6. $^1$H NMR (d$_4$-MeOH, 300 MHz) δ 7.47 (d, J=8.7 Hz, 2H), 7.03 (d, J=9.0 Hz, 2H), 4.40 (d, J=11.2 Hz, 1H), 4.27 (d, J=11.2 Hz, 1H), 3.83 (s, 3H), 2.82 (s, 3H), 2.43-2.38 (m, 2H), 1.95-1.81 (m, 2H), 1.44-1.23 (m, 6H), 0.82 (t, J=7.5 Hz, 2H). ESI MS found for C$_{17}$H$_{29}$B$_2$NO$_5$ m/z [353.6 (M+H)].

Example 28

Preparation of 2-amino-6-borono-2-(2-(4-phenyl-5,6-dihydropyridin-1(2H)-yl)ethyl)hexanoic acid dihydrochloride

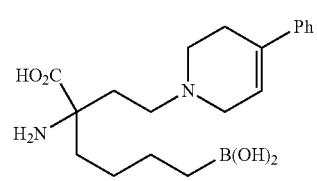

(28)

2-Amino-6-borono-2-(2-(4-phenyl-5,6-dihydropyridin-1(2H)-yl)ethyl)hexanoic acid dihydrochloride is prepared in a manner analogous to that set forth in Example 16, except 4-phenyl-1,2,3,6-tetrahydropyridine is used as the amine in step 6. $^1$H NMR (d$_4$-MeOH, 300 MHz) δ 7.67-7.64 (m, 1H), 7.50-7.45 (m, 2H), 7.40-7.31 (m, 2H), 6.14 (s, 1H), 2.97-2.71 (m, 2H), 2.49 (t, J=7.8 Hz, 2H), 2.08-1.92 (m, 4H), 1.59-1.19 (m, 8H), 0.84 (t, J=7.8 Hz, 2H). ESI MS found for C$_{19}$H$_{29}$B$_1$N$_2$O$_4$ m/z [325.5 (M+1)-2H$_2$O].

Example 29

Preparation of 2-amino-6-borono-2-(2-(6,7-dihydrothieno[3,2-c]pyridin-5(4H)-yl)ethyl)hexanoic acid dihydrochloride

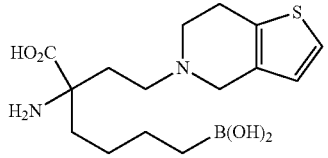

(29)

2-Amino-6-borono-2-(2-(6,7-dihydrothieno[3,2-c]pyridin-5(4H)-yl)ethyl)hexanoic acid dihydrochloride is prepared in a manner analogous to that set forth in Example 16, except 4,5,6,7-tetrahydrothieno[3,2-c]pyridine is used as the amine in step 6. $^1$H NMR (d$_4$-MeOH, 300 MHz) δ 7.42 (d, J=5.1 Hz, 1H), 6.91 (d, J=5.1 Hz, 1H), 3.60-3.53 (m, 2H), 2.50 (t, J=8.1 Hz, 2H), 2.08-1.88 (m, 2H), 1.59-1.21 (m, 10H), 0.84 (t, J=7.5 Hz, 2H). ESI MS found for C$_{15}$H$_{25}$B$_1$N$_2$O$_4$S$_1$ m/z [305.1 (M+1)-2H$_2$O].

Example 30

Preparation of 2-amino-6-borono-2-(2-(3-oxo-2,3,6,7-tetrahydro-1H-pyrazolo[4,3-c]pyridin-5(4H)-yl)ethyl)hexanoic acid dihydrochloride

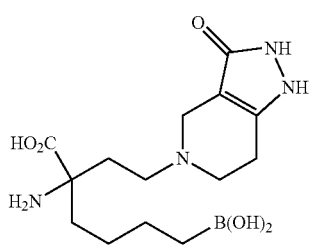

(30)

2-Amino-6-borono-2-(2-(3-oxo-2,3,6,7-tetrahydro-1H-pyrazolo[4,3-c]pyridin-5(4H)-yl)ethyl)hexanoic acid dihydrochloride is prepared in a manner analogous to that set forth in Example 16, except 4,5,6,7-tetrahydro-1H-pyrazolo[4,3-c]pyridin-3(2H)-one is used as the amine in step 6. $^1$H NMR (d$_4$-MeOH, 300 MHz) δ 7.23-7.08 (m, 2H), 3.19 (s, 2H), 2.54 (t, J=8.4 Hz, 2H), 2.08-1.89 (m, 4H), 1.50-1.28 (m, 8H), 0.84 (t, J=6.9 Hz, 2H). ESI MS found for C$_{14}$H$_{25}$B$_1$N$_2$O$_5$ m/z [341.3 (M+1)].

Example 31

Preparation of 2-amino-6-borono-2-(2-(4-(4-methoxyphenyl)-5,6-dihydropyridin-1(2H)-yl)ethyl)hexanoic acid dihydrochloride

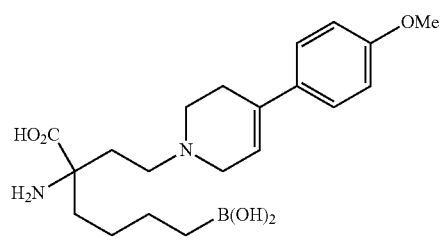

(31)

2-Amino-6-borono-2-(2-(4-(4-methoxyphenyl)-5,6-dihydropyridin-1(2H)-yl)ethyl)hexanoic acid dihydrochloride is prepared in a manner analogous to that set forth in Example 16, except 4-(4-methoxyphenyl)-1,2,3,6-tetrahydropyridine is used as the amine in step 6. $^1$H NMR (d$_4$-MeOH, 300 MHz) δ 7.42 (d, J=8.7 Hz, 2H), 6.92 (d, J=8.7 Hz, 2H), 6.40 (s, 1H), 3.80 (s, 3H), 2.88 (s, 2H), 2.50-2.43 (m, 2H), 2.05-1.88 (m, 4H), 1.59-1.23 (m, 8H), 0.84 (t, J=7.2 Hz, 2H). (ESI MS found for C$_{20}$H$_{31}$B$_1$N$_2$O$_5$ m/z [373.5 (M+1)–H$_2$O].

Example 32

Preparation of 2-amino-6-borono-2-(2-(piperazin-1-yl)ethyl)hexanoic acid trihydrochloride

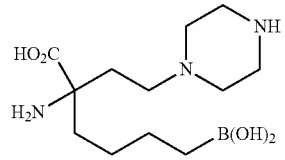

(32)

2-Amino-6-borono-2-(2-(piperazin-1-yl)ethyl)hexanoic acid trihydrochloride is prepared in a manner analogous to that set forth in Example 16, except tert-butyl piperazine-1-carboxylate is used as the amine in step 6. The final compound was isolated as the trihydrochloride salt. $^1$H NMR (D$_2$O, 300 MHz) δ 3.55-3.30 (m, 9H), 3.26-3.14 (m, 1H), 2.30-2.11 (m, 2H), 1.88-1.62 (m, 2H), 1.31-1.14 (m, 3H), 1.14-0.99 (m, 1H), 0.60 (t, J=7.2 Hz, 2H). ESI MS found for $C_{12}H_{26}BN_3O_4$ m/z [288.2 (M+1)].

Example 33

Preparation of 2-amino-6-borono-2-(2-((S)-2-(methoxymethyl)pyrrolidin-1-yl)ethyl)hexanoic acid dihydrochloride

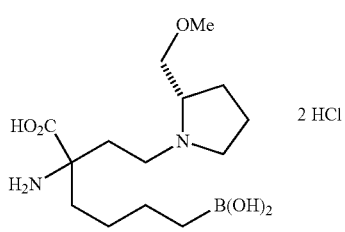

(33)

2-Amino-6-borono-2-(2-((S)-2-(methoxymethyl)pyrrolidin-1-yl)ethyl)hexanoic acid dihydrochloride is prepared in a manner analogous to that set forth in Example 16, except (S)-2-(methoxymethyl)pyrrolidine is used as the amine in step 6. $^1$H NMR (D$_2$O, 300 MHz) δ 3.63-3.38 (m, 5H), 3.21 (s, 3H), 3.07-2.95 (m, 2H), 2.24-1.60 (m, 8H), 1.32-1.17 (m, 3H), 1.15-0.98 (m, 1H), 0.60 (t, J=7.2 Hz, 2H). ESI MS found for $C_{14}H_{29}BN_2O_5$ m/z [317.2 (M+1)].

Example 34

Preparation of 2-amino-2-(2-(4-benzyl-4-hydroxypiperidin-1-yl)ethyl)-6-boronohexanoic acid dihydrochloride

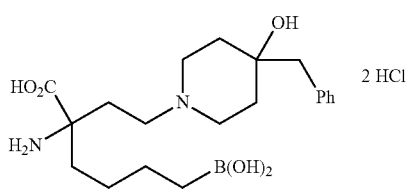

(34)

2-Amino-2-(2-(4-benzyl-4-hydroxypiperidin-1-yl)ethyl)-6-boronohexanoic acid dihydrochloride is prepared in a manner analogous to that set forth in Example 16, except 4-benzylpiperidin-4-ol is used as the amine in step 6. The final compound was isolated as the dihydrochloride salt. $^1$H NMR (D$_2$O, 300 MHz) δ 7.20-7.01 (m, 5H), 3.32-3.10 (m, 3H), 3.06-2.90 (m, 3H), 2.61 (s, 2H), 2.16 (t, J=8.4 Hz, 2H), 1.81-1.64 (m, 4H), 1.57 (d, J=14.7 Hz, 2H), 1.27-1.12 (m, 3H), 1.09-0.95 (m, 1H), 0.55 (t, J=7.2 Hz, 2H). ESI MS found for $C_{20}H_{33}BN_2O_5$ m/z [393.2 (M+1)].

Example 35

Preparation of 2-amino-6-borono-2-(2-(4-methylpiperazin-1-yl)ethyl)hexanoic acid trihydrochloride

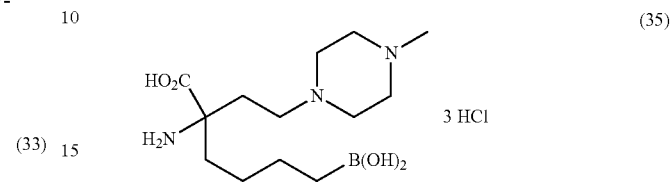

(35)

2-Amino-6-borono-2-(2-(4-methylpiperazin-1-yl)ethyl)hexanoic acid trihydrochloride is prepared in a manner analogous to that set forth in Example 16, except 1-methylpiperazine is used as the amine in step 6. The final compound was isolated as the trihydrochloride salt. $^1$H NMR (D$_2$O, 300 MHz) δ 3.90-3.12 (m, 9H), 2.84 (s, 3H), 2.30-2.11 (m, 2H), 1.87-1.63 (m, 3H), 1.33-1.14 (m, 3H), 1.14-0.97 (m, 1H), 0.60 (t, J=7.5 Hz, 2H). ESI MS found for $C_{13}H_{28}BN_3O_4$ m/z [302.2 (M+1)].

Example 36

Preparation of 2-amino-6-borono-2-(2-(3,4-dihydroisoquinolin-2(1H)-yl)ethyl)hexanoic acid dihydrochloride

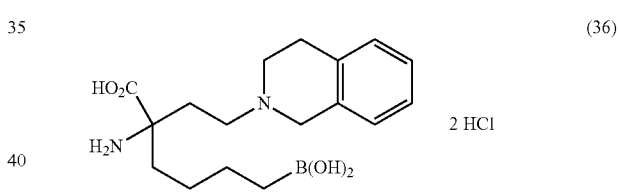

(36)

2-Amino-6-borono-2-(2-(3,4-dihydroisoquinolin-2(1H)-yl)ethyl)hexanoic acid dihydrochloride is prepared in a manner analogous to that set forth in Example 16, except 1,2,3,4-tetrahydroisoquinoline is used as the amine in step 6. $^1$H NMR (D$_2$O, 300 MHz) δ 7.22-7.10 (m, 3H), 4.45 (d$_{AB}$, J=15.0 Hz, 1H), 4.21 (d$_{AB}$, J=15.0 Hz, 1H), 3.72-3.62 (m, 1H), 3.48-3.00 (m, 4H), 2.38-2.28 (m, 2H), 1.92-1.69 (m, 3H), 1.35-1.20 (m, 3H), 1.18-1.03 (m, 1H), 0.62 (t, J=6.9 Hz, 2H). ESI MS found for $C_{17}H_{27}BN_2O_4$ m/z [335.2 (M+1)].

Example 37

Preparation of 2-amino-6-borono-2-(2-(diethylamino)ethyl)hexanoic acid dihydrochloride

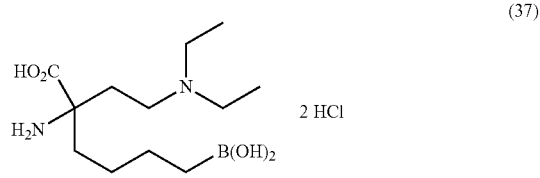 [SMILES: CCN(CC)CCC(N)(CCCCB(O)O)C(=O)O]

(37)

2-Amino-6-borono-2-(2-(diethylamino)ethyl)hexanoic acid dihydrochloride is prepared in a manner analogous to that set forth in Example 16, except diethylamine is used as the amine in step 6. $^1$H NMR (D$_2$O, 300 MHz) δ 3.28-3.14 (m, 1H), 3.06 (q, J=7.2 Hz, 4H), 3.08-2.95 (m, 1H), 2.21-2.11 (m, 2H), 1.89-1.68 (m, 2H), 1.31-1.17 (m, 3H), 1.09 (t, J=7.2 Hz, 6H), 1.08-0.98 (m, 1H), 0.60 (t, J=7.5 Hz, 2H). ESI MS found for C$_{12}$H$_{27}$BN$_2$O$_4$ m/z [275.2 (M+1)].

Example 38

Preparation of 2-amino-6-borono-2-(2-(4-oxopiperidin-1-yl)ethyl)hexanoic acid dihydrochloride

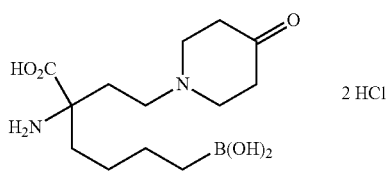

(38)

2 HCl

2-Amino-6-borono-2-(2-(4-oxopiperidin-1-yl)hexanoic acid dihydrochloride monohydrate is prepared in a manner analogous to that set forth in Example 16, except piperidin-4-one is used as the amine in step 6. $^1$H NMR (D$_2$O, 500 MHz) δ 3.54-3.47 (m, 2H), 3.32 (dt, J=5.0, 6.0 Hz, 1H), 3.15-3.07 (m, 3H), 2.28-2.18 (m, 2H), 2.01-1.84 (m, 5H), 1.78-1.72 (m, 1H), 1.37-1.27 (m, 3H), 1.20-1.10 (m, 1H), 0.70 (t, J=8.0 Hz, 2H). ESI MS found for C$_{13}$H$_{25}$BN$_2$O$_5$ m/z [283.6 (M+1–18) 7%, 265.5 (M+1–2×18) 100%].

Example 39

Preparation of 2-amino-6-borono-2-(2-(4-(trifluoromethyl)piperidin-1-yl)ethyl)hexanoic acid dihydrochloride

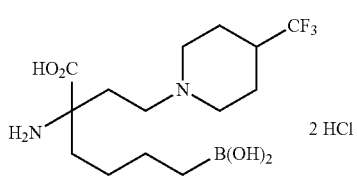

(39)

2 HCl

2-Amino-6-borono-2-(2-(4-(trifluoromethyl)piperidin-1-yl)ethyl)hexanoic acid dihydrochloride monohydrate is prepared in a manner analogous to that set forth in Example 16, except 4-(trifluoromethyl)piperidine is used as the amine in step 6. $^1$H NMR (D$_2$O, 500 MHz) δ 3.63 (t, J=12.0 Hz, 2H) 3.31 (ddd, J$_1$=12.0 Hz, J$_2$=10.0 Hz, J$_3$=6.0 Hz, 1H), 3.11 (ddd, J$_1$=12.0 Hz, J$_2$=11.0 Hz, J$_3$=6.0 Hz, 1H), 3.03-2.94 (m, 2H), 2.59-2.49 (m, 1H), 2.28-2.21 (m, 2H), 2.16-2.13 (m, 2H), 1.89-1.84 (m, 1H), 1.78-1.69 (m, 3H), 1.37-1.27 (m, 3H), 1.19-1.10 (m, 1H), 0.70 (t, J=8.0 Hz, 2H). $^{19}$F NMR −73.45 (s, 3F). ESI MS found for C$_{14}$H$_{26}$BF$_3$N$_2$O$_4$ m/z [337.6 (M+1–18) 13%, 319.5 (M+1–2×18) 100%].

Example 40

Preparation of 2-amino-6-borono-2-(2-((S)-2-(pyrrolidin-1-ylmethyl)pyrrolidin-1-yl)ethyl)hexanoic acid trihydrochloride

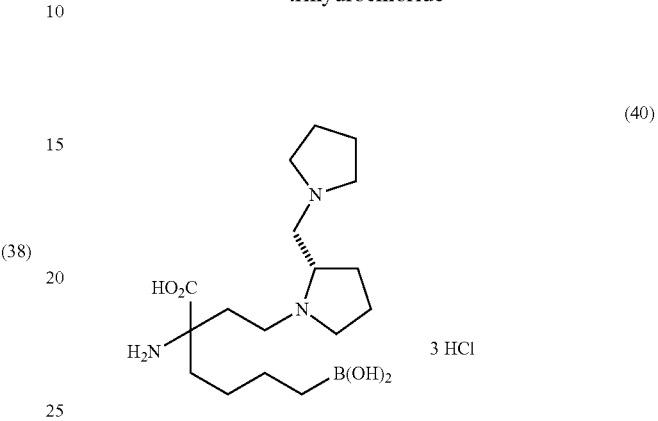

(40)

3 HCl

2-Amino-6-borono-2-(2-((S)-2-(pyrrolidin-1-ylmethyl)pyrrolidin-1-yl)ethyl)hexanoic acid trihydrochloride is prepared in a manner analogous to that set forth in Example 16, except (S)-1,2'-methylenedipyrrolidine is used as the amine in step 6. The final compound was isolated as the trihydrochloride salt and monohydrate. $^1$H NMR (D$_2$O, 500 MHz) δ 3.89-3.81 (m, 1H), 3.72-3.65 (m, 4H), 3.53 (dd, J$_1$=12.0 Hz, J$_2$=4.0 Hz, 1H), 3.43 (dd, J$_1$=12.0 Hz, J$_2$=6.0 Hz, 1H), 2.28-2.17 (m, 2H), 2.16-2.01 (m, 4H), 1.94-1.83 (m, 4H), 1.76-1.71 (m, 1H), 1.37-1.32 (m, 3H), 1.18-1.09 (m, 1H), 0.69 (t, J=8.0 Hz, 2H). ESI MS found for C$_{17}$H$_{34}$BN$_3$O$_4$ m/z [338.7 (M+1–18) 29%, 320.6 (M+1–2×18) 100%, 336.7 (M−1–18) 100%].

Example 41

Preparation of 2-amino-6-borono-2-(2-(4-methoxypiperidin-1-yl)ethyl)hexanoic acid dihydrochloride

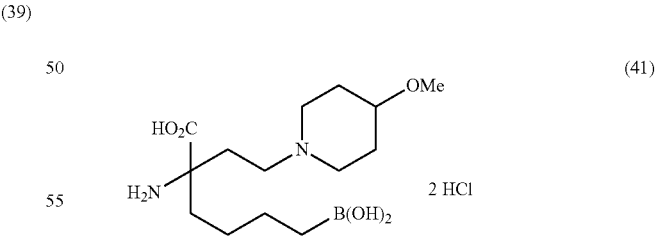

(41)

2 HCl

2-Amino-6-borono-2-(2-(4-methoxypiperidin-1-yl)ethyl)hexanoic acid dihydrochloride monohydrate is prepared in a manner analogous to that set forth in Example 16, except 4-methoxypiperidine is used as the amine in step 6. $^1$H NMR (D$_2$O, 500 MHz) δ 3.60-3.49 (m, 2H), [3.29 (s, 1$^{st}$ conformer), 3.26 (s, 2$^{nd}$ conformer), 3H], 3.33-3.24 (m, 2H), 3.12-3.04 (m, 2H), 3.02-2.93 (m, 1H), 1.88-1.75 (m, 3H), 1.57-1.48 (m, 1H), 1.38-1.27 (m, 3H), 1.19-1.09 (m, 1H), 0.68 (t, J=8.0 Hz, 2H). ESI MS found for $C_{14}H_{29}BN_2O_5$ m/z [299.6 (M+1−18) 15%, 281.5 (M+1−2×18) 100%, 297.6 (M−1−18) 75%].

Example 42

Preparation of 2-amino-2-(2-(2-(benzofuran-2-yl)pyrrolidin-1-yl)ethyl)-6-boronohexanoic acid dihydrochloride

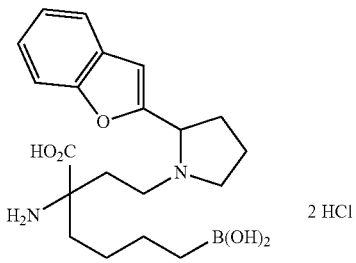

(42)

2-Amino-2-(2-(2-(benzofuran-2-yl)pyrrolidin-1-yl)ethyl)-6-boronohexanoic acid dihydrochloride monohydrate is prepared in a manner analogous to that set forth in Example 16, except 2-(benzofuran-2-yl)pyrrolidine is used as the amine in step 6. $^1$H NMR ($D_2O$, 500 MHz) δ 7.62 (dd, $J_1$=8.0 Hz, $J_2$=8.0 Hz, 1H), 7.51 (dd, $J_1$=8.0 Hz, $J_2$=4.0 Hz, 1H), 7.31-7.37 (m, 1H), 7.22-7.27 (m, 1H), [7.12 (s, $1^{st}$ diastereoisomer), 7.09 (s, $2^{nd}$ diastereoisomer), 1H], 4.78-4.61 (m, 3H), 3.82-3.75 (m, 1H), 3.59-3.52 (m, 1H), 3.40-3.31 (m, 1H), 3.25-3.12 (m, 1H), 2.52-2.40 (m, 2H), 2.30-2.12 (m, 3H), [1.97-1.93 (m, $1^{st}$ diastereoisomer), 2.05-2.00 (m, $2^{nd}$ diastereoisomer), 1H], 1.28-1.00 (m, 4H), [0.55-0.43 (m, $1^{st}$ diastereoisomer), 0.81-0.62 (m, $2^{nd}$ diastereoisomer), 2H]. ESI MS found for $C_{20}H_{29}BN_2O_5$ m/z [371.6 (M+1−18) 16%, 353.6 (M+1−2×18) 100%].

Example 43

Preparation of 2-amino-6-borono-2-(2-((2-hydroxyethyl)(methyl)amino)ethyl)hexanoic acid dihydrochloride

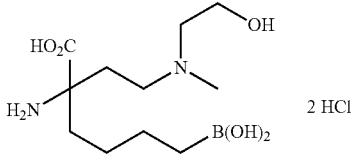

(43)

2-Amino-6-borono-2-(2-((2-hydroxyethyl)(methyl)amino)ethyl)hexanoic acid dihydrochloride monohydrate is prepared in a manner analogous to that set forth in Example 16, except 2-(methylamino)ethanol is used as the amine in step 6. $^1$H NMR ($D_2O$, 500 MHz) δ 3.81 (brt, J=5.0 Hz, 2H), 3.55-3.42 (m, 1H), 3.36-3.13 (m, 3H), [2.84 (s, $1^{st}$ rotamer), 2.83 (s, $2^{nd}$ rotamer), 3H], 2.27 (brt, J=7.0 Hz, 2H), 1.92-1.87 (m, 1H), 1.81-1.75 (m, 1H), 1.37-1.29 (m, 3H), 1.18-1.13 (m, 1H), 0.70 (t, J=7.0 Hz, 2H). ESI MS found for $C_{11}H_{25}BN_2O_5$ m/z [277.6 (M+1) 5%, 259.6 (M+1−18) 25%, 241.5 (M+1−2×18) 100%, 257.6 (M−1−18) 100%].

Example 44

Preparation of 2-amino-6-borono-2-(2-(3,3-difluoropyrrolidin-1-yl)ethyl)hexanoic acid dihydrochloride

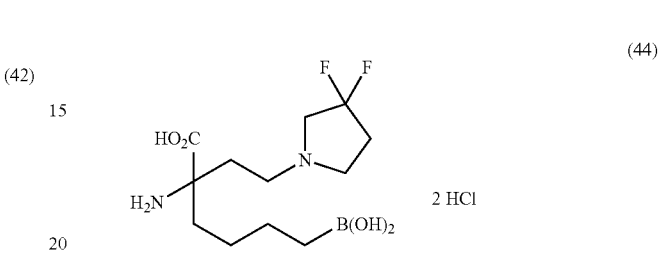

(44)

2-Amino-6-borono-2-(2-(3,3-difluoropyrrolidin-1-yl)ethyl)hexanoic acid dihydrochloride monohydrate is prepared in a manner analogous to that set forth in Example 16, except 3,3-difluoropyrrolidine is used as the amine in step 6. $^1$H NMR ($D_2O$, 500 MHz) δ 3.95-3.85 (m, 2H), 3.79-3.69 (m, 2H), 3.54 (ddd, $J_1$=12.0 Hz, $J_2$=10.0 Hz, $J_3$=6.0 Hz, 1H), 3.35 (ddd, $J_1$=12.0, $J_2$=10.0, $J_3$=5.0 Hz, 1H), 2.68-2.63 (m, 2H), 2.29-2.22 (m, 2H), 1.79 (ddd, $J_1$=15.0, $J_2$=12.0, $J_3$=5.0 Hz, 1H), 1.40-1.32 (m, 3H), 1.22-1.15 (m, 1H), 0.73 (t, J=7.0 Hz, 2H). ESI MS found for $C_{12}H_{23}BF_2N_2O_4$ m/z [291.5 (M+1−18) 17%, 273.5 (M+1−2×18) 100%, 307.6 (M−1) 29%, 289.5 (M−1−18) 100%].

Example 45

Preparation of 2-(2-(4-acetyl-4-phenylpiperidin-1-yl)ethyl)-2-amino-6-boronohexanoic acid dihydrochloride

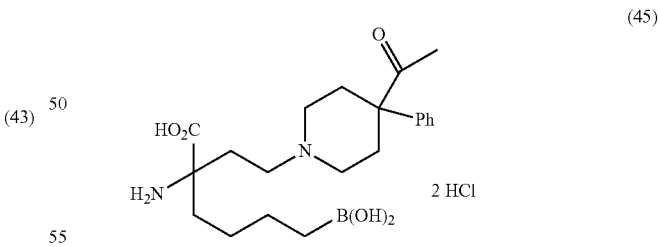

(45)

2-(2-(4-Acetyl-4-phenylpiperidin-1-yl)ethyl)-2-amino-6-boronohexanoic acid dihydrochloride monohydrate is prepared in a manner analogous to that set forth in Example 16, except 1-(4-phenylpiperidin-4-yl)ethanone is used as the amine in step 6. $^1$H NMR ($D_2O$, 500 MHz) δ 7.27-7.44 (m, 5H), 3.64-3.60 (m, 1H), 3.56-3.52 (m, 1H), 3.33-3.08 (m, 2H), 3.04-2.89 (m, 2H), 2.85-2.82 (m, 2H), 2.29-2.25 (m, 1H), 2.21-2.13 (m, 2H), 2.11-2.03 (m, 1H), [1.93 (s, $1^{st}$ conformer), 1.91 (s, $2^{nd}$ conformer), 3H], 1.88-1.69 (m, 2H), 1.37-1.25 (m, 3H), 1.16-1.09 (m, 1H), [0.69 (t, J=7.0 Hz, $1^{st}$ conformer), 0.67 (t, J=7.0 Hz, 2$^{nd}$ conformer), 2H]. ESI MS found for $C_{21}H_{33}BN_2O_5$ m/z [387.7 (M+1−18) 30%, 369.6 (M+1−2×18) 100%].

Example 46

Preparation of 2-amino-6-borono-2-(2-OR)-2-(trifluoromethyl)pyrrolidin-1-yl)ethyl)hexanoic acid dihydrochloride

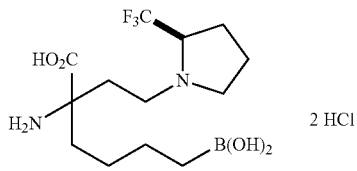

(46)

2-Amino-6-borono-2-(2-((R)-2-(trifluoromethyl)pyrrolidin-1-yl)ethyl)hexanoic acid dihydrochloride monohydrate is prepared in a manner analogous to that set forth in Example 16, except (R)-2-(trifluoromethyl)pyrrolidine is used as the amine in step 6. $^1$H NMR (D$_2$O, 500 MHz) δ 4.44-4.34 (m, 1H), 3.78-3.71 (m, 1H), [3.54-3.47 (m, 1$^{st}$ diastereoisomer), 3.69-3.65 (m, 2$^{st}$ diastereoisomer), 1H], [3.37-3.32 (m, 1$^{st}$ diastereoisomer), 3.46-3.41 (m, 2$^{st}$ diastereoisomer), 1H], 3.29-3.19 (m, 1H), 2.44-2.35 (m, 1H), 2.33-2.27 (m, 1H), 2.22-2.13 (m, 3H), 2.05-1.96 (m, 1H), 1.92-1.86 (m, 1H), 1.80-1.73 (m, 1H), 1.35-1.29 (m, 3H), 1.20-1.11 (m, 1H), 0.69 (t, J=7.0 Hz, 2H). $^{19}$F NMR [−71.29 (s, 1$^{st}$ diastereoisomer), −71.06 (s, 2$^{nd}$ diastereoisomer), 3F]. ESI MS found for $C_{13}H_{24}BF_3N_2O_4$ m/z [323.5 (M+1−18) 10%, 305.5 (M+1−2×18) 100%, 321.5 (M−1−18) 100%].

Example 47

Preparation of 2-amino-6-borono-2-(2-(4-fluoropiperidin-1-yl)ethyl) hexanoic acid dihydrochloride

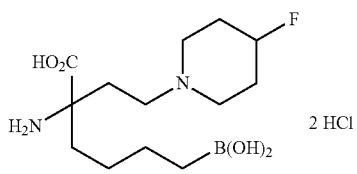

(47)

2-Amino-6-borono-2-(2-(4-fluoropiperidin-1-yl)ethyl) hexanoic acid dihydrochloride monohydrate is prepared in a manner analogous to that set forth in Example 16, except 4-fluoropiperidine is used as the amine in step 6. $^1$H NMR (D$_2$O, 500 MHz) δ 5.00 (brd, J=47 Hz, 0.7H), 4.85 (d sept. J=47 Hz 0.08H), 3.65-3.58 (m, 0.3H), 3.48-3.44 (m, 1.5H), 3.37-3.33 (m, 1H), 3.27-3.20 (m, 1.5H), 3.19-3.14 (m, 1H), 3.12-3.06 (m, 0.3H), 2.34-2.26 (m, 2H), 2.24-2.20 (m, 2H), 2.05-1.88 (m, 3H), 1.81 (ddd, J=14.0, 12.0, 4.0 Hz, 1H), 1.40-1.32 (m, 3H), 1.22-1.16 (m, 1H), 0.73 (t, J=7.0 Hz, 2H). $^{19}$F NMR [−188.10−−188.05 (m, 1$^{st}$ conformer), −177.96−−177.87 (m, 2$^{nd}$ conformer), 1F].

Example 48

Preparation of 2-amino-6-borono-2-(2-((4-fluoro-3-(trifluoromethyl)benzyl)(methyl)amino)ethyl)hexanoic acid dihydrochloride

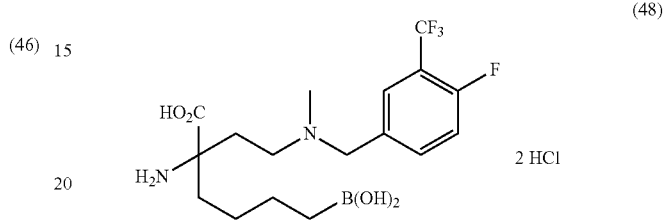

(48)

2-Amino-6-borono-2-(2-((4-fluoro-3-(trifluoromethyl)benzyl)(methyl)amino)ethyl)hexanoic acid dihydrochloride monohydrate is prepared in a manner analogous to that set forth in Example 16, except 1-(4-fluoro-3-(trifluoromethyl)phenyl)-N-methylmethanamine is used as the amine in step 6. $^1$H NMR (D$_2$O, 500 MHz) δ [7.80 (brs, 1$^{st}$ rotamer), 7.79 (brs, 2$^{nd}$ rotamer), 1H], 7.75-7.69 (m, 1H), 7.36 (dd, J$_1$=10.0 Hz, J$_2$=8.0 Hz, 1H), 4.45-4.36 (m, 1H), 4.32-4.23 (m, 1H), 3.43-3.37 (m, 1H), 3.13-3.05 (m, 1H), 2.79 (brs, 2$^{nd}$ rotamer), 3H], [2.76 (brs, 1$^{st}$ rotamer), 2.26 (dt, J$_1$=16.0 Hz, J$_2$=8.0 Hz, 1H), 2.18-2.06 (m, 1H), 1.86-1.66 (m, 1H), 1.46-0.98 (m, 5H), 0.69-0.57 (m, 2H). $^{19}$F NMR −112.29 (q, J=14.0 Hz, 1F), −60.85 (d, J=14.0 Hz, 3F). ESI MS found for $C_{17}H_{25}BF_4N_2O_4$ m/z [391.5 (M+1−18) 33%, 373.6 (M+1−2×18) 100%].

Example 49

Preparation of 2-amino-6-borono-2-(2-(4-methyl-1,4-diazepan-1-yl)ethyl)hexanoic acid dihydrochloride

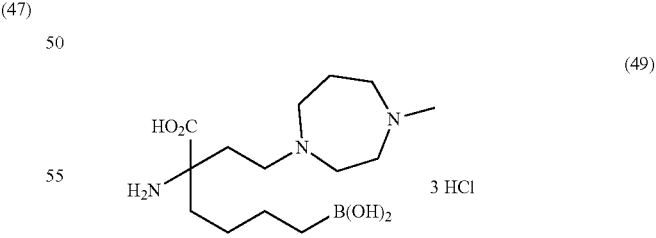

(49)

2-Amino-6-borono-2-(2-(4-methyl-1,4-diazepan-1-yl) ethyl)hexanoic acid dihydrochloride monohydrate is prepared in a manner analogous to that set forth in Example 16, except 1-methyl-1,4-diazepane is used as the amine in step 6. $^1$H NMR (D$_2$O, 500 MHz) δ 3.77-3.68 (m, 2H), 3.55-3.51 (m, 3H), 3.47-3.41 (m, 2H), 3.28-3.23 (m, 1H), 2.91 (s, 3H), 2.29-2.23 (m, 3H), 2.21-2.14 (m, 1H), 1.88-1.83 (m, 1H), 1.76-1.71 (m, 1H), 1.37-1.27 (m, 3H), 1.18-1.10 (m, 1H), 0.70 (t, J=8.0 Hz, 2H). ESI MS found for $C_{14}H_{30}BN_3O_4$ m/z [298.5 (M+1–18) 6%, 280.5 (M+1–2×18) 100%, 268.5 (M+1–3×18) 5%].

Example 50

Preparation of 2-amino-6-borono-2-(2-(4-(2-methoxyphenyl)piperazin-1-yl)ethyl)hexanoic acid dihydrochloride

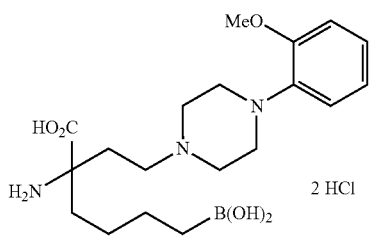

(50)

2-Amino-6-borono-2-(2-(4-(2-methoxyphenyl)piperazin-1-yl)ethyl)hexanoic acid dihydrochloride monohydrate is prepared in a manner analogous to that set forth in Example 16, except 1-(2-methoxyphenyl)piperazine is used as the amine in step 6. $^1$H NMR ($D_2O$, 500 MHz) δ 7.15 (ddd, $J_1$=8.0 Hz, $J_2$=8.0 Hz, $J_3$=1.0 Hz, 1H), 7.09 (dd, $J_1$=8.0 Hz, $J_2$=1.0 Hz, 1H), 7.01 (d, J=8.0 Hz, 1H), 6.95 (dd, $J_1$=8.0 Hz, $J_2$=8.0 Hz, 1H), 3.78 (s, 3H), 3.52-3.34 (m, 8H), 2.34-2.24 (m, 2H), 1.92-1.87 (m, 1H), 1.81-1.75 (m, 1H), 1.49-1.44 (m, 2H), 1.37-1.29 (m, 3H), 1.20-1.15 (m, 1H), 0.70 (t, J=8.0 Hz, 2H). ESI MS found for $C_{19}H_{32}BN_3O_5$ m/z [376.6 (M+1–18) 10%, 358.7 (M+1–2×18) 100%].

Example 51

Preparation of 2-amino-2-(2-(bis(2-aminoethyl)amino)ethyl)-6-boronohexanoic acid tetrahydrochloride

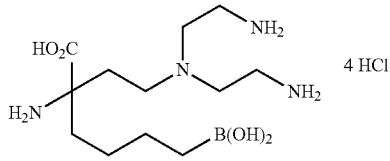

(51)

2-Amino-2-(2-(bis(2-aminoethyl)amino)ethyl)-6-boronohexanoic acid tetrahydrochloride is prepared in a manner analogous to that set forth in Example 16, except tert-butyl 2,2'-azanediylbis(ethane-2,1-diyl)dicarbamate is used as the amine in step 6. The final compound was isolated as the tetrahydrochloride salt and monohydrate. $^1$H NMR ($D_2O$, 500 MHz) δ 3.15-3.12 (m, 4H), 3.00-2.92 (m, 5H), 2.77 (ddd, $J_1$=14.0 Hz, $J_2$=7.0 Hz, $J_3$=6.0 Hz, 1H), 2.07 (t, J=7.0 Hz, 2H), 1.86 (ddd, $J_1$=18.0 Hz, $J_2$=14.0 Hz, $J_3$=4.0 Hz, 1H), 1.76 (ddd, $J_1$=18.0 Hz, $J_2$=14.0 Hz, $J_3$=4.0 Hz, 1H), 1.37-1.32 (m, 3H), 1.17-1.09 (m, 1H), 0.69 (t, J=7.0 Hz, 2H). ESI MS found for $C_{12}H_{29}BN_4O_4$ m/z [287.6 (M+1–18) 5%, 269.5 (M+1–2×18) 100%, 303.6 (M–1) 28%, 285.6 (M–1–18) 100%].

Example 52

Preparation of 1-(3-amino-7-borono-3-carboxyheptyl)piperidine-2-carboxylic acid dihydrochloride

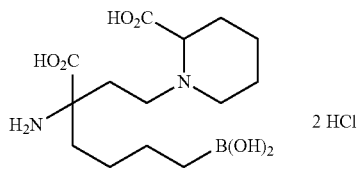

(52)

1-(3-Amino-7-borono-3-carboxyheptyl)piperidine-2-carboxylic acid dihydrochloride monohydrate is prepared in a manner analogous to that set forth in Example 16, except piperidine-2-carboxylate is used as the amine in step 6. $^1$H NMR ($D_2O$, 500 MHz) δ 3.98-3.88 (m, $1^{st}$ conformer, 1H), 3.64 (brd, J=13.0 Hz, 1H), 3.44 (dt, $J_1$=13.0 Hz, $J_2$=6.0 Hz, $2^{nd}$ conformer), 3.32-3.25 (m, 2H), 3.10 (dt, $J_1$=13.0 Hz, $J_2$=5.0 Hz, $2^{nd}$ conformer), 1H], [3.03-2.96 (m, $1^{st}$ conformer), 2.42-2.36 (m, 1H), 2.35-2.30 (m, 1H), 2.24 (brd, J=14.0 Hz, 1H), 1.94-1.88 (m, 2H), 1.84-1.81 (m, 2H), 1.78-1.72 (m, 1H), 1.70-1.64 (m, 1H), 1.55-1.50 (m, 1H), 1.38-1.32 (m, 3H), 1.21-1.16 (m, 1H), 0.72 (t; J=7.0 Hz, 2H). ESI MS found for $C_{12}H_{29}BN_4O_4$ m/z [317.5 (M+Na$^+$–2×18) 11%, 313.6 (M+1–18) 17%, 295.6 (M+1–2×18) 100%, 329.5 (M–1) 6%, 311.6 (M–1–18) 100%].

Example 53

Preparation of 1-(3-amino-7-borono-3-carboxyheptyl)piperidine-2-carboxylic acid dihydrochloride

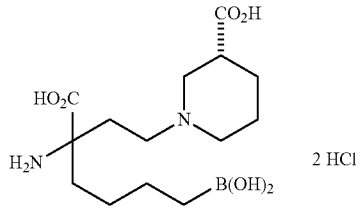

(53)

1-(3-Amino-7-borono-3-carboxyheptyl)piperidine-2-carboxylic acid dihydrochloride monohydrate is prepared in a manner analogous to that set forth in Example 16, except (R)-piperidine-3-carboxylate is used as the amine in step 6. $^1$H NMR ($D_2O$, 500 MHz) δ (two diastereoisomers+two conformers) 3.78 (brt, J=12.0 Hz, 0.35H), 3.73 (brt, J=12.0 Hz, 0.65H), 3.54 (brt, J=14.0 Hz, 0.65H), 3.43 (brt, J=14.0 Hz, 0.35H), 3.39-3.33 (m, 1H), 3.19-3.13 (m, 1H), 3.11-3.08 (m, 1H), 3.05-2.80 (m, 2H), 2.40-2.19 (m, 2H), 2.17-2.11 (m, 1H), 2.02 (brd, J=15.0 Hz, 0.65H), 1.94-1.67 (m, 3.70H), 1.55 (ddd, $J_1$=16.0 Hz, $J_2$=13.0 Hz, $J_3$=4.0 Hz, 0.65H), 1.39-1.33 (m, 3H), 1.22-1.15 (m, 1H), 0.74 (t, J=7.0 Hz, 2H). ESI MS found for $C_{12}H_{29}BN_4O_4$ m/z [317.4 (M+Na$^+$−2×18) 5%, 313.6 (M+1−18) 10%, 295.6 (M+1−2×18) 100%, 311.6 (M−1−18) 100%].

Example 54

Preparation of 2-amino-6-borono-2-(2-((S)-2-(dimethylcarbamoyl)pyrrolidin-1-yl)ethyl)hexanoic acid dihydrochloride

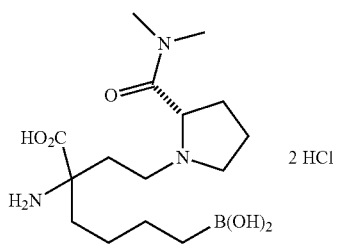

(54)

2-Amino-6-borono-2-(2-((S)-2-(dimethylcarbamoyl)pyrrolidin-1-yl)ethyl)hexanoic acid dihydrochloride monohydrate is prepared in a manner analogous to that set forth in Example 16, except (S)—N,N-dimethylpyrrolidine-2-carboxamide is used as the amine in step 6. ESI MS found for $C_{13}H_{26}BN_3O_5$ m/z [298.5 (M+1−18) 15%, 280.5 (M+1−2×18) 55%, 235.5 (M+1−2×18−45) 100%].

Example 55

Preparation of 2-amino-6-borono-2-(2-(isopropylamino)ethyl)hexanoic acid dihydrochloride

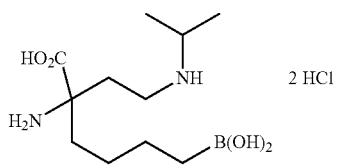

(55)

2-Amino-6-borono-2-(2-(isopropylamino)ethyl)hexanoic acid dihydrochloride monohydrate is prepared in a manner analogous to that set forth in Example 16, except isopropylamine is used as the amine in step 6. $^1$H NMR (D$_2$O, 500 MHz) δ 3.26 (septet, J=6.0 Hz, 1H), 3.10-3.0.5 (m, 1H), 2.84-2.80 (m, 1H), 2.12 (t, J=8.0 Hz, 2H), 1.80-1.71 (m, 2H), 1.34-1.27 (m, 3H), 1.19 (d, J=6.0 Hz, 6H), 1.11-1.07, (m, 1H), 0.58 (t, J=7.0 Hz, 2H). ESI MS found for $C_{11}H_{25}BN_2O_4$ m/z [261.6 (M+1) 3%, 243.5 (M+1−18) 30%, 225.5 (M+1−2×18) 100%, 207.5 (M+1−3×18) 62%, 501.9 (2 M−1−18) 13%, 259.6 (M−1) 23%, 241.5 (M−1−18) 100%].

Example 56

Preparation of (3S)-1-(3-amino-7-borono-3-carboxyheptyl)piperidine-3-carboxylic acid dihydrochloride

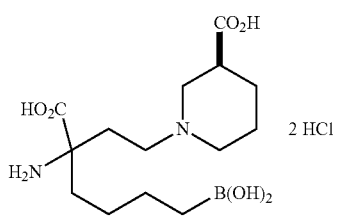

(56)

(3S)-1-(3-Amino-7-borono-3-carboxyheptyl)piperidine-3-carboxylic acid dihydrochloride monohydrate is prepared in a manner analogous to that set forth in Example 16, except (S)-ethyl piperidine-3-carboxylate is used as the amine in step 6. $^1$H NMR (D$_2$O, 500 MHz) δ (two diastereoisomers+two conformers) 3.79 (brt, J=12.0 Hz, 0.35H), 3.74 (brt, J=12.0 Hz, 0.65H), 3.55 (brt, J=12.0 Hz, 0.65H), 3.44 (brt, J=12.0 Hz, 0.35H), 3.41-3.33 (m, 1H), 3.21-3.15 (m, 1H), 3.13-2.95 (m, 2H), 2.92-2.81 (m, 1H), 2.42-2.11 (m, 3H), 2.03 (brd, J=14.0 Hz, 0.65H), 1.94-1.70 (m, 3.80H), 1.57 (dq, J=13.0, 4.0 Hz, 0.65H), 1.40-1.32 (m, 3H), 1.24-1.15 (m, 1H), 0.74 (t, J=7.0 Hz, 2H). ESI MS found for $C_{14}H_{27}BN_2O_6$ m/z [313.6 (M+1−18) 10%, 295.5 (M+1−2×18) 100%, 277.5 (M+1−3×18) 15%].

Example 57

Preparation of 1-(3-amino-7-borono-3-carboxyheptyl)-4-methylpiperidine-4-carboxylic acid

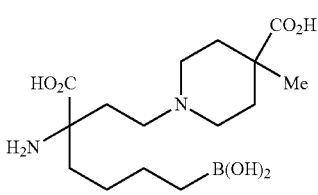

(57)

(2-(2-(4-Acetyl-4-methylpiperidin-1-yl)ethyl)-2-amino-6-boronohexanoic acid dihydrochloride monohydrate is prepared in a manner analogous to that set forth in Example 16, except 1-(4-methylpiperidin-4-yl)ethanone is used as the amine in step 6. $^1$H NMR (D$_2$O, 500 MHz) δ (two conformers in ratio 3/1) 3.48-3.40 (m, 2H), 3.34-3.21 (m, 1H), 3.15-3.11 (m, 0.5H), 3.08-3.02 (m, 1H), 2.96-2.87 (m, 1.5H), 2.28 (d, J=14.0 Hz, 1.5H), 2.23-2.19 (m, 2H), 2.06-2.01 (m, 0.5H), 1.88-1.82 (m, 1.5H), 1.77-1.71 (m, 1H), 1.61 (t, J=14.0 Hz, 1.5H), 1.34-1.27 (m, 3H), [1.25 (s, 1$^{st}$ conformer), 1.18 (s, 2$^{nd}$ conformer), 3H], 1.16-1.10 (m, 1H), 0.69 (t, J=8.0 Hz, 2H). ESI MS found for $C_{15}H_{29}BN_2O_6$ m/z [327.6 (M+1−18) 13%, 309.6 (M+1−2×18) 100%, 291.6 (M+1−3×18) 10%, 325.6 (M−1−18) 100%, 307.6 (M−1−2×18) 37%].

Example 58

Preparation of 2-amino-6-borono-2-(2-(2,3-dihydro-1H-inden-2-ylamino)ethyl)hexanoic acid dihydrochloride

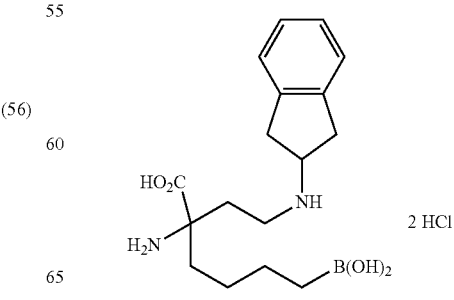

(58)

2-Amino-6-borono-2-(2-(2,3-dihydro-1H-inden-2-ylamino)ethyl)hexanoic acid dihydrochloride monohydrate is prepared in a manner analogous to that set forth in Example 16, except 2,3-dihydro-1H-inden-2-amine is used as the amine in step 6. $^1$H NMR (D$_2$O, 500 MHz) δ 7.26-7.24 (m, 2H), 7.21-7.19 (m, 2H), 4.09-4.04 (m, 1H), 3.35 (dd, J$_1$=17.0 Hz, J$_2$=7.0 Hz, 2H), 3.31-3.25 (m, 1H), 3.12-3.07 (m, 1H), 3.04 (dd, J$_1$=17.0 Hz, J$_2$=4.0 Hz, 2H), 2.18 (t, J=8.0 Hz, 2H), 1.91-1.86 (m, 1H), 1.79-1.73 (m, 1H), 1.38-1.27 (m, 3H), 1.20-1.11 (m, 1H), 0.71 (t, J=8.0 Hz, 2H). ESI MS found for C$_{13}$H$_{26}$BFN$_2$O$_4$ m/z [317.5 (M+1−18) 28%, 299.6 (M+1−2×18) 100%, 281.5 (M+1−3×18) 31%, 333.5 (M−1) 28%, 315.5 (M−1−18) 100%].

Example 59

Preparation of 2-amino-6-borono-2-(2-(3-hydroxyazetidin-1-yl)ethyl)hexanoic acid dihydrochloride

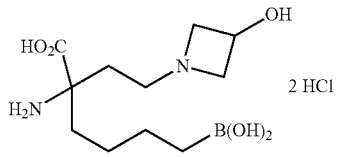

(59)

2-Amino-6-borono-2-(2-(3-hydroxyazetidin-1-yl)ethyl) hexanoic acid dihydrochloride monohydrate is prepared in a manner analogous to that set forth in Example 16, except azetidin-3-ol is used as the amine in step 6. $^1$H NMR (D$_2$O, 500 MHz) δ 4.65-4.60 (m, 1H), 4.50-4.46 (m, 1H), 4.21-4.17 (m, 1H), 4.10-4.08 (m, 1H), 3.86-3.82 (m, 1H), 3.48-3.37 (m, 1H), 3.30-3.19 (m, 1H), 2.09-2.04 (m, 2H), 1.90-1.85 (m, 1H), 1.78-1.73 (m, 1H), 1.35-1.28 (m, 3H), 1.19-1.10 (m, 1H), 0.70 (t, J=7.0 Hz, 2H). ESI MS found for C$_{11}$H$_{23}$BN$_2$O$_5$ m/z [275.5 (M+1) 5%, 257.5 (M+1−18) 11%, 239.4 (M+1−2×18) 100%, 273.5 (M−1) 10%, 255.5 (M−1−18) 100%].

Example 60

Preparation of 2-amino-6-borono-2-(2-(1-butylcyclopropylamino)ethyl)hexanoic acid dihydrochloride

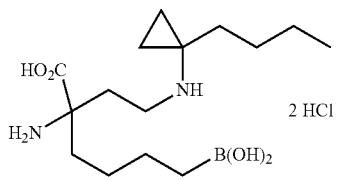

(60)

2-Amino-6-borono-2-(2-(1-butylcyclopropylamino) ethyl)hexanoic acid dihydrochloride is prepared in a manner analogous to that set forth in Example 16, except 1-butylcyclopropanamine is used as the amine in step 6 and dihydrate. $^1$H NMR (D$_2$O, 500 MHz) δ 3.33-3.27 (m, 1H), 3.12-3.07 (m, 1H), 2.15 (t, J=8.0 Hz, 2H), 1.91-1.86 (m, 1H), 1.79-1.73 (m, 1H), 1.66-1.56 (m, 2H), 1.36-1.30 (m, 3H), 1.26 (brs, 4H), 1.17-1.11 (m, 1H), 0.89 (s, 2H), 0.79-0.77 (m, 5H), 0.70 (t, J=7.0 Hz, 2H). ESI MS found for C$_{15}$H$_{31}$BN$_2$O$_4$ m/z [297.6 (M+1−18) 22%, 279.5 (M+1−2×18) 100%, 261.6 (M+1−3×18) 17%, 313.6 (M−1) 19%, 295.6 (M−1−18) 100%]. Anal. Calcd for C$_{15}$H$_{31}$BN$_2$O$_4$×2 HCl×2H$_2$O: C, 42.57; H, 8.81; N, 6.62. Found C, 41.19; H, 8.24; N, 6.57.

Example 61

Preparation of 2-amino-6-borono-2-(2-(1-(4-methoxybenzyl)cyclopropylamino)ethyl)hexanoic acid

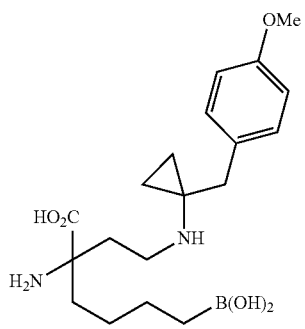

(61)

2-Amino-6-borono-2-(2-(1-(4-methoxyphenyl)cyclopropylamino)ethyl)hexanoic acid dihydrochloride is prepared in a manner analogous to that set forth in Example 16, except 1-(4-methoxyphenyl)cyclopropanamine is used as the amine in step 6 and dihydrate. $^1$H NMR (D$_2$O, 500 MHz) δ 7.26 (d, J=8.0 Hz, 2H), 6.92 (d, J=8.0 Hz, 2H), 3.73 (s, 3H), 3.29-3.249 (m, 1H), 3.11-3.05 (m, 1H), 2.97 (d, J=16.0 Hz, 1H), 2.93 (d, J=16.0 Hz, 1H), 2.07-2.00 (m, 2H), 1.78-1.73 (m, 1H), 1.67-1.62 (m, 1H), 1.34-1.29 (m, 2H), 1.27-1.21 (m, 1H), 1.12-1.07 (m, 1H), 1.00 (s, 2H), 0.94 (s, 2H), 0.69 (t, J=8.0 Hz, 2H). ESI MS found for C$_{19}$H$_{31}$BN$_2$O$_5$ m/z [361.6 (M+1−18) 16%, 343.6 (M+1−2×18) 100%, 325.5 (M+1−3×18) 16%, 377.7 (M−1) 17%, 359.6 (M−1−18) 100%]. Anal. Calcd for C$_{19}$H$_{31}$BN$_2$O$_5$×2HCl×2H$_2$O: C, 46.84; H, 7.65; N, 5.75. Found C, 46.94; H, 7.58; N, 5.95.

Example 62

Preparation of 2-amino-6-borono-2-(2-(4,5-dihydrothieno[2,3-c]pyridin-6(7H)-yl)ethyl)hexanoic acid dihydrochloride

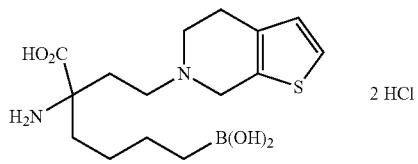

(62)

2-Amino-6-borono-2-(2-(4,5-dihydrothieno[2,3-c]pyridin-6(7H)-yl)ethyl)hexanoic acid dihydrochloride monohydrate is prepared in a manner analogous to that set forth in Example 16, except 4,5,6,7-tetrahydrothieno[2,3-c]pyridine is used as the amine in step 6. $^1$H NMR (D$_2$O, 500 MHz) δ 7.23 (d, J=5.0 Hz, 1H), 6.86 (d, J=5.0 Hz, 1H), [4.64 (d, J=14.0 Hz), 4.34 (d, J=14.0 Hz), 2H, AB system], 3.77-3.73 (m, 1H), 3.55-3.37 (m, 2H), 3.34-3.26 (m, 1H), 2.99 (brs, 2H), 2.35-2.30 (m, 2H), 1.88-0.93 (m, 1H), 1.76-1.82 (m, 1H), 1.29-1.39 (m, 3H), 1.12-1.19 (m, 1H), 0.70 (t, J=7.0 Hz, 2H). ESI MS found for $C_{15}H_{25}BN_2O_4S$ m/z [341.5 (M+1) 1%, 323.5 (M+1−18) 12%, 305.5 (M+1−2×18) 100%, 661.9 (2 M−1−18) 4%, (339.5 (M−1) 34%, 321.5 (M−1−18) 100%].

Example 63

Preparation of 2-amino-6-borono-2-(2-(3-(3,4-difluorophenyl)propylamino)ethyl)hexanoic acid dihydrochloride

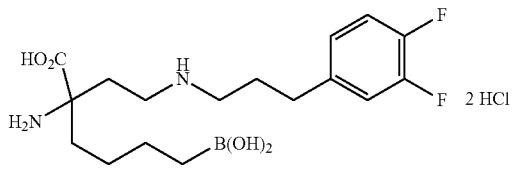

(63)

2-Amino-6-borono-2-(2-(3-(3,4-difluorophenyl)propylamino)ethyl)hexanoic acid dihydrochloride monohydrate is prepared in a manner analogous to that set forth in Example 16, except 3-(3,4-difluorophenyl)propan-1-amine is used as the amine in step 6. $^1$H NMR (D$_2$O, 500 MHz) δ 7.13-7.00 (m, 2H), 6.95-6.89 (m, 1H), 3.20-3.05 (m, 1H), 3.01-2.91 (m, 3H), 2.60 (t, J=8.0 Hz, 2H), 2.15 (t, J=8.0 Hz, 2H), 1.96-1.73 (m, 4H), 1.36-1.25 (m, 3H), 1.22-1.06 (m, 1H), 0.68 (t, J=7.0 Hz, 2H). $^{19}$F NMR −142.00 (d, J=22.0 Hz, 1F), −138.58 (d, J=22.0 Hz, 1F). ESI MS found for $C_{17}H_{27}BF_2N_2O_4$ m/z [355.6 (M+1−18) 20%, 337.6 (M+1−2×18) 90%, 319.5 (M+1−3×8) 100%, 371.6 (M−1) 20%, 353.6 (M−1-18) 100%].

Example 64

Preparation of 2-amino-6-borono-2-(2-(3-(2-chloro-5-(trifluoromethyl)phenyl)propylamino)ethyl)hexanoic acid dihydrochloride

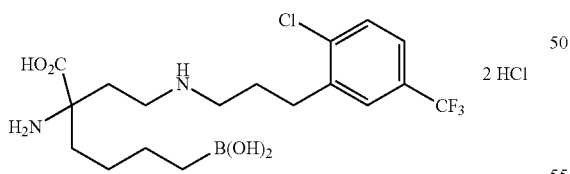

(64)

2-Amino-6-borono-2-(2-(3-(2-chloro-5 (trifluoromethyl) phenyl)propylamino)ethyl) hexanoic acid dihydrochloride monohydrate is prepared in a manner analogous to that set forth in Example 16, except 3-(2-chloro-5-(trifluoromethyl) phenyl)propan-1-amine is used as the amine in step 6. $^1$H NMR (D$_2$O, 500 MHz) δ 7.56 (s, 1H), 7.48 (d, J=8.0 Hz, 1H), 7.44 (d, J=8.0 Hz, 1H), 3.19-3.13 (m, 1H), 3.01 (t, J=8.0 Hz, 2H), 2.99-2.95 (m, 1H), 2.79 (t, J=8.0 Hz, 2H), 2.13 (t, J=8.0 Hz, 2H), 1.91 (tt, J=8.0, 8.0 Hz, 2H), 1.87-1.81 (m, 1H), 1.75-1.69 (m, 1H), 1.33-1.25 (m, 3H), 1.15-1.08 (m, 1H), 0.66 (t, J=7.0 Hz, 2H). $^{19}$F NMR −61.66 (s, 3F). ESI MS found for $C_{18}H_{27}BClF_3N_2O_4$ m/z [421.6/423.6 (M+1−18) 38%, 403.6/405.6 (M+1−2×18) 75%, 367.6 (M+1−2×18−Cl$^-$) 100%, 437.6/439.7 (M−1) 30%, 419.6/421.6 (M−1−18) 100%, 383.6 (M−1−18−Cl$^-$) 30%].

Example 65

Preparation of 2-amino-6-borono-2-(2-(3-(3-methoxyphenyl)propylamino)ethyl)hexanoic acid dihydrochloride

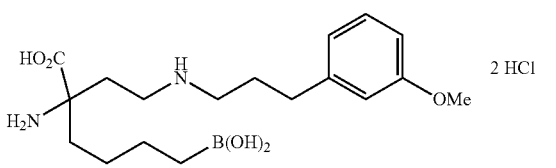

(65)

2-Amino-6-borono-2-(2-(3-(3-methoxyphenyl)propylamino)ethyl)hexanoic acid dihydrochloride monohydrate is prepared in a manner analogous to that set forth in Example 16, except 3-(3-methoxyphenyl)propan-1-amine is used as the amine in step 6. $^1$H NMR (D$_2$O, 500 MHz) δ 7.16-7.13 (m, 1H), 6.75-6.71 (m, 3H), 3.64 (s, 3H), 3.11-3.04 (m, 1H), 2.93-2.83 (m, 3H), 2.53 (t, J=8.0 Hz, 2H), 2.06 (t, J=8.0 Hz, 2H), 1.85-1.75 (m, 3H), 1.68-1.60 (m, 1H), 1.27-1.17 (m, 3H), 1.10-1.00 (m, 1H), 0.60 (t, J=8.0 Hz, 2H). ESI MS found for $C_{18}H_{31}BN_2O_5$ m/z [389.7 (M+Na$^+$) 5%, 331.6 (M+1−2× 18) 70%, 313.6 (M+1−3×18) 100%].

Example 66

Preparation of 2-amino-6-borono-2-(2-(3-(2,4-dichlorophenyl)propylamino)ethyl)hexanoic acid dihydrochloride

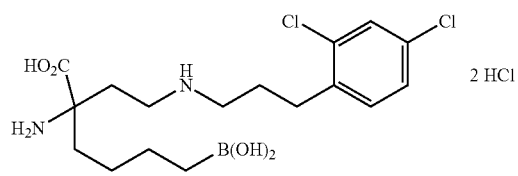

(66)

2-Amino-6-borono-2-(2-(3-(2,4-dichlorophenyl)propylamino)ethyl)hexanoic acid dihydrochloride is prepared in a manner analogous to that set forth in Example 16, except 3-(2,4-dichlorophenyl)propan-1-amine is used as the amine in step 6. $^1$H NMR (D$_2$O, 500 MHz) δ 7.24 (m, 1H), 7.06 (m, 2H), 3.12-3.06 (m, 1H), 2.95-2.89 (m, 3H), 2.58 (t, J=8.0 Hz, 2H), 2.11 (t, J=8.0 Hz, 2H), 1.84-1.74 (m, 3H), 1.70-1.65 (m, 1H), 1.25-1.15 (m, 3H), 1.10-1.00 (m, 1H), 0.56 (t, J=7.0 Hz, 2H). $^{13}$C NMR (D$_2$O) δ 23.24, 25.07, 25.10, 29.00, 31.30, 35.05, 42.84, 47.52, 62.48, 125.78, 127.14, 128.84, 131.25, 132.65, 133.84, 136.37, 172.94. ESI MS found for $C_{17}H_{27}BCl_2N_2O_4$ m/z [387.5 (M+1−18) 20%, 369.5 (M+1−

2×18) 100%, 385.5 (M−1−18) 100%]. Anal. Calcd for C$_{17}$H$_{27}$BCl$_2$N$_2$O$_4$: C, 42.67; H, 6.06); N, 5.85). Found: C, 42.53; H, 6.00; N, 5.68.

Example 67

Preparation of 2-amino-6-borono-2-(2-(tert-butylamino)ethyl)hexanoic acid dihydrochloride

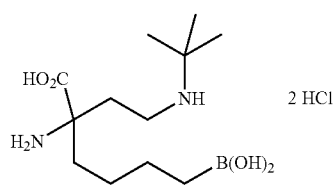

(67)

2-Amino-6-borono-2-(2-(tert-butylamino)ethyl)hexanoic acid dihydrochloride monohydrate is prepared in a manner analogous to that set forth in Example 16, except tert-butylamine is used as the amine in step 6. $^1$H NMR (D$_2$O, 500 MHz) δ 3.11-3.05 (m, 1H), 2.89-2.83 (m, 1H), 2.13-2.06 (m, 2H), 1.86-1.81 (m, 1H), 1.75-1.69 (m, 1H), 1.28-1.22 (m, 3H), 1.17 (s, 9H), 1.09-1.02 (m, 1H), 0.61 (t, J=8.0 Hz, 2H). ESI MS found for C$_{12}$H$_{27}$BN$_2$O$_4$ m/z [239.5 (M+1−2×18) 100%, 255.5 (M−1−18) 90%].

Example 68

Preparation of 2-amino-6-borono-2-(2-(cyclopropylamino)ethyl)hexanoic acid dihydrochloride

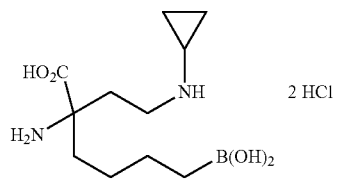

(68)

2-Amino-6-borono-2-(2-(cyclopropylamino)ethyl)hexanoic acid dihydrochloride monohydrate is prepared in a manner analogous to that set forth in Example 16, except cyclopropanamine is used as the amine in step 6. $^1$H NMR (D$_2$O, 500 MHz) δ 3.32-3.25 (m, 1H), 3.14-3.10 (m, 1H), 2.69-2.63 (m, 1H), 2.25-2.16 (m, 2H), 1.90-1.86 (m, 1H), 1.80-1.75 (m, 1H), 1.39-1.24 (m, 3H), 1.15-1.08 (m, 1H), 0.81-0.76 (m, 4H), 0.75-0.68 (m, 2H). ESI MS found for C$_{11}$H$_{23}$BN$_2$O$_4$ m/z [223.4 (M+1−2×18) 30%, 205.4 (M+1−3×18), 60%, 239.5 (M−1−18) 100%].

Example 69

Preparation of 2-amino-6-borono-2-(2-(4-methoxybenzylamino)ethyl) hexanoic acid dihydrochloride

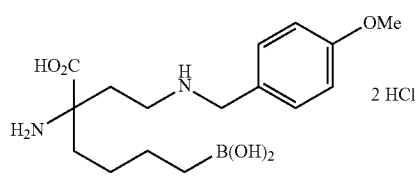

(69)

2-Amino-6-borono-2-(2-(4-methoxybenzylamino)ethyl) hexanoic acid dihydrochloride monohydrate is prepared in a manner analogous to that set forth in Example 16, except (4-methoxyphenyl)methanamine is used as the amine in step 6. $^1$H NMR (D$_2$O, 500 MHz) δ 7.28 (d, J=8.0 Hz, 2H), 6.70 (d, J=8.0 Hz, 2H), 4.09 (d, J=14.0 Hz, 1H), 4.06 (d, J=14.0 Hz, 1H), 3.69 (s, 3H), 3.19-3.14 (m, 1H), 3.02-2.96 (m, 1H), 2.16 (t, J=8.0 Hz, 2H), 1.82-1.77 (m, 1H), 1.72-1.67 (m, 1H), 1.30-1.18 (m, 3H), 1.10-1.02 (m, 1H), 0.61 (t, J=7.0 Hz, 2H). ESI MS found for C$_{16}$H$_{27}$BN$_2$O$_5$ m/z [319.6 (M−1−18) 100%, 321.5 (M+1−18) 60%, 303.6 (M+1−2×18) 100%].

Example 70

Preparation of 2-amino-2-(2-(benzylamino)ethyl)-6-boronohexanoic acid dihydrochloride

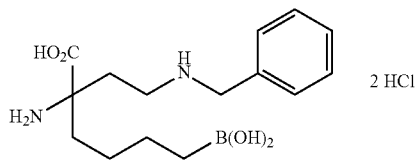

(70)

2-Amino-2-(2-(benzylamino)ethyl)-6-boronohexanoic acid dihydrochloride monohydrate is prepared in a manner analogous to that set forth in Example 16, except benzylamine is used as the amine in step 6. $^1$H NMR (D$_2$O, 500 MHz) δ 7.42-7.38 (m, 1H), 7.36-7.32 (m, 4H), 4.13 (s, 2H), 3.23-3.17 (m, 1H), 3.05-2.99 (m, 1H), 2.18 (t, J=8.0 Hz, 2H), 1.88-1.78 (m, 1H), 1.74-1.69 (m, 1H), 1.30-1.18 (m, 3H), 1.10-1.06 (m, 1H), 0.63 (t, J=7.0 Hz, 2H). ESI MS found for C$_{15}$H$_{25}$BN$_2$O$_4$ m/z [273.5 (M+1−2×18) 80%, 255.6 (M+1−3×18) 100%].

Example 71

Preparation of 2-amino-6-borono-2-(2-((2-(dimethylamino)ethyl)(methyl)amino)ethyl)hexanoic acid trihydrochloride

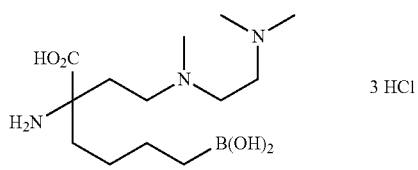

(71)

2-Amino-6-borono-2-(2-((2-(dimethylamino)ethyl)(methyl)amino)ethyl)hexanoic acid trihydrochloride is prepared in a manner analogous to that set forth in Example 16, except N1,N1,N2-trimethylethane-1,2-diamine is used as the amine in step 6. The final compound was isolated as the trihydrochloride salt and monohydrate. $^1$H NMR (D$_2$O, 500 MHz) δ 3.58-3.52 (m, 4H), 3.45-3.39 (m, 1H), 3.27-3.22 (m, 1H), 2.89 (s, 9H), 2.33-2.23 (m, 2H), 1.92-1.86 (m, 1H), 1.81-1.75 (m, 1H), 1.35-1.29 (m, 3H), 1.18-1.13 (m, 1H), 0.70 (t, J=8.0 Hz, 2H). ESI MS found for C$_{13}$H$_{30}$BN$_3$O$_4$ m/z [268.5 (M+1−2×18) 100%, 286.6 (M+1−18) 7%].

Example 72

Preparation of 2-amino-6-borono-2-(2-(cyclopentylamino)ethyl)hexanoic acid dihydrochloride

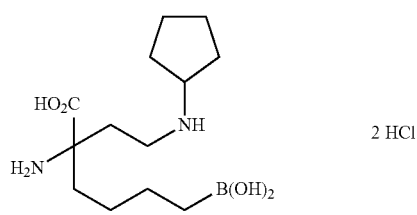
(72)

2-Amino-6-borono-2-(2-(cyclopentylamino)ethyl)hexanoic acid dihydrochloride monohydrate is prepared in a manner analogous to that set forth in Example 16, except cyclopentanamine is used as the amine in step 6. $^1$H NMR (D$_2$O, 500 MHz) δ 3.55-3.43 (m, 1H), 3.20-3.13 (m, 1H), 3.03-2.92 (m, 1H), 2.21-2.15 (m, 2H), 2.01-1.92 (m, 2H), 1.90-1.82 (m, 1H), 1.81-1.71 (m, 1H), 1.67-1.57 (m, 2H), 1.55-1.45 (m, 4H), 1.36-1.25 (m, 3H), 1.18-1.08 (m, 1H), 0.60-0.71 (m, 2H). ESI MS found for C$_{13}$H$_{27}$BN$_2$O$_4$ m/z [251.5 (M+1−2×18) 100%, 233.5 (M+1−3×18) 70%].

Example 73

Preparation of 2-amino-2-(2-((2-aminoethyl)(benzyl)amino)ethyl)-6-boronohexanoic acid trihydrochloride

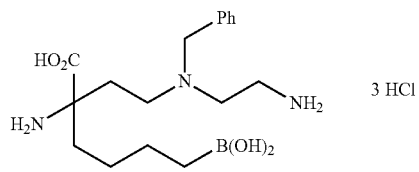
(73)

2-Amino-2-(2-((2-aminoethyl)(benzyl)amino)ethyl)-6-boronohexanoic acid trihydrochloride is prepared in a manner analogous to that set forth in Example 16, except tert-butyl 2-(benzylamino)ethylcarbamate is used as the amine in step 6. The final compound was isolated as the trihydrochloride salt and monohydrate. $^1$H NMR (D$_2$O, 500 MHz) δ 7.50-7.43 (m, 5H), [4.52 (d, J=13.0 Hz, 1H), 4.22 (d, J=13.0 Hz, 1H), AB-system], 3.56-3.50 (m, 1H), 3.46-3.37 (m, 4H), 3.24-3.19 (m, 1H), 2.31 (dt, J$_1$=16.0 Hz, J$_2$=8.0 Hz, 1H), 2.08-1.99 (m, 1H), 1.39-1.22 (m, 2H), 1.14-1.04 (m, 3H), 1.01-0.91 (m, 1H), 0.57 (t, J=6.0 Hz, 2H). ESI MS found for C$_{17}$H$_{30}$BN$_3$O$_4$ m/z [316.5 (M+1−2×18) 100%, 298.6 (M+1−3×18) 20%, 332.6 (M−1−18) 100%].

Example 74

Preparation of 2-amino-6-borono-2-(2-((4-isopropoxybenzyl)(methyl)amino)ethyl)hexanoic acid dihydrochloride

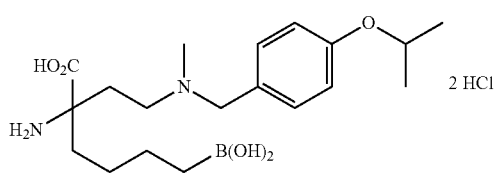
(74)

2-Amino-6-borono-2-(2-((4-isopropoxybenzyl)(methyl)amino)ethyl)hexanoic acid dihydrochloride monohydrate is prepared in a manner analogous to that set forth in Example 16, except 1-(4-isopropoxyphenyl)-N-methylmethanamine is used as the amine in step 6. $^1$H NMR (D$_2$O, 500 MHz) δ [7.36 (d, J=9.0 Hz, 2$^{nd}$ rotamer), 2H, 7.34 (d, J=9.0 Hz, 1$^{st}$ rotamer)], 6.99 (d, J=9.0 Hz, 2H), 4.67-4.61 (m, 1H), [4.30 (d, J=13.0 Hz, 1$^{st}$ rotamer), 4.28 (d, J=13.0 Hz, 2$^{nd}$ rotamer), 1H], [4.16 (d, J=13.0 Hz, 1$^{st}$ conformer), 4.09 (d, J=13.0 Hz, 2$^{nd}$ conformer), 1H], 3.24-3.14 (m, 1H), [3.05-3.11 (m, 2$^{nd}$ rotamer), 2.96-3.01 (m, 1$^{st}$ rotamer), 1H], [2.78 (s, 1$^{st}$ rotamer), 2.73 (s, 2$^{nd}$ rotamer), 3H], 2.31-2.21 (m, 1H), [2.15-2.09 (m, 2$^{nd}$ rotamer), 2.04-1.96 (m, 1$^{st}$ rotamer), 1H], 1.32-1.27 (m, 2H), 1.24 (d, J=6.0 Hz, 6H), 1.20-1.06 (m, 3H), 1.01-0.93 (m, 1H), [0.66 (t, J=8.0 Hz, 1$^{st}$ rotamer), 0.58 (t, J=8.0 Hz, 2$^{nd}$ rotamer), 2H]. ESI MS found for C$_{19}$H$_{33}$BN$_2$O$_5$ m/z [363.6 (M+1−18) 70%, 345.5 (M+1−2×18) 100%].

Example 75

Preparation of 2-amino-2-(2-(azetidin-1-yl)ethyl)-6-boronohexanoic acid dihydrochloride

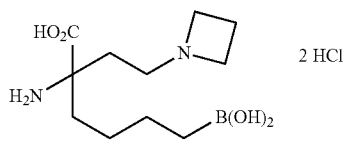
(75)

2-Amino-2-(2-(azetidin-1-yl)ethyl)-6-boronohexanoic acid dihydrochloride monohydrate is prepared in a manner analogous to that set forth in Example 16, except azetidine is used as the amine in step 6. $^1$H NMR (D$_2$O, 500 MHz) δ 4.24-4.15 (m, 2H), 4.05-3.93 (m, 2H), 3.39-3.32 (m, 1H), 3.22-3.13 (m, 1H), 2.54-2.41 (m, 1H), 2.39-2.29 (m, 1H), 2.00 (t, J=8.0 Hz, 2H), 1.88-1.80 (m, 1H), 1.77-1.67 (m, 1H), 1.36-1.23 (m, 3H), 1.19-1.08 (m, 1H), 0.69 (t, J=7.0 Hz, 2H).

ESI MS found for $C_{11}H_{23}BN_2O_4$ m/z [241.5 (M+1−18) 7%, 223.4 (M+1−2×18) 100%].

Example 76

Preparation of 2-amino-6-borono-2-(2-(4-phenylpiperazin-1-yl)ethyl)hexanoic acid dihydrochloride

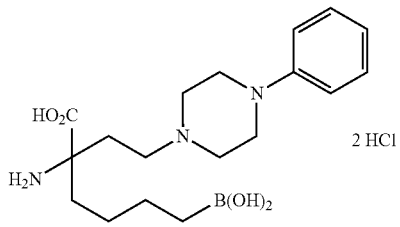

(76)

2-Amino-6-borono-2-(2-(4-phenylpiperazin-1-yl)ethyl) hexanoic acid dihydrochloride monohydrate is prepared in a manner analogous to that set forth in Example 16, except 1-phenylpiperazine is used as the amine in step 6. $^1$H NMR ($D_2O$, 500 MHz) δ 7.31 (t, J=8.0 Hz, 2H), 7.04 (d, J=8.0 Hz, 2H), 7.00 (t, J=8.0 Hz, 1H), 3.44-3.20 (m, 8H), 3.13-3.03 (m, 2H), 2.25-2.12 (m, 2H), 1.88-1.79 (m, 1H), 1.77-1.66 (m, 1H), 1.39-1.27 (m, 3H), 1.19-1.11 (m, 1H), 0.71 (t, J=8.0 Hz, 2H). ESI MS found for $C_{18}H_{30}BN_3O_4$ m/z [344.5 (M−1−18) 100%, 328.6 (M+1−2×18) 100%].

Example 77

Preparation of 2-amino-6-borono-2-(2-(4-(2-methoxyethyl)piperazin-1-yl)ethyl)hexanoic acid trihydrochloride

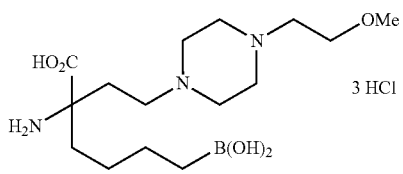

(77)

2-Amino-6-borono-2-(2-(4-(2-methoxyethyl)piperazin-1-yl)ethyl)hexanoic acid trihydrochloride monohydrate is prepared in a manner analogous to that set forth in Example 16, except 1-(2-methoxyethyl)piperazine is used as the amine in step 6. ESI MS found for $C_{15}H_{32}BN_3O_5$ m/z [310.6 (M+1−2×18) 89%, 328.6 (M+1−18) 3%, 326.6 (M−1−18) 13%].

Example 78

Preparation of 2-amino-6-borono-2-(2-((2-hydroxy-2-phenylethyl)(methyl)amino)ethyl)hexanoic acid dihydrochloride

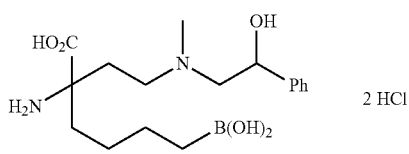

(78)

2-Amino-6-borono-2-(2-((2-hydroxy-2-phenylethyl)(methyl)amino)ethyl)hexanoic acid dihydrochloride monohydrate is prepared in a manner analogous to that set forth in Example 16, except 2-(methylamino)-1-phenylethanol is used as the amine in step 6. ESI MS found for $C_{17}H_{29}BN_2O_5$ m/z [317.5, (M+1−2×18) 20%, 299.5 (M+1−3×18) 100%].

Example 79

Preparation of 2-amino-6-borono-2-(piperidin-1-ylmethyl)hexanoic acid

Step 1: diethyl 2-(benzyloxycarbonylamino)-2-(but-3-enyl)malonate

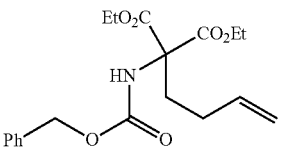 [SMILES: C=CCCC(NC(=O)OCc1ccccc1)(C(=O)OCC)C(=O)OCC]

A suspension of sodium hydride (510 mg, 21.24 mmol, 60% suspension) in dimethylformaamide (30 mL) was treated with diethyl carbobenzyloxy protected aminomalonate (6.0 g, 19.4 mmol) in dimethylformaamide (30 mL) at 0° C. After stirring for 30 minutes, bromobutene (2.89 g, 21.43 mmol, 1.92 mL) was added and the resulting solution was warmed to 90° C. and stirred an additional 4 h. The reaction mixture was diluted with ethyl acetate (200 mL) and washed successively with water (2×100 mL) and saturated aqueous sodium chloride (1×100 mL). After evaporating the organic layer to dryness the resulting residue was purified by combiflash (80 g silica column, eluted with 15-50% ethyl acetate in heptanes) to give diethyl 2-(benzyloxycarbonylamino)-2-(but-3-enyl)malonate (4.8 g, 67%). $^1$H NMR ($CDCl_3$) δ 7.36 (m, 5H), 7.26-6.93 (m, 1H), 6.20 (bs, 1H), 5.75 (m, 1H), 5.11 (s, 2H), 5.04-4.04 (m, 2H), 4.24 (m, 4H), 2.43 (m, 2H), 1.96-1.93 (m, 2H), 1.27-1.21 (m, 6H). MS found for $C_{19}H_{25}NO_6$ m/z [364 (M+$^1$)]

Step 2: 2-(benzyloxycarbonylamino)-2-(ethoxycarbonyl)hex-5-enoic acid

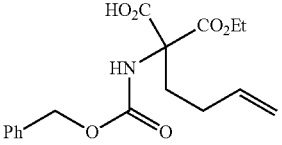 [SMILES: C=CCCC(NC(=O)OCc1ccccc1)(C(=O)O)C(=O)OCC]

A solution of diethyl 2-(benzyloxycarbonylamino)-2-(but-3-enyl)malonate (4.8 g, 13.23 mmol) in ethanol (45 mL) was cooled to −30° C. and treated with an aqueous solution of potassium hydroxide (1.55 g, 27.76 mmol in 15 mL water). After the addition was complete, the solution was warmed to 0° C. for 30 minutes followed by room temperature for 1 h. With the reaction complete, the mixture was acidified with AcOH (1.8 g) and extracted with ethyl acetate (1×50 mL). The aqueous layer was acidified to pH 3 with 3 N hydrochloric acid and extracted with ethyl acetate (2×50 mL). The combined organic layers were washed with saturated aqueous sodium chloride (1×50 mL), dried over $MgSO_4$ and concentrated to give 2-(benzyloxycarbonylamino)-2-(ethoxycarbonyl)hex-5-enoic acid (3.0 g, 68%). $^1$H NMR ($CDCl_3$) δ 10.00 (bs, 1H), 7.37 (m, 5H), 7.26-6.93 (m, 1H), 6.21 (bs, 1H), 5.76 (m, 1H), 5.94-5.22 (m, 4H), 4.27 (m, 2H) 2.43 (m, 2H), 1.96-1.93 (m, 2H), 1.27-1.21 (m, 3H). MS found for $C_{17}H_{21}NO_6$ m/z [336 (M+1)].

Step 3: ethyl 2-(benzyloxycarbonylamino)-2-(hydroxymethyl)hex-5-enoate

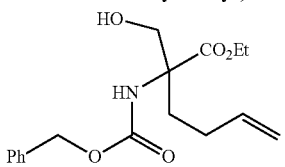

A solution of 2-(benzyloxycarbonylamino)-2-(ethoxycarbonyl)hex-5-enoic acid (1.54 g, 4.6 mmol) and triethylamine (557 mg, 5.52 mmol, 0.76 mL) in tetrahydrofuran (10 mL) was cooled to −30° C. and treated with ethyl chloroformate (522 mg, 4.82 mmol, 0.46 mL) and stirred for 30 minutes. A solution of sodium borohydride (175 mg, 4.6 mmol) in water (2 mL) was added and the mixture was stirred for 30 minutes. Once the reaction was complete, 3 N hydrochloric acid (1 mL) was added and the mixture was diluted with ethyl acetate (50 mL), washed with water (1×50 mL) and extracted with ethyl acetate (1×50 mL). The combined organic layers were concentrated and purified using a combiflash system (2×12 g silica gel column, eluting with 10-50% ethyl acetate in heptanes) to give ethyl 2-(benzyloxycarbonylamino)-2-(hydroxymethyl)hex-5-enoate (700 mg, 48%). $^1$H NMR (CDCl$_3$) δ 7.29 (m, 5H), 5.82 (bs, 1H), 5.68-5.62 (m, 1H), 5.03 (s, 1H), 4.94-4.86 (m, 2H), 4.17 (m, 2H) 3.76 (dd, J=11.4 Hz, 1H), 1.97 (m, 2H), 1.77 (m, 2H), 1.21 (t, J=7.2 Hz, 3H). MS found for C$_{17}$H$_{23}$NO$_5$ m/z [322 (M+1)].

Step 4: 3-benzyl 4-ethyl 4-(but-3-enyl)-2,2-dimethyloxazolidine-3,4-dicarboxylate

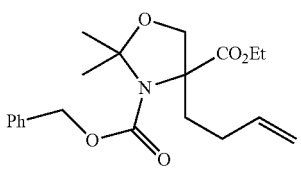

A solution of the ethyl 2-(benzyloxycarbonylamino)-2-(hydroxymethyl)hex-5-enoate 4 (820 mg, 2.55 mmol) in toluene (10 mL) was treated with 2,2-dimethoxy propane (2 mL) and 4-toluenesulfonic acid (100 mg). The mixture was heated under reflux for 1 h, cooled, concentrated and purified using a combiflash system (12 g silica gel column, eluting with 5-50% of ethyl acetate in heptanes) to give 3-benzyl 4-ethyl 4-(but-3-enyl)-2,2-dimethyloxazolidine-3,4-dicarboxylate (530 mg, 57%). $^1$H NMR (CDCl$_3$) δ 7.36 (m, 5H), 5.75 (m, 1H), 4.51 (m, 4H), 4.06 (m, 4H) 2.08 (m, 4H), 1.65 (2 s, 6H), 1.13 (t, J=7.1 Hz, 3H). MS found for C$_{20}$H$_{27}$NO$_5$ m/z [332 (M+1)].

Step 5: 3-benzyl 4-ethyl 2,2-dimethyl-4-(4-(4,4,5,5-tetramethyl-1,3,2-dioxaborolan-2-yl)butyl)oxazolidine-3,4-dicarboxylate

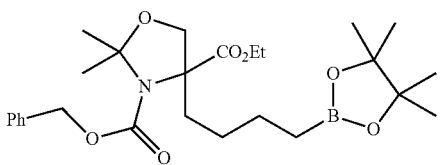 [SMILES: CCOC(=O)C1(CCCCB2OC(C)(C)C(C)(C)O2)COC(C)(C)N1C(=O)OCc1ccccc1]

While under an argon atmosphere, a solution of chloro(1,5-cyclooctadiene) iridium(I) dimer (15 mg, 0.022 mmol) and 1,2-bis(diphenyl-phosphino) ethane (18 mg, 0.044 mmol) in dichloromethane (5 mL) was treated with pinacol borane (225 mg, 1.76 mmol, 0.26 mL) and stirred for 15 minutes. To this mixture was added a solution of 3-benzyl 4-ethyl 4-(but-3-enyl)-2,2-dimethyloxazolidine-3,4-dicarboxylate (530 mg, 1.47 mmol) in dichloromethane (5 mL). After stirring for 19 h at room temperature the solution was concentrated and purified using a combiflash system (24 g column, eluting with 5-50% (ethyl acetate in heptanes) to give 3-benzyl 4-ethyl 2,2-dimethyl-4-(4-(4,4,5,5-tetramethyl-1,3,2-dioxaborolan-2-yl)butyl)oxazolidine-3,4-dicarboxylate (470 mg, 65%). $^1$H NMR (CDCl$_3$) δ: 7.22 (m, 5H), 5.01 (m, 2H), 3.91 (m, 4H), 2.20-2.01 (m, 1H), 1.75 (m, 1H), 1.51 (2s, 6H), 1.29 (m, 4H), 1.16 (s, 12H), 1.02 (t, J=7.2 Hz, 3H), 0.69 (t, 2H). MS found for C$_{26}$H$_{40}$BNO$_7$ m/z [490 (M+1), 522 (M+Na)].

Step 6: ethyl 2-(benzyloxycarbonylamino)-2-(hydroxymethyl)-6-(4,4,5,5-tetramethyl-1,3,2-dioxaborolan-2-yl)hexanoate

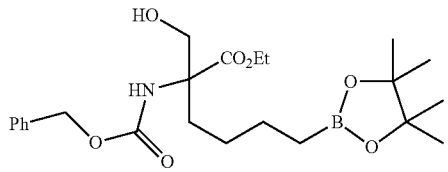 [SMILES: CCOC(=O)C(CO)(CCCCB1OC(C)(C)C(C)(C)O1)NC(=O)OCc1ccccc1]

While under an argon atmosphere, a solution of 3-benzyl 4-ethyl 2,2-dimethyl-4-(4-(4,4,5,5-tetramethyl-1,3,2-dioxaborolan-2-yl)butyl)oxazolidine-3,4-dicarboxylate (350 mg, 0.72 mmol) in dichloromethane (5 mL) was cooled to −40° C. and carefully treated with trimethylsilyltrifluoromethane sulfonate (1.09 g, 4.29 mmol, 0.94 mL). After stirring for 30 minutes the solution was warmed to 0° C. and stirred an additional 2 h, concentrated and purified using a combiflash system (12 g silica gel column, eluting with 20-100% ethyl acetate in heptanes) to give ethyl 2-(benzyloxycarbonylamino)-2-(hydroxymethyl)-6-(4,4,5,5-tetramethyl-1,3,2-dioxaborolan-2-yl)hexanoate (180 mg, 56%). $^1$HNMR (CDCl$_3$) δ 7.38-7.31 (m, 5H), 5.81 (bs, 1H), 5.10 (s, 2H), 4.25-4.23 (m, 3H), 3.84 (d, 1H), 2.84 (m, 1H), 1.76-1.68 (m, 1H), 1.41-1.35 (m, 2H), 1.28 (t, 3H), 1.23 (s, 12H), 1.11-1.03 (m, 1H), 1.29 (m, 4H), 0.75 (t, 2H). MS found for C$_{23}$H$_{36}$BNO$_7$ m/z [450 (M+1)].

Step 7: ethyl 2-(benzyloxycarbonylamino)-2-formyl-6-(4,4,5,5-tetramethyl-1,3,2-dioxaborolan-2-yl)hexanoate

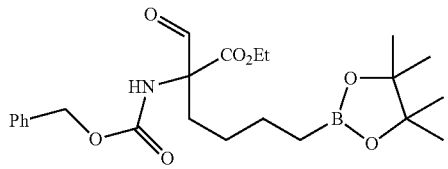 [SMILES: CCOC(=O)C(C=O)(CCCCB1OC(C)(C)C(C)(C)O1)NC(=O)OCc1ccccc1]

While under an argon atmosphere, a solution of oxalyl chloride (1.56 g, 12.4 mmol, 0.98 mL) in dichloromethane (15 mL) was cooled to −78° C. and treated with dimethyl sulfoxide (1.94 g, 1.8 mL, 24.84 mmol) and stirred for 10 minutes. To this mixture ethyl 2-(benzyloxycarbonylamino)-2-(hydroxymethyl)-6-(4,4,5,5-tetramethyl-1,3,2-dioxaborolan-2-yl)hexanoate (2.79 g, 6.21 mmol) in anhydrous dichloromethane (15 mL) was added and the mixture was stirred for 30 minutes. The reaction mixture was quenched by adding triethylamine (3.76 g, 5.2 mL, 37.26 mmol) at −78° C. and slowly warming the reaction mixture to room temperature. The mixture was diluted with dichloromethane (25 mL) and washed successively with water (2×25 mL) and saturated aqueous sodium chloride (25 mL). Organic layer was dried over magnesium sulfate, filtered and evaporated to dryness. The resulting residue was purified using a combiflash system (40 g column, eluted with 20-40% ethyl acetate in heptanes) to give ethyl 2-(benzyloxycarbonylamino)-2-formyl-6-(4,4,5,5-tetramethyl-1,3,2-dioxaborolan-2-yl)hexanoate (2.4 g, 86%). $^1$H NMR (CDCl$_3$) δ: 9.49 (s, 1H), 7.28 (m, 5H), 5.85 (bs, 1H), 5.03 (s, 2H), 4.17, 2.17-2.09 (m, 2H), 1.38-1.28 (m, 4H), 1.25-1.20 (m, 5H), 1.19 (s, 12H), 0.68 (t, J=7.8 Hz, 2H). MS found for C$_{23}$H$_{34}$BNO$_7$ m/z [471(M+Na)].

Step 8: ethyl 2-(benzyloxycarbonylamino)-2-(piperidin-1-ylmethyl)-6-(4,4,5,5-tetramethyl-1,3,2-dioxaborolan-2-yl)hexanoate

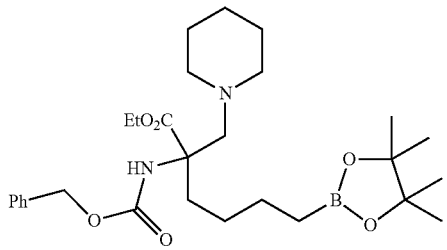 [SMILES: CCOC(=O)C(CCCCB1OC(C)(C)C(C)(C)O1)(CN1CCCCC1)NC(=O)OCc1ccccc1]

A solution of ethyl 2-(benzyloxycarbonylamino)-2-formyl-6-(4,4,5,5-tetramethyl-1,3,2-dioxaborolan-2-yl)hexanoate (0.503 g, 1.13 mmol), piperidine (0.39 mL, 4 mmol) and acetic acid (0.23 mL, 4 mmol) in 1,2-dichloroethane (20 mL) was stirred for 15 minutes then treated with sodium triacetoxyborohydride (0.85 g, 4 mmol). After stirring for 2 h at 65° C. the solution was cooled to room temperature and concentrated. The resulting residue was purified using a combiflash system (12 g silica gel column, 10-100% ethyl acetate in heptanes) to give ethyl 2-(benzyloxycarbonylamino)-2-(piperidin-1-ylmethyl)-6-(4,4,5,5-tetramethyl-1,3,2-dioxaborolan-2-yl)hexanoate (300 mg, 52%). $^1$H NMR (CDCl$_3$) δ: 7.36 (m, 5H), 6.05 (bs, 1H), 5.14 (d, 1H), 5.03 (d, J=11.2 Hz, 1H), 4.19 (m, 2H), 3.06 (d, J=13.8 Hz, 1H,), 2.59 (d, J=13.8 Hz, 1H), 2.34 (m, 4H), 2.15 (m, 1H), 1.78-1.70 (m, 1H), 1.45-1.25 (m, 12H), 1.22 (s, 12H), 1.02 (m, 1H), 0.73 (t, J=7.8 Hz, 2H). MS found for C$_{28}$H$_{45}$BN$_2$O$_7$ m/z[517(M+1)].

Step 9: 2-amino-6-borono-2-(piperidin-1-ylmethyl)hexanoic acid dihydrochloride

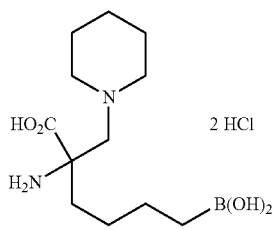

(79)

A solution of ethyl 2-(benzyloxycarbonylamino)-2-(piperidin-1-ylmethyl)-6-(4,4,5,5-tetramethyl-1,3,2-dioxaborolan-2-yl)hexanoate (0.26 g, 0.51 mmol) in 6 N HCl (20 mL) was heated to a gentle reflux for 48 h. After cooling to room temperature, the solution was washed with dichloromethane (5×15 mL) and concentrated (aqueous layer). The resulting residue was dissolved in water (3 mL) and passed through cation exchange resin Dowex 50-200 eluted with 2 N ammonia (4 g resin was loaded on a column, washed successively with water, 1 N HCl, water to neutral pH, 2 N ammonia solution and water to neutral pH). Fractions containing product were concentrated, diluted with minimal water, acidified with 6 N HCl, frozen and lyophilized to give 2-amino-6-borono-2-(piperidin-1-ylmethyl)hexanoic acid dihydrochloride. (60 mg, 43%). $^1$H NMR (D$_2$O) δ 3.64-3.53 (m, 1H), 3.34 (d, J=13.9 Hz, 1H), 3.05-3.03 (m, 2H), 2.93-2.91 (m, 3H), 1.76-1.67 (m, 5H), 1.53-1.46 (m, 3H), 1.31-1.30 (m, 3H), 1.09-1.07 (m, 1H), 0.70 (t, J=7.3 Hz, 2H). MS found for C$_{12}$H$_{25}$BN$_2$O$_4$ m/z[254(M−18+1)].

Example 80

Preparation of 2-amino-6-borono-2-((4-methylpiperazin-1-yl)methyl) hexanoic acid trihydrochloride

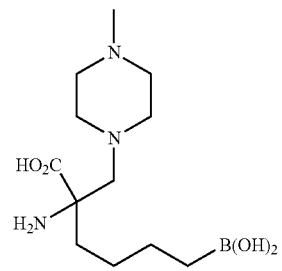

(80)

2-Amino-6-borono-2-((4-methylpiperazin-1-yl)methyl)hexanoic acid dihydrochloride is prepared in a manner analogous to that set forth in Example 79, except 1-methylpiperazine is used as the amine in step 8. The final compound was isolated as the trihydrochloride salt. $^1$HNMR (D$_2$O) δ 2.93 (d, J=14.2 Hz, 1H), 2.64 (bs 1H), 2.50 (d, J=14.3 Hz, 1H), 2.33 (s, 3H), 1.77-1.65 (m, 1H), 1.50-1.43 (m, 1H), 1.33-1.30 (m, 3H), 1.15-1.05 (m, 1H), 0.69 (t, J=8.2 Hz, 2H). MS found for C$_{12}$H$_{26}$BN$_3$O$_4$ m/z[270(M−18+1)].

Example 81

Preparation of 2-amino-6-borono-2-(morpholinomethyl)hexanoic acid dihydrochloride

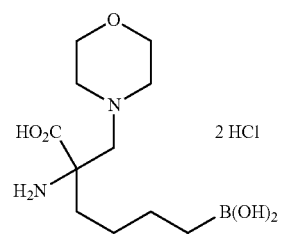

(81)

2-Amino-6-borono-2-(morpholinomethyl)hexanoic acid dihydrochloride is prepared in a manner analogous to that set forth in Example 79, except morpholine is used as the amine in step 8. The final compound was isolated as the dihydrochloride salt. $^1$H NMR (D$_2$O) δ 3.65 (m, 4H), 2.95 (d, J=14.3 Hz, 1H), 2.62-2.56 (m, 2H), 2.49 (d, J=14.4 Hz, 1H), 2.47-2.41 (m, 2H), 1.80-1.70 (m, 1H), 1.54-1.47 (m, 1H), 1.34-

1.32 (m, 3H), 1.16-1.12 (m, 1H), 0.72 (t, J=8.1 Hz, 2H). MS found for $C_{12}H_{23}BN_2O_5$ m/z[257.1 (M−18+1)].

Example 82

Preparation of 2-amino-6-borono-2-(hydroxymethyl)hexanoic acid hydrochloride

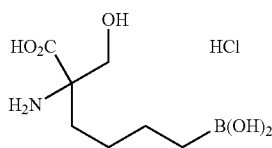

(82)

2-Amino-6-borono-2-(hydroxymethyl)hexanoic acid hydrochloride is prepared in a manner analogous to that set forth in Example 79, except in step 8 sodium borohydride is used instead of sodium triacetoxyborohydride and no amine is used. The final compound was isolated as the hydrochloride salt. $^1$HNMR ($D_2O$) δ 3.81 (d, J=12.0 Hz, 1H), 3.55 (d, J=12.0 Hz, 1H), 1.73-1.52 (m, 2H), 1.39-1.06 (m, 4H), 0.67 (t, J=7.4 Hz, 2H). MS found for $C_7H_{16}BNO_5$ m/z[188.1 (M−18+1)].

Example 83

Preparation of 2-amino-6-borono-2-((propylamino)methyl)hexanoic acid dihydrochloride

Step 1: diethyl 2-(but-3-enyl)-2-(tert-butoxycarbonylamino)malonate

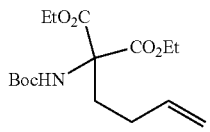

To a suspension of sodium hydride (8.7 g, 218 mmol, 60% suspension) in dimethylformaamide (250 mL) at 0° C. was added diethyl 2-(tert-butoxycarbonylamino)malonate (50.0 g, 182 mmol) in dimethylformaamide (250 mL). After stirring for 30 minutes, 4-bromobut-1-ene (29.5 g, 218 mmol, 22.2 mL) was added and the mixture was warmed to 90° C. After stirring an additional 4 h, the solution was cooled to room temperature and the solvents were removed by evaporation. The resulting residue was diluted with ethyl acetate (1.0 L), washed successively with water (2×250 mL), saturated aqueous sodium chloride (1×200 mL) and concentrated. Purification using a combiflash system (330 g silica column, eluted with 15-50% ethyl acetate in heptanes) gave diethyl 2-(but-3-enyl)-2-(tert-butoxycarbonylamino)malonate (54 g, 90%). $^1$H NMR ($CDCl_3$) δ 5.92 (bs, 1H), 5.79-5.71 (m, 1H), 5.03-4.93 (m, 2H), 4.24-4.19 (m, 4H), 2.36 (m, 2H), 1.96-1.93 (m, 2H), 1.42 (s, 9H), 1.27-1.24 (m, 6H).

Step 2: 2-(tert-butoxycarbonylamino)-2-(ethoxycarbonyl)hex-5-enoic acid

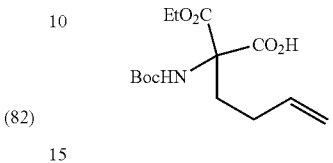

A solution of the diethyl 2-(but-3-enyl)-2-(tert-butoxycarbonylamino)malonate (10.0 g, 30.4 mmol) in ethanol (100 mL) was cooled to 0° C. and treated with aqueous sodium hydroxide (1 N, 31 mL). After stirring for 30 minutes, the cooling bath was removed and stirring was continued for an additional 19 h. The solvent was removed by evaporation and the resulting residue was diluted with water (150 mL) and washed with ethyl acetate (2×100 mL). The aqueous layer was acidified with concentrated hydrochloric acid to pH 2 and extracted with ethyl acetate (2×150 mL). The combined organic layers were washed with saturated aqueous sodium chloride (1×100 mL), dried over $MgSO_4$, filtered and concentrated to give 2-(tert-butoxycarbonylamino)-2-(ethoxycarbonyl)hex-5-enoic acid (8.2 g, 82%). $^1$H NMR ($CDCl_3$) δ 5.87-5.75 (m, 1H), 5.06-5.02 (m, 2H), 4.26 (m, 2H), 2.34 (m, 2H), 1.96-1.93 (m, 2H), 1.43 (s, 9H), 1.29 (m, 3H).

Step 3: ethyl 2-(tert-butoxycarbonylamino)-2-(hydroxymethyl)hex-5-enoate

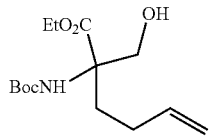 [SMILES: C=CCCC(CO)(NC(=O)OC(C)(C)C)C(=O)OCC]

A solution of the 2-(tert-butoxycarbonylamino)-2-(ethoxycarbonyl)hex-5-enoic acid (7.5 g, 24.9 mmol) and triethylamine (3.01 g, 29.9 mmol, 4.15 mL) in THF (10 mL) was cooled to −40° C. and treated with ethyl chloroformate (2.97 g, 27.4 mmol, 2.65 mL). After stirring for 30 minutes, the precipitate (triethylamine hydrochloride) was removed by filtration and the filtrate was collected and cooled to −40° C. A solution of sodiumborohydride (950 mg, 24.9 mmol) in water (10 mL) was added and the resulting solution was stirred for 30 minutes. After quenching the reaction mixture with 3 N hydrochloric acid (5 mL), the mixture was diluted with ethyl acetate (150 mL), washed with water (1×50 mL) and extracted with ethyl acetate (1×150 mL). The combined organic layers were concentrated, dried over $MgSO_4$, filtered and purified using a combiflash system (80 g silica gel column, eluting with 10-50% ethyl acetate in heptanes) to give ethyl 2-(tert-butoxycarbonylamino)-2-(hydroxymethyl)hex-5-enoate (5.6 g, 78%). $^1$H NMR ($CDCl_3$) δ 5.71-5.62 (m, 1H), 5.52 (bs, 1H), 4.96-4.87 (m, 2H), 4.20-4.12 (m, 2H) 4.07-4.03 (m, 2H), 3.73 (d, J=12.0 Hz, 1H), 2.22-1.62 (m, 4H), 1.37 (m, 9H), 1.22 (t, J=7.2 Hz, 3H).

Step 4: ethyl 2-(acetoxymethyl)-2-(tert-butoxycarbonylamino)hex-5-enoate

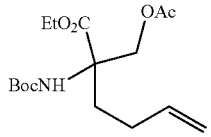 [SMILES: C=CCCC(COC(C)=O)(NC(=O)OC(C)(C)C)C(=O)OCC]

A solution of the ethyl 2-(tert-butoxycarbonylamino)-2-(hydroxymethyl)hex-5-enoate (10.0 g, 35 mmol) and dimethylaminopyridine (4.48 g, 35 mmol) in dichloromethane (100 mL) was treated with acetic anhydride and stirred at room temperature overnight. The solution was concentrated and the resulting residue purified using a combiflash system (89 g column, eluting with 20-50% ethyl acetate in heptanes) to give ethyl 2-(acetoxymethyl)-2-(tert-butoxycarbonylamino)hex-5-enoate (10 g, 80%). $^1$H NMR (CDCl$_3$) δ 5.78-5.68 (m, 1H), 5.55 (bs, 1H), 5.03-4.93 (m, 2H), 4.73 (d, J=11.0 Hz, 1H) 4.32 (d, J=11.0 Hz, 1H,), 4.20 (q, J=7.2 Hz, 2H), 2.36 (m, 1H), 2.07-2.05 (m, 1H), 2.02 (s, 3H), 1.89-1.75 (m, 2H), 1.43 (m, 9H), 1.27 (t, J=7.2 Hz, 3H). MS found for C$_{16}$H$_{27}$NO$_6$ m/z[330(M+1)].

Step 5: ethyl 2-(acetoxymethyl)-2-(tert-butoxycarbonylamino)-6-(4,4,5,5-tetramethyl-1,3,2-dioxaborolan-2-yl)hexanoate

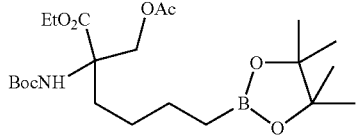 [SMILES: CCOC(=O)C(CCCCB1OC(C)(C)C(C)(C)O1)(COC(C)=O)NC(=O)OC(C)(C)C]

While under an argon atmosphere, a solution of chloro(1,5-cyclooctadiene)iridium(I) dimer (160 mg, 0.23 mmol) and 1,2-bis(diphenyl-phosphino) ethane (190 mg, 0.48 mmol) in dichloromethane (50 mL) was treated with pinacol borane (7.78 g, 61 mmol, 8.8 mL) and stirred for 15 minutes. To this mixture was added a solution of ethyl 2-(acetoxymethyl)-2-(tert-butoxycarbonylamino)hex-5-enoate (10 g, 30.4 mmol) in dichloromethane (50 mL). After stirring for 19 h at room temperature the solution was concentrated and purified using a combiflash system (120 g column, eluting with 5-50% ethyl acetate in heptanes) to give ethyl 2-(acetoxymethyl)-2-(tert-butoxycarbonylamino)-6-(4,4,5,5-tetramethyl-1,3,2-dioxaborolan-2-yl)hexanoate (7.5 g, 54%). $^1$H NMR (CDCl$_3$) δ 5.49 (bs, 1H), 4.72 (d, 1H), 4.33 (d, 1H), 4.23 (q, 2H), 2.18 (m, 1H), 2.01 (s, 3H), 1.69 (m, 2H), 1.43 (s, 9H), 1.29 (m, 4H), 1.23 (s, 12H), 0.88 (t, 3H), 0.74 (t, 2H). MS found for C$_{22}$H$_{40}$BNO$_8$ m/z [480(M+Na)].

Step 6: ethyl 2-(tert-butoxycarbonylamino)-2-(hydroxymethyl)-6-(4,4,5,5-tetramethyl-1,3,2-dioxaborolan-2-yl)hexanoate

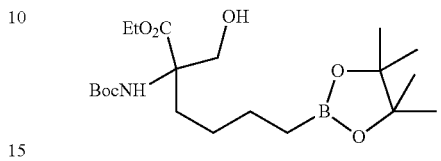

A solution of ethyl 2-(acetoxymethyl)-2-(tert-butoxycarbonylamino)-6-(4,4,5,5-tetramethyl-1,3,2-dioxaborolan-2-yl)hexanoate (12.0 g, 26.3 mmol) in ethanol (100 mL) was treated with solid potassium carbonate (3.62 g, 26.3 mmol) and stirred for 2 h. The solution was filtered and the filtrate was evaporated to dryness. The resulting residue was dissolved in ethyl acetate (150 mL) and washed successively with water (50 mL) and saturated aqueous sodium chloride (50 mL). Organic layer was concentrated and purified using a combiflash system (120 g column, eluting with 20-30% ethyl acetate in heptanes) to give ethyl 2-(tert-butoxycarbonylamino)-2-(hydroxymethyl)-6-(4,4,5,5-tetramethyl-1,3,2-dioxaborolan-2-yl)hexanoate (7.0 g, 78%). $^1$H NMR (CDCl$_3$) δ 5.25 (bs, 1H), 4.00 (m, 2H), 3.91 (d, J=11.3 Hz, 1H), 3.60 (d, J=11.3 Hz, 1H), 1.53-1.46 (m, 1H), 1.23 (s, 9H), 1.21-1.15 (m, 1H), 1.06 (m, 7H), 1.03 (s, 12H), 0.90 (m, 1H), 0.54 (t, J=7.8 Hz, 2H). MS found for C$_{20}$H$_{38}$BNO$_7$ m/z[438(M+Na)]

Step 7: ethyl 2-(tert-butoxycarbonylamino)-2-formyl-6-(4,4,5,5-tetramethyl-1,3,2-dioxaborolan-2-yl)hexanoate

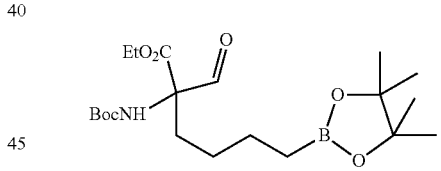

While under an argon atmosphere, a solution of oxalyl chloride (1.46 g, 0.88 mL, 11.6 mmol) in dichloromethane (15 mL) was cooled to −78° C. and treated with dimethyl sulfoxide (1.8 g, 1.64 mL, 23.2 mmol) and stirred for 10 minutes. To this mixture ethyl 2-(tert-butoxycarbonylamino)-2-(hydroxymethyl)-6-(4,4,5,5-tetramethyl-1,3,2-dioxaborolan-2-yl)hexanoate (2.4 g, 5.78 mmol) in anhydrous dichloromethane (15 mL) was added and the mixture was stirred for 30 minutes. The reaction mixture was quenched by adding triethylamine (3.5 g, 4.8 mL, 34.7 mmol) at −78° C. and slowly warming the reaction mixture to room temperature. The mixture was diluted with dichloromethane (25 mL) and washed successively with water (2×25 mL) and saturated aqueous sodium chloride (25 mL). Organic layer was dried over magnesium sulfate, filtered and evaporated to dryness. The resulting residue was purified using a combiflash system (40 g column, eluted with 20-40% ethyl acetate in heptanes) to give ethyl 2-(tert-butoxycarbonylamino)-2-formyl-6-(4,4,5,5-tetramethyl-1,3,2-dioxaborolan-2-yl)hexanoate (1.35 g, 57%). $^1$HNMR (CDCl$_3$) δ 9.58 (s, 1H), 5.64 (bs, 1H), 4.25 (m, 2H), 2.13 (m, 2H), 1.45 (m, 9H), 1.28 (m, 4H), 1.24 (s, 12H), 0.88 (t, J=6.4 Hz, 3H), 0.77 (t, J=7.9 Hz, 2H). MS found for $C_{20}H_{36}BNO_7$ m/z[436(M+Na)].

Step 8: ethyl 2-(tert-butoxycarbonylamino)-2-((propylamino)methyl)-6-(4,4,5,5-tetramethyl-1,3,2-dioxaborolan-2-yl)hexanoate

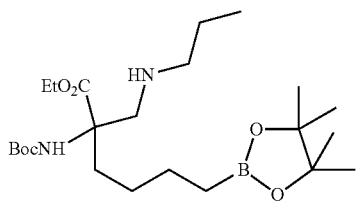 [SMILES: CCCNCC(CCCCB1OC(C)(C)C(C)(C)O1)(NC(=O)OC(C)(C)C)C(=O)OCC]

A slurry of ethyl 2-(tert-butoxycarbonylamino)-2-formyl-6-(4,4,5,5-tetramethyl-1,3,2-dioxaborolan-2-yl)hexanoate (172 mg, 0.42 mmol) and propylamine (40 μL, 0.49 mmol, 1.3 equiv) in 1,2-dichloroethane (3 mL) was treated with sodium triacetoxyborohydride (352 mg, 1.66 mmol, 4 equiv). Acetic acid (2 drops, ca 3-5 equiv) was added and the mixture stirred at room temperature for 17 hours then 60° C. for 1 hour. Once the reaction was complete, saturated aqueous sodium bicarbonate was added and the solution was extracted with dichloromethane. The organic extracts were washed with saturated aqueous NaCl, dried over MgSO4, filtered and concentrated. Purification by flash chromatography (0-60% ethyl acetate in hexane) gave ethyl 2-(tert-butoxycarbonylamino)-2-((propylamino)methyl)-6-(4,4,5,5-tetramethyl-1,3,2-dioxaborolan-2-yl)hexanoate as an oil (66 mg, 34%). $^1$H NMR (CDCl$_3$, 400 MHz) δ 4.16 (m, 2H), 3.5-3.3 (m, 2H), 3.2 (br m, 2H), 2.9 (m, 1H), 1.8-1.6 (m, 4H), 1.5-1.4 (m, 2H), 1.38 (s, 9H), 1.36-1.3 (m, 3H), 1.22 (t, J=7.2 Hz, 3H), 1.18 (s, 12H), 1.05 (m, 1H), 0.75 (t, J=7.4 Hz, 3H), 0.68 (t, J=7.5 Hz, 2H). ESI$^+$ MS: obsd m/z 457 (M+H)$^+$.

Step 9: 2-amino-6-borono-2-((propylamino)methyl)hexanoic acid (83)

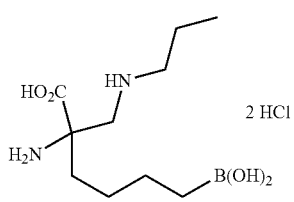

A solution of ethyl 2-(tert-butoxycarbonylamino)-2-((propylamino)methyl)-6-(4,4,5,5-tetramethyl-1,3,2-dioxaborolan-2-yl)hexanoate (66 mg, 0.14 mmol) in 6 N HCl (5 mL) and 1,4-dioxane (1 mL) was heated at 100° C. for 16 hrs. After cooling to room temperature, the reaction mixture was transferred to a separatory funnel, diluted with deionized water (5 mL) and washed with dichloromethane (6×25 mL). The aqueous layer was frozen (dry ice/acetone) and lyophilized to give 2-amino-6-borono-2-((propylamino)methyl)hexanoic acid as a dihydrochloride salt (40 mg). $^1$H NMR (D$_2$O, 400 MHz) δ 3.33 (d$_{AB}$, J$_{AB}$=13.7 Hz, 1H), 3.21 (d$_{AB}$, J$_{AB}$=13.7 Hz, 1H), 2.91-2.78 (m, 2H), 1.88-1.75 (m, 1H), 1.70-1.60 (m, 1H), 1.54-1.38 (m, 2H), 1.24-1.08 (m, 3H), 1.05-0.92 (m, 1H), 0.75-0.61 (m, 3H), 0.55-0.45 (m, 2H). ESI$^+$ MS: obsd m/z 229.1 (M−18H)$^+$, 211.1 (M−36+H)$^+$, ESI-MS: 227.1 (M−18−1)$^-$.

Example 84

Preparation of 2-amino-2-((benzylamino)methyl)-6-boronohexanoic acid (84)

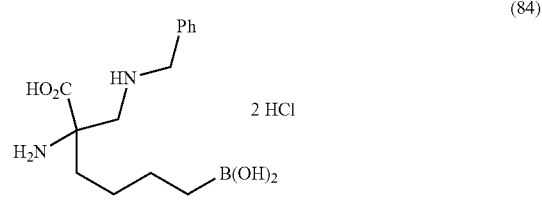 [SMILES: NC(CCCCB(O)O)(CNCc1ccccc1)C(=O)O]

2-Amino-2-((benzylamino)methyl)-6-boronohexanoic acid dihydrochloride is prepared in a manner analogous to that set forth in Example 83, except benzylamine is used as the amine in step 8. The final compound was isolated as the dihydrochloride salt. $^1$H NMR (D$_2$O, 400 MHz) δ 7.47-7.27 (m, 5H), 3.85 (d$_{AB}$, J$_{AB}$=13.4 Hz, 1H), 3.80 (d$_{AB}$, J$_{AB}$=13.4 Hz, 1H), 3.05 (d$_{AB}$, J$_{AB}$=13.2 Hz, 1H), 2.69 (d$_{AB}$, J$_{AB}$=13.2 Hz, 1H), 1.76-1.64 (m, 1H), 1.58-1.46 (m, 1H), 1.37-1.18 (m, 3H), 1.17-1.02 (m, 1H), 0.68 (t, J=7.8 Hz, 2H). ESI$^+$ MS: obsd m/z 277.1 (M−18+H)$^+$, 259.1 (M−36+H)$^+$, ESI-MS: 275.1 (M−18−1)$^-$.

Example 85

Preparation of 2-amino-6-borono-2-(((R)-2-hydroxypropylamino)methyl) hexanoic acid dihydrochloride (85)

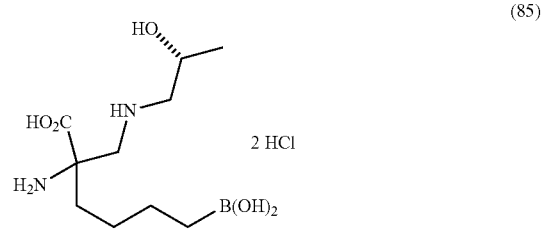 [SMILES: C[C@@H](O)CNCC(N)(CCCCB(O)O)C(=O)O]

2-Amino-6-borono-2-(((R)-2-hydroxypropylamino)methyl)hexanoic acid dihydrochloride is prepared in a manner analogous to that set forth in Example 83, except (R)-1-aminopropan-2-ol is used as the amine in step 8. The final compound was isolated as the dihydrochloride salt. $^1$H NMR (D$_2$O, 400 MHz) δ 3.89-3.80 (m, 1H), 3.70-3.40 (m, 4H), 3.31 (d$_{AB}$, J$_{AB}$=12.7 Hz, 1H), 2.05-1.93 (m, 1H), 1.87-1.74

(m, 1H), 1.48-1.35 (m, 3H), 1.33-1.18 (m, 3H), 0.77 (t, J=7.8 Hz, 2H). ESI⁺ MS: obsd m/z 227.1 (M−36+H)⁺, 243.1 (M−18−1)⁻.

Example 86

Preparation of 2-amino-6-borono-2-((butylamino)methyl)hexanoic acid dihydrochloride

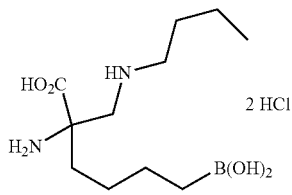

(86)

2-Amino-6-borono-2-((butylamino)methyl)hexanoic acid dihydrochloride is prepared in a manner analogous to that set forth in Example 83, except butan-1-amine is used as the amine in step 8. The final compound was isolated as the dihydrochloride salt. ¹H NMR (D₂O, 400 MHz) δ 3.38 (d$_{AB}$, J$_{AB}$=13.8 Hz, 1H), 3.24 (d$_{AB}$, J$_{AB}$=13.8 Hz, 1H), 3.10-2.94 (m, 2H), 1.92-1.82 (m, 1H), 1.75-1.65 (m, 1H), 1.65-1.53 (m, 2H), 1.40-1.21 (m, 4H), 1.22-1.1.08 (m, 1H), 0.68 (t, J=7.2 Hz, 2H). ESI⁺ MS: obsd m/z 243.1 (M−18+H)⁺, 225.1 (M−36+H)⁺, ESI-MS: 241.1 (M−18−1)⁻.

Example 87

Preparation of 2-amino-6-borono-2-((tetrahydro-2H-pyran-4-ylamino)methyl) hexanoic acid dihydrochloride

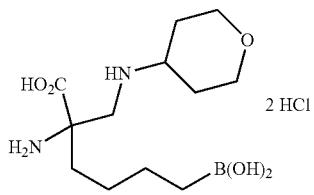

(87)

2-Amino-6-borono-2-((tetrahydro-2H-pyran-4-ylamino)methyl)hexanoic acid dihydrochloride is prepared in a manner analogous to that set forth in Example 83, except tetrahydro-2H-pyran-4-amine is used as the amine in step 8. The final compound was isolated as the dihydrochloride salt. ¹H NMR (D₂O, 400 MHz) δ 4.02-3.92 (m, 2H), 3.48-3.28 (m, 5H), 2.03-1.82 (m, 3H), 1.75-1.58 (m, 3H), 1.38-1.26 (m, 3H), 1.20-1.10 (m, 1H), 0.68 (t, J=7.2 Hz, 2H). ESI⁺ MS: obsd m/z 271.1 (M−18+H)⁺, 253.1 (M−36+H)⁺, ESI-MS: 269.1 (M−18−1)⁻.

Example 88

Preparation of 2-amino-6-borono-2-(((S)-1-hydroxy-4-methylpentan-2-ylamino)methyl)hexanoic acid dihydrochloride

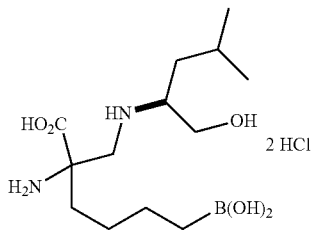

(88)

2-Amino-6-borono-2-(((S)-1-hydroxy-4-methylpentan-2-ylamino)methyl)hexanoic acid dihydrochloride is prepared in a manner analogous to that set forth in Example 83, except (R)-2-amino-4-methylpentan-1-ol is used as the amine in step 8. The final compound was isolated as the dihydrochloride salt. ¹H NMR (D₂O, 400 MHz) δ 3.87-3.70 (m, 1H), 3.65-3.48 (m, 1H), 3.46-3.40 (m, 1H), 3.39-3.33 (m, 1H), 3.33-3.27 (m, 1H), 3.24 (d$_{AB}$, J$_{AB}$=13.8 Hz, 1H), 1.95-1.85 (m, 1H), 1.77-1.65 (m, 1H), 1.62-1.52 (m, 1H), 1.50-1.40 (m, 2H), 1.39-1.27 (m, 3H), 1.20-1.08 (m, 1H), 0.86-0.78 (m, 6H), 0.68 (t, J=7.4 Hz, 2H). ESI⁺ MS: obsd m/z 269.1 (M−36+H)⁺, 285.1 (M−18−1)⁻.

Example 89

Preparation of 2-amino-6-borono-2-(((1R,2S)-2-hydroxy-1,2-diphenylethylamino)methyl) hexanoic acid dihydrochloride

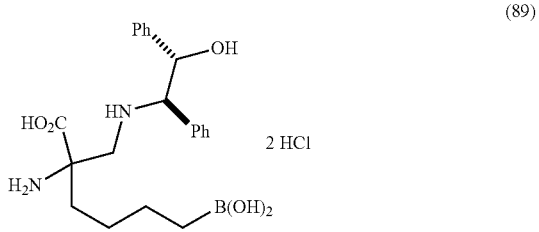 [SMILES: NC(CCCCB(O)O)(CN[C@H](c1ccccc1)[C@@H](O)c1ccccc1)C(=O)O]

(89)

2-Amino-6-borono-2-(((1R,2S)-2-hydroxy-1,2-diphenylethylamino)methyl) hexanoic acid dihydrochloride is prepared in a manner analogous to that set forth in Example 83, except (1S,2R)-2-amino-1,2-diphenylethanol is used as the amine in step 8. The final compound was isolated as the dihydrochloride salt. ¹H NMR (D₂O, 400 MHz) δ 7.46-7.00 (m, 10H), 5.37-5.04 (m, 1H), 4.57-4.46 (m, 1H), 3.35-2.85 (m, 2H), 1.96-1.82 (m, 1H), 1.76-1.60 (m, 1H), 1.56-1.44 (m, 1H), 1.39-1.26 (m, 2H), 1.26-0.87 (m, 2H), 0.74-0.56 (m, 2H). ESI⁺ MS: obsd m/z 383.1 (M−18+H)⁺, 365.1 (M−36+H)⁺, ESI-MS: 381.1 (M−18−1)⁻.

Example 90

Preparation of 2-amino-6-borono-2-(((S)-1-phenylethylamino)methyl) hexanoic acid dihydrochloride

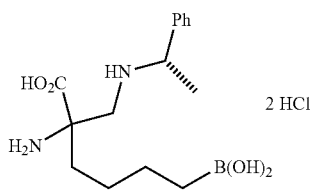

(90)

2-Amino-6-borono-2-(((S)-1-phenylethylamino)methyl) hexanoic acid dihydrochloride is prepared in a manner analogous to that set forth in Example 83, except (S)-1-phenylethanamine is used as the amine in step 8. The final compound was isolated as the dihydrochloride salt. $^1$H NMR (D$_2$O, 400 MHz) δ 7.48-7.32 (m, 5H), 4.50-4.37 (m, 1H), 3.30-3.12 (m, 1H), 3.08-2.98 (m, 1H), 1.92-1.70 (m, 1H), 1.68-1.54 (m, 4H), 1.37-1.17 (m, 3H), 1.18-0.96 (m, 1H), 0.73-0.55 (m, 2H). ESI⁺ MS: obsd m/z 291.1 (M−18+H)⁺.

Example 91

Preparation of 2-amino-6-borono-2-(((R)-1-hydroxypropan-2-ylamino)methyl)hexanoic acid dihydrochloride

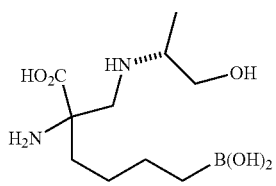

(91)

2-Amino-6-borono-2-(((R)-1-hydroxypropan-2-ylamino) methyl)hexanoic acid dihydrochloride is prepared in a manner analogous to that set forth in Example 83, except (R)-2-aminopropan-1-ol is used as the amine in step 8. The final compound was isolated as the dihydrochloride salt. $^1$H NMR (D$_2$O, 400 MHz) δ 4.07-3.87 (m, 2H), 3.80-3.71 (m, 1H), 3.51-3.27 (m, 2H), 3.17-3.02 (m, 1H), 2.99-2.80 (m, 1H), 1.95-1.81 (m, 1H), 1.79-1.65 (m, 1H), 1.45-1.35 (m, 1H), 1.32-1.18 (m, 2H), 1.15-0.90 (m, 3H), 0.61 (t, J=7.2 Hz, 2H). ESI⁺ MS: obsd m/z 227.1 (M−36+H)⁺.

Example 92

Preparation of 2-amino-6-borono-2-(2-(4-chlorophenoxy)ethyl)hexanoic acid hydrochloride Step 1: tert-butyl 4-(4-chlorophenoxy)-2-(diphenylmethyleneamino)butanoate

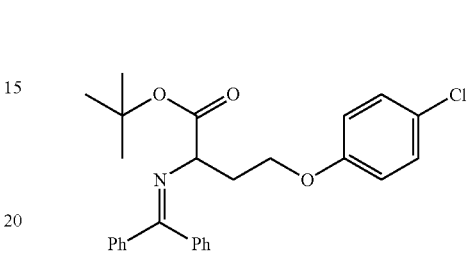

While under a nitrogen atmosphere, a solution of (benzhydrylidene-amino)-acetic acid tert-butyl ester (400 mg, 1.35 mmol) in tetrahydrofuran (7 mL) was cooled to −78° C. and treated with sodium bis(trimethylsilyl)amide (1.49 mL, 1.0 M in tetrahydrofuran, 1.49 mmol) in a dropwise manner. After the addition was complete, stirring was continued for 30 minutes and 1-(2-bromoethoxy)-4-chlorobenzene (398 mg, 1.69 mmol) was slowly added to the reaction mixture. Stirring was continued for 2 more hours, then slowly warmed to room temperature overnight. The resulting solution was poured into water, and extracted with ethyl acetate (3×). The combined organic phase was washed with saturated aqueous sodium chloride, dried over anhydrous magnesium sulfate, filtered and concentrated. Purification by flash column chromatography (silica gel, 0-20% ethyl acetate in heptane) gave tert-butyl 4-(4-chlorophenoxy)-2-(diphenylmethyleneamino)butanoate as a colorless oil (450 mg. 74%); MS (+CI): m/z for C$_{27}$H$_{28}$ClNO$_3$: expected 449.2. found 450.2 (M+H)⁺, 394.2 (M+H−isobutene)⁺.

Step 2: tert-butyl 2-(2-(4-chlorophenoxy)ethyl)-2-(diphenylmethyleneamino)-6-(4,4,5,5-tetramethyl-1,3,2-dioxaborolan-2-yl)hexanoate

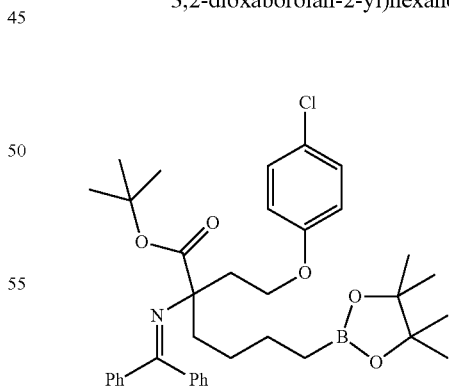

While under a nitrogen atmosphere, a solution of tert-butyl 4-(4-chlorophenoxy)-2-(diphenylmethyleneamino)butanoate (450 mg, 1.0 mmol) in tetrahydrofuran (7 mL) was cooled to −78° C. and treated with sodium bis(trimethylsilyl) amide (2.0 mL, 1.0 M in tetrahydrofuran, 2.0 mmol) in a dropwise manner. After the addition was complete, stirring was continued for 30 minutes and 2-(4-iodobutyl)-4,4,5,5- tetramethyl-[1,3,2]dioxaborolane (931 mg, 3.0 mmol) was slowly added to the reaction mixture. Stirring was continued for 2 more hours, and then slowly warmed to room temperature overnight. The resulting solution was poured into water, and extracted with ethyl acetate (3×). The combined organic phase was washed with saturated aqueous sodium chloride, dried over anhydrous magnesium sulfate, filtered and concentrated. Purification by flash column chromatography (silica gel, 0-15% ethyl acetate in heptane) gave tert-butyl 2-(2-(4-chlorophenoxy)ethyl)-2-(diphenylmethyleneamino)-6-(4,4,5,5-tetramethyl-1,3,2-dioxaborolan-2-yl)hexanoate as a colorless oil (486 mg. 77%); $^1$H NMR (CDCl$_3$, 300 MHz) $\delta_H$ 7.54 (d, J=7 Hz, 2H), 7.36 (m, 4H), 7.18-7.32 (m, 6H), 6.82 (d, J=9 Hz, 2H), 4.19 (m, 1H), 4.04 (m, 1H), 2.39 (ddd, J=14 Hz, J$_2$=9.5 Hz, J$_3$=5.0 Hz, 1H), 2.22 (ddd, J$_1$=13.5 Hz, J$_2$=9.5 Hz, J$_3$=5.0 Hz, 1H), 1.73 (m, 2H), 1.14-1.46 (m, 4H), 1.34 (s, 9H), 1.18 (s, 12H) and 0.76 (t, J=7 Hz, 2H); MS (+CI): m/z for C$_{37}$H$_{47}$BClNO$_5$: expected 631.3. found 632.3 (M+H)$^+$, 576.3 (M+H-isobutene)$^+$.

Step 3: 2-amino-6-borono-2-(2-(4-chlorophenoxy)ethyl)hexanoic acid

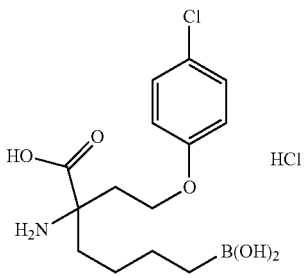

(92)

A solution of 2-(benzhydrylidene-amino)-2-[2-(4-chlorophenoxy)-ethyl]-6-(4,4,5,5-tetramethyl-[1,3,2]-dioxaborolan-2-yl)-hexanoic acid tert-butyl ester (486 mg) in 6 N HCl (6 ml) was warmed to 60° C. and stirred overnight. After cooling to room temperature, the reaction mixture was transferred to a separatory funnel, diluted with deionized water (6 ml) and washed with dichloromethane (3×). The aqueous layer was frozen in liquid nitrogen and lyophilized to give 2-amino-6-borono-2-(2-(4-chlorophenoxy)ethyl)hexanoic acid hydrochloride, as a colorless foam (125 mg, 85%); $^1$H NMR (D$^4$-MeOH, 300 MHz) $\delta_H$ 7.24 (2H, d, J=7 Hz, 2H), 6.94 (d, J=7 Hz, 2H), 4.18 (m, 2H), 2.52 (m, 1H), 2.46 (m, 1H), 1.92 (m, 2H), 1.22-1.52 (m, 4H) and 0.82 (t, J=7 Hz, 2H,); MS (+CI): m/z for C$_{14}$H$_{21}$BClNO$_5$: expected 329.1. found 330.2 (M+H)$^+$, 312.2 (M+H-H$_2$O)$^+$, 659.4 (2 M+H)$^+$, 641.4 (2 M+H-H$_2$O)$^+$.

Example 93

Preparation of 2-amino-6-borono-2-(2-(4-methoxyphenoxy)ethyl)hexanoic acid hydrochloride

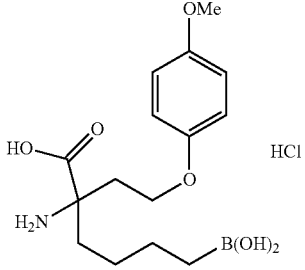

(93)

2-Amino-6-borono-2-(2-(4-methoxyphenoxy)ethyl)hexanoic acid hydrochloride is prepared in a manner analogous to that set forth in Example 92, except 1-(2-bromoethoxy)-4-methoxybenzene is used as the alkylating agent in step 1. $^1$H NMR (D$^4$-MeOH, 300 MHz) $\delta$ 6.91 (d, J=9 Hz, 2H), 6.85 (d, J=7 Hz, 2H), 4.12 (m, 2H), 3.74 (s, 3H), 2.46 (m, 1H), 2.34 (m, 1H), 1.96 (m, 2H), 1.22-1.66 (m, 4H) and 0.84 (t, J=7 Hz, 2H); MS (+CI): m/z for C$_{15}$H$_{24}$BClNO$_5$: expected 325.2. found 326.2 (M+H)$^+$, 308.2 (M+H-H$_2$O)$^+$.

Example 94

Preparation of 2-Amino-6-borono-2-[2-(2,4-dichlorophenoxy)-ethyl]-hexanoic acid hydrochloride

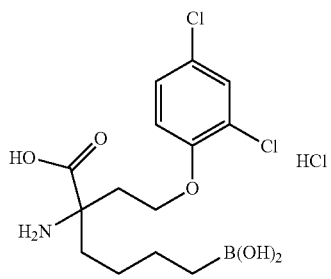

(94)

2-Amino-6-borono-2-[2-(2,4-dichlorophenoxy)-ethyl]-hexanoic acid is prepared in a manner analogous to that set forth in Example 92, except 1-(2-bromoethoxy)-2,4-dichlorobenzene is used as the alkylating agent in step 1. $^1$H NMR (D$^4$-MeOH, 300 MHz) $\delta$ 7.43 (d, J=2 Hz, 1H), 7.29 (dd, J$_1$=9.0 Hz, J$_2$=2.0 Hz, 1H), 7.09 (d, J=9 Hz, 1H), 4.30 (m, 1H), 4.21 (m, 1H), 2.53 (ddd. J$_1$=15.5 Hz, J$_2$=7.5 Hz, J$_3$=4.5 Hz, 1H), 2.44 (ddd. J$_1$=15.5 Hz, J$_2$=7.0 Hz, J$_3$=4.5 Hz, 1H), 2.01 (m, 2H), 1.46 (m, 3H), 1.32 (m, 1H) and 0.82 (t, J=7 Hz, 2H); MS (+CI): m/z for C$_{14}$H$_{20}$BCl$_2$NO$_5$: expected 363.1. found 364.2 (M+H)$^+$, 346.2 (M+H-H$_2$O)$^+$.

Example 95

Preparation of 2-Amino-6-borono-2-[2-(3-trifluoromethylphenoxy)-ethyl]-hexanoic acid hydrochloride

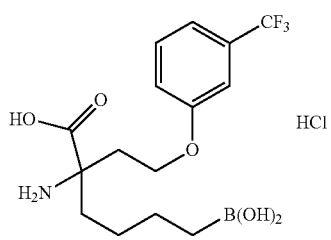

(95)

2-Amino-6-borono-2-[2-(3-trifluoromethylphenoxy)-ethyl]-hexanoic acid hydrochloride is prepared in a manner analogous to that set forth in Example 92, except 1-(2-bromoethoxy)-3-(trifluoromethyl)benzene is used as the alkylating agent in step 1. $^1$H NMR (D$^4$-MeOH, 300 MHz) $\delta$ 7.49 (t, J=8 Hz, 1H), 7.26 (m, 3H), 4.24 (m, 2H), 2.52 (m, 1H), 2.37 (m, 1H), 1.96 (m, 2H), 1.46 (m, 3H), 1.32 (m, 1H) and 0.83 (t, J=7 Hz, 2H); MS (+CI): m/z for C$_{15}$H$_{21}$BF$_3$NO$_5$: expected 363.21. found 364.2 (M+H)$^+$, 346.2 (M+H-H$_2$O)$^+$, 727.4 (2 M+H)$^+$, 709.4 (2M+H-H$_2$O)$^+$.

Example 96

Preparation of 2-Amino-6-borono-2-[3-(4-chlorophenoxy)-propyl]-hexanoic acid hydrochloride

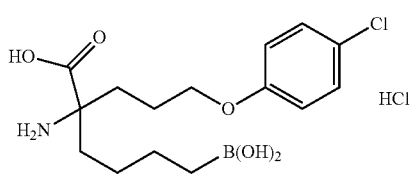
(96)

2-Amino-6-borono-2-[3-(4-chlorophenoxy)-propyl]-hexanoic acid hydrochloride is prepared in a manner analogous to that set forth in Example 92, except 1-(4-bromopropoxy)-4-chlorobenzene is used as the alkylating agent in step 1. $^1$H NMR (D$^4$-MeOH, 300 MHz) δ 7.24 (d, J=9 Hz, 2H), 6.90 (d, J=9 Hz, 2H), 3.98 (m, 2H), 1.68-2.19 (m, 6H), 1.44 (m, 3H), 1.27 (m, 1H) and 0.82 (t, J=7 Hz, 2H); MS (+CI): m/z for $C_{15}H_{23}BClNO_5$: expected 343.1. found 344.2 (M+H)$^+$, 326.2 (M+H−H$_2$O)$^+$.

Example 97

Preparation of 2-Amino-6-borono-2-methylhexanoic acid hydrochloride

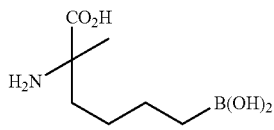
(97)

2-Amino-6-borono-2-methylhexanoic acid hydrochloride is prepared in a manner analogous to that set forth in Example 92, except methyliodide is used as the alkylating agent in step 1. $^1$H NMR (D$_2$O, 300 MHz) δ 1.89-1.82 (m, 1H), 1.79-1.68 (m, 1H), 1.48 (s, 3H), 1.47-1.25 (m, 3H), 1.22-1.13 (m, 1H), 0.69 (t, J=6.6 Hz, 2H). ESI MS found for $C_7H_{16}BNO_4$ m/z [190.1 (M+1)].

Example 98

Preparation of 2-amino-6-borono-2-(3-fluorobenzyl)hexanoic acid hydrochloride

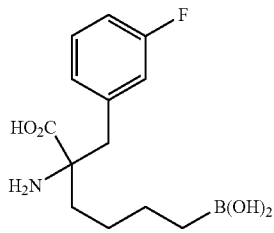
(98)

2-amino-6-borono-2-(3-fluorobenzyl)hexanoic acid hydrochloride is prepared in a manner analogous to that set forth in Example 92, except 1-(bromomethyl)-3-fluorobenzene is used as the alkylating agent in step 1. $^1$H NMR (CD$_3$OD, 300 MHz) δ 7.41-7.32 (m, 1H), 7.14-7.02 (m, 3H), 3.33 (d$_{AB}$, J=14.4 Hz, 1H), 3.14 (d$_{AB}$, J=14.4 Hz, 1H), 2.10-1.80 (m, 2H), 1.48-1.25 (m, 4H), 0.79 (t, J=6.9 Hz, 2H). ESI MS found for $C_{13}H_{19}BFNO_4$ m/z [284.2 (M+1)].

Example 99

Preparation of 2-amino-2-benzyl-6-boronohexanoic acid hydrochloride

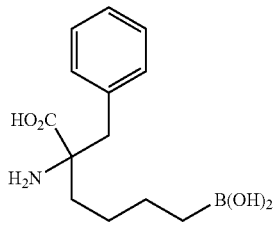
(99)

2-amino-2-benzyl-6-boronohexanoic acid hydrochloride is prepared in a manner analogous to that set forth in Example 92, except benzyl bromide is used as the alkylating agent in step 1. $^1$H NMR (D$_2$O, 300 MHz) δ 7.32-7.21 (m, 3H), 7.24-7.24 (m, 2H), 3.27 (d$_{A B}$, J=12.8 Hz, 1H), 3.04 (d$_{A B}$, J=12.8 Hz, 1H), 2.03-1.92 (m, 1H), 1.84-1.75 (m, 1H), 1.40-1.08 (m, 4H), 0.68 (t, J=7.2 Hz, 2H). ESI MS found for $C_{13}H_{20}BNO_4$ m/z [266.1 (M+1)].

Example 100

Preparation of 2-amino-6-borono-2-(3-methoxypropyl)hexanoic acid hydrochloride

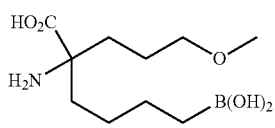
(100)

2-Amino-6-borono-2-(3-methoxypropyl)hexanoic acid hydrochloride is prepared in a manner analogous to that set forth in Example 92, except 1-bromo-3-methoxypropane is used as the alkylating agent in step 1. $^1$H NMR (D$_2$O, 300 MHz) δ 3.29 (t, J=6.6 Hz, 2H), 3.13 (s, 3H), 1.90-1.62 (m, 4H), 1.58-1.42 (m, 1H), 1.42-1.29 (m, 1H), 1.28-1.14 (m, 3H), 1.11-0.97 (m, 1H), 0.58 (t, J=7.5 Hz, 2H). ESI MS found for $C_{10}H_{22}BNO_5$ m/z [248.1 (M+1)].

Example 101

Preparation of 2-amino-6-borono-2-(3-hydroxypropyl)hexanoic acid hydrochloride

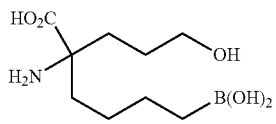
(101)

2-Amino-6-borono-2-(3-hydroxypropyl)hexanoic acid hydrochloride is prepared in a manner analogous to that set forth in Example 92, except 2-(3-bromopropoxy)tetrahydro-2H-pyran is used as the alkylating agent in step 1. $^1$H NMR ($D_2O$, 300 MHz) δ 3.42 (t, J=6.3 Hz, 2H), 1.96-1.64 (m, 4H), 1.55-1.41 (m, 1H), 1.40-1.19 (m, 4H), 1.11-0.96 (m, 1H), 0.60 (t, J=7.5 Hz, 2H). ESI MS found for $C_9H_{20}BNO_5$ m/z [234.1 (M+1)].

Example 102

Preparation of 2-((1H-imidazol-5-yl)methyl)-2-amino-6-boronohexanoic acid dihydrochloride

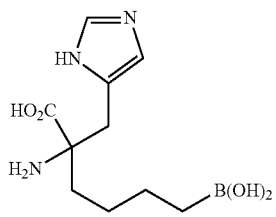
(102)

A solution of N-(diphenylmethylene)histidine (1-trityl) tert-butyl ester (400 mg, 0.65 mmol) in freshly distilled THF (4 mL) was cooled to −78° C. (under argon atmosphere) and treated with lithium bis(trimethylsilyl)amide (1.5 mmol, 1.5 mL, 1.0 M in THF). 2-(4-iodobutyl)-4,4,5,5-tetramethyl-1,3,2-dioxaborolane (401 mg, 1.30 mmol) was added in one portion and the reaction was warmed to 50° C. and heated for 8 h. After being complete by TLC, the reaction mixture was cooled to 0° C., diluted with ethyl acetate and washed successively with saturated aqueous $NaHCO_3$ and saturated aqueous NaCl, dried over $MgSO_4$, filtered and concentrated. Purification by MPLC (50% ethyl acetate in heptane) gave the crude product as an oil which was redissolved in 6N HCl (10 mL) and heated to 70° C. for 16 h. After cooling to room temperature, the reaction mixture was transferred to a separatory funnel, diluted with deionized water (10 mL) and washed with dichloromethane (5×10 mL). The aqueous layer was concentrated to give an off-white solid product (68 mg, 42%) as diHCl salt. $^1$H NMR ($D_2O$, 300 MHz) δ 8.51 (d, J=1.2 Hz, 1H), 7.25 (d, J=1.2 Hz, 1H), 3.30 ($d_{AB}$, J=15.9 Hz, 1H), 3.18 ($d_{AB}$, J=15.9 Hz, 1H), 1.92-1.78 (m, 1H), 1.70 (ddd, J=14.7, 12.0, 4.2 Hz, 1H), 1.32-1.16 (m, 3H), 1.16-0.99 (m, 1H), 0.59 (t, J=7.5 Hz, 2H). ESI MS found for $C_{10}H_{18}BN_3O_4$ m/z [256.2 (M+)].

Example 103

Preparation of 2-(4-boronobutyl)pyrrolidine-2-carboxylic acid hydrochloride

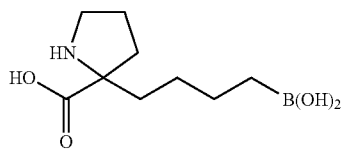
(103)

2-(4-Boronobutyl)pyrrolidine-2-carboxylic acid hydrochloride is prepared in a manner analogous to that set forth in Example 102, except di-tert-butyl pyrrolidine-1,2-dicarboxylate is used as the starting amino acid derivative in step 1. $^1$H NMR ($D_2O$, 300 MHz) δ 3.36-3.24 (m, 2H), 2.41-2.33 (m, 1H), 2.08-1.70 (m, 5H), 1.39-1.12 (m, 4H), 0.71 (t, J=7.2 Hz, 2H). ESI MS found for $C_9H_{18}BNO_4$ m/z [216.0 (M+1)].

Example 104

Preparation of 2-amino-6-borono-2-isobutylhexanoic acid hydrochloride

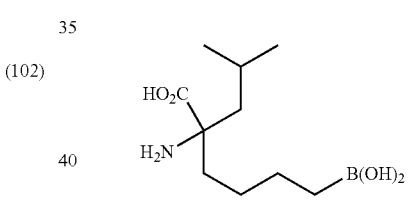
(104)

2-Amino-6-borono-2-isobutylhexanoic acid hydrochloride is prepared in a manner analogous to that set forth in Example 102, except tert-butyl 2-(diphenylmethyleneamino)-4-methylpentanoate is used as the starting amino acid derivative in step 1. $^1$H NMR ($D_2O$, 300 MHz) δ 1.80-1.47 (m, 5H), 1.29-1.15 (m, 3H), 1.08-0.94 (m, 1H), 0.75 (d, J=6.6 Hz, 3H), 0.70 (d, J=6.6 Hz, 3H), 0.58 (t, J=7.8 Hz, 2H). ESI MS found for $C_{10}H_{22}BNO_4$ m/z [232.1 (M+1)].

Example 105

Preparation of 2-amino-6-borono-2-isopropylhexanoic acid hydrochloride

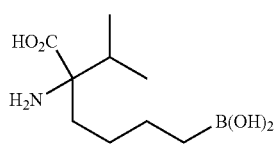
(105)

2-Amino-6-borono-2-isobutylhexanoic acid hydrochloride is prepared in a manner analogous to that set forth in Example 102, except tert-butyl 2-(diphenylmethyleneamino)-3-methylbutanoate is used as the starting amino acid derivative in step 1. $^1$H NMR (D$_2$O, 300 MHz) δ 2.08 (heptet, J=6.9 Hz, 1H), 1.78-1.70 (m, 2H), 1.31-1.15 (m, 3H), 1.10-0.97 (m, 1H), 0.84 (d, J=6.9 Hz, 3H), 0.82 (d, J=6.9 Hz, 3H), 0.61 (t, J=7.5 Hz, 2H). ESI MS found for C$_9$H$_{20}$BNO$_4$ m/z [218.1 (M+1)].

Example 106

Preparation of 2-amino-2-(4-boronobutyl)succinic acid hydrochloride

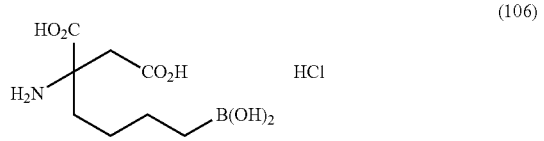 [SMILES: NC(CCCCB(O)O)(CC(=O)O)C(=O)O ; Cl]

(106)

2-Amino-2-(4-boronobutyl)succinic acid hydrochloride is prepared in a manner analogous to that set forth in Example 102, except di-tert-butyl 2-(diphenylmethyleneamino)succinate is used as the starting amino acid derivative in step 1. $^1$H NMR (D$_2$O, 500 MHz) δ 3.10 (d, J=18.0 Hz, 1H), 2.85 (d, J=18.0 Hz, 1H [AB system], 1.85-1.78 (m, 2H), 1.37-1.32 (m, 3H), 1.23-1.19 (m, 1H), 0.72 (t, J=7.0 Hz, 2H). ESI MS found for C$_8$H$_{16}$BNO$_6$ m/z [216.4, (M+1−18) 100%, 198.3 (M+1−2×18) 35%, 232.4 (M−1) 50%, 214.4 (M+1−18) 100%].

Example 107

Preparation of 2-amino-6-borono-2-((1-isopropyl-1H-imidazol-5-yl)methyl)hexanoic acid dihydrochloride

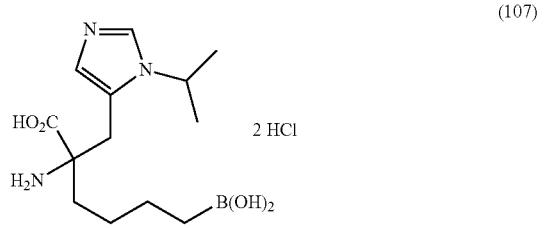 [SMILES: CC(C)n1cncc1CC(N)(CCCCB(O)O)C(=O)O]

(107)

A solution of tert-butyl 2-(tert-butoxycarbonylamino)-2-(2-oxoethyl)-6-(4,4,5,5-tetramethyl-1,3,2-dioxaborolan-2-yl)hexanoate (prepared in a manner analogous to that described in example 16) 100 mg (0.22 mmol) in methanol (1 mL) was treated with tosmethyl isocyanide (59 mg, 0.30 mmol) followed by iso-propyl amine (59 mg, 85 uL, 1.00 mmol) at room temperature. The reaction mixture was stirred at room temperature for 48 hours, then evaporated and purified by chromatography (chloroform:methanol; gradient 100:1 to 10:1) to give 35 mg of the alkylated product (white solid), which was redissolved in 6 N HCl (10 mL) and heated to 70° C. for 16 h. After cooling to room temperature, the reaction mixture was transferred to a separatory funnel, diluted with deionized water (10 mL) and washed with dichloromethane (5×10 mL). The aqueous layer was concentrated to give 2-amino-6-borono-2-((1-isopropyl-1H-imidazol-5-yl)methyl)hexanoic acid dihydrochloride as an off-white solid product (20 mg, 26% yield). $^1$H NMR (D$_2$O, 300 MHz) δ 8.71 (d, J=1.2 Hz, 1H), 7.24 (d, J=1.2 Hz, 1H), 4.45 (heptet, J=6.3 Hz, 1H), 3.35 (d$_{AB}$, J=16.2 Hz, 1H), 3.21 (d$_{AB}$, J=16.2 Hz, 1H), 1.98-1.86 (m, 1H), 1.82-1.68 (m, 1H), 1.38-1.20 (m, 3H), 1.37 (d, J=6.3 Hz, 3H), 1.32 (d, J=6.3 Hz, 3H), 1.17-1.03 (m, 1H), 0.62 (t, J=7.5 Hz, 2H). ESI MS found for C$_{13}$H$_{24}$BN$_3$O$_4$ m/z [298.2 (M+1)].

Example 108

Preparation of 2-amino-6-borono-2-(1-hydroxypropyl)hexanoic acid hydrochloride

Step 1: tert-butyl 2-(diphenylmethyleneamino)hex-5-enoate

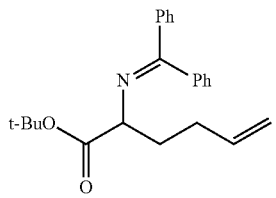 [SMILES: C=CCCC(N=C(c1ccccc1)c1ccccc1)C(=O)OC(C)(C)C]

While under a nitrogen atmosphere a stirred solution of (benzhydrylidene-amino)-acetic acid tert-butyl ester (5 g, 16.9 mmol) in THF (80 mL, 0.2 M) was carefully treated with sodium bis(trimethylsilyl)amide (18.6 mL, 1.0 M, 1.1 equiv) at −78° C. After stirring for 30 min, 4-bromo-but-1-ene (2.1 mL, 20.3 mmol, 1.2 equiv) was slowly added. The cooling bath was removed and the reaction mixture gradually warmed to room temperature and stirred for overnight. The solution was cooled to 0° C. and quenched with water. The resulting solution was diluted with ethyl acetate and washed successively with water and saturated aqueous NaCl, dried over MgSO$_4$, filtered and concentrated. Purification by MPLC (1-25% ethyl acetate in heptane) gave 2-(benzhydrylidene-amino)-hex-5-enoic acid tert-butyl ester as colorless oil (5.6 g, 15.9 mmol, 94%).

Step 2: tert-butyl 4-(but-3-enyl)-5-ethyl-2,2-diphenyloxazolidine-4-carboxylate

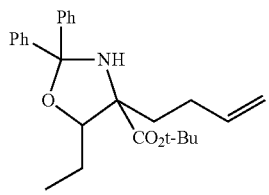 [SMILES: C=CCCC1(C(=O)OC(C)(C)C)NC(c2ccccc2)(c2ccccc2)OC1CC]

While under a nitrogen atmosphere, a stirred solution of 2-(benzhydrylidene-amino)-hex-5-enoic acid tert-butyl ester (350 mg, 1 mmol) in THF (5 mL, 0.2 M) was cooled to −78° C. and carefully treated with sodium bis(trimethylsilyl)amide (2 mL, 1 M, 2 equiv). After stirring 30 min, diethyl aluminum chloride (2.4 mL, 1 M, 2.4 equiv) was added and the reaction mixture was stirred an additional 30 min. Propionaldehyde (94 μl, 1.25 mmol, 1.25 eq) was added to the solution and the cooling bath was removed. After stirring overnight the reaction mixture was cooled to 0° C. and quenched with saturated NH₄Cl. The resulting solution was diluted with ethyl acetate and washed successively with water and saturated potassium sodium tartrate, dried over MgSO₄, filtered and concentrated. Purification by MPLC (1-40% ethyl acetate in heptane) gave 4-but-3-enyl-5-ethyl-2,2-diphenyl-oxazolidine-4-carboxylic acid tert-butyl ester (349 mg, 0.86 mmol, 86%).

Step 3: tert-butyl 5-ethyl-2,2-diphenyl-4-(4-(4,4,5,5-tetramethyl-1,3,2-dioxaborolan-2-yl)butyl)oxazolidine-4-carboxylate

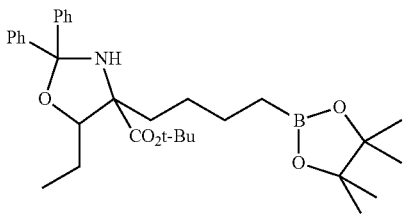 [SMILES: CCC1OC(c2ccccc2)(c2ccccc2)NC1(CCCCB1OC(C)(C)C(C)(C)O1)C(=O)OC(C)(C)C]

A solution of 4-but-3-enyl-5-ethyl-2,2-diphenyl-oxazolidine-4-carboxylic acid tert-butyl ester (230 mg, 0.56 mmol) in dichloromethane (2 mL, 0.3 M) was added chlorotris(triphenylphosphine)rhodium(I) (60 mg, 0.065 mmol, 10 mol %) at room temperature. After stirring for 30 min, 4,4,5,5-Tetramethyl-1,3,2-dioxaborolane (200 µl, 1.3 mmol, 2 eq) was added to the reaction mixture and stirred overnight. After quenching the reaction with water (3 mL), the resulting solution was diluted with ethyl acetate and washed successively with water and saturated aqueous NaCl, dried over MgSO₄, filtered and concentrated. Purification by MPLC (1-40% ethyl acetate in heptane) gave 5-Ethyl-2,2-diphenyl-4-[4-(4,4,5,5-tetramethyl-[1,3,2]dioxaborolan-2-yl)-butyl]-oxazolidine-4-carboxylic acid tert-butyl ester (152 mg, 0.28 mmol, 50%).

Step 4:
2-amino-6-borono-2-(1-hydroxypropyl)hexanoic acid hydrochloride

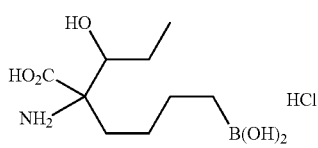
(108)

A solution of 5-ethyl-2,2-diphenyl-4-[4-(4,4,5,5-tetramethyl-[1,3,2]dioxaborolan-2-yl)-butyl]-oxazolidine-4-carboxylic acid tert-butyl ester (152 mg, 0.28 mmol) in 6 N HCl (4 ml) was stirred at 65° C. for 1 day. After cooling to room temperature, the reaction mixture was transferred to a separatory funnel, diluted with deionized water (3 ml) and washed with dichloromethane (3×4 mL). The aqueous layer was frozen in liquid nitrogen and lyophilized to give 2-amino-6-borono-2-(1-hydroxy-propyl)-hexanoic acid hydrochloride as white foam (20 mg, 0.074 mmol, 27%). ¹H NMR (D₂O, 300 MHz) δ 3.80 (dd, J=11.4, 1.8 Hz, 1H), 1.88-1.50 (m, 2H), 1.48-0.92 (m, 5H), 0.85 (t, J=7.6 Hz, 3H), 0.63 (t, J=7.6 Hz, 2H).

Example 109

Preparation of 2-amino-6-borono-2-(hydroxy(piperidin-4-yl)methyl)hexanoic acid dihydrochloride

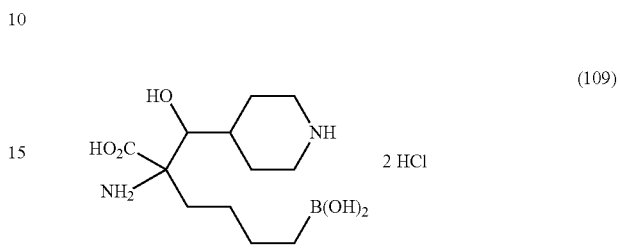
(109)

2-Amino-6-borono-2-(hydroxy(piperidin-4-yl)methyl)hexanoic acid dihydrochloride is prepared in a manner analogous to that set forth in Example 108, except tert-butyl 4-formylpiperidine-1-carboxylate is used as the aldehyde in step 2. ¹H NMR (D₂O, 300 MHz) δ 3.80 (d, J=2.9 Hz, 1H), 3.36-3.20 (m, 2H), 2.94-2.75 (m, 2H), 1.98-1.34 (m, 7H), 1.34-0.97 (m, 4H), 0.63 (t, J=7.6 Hz, 2H).

Example 110

Preparation of 2-amino-6-borono-2-(hydroxy(piperidin-3-yl)methyl)hexanoic acid dihydrochloride

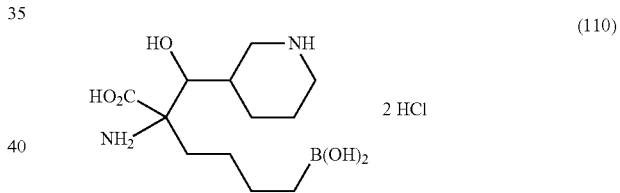
(110)

2-Amino-6-borono-2-(hydroxy(piperidin-3-yl)methyl)hexanoic acid dihydrochloride is prepared in a manner analogous to that set forth in Example 108, except tert-butyl 3-formylpiperidine-1-carboxylate is used as the aldehyde in step 2. ¹H NMR (D₂O, 300 MHz) δ 4.05-3.70 (m, 1H), 3.60-3.40 (m, 1H), 3.00-2.70 (m, 3H), 2.70-1.60 (m, 7H), 1.60-1.15 (m, 4H), 0.85 (t, J=7.1 Hz, 2H).

Example 111

Preparation of 2-amino-2-(4-boronobutyl)-6,6,6-trifluoro-3-hydroxyhexanoic acid hydrochloride

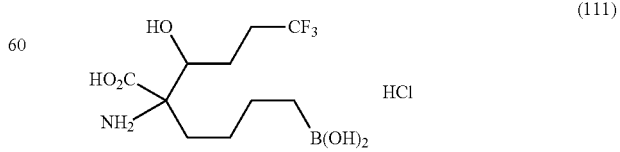
(111)

2-Amino-2-(4-boronobutyl)-6,6,6-trifluoro-3-hydroxyhexanoic acid hydrochloride is prepared in a manner analogous to that set forth in Example 108, except 4,4,4-trifluorobutanal is used as the aldehyde in step 2. $^1$H NMR (D$_2$O, 300 MHz) δ 3.98-3.84 (m, 1H), 2.50-2.12 (m, 2H), 2.06-1.66 (m, 4H), 1.47-1.12 (m, 4H), 0.75 (t, J=7.5 Hz, 2H).

Example 112

Preparation of 2-amino-6-borono-2-(hydroxy(pyridin-3-yl)methyl)hexanoic acid dihydrochloride

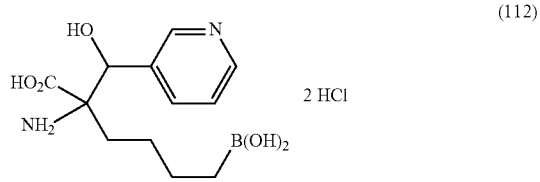 [SMILES: NC(CCCCB(O)O)(C(=O)O)C(O)c1cccnc1]

2-Amino-6-borono-2-(hydroxy(pyridin-3-yl)methyl)hexanoic acid dihydrochloride is prepared in a manner analogous to that set forth in Example 108, except nicotinaldehyde is used as the aldehyde in step 2. $^1$H NMR (D$_2$O, 300 MHz) δ 8.84 (s, 1H), 8.75 (d, J=5.9 Hz, 1H), 8.61 (d, J=8.2 Hz, 1H), 8.06 (dd, J=8.2, 5.9 Hz, 1H), 5.27 (s, 1H), 2.06-1.86 (m, 1H), 1.84-1.67 (m, 1H), 1.54-1.28 (m, 3H), 1.28-1.08 (m, 1H), 0.74 (t, J=7.8 Hz, 2H).

Example 113

Preparation of 2-amino-2-(azetidin-3-yl(hydroxy)methyl)-6-boronohexanoic acid dihydrochloride

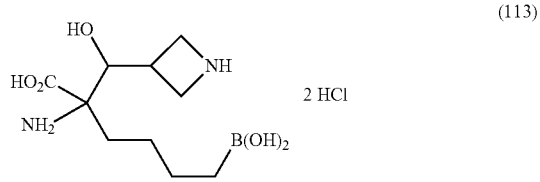 [SMILES: NC(CCCCB(O)O)(C(=O)O)C(O)C1CNC1]

2-Amino-2-(azetidin-3-yl(hydroxy)methyl)-6-boronohexanoic acid dihydrochloride is prepared in a manner analogous to that set forth in Example 108, except tert-butyl 3-formylazetidine-1-carboxylate is used as the aldehyde in step 2. $^1$H NMR (D$_2$O, 300 MHz) δ 4.11 (d, J=6.0 Hz, 1H), 4.07-3.78 (m, 4H), 3.40-3.10 (m, 1H), 1.85-1.36 (m, 7H), 1.32-0.92 (m, 4H), 0.60 (t, J=7.6 Hz, 2H).

Example 114

Preparation of 5-amino-6-oxo-6-phenylhexylboronic acid hydrochloride

Step 1: tert-butyl 2-benzoyl-2-(diphenylmethyleneamino)hex-5-enoate

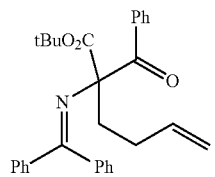

A solution of 2-(benzhydrylidene-amino)-hex-5-enoic acid tert-butyl ester (350 mg, 1 mmol) in THF (5 mL, 0.2 M) was cooled to −78° C. and treated with sodium bis(trimethylsilyl)amide (2.2 mL, 1.0 M, 2.2 equiv) drop wise over 5 min and stirred for 30 min. After adding benzoyl chloride (140 µl, 1.2 mmol, 1.2 eq), the reaction mixture was warmed up to room temperature and stirred for an additional 1.5 h. The solution was cooled to 0° C. and quenched with water (5 mL). The resulting solution was diluted with ethyl acetate and washed successively with water and saturated aqueous NaCl, dried over MgSO$_4$, filtered and concentrated. Purification by MPLC (1-40% ethyl acetate in heptane gave 2-(benzhydrylidene-amino)-2-benzoyl-hex-5-enoic acid tert-butyl ester (477 mg, 1 mmol, 100%).

Step 2: tert-butyl 2-benzoyl-2-(diphenylmethyleneamino)-6-(4,4,5,5-tetramethyl-1,3,2-dioxaborolan-2-yl)hexanoate

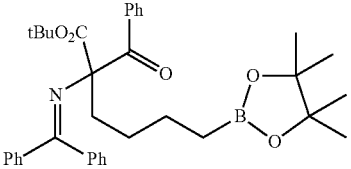 [SMILES: CC(C)(C)OC(=O)C(CCCCB1OC(C)(C)C(C)(C)O1)(N=C(c1ccccc1)c1ccccc1)C(=O)c1ccccc1]

A solution of 2-(benzhydrylidene-amino)-hex-5-enoic acid tert-butyl ester (530 mg, 1.17 mmol) in dichloromethane (3 mL, 0.4 M) was treated with chloro-1,5-cyclooctadiene iridium (I) dimer (24 mg, 0.036 mmol, 3 mol %) and 1,2-bis(diphenyl phosphino) ethane (28 mg, 0.07 mmol, 6 mol %) at room temperature. After stirring for 30 min, 4,4,5,5-tetramethyl-1,3,2-dioxaborolane (204 µl, 1.4 mmol, 1.2 eq) was added to the reaction mixture and stirring was continued overnight. The solution was quenched with water (3 mL). The resulting solution was diluted with ethyl acetate and washed successively with water and saturated aqueous NaCl, dried over MgSO$_4$, filtered and concentrated. Purification by MPLC (1-40% ethyl acetate in heptane) gave 2-(benzhydrylidene-amino)-2-benzoyl-6-(4,4,5,5-tetramethyl-[1,3,2]dioxaborolan-2-yl)-hexanoic acid tert-butyl ester (370 mg, 0.64 mmol, 54%).

Step 3: 5-amino-6-oxo-6-phenylhexylboronic acid hydrochloride

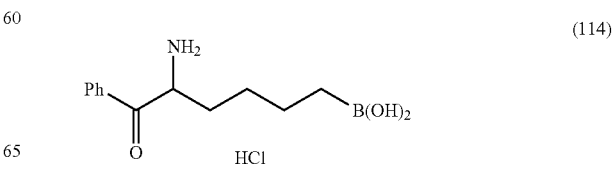

A solution of 2-(benzhydrylidene-amino)-2-benzoyl-6-(4,4,5,5-tetramethyl-[1,3,2]dioxaborolan-2-yl)-hexanoic acid tert-butyl ester (186 mg, 0.32 mmol) in 6 N HCl (6 mL) was stirred at 65° C. for 1 day. After cooling to room temperature, the reaction mixture was transferred to a separatory funnel, diluted with deionized water (5 mL) and washed with dichloromethane (3×5 mL). The aqueous layer was frozen in liquid nitrogen and lyophilized to give 2-amino-6-borono-1-phenyl-hexan-1-one (76.5 mg, 88%). $^1$H NMR (D$_2$O, 300 MHz) δ 8.04-7.60 (m, 2H), 7.77 (tt, J=7.6, 1.2 Hz, 1H), 7.61 (d, J=7.6 Hz, 2H), 5.18 (dd, J=7.5, 4.7 Hz, 1H), 2.15-1.82 (m, 2H), 1.5-1.2 (m, 4H), 0.69 (t, J=7.2 Hz, 2H).

Example 115

Preparation of 2-amino-6-borono-2-(2-((R)-pyrrolidin-2-yl)ethyl)hexanoic acid dihydrochloride

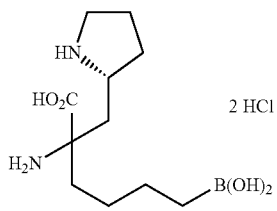

(115)

2-Amino-6-borono-2-(2-((R)-pyrrolidin-2-yl)ethyl)hexanoic acid dihydrochloride is prepared in a manner analogous to that set forth in Example 87-A below, except (R)-2-(1-(tert-butoxycarbonyl)pyrrolidin-2-yl)acetic acid is used as the carboxylic acid in step 1. $^1$H NMR (D$_2$O, 500 MHz) δ 3.52-3.48 (m, 1H), 3.21-3.11 (m, 2H), 2.35 (dd, J=16.0, 6.0 Hz, 1H), 2.19-2.12 (m, 2H), 1.96-1.89 (m, 1H), 1.85-1.79 (m, 2H) 1.70 (dt, J=14.0, 4.0 Hz, 1H), 1.60-1.52 (m, 1H), 1.29-1.21 (m, 3H), 1.12-1.05 (m, 1H), 0.62 (t, J=7.0 Hz, 2H). ESI MS found for C$_{11}$H$_{23}$BN$_2$O$_4$ m/z [481.9 (2M+1−2×18) 2%, 281.6 (M+Na$^+$) 5%, 263.6 (M+Na$^+$−18) 4%, 241.5 (M+1−18) 23%, 223.5 (M+1−2×18) 100%, 257.5 (M−1) 8%, 239.5 (M−1−18) 100%.].

Example 116

Preparation of 2-amino-6-borono-2-(2-(pyridin-2-yl)ethyl)hexanoic acid dihydrochloride

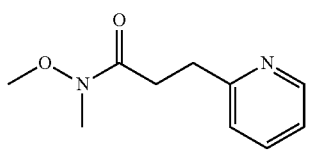

Step 1:
N-methoxy-N-methyl-3-(pyridin-2-yl)propanamide

A solution of 3-pyridin-2-yl-propionic acid (1.0 g, 6.62 mmol), DMAP (10 mg), and N,O-dimethylhydroxylamine hydrochloride (679 g, 7.0 mmol) and EDC (1.34 g, 7.0 mmol) in dichloromethane (40 mL) was treated with triethylamine (2.8 mL, 20.0 mmol). After stirring at room temperature overnight, the solution was poured into water, extracted with ethyl acetate (3×) and the combined organic phase was washed with saturated aqueous sodium chloride, dried over anhydrous magnesium sulfate, filtered and concentrated. Purification by column chromatography (silica gel, 30-100% ethyl acetate in heptane) gave N-methoxy-N-methyl-3-(pyridin-2-yl)propanamide (1.02 g, 78%) as a colorless oil. ESI MS found for C$_{10}$H$_{14}$N$_2$O$_2$ m/z [195.1 (M+1)].

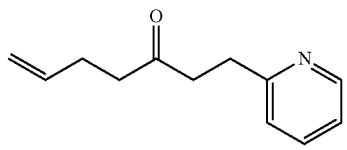

Step 2: 1-(pyridin-2-yl)hept-6-en-3-one

While under a nitrogen atmosphere, a solution of N-methoxy-N-methyl-3-(pyridin-2-yl)propanamide (1.00 g, 5.15 mmol), in tetrahydrofuran (10 mL) was cooled to 0° C. and treated with 4-butenylmagnesiun bromide (0.5 M in THF, 16 mL, 8.0 mmol) in a dropwise manner. The solution was stirred for 1 hour at 0° C. then allowed to warm to room temperature for 3 h. The resulting solution was poured into saturated aqueous sodium chloride (100 mL) and extracted with ethyl acetate (3×50 mL). The combined organic phase was washed with saturated aqueous sodium chloride, dried over anhydrous magnesium sulfate, filtered and concentrated. Purification by flash column chromatography (silica gel, 0-25% ethyl acetate in heptane) gave 1-(pyridin-2-yl)hept-6-en-3-one as a colorless oil (828 mg, 85%). ESI MS found for C$_{12}$H$_{15}$NO m/z [190.1 (M+1)].

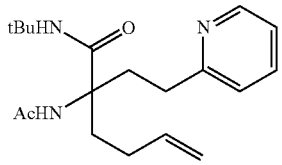

Step 3: 2-acetamido-N-tert-butyl-2-(2-(pyridin-2-yl)ethyl)hex-5-enamide

A solution of 1-(pyridin-2-yl)hept-6-en-3-one (825 mg, 4.36 mmol) and ammonium acetate (1.01 g, 13.09 mmol) in 2,2,2-trifluoroethanol (3 mL) was treated with tert-butyl isocyanide (730 mg, 0.99 mL, 8.80 mmol). After stirring at room temperature for 6 days, the reaction mixture was purified by flash column chromatography (crude reaction mixture loaded on the top of the column; silica gel, 0-10% methanol in dichloromethane) to give 2-acetamido-N-tert-butyl-2-(2-(pyridin-2-yl)ethyl)hex-5-enamide as white solid (1.37 g, 95%). ESI MS found for C$_{19}$H$_{29}$N$_3$O$_2$ m/z [332.2 (M+1)].

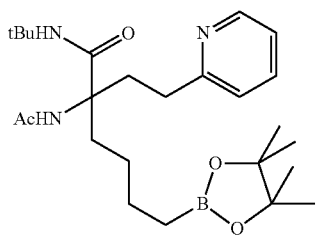

Step 6: 2-acetamido-N-tert-butyl-2-(2-(pyridin-2-yl)ethyl)-6-(4,4,5,5-tetramethyl-1,3,2-dioxaborolan-2-yl)hexanamide A solution of 2-acetamido-N-tert-butyl-2-(2-(pyridin-2-yl)ethyl)hex-5-enamide (810 mg, 2.45 mmol) in dichloromethane (4 mL), was treated with chloro-1,5-cyclooctadiene iridium(I) dimer (35 mg, 2 mol %) and 1,2-bis(diphenylphosphino)ethane (42 mg, 4 mol %). The solution was stirred at room temperature for 30 minutes and then 4,4,5,5-tetramethyl-[1,3,2]dioxaborolane (0.76 mL, 5.20 mmol) was added dropwise, and the reaction was then stirred overnight at room temperature. The reaction was poured into water and extracted with ethyl acetate (3×). The combined organic phase was washed with saturated aqueous sodium chloride, dried over anhydrous magnesium sulfate, filtered and concentrated. Purification by flash column chromatography (silica gel, 0-10% methanol in dichloromethane) gave 2-acetamido-N-tert-butyl-2-(2-(pyridin-2-yl)ethyl)-6-(4,4,5,5-tetramethyl-1,3,2-dioxaborolan-2-yl)hexanamide as a colorless oil (787 mg, 70%). ESI MS found for $C_{25}H_{42}BN_3O_4$ m/z [460.3 (M+1)].

(116)

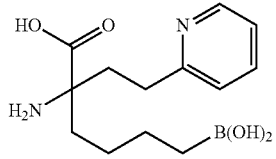

Step 7: 2-amino-6-borono-2-(2-(pyridin-2-yl)ethyl)hexanoic acid

The hydrolysis of 2-acetamido-N-tert-butyl-2-(2-(pyridin-2-yl)ethyl)-6-(4,4,5,5-tetramethyl-1,3,2-dioxaborolan-2-yl)hexanamide to form 2-amino-6-borono-2-(2-(pyridin-2-yl)ethyl)hexanoic acid was done in a manner analogous to that set forth in Example 1, Step 8. $^1$H NMR (D$_2$O, 300 MHz) δ 8.50 (ddd, J$_1$=6.0 Hz, J$_2$=1.5 Hz, J$_3$=0.6 Hz, 1H), 8.37 (ddd, J$_1$=9.6 Hz, J$_2$=7.8 Hz, J$_3$=1.8 Hz, 1H), 7.81-7.74 (m, 2H), 3.22-3.08 (m, 1H), 3.03-2.91 (m, 1H), 2.33-2.18 (m, 2H), 1.97-1.72 (m, 2H), 1.38-1.06 (m, 4H), 0.64 (t, J=7.5 Hz, 2H). ESI MS found for $C_{13}H_{21}BN_2O_4$ m/z [281.2 (M+1)].

Example 117

Preparation of 2-amino-6-borono-2-((1-(3,4-dichlorobenzyl)azetidin-3-yl)methyl)hexanoic acid dihydrochloride (117)

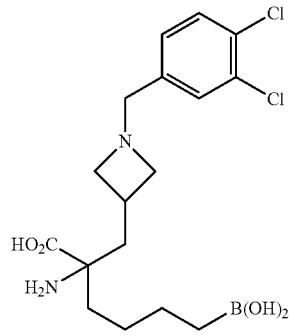

2-Amino-6-borono-2-((1-(3,4-dichlorobenzyl)azetidin-3-yl)methyl)hexanoic acid dihydrochloride was made from 1-Cbz-3-azetidineacetic acid in a manner analogous to that set forth in Example 139. $^1$H NMR (D$_2$O, 500 MHz) δ 7.55-7.45 (m, 2H), 7.29-7.17 (m, 1H), 4.17 (pseudo-t$_{AB}$, 2 H), 4.12-4.03 (m, 1H), 3.91-3.80 (m, 1H), 3.14-2.90 (m, 2H), 2.23-2.05 (m, 2H), 2.01-1.55 (m, 3H), 1.33-1.16 (m, 3H), 1.09-1.01 (m, 1H), 0.63 (t, J=7.2 Hz, 2H). ESI MS found for $C_{17}H_{25}BCl_2N_2O_4$ m/z [385.5 (M−18+1)].

Example 118

Preparation of 2-amino-6-borono-2-((1-(2,4-dichlorophenethyl)azetidin-3-yl)methyl)hexanoic acid dihydrochloride (118)

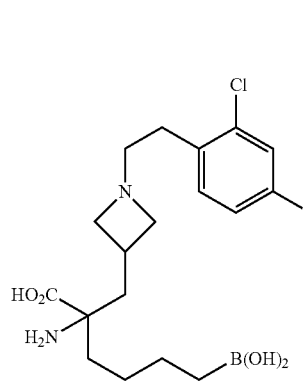

2-Amino-6-borono-2-((1-(2,4-dichlorophenethyl)azetidin-3-yl)methyl)hexanoic acid dihydrochloride was made from 1-Cbz-3-azetidineacetic acid in a manner analogous to that set forth in Example 116. $^1$H NMR (D$_2$O, 500 MHz) δ 7.55-7.30 (m, 3H), 3.55-3.45 (m, 1H), 3.31-3.20 (m, 1H), 3.18-2.90 (m, 4H), 2.77 (t, J=7.6 Hz, 1H), 2.12-2.05 (m, 1H), 2.02-1.61 (m, 5H), 1.32-1.17 (m, 3H), 1.13-1.00 (m, 1H), 0.65 (t, J=7.2 Hz, 2H). ESI MS found for $C_{18}H_{27}BCl_2N_2O_4$ m/z [397.5 (M−18+1)].

Example 119

Preparation of 2-amino-6-borono-2-(2-(3-(3,4-dichlorophenyl)thioureido) ethyl)hexanoic acid hydrochloride

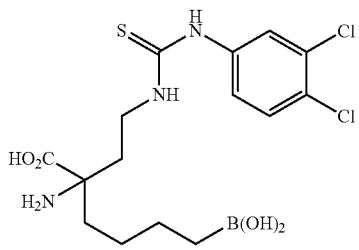

(119)

2-Amino-6-borono-2-(2-(3-(3,4-dichlorophenyl)thioureido) ethyl)hexanoic acid hydrochloride is prepared in a manner analogous to that set forth in Example 16, except tert-butyl 2-(diphenylmethyleneamino)acetate is used in step 1 and the following procedure is used for steps 6 and 7: a solution of aldehyde (5.92 mmol) and benzylamine (11.85 mmol) in dichloroethane was stirred at room temperature for 1 h, then treated with NaBH(OAc)₃ (17.76 mmol). After 16 h, the reaction was quenched with 5% solution of NaHCO₃ and extracted with dichloromethane. The organic extracts were washed successively with 1 M HCl, saturated aqueous sodium chloride, dried over MgSO₄ and concenrated. The crude product was purified by flash chromathography, dissolved in pyridine and treated with 3,4 dichlorophenylisothiocyanate (1.5 equivalents). After stirring overnight at room temperature, the reaction was concentrated, dissolved in dichloromethane, washed with 1 M HCl, saturated aqueous sodium chloride, dried over MgSO₄ and concentrated. Purification by flash chromatography gave the urea which was dissolved in ethanol and treated with Pd(OH)₂/C and hydrogen using a Parr apparatus. When reaction was complete the catalyst was filtered through a pad of celite and the filtrate was concentrated to dryness. The resulting oil was treated with 6 N HCl and heated to 100° C. for 6 h, cooled to room temperature and concentrated. Purification by HPLC gave amino-6-borono-2-(2-(3-(3,4-dichlorophenyl)thioureido) ethyl)hexanoic acid hydrochloride. ¹H NMR (D₂O, 500 MHz) δ 7.39 (d, J=8.4 Hz, 1H), 7.32 (s, 1H), 7.01 (d, J=8.4 Hz, 1H), 3.67-3.51 (m, 2H), 2.28-2.17 (m, 1H), 2.05-1.96 (m, 1H), 1.84-1.68 (m, 2H), 1.35-1.24 (m, 3H), 1.14-1.04 (m, 1H), 0.62 (t, J=7.0 Hz, 2H). ESI MS found for $C_{15}H_{22}BCl_2N_3O_4S$ m/z [404.5 (M−18+1)].

Example 120

Preparation of 2-amino-6-borono-2-(2-isobutyramidoethyl)hexanoic acid hydrochloride

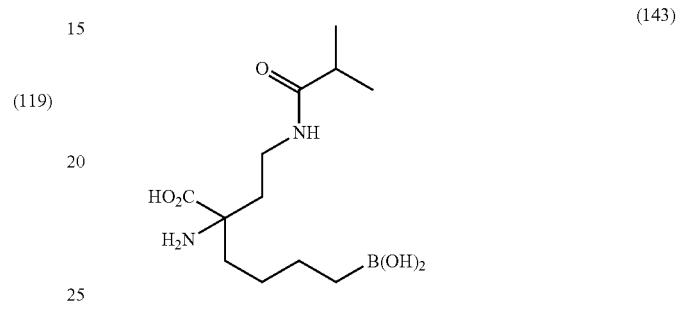

(143)

2-amino-6-borono-2-(2-isobutyramidoethyl)hexanoic acid hydrochloride is prepared in a manner analogous to that set forth in Example 119, except isobutyryl chloride is used instead of 3,4 dichlorophenylisocyanate. ¹H NMR (D₂O, 500 MHz) δ 3.22-3.15 (m, 2H), 2.32 (hept, J=6.3 Hz, 1H), 2.16-08 (m, 1H), 1.91-1.83 (m, 1H), 1.83-1.74 (m, 1H), 1.72-1.64 (m, 1H), 1.30-1.22 (m, 3H), 1.12-1.03 (m, 1H), 0.93 (d, J=6.3 Hz, 6H), 0.65 (t, J=7.5 Hz, 2H). ESI MS found for $C_{12}H_{25}BN_2O_5$ m/z [271.5 (M−18+1)].

Example 121

Preparation of 2-amino-6-borono-2-(2-(4-(4-chlorophenyl)piperidin-1-yl)ethyl)hexanoic acid dihydrochloride

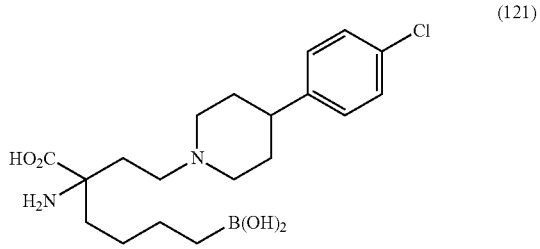 [SMILES: NC(CCCCB(O)O)(CCN1CCC(c2ccc(Cl)cc2)CC1)C(=O)O]

(121)

2-Amino-6-borono-2-(2-(4-(4-chlorophenyl)piperidin-1-yl)ethyl)hexanoic acid dihydrochloride is prepared in a manner analogous to that set forth in Example 16, except 4-(4-chlorophenyl)piperidine is used as the amine in step 6. ¹H NMR (D₂O, 300 MHz) δ 7.22 (d, J=8.4 Hz, 2H), 7.12 (d, J=8.4 Hz, 2H), 3.60-3.47 (m, 2H), 3.32-3.20 (m, 1H), 3.15-2.95 (m, 3H), 2.82-2.70 (m, 1H), 2.31-2.18 (m, 2H), 2.05-

1.65 (m, 6H), 1.35-1.15 (m, 3H), 1.15-1.01 (m, 1H), 0.63 (t, J=7.2 Hz, 2H). ESI MS found for $C_{19}H_{30}BClN_2O_4$ m/z [397.3 (M+1)].

Example 122

Preparation of 2-amino-6-borono-2-(2-(4-(4-chlorobenzyl)piperidin-1-yl)ethyl)hexanoic acid dihydrochloride

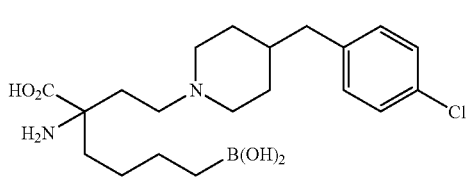

(122)

2-Amino-6-borono-2-(2-(4-(4-chlorobenzyl)piperidin-1-yl)ethyl)hexanoic acid dihydrochloride is prepared in a manner analogous to that set forth in Example 16, except 4-(4-chlorobenzyl)piperidine is used as the amine in step 6. $^1$H NMR (D$_2$O, 500 MHz) δ 7.20 (d, J=8.5 Hz, 2H), 7.05 (d, J=8.5 Hz, 2H), 3.45-3.38 (m, 2H), 3.21-3.15 (m, 1H), 3.04-2.96 (m, 1H), 2.82-2.74 (m, 2H), 2.45-2.41 (m, 2H), 2.20-2.14 (m, 2H), 1.85-1.68 (m, 5H), 1.35-1.20 (m, 5H), 1.13-1.04 (m, 1H), 0.64 (t, J=7.5 Hz, 2H). ESI MS found for $C_{20}H_{32}BClN_2O_4$ m/z [375.5 (M−2×18+1)].

Example 123

Preparation of 2-amino-2-(azetidin-3-ylmethyl)-6-boronohexanoic acid dihydrochloride

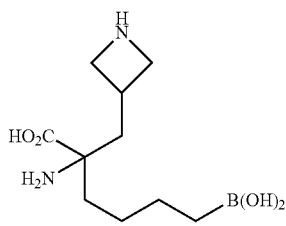

(123)

2-amino-2-(azetidin-3-ylmethyl)-6-boronohexanoic acid dihydrochloride is prepared in a manner analogous to that set forth in Example 116, except 2-(1-(tert-butoxycarbonyl)azetidin-3-yl)acetic acid is used as the carboxylic acid in step 1. $^1$H NMR (D$_2$O, 300 MHz) 3.63-3.50 (m, 1H), 3.08-2.90 (m, 3H), 2.68-2.43 (m, 2H), 2.12-1.94 (m, 1H), 1.82-1.64 (m, 2H), 1.32-1.00 (m, 4H), 0.61 (t, J=7.3 Hz, 2H). ESI MS found for $C_{10}H_{21}BN_2O_4$ m/z [245.3 (M+1)].

Example 124

Preparation of 2-amino-2-(2-(4-benzylpiperidin-1-yl)propyl)-6-boronohexanoic acid dihydrochloride

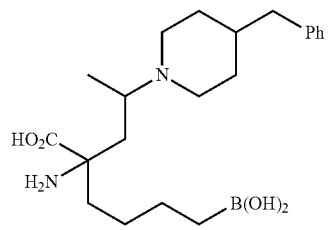

(124)

2-Amino-2-(2-(4-benzylpiperidin-1-yl)propyl)-6-boronohexanoic acid dihydrochloride is prepared in a manner analogous to that set forth in Example 16, except 3-bromo-2-methyl-propene is used as alkyl halide in step 2 and Step 6 is carried out using 4-benzylpiperidine using the following procedure: A mixture of the ketone (235 mg, 0.5 mmol), amine (0.088 ml, 0.5 mmol), and titanium(IV) isopropoxide (0.186 ml, 0.63 mmol) was stirred at room temperature under nitrogen. After 1 hr, the viscous solution was diluted with absolute ethanol (0.5 mL). Sodium cyanoborohydride (21 mg, 0.335 mL) was added, and the solution was stirred for 1 day. Water was added with stirring, and the resulting inorganic precipitate was filtered and washed with ethanol. The filtrate was then concentrated in vacuo. The crude product was dissolved in ethyl acetate, filtered to remove the remaining inorganic solids, and concentrated in vacuo. The product was then purified by flash chromatography. The aqueous layer was frozen in liquid nitrogen and lyophilized to give the title compound as a colorless foam (97 mg); $^1$H NMR (D$_2$O, 300 MHz) δ 7.28-7.18 (m, 2H), 7.18-7.09 (m, 3H), 3.37-3.08 (m, 3H), 3.03-2.70 (m, 2H), 2.51-2.26 (m, 4H), 1.90-1.57 (m, 6H), 1.44-1.02 (m, 8H), 0.64 (t, J=7.5 Hz, 2H); MS (+CI): m/z for $C_{21}H_{35}BN_2O_4$: expected 390.32. found 391.2 (M+H)$^+$, 373.3 (M+H−H$_2$O)$^+$.

Example 125

Preparation of 2-amino-2-(2-(4-benzylpiperidin-1-yl)ethyl)-6-boronohexanoic acid dihydrochloride

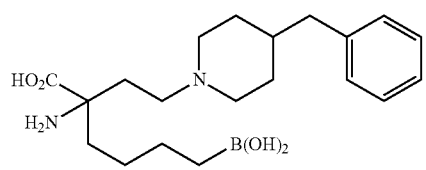

(125)

2-Amino-2-(2-(4-benzylpiperidin-1-yl)ethyl)-6-boronohexanoic acid is prepared in a manner analogous to that set forth in Example 16, except 4-benzylpiperidine is used as the amine in step 6. $^1$H NMR (D$_2$O, 300 MHz) δ 7.28-7.18 (m, 2H), 7.18-7.08 (m, 3H), 3.50-3.36 (m, 2H), 3.24-3.12 (m, 1H), 3.08-2.91 (m, 1H), 2.89-2.71 (m, 2H), 2.56-2.43 (m, 2H), 2.23-2.10 (m, 2H), 1.89-1.64 (m, 5H), 1.43-1.22 (m, 5H), 1.19-1.04 (m, 1H), 0.66 (t, J=7.2 Hz, 2H). ESI MS found for $C_{20}H_{33}BN_2O_4$ m/z [377.3 (M+1)].

Example 126

Preparation of 2-amino-6-borono-2-(2-(4-(4-(trifluoromethyl)benzyl)piperidine-1-yl)ethyl)hexanoic acid dihydrochloride

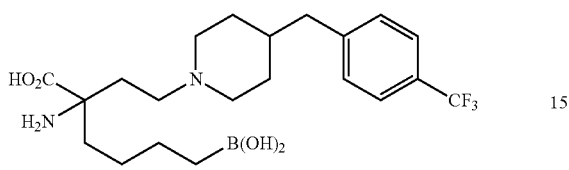

(126)

2-Amino-6-borono-2-(2-(4-(4-(trifluoromethyl)benzyl) piperidine-1-yl)ethyl)hexanoic acid dihydrochloride is prepared in a manner analogous to that set forth in Example 16, except 4-(4-(trifluoromethyl)benzyl)piperidine is used as the amine in step 6. $^1$H NMR ($D_2O$, 300 MHz) δ 7.53 (d, J=7.8 Hz, 2H), 7.27 (d, J=7.8 Hz, 2H), 3.50-3.36 (m, 2H), 3.27-3.12 (m, 1H), 3.07-2.91 (m, 1H), 2.90-2.71 (m, 2H), 2.61-2.51 (m, 2H), 2.22-2.09 (m, 2H), 1.90-1.62 (m, 5H), 1.45-1.19 (m, 5H), 1.17-1.04 (m, 1H), 0.67 (t, J=7.2 Hz, 2H). ESI MS found for $C_{21}H_{32}BF_3N_2O_4$ m/z [445.3 (M+1)].

Example 127

Preparation of 2-amino-6-borono-2-(2-(4-(4-fluorobenzyl)piperidin-1-yl)ethyl)hexanoic acid dihydrochloride

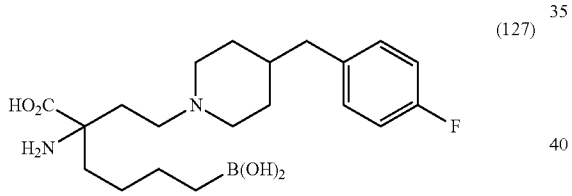

(127)

2-Amino-6-borono-2-(2-(4-(4-fluorobenzyl)piperidin-1-yl)ethyl)hexanoic acid dihydrochloride is prepared in a manner analogous to that set forth in Example 16, except 4-(4-fluorobenzyl)piperidine is used as the amine in step 6. $^1$H NMR ($D_2O$, 500 MHz) δ 7.09 (m, 2H), 6.92 (m, 2H), 3.48-3.39 (m, 2H), 3.24-3.12 (m, 1H), 3.06-2.94 (m, 1H), 2.83-2.74 (m, 2H), 2.44-2.37 (m, 2H), 2.25-2.17 (m, 2H), 1.88-1.78 (m, 1H), 1.76-1.64 (m, 4H), 1.33-1.20 (m, 5H), 1.15-1.02 (m, 1H), 0.64 (t, J=7.2 Hz, 2H). ESI MS found for $C_{21}H_{32}BF_3N_2O_4$ m/z [395.4 (M+1)].

Example 128

Preparation of 2-amino-6-borono-2-(2-(4,4-dimethylpiperidin-1-yl)ethyl)hexanoic acid dihydrochloride

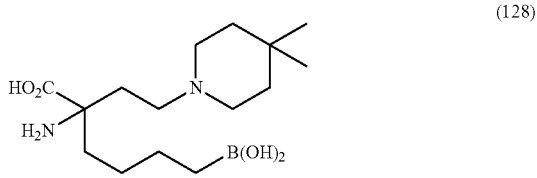 [SMILES: CC1(C)CCN(CCC(N)(CCCCB(O)O)C(=O)O)CC1]

(128)

2-Amino-6-borono-2-(2-(4,4-dimethylpiperidin-1-yl) ethyl)hexanoic acid is prepared in a manner analogous to that set forth in Example 16, except 4,4-dimethylpiperidine is used as the amine in step 6. $^1$H NMR ($D_2O$, 500 MHz) δ 3.33-3.19 (m, 3H), 3.12-2.94 (m, 3H), 2.29-2.20 (m, 2H), 1.90-1.82 (m, 1H), 1.80-1.74 (m, 1H), 1.53-1.48 (m, 4H), 1.33-1.25 (m, 3H), 1.16-1.08 (m, 1H), 0.89 (s, 3H), 0.85 (s, 3H), 0.66 (t, J=7.2 Hz, 2H). ESI MS found for $C_{15}H_{31}BN_2O_4$ m/z [315.7 (M+1)].

Example 129

Preparation of 2-amino-6-borono-2-(2-(4-propylpiperidin-1-yl)ethyl)hexanoic acid dihydrochloride

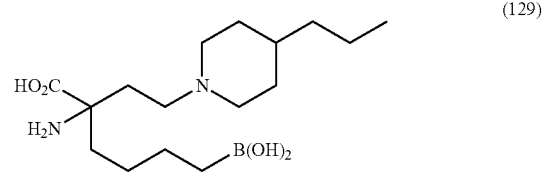 [SMILES: CCCC1CCN(CCC(N)(CCCCB(O)O)C(=O)O)CC1]

(129)

2-Amino-6-borono-2-(2-(4-propylpiperidin-1-yl)ethyl) hexanoic acid is prepared in a manner analogous to that set forth in Example 16, except 4-propylpiperidine is used as the amine in step 6. $^1$H NMR ($D_2O$, 500 MHz) δ 3.49-3.40 (m, 2H), 3.24-3.17 (m, 1H), 3.05-2.97 (m, 1H), 2.88-2.79 (m, 2H), 2.24-2.17 (m, 2H), 1.90-1.79 (m, 3H), 1.76-1.70 (m, 1H), 1.53-1.42 (m, 1H), 1.35-1.05 (m, 10H), 0.74 (t, J=6.9 Hz, 2H), 0.65 (t, J=7.2 Hz, 2H). ESI MS found for $C_{16}H_{33}BN_2O_4$ m/z [329.7 (M+1)].

Example 130

Preparation of 2-amino-6-borono-2-(2-(2-ethyl-1,2,3,4-tetrahydroisoquinolin-3-yl)ethyl)hexanoic acid dihydrochloride

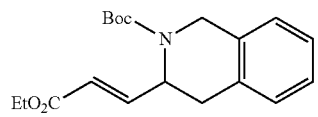

Step 1: Synthesis of (E)-tert-butyl 3-(3-ethoxy-3-oxoprop-1-enyl)-3,4-dihydroisoquinoline-2(1H)-carboxylate A solution of tert-butyl 3-formyl-3,4-dihydroisoquinoline-2(1H)-carboxylate (8.4 g, 32.2 mmol) in dry THF (200 mL, 0.16 M) was treated with (ethoxycarbonylmethylene)triphenylphosphorane (12.8 g, 37.0 mmol) in one portion. After stirring at room temperature overnight, the solvent was evaporated, and the resulting residue was dissolved in ether. Heptane was added and the precipitated triphenylphosphine oxide was filtered off. The filtrate was concentrated and purified by flash chromatography (5-20% ethyl acetate in hexane) affording (E)-tert-butyl 3-(3-ethoxy-3-oxoprop-1-enyl)-3,4-dihydroisoquinoline-2(1H)-carboxylate as yellow oil (8.7 g, 82%). $^1$H NMR (CDCl$_3$, 500 MHz) δ 7.21-7.14 (m, 2H), 7.14-7.07 (m, 2H), 6.74 (dd, J$_1$=15.8 Hz, J$_2$=4.8 Hz, 1H), 5.79 (dd, J$_1$=15.8 Hz, J$_2$=1.3 Hz, 1H), 4.72 (d, J=16.5 Hz, 1H), 4.35 (d, J=16.5 Hz, 1H), 4.11 (qw, J=14.4 Hz, 2H), 3.18 (dd, J$_1$=15.8 Hz, J$_2$=6.2 Hz 1H), 2.84 (d, J=15.8 Hz, 1H), 1.49 (s, 9H), 1.23 (t, J=14.4 Hz, 3H). ESI MS found for $C_{19}H_{25}NO_4$ m/z [354.4 (M+23)].

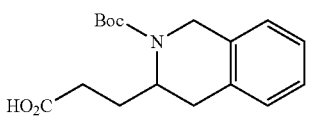

Step 2: Synthesis of 3-(2-(tert-butoxycarbonyl)-1,2,3,4-tetrahydroisoquinolin-3-yl)propanoic acid A solution of (E)-tert-butyl 3-(3-ethoxy-3-oxoprop-1-enyl)-3,4-dihydroisoquinoline-2(1H)-carboxylate (8.7 g, 26.3 mmol) and Pd/C (cat) in ethanol (150 mL, 0.18 M) was evacuated to remove air then treated with hydrogen via a balloon. After stirring for 4 h, 3 M sodium hydroxide was added to adjust the solution to pH 11 and the mixture was stirred overnight. The resulting solution was filtered, concentrated, acidified to pH 2 and extracted with ethyl acetate. The organic layer was dried over MgSO$_4$, filtered and concentrated to give 3-(2-(tert-butoxycarbonyl)-1,2,3,4-tetrahydroisoquinolin-3-yl)propanoic acid as a yellow oil (7.7 g, 96%). ESI MS found for $C_{17}H_{23}NO_4$ m/z [328.4 (M+23)]. The crude product was used without further purification.

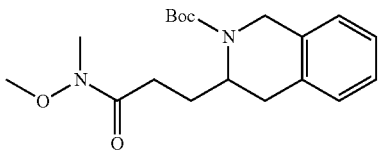 [SMILES: CON(C)C(=O)CCC1Cc2ccccc2CN1C(=O)OC(C)(C)C]

Step 3: Synthesis of tert-butyl 3-(3-(methoxy(methyl)amino)-3-oxopropyl)-3,4-dihydroisoquinoline-2(1H)-carboxylate A solution of 3-(2-(tert-butoxycarbonyl)-1,2,3,4-tetrahydroisoquinolin-3-yl)propanoic acid (7.7 g, 25.2 mmol) in dichloromethane (200 mL, 0.13 M) was treated with CDI (6.1 g, 37.8 mmol) in three portions over 10 min with vigorous stirring. After the addition was complete, the mixture was stirred for an additional 40 min and treated with N,O-dimethylhydroxylamine hydrochloride (3.7 g, 37.2 mmol) and stirred overnight. The resulting solution was washed successively with water, 1 M HCl, 1 M NaOH, sat'd aq sodium chloride, dried over anhydrous MgSO$_4$, filtered and concentrated to give tert-butyl 3-(3-(methoxy(methyl)amino)-3-oxopropyl)-3,4-dihydroisoquinoline-2(1H)-carboxylate as a yellow oil (8.6 g, 98%). LCMS, $C_{19}H_{28}N_2O_4$ m/z [371.4 (M+23)]. The crude product was used without further purification.

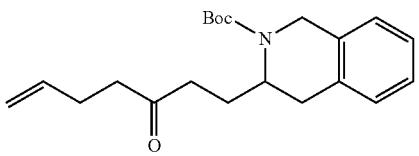 [SMILES: C=CCCC(=O)CCC1Cc2ccccc2CN1C(=O)OC(C)(C)C]

Step 4: Synthesis of tert-butyl 3-(3-oxohept-6-enyl)-3,4-dihydroisoquinoline-2(1H)-carboxylate While under an atmosphere of argon, a flame-dried round-bottomed flask was charged with magnesium (1.5 g, 62.9 mmol) a small crystal of I$_2$ and just enough dry THF to cover the magnesium. The mixture was heated to reflux until the color dissipated (about 10 min). Approximately 10% of a solution of 4-bromo-1-butene (61.7 mmol) in THF (100 mL) was added all at once. The remainder of the solution was added dropwise while maintaining a gentle reflux. After the addition was complete, heating was continued for 5 min (until almost all of the Mg had reacted). The newly formed Grignard reagent was then added to an ice cooled solution of tert-butyl 3-(3-(methoxy(methyl)amino)-3-oxopropyl)-3,4-dihydroisoquinoline-2(1H)-carboxylate (8.6 g, 24.7 mmol) in dry THF (100 mL). After stirring overnight at room temperature, the solution was poured into saturated aqueous ammonium chloride and extracted with ether (3×). The combined organic extracts were dried over MgSO$_4$, filtered and concentrated under reduced pressure to give tert-butyl 3-(3-oxohept-6-enyl)-3,4-dihydroisoquinoline-2(1H)-carboxylate (8.0 g, 95%). ESI MS found for $C_{21}H_{29}NO_3$ m/z [366.5 (M+23)]. The crude product was used without further purification.

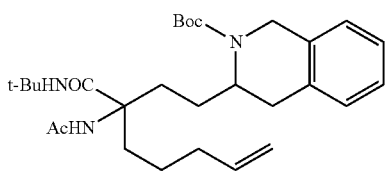

Step 5: Synthesis of tert-butyl 3-(3-acetamido-3-(tert-butylcarbamoyl)oct-7-enyl)-3,4-dihydroisoquinoline-2(1H)-carboxylate A solution of tert-butyl 3-(3-oxohept-6-enyl)-3,4-dihydroisoquinoline-2(1H)-carboxylate (2.0 g, 5.8 mmol), t-butyl isonitrile (2.7 mL, 23.3 mmol) and ammonium acetate 2.7 g (34.8 mmol) in 2,2,2-trifluoroethanol (3 mL, 1.9 M) was stirred at room temperature until thin-layer chromatography (TLC) indicated the starting ketone was consumed. Once complete, the reaction was diluted with ethyl acetate, quenched with 2 M HCl and extracted with ethyl acetate. The organic layer was washed successively with 2 M HCl and sat'd aq sodium chloride, dried over MgSO$_4$, filtered and concentrated. Purification by column chromatography (ethyl acetate in hexanes) gave tert-butyl 3-(3-acetamido-3-(tert-butylcarbamoyl)oct-7-enyl)-3,4-dihydroisoquinoline-2(1H)-carboxylate as yellow oil (1.5 g, 53%). ESI MS found for $C_{28}H_{43}N_3O_4$ m/z [508.6 (M+23)].

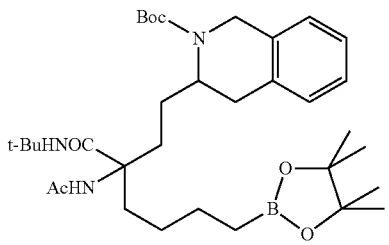

Step 6: Synthesis of tert-butyl 3-(3-acetamido-3-(tert-butylcarbamoyl)-7-(4,4,5,5-tetramethyl-1,3,2-dioxaborolan-2-yl)heptyl)-3,4-dihydroisoquinoline-2(1H)-carboxylate While under an atmosphere of argon, a solution of bis(1,5-dicyclooctadiene)diiridium(I) dichloride (54 mg, 3% mol), diphenylphosphinoethane (64 mg, 6% mol) and 4,4,5,5-tetramethyl-1,3,2-dioxaborolane (1.5 mL, 10.7 mmol) in dry dichloromethane (20 mL) was cooled to 0° C. A second solution of tert-butyl 3-(3-acetamido-3-(tert-butylcarbamoyl)oct-7-enyl)-3,4-dihydroisoquinoline-2(1H)-carboxylate (1.5 g, 2.67 mmol) in dry dichloromethane (20 mL) was added in one portion. After 4 h LCMS indicated all the starting olefin was consumed and the reaction was washed successively with water, sat'd aq sodium chloride, dried over MgSO$_4$, filtered and concentrated. Purification by flash chromatography (20-35% ethyl acetate in hexanes) gave tert-butyl 3-(3-acetamido-3-(tert-butylcarbamoyl)-7-(4,4,5,5-tetramethyl-1,3,2-dioxaborolan-2-yl)heptyl)-3,4-dihydroisoquinoline-2(1H)-carboxylate as a yellow oil (1.5 g, 93%). ESI MS found for $C_{34}H_{56}BN_3O_6$ m/z [614.7 (M+1), 633.7 (M+23)].

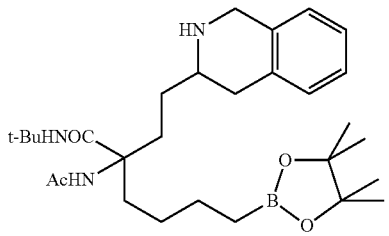

Step 7: Synthesis of 2-acetamido-N-tert-butyl-2-(2-(1,2,3,4-tetrahydroisoquinolin-3-yl)ethyl)-6-(4,4,5,5-tetramethyl-1,3,2-dioxaborolan-2-yl)hexanamide A solution of tert-butyl 3-(3-acetamido-3-(tert-butylcarbamoyl)-7-(4,4,5,5-tetramethyl-1,3,2-dioxaborolan-2-yl)heptyl)-3,4-dihydroisoquinoline-2(1H)-carboxylate in ethyl acetate was treated with a solution of HCl (g) in ethyl acetate (approximately 2 M). After stirring for 30 min the reaction was concentrated to dryness and the crude hydrochloride product was used without further purification.

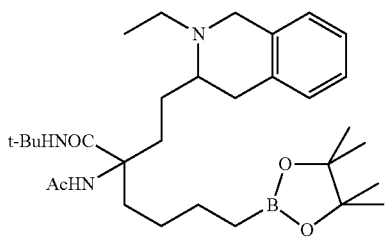

Step 8: Synthesis of 2-acetamido-N-tert-butyl-2-(2-(2-ethyl-1,2,3,4-tetrahydroisoquinolin-3-yl)ethyl)-6-(4,4,5,5-tetramethyl-1,3,2-dioxaborolan-2-yl)hexanamide A solution of acetaldehyde (0.06 mL, 1.1 mmol) and 2-acetamido-N-tert-butyl-2-(2-(1,2,3,4-tetrahydroisoquinolin-3-yl)ethyl)-6-(4,4,5,5-tetramethyl-1,3,2-dioxaborolan-2-yl)hexanamide (0.51 g, 1.0 mmol) in dichloromethane was stirred at room temperature for 1 h, then treated with sodium triacetoxyborohydride (0.63 g, 3 mmol). After stirring overnight, the reaction was quenched with 5% aq NaHCO$_3$ (W/V) and extracted with dichloromethane. The organic layer was washed successively with 1 M HCl, sat'd aq sodium chloride, dried over MgSO$_4$, filtered and concentrated. Purification by flash chromatography (1% methanol in chloroform) gave 2-acetamido-N-tert-butyl-2-(2-(2-ethyl-1,2,3,4-tetrahydroisoquinolin-3-yl)ethyl)-6-(4,4,5,5-tetramethyl-1,3,2-dioxaborolan-2-yl)hexanamide as an oil (0.45 g, 83%). ESI MS found for $C_{31}H_{52}BN_3O_4$ m/z [b.e.542.7 (M+1)].

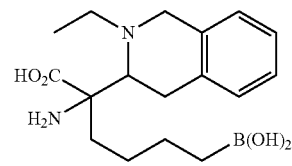

(130)

Step 9: Synthesis of 2-amino-6-borono-2-(2-(2-ethyl-1,2,3,4-tetrahydroisoquinolin-3-yl)ethyl)hexanoic acid A solution of 2-acetamido-N-tert-butyl-2-(2-(2-ethyl-1,2,3,4-tetrahydroisoquinolin-3-yl)ethyl)-6-(4,4,5,5-tetramethyl-1,3,2-dioxaborolan-2-yl)hexanamide (0.108 g, 0.2 mmol) in 6 N HCl was heated to reflux for 16 h, cooled to room temperature and concentrated to dryness. Purified by preparative HPLC (20% acetonitrile in water with 0.1% trifluoroacetic acid) gave 2-amino-6-borono-2-(2-(2-ethyl-1,2,3,4-tetrahydroisoquinolin-3-yl)ethyl)hexanoic acid as a white solid (90 mg, 83%). $^1$H NMR (D$_2$O, 500 MHz) δ 7.32-7.10 (m, 4H), 4.51-4.38 (m, 1H), 4.29-4.20 (m, 1H), 3.83-3.78 (m, 0.5H), 3.70-3.64 (m, 0.5H), 3.33-3.08 (m, 3H), 3.03-2.85 (m, 1H), 2.02-1.62 (m, 5.5H), 1.50-1.38 (m, 0.5H), 1.35-1.20 (m, 6H), 1.17-1.05 (m, 1H), 0.70-0.60 (m, 2H). ESI MS found for $C_{19}H_{31}BN_2O_4$ m/z [345.4 (M+1−18), 327.4 (M+1−2×18)].

Example 131

Preparation of 2-amino-6-borono-2-(2-(1,2,3,4-tetrahydroisoquinolin-3-yl)ethyl)hexanoic acid dihydrochloride

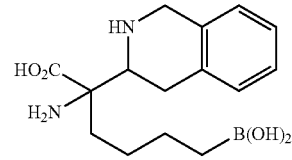

(131)

2-Amino-6-borono-2-(2-(1,2,3,4-tetrahydroisoquinolin-3-yl)ethyl)hexanoic acid dihydrochloride is prepared in a manner analogous to that set forth in Example 130, except steps 7 and 8 were omitted. $^1$H NMR (D$_2$O, 500 MHz) δ 7.29-7.13 (m, 4H), 4.33 (bs, 2H), 3.59-3.50 (m, 1H), 3.18 (dd, J$_1$=17.6 Hz, J$_2$=5.3 Hz, 1H), 2.87 (dd, J$_1$=17.6 Hz, J$_2$=10.6 Hz, 1H), 2.12-1.74 (m, 6H), 1.41-1.30 (m, 3H), 1.22-1.13 (m, 1H), 0.69 (t, J=7.2 Hz, 2H). ESI MS found for $C_{17}H_{27}BN_2O_4$ m/z [335.4 (M+1), 317.4 (M+1−18)].

Example 132

Preparation of 2-amino-6-borono-2-(2-(2-(4-chlorobenzyl)-1,2,3,4-tetrahydroisoquinolin-3-yl)ethyl)hexanoic acid dihydrochloride

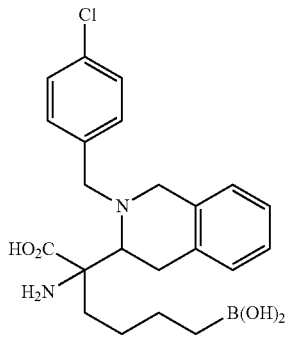

(132)

2-Amino-6-borono-2-(2-(2-(4-chlorobenzyl)-1,2,3,4-tetrahydroisoquinolin-3-yl)ethyl)hexanoic acid dihydrochloride is prepared in a manner analogous to that set forth in Example 130, except 4-chlorobenzaldehyde was used as the aldehyde in Step 8. $^1$H NMR ($D_2O$, 500 MHz) δ 7.47-7.06 (m, 8H), 4.45-4.11 (m, 4H), 3.83-3.64 (m, 1H), 3.32-3.20 (m, 1H), 3.07-2.90 (m, 1H), 2.05-1.40 (m, 6H), 1.39-1.21 (m, 3H), 1.22-1.06 (m, 1H), 0.71-0.60 (m, 2H). ESI MS found for $C_{24}H_{32}BClN_2O_4$ m/z [441.4/443.5 (M+1−18)].

Example 133

Preparation of 2-amino-6-borono-2-(2-(2-isopentyl-1,2,3,4-tetrahydroisoquinolin-3-yl)ethyl)hexanoic acid dihydrochloride

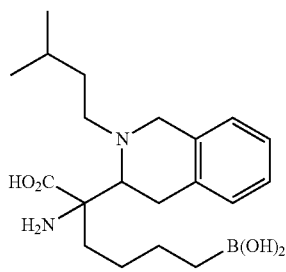

(156)

2-Amino-6-borono-2-(2-(2-isopentyl-1,2,3,4-tetrahydroisoquinolin-3-yl)ethyl)hexanoic acid dihydrochloride is prepared in a manner analogous to that set forth in Example 130, except isovaleraldehyde was used as the aldehyde in Step 8. $^1$H NMR ($D_2O$, 500 MHz) δ 7.34-7.10 (m, 4H), 4.50-4.38 (m, 1H), 4.31-4.18 (m, 1H), 3.82-3.75 (m, 0.5H), 3.70-3.62 (m, 0.5H), 3.28-2.85 (m, 4H), 2.00-1.41 (m, 9H), 1.35-1.20 (m, 3H), 1.18-1.06 (m, 1H), 0.86-0.75 (m, 6H), 0.70-0.60 (m, 2H). ESI MS found for $C_{22}H_{37}BN_2O_4$ m/z [427.2 (M+23), 387.5 (M+1−18)].

Example 134

Preparation of 2-amino-6-borono-2-(2-(2-(cyclohexylmethyl)-1,2,3,4-tetrahydroisoquinolin-3-yl)ethyl)hexanoic acid dihydrochloride

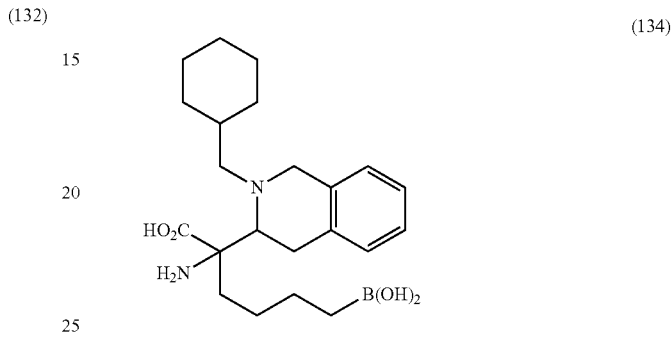

(134)

2-Amino-6-borono-2-(2-(2-(cyclohexylmethyl)-1,2,3,4-tetrahydroisoquinolin-3-yl)ethyl)hexanoic acid dihydrochloride is prepared in a manner analogous to that set forth in Example 130, except cyclohexanealdehyde was used as the aldehyde in Step 8. $^1$H NMR ($D_2O$, 500 MHz) δ 7.35-7.07 (m, 4H), 4.50-4.10 (m, 2H), 3.85-3.64 (m, 1H), 3.30-3.12 (m, 1H), 3.08-2.80 (m, 3H), 2.05-1.42 (m, 12H), 1.37-1.05 (m, 7H), 1.05-0.88 (m, 2H), 0.70-0.60 (m, 2H). ESI MS found for $C_{24}H_{39}BN_2O_4$ m/z [431.6 (M+1), 413.6 (M+1−18)].

Example 135

Preparation of 2-amino-6-borono-2-(2-(2-isobutyl-1,2,3,4-tetrahydroisoquinolin-3-yl)ethyl)hexanoic acid dihydrochloride

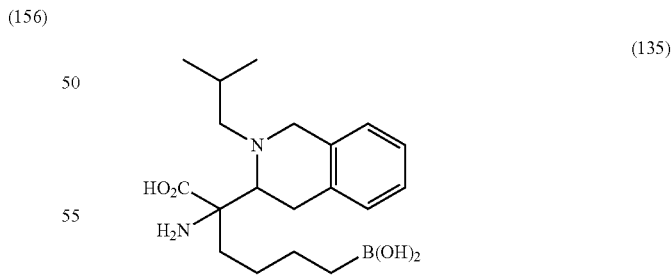

(135)

2-Amino-6-borono-2-(2-(2-isobutyl-1,2,3,4-tetrahydroisoquinolin-3-yl)ethyl)hexanoic acid dihydrochloride is prepared in a manner analogous to that set forth in Example 130, except isobutyraldehyde was used as the aldehyde in Step 8. $^1$H NMR ($D_2O$, 500 MHz) δ 7.36-7.05 (m, 4H), 4.52-4.12 (m, 2H), 3.83-3.65 (m, 1H), 3.30-3.15 (m, 1H), 3.08-2.81 (m, 3H), 2.15-1.96 (m, 3.5H), 1.90-1.70 (m, 3H), 1.53-1.45 (m, 0.5H), 1.35-1.27 (m, 3H), 1.18-1.07 (m, 1H), 1.01-0.85 (m, 6H), 0.70-0.60 (m, 2H). ESI MS found for $C_{21}H_{35}BN_2O_4$ m/z [391.5 (M+1), 373.5 (M+1–18)].

Example 136

Preparation of 6-borono-2-(3-(3,4-dichlorobenzylamino)propyl)-2-(methylamino)hexanoic acid dihydrochloride

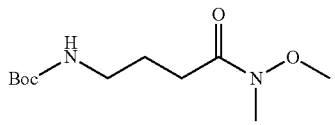 [SMILES: CON(C)C(=O)CCCNC(=O)OC(C)(C)C]

Step 1: Synthesis of tert-butyl 4-(methoxy(methyl)amino)-4-oxobutylcarbamate While under an atmosphere of argon, a room temperature solution of 4-(tert-butoxycarbonylamino) butanoic acid (20 g, 0.098 mol) in dichloromethane (280 mL, 0.35 M) was treated with CDI (17.6 g, 0.108 mol). After 1.5 hr, O,N-dimethylhydroxylamine hydrochloride (10.6 g; 0.108 mol) was added, and the resulting solution was stirred overnight. The mixture was added to a separatory funnel, diluted with dichloromethane (220 mL) and washed successively with 2 M HCl (2×), 1 M NaOH and sat'd aq sodium chloride, dried over MgSO$_4$, filtered and concentrated to give tert-butyl 4-(methoxy(methyl)amino)-4-oxobutylcarbamate (23.8 g, 98%). ESI MS found for $C_{11}H_{22}N_2O_4$ m/z [269.4 (M+Na$^+$)].

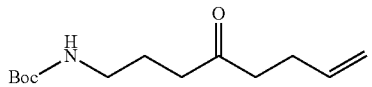 [SMILES: C=CCCC(=O)CCCNC(=O)OC(C)(C)C]

Step 2: Synthesis of tert-butyl 4-oxooct-7-enylcarbamate

While under an atmosphere of nitrogen, a flame-dried round-bottomed flask was charged with magnesium (3.95 g, 0.162 mol) a small crystal of I$_2$ and just enough dry THF to cover the magnesium. The mixture was heated to reflux until the color dissipated (about 10 min.). Next, a solution of 4-bromo-1-butene (16.4 mL, 0.162 mmol) in dry THF (70 mL) was added and heating was continued for 10 min. After cooling to room temperature, the newly formed Grignard reagent was then added to a ice-cooled solution of tert-butyl 4-(methoxy(methyl)amino)-4-oxobutylcarbamate (10 g, 0.041 mol) in dry THF (100 mL). After stirring overnight at room temperature, the solution was poured into saturated aqueous ammonium chloride (70 mL) and extracted with ether (2×). The organic extracts were combined and washed successively with 1.0 M aq HCl and sat'd aq sodium chloride, dried over MgSO$_4$, filtered and concentrated. Purification by flash column chromatography (15-30% ethyl acetate in hexanes) gave tert-butyl 4-oxooct-7-enylcarbamate as a colorless oil (6.04 g, 62%). ESI MS found for $C_{13}H_{23}NO_3$ m/z [264.3 (M+Na$^+$)].

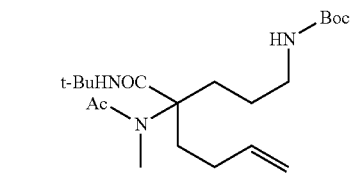

Step 3: Synthesis of tert-butyl 4-(tert-butylcarbamoyl)-4-(N-methylacetamido)oct-7-enylcarbamate A solution of tert-butyl 4-oxooct-7-enylcarbamate (300 mg; 1.24 mmol), methylammonium acetate (680 mg, 7.46 mmol) in 2,2,2-trifluoroethanol (2 mL) was treated with tert-butyl isocyanide (0.56 mL, 5.0 mmol) and stirred at room temperature for 5 days. Ethyl acetate (5 mL) and 2 M aq HCl (2 mL) were added and the solution was vigorously stirred for 3 additional hrs. The phases were separated and the organic phase was washed successively with water and sat'd aq sodium chloride, dried over MgSO$_4$, filtered and concentrated. The crude viscous yellow oil residue was purified by flash column chromatography (2% methanol in dichloromethane) to give tert-butyl 4-(tert-butylcarbamoyl)-4-(N-methylacetamido)oct-7-enylcarbamate (130 mg, 26%). $^1$H NMR (CDCl$_3$, 500 MHz) δ 5.81-5.73 (m, 1H), 5.40 (s, 1H), 5.05-4.96 (m, 2H), 4.62 (bs, 1H), 3.15-3.09 (m, 2H), 3.01 (s, 3H) 2.17-2.12 (m, 2H), 2.10 (s, 3H) 2.04-1.94 (m, 2H), 1.77-1.71 (m, 2H), 1.43 (s, 9H), 1.38-1.34 (m, 2H), 1.32 (s, 9H). ESI MS found for $C_{21}H_{39}N_3O_4$ m/z [420.5 (M+Na$^+$), 442.4 (M+HCOO$^-$), 396.6 (M–1)].

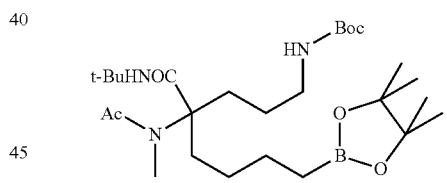

Step 4: Synthesis of tert-butyl 4-(tert-butylcarbamoyl)-4-(N-methylacetamido)-8-(4,4,5,5-tetramethyl-1,3,2-dioxaborolan-2-yl)octylcarbamate While under an atmosphere of argon, a solution of bis(1,5-dicyclooctadiene)diiridium(I)dichloride (6 mg; 0.009 mmol) and diphenylphosphinoethane (7 mg, 0.018 mmol) in dichloromethane (1 mL) was cooled to 0° C. and treated with 4,4,5,5-tetramethyl-1,3,2-dioxaborolane (0.174 mL, 1.2 mmol). After stirring for 30 min, a solution of tert-butyl 4-(tert-butylcarbamoyl)-4-(N-methylacetamido)oct-7-enylcarbamate (120 mg, 0.3 mmol) in dichloromethane (4 mL) was added and the solution was stirred an additional 16 h. Dichloromethane (10 mL) was added, and the solution was washed successively with water and sat'd aq sodium chloride, dried over MgSO$_4$, filtered and concentrated. Purification by column chromatography (3% methanol in dichloromethane) gave tert-butyl 4-(tert-butylcarbamoyl)-4-(N-methylacetamido)-8-(4,4,5,5-tetramethyl-1,3,2-dioxaborolan-2-yl)octylcarbamate (142 mg, 90%). ESI MS found for $C_{27}H_{52}BN_3O_6$ m/z [548.7 (M+Na$^+$), 526.7 (M+1), 570.8 (M+HCOO$^-$), 524.6 (M−1)].

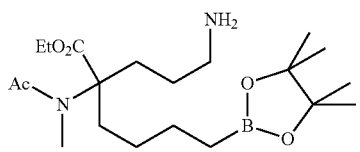 [SMILES: CCOC(=O)C(CCCN)(CCCCB1OC(C)(C)C(C)(C)O1)N(C)C(C)=O]

Step 5: Synthesis of ethyl 2-(3-aminopropyl)-2-(N-methylacetamido)-6-(4,4,5,5-tetramethyl-1,3,2-dioxaborolan-2-yl)hexanoate hydrochloride A solution of tert-butyl 4-(tert-butylcarbamoyl)-4-(N-methylacetamido)-8-(4,4,5,5-tetramethyl-1,3,2-dioxaborolan-2-yl)octylcarbamate (140 mg, 0.266 mmol) in ethyl acetate (2 mL) was treated with anh HCl (2 N in ethyl acetate, 10 mL) and stirred at room temp. After 30 min, the solution was concentrated to give crude ethyl 2-(3-aminopropyl)-2-(N-methylacetamido)-6-(4,4,5,5-tetramethyl-1,3,2-dioxaborolan-2-yl)hexanoate hydrochloride as a white solid (130 mg). ESI MS found for $C_{20}H_{39}BN_2O_5$ m/z [399.5 (M+1)]. This material was used without further purification.

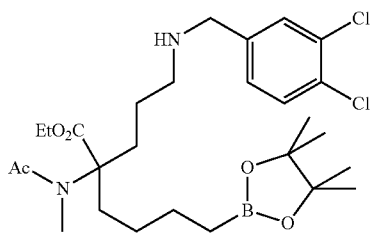 [SMILES: CCOC(=O)C(CCCCB1OC(C)(C)C(C)(C)O1)(CCCNCc1ccc(Cl)c(Cl)c1)N(C)C(C)=O]

Step 6: Synthesis of ethyl 2-(3-(3,4-dichlorobenzylamino)propyl)-2-(N-methylacetamido)-6-(4,4,5,5-tetramethyl-1,3,2-dioxaborolan-2-yl)hexanoate hydrochloride A solution of 3,4-dichlorobenzaldehyde (55 mg, 0.31 mmol) and ethyl 2-(3-aminopropyl)-2-(N-methylacetamido)-6-(4,4,5,5-tetramethyl-1,3,2-dioxaborolan-2-yl)hexanoate hydrochloride (120 mg, 0.26 mmol) in dichloromethane (3 mL) was stirred at room temperature. After 30 min, sodium triacetoxyborohydride (138 mg, 0.65 mmol) was added in one portion and stirring was continuated overnight. Once complete, the solution was diluted with dichloromethane (10 mL), quenched with aq 5% NaHCO$_3$ (W/V, 5 mL) and stirred vigorously for 30 min. The layers were separated and the organic phase was washed with water and sat'd aq sodium chloride, dried over MgSO$_4$, filtered and concentrated. Purification by flash column chromatography (2-20% methanol in dichloromethane) gave ethyl 2-(3-(3,4-dichlorobenzylamino)propyl)-2-(N-methylacetamido)-6-(4,4,5,5-tetramethyl-1,3,2-dioxaborolan-2-yl)hexanoate (78 mg). ESI MS found for $C_{27}H_{43}BCl_2N_2O_5$ m/z [557.6/559.6 (M+1)].

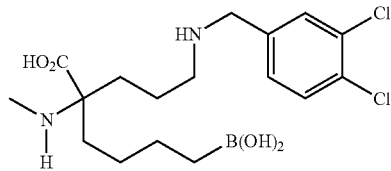

(136)

Step 7: Synthesis of 6-borono-2-(3-(3,4-dichlorobenzylamino)propyl)-2-(methylamino)hexanoic acid dihydrochloride.

A solution of ethyl 2-(3-(3,4-dichlorobenzylamino)propyl)-2-(N-methylacetamido)-6-(4,4,5,5-tetramethyl-1,3,2-dioxaborolan-2-yl)hexanoate (76 mg) in aq 6 M HCl was heated to reflux for 16 h, concentrated to dryness and purified by preparative HPLC. The resulting residue was redissolved in 2 N HCl and evaporated to give 6-borono-2-(3-(3,4-dichlorobenzylamino)propyl)-2-(methylamino)hexanoic acid dihydrochloride (19 mg, 12%-3 steps). $^1$H NMR (D$_2$O, 500 MHz) δ 7.55 (bs, 1H), 7.51 (d, J=7.5 Hz, 1H), 7.28 (d, J=7.5 Hz, 1H), 4.12 (s, 2H), 3.02 (t, J=7.2 Hz, 2H), 2.55 (s, 3H), 1.91-1.68 (m, 5H), 1.60-1.49 (m, 1H), 1.38-1.29 (m, 2H), 1.28-1.19 (m, 1H), 1.14-1.04 (m, 1H), 0.70 (t, J=7.2 Hz, 2H). ESI MS found for $C_{17}H_{27}BCl_2N_2O_4$ m/z [405.4/407.4 (M+1)].

Example 137

Preparation of 6-borono-2-(methylamino)-2-(3-(pyrrolidin-1-yl)propyl)hexanoic acid dihydrochloride

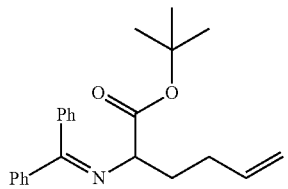

Step 1: Preparation of tert-butyl 2-(diphenylmethyleneamino)hex-5-enoate

While under an atmosphere of argon, a solution of N-(diphenylmethylene)glycine tert-butyl ester (6.30 g, 21.33 mmol) and 4-bromo-butene (3.45 g, 25.56 mmol) in freshly distilled THF (50 mL) was cooled to −78° C. and treated with sodium bis(trimethylsilyl)amide (23.4 mL, 1.0 M in THF). Once the addition was complete, the reaction was warmed to room temperature and stirred for 16 h, cooled to 0° C., diluted with ethyl ether and washed successively with saturated aqueous NaHCO$_3$ and saturated aqueous NaCl, dried over MgSO$_4$, filtered and concentrated. Rapid purification by MPLC (1-25% ethyl acetate in heptane over 8 CV) gave product tert-butyl 2-(diphenylmethyleneamino)hex-5-enoate as a colorless oil (7.00 g, 94%). R$_f$ 0.50 (30% ethyl acetate in heptane).

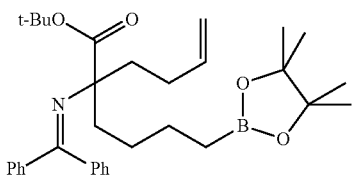 [SMILES: C=CCCC(CCCCB1OC(C)(C)C(C)(C)O1)(N=C(c1ccccc1)c1ccccc1)C(=O)OC(C)(C)C]

Step 2: Preparation of tert-butyl 2-(diphenylmethyleneamino)-2-(4-(4,4,5,5-tetramethyl-1,3,2-dioxaborolan-2-yl)butyl)hex-5-enoate While under an atmosphere of argon, a solution of tert-butyl 2-(diphenylmethyleneamino)hex-5-enoate (7.00 g, 20.06 mmol) in freshly distilled (THF 50 mL) was cooled to −78° C. and treated with sodium bis(trimethylsilyl)amide (60 mL, 1.0 M in THF). After stirring for 10 min 2-(4-iodobutyl)-4,4,5,5-tetramethyl-1,3,2-dioxaborolane (12.4 g, 40.0 mmol) was added and the reaction was warmed to room temperature and stirred for 16 h. Next, the reaction mixture was cooled to 0° C., diluted with ethyl ether and washed successively with saturated aqueous $NaHCO_3$ and saturated aqueous NaCl, dried over $MgSO_4$, filtered and concentrated. Purification by MPLC (1-20% ethyl acetate in heptane with 0.5% triethylamine over 6 CV) gave tert-butyl 2-(diphenylmethyleneamino)-2-(4-(4,4,5,5-tetramethyl-1,3,2-dioxaborolan-2-yl)butyl)hex-5-enoate as a colorless oil (8.50 g, 80%). $R_f$ 0.55 (30% ethyl acetate in heptane). ESI MS found for $C_{33}H_{46}BNO_4$ m/z [532.5 (M+1)].

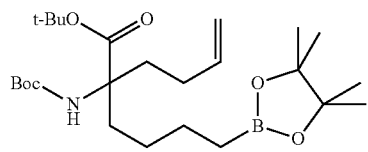 [SMILES: C=CCCC(CCCCB1OC(C)(C)C(C)(C)O1)(NC(=O)OC(C)(C)C)C(=O)OC(C)(C)C]

Step 3: Preparation of tert-butyl 2-(tert-butoxycarbonylamino)-2-(4-(4,4,5,5-tetramethyl-1,3,2-dioxaborolan-2-yl)butyl)hex-5-enoate A solution of tert-butyl 2-(diphenylmethyleneamino)-2-(4-(4,4,5,5-tetramethyl-1,3,2-dioxaborolan-2-yl)butyl)hex-5-enoate (5.31 g, 10.0 mmol) in diethyl ether (25 mL) was treated with 1 N HCl (25 mL). After stirring 4 h, sodium bicarbonate (8.4 g, 0.1 mol) and di-tert-butyl carbonate (2.40 g, 11.0 mmol) were sequentially added. After 16 h, the layers were separated and the aqueous layer was extracted with ethyl acetate. The combined organic layers were washed with saturated aqueous NaCl, dried over $MgSO_4$, filtered and concentrated. Purification by MPLC (0-20% ethyl acetate in heptane over 8 CV) gave tert-butyl 2-(tert-butoxycarbonylamino)-2-(4-(4,4,5,5-tetramethyl-1,3,2-dioxaborolan-2-yl)butyl)hex-5-enoate as a colorless oil (3.64 g, 78%). $R_f$ 0.55 (30% ethyl acetate in heptane); ESI MS found for $C_{25}H_{46}BNO_6$ m/z [468.3 (M+1)].

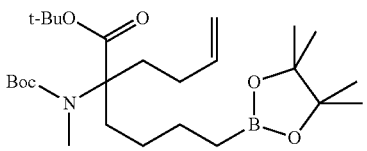 [SMILES: C=CCCC(CCCCB1OC(C)(C)C(C)(C)O1)(C(=O)OC(C)(C)C)N(C)C(=O)OC(C)(C)C]

Step 5: Preparation of tert-butyl 2-(tert-butoxycarbonyl(methyl)amino)-2-(4-(4,4,5,5-tetramethyl-1,3,2-dioxaborolan-2-yl)butyl)hex-5-enoate While under an atmosphere of argon, a solution of tert-butyl 2-(tert-butoxycarbonylamino)-2-(4-(4,4,5,5-tetramethyl-1,3,2-dioxaborolan-2-yl)butyl)hex-5-enoate (1.35 g, 2.89 mmol) in freshly distilled (THF 5 mL) was cooled to 0° C. and treated with sodium bis(trimethylsilyl)amide (6 mL, 1.0 M in THF) under argon. After stirring for 10 min, iodomethane (2.04 g, 14.4 mmol) was added and the reaction was warmed to room temperature and stirred for 16 h. After being complete by TLC, the reaction mixture was cooled to 0° C., diluted with ethyl ether and washed with saturated aqueous NaCl, dried over $MgSO_4$, filtered and concentrated. Purification by MPLC (1-20% ethyl acetate in heptane with 0.5% triethylamine over 8 CV) gave tert-butyl 2-(tert-butoxycarbonyl(methyl)amino)-2-(4-(4,4,5,5-tetramethyl-1,3,2-dioxaborolan-2-yl)butyl)hex-5-enoate as a colorless oil (1.27 g, 91%). $R_f$ 0.35 (20% ethyl acetate in heptane). ESI MS found for $C_{26}H_{48}BNO_6$ m/z [482.3 (M+1)].

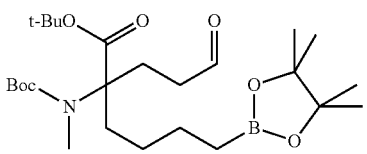 [SMILES: CN(C(=O)OC(C)(C)C)C(CCC=O)(CCCCB1OC(C)(C)C(C)(C)O1)C(=O)OC(C)(C)C]

Step 6: Preparation of tert-butyl 2-(tert-butoxycarbonyl(methyl)amino)-2-(3-oxopropyl)-6-(4,4,5,5-tetramethyl-1,3,2-dioxaborolan-2-yl)hexanoate A solution of tert-butyl 2-(tert-butoxycarbonyl(methyl)amino)-2-(4-(4,4,5,5-tetramethyl-1,3,2-dioxaborolan-2-yl)butyl)hex-5-enoate (1.10 g, 2.29 mmol) in dichloromethane (30 mL) was cooled to −78° C. and treated with ozone until a pale blue-gray color appeared. After TLC indicated the absence of starting material, the ozone inlet tube was replaced with nitrogen and nitrogen was bubbled through the solution for 20 min to remove any excess ozone. Triphenylphosphine (1.50 g, 5.72 mmol, 2.5 equiv) was added in one portion, the cooling bath was removed and the mixture was stirred for 4 h. The solution was concentrated and purified by MPLC (0-40% ethyl acetate in heptane) gave tert-butyl 2-(tert-butoxycarbonyl(methyl)amino)-2-(3-oxopropyl)-6-(4,4,5,5-tetramethyl-1,3,2-dioxaborolan-2-yl)hexanoate as a colorless oil (780 mg, 70%). $R_f$ 0.40 (30% ethyl acetate in heptane). ESI MS found for $C_{25}H_{46}BNO_7$ m/z [484.3 (M+1)].

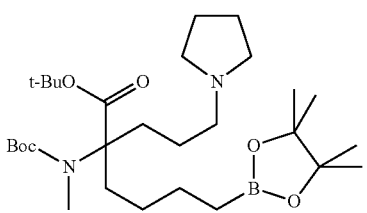 [SMILES: CN(C(=O)OC(C)(C)C)C(CCCCB1OC(C)(C)C(C)(C)O1)(CCCN1CCCC1)C(=O)OC(C)(C)C]

Step 6: Preparation of tert-butyl 2-(tert-butoxycarbonyl(methyl)amino)-2-(3-(pyrrolidin-1-yl)propyl)-6-(4,4,5,5-tetramethyl-1,3,2-dioxaborolan-2-yl)hexanoate A solution of tert-butyl 2-(tert-butoxycarbonyl(methyl)amino)-2-(3-oxopropyl)-6-(4,4,5,5-tetramethyl-1,3,2-dioxaborolan-2-yl)hexanoate (193 mg, 0.40 mmol, 1.0 equiv) and pyrrolidine (43 mg, 0.60 mmol, 1.5 equiv) in 1,2-dichloroethane (2 mL) was treated with sodium triacetoxyborohydride (168 mg, 0.80 mmol) in one portion. After stirring at room temperature overnight, the reaction mixture was quenched with saturated aqueous NaHCO$_3$ (1 mL) and stirred for an additional 5 min. The resulting mixture was added to a separatory funnel, diluted with saturated aqueous NaCl (5 mL) and extracted with dichloromethane (2×10 mL). The organic layer was dried over MgSO$_4$, filtered and concentrated under reduced pressure. Purification by flash column chromatography eluting with gradient 1-10% methanol in chloroform gave tert-butyl 2-(tert-butoxycarbonyl(methyl)amino)-2-(3-(pyrrolidin-1-yl)propyl)-6-(4,4,5,5-tetramethyl-1,3,2-dioxaborolan-2-yl)hexanoate as an oil (186 mg, 88%). R$_f$ 0.35 (10% methanol in dichloromethane). ESI MS found for C$_{29}$H$_{55}$BN$_2$O$_6$ m/z [539.4 (M+1)].

(137)

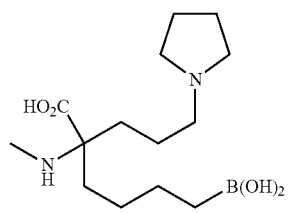

Step 7: Preparation of 6-borono-2-(methylamino)-2-(3-(pyrrolidin-1-yl)propyl)hexanoic acid dihydrochloride A solution of tert-butyl 2-(tert-butoxycarbonyl(methyl)amino)-2-(3-(pyrrolidin-1-yl)propyl)-6-(4,4,5,5-tetramethyl-1,3,2-dioxaborolan-2-yl)hexanoate (183 mg, 0.33 mmol) in 6 N hydrochloric acid (5 mL) was stirred at 95° C. overnight. After cooling to room temperature, the reaction mixture was transferred to a separatory funnel, diluted with deionized water (5 mL) and washed with dichloromethane (3×). The aqueous layer was frozen in liquid nitrogen and lyophilized to give 6-borono-2-(methylamino)-2-(3-(pyrrolidin-1-yl)propyl)hexanoic acid dihydrochloride, as a colorless foam (81 mg, 80%). $^1$H NMR (D$_2$O, 300 MHz) δ 3.55-3.45 (m, 2H), 3.14-3.05 (m, 2H), 2.98-2.87 (m, 2H), 2.53 (s, 3H), 2.03-1.92 (m, 2H), 1.92-1.76 (m, 6H), 1.76-1.64 (m, 1H), 1.62-1.48 (m, 1H), 1.36-1.14 (m, 3H), 1.14-0.98 (m, 1H), 0.64 (t, J=7.2 Hz, 2H). ESI MS found for C$_{14}$H$_{29}$BN$_2$O$_4$ m/z [301.2 (M+1)].

Example 138

Preparation of 6-borono-2-(3-(2,3-dihydro-1H-inden-2-ylamino)propyl)-2-(methylamino)hexanoic acid dihydrochloride (138)

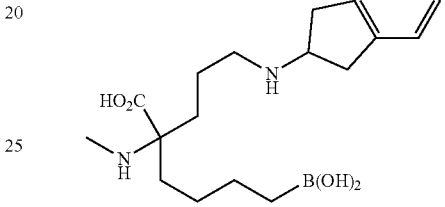

6-Borono-2-(3-(2,3-dihydro-1H-inden-2-ylamino)propyl)-2-(methylamino)hexanoic acid dihydrochloride is prepared in a manner analogous to that set forth in Example 137, except 2,3-dihydro-1H-inden-2-amine was used as the amine in Step 6. $^1$H NMR (D$_2$O, 300 MHz) δ 7.15-7.04 (m, 4H), 3.94-3.82 (m, 1H), 3.25-3.16 (m, 2H), 3.11-2.80 (m, 4H), 2.47 (s, 3H), 1.89-1.40 (m, 6H), 1.27-1.07 (m, 3H), 1.07-0.92 (m, 1H), 0.58 (t, J=7.5 Hz, 2H). ESI MS found for C$_{19}$H$_{31}$BN$_2$O$_4$ m/z [363.3 (M+1)].

Example 139

Preparation of 6-borono-2-(3-(4-chlorobenzylamino)propyl)-2-(methylamino)hexanoic acid dihydrochloride (139)

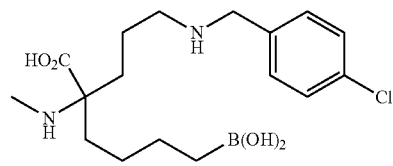

6-Borono-2-(3-(4-chlorobenzylamino)propyl)-2-(methylamino)hexanoic acid dihydrochloride is prepared in a manner analogous to that set forth in Example 137, except 4-chlorobenzylamine was used as the amine in Step 6. $^1$H NMR (D$_2$O, 300 MHz) δ 7.32-7.18 (m, 4H), 4.01 (s, 2H), 2.90 (t, J=7.2 Hz, 2H), 2.46 (s, 3H), 1.84-1.38 (m, 6H), 1.28-1.04 (m, 3H), 1.04-0.92 (m, 1H), 0.56 (t, J=7.5 Hz, 2H). ESI MS found for $C_{17}H_{28}BClN_2O_4$ m/z [371.2 (M+1)].

Example 140

Preparation of 2-amino-6-borono-2-(3-(2,4-dichlorophenethylamino)propyl)hexanoic acid dihydrochloride

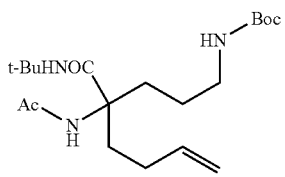

Step 1: Synthesis of tert-butyl 4-acetamido-4-(tert-butylcarbamoyl)oct-7-enylcarbamate A solution of tert-butyl 4-oxooct-7-enylcarbamate (Example 159, 2.17 g, 8.99 mmol) and ammonium acetate (4.16 g, 53.9 mmol) in 2,2,2-trifluoroethanol (7 mL) was treated with tert-butyl isocyanide (4.1 mL, 35.9 mmol) and stirred at room temperature for 3 days. Ethyl acetate (15 mL) and 2 M aq HCl (10 mL) were added and the solution was vigorously stirred for an additional 3 hrs. The phases were separated and the organic phase was washed successively with water and sat'd aq sodium chloride, dried over MgSO$_4$, filtered and concentrated. The crude viscous yellow residue was purified by flash column chromatography (5-50% ethyl acetate in hexanes) to give tert-butyl 4-acetamido-4-(tert-butylcarbamoyl)oct-7-enylcarbamate (2.27 g, 66%). $^1$H NMR (CDCl$_3$, 500 MHz) δ 6.97 (s, 1H), 5.79-5.70 (m, 1H), 5.56 (s, 1H), 4.99-4.92 (m, 2H), 4.55 (bs, 1H), 3.08-3.06 (m, 2H), 2.78-2.67 (m, 2H), 2.03-1.93 (m, 1H), 1.99 (s, 3H), 1.84-1.76 (m, 1H), 1.42 (s, 9H), 1.38-1.34 (m, 2H), 1.36 (s, 9H), 1.29-1.24 (m, 2H), ESI MS found for $C_{20}H_{37}N_3O_4$ m/z [406.5 (M+Na$^+$), 384.6 (M+1), 382.5 (M−1)].

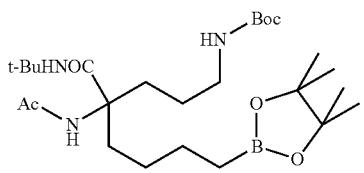

Step 2: Synthesis of tert-butyl 4-acetamido-4-(tert-butylcarbamoyl)oct-7-enylcarbamate While under an atmosphere of argon, a solution of bis(1,5-dicyclooctadiene)diiridium(I)dichloride (26.2 mg; 0.039 mmol) and diphenylphosphinoethane (31 mg, 0.078 mmol) in dichloromethane (3 mL) was cooled to 0° C. and treated with 4,4,5,5-tetramethyl-1,3,2-dioxaborolane (0.76 mL, 5.2 mmol). After stirring for 30 min, a solution of tert-butyl 4-acetamido-4-(tert-butylcarbamoyl)oct-7-enylcarbamate (500 mg, 1.3 mmol) in dichloromethane (15 mL) was added and the solution was stirred an additional 16 h. Dichloromethane (20 mL) was added, and the solution was washed successively with water and sat'd aq sodium chloride, dried over MgSO$_4$, filtered and concentrated. Purification by column chromatography (3% methanol in dichloromethane) gave tert-butyl 4-acetamido-4-(tert-butylcarbamoyl)oct-7-enylcarbamate (530 mg, 80%). ESI MS found for $C_{26}H_{50}BN_3O_6$ m/z [534.6 (M+Na$^+$), 512.6 (M+1), 510.5 (M−1)].

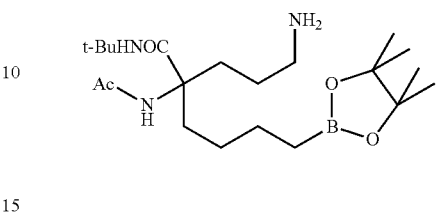

Step 3: Synthesis of 2-acetamido-2-(3-aminopropyl)-N-tert-butyl-6-(4,4,5,5-tetramethyl-1,3,2-dioxaborolan-2-yl)hexanamide A solution of tert-butyl 4-acetamido-4-(tert-butylcarbamoyl)oct-7-enylcarbamate (530 mg, 1.04 mmol) in ethyl acetate (5 mL) was treated with anh HCl (2 N in ethyl acetate, 15 mL) and stirred at room temp. After 30 min, the solution was concentrated to give crude 2-acetamido-2-(3-aminopropyl)-N-tert-butyl-6-(4,4,5,5-tetramethyl-1,3,2-dioxaborolan-2-yl)hexanamide hydrochloride as a white solid (459 mg, 99%). ESI MS found for $C_{21}H_{42}BN_3O_4$ m/z [434.6 (M+Na$^+$), 412.6 (M+1), 410.5 (M−1)]. This material was used without further purification.

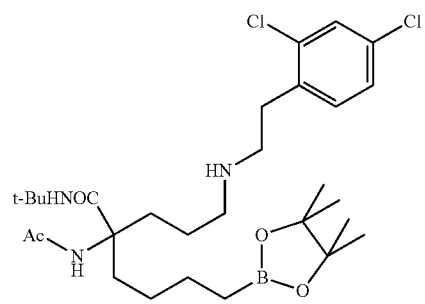

Step 4: Synthesis of 2-acetamido-N-tert-butyl-2-(3-(2,4-dichlorophenethylamino)propyl)-6-(4,4,5,5-tetramethyl-1,3,2-dioxaborolan-2-yl)hexanamide A solution of (2,4-dichlorophenyl)acetaldehyde (0.8 mmol) and 2-acetamido-2-(3-aminopropyl)-N-tert-butyl-6-(4,4,5,5-tetramethyl-1,3,2-dioxaborolan-2-yl)hexanamide hydrochloride (260 mg, 0.58 mmol) in dichloromethane (5 mL) was stirred at room temperature. After 30 min, sodium triacetoxyborohydride (310 mg, 1.45 mmol) was added in one portion and stirring was continued overnight. Once complete, the solution was diluted with dichloromethane (10 mL), quenched with aq 5% NaHCO$_3$ (W/V, 5 mL) and stirred vigorously for 30 min. The layers were separated and the organic phase was washed with water and sat'd aq sodium chloride, dried over MgSO$_4$, filtered and concentrated. Purification by flash column chromatography (1-20% methanol in dichloromethane) gave 2-acetamido-N-tert-butyl-2-(3-(2,4-dichlorophenethylamino)propyl)-6-(4,4,5,5-tetramethyl-1,3,2-dioxaborolan-2-yl)hexanamide (140 mg, 47%). ESI MS found for $C_{29}H_{48}BCl_2N_3O_4$ m/z [584.6/586.6 (M+1)].

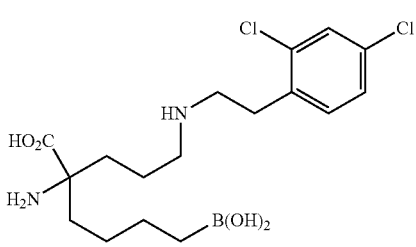

(140)

Step 5: Synthesis of 2-amino-6-borono-2-(3-(2,4-dichlorophenethylamino)propyl)hexanoic acid A solution of 2-acetamido-N-tert-butyl-2-(3-(2,4-dichlorophenethylamino)propyl)-6-(4,4,5,5-tetramethyl-1,3,2-dioxaborolan-2-yl)hexanamide (140 mg) in aq 6 M HCl was heated to reflux for 16 h, concentrated to dryness and purified by preparative HPLC. The residue was redissolved in 2 N HCl and evaporated to give 2-amino-6-borono-2-(3-(2,4-dichlorophenethylamino)propyl)hexanoic acid dihydrochloride (110 mg, 98%). $^1$H NMR (D$_2$O, 500 MHz) δ 7.45 (bs, 1H), 7.23 (bs, 2H), 3.19 (t, J=7.5 Hz, 2H), 3.06-2.95 (m, 4H), 1.91-1.71 (m, 5H), 1.60-1.49 (m, 1H), 1.34-1.25 (m, 3H), 1.17-1.08 (m, 1H), 0.69 (t, J=7.2 Hz, 2H). ESI MS found for C$_{17}$H$_{27}$BCl$_2$N$_2$O$_4$ m/z [387.5/389.4 (M+1−18)].

Example 141

Preparation of 2-amino-6-borono-2-(3-(3,4-dichlorobenzylamino)propyl)hexanoic acid dihydrochloride

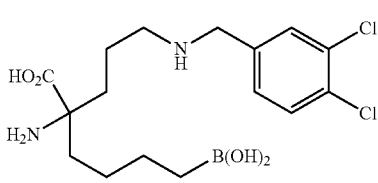

(141)

2-Amino-6-borono-2-(3-(3,4-dichlorobenzylamino)propyl)hexanoic acid dihydrochloride is prepared in a manner analogous to that set forth in Example 140, except 3,4-dichlorobenzaldehyde was used as the aldehyde in Step 4. $^1$H NMR (D$_2$O, 500 MHz) δ 7.57-7.48 (m, 2H), 7.30-7.26 (m, 1H), 4.11 (s, 2H), 3.00 (t, J=7.5 Hz, 2H), 1.90-1.68 (m, 5H), 1.63-1.51 (m, 1H), 1.35-1.25 (m, 3H), 1.17-1.09 (m, 1H), 0.69 (t, J=7.2 Hz, 2H). ESI MS found for C$_{16}$H$_{25}$BCl$_2$N$_2$O$_4$ m/z [391.4/393.4 (M+1)].

Example 142

Preparation of 2-amino-6-borono-2-(2-(4-(4-chlorobenzyl)piperidin-1-yl)ethyl)hexanoic acid dihydrochloride

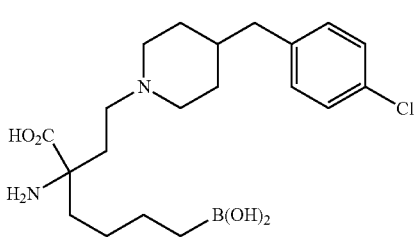

(142)

2-Amino-6-borono-2-(2-(4-(4-chlorobenzyl)piperidin-1-yl)ethyl)hexanoic acid dihydrochloride is prepared in a manner analogous to that set forth in Example 16, except 4-(4-chlorobenzyl)piperidine was used as the aldehyde in Step 6. $^1$H NMR (D$_2$O, 500 MHz) δ 7.20 (d, J=8.5 Hz, 2H), 7.05 (d, J=8.5 Hz, 2H), 3.45-3.38 (m, 2H), 3.21-3.15 (m, 1H), 3.04-2.96 (m, 1H), 2.82-2.74 (m, 2H), 2.45-2.41 (m, 2H), 2.20-2.14 (m, 2H), 1.85-1.68 (m, 5H), 1.35-1.20 (m, 5H), 1.13-1.04 (m, 1H), 0.64 (t, J=7.5 Hz, 2H). ESI MS found for C$_{20}$H$_{32}$BClN$_2$O$_4$ m/z [375.5 (M−2×18+1)].

Example 143

Preparation of 2-amino-6-borono-2-(2-((S)-pyrrolidin-2-yl)ethyl)hexanoic acid dihydrochloride

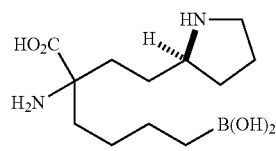

(143)

2-Amino-6-borono-2-(2-((S)-pyrrolidin-2-yl)ethyl)hexanoic acid dihydrochloride is prepared in a manner analogous to that set forth in Example 130, except 1-(tert-butoxycarbonyl)pyrrolidine-2-carboxylic acid was used as the carboxylic acid in Step 1. $^1$H NMR (D$_2$O, 300 MHz) δ 3.48-3.36 (m, 1H), 3.23-3.10 (m, 2H), 2.19-2.04 (m, 1H), 2.00-1.45 (m, 9H), 1.37-1.21 (m, 3H), 1.19-1.03 (m, 1H), 0.64 (t, J=7.5 Hz, 2H). ESI MS found for C$_{12}$H$_{25}$BN$_2$O$_4$ m/z [273.2 (M+1), 255.2 (M+1−18)].

Example 144

Preparation of 6-borono-2-(methylamino)-2-(2-((S)-pyrrolidin-2-yl)ethyl)hexanoic acid dihydrochloride

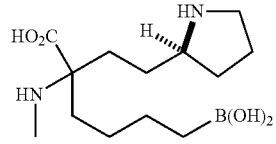

(167)

6-Borono-2-(methylamino)-2-(2-((S)-pyrrolidin-2-yl)ethyl)hexanoic acid dihydrochloride is prepared in a manner analogous to that set forth in Example 130, except 1-(tert-butoxycarbonyl)pyrrolidine-2-carboxylic acid was used as the carboxylic in Step 1 and methylammonium acetate was used in place of ammonium acetate in step 5. $^1$H NMR (D$_2$O, 300 MHz) δ 3.48-3.34 (m, 1H), 3.23-3.10 (m, 2H), 2.52 (bs, 3H), 2.18-2.04 (m, 1H), 2.00-1.70 (m, 6H), 1.70-1.40 (m, 3H), 1.37-1.16 (m, 3H), 1.14-0.97 (m, 1H), 0.63 (t, J=7.2 Hz, 2H). ESI MS found for C$_{13}$H$_{27}$BN$_2$O$_4$ m/z [287.3 (M+1), 269.3 (M+1−18)].

Example 145

Preparation of 6-borono-2-(4-chlorobenzylamino)hexanoic acid hydrochloride

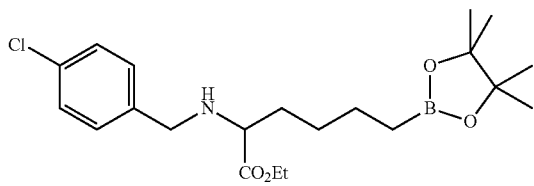 [SMILES: CCOC(=O)C(CCCCB1OC(C)(C)C(C)(C)O1)NCc1ccc(Cl)cc1]

Step 1: Preparation of ethyl 2-(4-chlorobenzylamino)-6-(4,4,5,5-tetramethyl-1,3,2-dioxaborolan-2-yl)hexanoate A solution of ethyl 2-amino-6-(4,4,5,5-tetramethyl-1,3,2-dioxaborolan-2-yl)hexanoate (119 mg, 0.42 mmol) in 1,2-dichloroethane (1 mL) was treated with 4-chlorobenzaldehyde (89 mg, 0.63 mmol). After stirring for 10 minutes, sodium triacetoxyborohydride (230 mg, 1.05 mmol) was added and stirring was continued for 18 hours. The reaction was diluted with ethyl acetate, washed with saturated aq sodium bicarbonate and sat'd aq sodium chloride, dried over $MgSO_4$, and concentrated. Purification by column chromatography (4-32% ethyl acetate in heptane afford ethyl 2-(4-chlorobenzylamino)-6-(4,4,5,5-tetramethyl-1,3,2-dioxaborolan-2-yl)hexanoate (59 mg, 34%). $R_f$ 0.28 (20% ethyl acetate in heptane). $^1$H NMR ($CDCl_3$, 300 MHz) δ 7.29-7.25 (m, 4H), 4.21 (q, J=7.7 Hz, 2H), 3.78, 3.58 (ABq, $J_{AB}$=13.2 Hz, 2H), 3.20 (t, J=7.0 Hz, 1H), 1.80-1.57 (m, 2H), 1.42-1.34 (m, 4H), 1.30-1.21 (m, 15H), 0.77 (t, J=7.0 Hz, 2H). ESI MS found for $C_{21}H_{33}B_1Cl_1N_1O_4$ m/z [410.1 (M+1)].

(145)

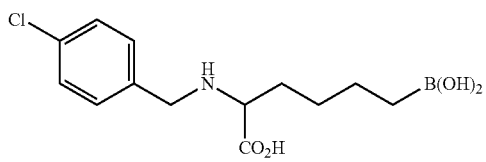

Step 2: Preparation of 6-borono-2-(4-chlorobenzylamino)hexanoic acid hydrochloride A solution of ethyl 2-(4-chlorobenzylamino)-6-(4,4,5,5-tetramethyl-1,3,2-dioxaborolan-2-yl)hexanoate (59 mg) in aq 6 M HCl was heated to reflux for 16 h, concentrated to dryness and purified by preparative HPLC. The residue was redissolved in 2 N HCl and evaporated to give 6-borono-2-(4-chlorobenzylamino)hexanoic acid hydrochloride (36 mg, 83%). $^1$H NMR ($CD_3OD$, 300 MHz) δ 7.56-7.46 (m, 4H), 4.23 (s, 2H), 4.09-3.98 (m, 1H), 2.02-1.91 (m, 2H), 1.52-1.37 (m, 4H), 0.81 (t, J=7.0 Hz, 2H). ESI MS found for $C_{13}H_{19}B_1Cl_1N_1O_4$ m/z [300.2 (M+1)].

Example 146

Preparation of 6-borono-2-(methylamino)hexanoic acid hydrochloride

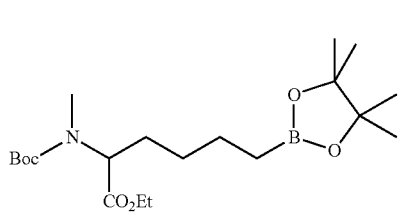 [SMILES: CCOC(=O)C(CCCCB1OC(C)(C)C(C)(C)O1)N(C)C(=O)OC(C)(C)C]

Step 1: Preparation of ethyl 2-(tert-butoxycarbonyl(methyl)amino)-6-(4,4,5,5-tetramethyl-1,3,2-dioxaborolan-2-yl)hexanoate A solution of ethyl 2-(tert-butoxycarbonylamino)-6-(4,4,5,5-tetramethyl-1,3,2-dioxaborolan-2-yl)hexanoate (104 mg, 0.27 mmol) in THF (2.7 mL) was cooled to 0° C. and treated with methyl iodide (0.084 mL, 1.35 mmol) and NaHMDS (0.41 mL, 1 M solution in THF, 0.41 mmol). After stirring for 16 h at room temperature, additional methyl iodide (0.042 mL, 0.77 mmol) was added and the mixture was warmed to 35° C. for 6 hours. The reaction was quenched with saturated $NH_4Cl$ solution (2 mL), diluted with ethyl acetate, washed with saturated aqueous sodium bicarbonate solution, sat'd aq sodium chloride, dried over $MgSO_4$ and concentrated. Purification by column chromatography (5-40% ethyl acetate in heptane) gave ethyl 2-(tert-butoxycarbonyl(methyl)amino)-6-(4,4,5,5-tetramethyl-1,3,2-dioxaborolan-2-yl)hexanoate (59 mg, 55%). $R_f$ 0.34 (20% ethyl acetate in heptane). $^1$H NMR ($CDCl_3$, 300 MHz) δ 4.72-4.68, 4.43-4.38 (m, 1H, rotamers), 4.15 (q, J=7.3 Hz, 2H), 2.81, 2.77 (s, 3H, rotamers), 1.87-1.61 (m, 2H), 1.53-1.23 (m, 28H), 0.78 (t, J=7.3 Hz, 2H). ESI MS found for $C_{20}H_{38}B_1N_1O_6$ m/z [400.5 (M+1)].

(169)

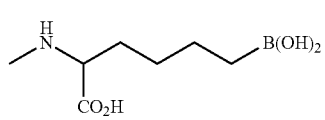

Step 2: Preparation of 6-borono-2-(methylamino)hexanoic acid

A solution of ethyl 2-(tert-butoxycarbonyl(methyl)amino)-6-(4,4,5,5-tetramethyl-1,3,2-dioxaborolan-2-yl)hexanoate (59 mg) in aq 6 M HCl was heated to reflux for 16 h, concentrated to dryness and purified by preparative HPLC. The residue was redissolved in 2 N HCl and evaporated to give 6-borono-2-(methylamino)hexanoic acid as a white solid (24 mg, 72%). $^1$H NMR ($CD_3OD$, 300 MHz) δ 3.94 (t, J=5.9 Hz), 2.72 (s, 3H), 1.45-1.34 (m, 4H), 0.81 (t, J=7.0 Hz, 2H). ESI MS found for $C_7H_{16}B_1N_1O_4$ m/z [190.0 (M+1)].

Example 147

Preparation of 2-amino-6-borono-2-(3-(piperidin-1-yl)propyl)hexanoic acid dihydrochloride

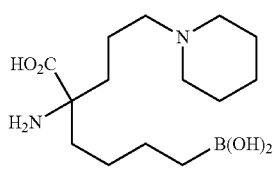

(170)

2-Amino-6-borono-2-(3-(piperidin-1-yl)propyl)hexanoic acid dihydrochloride is prepared in a manner analogous to that set forth in Example 137, except step 5 was omitted and piperidine was used as the amine in Step 6. $^1$H NMR (CD$_3$OD, 300 MHz) δ 3.60-3.49 (m, 2H), 3.24-2.93 (m, 4H), 1.99-1.79 (m, 10H), 1.45-1.29 (m, 6H), 0.83 (t, J=6.6 Hz, 2H). ESI MS found for $C_{14}H_{29}B_1N_2O_4$ m/z [301.10 (M+$^1$)].

Example 148

Preparation of 6-borono-2-(methylamino)-2-(3-(piperidin-1-yl)propyl)hexanoic acid dihydrochloride

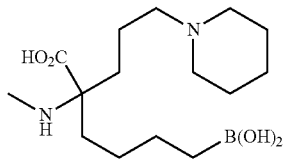

(148)

6-Borono-2-(methylamino)-2-(3-(piperidin-1-yl)propyl)hexanoic acid dihydrochloride is prepared in a manner analogous to that set forth in Example 137, except piperidine was used as the amine in Step 6. $^1$H NMR (D$_2$O, 300 MHz) δ 3.37 (d, J=13.2 Hz, 2H), 2.98 (t, J=6.6 Hz, 2H), 2.79 (t, J=12.5 Hz. 2H), 2.49 (s, 3H), 1.83-1.39 (m, 10H). 1.35-1.01 (m, 6H), 0.67 (t, J=7.7 Hz, 2H). ESI MS found for $C_{15}H_{31}B_1N_2O_4$ m/z [315.4 (M+1)].

Example 149

Preparation of 6-borono-2-(methylamino)-2-(2-(piperidin-1-yl)ethyl)hexanoic acid dihydrochloride

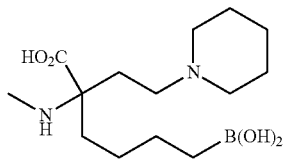

(149)

6-Borono-2-(methylamino)-2-(2-(piperidin-1-yl)ethyl) hexanoic acid dihydrochloride is prepared in a manner analogous to that set forth in Example 137, except allyl iodide was used as the alkylation agent in step 1 and piperidine was used as the amine in Step 6. $^1$H NMR (D$_2$O, 300 MHz) δ 3.48 (br t, J=12.1 Hz), 3.22-3.11 (m, 1H), 3.03-2.76 (m, 3H), 2.52 (s, 3H), 2.23-2.03 (m, 2H), 1.85-1.51 (m, 8H), 1.40-1.03 (m, 6H), 0.67 (t, J=7.7 Hz, 2H). ESI MS found for $C_{14}H_{29}B_1N_2O_4$ m/z [301.4 (M+1)].

II. Synthesis of Formula II Compounds

In addition to the foregoing methodologies that are generally applicable to all compounds described herein, the present invention also provides methodologies that are more specific to compounds of Formula II. Thus, in one embodiment, a Formula II compound synthesis is accomplished using the Ugi reaction (Doemling, A., Chem. Rev. 2006, 106, 17-89. This method is illustrated in Scheme A-I. Thus, treating a ketone or an aldehyde (A-3), with an isocyanate such as tert-butyl isocyanate and an amine source like ammonium acetate gives an amino acid derivative in which the carboxylic acid is protected as a tert-butylamide and the α-amine group is protected as an acetamide. By using different isocyanates and amines as starting materials, therefore, a series of amino acid precursors are obtained in which the amine and carboxylic acid groups are orthogonally protected. If optically active products are desired chiral optically pure isocyanates and/or amine sources can be used. The reactions using these reagents may be enantioselective or, at least, provide diastereomeric mixtures of products that can be resolved using analytical separation techniques known in the chemical art.

Scheme A-I

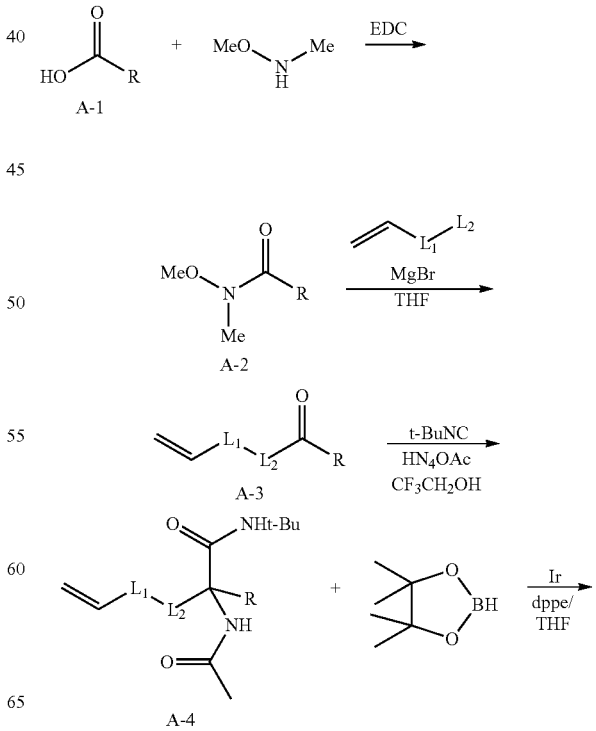

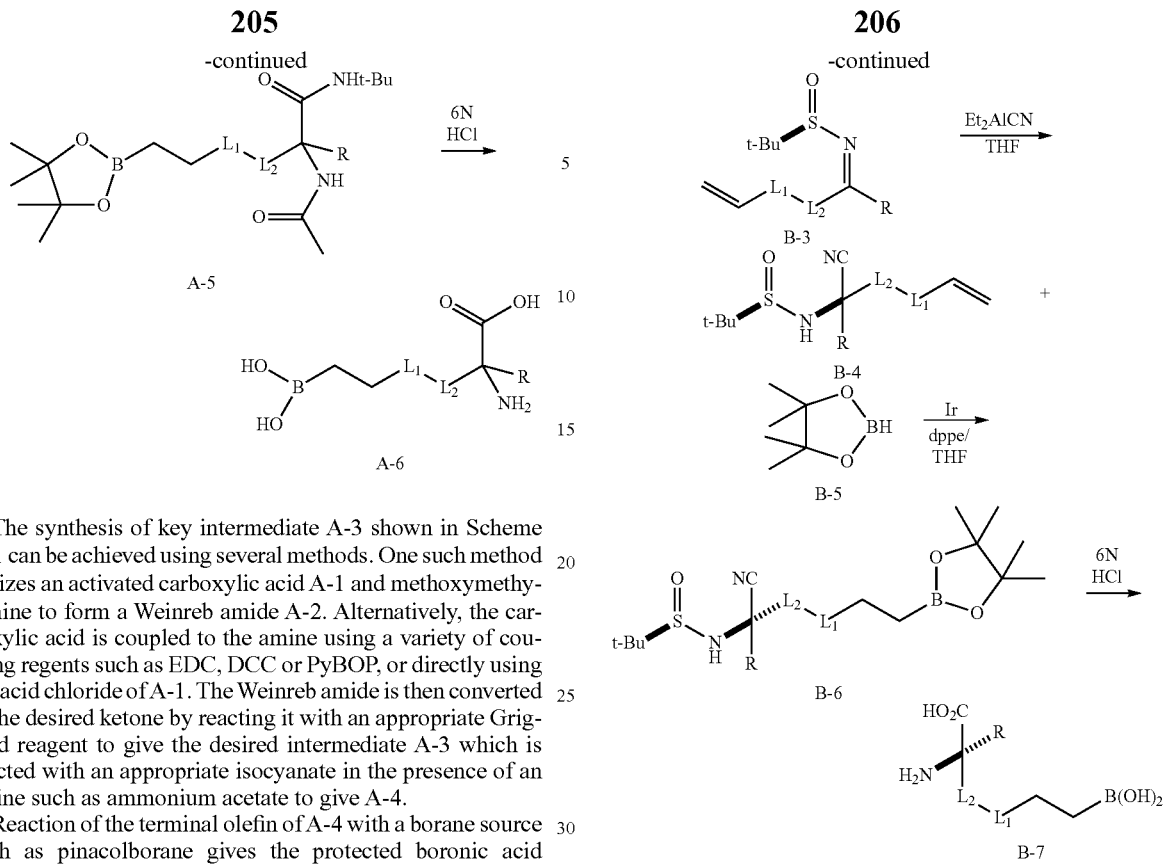

The synthesis of key intermediate A-3 shown in Scheme A-1 can be achieved using several methods. One such method utilizes an activated carboxylic acid A-1 and methoxymethylamine to form a Weinreb amide A-2. Alternatively, the carboxylic acid is coupled to the amine using a variety of coupling regents such as EDC, DCC or PyBOP, or directly using the acid chloride of A-1. The Weinreb amide is then converted to the desired ketone by reacting it with an appropriate Grignard reagent to give the desired intermediate A-3 which is reacted with an appropriate isocyanate in the presence of an amine such as ammonium acetate to give A-4.

Reaction of the terminal olefin of A-4 with a borane source such as pinacolborane gives the protected boronic acid derivative (A-5), which upon deprotection gives the target compound, an α-borono amino acid A-6.

Those skilled in the art of organic synthesis will recognize that several methods exist for the asymmetric synthesis of substituted amino acids. See, for example, Vogt, H. and Brase, S. *Organic & Biomolecular Chemistry* 2007, 5, 406-430.

In another embodiment, Formula II compounds are synthesized using the general protocol illustrated in Scheme B-I. Thus, reaction of the ketone intermediate B-1 (prepared using methods outlines in Scheme A-I), with a chiral auxiliary such as (R) or (S)—N-tert-butanesulfinamide (B-2) in the presence of a Lewis acid like Ti(OEt)$_4$ results in the formation of the corresponding tert-butanesulfinyl imine B-3. See Ellman, J. A.; Owens, T. D. and Tang, T. P. *Acc. Chem. Res.* 2002, 35, 984-995.

The stereoselective introduction of cyanide is achieved by reacting tert-butanesulfinyl imine B-3 with Et$_2$AlCN. If the corresponding aminonitrile product B-4 is obtained as a mixture of two isomers, then the isomeric mixture is resolved using chromatography. Subsequent hydroboration of the terminal double bond using a wide variety of borane reagents, such as pinacol borane in the presence of an iridium catalyst gives the corresponding pinacol borane intermediate B-6. Hydrolysis of intermediate B-6 using a strong acid like 6 N HCl converts the cyano group to a carboxylic acid group and deprotects the dioxaborane moiety to give the target compound B-7.

Those having skill in the art will recognize that the starting materials and reaction conditions may be varied, the sequence of the reactions altered, and additional steps can be employed to synthesize compounds according to Formula II, as demonstrated by the following examples. As stated above, in some cases, protection of certain reactive functionalities may be necessary to achieve some of the above transformations. In general, the need for such protecting groups as well as the conditions necessary to attach and remove such groups will be apparent to those skilled in the art of organic synthesis.

The disclosures of all articles and references mentioned in this application, including patents, are incorporated herein by reference. The preparation of compounds of the present invention is illustrated further by the following examples, which are not to be construed as limiting the invention in scope or spirit to the specific procedures and compounds described in them.

EXEMPLARY FORMULA II COMPOUNDS

Example 1-A 2-amino-6-borono-2-(5'Trifluoromethyl-3,4,5,6-tetrahydro-2H-[1,2']bipyridinyl-4-yl)-hexanoic acid hydrochloride

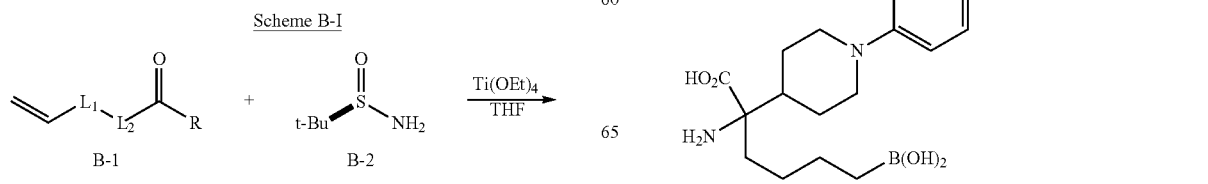

2-Amino-6-borono-2-(5'-trifluoromethyl-3,4,5,6-tetrahydro-2H-[1,2']bipyridinyl-4-yl)-hexanoic acid was prepared in a manner analogous to Example 116, except 5-trifluoromethyl-3,4,5,6-tetrahydro-2H-[1,2']bipyridinyl-4-carboxylic acid was used in step 1. The product was isolated as a white solid. $^1$H NMR (D$_2$O, 300 MHz) δ 8.12, (s, 1H), 7.98 (d, J=9.5 Hz, 1H), 7.28 (dd, J$_1$=9.5 Hz, J$_2$=1 Hz, H), 4.15 (m, 2H), 3.20 (m, 2H), 2.22 (m, 1H), 1.99 (d, J=12.5 Hz, 1H), 1.72-1.88 (m, 3H), 1.61 (qd, J$_1$=12.5 Hz, J$_2$=3.5 Hz, 1H), 1.22-1.39 (m, 4H), 1.09 (m, 1H) and 0.65 (t, J=7 Hz, 2H); MS (+CI): m/z for C$_{17}$H$_{25}$BF$_3$N$_3$O$_4$: expected 403.2. found 404.2 (M+H)$^+$, 386.3 (M+H–H$_2$O)$^+$, 367.9 (M+H-2H$_2$O)$^+$.

Example 2-A 2-amino-6-borono-2-[(4-Trifluoromethyl-pyrimidin-2yl)-piperidin-4-yl)-hexanoic acid hydrochloride

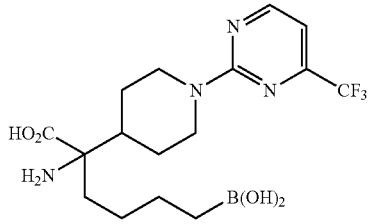

(2-A)

2-Amino-6-borono-2-[(4-trifluoromethyl-pyrimidin-2-yl)-piperidin-4-yl]-hexanoic acid was prepared in a manner analogous to Example 116, except 1-(4-trifluoromethyl-pyrimidin-2-yl)-piperidine-4-carboxylic acid was used in step 1. The product was isolated as its hydrochloride salt as a white solid. $^1$H NMR (D$_2$O, 300 MHz) δ 8.38, (d, J=5.5 Hz, 1H), 6.97 (d, J=5.5 Hz, 1H), 4.53 (m, 2H), 2.97 (m, 2H), 2.18 (m, 1H), 1.79-1.92 (m, 3H), 1.66, (m, 1H), 1.47 (qd, J$_1$=13 Hz, J$_2$=4 Hz, 1H), 1.17-1.34 (m, 4H), 1.09 (m, 1H) and 0.65 (t, J=7.5 Hz, 2H); MS (+CI): m/z for C$_{16}$H$_{24}$BF$_3$N$_4$O$_4$: expected 404.2. found 405.2 (M+H)$^+$, 387.2 (M+H–H$_2$O)$^+$, 369.1 (M+H–2H$_2$O)$^+$.

Example 3-A 2-amino-6-borono-2-[(2-Trifluoromethyl-quinolin-4-yl)-piperidin-4-yl)-hexanoic acid hydrochloride

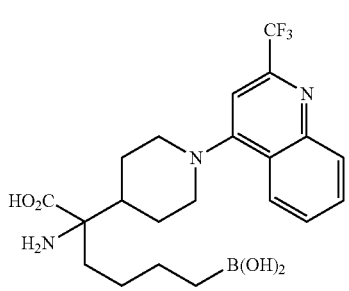

(3-A)

2-Amino-6-borono-2-[(2-trifluoromethyl-quinolin-4-yl)-piperidinyl-4-yl]-hexanoic acid was prepared in a manner analogous to Example 116, except 1-(2-trifluoromethyl-quinolin-4-yl)-piperidine-4-carboxylic acid in step 1. The product was isolated as its hydrochloride salt as a pale yellow solid. $^1$H NMR (D$_2$O, 300 MHz) δ 7.99, (d, J=7.5 Hz, 1H), 7.74-7.85 (m, 2H), 7.55 (ddd, J$_1$=8.5 Hz, J$_2$=6.5 Hz, J$_3$=2.5 Hz, 1H), 7.28 (s, 1H), 4.35 (m, 2H), 3.46 (m, 2H), 2.29 (m, 1H,), 2.01 (m, 1H), 1.75-1.89 (m, 3H), 1.49, (m, 1H), 1.22-1.36 (m, 4H), 1.12 (m, 1H) and 0.67 (t, J=7.5 Hz, 2H); MS (+CI): m/z for C$_{21}$H$_{27}$BF$_3$N$_3$O$_4$: expected 453.2. found 454.4 (M+H)$^+$, 436.4 (M+H–H$_2$O)$^+$, 418.0 (M+H-2H$_2$O)$^+$.

Example 4-A 2-amino-6-borono-2-[(6-chlorobenzoxazol-2-yl)-piperidin-4-yl)-hexanoic acid hydrochloride

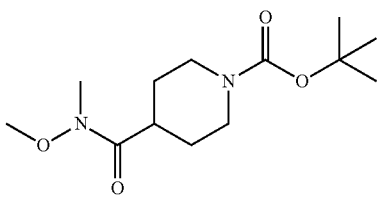 [SMILES: CON(C)C(=O)C1CCN(C(=O)OC(C)(C)C)CC1]

Step 1: tent-Butyl-4-[methoxy(methyl)carbamoyl]piperidine-1-carboxylate

EDC (6.29 g, 32.8 mmol) was added in several portions to a stirring solution of piperidine-1,4-dicarboxylic acid, mono tert-butyl ester (5.0 g, 21.8 mmol), DMAP (10 mg), and N,O-dimethylhydroxylamine hydrochloride (3.21 g, 32.8 mmol) in dichloromethane (100 mL). To the resultant solution was added dropwise triethylamine (9.4 mL, 65.6 mmol), and the reaction mixture was stirred at room temperature overnight. The next day, the reaction mixture was poured into water, and the aqueous layer was extracted using ethyl acetate (3×). The combined organic phase was washed with saturated aqueous sodium chloride, dried over anhydrous magnesium sulfate, filtered and concentrated in vacuo to give a colorless oil. Purification by column chromatography (silica gel, 0-40% ethyl acetate in heptane) gave tert-butyl-4-[methoxy(methyl)-carbamoyl]-piperidine-1-carboxylate (5.04 g, 85%) as a colorless oil; $^1$H NMR (CDCl$_3$, 300 MHz) δ 4.16 (m, 2H), 3.70 (s, 3H), 3.17 (s, 3H), 2.72-2.86 (m, 3H), 1.62-1.75 (m, 4H) and 1.44 (s, 9H).

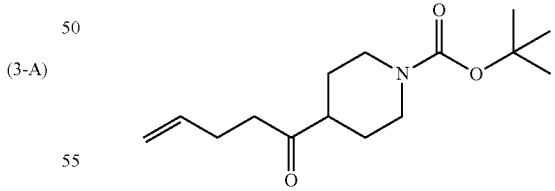

Step 2:
tent-Butyl-4-pent-4-enoyl-piperidine-1-carboxylate

A solution of tert-butyl-4-[methoxy(methyl)-carbamoyl]-piperidine-1-carboxylate (5.04 g, 18.53 mmol), in tetrahydrofuran (50 mL) maintained under an atmosphere of nitrogen was cooled to 0° C. To this cold solution was added a THF solution of 4-butenylmagnesiun bromide (0.5 M in THF, 45 mL, 22.5 mmol) in a dropwise manner. The solution was stirred for 1 hour at 0° C. then allowed to warm to room temperature overnight. The resulting solution was poured into water, acidified to pH 3-4 with 1 N hydrochloric acid, and extracted with ethyl acetate (3×). The combined organic phase was washed with saturated aqueous sodium chloride, dried over anhydrous magnesium sulfate, filtered and concentrated in vacuo. Purification by flash column chromatography (silica gel, 0-25% ethyl acetate in heptane) gave tert-butyl-4-pent-4-enoylpiperidine-1-carboxylate as a colorless oil (4.37 g, 88%); $^1$H NMR (CDCl$_3$, 300 MHz) δ 5.79 (m, 1H), 4.98 (m, 2H), 4.10 (m, 2H), 2.76 (t, J=11.5 Hz, 2H), 2.54 (m, 2H), 2.46 (tt, J$_1$=11.5 Hz, J$_2$=3.5 Hz, 1H), 2.32 (m, 2H), 1.78 (m, 2H), 1.48-1.58 (m, 2H) and 1.45 (s, 9H).

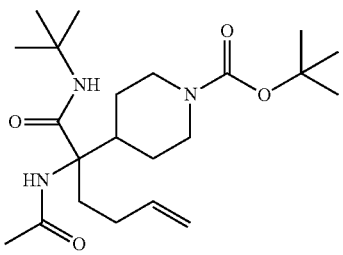 [SMILES: C=CCCC(NC(C)=O)(C(=O)NC(C)(C)C)C1CCN(C(=O)OC(C)(C)C)CC1]

Step 3: tert-butyl 4-(1-acetylamino)-1-tert-butylcarbamoyl-pent-4-enyl)-piperidine-1-carboxylate A solution of tert-butyl-4-pent-4-enoylpiperidine-1-carboxylate (4.37 g, 16.36 mmol) and ammonium acetate (5.11 g, 65.5 mmol) in 2,2,2-trifluoroethanol (4 mL) was treated with tert-butyl isocyanide (2.72 g, 3.70 mL, 32.75 mmol). After stirring at room temperature for 8 days, the reaction mixture was added to a separatory funnel, diluted with water (100 mL) and extracted with ethyl acetate (2×100 mL). The organic layer was washed with saturated aqueous sodium chloride, dried over MgSO$_4$, filtered and concentrated. Purification by flash column chromatography (silica gel, 10-60% ethyl acetate in heptane) gave tert-butyl 4-(lacetylamino)-1-tert-butylcarbamoyl-pent-4-enyl)piperidine-1-carboxylate as white solid (5.4 g, 81%). $^1$H NMR (CDCl$_3$, 300 MHz) δ 6.99 (s, NH, 1H), 5.78 (m, 1H), 5.49 (s, NH, 1H), 4.97 (m, 2H), 4.12 (m, 2H), 2.96 (ddd, J$_1$=16.5 Hz, J$_2$=11.5 Hz, J$_3$=5.5 Hz, 1H), 2.62 (m, 2H), 2.35 (tt, J$_1$=12.5 Hz J$_2$=3 Hz, 1H), 2.10-1.96 (m, 1H), 2.00 (s, 3H), 1.64-1.86 (m, 3H), 1.48 (m, 1H), 1.43 (s, 9H), 1.36 (s, 9H), 1.20-1.28 (m, 1H), 1.10 (m, 1H).

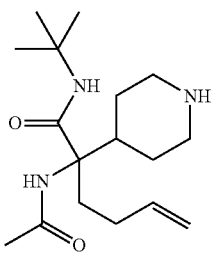 [SMILES: C=CCCC(NC(C)=O)(C(=O)NC(C)(C)C)C1CCNCC1]

Step 4: 2-acetylamino-2-piperidin-4-yl-hex-5-enoic acid tert-butylamide hydrochloride 4 N hydrogen chloride in dioxane (13.2 ml, 52.7 mmol) was added to a stirred dioxane (30 mL) solution of tert-butyl 4-(lacetylamino)-1-tert-butylcarbamoyl-pent-4-enyl)piperidine-1-carboxylate (5.4 g, 13.2 mmol). The reaction mixture was stirred for 2 hrs at room temperature and then concentrated in vacuo to give the title compound as a white solid, which was used without further purification (4.5 g, 99%). $^1$H NMR (CDCl$_3$, 300 MHz) δ 9.51 (br s, 2×NH, 2H), 7.26 (s, NH, 1H), 5.74 (m, vinyl CH+NH, 2H), 4.97 (m, 2H), 3.50 (m, 2H), 2.86 (m, 3H), 2.62 (m, 1H), 2.05 (s, 3H), 1.62-2.02 (m, 6H), 1.51 (m, 1H), 1.41 (s, 9H), 1.21-1.36 (m, 1H).

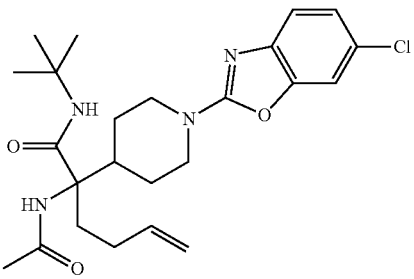 [SMILES: C=CCCC(NC(C)=O)(C(=O)NC(C)(C)C)C1CCN(c2nc3ccc(Cl)cc3o2)CC1]

Step 5: 2-acetamido-N-tert-butyl-2-(1-(6-chlorobenzo[d]oxazol-2-yl)piperidin-4-yl)hex-5-enamide Hunigs base (2.5 mL) was added to a stirred suspension of 2-acetylamino-2-piperidin-4-yl-hex-5-enoic acid tert-butylamide hydrochloride (250 mg, 0.73 mmol) and 2,6-dichlorobenzoxazole (172 mg, 0.91 mmol) in anhydrous dimethylacetamide (5 mL). The reaction was stirred at 95° C. overnight under an atmosphere of nitrogen. After heating over night, the reaction mixture was cooled to room temperature and then diluted with diethyl ether. The organic layer was washed with saturated aqueous sodium chloride (3×), dried over MgSO$_4$, filtered and concentrated. The crude product was purified by flash column chromatography (silica gel, 20-80% ethyl acetate in heptane) to give 2-acetamido-N-tert-butyl-2-(1-(6-chlorobenzo[d]oxazol-2-yl)piperidin-4-yl) hex-5-enamide as an off-white solid (240 mg, 72%). $^1$H NMR (CDCl$_3$, 300 MHz) δ 7.24 (d, J=2 Hz, 1H), 7.21 (d, J=8.5 Hz, 1H), 7.12 (dd, J$_1$=8.5 Hz, J$_2$=2 Hz, 1H), 7.02 (s, NH, 1H), 5.79 (m, 1H), 5.50 (s, NH, 1H), 4.98 (m, 2H), 4.34 (m, 2H), 3.00 (m, 3H), 2.49 (tt, J$_1$=12.5 Hz, J$_2$=3 Hz, 1H), 2.10-1.96 (m, 1H), 2.03 (s, 3H), 1.74-1.93 (m, 3H), 1.49 (m, 1H), 1.33 (s, 9H), 1.18-1.28 (m, 2H).

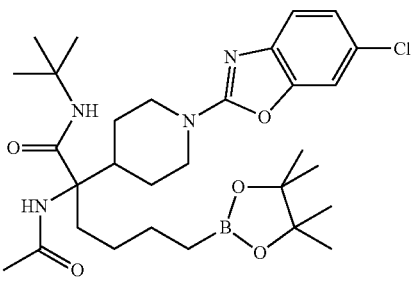 [SMILES: CC(=O)NC(CCCCB1OC(C)(C)C(C)(C)O1)(C(=O)NC(C)(C)C)C1CCN(c2nc3ccc(Cl)cc3o2)CC1]

Step 6: 2-acetamido-N-tert-butyl-2-(1-(6-chlorobenzo[d]oxazol-2-yl)piperidin-4-yl)-6-(4,4,5,5-tetramethyl-1,3,2-dioxaborolan-2-yl)hexanamide A solution of 2-acetamido-N-tert-butyl-2-(1-(6-chlorobenzo[d]oxazol-2-yl)piperidin-4-yl)hex-5-enamide (240 mg, 0.52 mmol) in dichloromethane (4 mL), was treated with chloro-1,5-cyclooctadiene iridium(I) dimer (10.4 mg, 3 mol %) and 1,2-bis(diphenylphosphino) ethane (12.2 mg, 6 mol %). The solution was stirred at room temperature for 30 minutes and then 4,4,5,5-tetramethyl-[1,3,2]dioxaborolane (0.152 mL, 1.04 mmol) was added dropwise, and the reaction was stirred overnight at room temperature. The next day, the reaction mixture was poured into water and extracted with ethyl acetate (3×). The combined organic phase was washed with saturated aqueous sodium chloride, dried over anhydrous magnesium sulfate, filtered and concentrated in vacuo. Purification of the crude product by flash column chromatography (silica gel, 30-100% ethyl acetate in heptane) gave 2-acetamido-N-tert-butyl-2-(1-(6-chlorobenzo[d]oxazol-2-yl)piperidin-4-yl)-6-(4,4,5,5-tetramethyl-1,3,2-dioxaborolan-2-yl)hexanamide as a colorless oil (212 mg, 69%). $^1$H NMR (CDCl$_3$, 300 MHz) δ 7.24 (d, J=2 Hz, 1H), 7.20 (d, J=8.5 Hz, 1H), 7.12 (dd, J$_1$=8.5 Hz, J$_2$=2 Hz, 1H), 6.97 (s, NH, 1H), 5.48 (s, NH, 1H), 4.32 (m, 2H), 3.02 (m, 2H), 2.84 (m, 1H), 2.47 (tt, J$_1$=12.5 Hz, J$_2$=3 Hz, 1H), 2.01 (s, 3H), 1.86 (m, 2H), 1.30-1.55 (m, 6H), 1.34 (s, 9H), 1.24 (s, 12H), 1.02-1.22 (m, 1H), 0.75 (t, J=7.5 Hz, 2H).

(4-A)

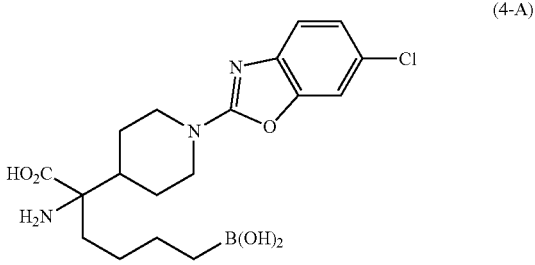 [SMILES: NC(CCCCB(O)O)(C(=O)O)C1CCN(c2nc3ccc(Cl)cc3o2)CC1]

Step 7: 2-amino-6-borono-2-(1-(6-chlorobenzo[d]oxazol-2-yl)piperidin-4-yl)hexanoic acid A solution of 2-acetamido-N-tert-butyl-2-(1-(6-chlorobenzo[d]oxazol-2-yl)piperidin-4-yl)-6-(4,4,5,5-tetramethyl-1,3,2-dioxaborolan-2-yl)hexanamide (212 mg) in 6 N HCl (15 mL) was stirred at 90° C. for 1 day. After cooling to room temperature, the reaction mixture was transferred to a separatory funnel, diluted with deionized water (10 mL) and washed with dichloromethane (3×). The aqueous solution was concentrated and purified by RP-HPLC (10-100% acetonitrile in water) to give the product, 2-amino-6-borono-2-(1-(6-chlorobenzo[d]oxazol-2-yl)piperidin-4-yl)hexanoic acid as its dihydrochloride salt and as a white solid (55 mg). $^1$H NMR (D$_2$O, 300 MHz) δ 7.40 (d, J=2 Hz, 1H), 7.24 (dd, J$_1$=8.5 Hz, J$_2$=2 Hz, 1H), 7.14 (d, J=8.5 Hz, 1H), 4.14 (m, 2H), 3.30 (t, J=13 Hz, 2H), 2.21 (m, 1H), 1.98 (m, 1H), 1.80 (m, 3H), 1.64 (m, 1H), 1.38 (m, 1H), 1.20-1.32 (m, 3H), 1.06 (m, 1H), 0.61 (t, J=7.5 Hz, 2H); MS (+CI): m/z for C$_{18}$H$_{25}$BClN$_3$O$_5$: expected 409.2. found 431.7 (M+Na)$^+$, 410.3 (M+H)$^+$, 392.0 (M+H–H$_2$O)$^+$, 374.4 (M+H-2H$_2$O)$^+$.

Example 5-A 2-amino-6-borono-2-(1-(5-fluoro-3,8-dimethylquinolin-2-yl)piperidin-4-yl)hexanoic acid dihydrochloride (5-A)

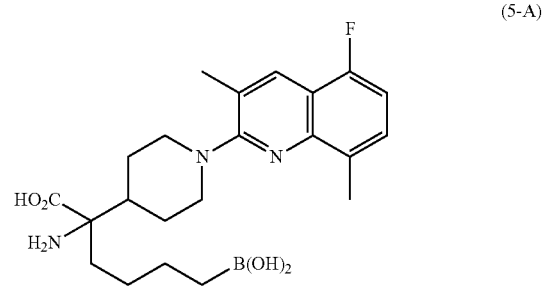 [SMILES: Cc1cc2c(F)ccc(C)c2nc1N1CCC(C(N)(CCCCB(O)O)C(=O)O)CC1]

2-Amino-6-borono-2-(1-(5-fluoro-3,8-dimethylquinolin-2-yl)piperidin-4-yl)hexanoic acid was prepared in a manner analogous to Example 4-A, except 2-chloro-5-fluoro-3,8-dimethylquinoline was used as the heteroaryl coupling partner in step 5. The title compound was isolated as its dihydrochloride salt, as a white solid (54 mg). $^1$H NMR (D$_2$O, 300 MHz) δ 8.27 (s, 1H), 7.44 (dd, J$_1$=9 Hz, J$_2$=5.5 Hz, 1H), 7.05 (t, J=9 Hz, 1H), 4.10 (m, 2H), 3.36 (m, 2H), 2.41 (s, 3H), 2.38 (s, 3H), 2.36-2.51 (m, 1H), 2.03 (m, 1H), 1.74-1.93 (m, 4H), 1.49 (m, 1H), 1.20-1.38 (m, 3H), 1.11 (m, 1H) and 0.68 (t, J=7 Hz, 2H); MS (+CI): m/z for C$_{22}$H$_{31}$BFN$_3$O$_4$: expected 431.2. found 432.4 (M+H)$^+$, 414.4 (M+H—H$_2$O)$^+$, 396.0 (M+H-2H$_2$O)$^+$.

Example 6-A

2-Amino-6-borono-2-[2-(4-trifluoromethyl-quinolin-2-yl)-piperidin-4-yl]hexanoic acid dihydrochloride (6-A)

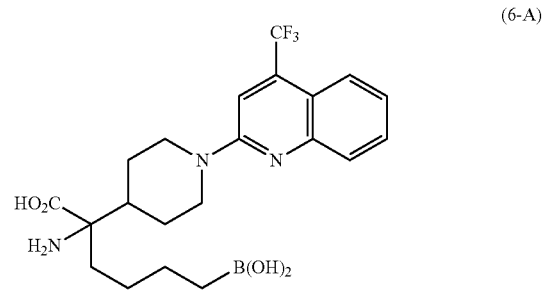 [SMILES: NC(CCCCB(O)O)(C(=O)O)C1CCN(c2cc(C(F)(F)F)c3ccccc3n2)CC1]

2-Amino-6-borono-2-[2-(4-trifluoromethyl-quinolin-2-yl)-piperidin-4-yl]-hexanoic acid was prepared in a manner analogous to Example 4-A, except 2-chloro-4-trifluoromethyl-quinoline was used as the heteroaryl coupling partner in step 5. The title compound was isolated as its dihydrochloride salt, as a white solid (90 mg). $^1$H NMR (D$_2$O, 300 MHz) δ 7.90 (d, J=7.5 Hz, 1H), 7.73 (m, 2H), 7.64 (s, 1H), 7.47 (ddd, J$_1$=8.5 Hz, J$_2$=6.5 Hz J$_3$=2 Hz, 1H), 4.44 (m, 2H), 3.34 (m, 2H), 2.27 (m, 1H), 2.05 (m, 1H), 1.83 (m, 3H), 1.66 (m, 1H), 1.24-1.43 (m, 4H), 1.11 (m, 1H) and 0.67 (t, J=7 Hz, 2H); MS (+CI): m/z for $C_{21}H_{27}BF_3N_3O_4$: expected 453.2. found 454.5 (M+H)$^+$, 436.5 (M+H–H$_2$O)$^+$, 418.0 (M+H-2H$_2$O)$^+$.

Example 7-A 2-amino-6-borono-2-[2-(6-methyl-4-trifluoromethyl-pyridin-2-yl)-piperidin-4-yl]-hexanoic acid

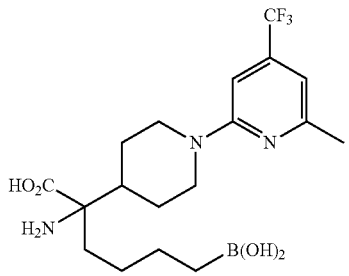

(7-A)

2-Amino-6-borono-2-[2-(6-methyl-4-trifluoromethyl-pyridin-2-yl)-piperidin-4-yl]-hexanoic acid was prepared in a manner analogous to Example 4-A, except 2-chloro-6-methyl-4-trifluoromethyl-pyridine was used as the heteroaryl coupling partner in step 5. The title compound was isolated as its dihydrochloride salt, as a white solid (118 mg). $^1$H NMR (D$_2$O, 300 MHz) δ 7.30 (s, 1H), 6.82 (s, 1H), 4.18 (m, 2H), 3.18 (m, 2H), 2.42 (s, 3H), 2.23 (m, 1H), 1.96 (m, 1H), 1.83 (m, 3H), 1.72 (m, 1H), 1.59 (td, J$_1$=13 Hz, J$_2$=4 Hz, 1H), 1.23-1.38 (m, 3H), 1.10 (m, 1H) and 0.66 (t, J=7.5 Hz, 2H); MS (+CI): m/z for $C_{18}H_{27}BF_3N_3O_4$: expected 417.2. found 418.0 (M+H)$^+$, 400.1 (M+H–H$_2$O)$^+$, 382.2 (M+H-2H$_2$O)$^+$.

Example 8-A 2-amino-6-borono-2-[2-(6-methyl-4-trifluoromethyl-pyridin-2-yl)-piperidin-4-yl]-hexanoic acid dihydrochloride

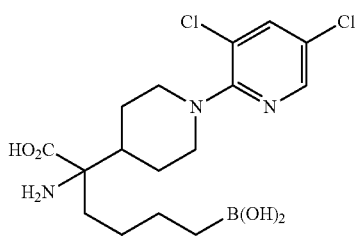

(8-A)

2-Amino-6-borono-2-[2-(3,5-dichloro-pyridin-2-yl)-piperidin-4-yl]-hexanoic acid was prepared in a manner analogous to Example 4-A, except 2,3,5-trichloro-pyridine was used as the heteroaryl coupling partner in step 5. The title compound was isolated as its dihydrochloride salt, as a white solid (63 mg). $^1$H NMR (D$_2$O, 300 MHz) δ 8.04 (d, J=2.5 Hz, 1H), 8.01 (dd, J$_1$=3 Hz, J$_2$=2.5 Hz, 1H), 3.85 (m, 2H), 3.04 (m, 2H), 2.14 (m, 1H), 1.92 (m, 1H), 1.82 (m, 2H), 1.70 (m, 2H), 1.46 (m, 1H), 1.28 (m, 3H), 1.08 (m, 1H) and 0.64 (t, J=7.5 Hz, 2H); MS (+CI): m/z for $C_{16}H_{24}BCl_2N_3O_4$: expected 403.1. found 404.2 (M+H)$^+$, 386.3 (M+H–H$_2$O)$^+$, 368.1 (M+H-2H$_2$O)$^+$.

Example 9-A 2-amino-6-borono-2-[2-(4-trifluoromethyl-pyridin-2-yl)-piperidin-4-yl]-hexanoic acid dihydrochloride

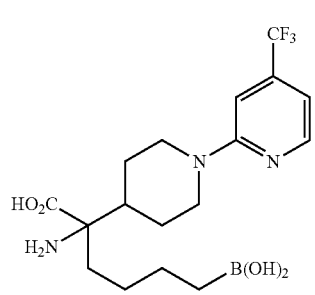

(9-A)

2-Amino-6-borono-2-[2-(4-trifluoromethylpyridin-2-yl)-piperidin-4-yl]-hexanoic acid was prepared in a manner analogous to Example 4-A, except 2-chloro-4-trifluoromethylpyridine was used as the heteroaryl coupling partner in step 5. The title compound was isolated as its dihydrochloride salt, as a white solid (58 mg). $^1$H NMR (D$_2$O, 300 MHz) δ 7.87 (d, J=7 Hz, 1H), 7.53, (s, 1H), 6.97 (dd, J$_1$=7 Hz, J$_2$=1.5 Hz, 1H), 4.17 (m, 2H), 3.22 (m, 2H), 2.21 (m, 1H), 1.98 (m, 1H), 1.72-1.86 (m, 3H), 1.59 (m, 1H), 1.25-1.40 (m, 4H), 1.10 (m, 1H) and 0.68 (t, J=7.5 Hz, 2H); MS (+CI): m/z for $C_{17}H_{25}BF_3N_3O_4$: expected 403.2. found 404.4 (M+H)$^+$, 386.2 (M+H–H$_2$O)$^+$, 368.3 (M+H-2H$_2$O)$^+$.

Example 10-A 2-amino-6-borono-2-(1-(3-chloro-5-(trifluoromethyl)pyridin-2-yl)piperidin-4-yl)hexanoic acid dihydrochloride

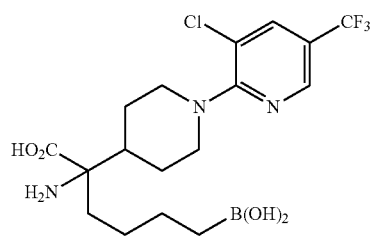

(10-A)

2-Amino-6-borono-2-(1-(3-chloro-5-(trifluoromethyl)pyridin-2-yl)piperidin-4-yl)hexanoic acid was prepared in a manner analogous to Example 4-A, except 2,3-dichloro-5-trifluoromethylpyridine was used as the heteroaryl coupling partner in step 5. The title compound was isolated as its dihydrochloride salt, as a white solid (93 mg). $^1$H NMR (D$_2$O, 300 MHz) δ 8.27 (dd, J$_1$=2 Hz, J$_2$=1 Hz, 1H), 8.06, (d, J=2 Hz, 1H), 3.94 (m, 2H), 2.87 (m, 2H), 2.09 (m, 1H), 1.78-1.93 (m, 3H), 1.57-1.69 (m, 2H), 1.25-1.42 (m, 4H), 1.10 (m, 1H) and 0.66 (t, J=7 Hz, 2H); MS (+CI): m/z for $C_{17}H_{24}BClF_3N_3O_4$: expected 437.15. found 438.5 (M+H)$^+$, 420.1 (M+H−H$_2$O)$^+$, 402.1 (M+H-2H$_2$O)$^+$.

Example 11-A 2-amino-6-borono-2-[(6-chlorobenzothiazol-2-yl)-piperidin-4-yl]-hexanoic acid dihydrochloride

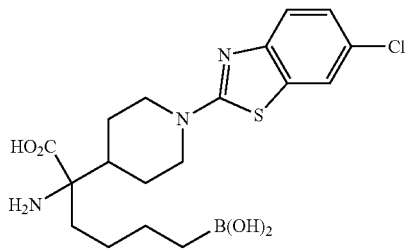

(11-A)

2-Amino-6-borono-2-[(6-chlorobenzothiazol-2-yl)-piperidin-4-yl]-hexanoic acid was prepared in a manner analogous to Example 4-A, except 2,6-dichlorobenzothiazole was used as the heteroaryl coupling partner in step 5. The title compound was isolated as its dihydrochloride salt, as a white solid (117 mg). $^1$H NMR (D$_2$O, 300 MHz) δ 7.62 (d, J=2 Hz, 1H), 7.35 (dd, J$_1$=8.5 Hz, J$_2$=2 Hz, 1H), 7.27 (d, J=8.5 Hz, 1H), 3.96 (m, 2H), 3.40 (t, J=13 Hz, 2H), 2.20 (m, 1H), 2.02 (m, 1H), 1.80 (m, 3H), 1.68 (m, 1H), 1.42 (m, 1H), 1.24-1.32 (m, 3H), 1.09 (m, 1H), 0.66 (t, J=7.5 Hz, 2H); MS (+CI): m/z for $C_{18}H_{25}BClN_3O_4S$: expected 425.1. found 426.0 (M+H)$^+$, 408.2 (M+H−H$_2$O)$^+$, 390.1 (M+H-2H$_2$O)$^+$.

Example 12-A (R)-2-amino-6-borono-2-((S)-1-(4-chlorophenyl)pyrrolidin-3-yl)hexanoic acid hydrochloride

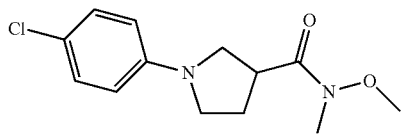 [SMILES: CON(C)C(=O)C1CCN(c2ccc(Cl)cc2)C1]

Step 1: 1-(4-chlorophenyl)-pyrrolidine-3-carboxylic acid, methoxy-methyl amide EDC (1.70 g, 8.86 mmol) was added portionwise to a stirred solution of 1-(4-chloro-phenyl)-pyrrolidine-3-carboxylic acid (1.0 g, 4.43 mmol), DMAP (5 mg) and N,O-dimethylhydroxylamine hydrochloride (865 mg, 8.86 mmol) in dichloromethane (20 mL). To this solution was added dropwise triethylamine (1.79 g, 2.47 mL, 17.7 mmol) and the reaction mixture was stirred at room temperature overnight. At the end of stirring, the reaction mixture was poured into water, and extracted with ethyl acetate (3×). The combined organic phase was washed with saturated aqueous sodium chloride, dried over anhydrous magnesium sulfate, filtered and concentrated in vacuo to give the title compound as a white solid (1.10 g. 98%); $^1$H NMR (CDCl$_3$, 300 MHz) δ 7.14 (d, J=8 Hz, 2H), 6.46 (d, J=8 Hz, 2H), 3.74 (s, 3H), 3.50-3.56 (m, 2H), 3.40-3.47 (m, 2H), 3.33 (m, 1H), 3.23 (s, 3H), 2.20-2.36 (m, 2H).

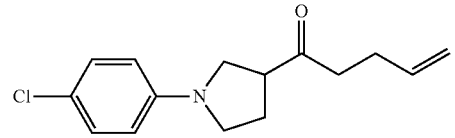 [SMILES: C=CCCC(=O)C1CCN(c2ccc(Cl)cc2)C1]

Step 2: 1-[1-(4-chlorophenyl)-pyrrolidin-3-yl]-pent-4-en-1-one

A solution of 1-(4-chlorophenyl)-pyrrolidine-3-carboxylic acid and methoxy-methyl amide (1.1 g, 4.1 mmol) in tetrahydrofuran (20 mL) was cooled to 0° C. while maintaining the solution under an atmosphere of nitrogen. To the cold solution was added a THF solution of 4-butenylmagnesium bromide (0.5M in THF, 16.4 mL, 8.2 mmol) in a dropwise manner. After stirring for 1 hour the bath was removed and stirring was continued overnight. The resulting solution was poured into water, acidified to pH 3-4 with 1 N hydrochloric acid and extracted with ethyl acetate (3×). The combined organic phase was washed with saturated aqueous sodium chloride, dried over anhydrous magnesium sulfate, filtered and concentrated. Purification of the crude by flash column chromatography (silica gel, 0-25% ethyl acetate in heptane) gave the title compound as a colorless oil (940 mg, 87%); $^1$H NMR (CDCl$_3$, 300 MHz) δ 7.15 (d, J=9 Hz, 2H), 6.46 (d, J=9 Hz, 2H), 5.81 (m, 1H), 5.12 (m, 2H), 3.54 (m, 2H), 3.26-3.39 (m, 3H), 2.62 (m, 2H), 2.36 (m, 2H) and 2.12-2.26 (m, 2H).

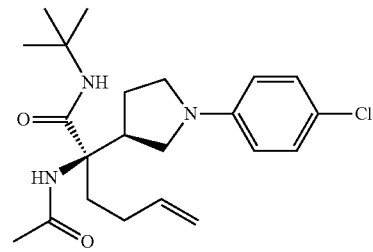 [SMILES: C=CCC[C@](NC(C)=O)(C(=O)NC(C)(C)C)[C@H]1CCN(c2ccc(Cl)cc2)C1]

Step 3: (2S,3'S)-2-Acetylamino-2-[1-(4-chlorophenyl)-pyrrolidin-3-yl]hex-5-enoic acid, tert-butylamide A solution of 1-[1-(4-chlorophenyl)-pyrrolidin-3-yl]-pent-4-en-1-one (940 mg, 3.57 mmol) and ammonium acetate (1.381 g, 17.85 mmol) in 2,2,2-trifluoroethanol (2 mL) was treated with tert-butyl isocyanide (594 mg, 810 μL, 7.15 mmol). After stirring at room temperature for 8 days, the reaction mixture was added to a separatory funnel, diluted with water (20 mL) and extracted with ethyl acetate (2×30 mL). The organic layer was washed with saturated aqueous sodium chloride, dried over MgSO$_4$, filtered and concentrated. Purification of the crude by flash column chromatography (silica gel, 20-70% ethyl acetate in heptane) gave (2S, 3'S)-2-acetylamino-2-[1-(4-chlorophenyl)-pyrrolidin-3-yl]-hex-5-enoic acid, tert-butylamide as a colorless oil (602 mg, 42%) and (2R,3'S)-2-acetylamino-2-[1-(4-chlorophenyl)-pyrrolidin-3-yl]-hex-5-enoic acid, tert-butylamide as a colorless oil (500 mg, 35%). The $^1$H NMR frequencies for (2S, 3'S)-2-acetylamino-2-[1-(4-chlorophenyl)-pyrrolidin-3-yl]-hex-5-enoic acid, tert-butylamide are as follows: $^1$H NMR (CDCl$_3$, 300 MHz) δ 7.12 (d, J=9 Hz, 2H), 6.98 (s, NH, 1H), 6.44 (d, J=9 Hz, 2H), 5.73-5.86 (m, NH, 1H), 5.79 (s, 1H), 5.00 (m, 2H), 3.02-3.38 (m, 6H), 1.80-2.10 (m, 4H), 2.01 (s, 3H), 1.55 (m, 1H), 1.37 (s, 9H).

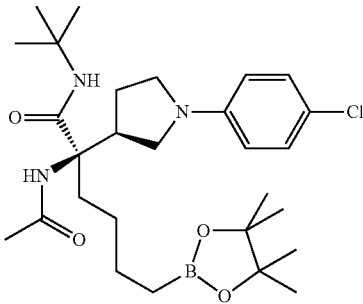 [SMILES: CC(=O)N[C@@](CCCCB1OC(C)(C)C(C)(C)O1)(C(=O)NC(C)(C)C)[C@H]1CCN(c2ccc(Cl)cc2)C1]

Step 4: (2S,3'S)-2-Acetylamino-2-[1-(4-chlorophenyl)-pyrrolidin-3-yl]tetramethyl-[1,3,2]-dioxaborolan-2-yl) hexanoic acid, tert-butylamide A solution of (2S,3'S)-2-Acetylamino-2-[1-(4-chlorophenyl)-pyrrolidin-3-yl]-hex-5-enoic acid, tert-butylamide (600 mg, 1.48 mmol) in dichloromethane (10 mL), was treated with chloro-1,5-cyclooctadiene iridium(I) dimer (30 mg, 3 mol %) and 1,2-bis(diphenylphosphino)ethane (36 mg, 6 mol %). The solution was stirred at room temperature for 30 minutes and then 4,4,5,5-tetramethyl-[1,3,2]dioxaborolane (0.43 mL, 2.96 mmol) was added dropwise, and the reaction was then stirred overnight at room temperature. The reaction was poured into water and extracted with ethyl acetate (3×). The combined organic phase was washed with saturated aqueous sodium chloride, dried over anhydrous magnesium sulfate, filtered and concentrated in vacuo. Purification of the crude product by flash column chromatography (silica gel, 30-100% ethyl acetate in heptane) gave (2S,3'S)-2-acetylamino-2-[1-(4-chlorophenyl)-pyrrolidin-3-yl]-6-(4,4,5,5-tetramethyl-[1,3,2]-dioxaborolan-2-yl) hexanoic acid, tert-butylamide as a colorless oil (568 mg, 72%). $^1$H NMR (CDCl$_3$, 300 MHz) δ 7.11 (d, J=8.5 Hz, 2H), 6.93 (s, NH, 1H), 6.43 (d, J=9 Hz, 2H), 5.77 (s, NH, 1H), 3.16-3.38 (m, 4H), 2.94-3.06 (m, 2H), 1.92-2.06 (m, 2H), 1.99 (s, 3H), 1.84 (m, 1H), 1.16-1.52 (m, 4H), 1.35 (s, 9H), 1.23 (s, 12H) and 0.76 (t, J=7.5 Hz, 2H).

(12-A)

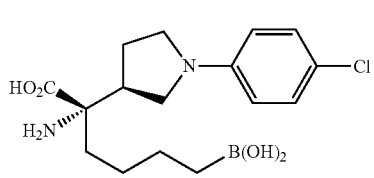

Step 5: (2S,3'S)-2-Amino-6-borono-2-[1-(4-chlorophenyl)-pyrrolidin-3-yl]-hexanoic acid A solution of (2S,3'S)-2-Acetylamino-2-[1-(4-chlorophenyl)-pyrrolidin-3-yl]-6-(4,4,5,5-tetramethyl-[1,3,2]-dioxaborolan-2-yl)-hexanoic acid, tert-butylamide (560 mg) in 6 N HCl (15 mL) was stirred at 90° C. for 1 day. After cooling to room temperature, the reaction mixture was transferred to a separatory funnel, diluted with deionized water (10 mL) and washed with dichloromethane (3×). The aqueous solution was concentrated in vacuo. Purification by RP-HPLC (10-100% acetonitrile in water) gave the desired product, (2S, 3'S)-2-Amino-6-borono-2-[1-(4-chlorophenyl)-pyrrolidin-3-yl]-hexanoic acid as its dihydrochloride salt, as a white solid (92 mg). $^1$H NMR (D$_2$O, 300 MHz) δ 7.36 (d, J=8.5 Hz, 2H), 7.12 (d, J=9 Hz, 2H), 3.74 (dd, J$_1$=11 Hz, J$_2$=9 Hz, 1H), 3.42-3.62 (m, 3H), 3.01 (quint. J=9 Hz, 1H), 2.20 (m, 2H), 1.96 (m, 1H), 1.79 (m, 1H), 1.26-1.40 m, (3H), 1.12 (m, 1H), 0.67 (t, J=7.5 Hz, 2H); MS (+CI): m/z for C$_{16}$H$_{24}$BClN$_2$O$_4$: expected 354.15. found 355.1 (M+H)$^+$, 319.4 (M+H-2H$_2$O)$^+$.

Example 13-A (2R,3'S)-2-amino-6-borono-2-[1-(4-chlorophenyl)-pyrrolidin-3-yl]hexanoic acid dihydrochloride (13-A)

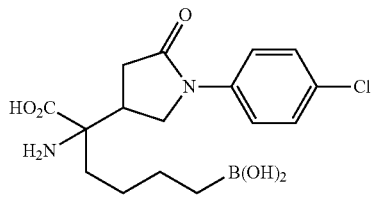

(2R,3'S)-2-Amino-6-borono-2-[1-(4-chlorophenyl)-pyrrolidin-3-yl]-hexanoic acid was prepared in a manner analogous to Example 12-A, except the second isomer was used from step 3. After RP-HPLC purification (10-100% acetonitrile in water) it was isolated as a white solid (92 mg). $^1$H NMR (D$_2$O, 300 MHz) δ 7.35 (2H, d, J=8.5 Hz, 2H), 7.14 (d, J=8 Hz, 2H), 3.82 (dd, J$_1$=11 Hz, J$_2$=9.5 Hz, 1H), 3.67 (dd, J$_1$=11 Hz, J$_2$=8.5 Hz, 1H), 3.58 (dd, J$_1$=8.5 Hz, J$_2$=6 Hz, 2H), 2.94 (quint. J=9 Hz, 1H), 2.31 (m, 1H), 1.70-1.91 (m, 3H), 1.24-1.36 (m, 3H), 1.12 (m, 1H), 0.63 (t, J=7.5 Hz, 2H—); MS (+CI): m/z for C$_{16}$H$_{24}$BClN$_2$O$_4$: expected 354.15. found 355.1 (M+H)$^+$, 337.5 (M+H–H$_2$O)$^+$, 319.2 (M+H-2H$_2$O)$^+$.

Example 14-A 2-amino-6-borono-2-[1-(4-chlorophenyl)-5-oxo-pyrrolidin-3-yl]hexanoic acid hydrochloride (14-A)

2-Amino-6-borono-2-[1-(4-chlorophenyl)-5-oxo-pyrrolidin-3-yl]-hexanoic acid was prepared in a manner analogous to Example 12-A, except 1-(4-chlorophenyl)-5-oxo-pyrrolidine-3-carboxylic acid was used as the carboxylic acid in step 1. After RP-HPLC purification (10-100% acetonitrile in water), the title compound was isolated as a white solid (19 mg). $^1$H NMR (D$_2$O, 300 MHz) δ 7.29 (d, J=9 Hz, 2H), 7.26 (d, J=9 Hz, 2H), 3.84-3.98 (m, 2H), 3.05 (quint. J=8.5 Hz, 1H), 2.74 (dd, J$_1$=17.5 Hz, J$_2$=9 Hz, 1H), 2.46 (dd, J$_1$=17.5 Hz, J$_2$=9 Hz, 1H), 1.70-1.96 (m, 2H), 1.24-1.46 (m, 3H), 1.15 (m, 1H), 0.65 (t, J=7.5 Hz, 2H); MS (+Cl): m/z for C$_{16}$H$_{22}$BClN$_2$O$_5$: expected 368.1. found 369.0 (M+H)$^+$, 351.0 (M+H–H$_2$O)$^+$, 331.1 (M+H-2H$_2$O)$^+$.

Example 15-A (R)-2-amino-2-((1S,3R)-3-aminocyclopentyl)-6-boronohexanoic acid dihydrochloride

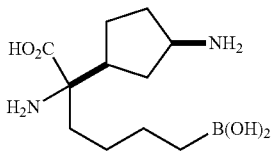

(15-A)

(R)-2-Amino-2-((1S,3R)-3-aminocyclopentyl)-6-boronohexanoic acid dihydrochloride is prepared in a manner analogous to that set forth in Example 116, except (1S,3R)-3-(tert-butoxycarbonylamino)cyclopentanecarboxylic acid is used as the acid in step 1. $^1$H NMR (D$_2$O, 300 MHz) δ 3.7-3.5 (m, 1H), 2.63-1.38 (m, 9H), 1.38-1.20 (m, 3H), 1.15-1.0 (m, 1H), 0.67 (t, J=7.6 Hz, 2H). ESI MS found for C$_{11}$H$_{23}$BN$_2$O$_4$ m/z [259.4 (M+1)].

Example 16-A (R)-2-amino-2-((1S,3S)-3-aminocyclopentyl)-6-boronohexanoic acid dihydrochloride

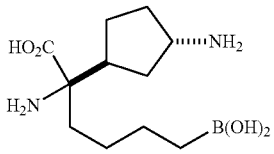

(16-A)

(R)-2-Amino-2-((1S,3S)-3-aminocyclopentyl)-6-boronohexanoic acid dihydrochloride is prepared in a manner analogous to that set forth in Example 116, except (1S,3S)-3-(tert-butoxycarbonylamino)cyclopentanecarboxylic acid is used as the acid in step 1. $^1$H NMR (D$_2$O, 300 MHz) δ 3.63-3.49 (m, 1H), 2.60-1.34 (m, 9H), 1.34-1.14 (m, 3H), 1.13-0.96 (m, 1H), 0.64 (t, J=7.6 Hz, 2H). ESI MS found for C$_{11}$H$_{23}$BN$_2$O$_4$ m/z [241.7 (M+1-H$_2$O)].

Example 17-A (S)-2-amino-2-((1R,3S)-3-aminocyclopentyl)-6-boronohexanoic acid dihydrochloride

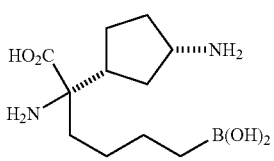

(17-A)

(S)-2-Amino-2-((1R,3S)-3-aminocyclopentyl)-6-boronohexanoic acid dihydrochloride is prepared in a manner analogous to that set forth in Example 116, except (1R,3S)-3-(tert-butoxycarbonylamino)cyclopentanecarboxylic acid is used as the acid in step 1. $^1$H NMR (D$_2$O, 300 MHz) δ 3.65-3.47 (m, 1H), 2.62-1.36 (m, 9H), 1.34-1.14 (m, 3H), 1.13-0.96 (m, 1H), 0.63 (t, J=7.6 Hz, 2H). ESI MS found for C$_{11}$H$_{23}$BN$_2$O$_4$ m/z [259.1 (M+1)].

Example 18-A 2-amino-2-(azetidin-3-yl)-6-boronohexanoic acid dihydrochloride

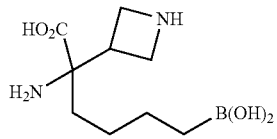

(18-A)

2-Amino-2-(azetidin-3-yl)-6-boronohexanoic acid dihydrochloride is prepared in a manner analogous to that set forth in Example 116, except 1-(tert-butoxycarbonyl)azetidine-3-carboxylic acid is used as the acid in step 1. $^1$H NMR (D$_2$O, 300 MHz) δ 4.74-4.57 (m, 1H), 4.45-4.2 (m, 1H), 3.47-2.99 (m, 3H), 1.98-1.67 (m, 2H), 1.42-1.20 (m, 4H), 0.73-0.62 (m, 2H). ESI MS found for C$_9$H$_{19}$BN$_2$O$_4$ m/z [253.4 (M+Na)].

Example 19-A

Preparation of 2-amino-6-borono-2-(morpholin-2-yl)hexanoic acid dihydrochloride

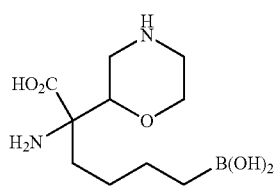

(19-A)

2-Amino-6-borono-2-(morpholin-2-yl)hexanoic acid dihydrochloride is prepared in a manner analogous to that set forth in Example 116, except 4-(tert-butoxycarbonyl)morpholine-2-carboxylic acid is used as the acid in step 1. $^1$H NMR (CD$_3$OD, 300 MHz) δ 4.26-4.13 (m, 2H), 3.96 (td, J=12.3, 2.7 Hz, 1H), 3.60-3.40 (m, 2H), 3.40-3.28 (m, 1H), 3.17 (td, J=12.6, 4.2 Hz, 1H), 2.02-1.86 (m, 2H), 1.5-1.36 (m, 3H), 1.34-1.18 (m, 1H), 0.83 (t, J=7.5 Hz, 2H). ESI MS found for C$_{10}$H$_{21}$BN$_2$O$_5$ m/z [243.1 (M+1-H$_2$O)].

Example 20-A

Preparation of 2-amino-2-(4-aminocyclohexyl)-6-boronohexanoic acid dihydrochloride

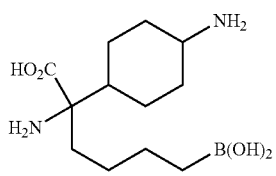

(20-A)

2-Amino-2-(4-aminocyclohexyl)-6-boronohexanoic acid dihydrochloride is prepared in a manner analogous to that set forth in Example 116, except 4-(tert-butoxycarbonylamino)cyclohexanecarboxylic acid is used as the acid in step 1. $^1$H NMR (D$_2$O, 300 MHz) δ 3.15-2.92 (m, 1H), 2.05-1.42 (m, 3H), 1.40-0.92 (m, 7H), 0.62 (t, J=7.4 Hz, 2H). ESI MS found for C$_{12}$H$_{25}$BN$_2$O$_4$ m/z [273.2 (M+1)].

Example 21-A

Preparation of 2-amino-6-borono-2-[cis-4-(4-chlorobenzylamino)-cyclohexyl]hexanoic acid dihydrochloride

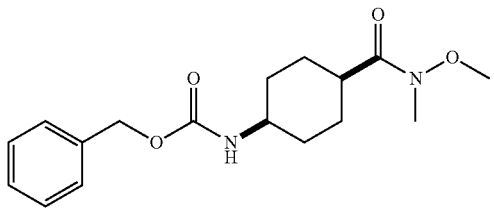

Step 1: benzyl cis-4-(methoxy(methyl)carbamoyl)cyclohexylcarbamate

EDC (6.9 g, 36 mmol) was added in several portions to a stirring solution of cis-4-benzyloxycarbonylamino-cyclohexanecarboxylic acid (5.0 g, 18 mmol), DMAP (10 mg), HOBt (10 mg) and N,O-dimethylhydroxylamine hydrochloride (3.5 g, 36 mmol) in dichloromethane (100 mL). To this solution was added dropwise triethylamine (10 mL, 72.0 mmol), and the reaction mixture was allowed to stir at room temperature overnight. After completion of stirring, the reaction mixture was poured into water and the aqueous layer was extracted with ethyl acetate (3×). The combined organic phase was washed with saturated aqueous sodium chloride, dried over anhydrous magnesium sulfate, filtered and concentrated in vacuo to give benzyl cis-4-(methoxy(methyl)carbamoyl)cyclohexylcarbamate as a colorless oil (5.48 g, 17.1 mmol, 95%). $^1$H NMR (CDCl$_3$, 300 MHz) δ 7.38-7.28 (m, 5H), 5.09 (bs, 2H), 5.02 (m, 1H), 3.92-3.82 (m, 1H), 3.69 (s, 3H), 3.17 (s, 3H), 2.81-2.68 (m, 1H), 1.91-1.78 (m, 2H), 1.74-1.6 (m, 6H).

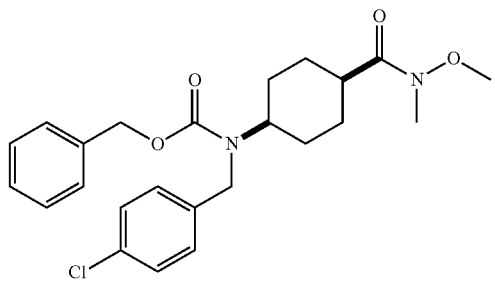

Step 2: benzyl 4-chlorobenzyl(cis-4-(methoxy(methyl)carbamoyl)cyclohexyl)carbamate A solution of benzyl cis-4-(methoxy(methyl)carbamoyl)cyclohexylcarbamate in DMF (12 mL) under an atmosphere of nitrogen was cooled to 0° C., followed by treatment with sodium hydride (150 mg of 60 wt % NaH in oil, 3.75 mmol). After stirring at room temperature for 30 min, the reaction mixture was cooled to 0° C. and charged with 4-chlorobenzyl bromide (793 g, 3.75 mmol). The resulting solution was warmed slowly to room temperature and stirred for another 16 hr prior to partitioning of the solution between saturated aqueous NaHCO$_3$ and ethyl acetate. The aqueous layer was further extracted with additional ethyl acetate. After separating the organic layer, the combined organic layer was washed with saturated aqueous sodium chloride, dried using MgSO$_4$, filtered, and concentrated to give benzyl 4-chlorobenzyl(cis-4-(methoxy(methyl)carbamoyl)cyclohexyl)carbamate as a colorless oil (1.19 g, 2.67 mmol, 86.0%). $^1$H NMR (CDCl$_3$, 300 MHz) δ 7.45-7.05 (m, 9H), 5.09 (bs, 2H), 4.41 (bs, 2H), 4.30-4.04 (m, 1H), 3.65 (s, 3H), 3.14 (s, 3H), 2.91 (m, 1H), 2.02-1.84 (m, 4H), 1.70-1.47 (m, 4H).

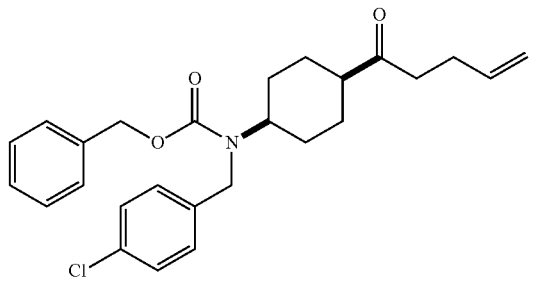

Step 3: 1-benzyl 4-chlorobenzyl(cis-4-pent-4-enoyl-cyclohexyl)carbamate

A solution of benzyl 4-chlorobenzyl(cis-4-(methoxy(methyl)carbamoyl)cyclohexyl) carbamate (1.19 g, 2.69 mmol), in tetrahydrofuran (15 mL), maintained under an inert atmosphere of nitrogen was cooled to 0° C. prior to reaction with 4-butenylmagnesiun bromide (0.5 M in THF, 13.4 mL, 6.7 mmol) which was added as a THF solution dropwise. After stirring for 1 hour at 0° C. the reaction mixture was warmed to room temperature overnight, poured into water, acidified to pH 3-4 with 1 N hydrochloric acid and extracted with ethyl acetate (3×). The combined organic phase was washed with saturated aqueous sodium chloride, dried over anhydrous magnesium sulfate, filtered and concentrated in vacuo. Purification by flash column chromatography gave 1-benzyl 4-chlorobenzyl(cis-4-pent-4-enoylcyclohexyl)carbamate as a colorless oil (0.98 g, 2.22 mmol, 83%). $^1$H NMR (CDCl$_3$, 300 MHz) δ 7.44-7.02 (m, 9H), 5.84-5.68 (m, 1H), 5.13 (bs, 2H), 5.05-4.92 (m, 2H), 4.34 (bs, 2H), 4.20-4.00 (m, 1H), 2.58 (m, 3H), 2.33-2.), 2.24 (m, 2H 19-2.07 (m, 2H), 1.7-1.4 (m, 6H).

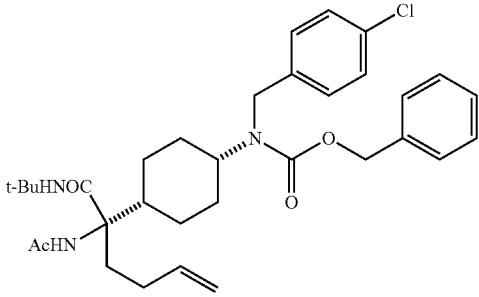

Step 4: benzyl (1R,4s)-4-((S)-2-acetamido-1-(tert-butylamino)-1-oxohex-5-en-2-yl)cyclohexyl(4-chlorobenzyl)carbamate Tert-Butyl isocyanide (0.627 mL, 5.55 mmol) was added to a stirred slurry of 1-benzyl 4-chlorobenzyl(cis-4-pent-4-enoylcyclohexyl)carbamate (978 mg, 2.22 mmol) and ammonium acetate (856 mg, 11.1 mmol) in 2,2,2-trifluoroethanol (2 mL). After stirring at room temperature for 8 days, the reaction mixture was poured into water and extracted with ethyl acetate (3×). The combined organic phase was washed with saturated aqueous sodium chloride, dried over anhydrous magnesium sulfate, filtered and concentrated in vacuo. Purification of the crude reaction by flash column chromatography gave benzyl (1R,4s)-4-((S)-2-acetamido-1-(tert-butylamino)-1-oxohex-5-en-2-yl)cyclohexyl(4-chlorobenzyl)carbamate as a colorless oil (850 mg, 1.5 mmol, 68%); $^1$H NMR (CDCl$_3$, 300 MHz) δ 7.39-6.9 (m, 9H), 5.84-5.68 (m, 1H), 5.54 (bs, 1H), 5.24-5.04 (m, 2H), 5.02-4.91 (m, 2H), 4.44-4.28 (bs, 2H), 4.1-3.9 (m, 1H), 2.97-2.82 (m, 1H), 2.23-1.93 (m, 5H), 1.90-1.65 (m, 5H), 1.51-0.96 (m, 14H).

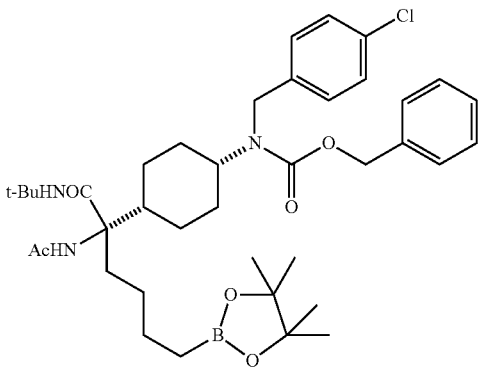

Step 5: benzyl (1R,4s)-4-((S)-2-acetamido-1-(tert-butylamino)-1-oxo-6-(4,4,5,5-tetramethyl-1,3,2-dioxaborolan-2-yl)hexan-2-yl)cyclohexyl(4-chlorobenzyl)carbamate A solution of benzyl (1R,4s)-4-((S)-2-acetamido-1-(tert-butylamino)-1-oxohex-5-en-2-yl)cyclohexyl(4-chlorobenzyl)carbamate (850 mg, 1.5 mmol) in dichloromethane (4 mL) was treated with chloro-1,5-cyclooctadiene iridium(I) dimer (30 mg, 3 mol %) and 1,2-bis(diphenylphosphino)ethane (36 mg, 6 mol %). After stirring for 30 minutes, 4,4,5,5-tetramethyl-[1,3,2]dioxaborolane (0.44 mL, 3 mmol) was added dropwise and the stirring was continued overnight. The reaction was poured into water and extracted with ethyl acetate (3×). The combined organic phase was washed with saturated aqueous sodium chloride, dried over anhydrous magnesium sulfate, filtered and concentrated in vacuo. Purification by flash column chromatography gave benzyl (1R,4s)-4-((S)-2-acetamido-1-(tert-butylamino)-1-oxo-6-(4,4,5,5-tetramethyl-1,3,2-dioxaborolan-2-yl)hexan-2-yl)cyclohexyl(4-chlorobenzyl)carbamate as a colorless oil (770 mg, 1.10 mmol, 74%); $^1$H NMR (CDCl$_3$, 300 MHz) δ 7.4-6.85 (m, 9H), 5.43 (br s, 1H), 5.25-5.0 (m, 2H), 4.44-4.28 (m, 2H), 4.08-3.72 (m, 2H), 2.80-2.64 (m, 1H), 2.22-2.04 (m, 1H), 1.98-1.90 (m, 4H), 1.90-1.62 (m, 4H), 1.46-0.93 (m, 29H), 0.725 (t, J=7.6 Hz, 2H).

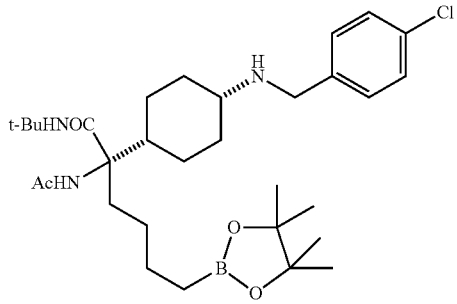

Step 6: (S)-2-acetamido-N-tert-butyl-2-((1s,4R)-4-(4-chlorobenzylamino)cyclohexyl)-6-(4,4,5,5-tetramethyl-1,3,2-dioxaborolan-2-yl)hexanamide A methanolic solution of benzyl (1R,4s)-4-((S)-2-acetamido-1-(tert-butylamino)-1-oxo-6-(4,4,5,5-tetramethyl-1,3,2-dioxaborolan-2-yl)hexan-2-yl)cyclohexyl(4-chlorobenzyl)carbamate (770 mg, 1.1 mmol, 10 mL methanol), was degassed using argon in a 100 mL round bottom flask which had been saturated with an atmosphere of argon. To this solution was added palladium (25 mg, 10 wt % on active carbon, wet, Degussa type E101 NE/W). After bubbling argon through this solution for 10 minutes, argon gas was replaced with a slow stream of hydrogen. After 1.5 h the reaction was complete and solution was purged with argon, filtered through the Celite 545 and the filter cake washed with methanol. The methanol solution was concentrated to give and collected solvents evaporated to give crude (S)-2-acetamido-N-tert-butyl-2-((1s,4R)-4-(4-chlorobenzylamino)cyclohexyl)-6-(4,4,5,5-tetramethyl-1,3,2-dioxaborolan-2-yl)hexanamide (660 mg 100%) which was used without further purification.

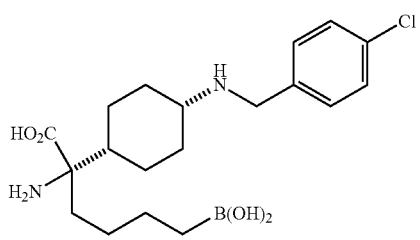

(21-A)

Step 7: (S)-2-amino-6-borono-2-((1s,4R)-4-(4-chlorobenzylamino)cyclohexyl)hexanoic acid dihydrochloride A solution of (S)-2-acetamido-N-tert-butyl-2-((1s,4R)-4-(4-chlorobenzylamino)cyclohexyl)-6-(4,4,5,5-tetramethyl-1,3,2-dioxaborolan-2-yl)hexanamide (195 mg) in 6 N HCl (6 mL) was stirred at 95° C. for 24 hours. After cooling to room temperature, the reaction mixture was transferred to a separatory funnel, diluted with deionized water (10 mL) and washed with dichloromethane (3×). The aqueous layer was frozen in liquid nitrogen and lyophilized to give (S)-2-amino-6-borono-2-((1s,4R)-4-(4-chlorobenzylamino)cyclohexyl) hexanoic acid dihydrochloride (105 mg), $^1$H NMR (D$_2$O, 300 MHz) δ 7.40-7.24 (m, 4), 4.10 (s, 2H), 3.50-2.94 (m, 1H), 2.22-2.06 (m, 2H), 1.98-1.84 (m, 1H), 1.78-1.52 (m, 4H), 1.44-1.10 (m, 6H), 1.10-0.88 (m, 2H), 0.63 (t, J=7.6 Hz, 2H); MS (+CI): m/z for C$_{19}$H$_{30}$BClN$_2$O$_4$: found 379.6 (M+1-H$_2$O)$^+$.

Example 22-A

Preparation of (S)-2-amino-6-borono-2-((1r,4S)-4-(4-chlorobenzylamino)cyclohexyl)hexanoic acid dihydrochloride

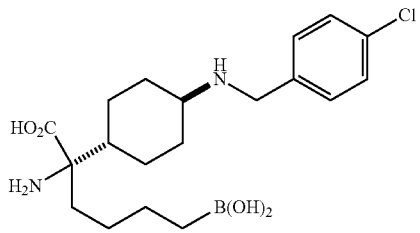

(22-A)

(S)-2-Amino-6-borono-2-((1r,4S)-4-(4-chlorobenzylamino)cyclohexyl)hexanoic acid dihydrochloride is prepared in a manner analogous to that set forth in Example 21-A, except trans-4-tert-butoxycarbonylamino-cyclohexanecarboxylic acid is used as the acid in step 1. $^1$H NMR (D$_2$O, 300 MHz) δ 7.33 (d, J=7.8 Hz, 2H), 7.27 (d, J=8.4 Hz, 2H), 4.09 (s, 2H), 3.08-2.96 (m, 1H), 2.20-2.07 (m, 2H), 1.98-1.85 (m, 1H), 1.78-1.56 (m, 4H), 1.43-1.10 (m, 6H), 1.10-0.90 (m, 2H), 0.63 (t, J=7.6 Hz, 2H); MS (+CI): m/z for C$_{19}$H$_{30}$BClN$_2$O$_4$: found 397.4 (M+1)$^+$.

Example 23-A

Preparation of 2-amino-6-borono-2-(1-cyclohexylpiperidin-4-yl)hexanoic acid dihydrochloride

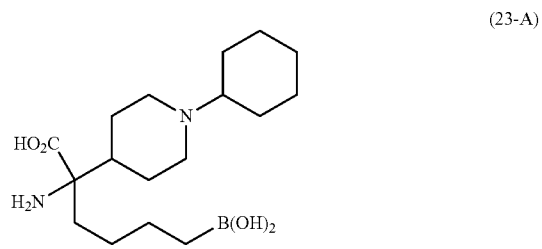 [SMILES: NC(CCCCB(O)O)(C(=O)O)C1CCN(C2CCCCC2)CC1]

(23-A)

2-Amino-6-borono-2-(1-cyclohexylpiperidin-4-yl)hexanoic acid dihydrochloride is prepared in a manner analogous to that set forth in Example 118, except cyclohexanone is used in place of benzaldehyde in step 6 with a reaction time of 18 h. $^1$H NMR (MeOH-d$_6$, 400 MHz) δ 3.61 (m, 2H), 3.16 (m, 3H), 2.32-2.05 (m, 5H), 1.97 (m, 5H), 1.78 (m, 2H), 1.55-1.35 (m, 7H), 1.33 (m, 2H), 0.86 (bt, J=7.2 Hz, 2H). ESI$^+$ MS found for C$_{17}$H$_{33}$BN$_2$O$_4$ m/z 323.4 (M−18+H); ESI$^-$ MS m/z 339.5 (M−H), 321.4 (M−18−H).

Example 24-A

Preparation of 2-amino-6-borono-2-(1-cyclopentylpiperidin-4-yl)hexanoic acid dihydrochloride

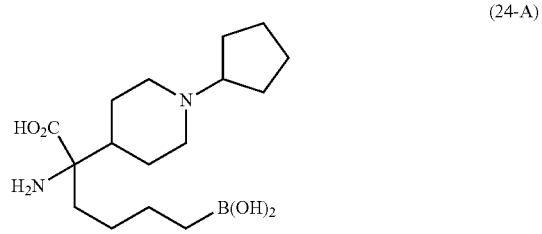 [SMILES: NC(CCCCB(O)O)(C(=O)O)C1CCN(C2CCCC2)CC1]

(24-A)

2-Amino-6-borono-2-(1-cyclopentylpiperidin-4-yl)hexanoic acid dihydrochloride is prepared in a manner analogous to that set forth in Example 118, except cyclopentanone is used in place of benzaldehyde in step 6 with a reaction time of >18 h. $^1$H NMR (D$_2$O, 400 MHz) δ 3.61 (m, 2H), 3.39 (m, 1H), 2.90 (m, 2H), 2.04 (m, 3H), 1.88-1.20 (m, 15H), 1.10 (m, 1H), 0.69 (bt, J=7.6 Hz, 2H). ESI+ MS found for $C_{16}H_{31}BN_2O_4$ m/z 309.4 (M−18+H); ESI− MS m/z 325.4 (M−H), 307.4 (M−18−H).

Example 25-A

Preparation of 2-amino-6-borono-2-[1-(4,4-dimethylcyclohexyl)piperidin-4-yl]hexanoic acid dihydrochloride

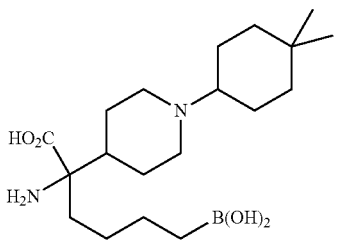

(25-A)

2-Amino-6-borono-2-[1-(4,4-dimethylcyclohexyl)piperidin-4-yl]hexanoic acid dihydrochloride is prepared in a manner analogous to that set forth in Example 118, except 4,4-dimethylcyclohexanone is used in place of benzaldehyde in step 6 with a reaction time of 24 h. $^1$H NMR (D$_2$O, 400 MHz) δ 3.53 (m, 2H), 3.00 (m, 3H), 2.10 (m, 2H), 1.90-1.70 (m, 6H), 1.65-1.40 (m, 5H), 1.35-1.05 (m, 6H), 0.80 (s, 6H), 0.69 (bt, J=7.6 Hz, 2H). ESI+ MS found for $C_{19}H_{37}BN_2O_4$ m/z 351.5 (M−18+H); ESI− MS m/z 367.5 (M−H), 349.5 (M−18−H).

Example 26-A

Preparation of 2-amino-6-borono-2-[1-(4-chlorobenzoyl)piperidin-4-yl]hexanoic acid hydrochloride

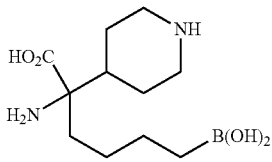 [SMILES: NC(CCCCB(O)O)(C(=O)O)C1CCNCC1]

Step 1:
2-Amino-6-borono-2-(piperidin-4-yl)hexanoic acid dihydrochloride

A solution of benzyl 4-[1-(tert-butylamino)-1-oxo-2-acetamido-6-(4,4,5,5-tetramethyl-1,3,2-dioxaborolan-2-yl)hexan-2-yl]piperidine-1-carboxylate (Example 118, Step 4, 9.00 g, 15.7 mmol) in 6 N HCl (157 mL) was heated at reflux for 18 h. After cooling to room temperature, the reaction mixture was washed with dichloromethane (2×50 mL). The aqueous layer was concentrated under reduced pressure, and the gummy residue was azeotroped twice from toluene and dried under high vacuum to give 2-amino-6-borono-2-(piperidin-4-yl)hexanoic acid dihydrochloride (6.84 g, >99% yield, contaminated with approx. 1 equivalent of tert-butylamine hydrochloride formed in the reaction) as an off-white foam which was used without further purification. ESI+ MS found for $C_{11}H_{23}BN_2O_4$ m/z 241.3 (M−18+H); ESI− MS m/z 357.3 (M−H), 239.3 (M−18−H).

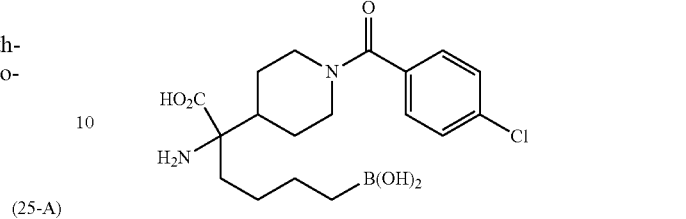

(26-A)

Step 2: 2-Amino-6-borono-2-[1-(4-chlorobenzoyl)piperidin-4-yl]hexanoic acid hydrochloride To a stirring solution of crude 2-amino-6-borono-2-(piperidin-4-yl)hexanoic acid dihydrochloride (150 mg, 0.371 mmol) in dry DMF (7.4 mL) under nitrogen was added triethylamine (0.31 mL, 2.23 mmol) to give a white slurry. 4-Chlorobenzoyl chloride (0.106 mL, 0.835 mmol) was added dropwise to the slurry, and the reaction mixture was stirred at room temperature overnight. The mixture was diluted with water (15 mL) and extracted with ethyl acetate (2×20 mL), and the organic phase was back-extracted with 1 N HCl (15 mL). The organic layer was discarded, and all aqueous layers were combined and washed with ethyl acetate (2×15 mL). The aqueous layer was concentrated under reduced pressure to give the crude product which was purified by reverse phase HPLC [Phenomenex Luna 250×30.00 mm, 10 micron column. 40 mL/min flow rate. Gradient: solvent A is 0.07% TFA in acetonitrile; solvent B is 0.10% TFA in water; 5% to 50% A over 24 min, then 50% to 100% A over 1 min]. Product fractions were pooled and concentrated, and the residue was taken up in 0.5N HCl (3 mL)/acetonitrile (6 mL) and concentrated. The residue was once again treated with 0.5N HCl (3 mL)/acetonitrile (6 mL) and concentrated and dried under high vacuum overnight to give 2-amino-6-borono-2-[1-(4-chlorobenzoyl)piperidin-4-yl]hexanoic acid hydrochloride (75 mg, 47%) as a faint yellow solid. $^1$H NMR (MeOH-d$_6$, 400 MHz) δ 7.51 (d, J=8.4 Hz, 2H), 7.42 (d, J=8.4 Hz, 2H), 4.77 (m, 1H), 3.82 (m, 1H), 3.19 (m, 1H), 2.85 (m, 1H), 2.25 (m, 1H), 2.10-1.40 (m, 8H), 1.28 (m, 2H), 0.85 (bt, J=7.2 Hz, 2H). ESI+ MS found for $C_{18}H_{26}BClN_2O_5$ m/z 379.3 (M−18+H); ESI+ MS m/z 395.4 (M−H), 377.4 (M−18−H).

Example 27-A

Preparation of 2-amino-6-borono-2-[1-acetylpiperidin-4-yl]hexanoic acid hydrochloride

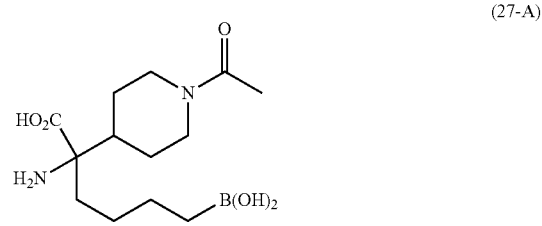 [SMILES: CC(=O)N1CCC(C(N)(CCCCB(O)O)C(=O)O)CC1]

(27-A)

To a stirring solution of crude 2-amino-6-borono-2-(piperidin-4-yl)hexanoic acid dihydrochloride (Example 26-A, Step 1, 250 mg, 0.618 mmol) in dry DMF (13 mL) under nitrogen was added triethylamine (0.69 mL, 4.95 mmol) to give a white slurry. The resultant slurry was treated with acetic anhydride (0.131 mL, 1.39 mmol), added dropwise, and the reaction mixture was stirred at room temperature for 2.5 h. The mixture was then diluted with ice water (10 mL) and 3 N HCl (5 mL) prior to extraction with ethyl acetate (2×25 mL). The aqueous layer was concentrated under reduced pressure to give the crude product which was purified by reverse phase HPLC [Phenomenex Luna 250×30.00 mm, 10 micron column. 40 mL/min flow rate. Gradient: solvent A is 0.07% TFA in acetonitrile; solvent B is 0.10% TFA in water; 2% A for 2 min, 2% to 20% A over 23 min, then 20% to 100% A over 1 min.] Product fractions were pooled and concentrated, and the residue was taken up in 0.25N HCl (3 mL)/acetonitrile (8 mL) and concentrated. The residue was once again treated with 0.25N HCl (3 mL)/acetonitrile (8 mL) and concentrated and dried under high vacuum overnight to give 2-amino-6-borono-2-[1-acetylpiperidin-4-yl]hexanoic acid hydrochloride (110 mg, 53%) as a white solid. $^1$H NMR (D$_2$O, 400 MHz) δ 4.38 (bt, J=12 Hz, 1H), 3.92 (bt, J=12 Hz, 1H), 3.03 (m, 1H), 2.55 (m, 1H), 2.11 (m, 1H), 2.00 (s, 3H), 1.87-1.78 (m, 3H), 1.55 (m, 1H), 1.50-1.00 (m, 6H), 0.68 (t, J=7.2 Hz, 2H). ESI$^+$ MS found for C$_{13}$H$_{25}$BN$_2$O$_5$ m/z 583.3 (2M−18+H), 565.6 (2M−2×18+H), 283.4 (M−18+H), 265.3 (M−2×18+H); ESI$^−$ MS m/z 581.6 (2M−18−H), 299.4 (M−H), 281.4 (M−18−H).

Example 28-A

Preparation of 2-amino-6-borono-2-{1-[(4-fluorophenyl)acetyl]-piperidin-4-yl}hexanoic acid hydrochloride

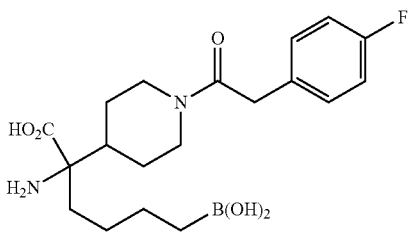

(28-A)

A solution of 4-fluorobenzeneacetic acid (126 mg, 0.816 mmol), N-(3-dimethylaminopropyl)-N'-ethylcarbodiimide hydrochloride (156 mg, 0.816 mmol) and 1-hydroxybenzotriazole hydrate (125 mg, 0.816 mmol) in dry DMF (4 mL) was stirred for 30 minutes under an atmosphere of nitrogen. To the stirring solution was added a solution of crude 2-amino-6-borono-2-(piperidin-4-yl)hexanoic acid dihydrochloride (Example 26-A, Step 1, 150 mg, 0.371 mmol) in dry DMF (4 mL) in one portion. Triethylamine (0.31 mL, 2.23 mmol) was added and the resulting opaque mixture was stirred at room temperature for 1.75 hours. At the end of the reaction the solution was diluted with 1 N HCl and washed with ethyl acetate (2×), prior to concentration of the combined organic layers. The crude product was purified by reverse phase HPLC [Phenomenex Luna 250×30.00 mm, 10 micron column. 40 mL/min flow rate. Gradient: solvent A is 0.07% TFA in acetonitrile; solvent B is 0.10% TFA in water. Run 1—5% to 50% A over 24 min, then 50% to 100% A over 1 min. Run 2—5% to 40% A over 24 min, then 40% to 100% A over 1 min. Run 3—5% to 30% A over 24 min, then 30% to 100% A over 1 min]. Product fractions were pooled and concentrated, and the residue was taken up in 0.5N HCl (4 mL)/acetonitrile (6 mL) and concentrated. The residue was once again treated with 0.5N HCl (4 mL)/acetonitrile (6 mL) and concentrated and dried under high vacuum overnight to give 2-amino-6-borono-2-{1-[(4-fluorophenyl)acetyl]piperidin-4-yl}hexanoic acid hydrochloride (56 mg, 35%) as a white solid. $^1$H NMR (MeOH-d$_6$, 400 MHz) δ 7.28 (m, 2H), 7.07 (m, 2H), 4.69 (m, 1H), 4.15 (m, 1H), 3.78 (m, 2H), 3.08 (m, 1H), 2.63 (m, 1H), 2.14 (m, 1H), 1.89 (m, 3H), 1.64 (m, 1H), 1.45 (m, 4H), 1.30-0.95 (m, 2H), 0.84 (bt, J=6.8 Hz, 2H). ESI$^+$ MS found for C$_{19}$H$_{28}$BFN$_2$O$_5$ m/z 377.3 (M−18+H), 359.4 (M−2×18+H); ESI$^−$ MS m/z 393.4 (M−H), 375.4 (M−18−H).

Example 29-A

Preparation of 2-amino-6-borono-2-{1-[(4-chlorophenyl)acetyl]-piperidin-4-yl}hexanoic acid hydrochloride

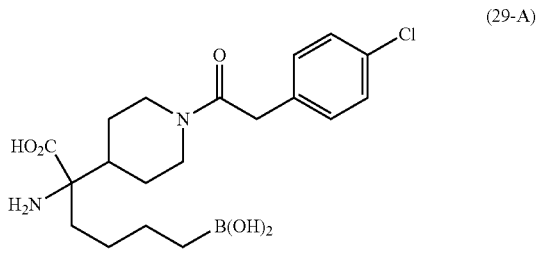 [SMILES: NC(CCCCB(O)O)(C(=O)O)C1CCN(C(=O)Cc2ccc(Cl)cc2)CC1]

(29-A)

2-Amino-6-borono-2-{1-[(4-chlorophenyl)acetyl]-piperidin-4-yl}hexanoic acid hydrochloride is prepared in a manner analogous to that set forth in Example 28-A, except 4-chlorophenylacetic acid is used in place of 4-fluorobenzeneacetic acid. $^1$H NMR (MeOH-d$_6$, 400 MHz) δ 7.34 (m, 2H), 7.25 (m, 2H), 4.70 (bd, J=13.2 Hz, 1H), 4.14 (bd, J=12.8 Hz, 1H), 3.79 (m, 2H), 3.08 (m, 1H), 2.63 (m, 1H), 2.14 (m, 1H), 1.89 (m, 3H), 1.64 (m, 1H), 1.45 (m, 4H), 1.30-0.95 (m, 2H), 0.84 (bt, J=6.8 Hz, 2H). ESI$^+$ MS found for C$_{19}$H$_{28}$BClN$_2$O$_5$ m/z 393.3 (M−18+H), 375.3 (M−2×18+H); ESI$^−$ MS m/z 409.4 (M−H), 391.4 (M−18−H).

Example 30-A

Preparation of 2-amino-6-borono-2-[1-benzoylpiperidin-4-yl]hexanoic acid hydrochloride

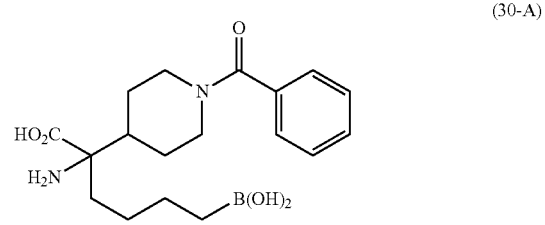 [SMILES: NC(CCCCB(O)O)(C(=O)O)C1CCN(C(=O)c2ccccc2)CC1]

(30-A)

2-Amino-6-borono-2-[1-benzoylpiperidin-4-yl]hexanoic acid hydrochloride is prepared in a manner analogous to that set forth in Example 28-A, except benzoic acid is used in place of 4-fluorobenzeneacetic acid. $^1$H NMR (D$_2$O, 400 MHz) δ 7.41 (m, 3H), 7.30 (m, 2H), 4.53 (bt, J=12 Hz, 1H), 3.72 (bt, J=12 Hz, 1H), 3.05 (m, 1H), 2.80 (m, 1H), 2.16 (bt, J=13 Hz, 1H), 1.95 (m, 1H), 1.83 (m, 2H), 1.71 (m, 1H), 1.55-1.05 (m, 6H), 0.68 (bt, J=7.2 Hz, 2H). ESI$^+$ MS found for C$_{18}$H$_{27}$BN$_2$O$_5$ m/z 345.4 (M−18+H), 327.4 (M−2×18+H); ESI$^-$ MS m/z 361.4 (M−H), 343.4 (M−18−H).

Example 31-A

Preparation of 2-amino-6-borono-2-{1-[(4-chlorobenzyl)carbamoyl]-piperidin-4-yl}hexanoic acid hydrochloride

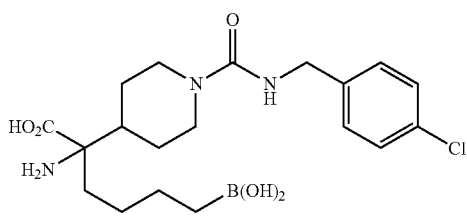

(31-A)

A stirred solution of crude 2-amino-6-borono-2-(piperidin-4-yl)hexanoic acid dihydrochloride (Example 26-A, Step 1, 0.240 g, 0.594 mmol) in dry DMF (12 mL) under nitrogen was treated with triethylamine (0.662 mL, 4.75 mmol) to give a white slurry. 1-chloro-4-(isocyanatomethyl)benzene (0.177 mL, 1.34 mmol) was added dropwise, and the resulting opaque mixture was stirred at room temperature for 1 h. The mixture was diluted with 1 N HCl (15 mL) and washed with ethyl acetate (2×20 mL), and the aqueous layer was concentrated under reduced pressure to give the crude product which was purified by reverse phase HPLC [Phenomenex Luna 250×30.00 mm, 10 micron column. 40 mL/min flow rate. Gradient: solvent A is 0.07% TFA in acetonitrile; solvent B is 0.10% TFA in water; 5% to 50% A over 24 min, then 50% to 100% A over 1 min]. Product fractions were pooled and concentrated, and the residue was taken up in 0.5N HCl (5 mL)/acetonitrile (8 mL) and concentrated. The residue was once again treated with 0.5N HCl (5 mL)/acetonitrile (8 mL) and concentrated and dried under high vacuum overnight to give 2-amino-6-borono-2-{1-[(4-chlorobenzyl)carbamoyl]-piperidin-4-yl}hexanoic acid hydrochloride (92 mg, 34%) as an off-white solid. $^1$H NMR (D$_2$O, 400 MHz) δ 7.26 (m, 2H), 7.15 (m, 2H), 4.19 (s, 2H), 3.95 (bt, J=14.6 Hz, 2H), 2.75 (bt, J=12.8 Hz, 2H), 2.06 (bt, J=12.4 Hz, 1H), 1.81 (m, 3H), 1.53 (bd, J=12.8 Hz, 1H), 1.32 (m, 4H), 1.11 (m, 2H), 0.69 (t, J=7.6 Hz, 2H). ESI$^+$ MS found for C$_{19}$H$_{29}$BClN$_3$O$_5$ m/z 408.4 (M−18+H); ESI$^-$ MS m/z 424.4 (M−H), 406.4 (M−18−H).

Example 32-A

Preparation of 2-amino-6-borono-2-{1-[(4-chlorophenyl)-carbamoyl]piperidin-4-yl}hexanoic acid hydrochloride

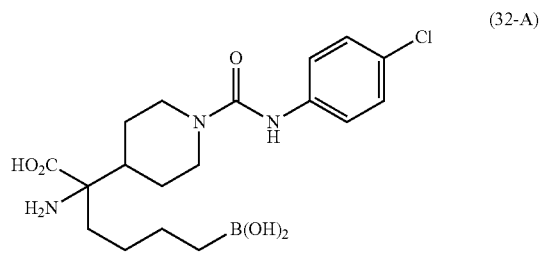 [SMILES: NC(CCCCB(O)O)(C(=O)O)C1CCN(C(=O)Nc2ccc(Cl)cc2)CC1]

(32-A)

2-Amino-6-borono-2-{1-[(4-chlorophenyl)carbamoyl]piperidin-4-yl}hexanoic acid hydrochloride is prepared in a manner analogous to that set forth in Example 31-A, except 1-chloro-4-isocyanatobenzene is used in place of 1-chloro-4-(isocyanatomethyl)benzene. $^1$H NMR (D$_2$O, 400 MHz) δ 7.25 (d, J=8 Hz, 2H), 7.09 (d, J=8 Hz, 2H), 4.07 (bt, J=14.4 Hz, 2H), 2.83 (bt, J=12.6 Hz, 2H), 2.08 (bt, J=12 Hz, 1H), 1.82 (m, 3H), 1.56 (bd, J=12.4 Hz, 1H), 1.50-1.05 (m, 6H), 0.69 (t, J=7.6 Hz, 2H). ESI$^+$ MS found for C$_{18}$H$_{27}$BClN$_3$O$_5$ m/z 394.3 (M−18+H), 376.3 (M−2×18+H); ESI$^-$ MS m/z 410.4 (M−H), 392.4 (M−18−H).

Example 33-A

Preparation of 2-amino-6-borono-2-(1-{[2-(4-fluorophenyl)ethyl]-carbamoyl}piperidin-4-yl)hexanoic acid hydrochloride

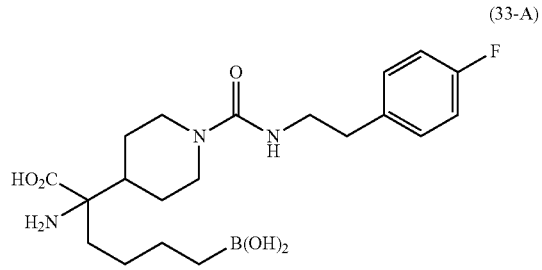 [SMILES: NC(CCCCB(O)O)(C(=O)O)C1CCN(C(=O)NCCc2ccc(F)cc2)CC1]

(33-A)

2-Amino-6-borono-2-(1-{[2-(4-fluorophenyl)ethyl]carbamoyl}piperidin-4-yl)hexanoic acid hydrochloride is prepared in a manner analogous to that set forth in Example 31-A, except 4-fluorophenethyl isocyanate is used in place of 1-chloro-4-(isocyanatomethyl)-benzene. $^1$H NMR (D$_2$O, 400 MHz) δ 7.12 (dd, J$_1$=8 Hz, J$_2$=5.6 Hz, 2H), 6.97 (t, J=8.8 Hz, 2H), 3.80 (bt, J=12.8 Hz, 2H), 3.27 (t, J=6.8 Hz, 2H), 2.65 (m, 4H), 1.99 (bt, J=12.8 Hz, 1H), 1.81 (m, 2H), 1.73 (bd, J=12.8 Hz, 1H), 1.49 (bd, J=12.4 Hz, 1H), 1.40-1.23 (m, 4H), 1.20-0.95 (m, 2H), 0.70 (t, J=7.6 Hz, 2H). ESI$^+$ MS found for $C_{20}H_{31}BFN_3O_5$ m/z 406.4 (M−18+H), 388.3 (M−2×18+H); ESI⁻ MS m/z 422.5 (M−H), 404.5 (M−18−H).

Example 34-A

Preparation of 2-amino-6-borono-2-(1-{[(4-chlorophenyl)amino]carbonothioyl}piperidin-4-yl)hexanoic acid hydrochloride

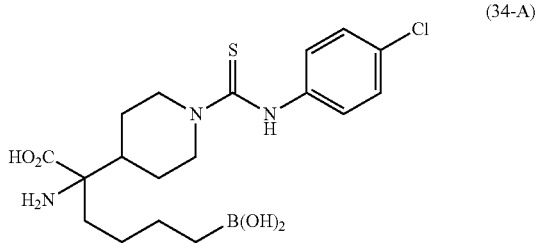 [SMILES: NC(CCCCB(O)O)(C(=O)O)C1CCN(C(=S)Nc2ccc(Cl)cc2)CC1]

(34-A)

2-Amino-6-borono-2-(1-{[(4-chlorophenyl)amino]carbonothioyl}piperidin-4-yl)hexanoic acid hydrochloride is prepared in a manner analogous to that set forth in Example 31-A, except 4-chlorophenyl isothiocyanate is used in place of 1-chloro-4-(isocyanatomethyl)-benzene and the clean product fractions isolated from HPLC purification are handled in the following manner. Pooled fractions are concentration under reduced pressure at 35° C. to remove acetonitrile and frozen prior to lyophilization to remove water. The residue is taken up in ~1 N HCl (10 mL) and frozen and lyophilized. Once again, the residue is taken up in ~1 N HCl (10 mL) and frozen and lyophilized to give the title compound. ¹H NMR (D₂O, 400 MHz) δ 7.31 (d, J=8.9 Hz, 2H), 7.08 (d, J=8.8 Hz, 2H), 4.70 (m, 2H), 3.08 (bt, J=13.2 Hz, 2H), 2.20 (bt, J=12.4 Hz, 1H), 1.87 (m, 3H), 1.65 (bd, J=13.2 Hz, 1H), 1.53 (qd, J₁=12.8 Hz, J₂=3.6 Hz, 1H), 1.33 (m, 4H), 1.14 (m, 1H), 0.70 (t, J=7.6 Hz, 2H). ESI⁺ MS found for $C_{18}H_{27}BClN_3O_4S$ m/z 410.4 (M−18+H); ESI⁻ MS m/z 426.5 (M−H), 408.4 (M−18−H).

Example 35-A

Preparation of 2-amino-6-borono-2-((S)-1-(4-chlorophenylcarbamothioyl)-pyrrolidin-3-yl)hexanoic acid hydrochloride

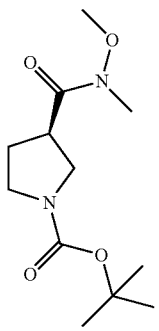 [SMILES: CON(C)C(=O)[C@@H]1CCN(C(=O)OC(C)(C)C)C1]

Step 1: tent-Butyl (3R)-3-[methoxy(methyl)carbamoyl]pyrrolidine-1-carboxylate In a 500 mL round-bottomed flask under a positive pressure of nitrogen, was added a methylene chloride (125 mL) solution of (R)—N-Boc-pyrroldine-3-carboxylic acid (7.00 g, 0.0325 mol). This solution was cooled to 0° C. using an ice/water bath and treated sequentially with, N-(3-dimethylaminopropyl)-N'-ethylcarbodiimide hydrochloride (7.48 g, 0.0390 mol) and 1-hydroxybenzotriazole (5.29 g, 0.0391 mol) in single portions. Following the addition of the coupling agents, the reaction mixture became cloudy, but upon further stirring a clear solution was obtained. The reaction mixture was stirred at 0° C. for 20 min then charged with N,O-dimethylhydroxylamine hydrochloride (4.78 g, 0.0490 mol) and triethylamine (13.5 mL, 0.0968 mol). The cooling bath was removed and the reaction mixture was allowed to warm to room temperature with stirring over a period of 1 h. The resulting solution was diluted with dichloromethane (600 mL) and 1 N HCl (1000 mL), mixed thoroughly and separated. The organic layer was washed with saturated aqueous sodium bicarbonate (300 mL) and saturated aqueous sodium chloride (300 mL), then dried over Na₂SO₄, filtered and concentrated to give tert-butyl (3R)-3-[methoxy(methyl)carbamoyl]pyrrolidine-1-carboxylate as a colorless oil (7.00 g; 83%). ¹H NMR (400 MHz, CDCl₃) δ 3.73 (s, 3H), 3.60-3.37 (m, 4H), 3.21 (s, 3H), 2.35-2.09 (m, 3H) 1.47 (s, 9H); ESI MS found for $C_{12}H_{22}N_2O_4$ m/z [159.1 (M+1-Boc)]

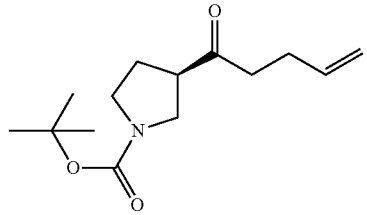 [SMILES: C=CCCC(=O)[C@@H]1CCN(C(=O)OC(C)(C)C)C1]

Step 2: tent-Butyl (3R)-3-hex-5-enoylpyrrolidine-1-carboxylate

In a 500 mL single necked round bottomed flask, a solution of tert-butyl (3R)-3-[methoxy(methyl)carbamoyl]pyrrolidine-1-carboxylate (7.00 g, 27.1 mmol) in tetrahydrofuran (100 mL) was cooled to 0° C. and treated with 0.5 M THF solution of 3-butenylmagnesium bromide (130 mL, 65 mmol) via a pressure equalizing addition funnel over a period of 20 minutes. Once the addition was complete, the cooling bath was removed and the mixture was allowed to warm to room temperature and stir for an additional 4 h. The reaction mixture was carefully quenched with 1 N HCl (300 mL) and stirred for an additional 20 min. The aqueous layer was extracted with ethyl acetate (3×200 mL) and the combined organic layers were dried over Na₂SO₄, filtered and concentrated to a yellow oil. Purification of the crude product by flash column chromatography (silica gel, 10% ethyl acetate in hexanes) afforded tert-butyl (3R)-3-hex-5-enoylpyrrolidine-1-carboxylate (6.62 g; 96%) as a light yellow oil. ¹H NMR (400 MHz, CDCl₃) δ 5.73-5.69 (m, 1H), 4.99-4.91 (m, 2H), 3.61-3.42 (m, 2H), 3.13-3.05 (m, 1H), 2.50 (t, J=7.2 Hz, 2H), 2.26 (q, J=7.2 Hz, 2H), 2.11-1.90 (m, 3H), 1.38 (s, 9H); ESI MS found for $C_{14}H_{23}NO_3$ m/z [154.1 (M+1-Boc)].

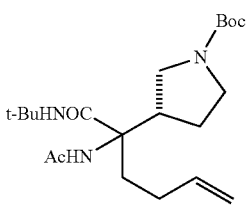

Step 3: 2-Acetamido-N-tert-butyl-2-[(3R)-1-tert-butylcarboxylpyrrolidin-3-yl]hex-5-enamide A solution of tert-butyl (3R)-3-hex-5-enoylpyrrolidine-1-carboxylate (1.00 g, 3.95 mmol), ammonium acetate (761 mg, 9.87 mmol) and tert-butyl isocyanide (2 mL, 30 mmol) in 2,2,2-trifluoroethanol (2 mL) was sealed in a 10 mL microwave vial. The reaction mixture was irradiated in a CEM microwave at 85° C. for 1.5 h. After cooling to room temperature, the solution was diluted with ethyl acetate (75 mL) and washed with saturated aqueous sodium bicarbonate (30 mL), water (30 ml) and saturated aqueous sodium chloride (30 ml). The organic layer was dried over $Na_2SO_4$, filtered and concentrated. Purification by flash column chromatography (silica gel, eluting with 20% ethyl acetate in hexanes) afforded recovered starting material (0.265 g, 27%) and 2-acetamido-N-tert-butyl-2-[(3R)-1-tert-butylcarboxylpyrrolidin-3-yl]hex-5-enamide as a mixture of diastereomers (1.06 g, 68%); ESI MS found for $C_{21}H_{37}N_3O_4$ m/z.

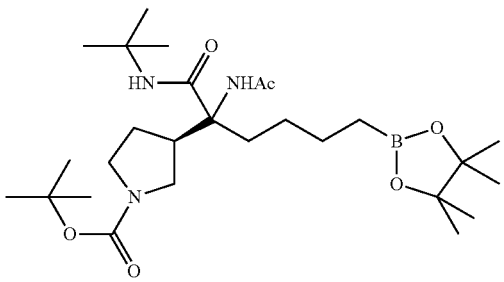 [SMILES: CC(=O)NC(CCCCB1OC(C)(C)C(C)(C)O1)(C(=O)NC(C)(C)C)[C@@H]1CCN(C(=O)OC(C)(C)C)C1]

Step 4: tert-butyl (3R)-3-[1-acetamido-1-(tert-butylcarbamoyl)-5-(4,4,5,5-tetramethyl-1,3,2-dioxaborolan-2-yl)pentyl]pyrrolidine-1-carboxylate In a 50 mL round bottomed flask a solution of bis(1,5-cyclooctadiene)diiridium(I) dichloride (92 mg, 0.14 mmol) and 1,2-bis(diphenylphosphino)ethane (117 mg, 0.294 mmol) in tetrahydrofuran (12 mL) was stirred for 5 min prior to cooling to 0° C. using an ice/water bath. After 15 min, 4,4,5,5-tetramethyl-1,3,2-dioxaborolane (600 uL, 4 mmol) was added in a single portion via syringe. After an additional 5 min at 0° C. the solution was warmed to room temperature and stirred for an additional 15 min. The reaction was then cooled once more in an ice/water bath and stirred for 10 min. From a separate flask, a THF solution (4 mL) of 2-acetamido-N-tert-butyl-2-[(3R)-1-tert-butylcarboxylpyrrolidin-3-yl]hex-5-enamide (1.06 g, 2.68 mmol) in tetrahydrofuran (4 mL) was transferred via syringe into the reaction mixture while it continued to stir at 0° C. for 10 minutes. The cold reaction mixture is then allowed to warm to room temperature and stirred for an additional 4 hours, prior to quenching the reaction by pouring it into a solution of saturated aqueous sodium bicarbonate (20 mL) and ethyl acetate (20 mL). After extraction, the organic layer was separated and the aqueous layer was further extracted using ethyl acetate (2×20 mL). The combined organic extracts were dried over $Na_2SO_4$, filtered and concentrated to afford tert-butyl (3R)-3-[1-acetamido-1-(tert-butylcarbamoyl)-5-(4,4,5,5-tetramethyl-1,3,2-dioxaborolan-2-yl)pentyl]pyrrolidine-1-carboxylate (1.46 g) as an oil, which was used without additional purification. ESI MS found for $C_{27}H_{50}BN_3O_6$ m/z 524.5 $(M+H)^+$; 522.7 $(M-H)^-$.

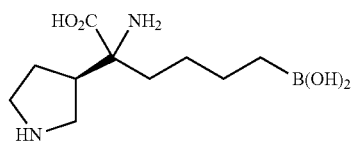 [SMILES: NC(CCCCB(O)O)(C(=O)O)[C@@H]1CCNC1]

Step 5: (R)-2-amino-6-borono-2-((R)-pyrrolidin-3-yl)hexanoic acid

In a 50 ML round bottom flask, tert-butyl (3R)-3-[1-acetamido-1-(tert-butylcarbamoyl)-5-(4,4,5,5-tetramethyl-1,3,2-dioxaborolan-2-yl)pentyl]pyrrolidine-1-carboxylate (1.41 g, 2.69 mmol) was dissolved in 1,4-dioxane (10 mL). To this solution was added a 6M aqueous solution of hydrogen chloride (10 mL) in a single portion and the reaction was heated under refluxing conditions for 18 h. At the end of 18 hours the reaction mixture was cooled to room temperature prior to dilution with water (10 mL). The aqueous layer was washed with ethyl acetate (20 mL) and concentrated in vacuo prior to lyophilization to afford (R)-2-amino-6-borono-2-((R)-pyrrolidin-3-yl)hexanoic acid dihydrochloride (0.657 g) as a mixture of diastereomers. The crude foam was used without purification in the next step. ESI MS found for $C_{10}H_{21}BN_2O_4$ m/z 227.2 $(M+H-water)^+$.

(35-A)

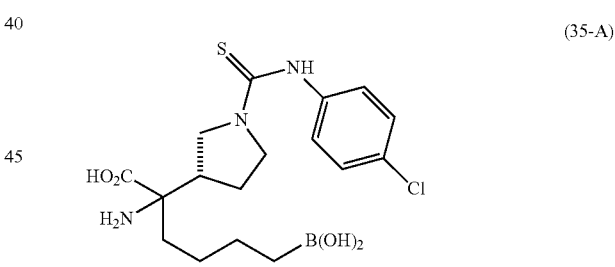

Step 6: 2-amino-6-borono-2-((S)-1-(4-chlorophenylcarbamothioyl)pyrrolidin-3-yl)hexanoic acid hydrochloride A solution of (R)-2-amino-6-borono-2-((R)-pyrrolidin-3-yl)hexanoic acid (200 mg, 0.8 mmol) and triethylamine (700 mg, 6 mmol) in N,N-dimethylformamide (4 mL, 50 mmol) was treated with 4-chlorophenyl isothiocyanate (300 mg, 1.8 mmol) in a single portion. After stirring at room temperature for 30 min, the reaction was diluted with 1 N HCl (20 mL) and washed with ethyl acetate (20 mL). The aqueous solution was concentrated and purified by HPLC to give 2-amino-6-borono-2-((S)-1-(4-chlorophenylcarbamothioyl)pyrrolidin-3-yl)hexanoic acid hydrochloride hydrochloride (81 mg, 20%). $^1$H NMR (400 MHz, $D_2O$, Mixture of diastereoisomers) δ 7.40-7.23 (m, 4H), 4.29-3.46 (m, 4H), 2.95-2.81 (m, 1H), 2.41-1.76 (m, 4H), 1.58-1.40 (br. m, 2H), 1.36-1.20 (br, m, 1H), 0.90-0.80 (br. m, 2H); MS ESI found for $C_{17}H_{25}BClN_3O_4S$ m/z (M-water+H)$^+$396.2; MS (ESI–) m/z (M–H)$^-$ 412.3, (M-water-H)$^-$ 394.3

Example 36-A

Preparation of 2-amino-6-borono-2-((S)-1-(4-chlorophenylcarbamoyl)pyrrolidin-3-yl)hexanoic acid hydrochloride

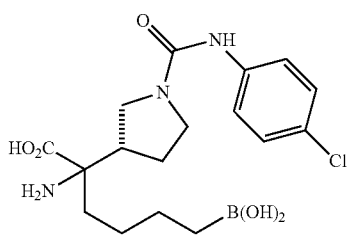

(36-A)

A solution of (R)-2-amino-6-borono-2-((R)-pyrrolidin-3-yl)hexanoic acid (Example 35-A, Step 5, 200 mg, 0.8 mmol) and triethylamine (900 uL, 6 mmol) in N,N-dimethylformamide (4 mL, 50 mmol) was treated with 4-chlorobenzene isocyanate-(280 mg, 1.8 mmol) in a single portion. After stirring at room temperature for 30 min, the reaction was diluted with 1 N HCl (20 mL) and washed with ethyl acetate (20 mL). The aqueous solution was concentrated and purified by HPLC to give 2-amino-6-borono-2-((S)-1-(4-chlorophenylcarbamoyl)pyrrolidin-3-yl)hexanoic acid (0.021 g, 6%). $^1$H NMR (400 MHz, D$_2$O, Mixture of diastereoisomers) δ 7.26 (d, J=8.1 Hz, 2H), 7.14 (d, J=8.1 Hz, 2H), 3.70-3.48 (br, m, 2H), 3.99-3.08 (br, m, 2H), 2.79-2.65 (br, m, 1H), 2.30-1.75 (br. m, 4H), 1.54-1.44 (br. m, 2H), 1.35-1.27 (br. m, 1H), 0.87 (t, J=6.5 Hz, 2H),.; MS (ESI$^+$) found for $C_{17}H_{25}ClBN_3O_5$ m/z (M-water+H)$^+$ 380.2; MS; (M-water+Na)$^+$ 403.3

Example 37-A

Preparation 2-amino-6-borono-2-((S)-1-(4-fluorobenzyl)pyrrolidin-3-yl)hexanoic acid dihydrochloride

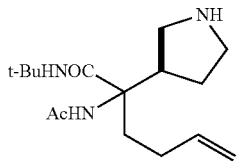

Step 1: 2-acetamido-N-tert-butyl-2((R)-pyrrolidin-3-yl)hex-5-enamide

To a 100 mL round bottomed flask containing a solution of 2-acetamido-N-tert-butyl-2-[(3R)-1-tert-butylcarboxylpyrrolidin-3-yl]hex-5-enamide (Example 35-A, Step 3, 1.42 g, 3.59 mmol) in methylene chloride (20 mL, 300 mmol) was added trifluoroacetic acid (2.4 mL, 31 mmol) in a single portion via syringe. After stirring for 4 h, the solution was poured into saturated aqueous sodium bicarbonate (100 mL) and the aqueous layer was extracted with 10% TFE in DCM (2×50 mL). The combined organic extracts were dried over Na$_2$SO$_4$, filtered and concentrated to give 2-acetamido-N-tert-butyl-2-[(3R)-pyrrolidin-3-yl]hex-5-enamide (0.95 g, 90%) as a light yellow oil. Used without further purification in subsequent step. $^1$H NMR (400 MHz, CDCl$_3$, Mixture of diastereoisomers) δ 7.80 (br. s, 0.5H), 7.60 (br. s, 0.5H), 7.45 (br. s, 0.5H), 1.96-165 (br. s, 0.5H), 1.80-1.55 (m, 4H), 1.36-1.34 (2×s, 9H), ESI MS found for $C_{16}H_{29}N_3O_2$ m/z 296.3 (M+H)$^+$.

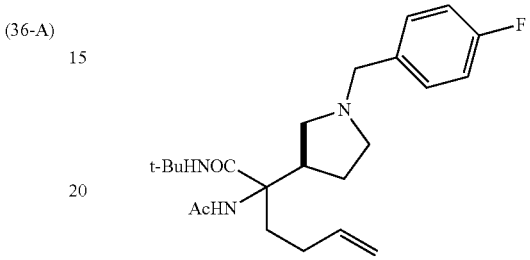

Step 2: 2-acetamido-N-tert-butyl-2-((R)-1-(4-fluorobenzyl)pyrrolidin-3-yl)hex-5-enamide A solution of 2-acetamido-N-tert-butyl-2-[(3R)-pyrrolidin-3-yl]hex-5-enamide (315 mg, 1.07 mmol), 4-fluorobenzaldehyde (140 uL, 1.3 mmol) and acetic acid (60 uL, 1 mmol) in methylene chloride (10 mL, 200 mmol) was stirred for 10 minutes prior to the addition of sodium triacetoxyborohydride (377 mg, 1.78 mmol) in a single portion. After stirring at room temperature overnight, the reaction was quenched with 1 N NaOH (10 mL). The organic layer thus obtained was separated and the aqueous layer further extracted with DCM (3×10 mL). The combined organic extracts were dried over Na$_2$SO$_4$, filtered and concentrated to give 2-acetamido-N-tert-butyl-2-((R)-1-(4-fluorobenzyl) pyrrolidin-3-yl)hex-5-enamide (0.387 g, 89.9%) as an oil. The oil was used in the next step without purification. ESI MS found for $C_{23}H_{34}FN_3O_2$ m/z 404.3 (M+H)$^+$.

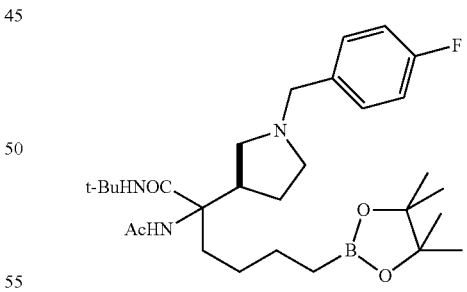

Step 3: 2-acetamido-N-tert-butyl-2-((R)-1-(4-fluorobenzyl)pyrrolidin-3-yl)-6-(4,4,5,5-tetramethyl-1,3,2-dioxaborolan-2-yl)hexanamide A solution of bis(1,5-cyclooctadiene)diiridium(I) dichloride (35.0 mg, 0.0520 mmol) and 1,2-bis(diphenylphosphino)-ethane (44 mg, 0.11 mmol) in tetrahydrofuran (5 mL, 60 mmol) was cooled to 0° C. After stirring for 10 min 4,4,5,5-tetramethyl-1,3,2-dioxaborolane (120 uL, 0.83 mmol) was added in a single portion via syringe and the reaction mixture was stirred at 0° C. for 5 min before warming to room temperature and stirring an additional 15 min. The reaction mixture was recooled to 0° C. and treated with 2-acetamido-N-tert-butyl-2-[(3R)-1-(4-fluorobenzyl)pyrrolidin-3-yl]hex-5-enamide (210 mg, 0.52 mmol) in tetrahydrofuran (3 mL, 40 mmol) in a single portion. After stirring for 10 min at 0° C., the reaction was warmed to room temperature and stirred an additional 4 h. The mixture was diluted with aqueous sodium bicarbonate, extracted with DCM (3×50 mL), dried over Na$_2$SO$_4$, filtered and concentrated to give 2-acetamido-N-tert-butyl-2-((R)-1-(4-fluorobenzyl)pyrrolidin-3-yl)-6-(4,4,5,5-tetramethyl-1,3,2-dioxaborolan-2-yl)hexanamide as a light orange oil that was used without further purification. ESI MS found for C$_{29}$H$_{47}$BFN$_3$O$_4$ m/z 532.3 (M+H)$^+$

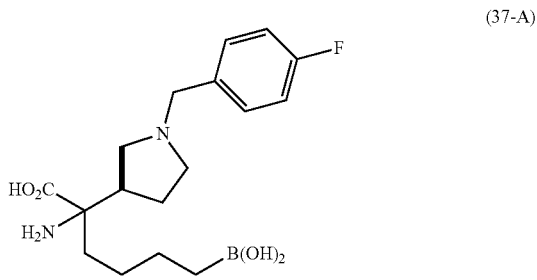

(37-A)

Step 4: 2-amino-6-borono-2-((R)-1-(4-fluorobenzyl)pyrrolidin-3-yl)hexanoic acid dihydrochloride An aqueous solution of 2-acetamido-N-tert-butyl-2-((R)-1-(4-fluorobenzyl)pyrrolidin-3-yl)-6-(4,4,5,5-tetramethyl-1,3,2-dioxaborolan-2-yl)hexanamide (0.280 g, 0.527 mmol) in 6M hydrogen chloride (10 mL, 60 mmol) was heated under reflux overnight. The reaction was cooled to room temperature, diluted with 20 mL of water, and washed with ethyl acetate (20 mL). The aqueous layer was purified by HPLC (3 injections) using a 5-20% acetonitrile in water. The fractions corresponding to the desired product were concentrated and lyophilized to give 2-amino-6-borono-2-((R)-1-(4-fluorobenzyl)pyrrolidin-3-yl)hexanoic acid dihydrochloride as white powder, which became oily upon exposure to air (hydroscopic). (0.003 g, 2%). $^1$H NMR (400 MHz, CDCl$_3$, Mixture of diastereoisomers) δ 7.41 (dd, J$_1$=8.1 Hz, J$_2$=6.5 Hz, 2H), 7.12 (t, J=8.1 Hz, 2H), 4.35-4.25 (br, m, 2H), 3.77-3.09 (br. m, 3H), 2.99-2.60 (br. m, 1H), 2.39-1.57 (br. m, 4H), 1.34-1.18 (br. m, 2H), 1.15-1.03 (br. m, 1H), 0.70-0.61 (m, 2H),; ESI MS found for C$_{17}$H$_{26}$BFN$_2$O$_4$ m/z 335.3 (M+H-water)$^+$; 351.4 (M–H)$^-$; 333.4 (M–H-water)$^-$.

Example 38-A

Preparation of 2-amino-6-borono-2-OR)-1-(4-(trifluoromethyl)benzyl)pyrrolidin-3-yl)hexanoic acid dihydrochloride

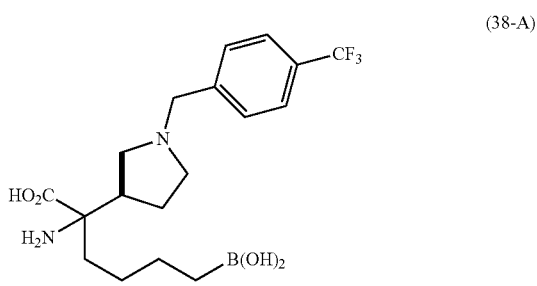

(38-A)

2-Amino-6-borono-2-((R)-1-(4-(trifluoromethyl)benzyl)pyrrolidin-3-yl)hexanoic acid was prepared in a manner analogous to that set forth in Example 37-A except that 4-trifluoromethylbenzaldehyde was used in step 2. $^1$H NMR (400 MHz, D$_2$O, Mixture of diastereoisomers) δ 7.73 (d, J=8.1 Hz, 2H), 7.58 (d, J=8.1 Hz, 2H), 4.41 (s, 2H), 2.82-3.63 (m, 4H), 2.42-1.58 (m, 4H), 1.38-1.20 (m, 2H), 1.18-1.03 (m, 1H), 0.72-0.63 (m, 2H),; ESI MS found for C$_{18}$H$_{26}$BF$_3$N$_2$O$_4$ m/z 385.3 (M+H-water)$^+$; 401.4 (M–H)$^-$; 383.4 (M–H-water)$^-$.

Example 39-A

Preparation of 2-amino-6-borono-2-((R)-1-(4-methylbenzyl)pyrrolidin-3-yl)hexanoic acid dihydrochloride

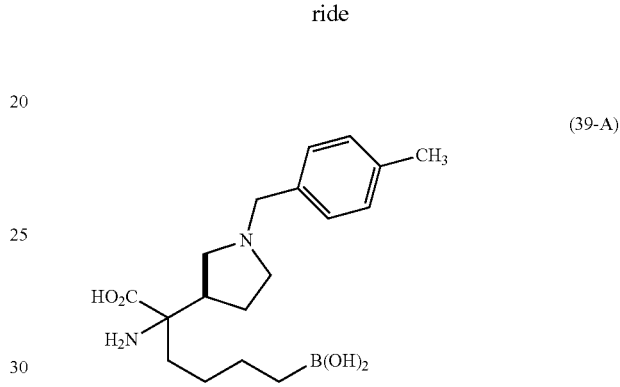

(39-A)

2-Amino-6-borono-2-((R)-1-(4-methylbenzyl)pyrrolidin-3-yl)hexanoic acid dihydrochloride was prepared in a manner analogous to that set forth in Example 37-A except that 4-methylbenzaldehyde was used in step 2 $^1$H NMR (400 MHz, D$_2$O, mixture of diastereoisomers) δ 7.22 (d, J=8.1 Hz, 2H), 7.18 (d, J=8.1 Hz, 2H), 4.30-4.11 (m, 2H), 3.69-3.28 (m, 3H), 3.24-2.66 (m, 2H), 2.33-2.02 (m, 4H), 1.92-1.55 (m, 3H), 1.34-1.17 (m, 2H), 1.15-1.00 (m, 1H), 0.67-0.57 (m, 2H),; ESI MS found for C$_{18}$H$_{29}$BN$_2$O$_4$ m/z 349.5 (M+H)$^+$; 331.4 (M+H-water)$^+$; 347.5 (M–H)$^-$; 329.4 (M–H-water)$^-$.

Example 40-A

Preparation of 2-amino-6-borono-2-((R)-1-(2-nitrophenylsulfonyl)pyrrolidin-3-yl)hexanoic acid

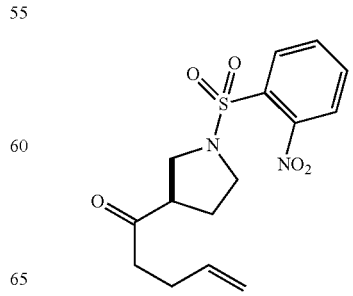

Step 1: (R)-1-(1-(2-nitrophenylsulfonyl)pyrrolidin-3-yl)pent-4-en-1-one

To a solution of (R)-tert-butyl 3-pent-4-enoylpyrrolidine-1-carboxylate (300 mg, 1 mmol) in methylene chloride (5 mL, 80 mmol) was added trifluoroacetic acid (2 mL, 20 mmol) and the resultant mixture was stirred at room temperature for 1 h. The crude reaction mixture was then concentrated to obtain a crude oil which was re-dissolved in methylene chloride (5 mL, 80 mmol) prior to the addition of triethylamine (1 mL, 7 mmol). This solution was cooled to 0° C. before adding 2-nitrobenzenesulfonyl chloride (450 mg, 2.0 mmol) in a single portion. The reaction mixture, which immediately turned blue in color, was stirred overnight at room temperature. At the end of the reaction, the solution was diluted with saturated aqueous sodium bicarbonate (50 mL) to give two layers which were separated. The aqueous layer was further extracted with methylene chloride (2×20 mL) and the combined organic layers were dried over $Na_2SO_4$, filtered and concentrated to give a blue oil, which was purified by flash column chromatography (silica gel, eluting with 0-100% ethyl acetate in hexanes) to give (R)-1-(1-(2-nitrophenylsulfonyl)pyrrolidin-3-yl)pent-4-en-1-one (305 mg, 80%). $^1$H NMR (400 MHz, $CDCl_3$) δ 8.07-8.03 (m, 1H), 7.76-7.70 (m, 2H), 7.66-7.62 (m, 1H), 5.78 (ddt, $J_1$=17.0 Hz, $J_2$=10.4 Hz, $J_3$=6.5 Hz, 1H), 5.07-4.97 (m, 2H), 3.70 (dd, $J_1$=12.0 Hz, $J_2$=8.0 Hz, 1H) 3.61 (dd, $J_1$=12.0 Hz, $J_2$=8.1 Hz, 1H), 3.52 (t, J=8.1 Hz, 2H), 3.24 (p, J=8.0 Hz, 1H), 2.59 (td, $J_1$=7.3 Hz, $J_2$=3.6 Hz, 2H), 2.32 (q, J=6.8 Hz, 2H), 2.24-2.16 (m, 1H), 2.14-2.05 (m, 1H), 1.28 (ddd, $J_1$=17.8 Hz, $J_2$=10.6 Hz, $J_3$=7.3 Hz, 1H); ESI MS found for $C_{15}H_{18}N_2O_5S$ m/z 339.3 (M+H)$^+$.

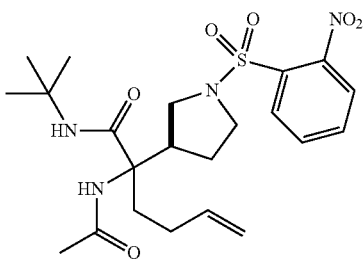

Step 2: 2-acetamido-N-tert-butyl-2-((R)-1-(2-nitrophenylsulfonyl)pyrrolidin-3-yl)hex-5-enamide A solution of (R)-1-(1-(2-nitrophenylsulfonyl)pyrrolidin-3-yl)pent-4-en-1-one (1.03 g, 3.04 mmol) and ammonium acetate (0.548 g, 7.11 mmol) in 2,2,2-trifluoroethanol (1.5 mL, 2.0 mmol) was treated with tert-butyl isocyanide (1.5 mL, 24 mmol) followed by stirring at room temperature. After 8 hours, an additional 0.5 mL of isocyanate was added and the temperature of the reaction was increased to 40° C. After stirring overnight at 40° C., the crude reaction was partitioned between ethyl acetate and saturated aqueous sodium bicarbonate. The organic layer was separated, dried over $Na_2SO_4$, filtered and concentrated prior to purification of the crude oil by flash column chromatography (silica gel, using 0-100% ethyl acetate in hexanes) to give 2-acetamido-N-tert-butyl-2-((R)-1-(2-nitrophenylsulfonyl)pyrrolidin-3-yl)hex-5-enamide (1.00 g, 68.4%) as a brown foam. $^1$H NMR (400 MHz, $CDCl_3$, mixture of diastereoisomers) δ 8.07-8.02 (m, 1H), 7.81-7.71 (m, 2H), 7.64-7.59 (m, 1H), 6.85 (2×s, 1H), 5.98-5.63 (br, m, 2H), 5.06-4.95 (m, 2H), 3.61-2.90 (m, 6H), 2.02-2.00 (2×s, 3H), 1.95-1.41 (m, 5H), 1.38-1.36 (2×s, 9H),; ESI MS found for $C_{22}H_{32}N_4O_6S$ m/z 481.2 (M+H)$^+$; 479.3 (M−H)$^−$.

Step 3: 2-acetamido-N-tert-butyl-2-((R)-1-(2-nitrophenylsulfonyl)pyrrolidin-3-yl)-6-(4,4,5,5-tetramethyl-1,3,2-dioxaborolan-2-yl)hexanamide In a 50 mL round bottomed flask, a solution of bis(1,5-cyclooctadiene)diiridium(I) dichloride (72 mg, 0.11 mmol) and 1,2-bis(diphenylphosphino)-ethane (84 mg, 0.21 mmol) in tetrahydrofuran (10 mL, 100 mmol) was cooled to 0° C., stirred for 15 min and treated with 4,4,5,5-tetramethyl-1,3,2-dioxaborolane (450 uL, 3.1 mmol). After additional stirring for 5 min the cooling bath was removed and the reaction mixture was allowed to warm to room temperature with stirring a period of 15 min. The reaction mixture was then recooled to 0° C. and treated with a solution of 2-acetamido-N-tert-butyl-2-((R)-1-(2-nitrophenylsulfonyl)pyrrolidin-3-yl)hex-5-enamide (1.00 g, 2.08 mmol) in tetrahydrofuran (2 mL, 20 mmol) added in a dropwise manner via syringe. After stirring for 5 min at 0° C. the reaction was warmed to room temperature and stirred until the desired product was obtained in good yield. The reaction mixture was quenched by pouring the crude into a saturated solution of aqueous sodium carbonate (50 mL). The aqueous layer was extracted using ethyl acetate (3×30 mL), and the combined organic layers were washed with saturated aqueous sodium chloride (20 mL), dried over $Na_2SO_4$, filtered and concentrated to give 2-acetamido-N-tert-butyl-2-((R)-1-(2-nitrophenylsulfonyl)pyrrolidin-3-yl)-6-(4,4,5,5-tetramethyl-1,3,2-dioxaborolan-2-yl)hexanamide (1.20 g, 94.8%) as a foam. The titled compound was used without further purification. ESI MS found for $C_{28}H_{45}N_4O_8BS$ m/z 609.5 (M+H)$^+$; 607.5 (M−H)$^−$.

(40-A)

Step 4: 2-amino-6-borono-2-((R)-1-(2-nitrophenylsulfonyl)pyrrolidin-3-yl)hexanoic acid A solution of 2-acetamido-N-tert-butyl-2-((R)-1-(2-nitrophenylsulfonyl)pyrrolidin-3-yl)-6-(4,4,5,5-tetramethyl-1,3, 2-dioxaborolan-2-yl)hexanamide (500 mg, 0.8 mmol) in 1,4-dioxane (3 mL, 40 mmol) was treated with a 6M aqueous solution of hydrogen chloride (6 mL, 40 mmol) followed by heating to 100° C. for 24 h. At the end of the 24 hour period, the reaction mixture was diluted with water and filtered. The filtrate that was obtained was purified by HPLC using 5%-50% acetonitrile in water over 30 min. The product-containing fractions were concentrated, then dissolved in 1N HCl and frozen prior to lyophilization to afford 2-amino-6-borono-2-((R)-1-(2-nitrophenylsulfonyl)pyrrolidin-3-yl) hexanoic acid (79 mg, 20%) as a white foam. $^1$H NMR (400 MHz, DMSO-$d_6$, Mixture of diastereoisomers) δ 8.55-8.35 (2H), 8.05-7.98 (m, 2H), 7.96-7.85 (m, 2H), 5.83 (t, J=6.5 Hz, 2H), 3.70-3.14 (m, 4H), 2.78-2.65 (m, 1H), 2.19-1.60 (m, 4H), 1.47-1.23 (m, 3H), 1.14-1.00 (m, 1H); ESI MS found for $C_{16}H_{24}BN_3O_8S$ m/z 412.1 [M−OH]$^+$; 410.2 (M−H$_2$O)$^-$.

Example 41-A

Preparation of 2-amino-6-borono-2-(1-phenethylpiperidin-4-yl)hexanoic acid

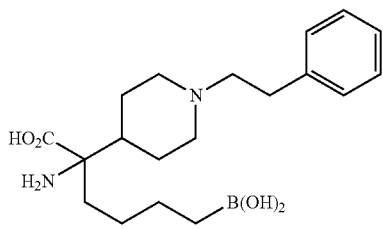

(41-A)

2-Amino-6-borono-2-(1-phenethylpiperidin-4-yl)hexanoic acid is prepared in a manner analogous to that set forth in Example 118, except 3-phenylethanal is used as the aldehyde in step 6. $^1$H NMR (D$_2$O, 300 MHz) δ 7.35-7.28 (m, 2H), 7.30-7.20 (m, 3H), 3.71-3.62 (m, 2H), 3.35-3.25 (m, 2H), 3.04-2.90 (m, 4H), 2.2-2.05 (m, 2H), 1.93-1.75 (m, 4H), 1.55-1.45 (m, 1H), 1.38-1.22 (m, 3H), 1.18-1.05 (m, 1H), 0.69 (t, J=7.2 Hz, 2H). ESI MS found for $C_{19}H_{31}BN_2O_4$ m/z [363.2 (M+$^1$)].

Example 42-A

Preparation of 2-amino-6-borono-2-(1-(3,4-dichlorophenylcarbamoyl)piperidin-4-yl)hexanoic acid

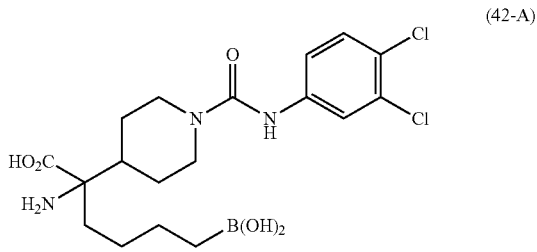 [SMILES: NC(CCCCB(O)O)(C(=O)O)C1CCN(C(=O)Nc2ccc(Cl)c(Cl)c2)CC1]

(42-A)

2-Amino-6-borono-2-(1-(3,4-dichlorophenylcarbamoyl) piperidin-4-yl)hexanoic acid is prepared in a manner analogous to that set forth in Example 31-A, except that 1,2-dichloro-4-isocyanatobenzene is used as the isocyanate. $^1$H NMR (D$_2$O, 500 MHz) δ 7.33-7.25 (m, 2H), 7.01-6.96 (m, 1H), 4.01 (t, J=11.4 Hz, 2H), 2.80 (t, J=11.1 Hz, 2H), 2.08-2.01 (m, 1H), 1.83-1.77 (m, 3H), 1.58-1.51 (m, 1H), 1.47-1.32 (m, 1H), 1.33-1.18 (m, 3H), 1.18-1.04 (m, 2H), 0.65 (t, J=7.2 Hz, 2H). ESI MS found for $C_{18}H_{27}BCl_2N_3O_5$ m/z [428.5 (M−18+1)].

Example 43-A

Preparation of 2-amino-6-borono-2-(1-(4-chlorobenzylcarbamothioyl)piperidin-4-yl)hexanoic acid

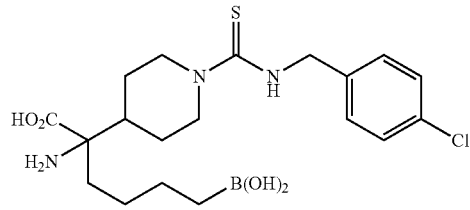

(43-A)

2-Amino-6-borono-2-(1-(4-chlorobenzylcarbamothioyl) piperidin-4-yl)hexanoic acid is prepared in a manner analogous to that set forth in Example 31-A, except that 1-chloro-4-(isothiocyanatomethyl)benzene is used as the isocyanate. $^1$H NMR (D$_2$O, 300 MHz) δ 7.21 (d, J=8.4 Hz, 2H), 7.09 (d, J=8.4 Hz, 2H), 4.62 (bs, 2H), 4.59 (m, 2H), 2.95 (bt, J=11.4 Hz, 2H), 2.14 (bt, J=11.4 Hz, 1H), 1.85-1.70 (m, 3H), 1.62-1.51 (m, 1H), 1.48-1.00 (m, 6H), 0.63 (t, J=7.5 Hz, 2H). ESI MS found for $C_{19}H_{29}BClN_3O_4S$ m/z [442.6 (M+1)].

Example 44-A

Preparation of 2-amino-6-borono-2-(1-(3-chloro-4-methylphenylcarbamothioyl)piperidin-4-yl)hexanoic acid

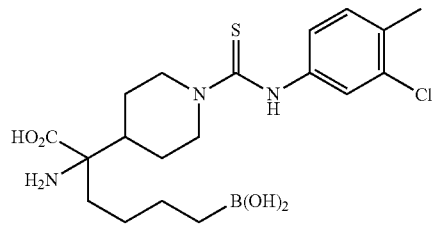

(44-A)

2-Amino-6-borono-2-(1-(3-chloro-4-methylphenylcarbamothioyl)piperidin-4-yl)hexanoic acid was prepared in a manner analogous to that set forth in Example 32-A, except that 2-chloro-4-isothiocyanato-1-methylbenzene is used as the isocyanate.

Example 45-A

Preparation of 2-amino-6-borono-2-(1-(naphthalen-1-ylcarbamothioyl)piperidin-4-yl)hexanoic acid

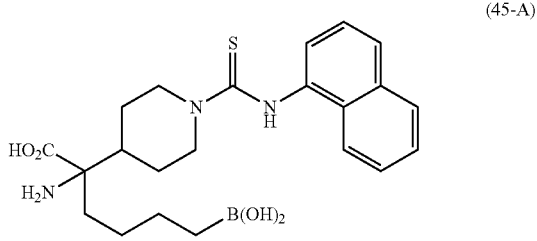 [SMILES: NC(CCCCB(O)O)(C(=O)O)C1CCN(C(=S)Nc2cccc3ccccc23)CC1]

(45-A)

2-Amino-6-borono-2-(1-(naphthalen-1-ylcarbamothioyl)piperidin-4-yl)hexanoic acid is prepared in a manner analogous to that set forth in Example 32-A, except that 1-isothiocyanatonaphthalene is used as the isocyanate. $^1$H NMR (D$_2$O, 300 MHz) δ 7.87-7.78 (m, 2H), 7.70-7.64 (m, 1H), 7.46-7.37 (m, 3H), 7.22-7.17 (m, 1H), 4.60-4.55 (m, 2H), 3.06 (bt, J=11.4 Hz, 2H), 2.20 (bt, J=11.4 Hz, 1H), 1.92-1.76 (m, 3H), 1.70-1.50 (m, 2H), 1.40-1.20 (m, 4H), 1.18-1.03 (m, 1H), 0.67 (t, J=7.2 Hz, 2H). ESI MS found for C$_{22}$H$_{30}$BN$_3$O$_4$S m/z [444.6 (M+1)].

Example 46-A

Preparation of 2-amino-6-borono-2-(1-(3-(4-chlorophenyl)propyl)piperidin-4-yl)hexanoic acid

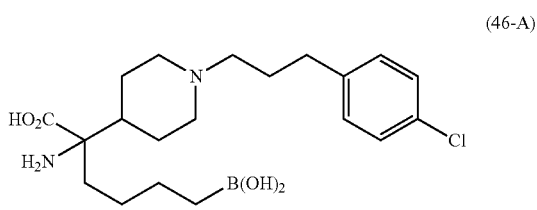 [SMILES: NC(CCCCB(O)O)(C(=O)O)C1CCN(CCCc2ccc(Cl)cc2)CC1]

(46-A)

2-Amino-6-borono-2-(1-(3-(4-chlorophenyl)propyl)piperidin-4-yl)hexanoic acid is prepared in a manner analogous to that set forth in Example 118, except that 3-(4-chlorophenyl)propanal is used as the aldehyde in step 6. $^1$H NMR (D$_2$O, 300 MHz) δ 7.16 (d, J=8.4 Hz, 2H), 7.04 (d, J=8.4 Hz, 2H), 3.54-3.45 (m, 2H), 2.97-2.88 (m, 2H), 2.87-2.72 (m, 2H), 2.58-2.50 (m, 2H), 2.10-1.95 (m, 1H), 1.96-1.85 (m, 1H), 1.88-1.62 (m, 6H), 1.48-1.32 (m, 1H), 1.30-1.15 (m, 3H), 1.09-0.98 (m, 1H), 0.60 (t, J=7.2 Hz, 2H). ESI MS found for C$_{20}$H$_{32}$BClN$_2$O$_4$ m/z [393.6 (M–18+1)].

Example 47-A

Preparation of 2-amino-6-borono-2-(1-(2,4-dichlorophenethyl)piperidin-4-yl)hexanoic acid

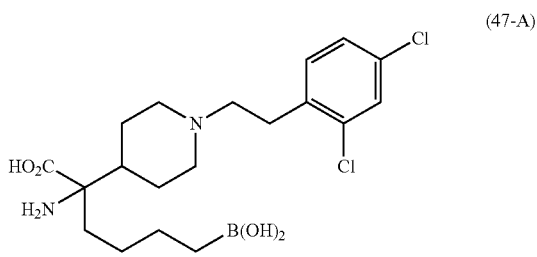 [SMILES: NC(CCCCB(O)O)(C(=O)O)C1CCN(CCc2ccc(Cl)cc2Cl)CC1]

(47-A)

2-Amino-6-borono-2-(1-(2,4-dichlorophenethyl)piperidin-4-yl)hexanoic acid is prepared in a manner analogous to that set forth in Example 118, except that 2-(2,4-dichlorophenyl)acetaldehyde is used as the aldehyde in step 6. $^1$H NMR (D$_2$O, 500 MHz) δ 7.41 (s, 1H), 7.20 (bs, 2H), 3.26-3.17 (m, 2H), 3.09-3.01 (m, 2H), 3.00-2.89 (m, 2H), 2.11-2.02 (m, 2H), 1.88-1.70 (m, 4H), 1.51-1.42 (m, 1H), 1.34-1.20 (m, 3H), 1.12-1.02 (m, 1H), 0.67 (t, J=7.2 Hz, 2H). ESI MS found for C$_{19}$H$_{29}$BCl$_2$N$_2$O$_4$ m/z [413.6 (M–18+1)].

Example 48-A

Preparation of 2-amino-6-borono-2-(1-(3,4-difluorobenzyl)piperidin-4-yl)hexanoic acid

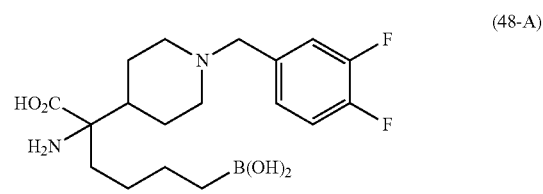

(48-A)

2-Amino-6-borono-2-(1-(3,4-difluorobenzyl)piperidin-4-yl)hexanoic acid is prepared in a manner analogous to that set forth in Example 118, except that 3,4-difluorobenzaldehyde is used as the aldehyde in step 6. $^1$H NMR (D$_2$O, 300 MHz) δ 7.35-7.05 (m, 3H), 4.14 (s, 2H), 3.50-3.36 (m, 2H), 2.94-2.84 (m, 2H), 2.16-1.95 (m, 2H), 1.86-1.54 (m, 4H), 1.50-1.35 (m, 1H), 1.36-1.14 (m, 3H), 1.14-0.97 (m, 1H), 0.65 (t, J=7.2 Hz, 2H). ESI MS found for C$_{18}$H$_{27}$BF$_2$N$_2$O$_4$ m/z [385.1 (M+1)].

Example 49-A

Preparation of 2-amino-6-borono-2-(1-(4-chloro-3-fluorobenzyl)piperidin-4-yl)hexanoic acid

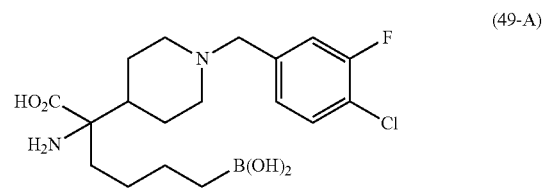 [SMILES: NC(CCCCB(O)O)(C(=O)O)C1CCN(Cc2ccc(F)c(F)c2)CC1]

(49-A)

2-Amino-6-borono-2-(1-(4-chloro-3-fluorobenzyl)piperidin-4-yl)hexanoic acid is prepared in a manner analogous to that set forth in Example 118, except 4-chloro-3-fluoro benzaldehyde is used as the aldehyde in step 6. $^1$H NMR (D$_2$O, 300 MHz) δ 7.51-7.43 (m, 1H), 7.32-7.23 (m, 1H), 7.22-7.10 (m, 1H), 4.13 (s, 2H), 3.51-3.38 (m, 2H), 2.98-2.82 (m, 2H), 2.18-1.94 (m, 2H), 1.88-1.61 (m, 4H), 1.50-1.32 (m, 1H), 1.33-1.14 (m, 3H), 1.13-0.96 (m, 1H), 0.61 (t, J=7.2 Hz, 2H). ESI MS found for C$_{18}$H$_{27}$BClFN$_2$O$_4$ m/z [401.2 (M+1)].

Example 50-A

Preparation of 2-amino-6-borono-2-(1-(3-(3-chloro-5-fluorophenyl) propyl)piperidin-4-yl)hexanoic acid

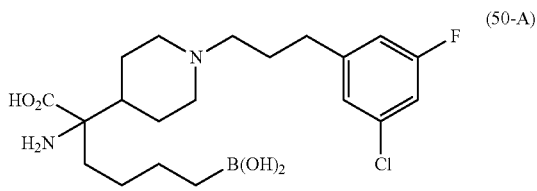 [SMILES: NC(CCCCB(O)O)(C(=O)O)C1CCN(CCCc2cc(F)cc(Cl)c2)CC1]
(50-A)

2-Amino-6-borono-2-(1-(3-(3-chloro-5-fluorophenyl)propyl)piperidin-4-yl)hexanoic acid is prepared in a manner analogous to that set forth in Example 118, except that 3-(3-chloro-5-fluorophenyl)propanal is used as the aldehyde in step 6. $^1$H NMR (D$_2$O, 300 MHz) δ 7.01-6.91 (m, 2H), 6.86-6.78 (m, 1H), 3.55-3.45 (m, 2H), 2.97-2.85 (m, 2H), 2.86-2.74 (m, 2H), 2.60-2.49 (m, 2H), 2.09-1.60 (m, 8H), 1.48-1.35 (m, 1H), 1.35-1.15 (m, 3H), 1.10-0.97 (m, 1H), 0.62 (t, J=7.5 Hz, 2H). ESI MS found for C$_{20}$H$_{31}$BClFN$_2$O$_4$ m/z [429.5 (M+1)].

Example 51-A

Preparation of 2-amino-6-borono-2-(1-((4-fluoronaphthalen-1-yl)methyl)piperidin-4-yl)hexanoic acid

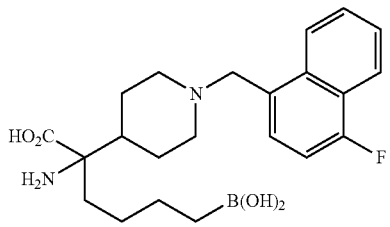
(51-A)

2-Amino-6-borono-2-(1-((4-fluoronaphthalen-1-yl)methyl)piperidin-4-yl)hexanoic acid is prepared in a manner analogous to that set forth in Example 118, except that 4-fluoro-1-naphthaldehyde is used as the aldehyde in step 6. $^1$H NMR (D$_2$O, 300 MHz) δ 8.03 (d, J=8.4 Hz, 1H), 7.95 (d, J=8.4 Hz, 1H), 7.64-7.44 (m, 3H), 7.10 (t, J=8.4 Hz, 1H), 4.60 (bs, 2H), 3.51-3.40 (m, 2H), 3.11-2.97 (m, 2H), 2.20-2.04 (m, 1H), 2.00-1.85 (m, 1H), 1.80-1.60 (m, 4H), 1.46-1.31 (m, 1H), 1.30-1.10 (m, 3H), 1.10-0.95 (m, 1H), 0.59 (t, J=7.2 Hz, 2H). ESI MS found for C$_{22}$H$_{30}$BFN$_2$O$_4$ m/z [417.1 (M+1)].

Example 52-A

Preparation of 2-amino-6-borono-2-(1-(3-(2,4-difluorophenyl)propyl)piperidin-4-yl)hexanoic acid dihydrochloride

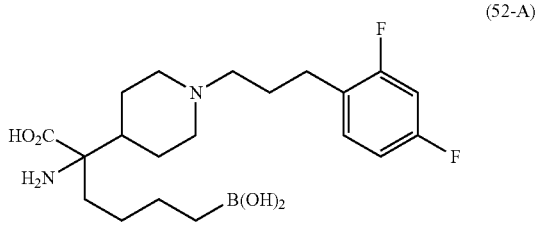 [SMILES: NC(CCCCB(O)O)(C(=O)O)C1CCN(CCCc2ccc(F)cc2F)CC1]
(52-A)

2-Amino-6-borono-2-(1-(3-(2,4-difluorophenyl)propyl)piperidin-4-yl)hexanoic acid dihydrochloride is prepared in a manner analogous to that set forth in Example 118, except that 3-(2,4-difluorophenyl)propanal is used as the aldehyde in step 6. $^1$H NMR (D$_2$O, 500 MHz) δ 7.22-7.15 (m, 1), 6.88-6.70 (m, 2H), 3.60-3.49 (m, 2H), 3.05-3.94 (m, 2H), 2.93-2.83 (m, 2H), 2.66-2.58 (m, 2H), 2.15-2.02 (m, 2H), 1.98-1.70 (m, 6H), 1.50-1.41 (m, 1H), 1.39-1.25 (m, 3H), 1.15-1.05 (m, 1H), 0.70 (t, J=7.2 Hz, 2H). ESI MS found for C$_{20}$H$_{31}$BF$_2$N$_2$O$_4$ m/z [395.7 (M+1−18)].

Example 53-A

Preparation of 2-amino-6-borono-2-(1-(2-(trifluoromethyl)benzyl)piperidin-4-yl)hexanoic acid dihydrochloride

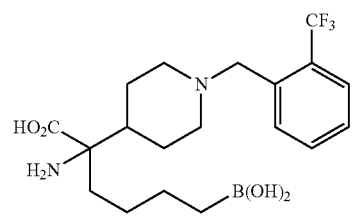
(53-A)

2-Amino-6-borono-2-(1-(2-(trifluoromethyl)benzyl)piperidin-4-yl)hexanoic acid is prepared in a manner analogous to that set forth in Example 118, except that 2-(trifluoromethyl)benzaldehyde is used as the aldehyde in step 6. $^1$H NMR (D$_2$O, 300 MHz) δ 7.79-7.74 (m, 1H), 7.67-7.52 (m, 3H), 4.39 (s, 2H), 3.62-3.48 (m, 2H), 3.14-3.00 (m, 2H), 2.15-1.95 (m, 2H), 1.87-1.65 (m, 4H), 1.55-1.38 (m, 1H), 1.35-1.20 (m, 3H), 1.15-0.96 (m, 1H), 0.65 (t, J=7.5 Hz, 2H). ESI MS found for C$_{19}$H$_{28}$BF$_3$N$_2$O$_4$ m/z [417.2 (M+1)].

Example 54-A

Preparation of 2-amino-6-borono-2-(1-(2-morpholinobenzyl)piperidin-4-yl)hexanoic acid dihydrochloride

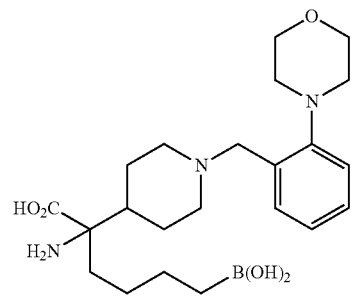
(54-A)

2-Amino-6-borono-2-(1-(2-morpholinobenzyl)piperidin-4-yl)hexanoic acid is prepared in a manner analogous to that set forth in Example 118, except that 2-morpholinobenzaldehyde is used as the aldehyde in step 6. $^1$H NMR (D$_2$O, 300 MHz) δ 7.43 (dd, J$_1$=8.7 Hz, J$_2$=1.5 Hz, 1H), 7.36-7.30 (m, 2H), 7.18 (dd, J$_1$=8.4 Hz, J$_2$=1.2 Hz, 1H), 4.32 (s, 2H), 3.82-3.75 (m, 4H), 3.55-3.45 (m, 2H), 3.10-2.95 (m, 2H), 3.90-3.82 (m, 4H), 2.18-1.98 (m, 2H), 1.89-1.70 (m, 4H), 1.50-1.35 (m, 1H), 1.35-1.20 (m, 3H), 1.15-0.99 (m, 1H), 0.64 (t, J=7.2 Hz, 2H). ESI MS found for C$_{22}$H$_{36}$BN$_3$O$_5$ m/z [434.1 (M+1)].

Example 55-A

Preparation of 2-amino-2-(1-(biphenyl-2-ylmethyl)piperidin-4-yl)-6-boronohexanoic acid dihydrochloride

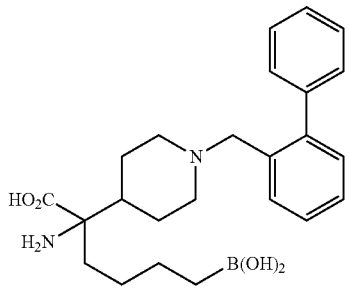

(55-A)

2-Amino-2-(1-(biphenyl-2-ylmethyl)piperidin-4-yl)-6-boronohexanoic acid is prepared in a manner analogous to that set forth in Example 118, except that biphenyl-2-carbaldehyde is used as the aldehyde in step 6. $^1$H NMR (D$_2$O, 300 MHz) δ 7.53-7.24 (m, 9H), 4.29 (s, 2H), 3.32-3.18 (m, 2H), 2.58-2.42 (m, 2H), 1.90-1.75 (m, 2H), 1.73-1.52 (m, 4H), 1.52-1.48 (m, 1H), 1.35-1.10 (m, 3H), 1.10-0.95 (m, 1H), 0.62 (t, J=7.2 Hz, 2H). ESI MS found for C$_{24}$H$_{33}$BN$_2$O$_4$ m/z [425.2 (M+1)].

Example 56-A

Preparation of 2-amino-6-borono-2-(1-(quinolin-8-ylmethyl)piperidin-4-yl)hexanoic acid dihydrochloride

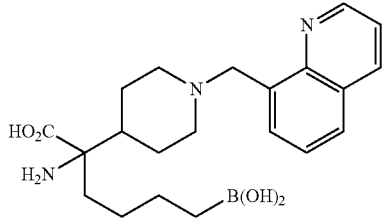

(56-A)

2-Amino-6-borono-2-(1-(quinolin-8-ylmethyl)piperidin-4-yl)hexanoic acid is prepared in a manner analogous to that set forth in Example 118, except that quinoline-8-carbaldehyde is used as the aldehyde in step 6. $^1$H NMR (D$_2$O, 300 MHz) δ 8.98 (bd, J=4.3 Hz, 1H), 8.82 (d, J=8.2 Hz, 1H), 8.21 (d, J=8.4 Hz, 1H), 8.04 (d, J=8.0 Hz, 1H), 7.89-7.75 (m, 4H), 4.85 (s, 2H), 3.65-3.50 (m, 2H), 3.20-3.03 (m, 2H), 2.22-2.08 (m, 1H), 2.10-1.96 (m, 1H), 1.88-1.65 (m, 4H), 1.54-1.38 (m, 1H), 1.38-1.17 (m, 3H), 1.15-0.99 (m, 1H), 0.67 (t, J=7.5 Hz, 2H). ESI MS found for C$_{21}$H$_{30}$BN$_3$O$_4$ m/z [400.5 (M+1)].

Example 57-A

Preparation of 2-amino-6-borono-2-(1-(2-(pyridin-3-yl)benzyl)piperidin-4-yl)hexanoic acid dihydrochloride

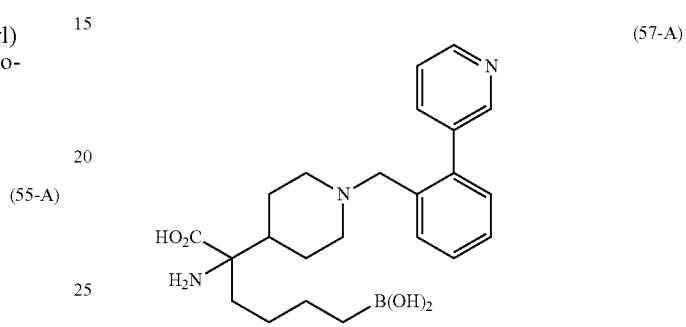

(57-A)

2-Amino-6-borono-2-(1-(2-(pyridin-3-yl)benzyl)piperidin-4-yl)hexanoic acid is prepared in a manner analogous to that set forth in Example 118, except that 2-(pyridin-3-yl)benzaldehyde is used as the aldehyde in step 6. $^1$H NMR (D$_2$O, 300 MHz) δ 8.82-8.75 (m, 2H), 8.56-8.50 (m, 1H), 8.12-8.05 (m, 1H), 7.65-7.53 (m, 3H), 7.38-7.34 (m, 1H), 4.25 (s, 2H), 3.44-3.35 (m, 2H), 2.68-2.51 (m, 2H), 1.96-1.80 (m, 2H), 1.70-1.52 (m, 4H), 1.52-1.48 (m, 1H), 1.35-1.10 (m, 3H), 1.10-0.95 (m, 1H), 0.66 (t, J=7.5 Hz, 2H). ESI MS found for C$_{23}$H$_{32}$BN$_3$O$_4$ m/z [426.3 (M+1)].

Example 58-A

Preparation of 2-amino-6-borono-2-(1-((3'-methoxybiphenyl-2-yl)methyl)piperidin-4-yl)hexanoic acid dihydrochloride

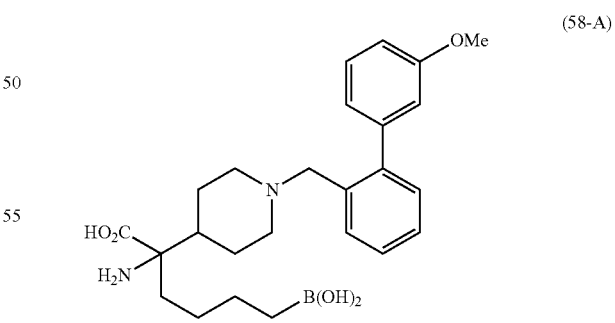

(58-A)

2-Amino-6-borono-2-(1-((3'-methoxybiphenyl-2-yl)methyl)piperidin-4-yl)hexanoic acid is prepared in a manner analogous to that set forth in Example 118, except that 3'-methoxybiphenyl-2-carbaldehyde is used as the aldehyde in step 6. $^1$H NMR (D$_2$O, 300 MHz) δ 7.52-7.28 (m, 5H), 7.00-6.83 (m, 3H), 4.28 (s, 2H), 3.73 (s, 3H), 3.32-3.22 (m, 2H), 2.60-2.45 (m, 2H), 1.90-1.75 (m, 2H), 1.70-1.50 (m, 4H), 1.38-1.10 (m, 4H), 1.10-0.94 (m, 1H), 0.62 (t, J=7.5 Hz, 2H). ESI MS found for $C_{25}H_{35}BN_2O_5$ m/z [455.4 (M+1)].

Example 59-A

Preparation of 2-amino-6-borono-2-(1-(3,4-difluorophenethyl)piperidin-4-yl)hexanoic acid acid dihydrochloride

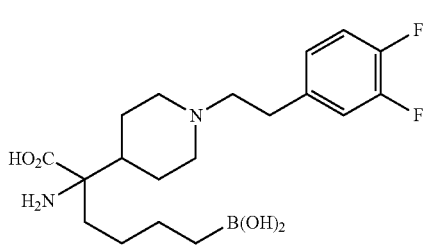

(59-A)

2-Amino-6-borono-2-(1-(3,4-difluorophenethyl)piperidin-4-yl)hexanoic acid is prepared in a manner analogous to that set forth in Example 118, except that 2-(3,4-difluorophenyl)acetaldehyde is used as the aldehyde in step 6. $^1$H NMR (D$_2$O, 300 MHz) δ 7.15-7.03 (m, 2H), 6.97-6.90 (m, 1H), 3.63-3.51 (m, 2H), 3.28-3.15 (m, 2H), 2.99-2.80 (m, 4H), 2.10-1.97 (m, 2H), 1.87-1.63 (m, 4H), 1.52-1.35 (m, 1H), 1.35-1.15 (m, 3H), 1.14-0.98 (m, 1H), 0.65 (t, J=7.2 Hz, 2H). ESI MS found for $C_{19}H_{29}BF_2N_2O_4$ m/z [399.2 (M+1)].

Example 60-A

Preparation of 2-amino-6-borono-2-(1-(chroman-8-ylmethyl)piperidin-4-yl)hexanoic acid dihydrochloride

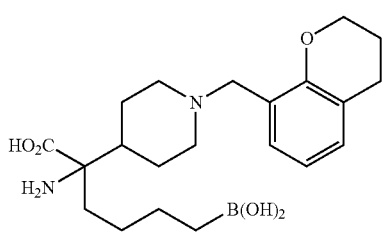

(60-A)

2-Amino-6-borono-2-(1-(chroman-8-ylmethyl)piperidin-4-yl)hexanoic acid is prepared in a manner analogous to that set forth in Example 118, except that chroman-8-carbaldehyde is used as the aldehyde in step 6. $^1$H NMR (D$_2$O, 300 MHz) δ 7.12 (d, J=8.2 Hz, 1H), 7.06 (d, J=8.2 Hz, 1H), 6.80 (dd, J$_1$=8.2 Hz, J$_2$=8.2 Hz, 1H), 4.17-4.09 (m, 4H), 3.52-3.42 (m, 2H), 3.00-2.86 (m, 2H), 2.71-2.64 (m, 2H), 2.09-1.95 (m, 2H), 1.91-1.64 (m, 6H), 1.49-1.34 (m, 1H), 1.35-1.18 (m, 3H), 1.16-0.99 (m, 1H), 0.64 (t, J=7.5 Hz, 2H). ESI MS found for $C_{21}H_{33}BN_2O_5$ m/z [405.3 (M+1)].

Example 61-A

Preparation of 2-amino-6-borono-2-(1-(indolin-7-ylmethyl)piperidin-4-yl)hexanoic acid dihydrochloride

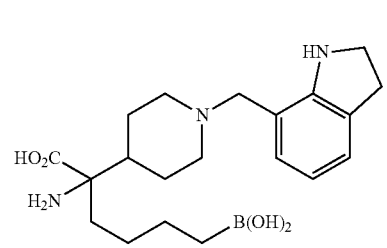

(61-A)

2-Amino-6-borono-2-(1-(indolin-7-ylmethyl)piperidin-4-yl)hexanoic acid is prepared in a manner analogous to that set forth in Example 118, except that indoline-7-carbaldehyde is used as the aldehyde in step 6. $^1$H NMR (D$_2$O, 300 MHz) δ 7.54-7.36 (m, 3H), 4.30 (s, 2H), 3.80 (t, J=7.8 Hz, 2H), 3.60-3.45 (m, 2H), 3.25 (t, J=7.8 Hz, 2H), 3.11-2.95 (m, 2H), 2.13-1.98 (m, 2H), 1.90-1.65 (m, 4H), 1.50-1.35 (m, 1H), 1.38-1.14 (m, 3H), 1.16-0.99 (m, 1H), 0.66 (t, J=7.2 Hz, 2H). ESI MS found for $C_{20}H_{32}BN_3O_4$ m/z [390.3 (M+1)].

Example 62-A

Preparation of 2-amino-6-borono-2-(1-((1,3-dimethyl-1H-pyrazol-5-yl)methyl)piperidin-4-yl)hexanoic acid dihydrochloride

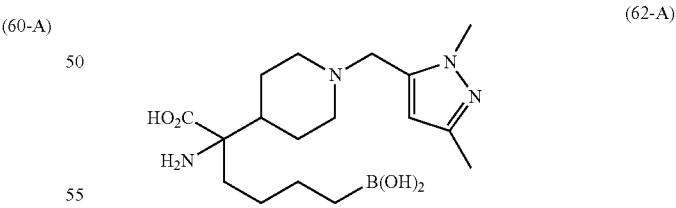

(62-A)

2-Amino-6-borono-2-(1-((1,3-dimethyl-1H-pyrazol-5-yl)methyl)piperidin-4-yl)hexanoic acid is prepared in a manner analogous to that set forth in Example 118, except that 1,3-dimethyl-1H-pyrazole-5-carbaldehyde is used as the aldehyde in step 6. $^1$H NMR (D$_2$O, 300 MHz) δ 6.30 (s, 1H), 4.32 (s, 2H), 3.73 (s, 3H), 3.58-3.47 (m, 2H), 3.07-2.94 (m, 2H), 2.12 (s, 3H), 2.11-2.00 (m, 2H), 1.90-1.68 (m, 4H), 1.51-1.4

(m, 1H), 1.36-1.22 (m, 3H), 1.18-1.04 (m, 1H), 0.66 (t, J=7.2 Hz, 2H). ESI MS found for $C_{17}H_{31}BN_4O_4$ m/z [367.4 (M+1)].

Example 63-A

Preparation of 2-amino-6-borono-2-(1-(3-(4-(trifluoromethyl)phenyl)propyl)piperidin-4-yl)hexanoic acid dihydrochloride

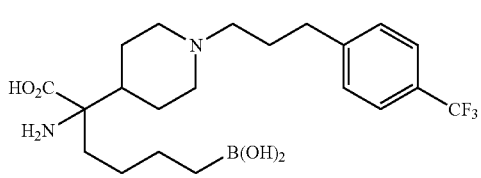

(63-A)

2-Amino-6-borono-2-(1-(3-(4-(trifluoromethyl)phenyl)propyl)piperidin-4-yl)hexanoic acid is prepared in a manner analogous to that set forth in Example 118, except that 3-(4-(trifluoromethyl)phenyl)propanal is used as the aldehyde in step 6. $^1$H NMR (D$_2$O, 300 MHz) δ 7.56 (d, J=8.6 Hz, 1H), 7.32 (d, J=8.6 Hz, 1H), 3.60-3.47 (m, 2H), 3.03-2.92 (m, 2H), 2.92-2.75 (m, 2H), 2.72-2.61 (m, 2H), 2.11-1.88 (m, 4H), 1.90-1.64 (m, 4H), 1.52-1.35 (m, 1H), 1.35-1.15 (m, 3H), 1.16-0.99 (m, 1H), 0.65 (t, J=7.2 Hz, 2H). ESI MS found for $C_{21}H_{32}BF_3N_2O_4$ m/z [445.2 (M+1)].

Example 64-A

Preparation of 2-amino-6-borono-2-(1-(4-(3,4-dichlorophenoxy)benzyl)piperidin-4-yl)hexanoic acid dihydrochloride

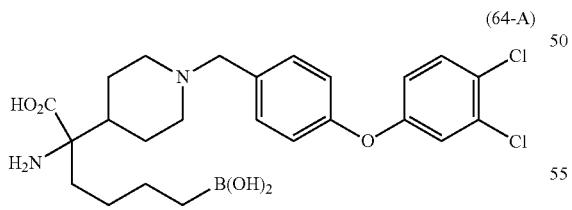

(64-A)

2-Amino-6-borono-2-(1-(4-(3,4-dichlorophenoxy)benzyl)piperidin-4-yl)hexanoic acid is prepared in a manner analogous to that set forth in Example 118, except that 4-(3,4-dichlorophenoxy)benzaldehyde is used as the aldehyde in step 6. $^1$H NMR (D$_2$O, 300 MHz) δ 7.44-7.36 (m, 2H), 7.20-7.03 (m, 4H), 6.89 (dd, J$_1$=8.8 Hz, J$_2$=3.0 Hz, 1H), 4.14 (s, 2H), 3.54-3.48 (m, 2H), 2.98-2.84 (m, 2H), 2.10-1.95 (m, 2H), 1.85-1.64 (m, 4H), 1.50-1.32 (m, 1H), 1.35-1.18 (m, 3H), 1.16-1.01 (m, 1H), 0.66 (t, J=7.5 Hz, 2H). ESI MS found for $C_{24}H_{31}BCl_2N_2O_5$ m/z [509.3 (M+1), 511.3 (M+1)].

Example 65-A

Preparation of 2-(1-(3-((1H-pyrazol-1-yl)methyl)benzyl)piperidin-4-yl)-2-amino-6-boronohexanoic acid dihydrochloride

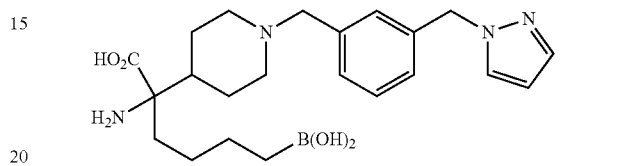

(65-A)

2-(1-(3-((1H-pyrazol-1-yl)methyl)benzyl)piperidin-4-yl)-2-amino-6-boronohexanoic acid is prepared in a manner analogous to that set forth in Example 118, except that 3-((1H-pyrazol-1-yl)methyl)benzaldehyde is used as the aldehyde in step 6. $^1$H NMR (D$_2$O, 300 MHz) δ 7.82 (d, J=2.6 Hz, 1H), δ 7.66 (d, J=2.6 Hz, 1H), 7.41-7.18 (m, 4H), 6.41 (dd, J$_1$=2.6 Hz, J$_2$=2.6 Hz, 1H), 5.39 (s, 2H), 4.15 (s, 2H), 3.50-3.38 (m, 2H), 2.97-2.82 (m, 2H), 2.15-1.92 (m, 2H), 1.87-1.62 (m, 4H), 1.49-1.32 (m, 1H), 1.35-1.18 (m, 3H), 1.16-0.99 (m, 1H), 0.64 (t, J=7.5 Hz, 2H). ESI MS found for C22H33BN4O4 $C_{22}H_{33}BN_2O_4$ m/z [429.3 (M+1)].

Example 66-A

Preparation of 2-amino-6-borono-2-(1-(3-(2,4-dichlorophenyl)propyl)piperidin-4-yl)hexanoic acid dihydrochloride

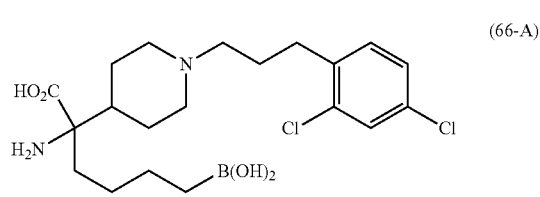 [SMILES: NC(CCCCB(O)O)(C(=O)O)C1CCN(CCCc2ccc(Cl)cc2Cl)CC1]

(66-A)

2-Amino-6-borono-2-(1-(3-(2,4-dichlorophenyl)propyl)piperidin-4-yl)hexanoic acid is prepared in a manner analogous to that set forth in Example 118, except that 3-(2,4-dichlorophenyl)propanal is used as the aldehyde in step 6. $^1$H NMR (D$_2$O, 500 MHz) δ 7.42 (s, 1H), 7.22 (bs, 2H), 3.65-3.55 (m, 2H), 3.14-3.05 (m, 2H), 3.00-2.97 (m, 2H), 2.75-2.67 (m, 2H), 2.29-2.19 (m, 1H), 2.17-2.08 (m, 1H), 2.02-1.79 (m, 6H), 1.62-1.50 (m, 1H), 1.45-1.29 (m, 3H), 1.21-

1.10 (m, 1H), 0.63 (t, J=7.2 Hz, 2H). ESI MS found for $C_{20}H_{31}BCl_2N_2O_4$ m/z [427.7 (M+1−18)].

Example 67-A

Preparation of 2-amino-2-((R)-1-benzylpyrrolidin-3-yl)-6-boronohexanoic acid dihydrochloride

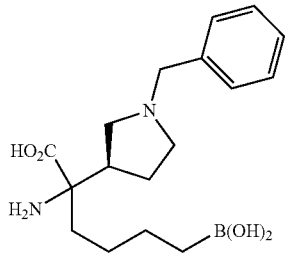

(67-A)

2-Amino-2-((R)-1-benzylpyrrolidin-3-yl)-6-boronohexanoic acid dihydrochloride is prepared in a manner analogous to that set forth in Example 118, except (R)-1-(tert-butoxycarbonyl)pyrrolidine-3-carboxylic acid is used as the carboxylic acid in step 1. ESI MS found for $C_{17}H_{27}BN_2O_4$ m/z [335.2 (M+1)].

Example 68-A

Preparation of 2-amino-2-((S)-1-benzylpyrrolidin-3-yl)-6-boronohexanoic acid dihydrochloride

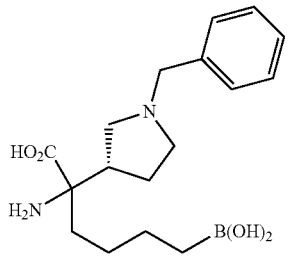

(68-A)

2-Amino-2-((S)-1-benzylpyrrolidin-3-yl)-6-boronohexanoic acid dihydrochloride is prepared in a manner analogous to that set forth in Example 118, except (S)-1-(tert-butoxycarbonyl)pyrrolidine-3-carboxylic acid is used as the carboxylic acid in step 1. ESI MS found for $C_{17}H_{27}BN_2O_4$ m/z [335.1 (M+1)].

Example 69-A

Preparation of 2-amino-6-borono-2-((S)-1-(3,4-dichlorobenzyl)piperidin-3-yl)hexanoic acid dihydrochloride

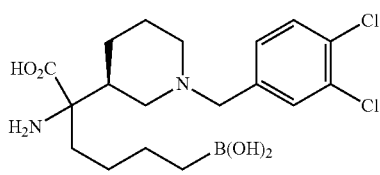

(69-A)

2-Amino-6-borono-2-((S)-1-(3,4-dichlorobenzyl)piperidin-3-yl)hexanoic acid dihydrochloride is prepared in a manner analogous to that set forth in Example 118, except (S)-1-(tert-butoxycarbonyl)piperidine-3-carboxylic acid is used as the carboxylic acid in step 1 and 3,4-dichlorobenzaldehyde is used as the aldehyde in step 6. ESI MS found for $C_{18}H_{27}BCl_2N_2O_4$ m/z [417.4 (M+1)].

Example 71-A

Preparation of (R)-2-amino-2-(1-benzylpiperidin-4-yl)-6-boronohexanoic acid

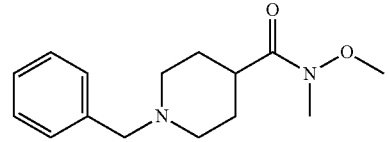 [SMILES: CON(C)C(=O)C1CCN(Cc2ccccc2)CC1]

Step 1: 1-benzyl-N-methoxy-N-methylpiperidine-4-carboxamide

A solution of ethyl 1-benzylpiperidine-4-carboxylate (10.0 g, 40.4 mmol) and N,O-dimethylhydroxylamine hydrochloride (6.12 g, 62.6 mmol) in THF (80 mL) was cooled to 0° C. prior to the addition of i-PrMgCl (121.2 mmol, 60.6 mL, 2 M in THF) dropwise. The reaction was stirred for 1 h, then quenched by addition of saturated aqueous ammonium chloride (90 mL). The aqueous and organic layers were separated. The separated aqueous phase was further extracted with ethyl acetate. The combined organic layers were washed with saturated aqueous sodium chloride, dried over MgSO$_4$, and concentrated in vacuo. The residue was chromatographed on silica gel (2-18% methanol in dichloromethane) to afford the desired product (8.88 g, 84%). $R_f$ 0.45 (10% MeOH/CH$_2$Cl$_2$). $^1$H NMR (CDCl$_3$, 300 MHz) δ 7.40-7.20 (m, 5H), 3.69 (s, 3H), 3.51 (s, 2H), 3.17 (s, 3H), 2.94 (d, 2H, J=11.4 Hz), 2.63-2.66 (m, 1H), 2.01 (td, J=11.7, 2.9 Hz, 2H), 1.83 (qd, J=12.8, 3.7 Hz, 2H), 1.72-1.67 (m, 2H). ESI MS found for $C_{15}H_{22}N_2O_2$ m/z [263.3 (M+1)].

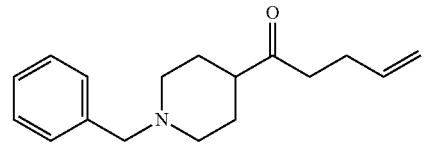 [SMILES: C=CCCC(=O)C1CCN(Cc2ccccc2)CC1]

Step 2: 1-(1-benzylpiperidin-4-yl)pent-4-en-1-one

A solution of 1-benzyl-N-methoxy-N-methylpiperidine-4-carboxamide (8.88 g, 33.0 mmol) in THF (40 mL, 0.8 M) was cooled to 0° C. and treated with a 0.5 M solution of 3-butenylmagnesium bromide (51 mmol, 102 mL) in a dropwise manner. After stirring for 4 h the reaction was quenched with 1 N HCl (24 mL), neutralized with 5% aqueous sodium bicarbonate and diluted with ethyl acetate. The layers were separated and the aqueous phase was extracted with ethyl acetate. The combined organic layers were washed with saturated aqueous sodium chloride, dried over MgSO$_4$, and concentrated in vacuo. The residue was chromatographed on silica (2-20% methanol in dichloromethane) to afford the desired product (4.95 g, 57%). $R_f$ 0.22 (10% MeOH/CH$_2$Cl$_2$). $^1$H NMR (CDCl$_3$, 300 MHz) δ 7.38-7.21 (m, 5H), 5.82-5.76 (m, 1H), 5.15-4.95 (m, 2H), 3.50 (s, 2H), 2.91 (d, J=11.2 Hz, 2H), 2.54 (t, J=7.3 Hz, 2H), 2.39-2.23 (m, 3H), 2.06-1.97 (m, 2H), 1.82-1.61 (m, 4H). ESI MS found for $C_{17}H_{23}NO$ m/z [258.2 (M+1)].

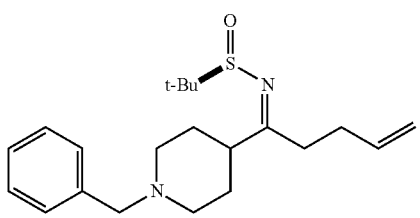 [SMILES: C=CCC/C(=N/[S@](=O)C(C)(C)C)C1CCN(Cc2ccccc2)CC1]

Step 3: (R,Z)—N-(1-(1-benzylpiperidin-4-yl)pent-4-enylidene)-2-methylpropane-2-sulfinamide A solution of 1-(1-benzylpiperidin-4-yl)pent-4-en-1-one (6.11 g, 21.3 mmol) and (R)-2-methylpropane-2-sulfinamide (3.62 g, 27.6 mmol) in THF (71 mL, 0.3 M) was treated with titanium (IV) ethoxide (12.6 g, 55.3 mmol) and heated to 70° C. overnight. Because the reaction was incomplete, additional portions of (R)-2-methylpropane-2-sulfinamide (1.81 g, 13.8 mmol) and titanium (IV) ethoxide (6.3 g, 27.7 mmol) were added and the mixture was heated to 75° C. for 6 more hours. The reaction was quenched by pouring it slowly into rapidly stirred saturated aqueous sodium chloride (100 mL) and filtering through Celite. The Celite pad was washed with ethyl acetate (3×) and the combined organics were washed with saturated aqueous sodium chloride, dried over MgSO$_4$, and concentrated in vacuo. The residue was chromatographed on silica gel (60% ethyl acetate in heptane) to afford the desired product (3.24 g, 42%). R$_f$ 0.44 (EtOAc). $^1$H NMR (CDCl$_3$, 300 MHz) δ 7.34-7.19 (m, 5H), 5.88-5.75 (m, 1H), 5.09-4.94 (m, 2H), 3.50 (d, J=5.5 Hz, 2H), 2.97-2.83 (m, 2H), 2.74-2.70 (m, 1H), 2.55-2.23 (m, 4H), 2.00 (t, J=8.8 Hz, 2H), 1.77-1.63 (m, 4H), 1.23 (s, 9H). ESI MS found for C$_{21}$H$_{32}$N$_2$OS m/z [361.4 (M+1)].

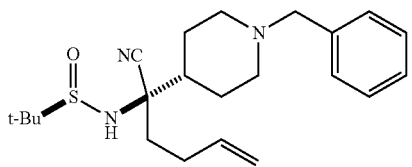

Step 4: (R)—N—((R)-1-(1-benzylpiperidin-4-yl)-1-cyanopent-4-enyl)-2-methylpropane-2-sulfinamide A solution of (R,Z)—N-(1-(1-benzylpiperidin-4-yl)pent-4-enylidene)-2-methylpropane-2-sulfinamide (2.74 g, 7.6 mmol) in THF (130 mL, 0.06 M) was cooled to −78° C. Separately, a 1 M solution of Et$_2$AlCN (11.4 mmol, 11.4 mL) was dissolved in THF (20 mL) and cooled to −78° C. iPrOH (0.64 mL, 8.26 mmol) was added dropwise and the solution was warmed to RT over 20 min, then added dropwise to the sulfinamide solution. The reaction was allowed to warm gradually to RT and stirred overnight. The reaction was quenched with saturated aqueous ammonium chloride (50 mL) and filtered through Celite. The Celite pad was washed with ethyl acetate (3×) and the combined organics were washed saturated aqueous sodium chloride, dried over MgSO$_4$, and concentrated in vacuo. The residue was chromatographed on silica gel (1-9% methanol in dichloromethane and again with 2-5% methanol in ethyl acetate) to afford the desired product (1.99 g, 67%) along with its undesired diastereoisomer (0.46 g, 15%). R$_f$ 0.26 (10% MeOH/CH$_2$Cl$_2$). $^1$H NMR (CDCl$_3$, 300 MHz) δ 7.31-7.25 (m, 5H), 5.83-5.78 (m, 1H), 5.13-5.03 (m, 2H), 3.51 (d, J=1.5 Hz, 2H), 3.41 (s, 1H), 3.00 (d, J=11.0 Hz, 2H), 2.34-2.29 (m, 2H), 2.05-1.83 (m, 6H), 1.60-1.44 (m, 3H), 1.25 (s, 9H). ESI MS found for C$_{22}$H$_{33}$N$_3$OS m/z [388.4 (M+1)].

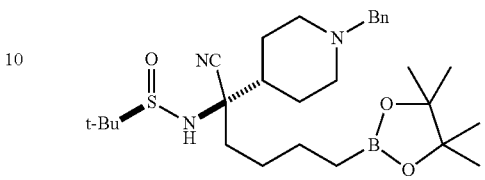

Step 5: (R)—N—((R)-1-(1-benzylpiperidin-4-yl)-1-cyano-5-(4,4,5,5-tetramethyl-1,3,2-dioxaborolan-2-yl)pentyl)-2-methylpropane-2-sulfinamide A solution of (R)—N—((R)-1-(1-benzylpiperidin-4-yl)-1-cyanopent-4-enyl)-2-methylpropane-2-sulfinamide (364 mg, 0.94 mmol), [Ir(COD)Cl]$_2$ (31 mg, 0.047 mmol) and dppe (37 mg, 0.094 mmol) in dichloromethane (9.4 mL) was stirred for 20 min then treated with pinacolborane (180 mg, 1.41 mmol). After stirring overnight at room temperature, the reaction was diluted with ethyl acetate, washed with saturated aqueous sodium chloride, dried over MgSO$_4$, and concentrated. The resulting residue was purified by flash column chromatography (silica gel, eluting with 1-10% methanol in dichloromethane) to afford the desired product (170 mg, 35%). R$_f$ 0.43 (10% MeOH/CH$_2$Cl$_2$). $^1$H NMR (CDCl$_3$, 300 MHz) δ 7.34-7.24 (m, 5H), 3.50 (s, 2H), 3.34 (s, 1H), 2.98 (d, J=11.4 Hz, 2H), 2.03-1.94 (m, 2H), 1.87-1.71 (m, 3H), 1.60-1.40 (m, 8H), 1.26 (s, 9H), 1.24 (s, 12H), 0.81 (t, J=7.3 Hz, 2H). ESI MS found for C$_{28}$H$_{46}$BN$_3$O$_3$S m/z [515.9 (M+1)].

(71-A)

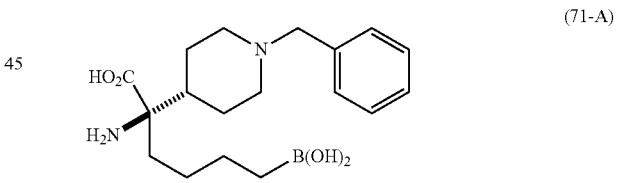

Step 6: (R)-2-amino-2-(1-benzylpiperidin-4-yl)-6-boronohexanoic acid (R)—N—((R)-1-(1-benzylpiperidin-4-yl)-1-cyano-5-(4,4,5,5-tetramethyl-1,3,2-dioxaborolan-2-yl)pentyl)-2-methylpropane-2-sulfinamide (170 mg, 0.33 mmol) was treated with 6 N HCl (3.3 mL) and heated to 105° C. After stirring overnight, the reaction was diluted with water, washed dichloromethane, and concentrated. The resulting residue was azeotroped with toluene, dried under high vacuum and purified by HPLC (10-100% acetonitrile/H$_2$O) to yield the desired product (39 mg, 34%). $^1$H NMR (CD$_3$OD, 300 MHz) δ 7.56-7.43 (m, 5H), 4.29 (s, 2H), 3.47 (br, 2H), 3.06 (br, 2H), 2.76 (br, 1H), 2.54 (t, J=7.0 Hz, 2H), 2.11 (d, J=13.9 Hz, 2H), 1.77 (br, 2H), 1.59-1.44 (m, 2H), 1.40-1.29 (m, 2H), 0.78 (t, J=8.1 Hz, 2H). ESI MS found for $C_{18}H_{29}BN_2O_4$ m/z [331.2 (M+1)−$H_2O$].

Example 72-A

Preparation of 2-amino-2-(azepan-4-yl)-6-boronohexanoic acid dihydrochloride

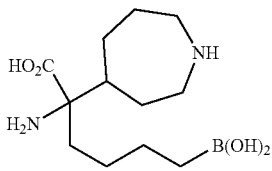

(72-A)

2-Amino-2-(azepan-4-yl)-6-boronohexanoic acid dihydrochloride is prepared in a manner analogous to that set forth in Example 118, except 1-(benzyloxycarbonyl)azepane-4-carboxylic acid was used as the acid in step 1 and Steps 5 and 6 were omitted. $^1$H NMR ($D_2O$, 300 MHz) δ 3.39-3.26 (m, 1H), 3.26-3.15 (m, 1H), 3.12-2.97 (m, 2H), 2.20-1.40 (m, 9H), 1.35-1.13 (m, 3H), 1.13-0.99 (m, 1H), 0.65 (t, J=7.2 Hz, 2H). ESI MS found for $C_{12}H_{25}BN_2O_4$ m/z [272.2 (M+1), 255.0 (M+1−18)].

Example 73-A

Preparation of 2-amino-6-borono-2-(1-(3,4-dichlorobenzyl)azepan-4-yl)hexanoic acid dihydrochloride

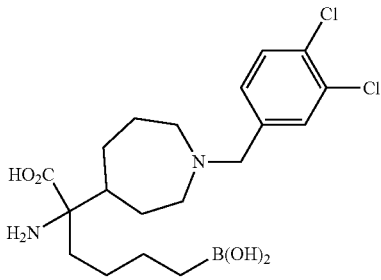

(73-A)

2-Amino-6-borono-2-(1-(3,4-dichlorobenzyl)azepan-4-yl)hexanoic acid dihydrochloride is prepared in a manner analogous to that set forth in Example 118, except 1-(benzyloxycarbonyl)azepane-4-carboxylic acid was used as the acid in step 1 and 3,4-dichlorobenzaldehyde was used as the aldehyde in Step 6. $^1$H NMR ($D_2O$, 300 MHz) δ 7.54 (bs, 1H), 7.48 (d, J=7.8 Hz, 1H), 7.26 (bd, J=7.8 Hz, 1H), 4.20 (bs, 2H), 3.52-2.90 (m, 4H), 2.31-2.10 (m, 1H), 2.11-1.44 (m, 8H), 1.35-1.14 (m, 3H), 1.16-0.98 (m, 1H), 0.64 (t, J=7.5 Hz, 2H).

ESI MS found for $C_{19}H_{29}BCl_2N_2O_4$ m/z [431.2&433.2 (M+1), 413.1&315.1 (M+1−18)].

Example 74-A

Preparation of cis-2-amino-2-(3-(benzylamino)cyclobutyl)-6-boronohexanoic acid dihydrochloride

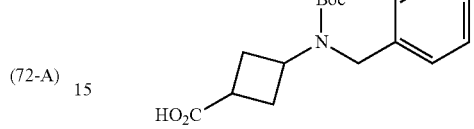

Step 1: Synthesis of 3-(benzyl(tert-butoxycarbonyl)amino)cyclobutanecarboxylic acid A solution of 3-oxo-1 cyclobutane carboxylic acid (4 g, 35 mmol, 1 eq), benzyl amine (19 ml, 175 mmol, 5 eq), and acetic acid (2.1 mL, 35 mmol, 1 eq) in 1,2-dichloroethane was stirred at room temperature for 1 h. Sodium triacetoxyborohydride (11.1 g, 52.5 mmol, 1.5 eq) was added and stirring was continued for 2 days, the solution was basified to pH 13 with aq NaOH (1 N) and washed with dichloromethane. The aqueous layer was charged with di-tert-butyl dicarbonate (45 g, 210 mmol, 6 eq) and stirred overnight. After acidifying to pH 5, the reaction mixture was extracted with ethyl acetate, washed with sat'd aq sodium chloride, dried over $MgSO_4$, filtered and concentrated. Purification by flash chromatography (1-20% methanol in dichloromethane) gave 3-(benzyl(tert-butoxycarbonyl)amino)cyclobutanecarboxylic acid as a white solid (7.96 g, 24.3 mmol, 69%). ESI MS found for $C_{17}H_{23}BNO_4$ m/z [304 (M−1)].

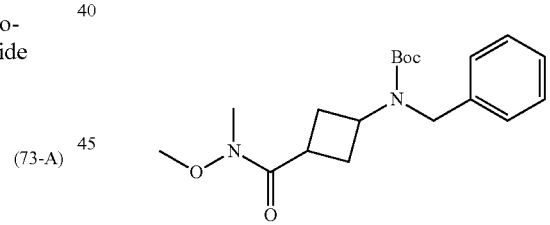

Step 2: Synthesis of tert-butyl benzyl(3-(methoxy(methyl)carbamoyl)cyclobutyl) carbamate A solution of 3-(benzyl(tert-butoxycarbonyl)amino)cyclobutanecarboxylic acid (4.96 g, 15.2 mmol) in dichloromethane (80 mL, 0.19 M) was treated with EDC (5.8 g, 30.3 mmol, 2 eq), N,O-dimethylhydroxylamine hydrochloride (3.0 g, 30.3 mmol, 2 eq), and triethyl amine (8.5 mL, 60.7 mmol, 4 eq) and stirred for 16 h. The resulting solution was washed successively with water, 1 M HCl, sat'd aq sodium chloride, dried over anhydrous $MgSO_4$, filtered and concentrated. Purification by flash chromatography (1-20% methanol in dichloromethane) gave tert-butyl benzyl(3-(methoxy(methyl)carbamoyl)cyclobutyl) carbamate as an off-white solid (4.04 g, 72%). $^1$H NMR ($CD_3OD$, 300 MHz) δ 7.40-7.16 (m, 5H), 4.60-4.20 (m, 1H), 4.52 (brs, 2H), 3.77 (s, 3H), 3.22-3.00 (brs, 4H), 2.60-2.20 (m, 4H), 1.58-1.08 (brs, 9H), LCMS, $C_{19}H_{28}N_2O_4$ m/z [349 (M+1), 371.3 (M+23)].

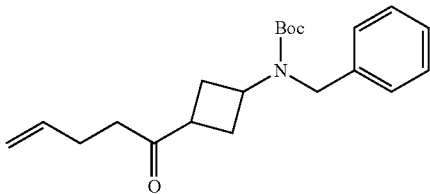 [SMILES: C=CCCC(=O)C1CC(N(Cc2ccccc2)C(=O)OC(C)(C)C)C1]

Step 3: Synthesis of tert-butyl benzyl(3-pent-4-enoylcyclobutyl)carbamate

While under a nitrogen atmosphere, a solution of tert-butyl benzyl(3-(methoxy(methyl)carbamoyl)cyclobutyl) carbamate (8.68 g, 23.5 mmol, 1 eq), in tetrahydrofuran (100 mL) was cooled to 0° C. and treated with 4-butenylmagnesiun bromide (0.5 M in THF, 70.4 mL, 35.2 mmol, 1.5 eq) dropwise. After stirring for 0.5 hour at 0° C., the reaction mixture was warmed to room temperature for an additional 3 h. Once complete, the reaction mixture was poured into water, acidified to pH 3-4 with 1 N hydrochloric acid and extracted with ethyl acetate (3×). The combined organic layers was washed with saturated aqueous sodium chloride, dried over anhydrous magnesium sulfate, filtered and concentrated. Purification by flash column chromatography (silica gel, 0-40% ethyl acetate in heptane) gave tert-butyl benzyl(3-pent-4-enoylcyclobutyl)carbamate as a colorless oil (7.7 g, 21.1 mmol, 90%). $^1$H NMR (CDCl$_3$, 300 MHz) δ 7.33-7.11 (m, 5H), 5.84-5.67 (m, 1H), 5.04-4.92 (m, 2H), 4.45 (brs, 3H), 2.89-2.70 (m, 1H), 2.48-2.15 (m, 8H), 1.5-1.08 (brs, 9H), ESI MS found for $C_{21}H_{29}NO_3$ m/z [366.2 (M+23)].

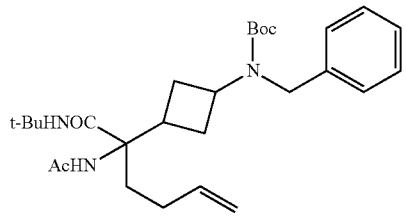

Step 4: Synthesis of tert-butyl 3-(2-acetamido-1-(tert-butylamino)-1-oxohex-5-en-2-yl)cyclobutyl (benzyl)carbamate A solution of tert-butyl benzyl(3-pent-4-enoylcyclobutyl) carbamate (7.7 g, 21.1 mmol, 5 eq), t-butyl isonitrile (12 mL, 106 mmol, 10 eq) and ammonium acetate (16.3 g, 212 mmol) in 2,2,2-trifluoroethanol (24 mL, 0.9 M) was stirred at room temperature for 3 days. The reaction mixture was diluted with ethyl acetate, quenched with 2 M HCl and extracted with ethyl acetate. The organic layer was washed successively with 2 M HCl and sat'd aq sodium chloride, dried over MgSO$_4$, filtered and concentrated. Purification by column chromatography (ethyl acetate in hexanes) gave cis-tert-butyl 3-(2-acetamido-1-(tert-butylamino)-1-oxohex-5-en-2-yl)cyclobutyl (benzyl)carbamate as a yellow solid (8.9 g, 17.5 mmol, 83%). $^1$H NMR (CDCl$_3$, 300 MHz) δ 7.32-7.10 (m, 6H), 6.08 (brs, 1H), 5.80-5.64 (m, 1H), 5.01-4.87 (m, 2H), 4.42 (brs, 2H), 4.41-4.08 (m, 1H), 2.79-2.58 (m, 1H), 2.40-1.99 (m, 8H), 1.98-1.80 (m, 3H), 1.56-1.08 (m, 18H), ESI MS found for $C_{28}H_{43}N_3O_4$ m/z [508.2 (M+23)] and trans-tert-butyl 3-(2-acetamido-1-(tert-butylamino)-1-oxohex-5-en-2-yl)cyclobutyl(benzyl)carbamate as a white foam (1.1 g, 2.2 mmol, 10%). $^1$H NMR (CDCl$_3$, 300 MHz) δ 7.32-7.11 (m, 5H), 6.79 (brs, 1H), 5.83-5.68 (m, 1H), 5.56 (brs, 1H), 5.02-4.88 (m, 2H), 4.54-4.37 (m, 2H), 4.35-4.16 (m, 1H), 2.94-2.75 (m, 2H), 2.51-2.39 (m, 1H), 2.38-2.19 (m, 2H), 2.18-1.90 (m, 5H), 1.86-1.70 (m, 1H), 1.67-1.58 (m, 1H), 1.47-1.22 (m, 18H), ESI MS found for $C_{28}H_{43}N_3O_4$ m/z [486.5 (M+1), 508.0 (M+23)].

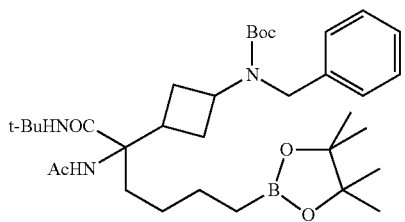

Step 5: Synthesis of cis-tert-butyl 3-(2-acetamido-1-(tert-butylamino)-1-oxo-6-(4,4,5,5-tetramethyl-1,3,2-dioxaborolan-2-yl)hexan-2-yl)cyclobutyl(benzyl) carbamate After stirring for 30 min, a solution of cis-tert-butyl 3-(2-acetamido-1-(tert-butylamino)-1-oxohex-5-en-2-yl)cyclobutyl(benzyl)carbamate (5.34 g, 10.5 mmol), chloro-1,5-cyclooctadiene iridium(I) dimer (212 mg, 0.32 mmol, 3 mol %) and 1,2-bis(diphenylphosphino)ethane (252 mg, 0.63 mmol, 6 mol %) in dichloromethane (50 mL) was cooled to 0° C. and carefully treated with 4,4,5,5-tetramethyl-[1,3,2]dioxaborolane (3.1 mL, 21.1 mmol, 2 eq) over 5 min. After slowly warming to room temperature and stirring overnight, the reaction was poured into water and extracted with ethyl acetate (3×). The combined organic phase was washed with saturated aqueous sodium chloride, dried over anhydrous magnesium sulfate, filtered and concentrated. Purification by flash column chromatography (silica gel, 10-40% ethyl acetate in heptane) gave cis-tert-butyl 3-(2-acetamido-1-(tert-butylamino)-1-oxo-6-(4,4,5,5-tetramethyl-1,3,2-dioxaborolan-2-yl)hexan-2-yl)cyclobutyl(benzyl)carbamate (4.8 g, 7.83 mmol, 74%). ESI MS found for $C_{34}H_{56}BN_3O_6$ m/z [614.2 (M+1), 636.2 (M+23)].

(74-A)

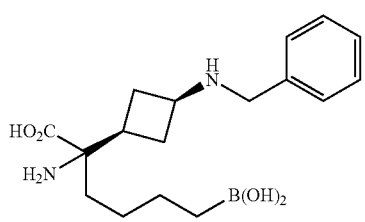

Step 6: cis-2-amino-2-(3-(benzylamino)cyclobutyl)-6-boronohexanoic acid dihydrochloride A solution of cis-tert-butyl 3-(2-acetamido-1-(tert-butylamino)-1-oxo-6-(4,4,5,5-tetramethyl-1,3,2-dioxaborolan-2-yl)hexan-2-yl)cyclobutyl(benzyl)carbamate (200 mg, 0.33 mmol) in 6 N HCl was heated to reflux for 16 h, cooled to room temperature and concentrated to dryness. Purification by preparative HPLC (20% acetonitrile in water with 0.1% trifluoroacetic acid) followed by treatment with aq HCl and evaporation gave cis-2-amino-6-borono-2-(3-benzylaminocyclobutyl)-hexanoic acid dihydrochloride as a white solid (73.6 mg, 0.23 mmol, 70%). $^1$H NMR (D$_2$O) δ 7.42-7.29 (m, 5H), 4.03 (s, 2H), 3.63-3.50 (m, 1H), 2.58-2.43 (m, 1H), 2.43-2.12 (m, 3H), 1.97-1.72 (m, 2H), 1.68-1.52 (m, 1H), 1.36-0.96 (m, 4H), 0.65 (t, J=7.5 Hz, 2H). MS found for $C_{17}H_{27}BN_2O_4$ m/z[317(M−18+1)].

Example 75-A

Preparation of trans-2-amino-2-(3-(benzylamino)cyclobutyl)-6-boronohexanoic acid dihydrochloride

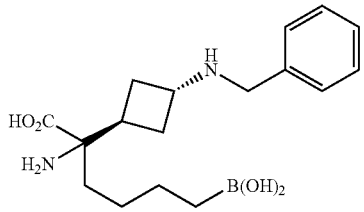

(75-A)

Trans-2-amino-2-(3-(benzylamino)cyclobutyl)-6-boronohexanoic acid dihydrochloride is prepared in a manner analogous to that set forth in Example 74-A, except trans-tert-butyl 3-(2-acetamido-1-(tert-butylamino)-1-oxohex-5-en-2-yl)cyclobutyl(benzyl)carbamate is used as the alkene in step 4. $^1$H NMR (D$_2$O) δ 7.42-7.27 (m, 5H), 4.02 (s, 2H), 3.72-3.57 (m, 1H), 3.01-2.84 (m, 1H), 2.64-2.48 (m, 1H), 2.40-2.20 (m, 3H), 1.93-1.76 (m, 1H), 1.68-1.55 (m, 1H), 1.35-0.96 (m, 4H), 0.64 (t, J=7.5 Hz, 2H). MS found for $C_{17}H_{27}BN_2O_4$ m/z[317(M−18+1)].

Example 76-A

Preparation of cis-2-amino-6-borono-2-(3-(4-(trifluoromethoxy)benzylamino)cyclobutyl)hexanoic acid dihydrochloride

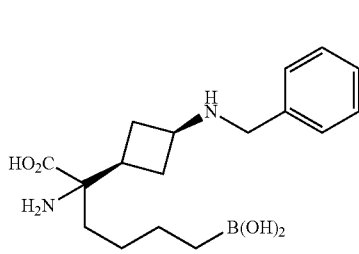

(76-A)

Cis-2-amino-6-borono-2-(3-(4-(trifluoromethoxy)benzylamino)cyclobutyl) hexanoic acid dihydrochloride is prepared in a manner analogous to that set forth in Example 74-A, except 4'-trifluoromethoxybenzylamine is used as the amine in step 1. $^1$H NMR (CD$_3$OD) δ 7.66 (dt, J=8.7, 2.4 Hz, 2H), 7.37 (dd, J=8.7, 0.9 Hz, 2H), 4.18 (s, 2H), 3.81-3.67 (m, 1H), 2.75-2.58 (m, 1H), 2.57-2.34 (m, 3H), 2.33-2.19 (m, 1H), 2.06-1.90 (m, 1H), 1.86-1.72 (m, 1H), 1.54-1.36 (m, 3H), 1.34-1.13 (m, 1H), 0.83 (t, J=7.4 Hz, 2H). MS found for $C_{18}H_{26}BF_3N_2O_5$ m/z[419(M+1)].

Example 77-A

Preparation of cis-2-amino-2-(3-(biphenyl-4-ylmethylamino)cyclobutyl)-6-boronohexanoic acid dihydrochloride

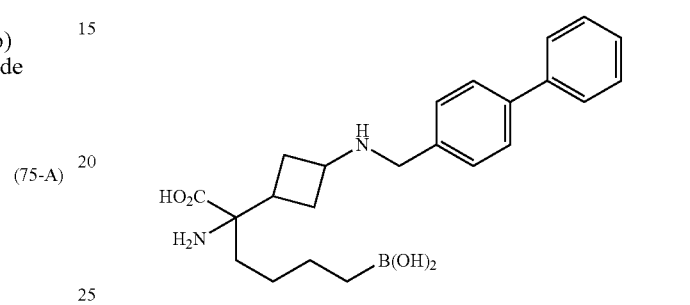

(77-A)

Cis-2-amino-2-(3-(biphenyl-4-ylmethylamino)cyclobutyl)-6-boronohexanoic acid dihydrochloride is prepared in a manner analogous to that set forth in Example 74-A, except biphenyl-4-ylmethanamine is used as the amine in step 1. $^1$H NMR (CD$_3$OD) δ 7.75-7.69 (m, 2H), 7.67-7.57 (m, 4H), 7.49-7.42 (m, 2H), 7.41-7.13 (m, 1H), 4.19 (s, 2H), 3.82-3.65 (m, 1H), 2.75-2.60 (m, 1H), 2.58-2.34 (m, 3H), 2.32-2.18 (m, 1H), 2.06-1.92 (m, 1H), 1.86-1.72 (m, 1H), 1.54-1.36 (m, 3H), 1.32-1.15 (m, 1H), 0.83 (t, J=7.5 Hz, 2H). MS found for $C_{23}H_{31}BN_2O_4$ m/z[411 (M+1)].

Example 78-A

Preparation of cis-2-amino-6-borono-2-(3-((6-chlorobenzo[d][1,3]dioxol-5-yl)methylamino)cyclobutyl)hexanoic acid dihydrochloride

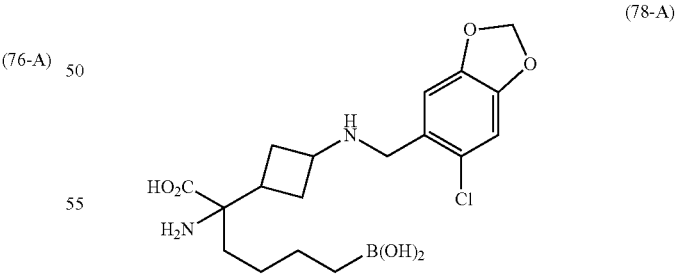

(78-A)

Cis-2-amino-6-borono-2-((6-chlorobenzo[d][1,3]dioxol-5-yl)methylamino)cyclobutyl)hexanoic acid dihydrochloride is prepared in a manner analogous to that set forth in Example 74-A, except (6-chlorobenzo[d][1,3]dioxol-5-yl)methanamine is used as the amine in step 1. $^1$H NMR (CD$_3$OD) δ 7.13 (s, 1H), 7.03 (s, 1H), 6.06 (s, 2H), 4.20 (s, 2H), 3.82-3.70 (m, 1H), 2.76-2.61 (m, 1H), 2.60-2.36 (m, 3H), 2.32-2.18 (m, 1H), 2.06-1.90 (m, 1H), 1.88-1.72 (m, 1H), 1.54-1.34 (m, 3H), 1.32-1.14 (m, 1H), 0.83 (t, J=7.2 Hz, 2H). MS found for $C_{18}H_{26}BClN_2O_6$ m/z[413.0 (M+1)].

Example 79-A

Preparation of cis-2-amino-6-borono-2-(3-(quinolin-8-ylmethylamino)cyclobutyl)hexanoic acid dihydrochloride

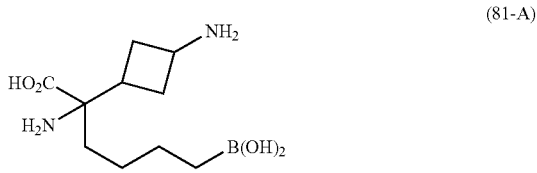 [SMILES: NC1CC(C(N)(CCCCB(O)O)C(=O)O)C1]

(79-A)

Cis-2-amino-6-borono-2-(3-(quinolin-8-ylmethylamino)cyclobutyl)hexanoic acid dihydrochloride is prepared in a manner analogous to that set forth in Example 74-A, except quinolin-8-ylmethanamine is used as the amine in step 1. $^1$H NMR (CD$_3$OD) δ 9.20 (dd, J=5.1, 1.5 Hz, 1H), 9.00 (dd, J=8.7, 1.5 Hz, 1H), 8.33 (dd, J=8.4, 1.2 Hz, 1H), 8.29 (dd, J=7.2, 1.2 Hz, 1H), 8.01 (dd, J=8.4, 5.1 Hz, 1H), 7.92 (dd, J=8.4, 7.2 Hz, 1H), 4.84 (s, 2H), 4.08-3.92 (m, 1H), 2.80-2.32 (m, 5H), 2.08-1.92 (m, 1H), 1.89-1.74 (m, 1H), 1.54-1.36 (m, 3H), 1.34-1.15 (m, 1H), 0.83 (t, J=7.5 Hz, 2H). MS found for $C_{20}H_{28}BN_3O_4$ m/z[386(M+1)].

Example 80-A

Preparation of cis-2-amino-6-borono-2-(3-(naphthalen-1-ylmethylamino)cyclobutyl)hexanoic acid dihydrochloride

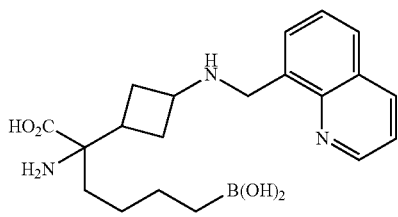

(80-A)

Cis-2-amino-6-borono-2-(3-(naphthalen-1-ylmethylamino)cyclobutyl)hexanoic acid dihydrochloride is prepared in a manner analogous to that set forth in Example 74-A, except naphthalen-1-ylmethanamine is used as the amine in step 1. $^1$H NMR (CD$_3$OD) δ 8.20-8.14 (m, 1H), 8.03-7.96 (m, 2H), 7.76-7.66 (m, 2H), 7.64-7.53 (m, 2H), 4.66 (s, 2H), 3.96-3.77 (m, 1H), 2.76-2.62 (m, 1H), 2.60-2.36 (m, 0.3H), 2.35-2.21 (m, 1H), 2.05-1.89 (m, 1H), 1.88-1.72 (m, 1H), 1.53-1.35 (m, 3H), 1.34-1.13 (m, 1H), 0.82 (t, J=7.5 Hz, 2H). MS found for $C_{21}H_{29}BN_2O_4$ m/z[385(M+1)].

Example 81-A

Preparation of cis-2-amino-2-(3-aminocyclobutyl)-6-boronohexanoic acid dihydrochloride

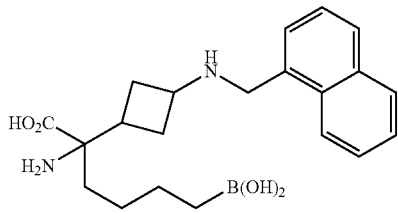

(81-A)

2-Amino-2-(3-aminocyclobutyl)-6-boronohexanoic acid dihydrochloride is prepared in a manner analogous to that set forth in Example 118, except (1s,3s)-3-(tert-butoxycarbonylamino)cyclobutane carboxylic acid was used as the acid in step 1 and Steps 5 and 6 were omitted. $^1$H NMR (D$_2$O, 300 MHz) δ 3.62-3.52 (m, 1H), 2.58-2.31 (m, 3H), 2.21 (q, J=10.3 Hz, 1H), 1.92-1.78 (m, 2H), 1.65-1.55 (m, 1H), 1.36-1.20 (m, 3H), 1.18-1.01 (m, 1H), 0.66 (t, J=7.7 Hz, 2H). ESI MS found for $C_{10}H_{21}B_1N_2O_4$ m/z [245.1 (M+1)].

Example 82-A

Preparation of cis-2-amino-6-borono-2-(3-(4-chlorobenzylamino)cyclobutyl)hexanoic acid dihydrochloride

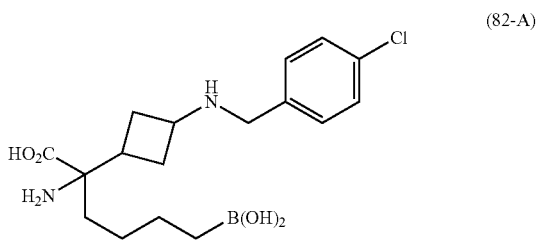 [SMILES: NC(CCCCB(O)O)(C(=O)O)C1CC(NCc2ccc(Cl)cc2)C1]

(82-A)

Cis-2-amino-6-borono-2-(3-(4-chlorobenzylamino)cyclobutyl)hexanoic acid dihydrochloride is prepared in a manner analogous to that set forth in Example 118, except (1s,3s)-3-(tert-butoxycarbonylamino)cyclobutane carboxylic acid was used as the acid in step 1 and 4-chlorobenzaldehyde is used as the aldehyde in Step 6. $^1$H NMR (D$_2$O, 300 MHz) δ 7.38 (d, J=8.4 Hz, 2H), 7.30 (d, J=8.4 Hz, 2H), 4.02 (s, 3H), 3.61-3.53 (m, 1H), 2.45-2.20 (m, 4H), 1.94-1.69 (m, 2H), 1.56-1.45 (m, 1H), 1.32-1.03 (m, 4H), 0.66 (t, J=7.7 Hz, 2H). ESI MS found for $C_{17}H_{26}B_1Cl_1N_2O_4$ m/z [369.3 (M+1)].

Example 83-A

Preparation of cis-2-amino-6-borono-2-(3-(isobutylamino)cyclobutyl)hexanoic acid dihydrochloride

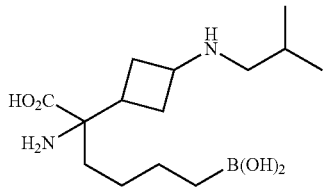

(83-A)

Cis-2-amino-6-borono-2-(3-(isobutylamino)cyclobutyl) hexanoic acid dihydrochloride is prepared in a manner analogous to that set forth in Example 118, except (1s,3s)-3-(tert-butoxycarbonylamino)cyclobutane carboxylic acid was used as the acid in step 1 and isobutyraldehyde is used as the aldehyde in Step 6. ESI MS found for $C_{14}H_{29}B_1N_2O_4$ m/z [301.1 (M+1)].

Example 84-A

Preparation of cis-2-Amino-6-borono-2-[4-(4-Chlorobenzoyl)-cyclohexyl]hexanoic acid hydrochloride Step 1: cis-4-(4-Chlorobenzoyl)-cyclohexanecarboxylic acid, methoxy-methyl amide

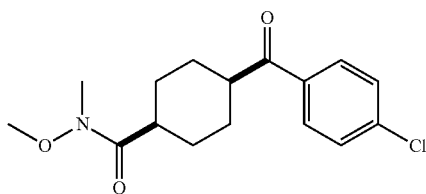

EDC (2.87 g, 15.0 mmol) was added portionwise to a stirred solution of cis-4-(4-chlorobenzoyl)-cyclohexanecarboxylic acid (2.0 g, 7.5 mmol), DMAP (5 mg), HOBt (5 mg) and N,O-dimethylhydroxylamine hydrochloride (1.46 g, 15 mmol) in dichloromethane (40 mL). Triethylamine (2.28 g, 3.14 mL, 22.5 mmol) was added dropwise, and the reaction mixture was stirred at room temperature overnight. The resulting solution was poured into water, and extracted with ethyl acetate (3×). The combined organic phase was washed with saturated aqueous sodium chloride, dried over anhydrous magnesium sulfate, filtered and concentrated in vacuo to give cis-4-(4-chlorobenzoyl)-cyclohexanecarboxylic acid, methoxy-methyl amide as a colorless oil (1.6 g. 69%); $^1$H NMR (CDCl$_3$, 300 MHz) δ 7.82 (d, J=8.5 Hz, 2H,), 7.41 (d, J=8.5 Hz, 2H), 3.69 (s, 3H), 3.35 (quin, J=5 Hz, 1H), 3.16 (s, 3H), 2.80 (sept, J=4 Hz, 1H), 2.15 (m, 2H), 1.89 (m, 2H), 1.72 (m, 4H).

Step 2: cis-4-[2-(4-Chlorophenyl)-[1,3]dioxolan-2-yl]-cyclohexanecarboxylic acid, methoxy-methyl amide

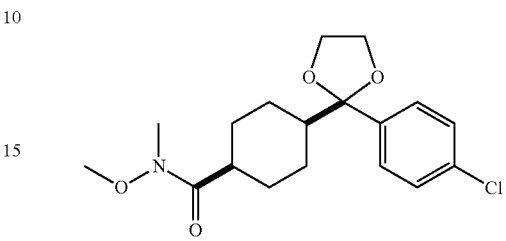

A solution of cis-4-(4-chlorobenzoyl)-cyclohexanecarboxylic acid, methoxy-methyl amide (1.6 g, 5.17 mmol), triethylorthoformate (843 mg, 0.95 mL, 5.7 mmol), ethylene glycol (1.6 g, 1.45 mL, 25.9 mmol) and toluenesulfonic acid monohydrate (50 mg) in toluene (50 mL) was stirred overnight at 60° C., and then cooled to room temperature and concentrated to dryness in vacuo. The reaction mixture was redissolved in ethyl acetate, washed with saturated aqueous sodium chloride, dried over anhydrous magnesium sulfate, filtered and concentrated in vacuo. Purification by flash column chromatography (silica gel, 0-30% ethyl acetate in heptane) gave cis-4-[2-(4-chlorophenyl)-[1,3]-dioxolan-2-yl]-cyclohexanecarboxylic acid, methoxy-methyl amide as a colorless oil (1.36 g, 74%); $^1$H NMR (CDCl$_3$, 300 MHz) δ 7.33 (d, J=8.5 Hz,), 7.27 (d, J=8.5 Hz, 2H), 3.96 (m, 2H), 3.68 (m, 2H), 3.64 (s, 3H), 3.14 (s, 3H), 2.83 (m, 1H), 1.96 (m, 2H), 1.76 (m, 1H), 1.67 (m, 3H) and 1.47 (m, 4H); MS (+CI): m/z for $C_{18}H_{24}ClNO_4$: expected 353.1. found 354.2 (M+H)$^+$.

Step 3: cis-1-{4-[2-(4-Chlorophenyl)-[1,3]-dioxolan-2-yl]-cyclohexyl}pent-4-en-1-one

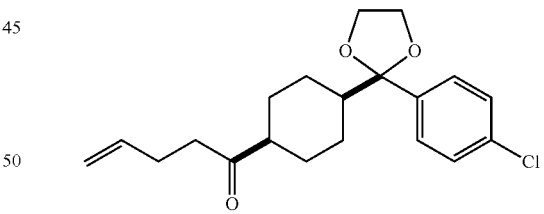

While under a nitrogen atmosphere, a solution of cis-4-[2-(4-chlorophenyl)-[1,3]-dioxolan-2-yl]-cyclohexanecarboxylic acid, methoxy-methyl amide (1.36 g, 3.85 mmol), in tetrahydrofuran (10 mL) was cooled to 0° C. and treated with 4-butenylmagnesiun bromide (0.5 M in THF, 19.24 mL, 9.62 mmol) in a dropwise manner. The solution was stirred for 1 hour at 0° C. then allowed to warm to room temperature overnight. The resulting solution was poured into water, acidified to pH 3-4 with 1 N hydrochloric acid, and extracted with ethyl acetate (3×). The combined organic phase was washed with saturated aqueous sodium chloride, dried over anhydrous magnesium sulfate, filtered and concentrated in vacuo. Purification by flash column chromatography (silica gel, 0-25% ethyl acetate in heptane) gave cis-1-{4-[2-(4- chlorophenyl)-[1,3]-dioxolan-2-yl]-cyclohexyl}pent-4-en-1-one as a colorless oil (1.13 g, 84%); $^1$H NMR (CDCl$_3$, 300 MHz) δ 7.31 (d, J=7.5 Hz, 2H), 7.27 (d, J=7.5 Hz, 2H), 5.78 (m, 1H), 4.96 (m, 2H), 3.94 (m, 2H), 3.68 (m, 2H), 2.50 (m, 3H), 2.30 (m, 2H), 2.15 (dd, J=13, 3 Hz, 2H), 1.76 (tt, J=11, 3 Hz, 1H), 1.36-1.56 (m, 4H) and 1.25 (td, J=13, 3 Hz, 2H); MS (+CI): m/z for C$_{20}$H$_{25}$ClO$_3$: expected 348.2. found 349.2 (M+H)$^+$.

Step 4: cis-2-Acetylamino-2-{4-[2-(4-Chlorophenyl)-[1,3]-dioxolan-2-yl]-cyclohexyl}hex-5-enoic acid, tert-butylamide

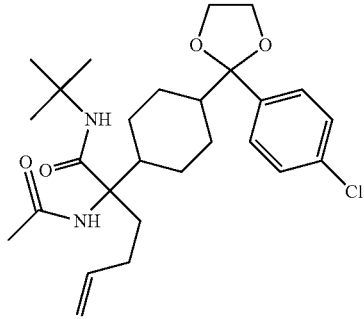 [SMILES: C=CCCC(NC(C)=O)(C(=O)NC(C)(C)C)C1CCC(C2(c3ccc(Cl)cc3)OCCO2)CC1]

tert-Butyl isocyanide (404 mg, 0.55 mL, 4.86 mmol) was added to a stirred slurry of cis-1-{4-[2-(4-chlorophenyl)-[1,3]-dioxolan-2-yl]-cyclohexyl}pent-4-en-1-one (1.13 g, 3.24 mmol) and ammonium acetate (999 mg, 12.96 mmol) in 2,2,2-trifluoroethanol (0.5 mL), and the resultant slurry was stirred at room temperature. After 8 days the reaction was poured into water and extracted with ethyl acetate (3×). The combined organic phase was washed with saturated aqueous sodium chloride, dried over anhydrous magnesium sulfate, filtered and concentrated in vacuo. Purification by flash column chromatography (silica gel, 10-50% ethyl acetate in heptane) gave cis-2-acetylamino-2-{4-[2-(4-chlorophenyl)-[1,3]-dioxolan-2-yl]-cyclohexyl}hex-5-enoic acid, tert-butylamide as a colorless oil (1.16 g, 71%); $^1$H NMR (CDCl$_3$, 300 MHz) δ 7.29 (m, 4H), 6.96 (br s, 1H NH), 5.76 (m, 1H), 5.44 (br s, NH, 1H), 4.94 (m, 2H), 3.94 (m, 2H), 3.68 (m, 2H), 2.93 (ddd, J$_1$=16.5 hz, J$_2$=11.5 Hz, J$_3$=5.0 Hz, 1H), 1.90-2.08 (m, 2H), 1.96 (s, 3H), 1.60-1.86 (m, (6H), 1.42 (m, 1H), 1.34 (s, 9H), 1.06 (m, 3H) and 0.86 (m, 1H).

Step 5: cis-2-Acetylamino-2-{-4-[2-(4-Chlorophenyl)-[1,3]-dioxolan-2-yl]-cyclohexyl}-6-(4,4,5,5-tetramethyl-[1,3,2]-dioxaboron-2-yl)-hex-5-enoic acid, tert-butylamide

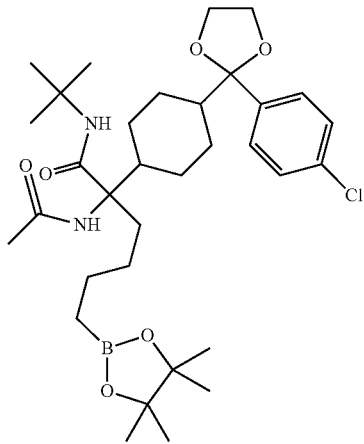 [SMILES: CC(=O)NC(CCCCB1OC(C)(C)C(C)(C)O1)(C(=O)NC(C)(C)C)C1CCC(C2(c3ccc(Cl)cc3)OCCO2)CC1]

A solution of cis-2-acetylamino-2-{4-[2-(4-Chlorophenyl)-[1,3]-dioxolan-2-yl]-cyclo-hexyl}-hex-5-enoic acid, tert-butylamide (1.13 g, 2.3 mmol) in dichloromethane (10 mL), was treated with chloro-1,5-cyclooctadiene iridium(I) dimer (46 mg, 3 mol %) and 1,2-bis(diphenylphosphino) ethane (55 mg, 6 mol %). The solution was stirred at room temperature for 30 minutes and then 4,4,5,5-tetramethyl-[1,3,2]dioxaborolane (588 mg, 0.67 mL, 4.6 mmol) was added dropwise, and the reaction was then stirred overnight at room temperature. The reaction was poured into water and extracted with ethyl acetate (3×). The combined organic phase was washed with saturated aqueous sodium chloride, dried over anhydrous magnesium sulfate, filtered and concentrated in vacuo. Purification by flash column chromatography (silica gel, 10-40% ethyl acetate in heptane) gave cis-2-acetylamino-2-{4-[2-(4-chlorophenyl)-[1,3]-dioxolan-2-yl]-cyclohexyl}-6-(4,4,5,5-tetramethyl-[1,3,2]-dioxaboron-2-yl)-hex-5-enoic acid, tert-butylamide as a colorless oil (970 mg, 68%); $^1$H NMR (CDCl$_3$, 300 MHz) δ 7.28 (m, 4H), 6.92 (br s, NH, 1H), 5.41 (br s, NH, 1H), 3.94 (m, 2H), 3.67 (m, 2H), 2.76 (m, 1H), 1.90-2.08 (m, 2H), 1.94 (s, 3H), 1.60-1.86 (m, 4H), 1.18-1.42 (m, 5H), 1.32 (s, 9H), 1.23 (s, 12H), 0.90-1.10 (m, 4H) and 0.72 (t, J=7.5 Hz, 2H); MS (+CI): m/z for C$_{33}$H$_{52}$BClN$_2$O$_6$: expected 618.4. found 619.3 (M+H)$^+$, 641.4 (M+Na)$^+$.

Step 6: (R)-2-amino-6-borono-2-((1s,4S)-4-(4-chlorobenzoyl)cyclohexyl)hexanoic acid

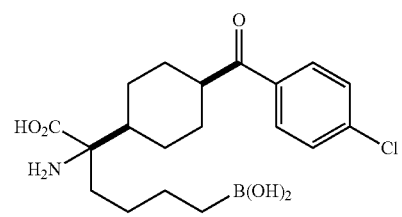

(84-A)

A solution of cis-2-acetylamino-2-{4-[2-(4-chlorophenyl)-[1,3]-dioxolan-2-yl]-cyclohexyl}-6-(4,4,5,5-tetramethyl-[1,3,2]-dioxaboron-2-yl)-hex-5-enoic acid, tert-butylamide (970 mg) in 6 N HCl (15 mL) was stirred at 90° C. for 1 day. After cooling to room temperature, the reaction mixture was transferred to a separatory funnel, diluted with deionized water (10 mL) and washed with dichloromethane (3×). The aqueous layer was frozen in liquid nitrogen and lyophilized to give title compound (545 mg, 88%). $^1$H NMR (D$_2$O, 300 MHz) δ 7.77 (d, J=7.0 Hz, 2H), 7.38 (dd, J=7.0 Hz, 2H), 3.24 (m, 1H), 1.76 (m, 6H), 1.54 (m, 1H), 1.24 (m, 6H), 1.06 (m, 2H) and 0.64 (t, J=6.5 Hz, 2H); MS (+CI): m/z for C$_{19}$H$_{27}$BClNO$_5$: expected 395.2. found 396.2 (M+H)$^+$, 378.2 (M+H−H$_2$O)$^+$.

Example 85-A

Preparation of 2-amino-6-borono-2-(1-(5-chloropyridin-2-yl)piperidin-4-yl)hexanoic acid hydrochloride Step 1: 5'-Chloro-3,4,5,6-tetrahydro-2H-[1,2']bipyridinyl-4-carboxylic acid, methoxy-methyl-amide

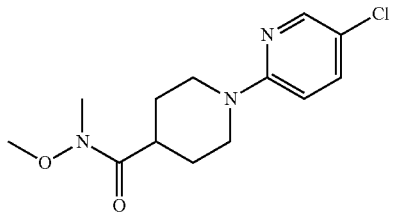 [SMILES: CON(C)C(=O)C1CCN(c2ccc(Cl)cn2)CC1]

EDC (1.61 g, 8.4 mmol) was added portionwise to a stirred solution of 5'-chloro-3,4,5,6-tetrahydro-2H-[1,2']bipyridinyl-4-carboxylic acid hydrochloride (1.16 g, 4.19 mmol), DMAP (5 mg), HOBt (5 mg) and N,O-dimethylhydroxylamine hydrochloride (818 mg, 8.4 mmol) in dichloromethane (20 mL). Triethylamine (1.69 g, 2.33 mL, 16.8 mmol) was added dropwise, and the reaction mixture was stirred at room temperature overnight. The resulting solution was poured into water and extracted with ethyl acetate (3×). The combined organic phase was washed with saturated aqueous sodium chloride, dried over anhydrous magnesium sulfate, filtered and concentrated in vacuo to give 5'-chloro-3,4,5,6-tetrahydro-2H-[1,2']bipyridinyl-4-carboxylic acid, methoxy-methyl-amide as a white solid (1.05 g. 86%); $^1$H NMR (CDCl$_3$, 300 MHz) δ 8.05 (d, J=2.5 Hz, 1H), 7.36 (dd, J$_1$=9.0 Hz, J$_2$=2.5 Hz, 1H), 6.57 (d, J=9.0 Hz, 1H), 4.25 (dt, J$_1$=13.0 Hz, J$_2$=3.0 Hz, 1H), 3.69 (s, 3H), 3.16 (s, 3H), 2.88 (m, 3H), and 1.78 (m, 4H); MS (+CI): m/z for C$_{13}$H$_{18}$ClN$_3$O$_2$: expected 283.1. found 284.2 (M+H)$^+$.

Step 2: 1-(5'-chloro-3,4,5,6-tetrahydro-2H-[1,2']bipyridinyl-4-yl)-pent-4-en-1-one

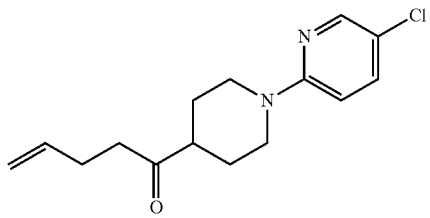 [SMILES: C=CCCC(=O)C1CCN(c2ccc(Cl)cn2)CC1]

While under a nitrogen atmosphere, a solution of 5'-chloro-3,4,5,6-tetrahydro-2H-[1,2']bipyridinyl-4-carboxylic acid, methoxy-methyl-amide (1.0 g, 3.5 mmol), in tetrahydrofuran (10 mL) was cooled to 0° C. and treated with 4-butenylmagnesiun bromide (0.5 M in THF, 17.6 mL, 8.8 mmol) dropwise. After stirring for 1 hour at 0° C. and room temperature overnight the reaction mixture was poured into water, acidified to pH 3-4 with 1N hydrochloric acid and extracted with ethyl acetate (3×). The combined organic phase was washed with saturated aqueous sodium chloride, dried over anhydrous magnesium sulfate, filtered and concentrated in vacuo. Purification by flash column chromatography (silica gel, 0-25% ethyl acetate in heptane) gave 1-(5'-chloro-3,4,5,6-tetrahydro-2H-[1,2']bipyridinyl-4-yl)-pent-4-en-1-one as a colorless oil (904 mg, 93%); $^1$H NMR (CDCl$_3$, 300 MHz) δ 8.05 (d, J=2.5 Hz, 1H), 7.42 (dd, J$_1$=9.0 Hz, J$_2$=2.5 Hz, 1H), 6.62 (d, J=9.0 Hz, 1H), 5.80 (m, 1H), 5.04 (m, 2H), 4.23 (m, 2H), 2.92 (m, 2H), 2.59 (m, 3H), 2.36 (m, 2H), 1.98 (m, 2H) and 1.70 (m, 2H); MS (+CI): m/z for C$_{15}$H$_{19}$ClN$_2$O: expected 278.1. found 279.2 (M+H)$^+$.

Step 3: 2-Acetylamino-2-(5'-Chloro-3,4,5,6-tetrahydro-2H-[1,2']bipyridinyl-4-yl)-hex-5-enoic acid, tert-butylamide

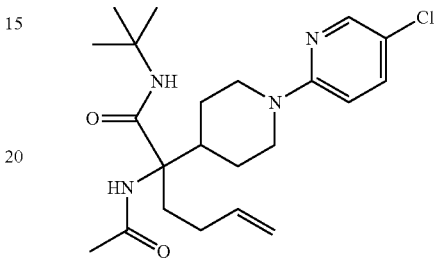

tert-Butyl isocyanide (538 mg, 0.73 mL, 6.48 mmol) was added to a stirred slurry of 1-(5'-chloro-3,4,5,6-tetrahydro-2H-[1,2']bipyridinyl-4-yl)-pent-4-en-1-one (900 mg, 3.24 mmol) and ammonium acetate (1.0 g, 12.96 mmol) in 2,2,2-trifluoroethanol (0.5 mL). After stirring at room temperature for 5 days, the reaction mixture was poured into water and extracted with ethyl acetate (3×). The combined organic phase was washed with saturated aqueous sodium chloride, dried over anhydrous magnesium sulfate, filtered and concentrated in vacuo. Purification by flash column chromatography (silica gel, 10-40% ethyl acetate in heptane) gave the title compound as a white solid (1.02 g, 74%); $^1$H NMR (CDCl$_3$, 300 MHz) δ 8.06 (dd, J$_1$=2.5 Hz, J$_2$=0.5 Hz, 1H), 7.37 (dd, J$_1$=9 Hz, J$_2$=2.5 Hz, 1H), 7.01 (br s, NH, 1H), 6.55 (dd, J$_1$=9.0 Hz, J$_2$=0.5 Hz, 1H), 5.78 (m, 1H), 5.50 (br s, NH, 1H), 4.97 (m, 2H), 4.38 (m, 1H), 4.14 (m, 1H), 3.00 (ddd, J$_1$=14.5 Hz, J$_2$=11.5 Hz, J$_3$=5.0 Hz, 1H), 2.72 (td, J$_1$=13 Hz, J$_2$=2.5 Hz, 2H), 2.44 (tt, J$_1$=2.5 Hz, J$_2$=3 Hz, 1H), 1.97-2.08 (m, 1H), 2.00 (s, 3H), 1.80 (m, 3H), 1.20-1.52 (m, 3H) and 1.30 (s, 9H).

Step 4: 2-acetylamino-2-(5'-chloro-3,4,5,6-tetrahydro-2H-[1,2']bipyridinyl-4-yl)-6-(4,4,5,5-tetramethyl-[1,3,2]-dioxaborolan-2-yl)hexanoic acid, tert-butylamide

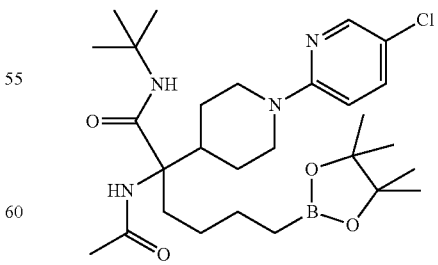

A solution of 2-acetylamino-2-(5'-chloro-3,4,5,6-tetrahydro-2H-[1,2]bipyridinyl-4-yl)-hex-5-enoic acid, tert-butylamide (1.0 g, 2.38 mmol) in dichloromethane (10 mL) was treated with chloro-1,5-cyclooctadiene iridium(I) dimer (48 mg, 3 mol %) and 1,2-bis(diphenylphosphino)ethane (57 mg, 6 mol %) under an atmosphere of nitrogen. The solution was stirred at room temperature for 30 minutes and then 4,4,5,5-tetramethyl-[1,3,2]dioxaborolane (609 mg, 0.69 mL, 4.76 mmol) was added dropwise, and the reaction was then stirred overnight at room temperature. The reaction was poured into water and extracted with ethyl acetate (3×). The combined organic phase was washed with saturated aqueous sodium chloride, dried over anhydrous magnesium sulfate, filtered and concentrated in vacuo. Purification by flash column chromatography (silica gel, 10-40% ethyl acetate in heptane) gave the title compound as a white solid (1.07 g, 82%); $^1$H NMR (CDCl$_3$, 300 MHz) δ 8.05 (d, J=2 Hz, 1H), 7.35 (dd, J$_1$=9.0 Hz, J$_2$=2.5 Hz, 1H), 6.96 (br s, NH, 1H), 6.53 (d, J=9.0 Hz, 1H), 5.78 (m, 1H), 5.46 (br s, NH, 1H), 4.36 (d, J=13 Hz, 1H), 4.12 (d, J=13 Hz, 1H), 2.83 (td, J$_1$=13.5 Hz, J$_2$=5 Hz, 1H), 2.72 (td, J$_1$=12.5 Hz, J$_2$=2 Hz, 2H), 2.42 (tt, J$_1$=12 Hz, J$_2$=3 Hz, 1H), 1.97 (s, 3H), 1.77 (m, 2H), 1.32-1.48 (m, 4H), 1.28 (s, 9H), 1.20 (s, 12H), 1.03-1.25 (m, 2H) and 0.72 (t, J=7.5 Hz, 2H); MS (+CI): m/z for C$_{28}$H$_{46}$BClN$_4$O$_4$: expected 548.3. found 549.3 (M+H)$^+$, 571.3 (M+Na)$^+$.

Step 5: 2-amino-6-borono-2-(1-(5-chloropyridin-2-yl)piperidin-4-yl)hexanoic acid

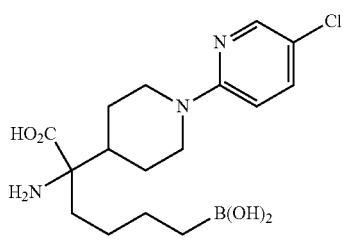

(85-A)

A solution of 2-acetylamino-2-(5'-chloro-3,4,5,6-tetrahydro-2H-[1,2']bipyridinyl-4-yl)-6-(4,4,5,5-tetramethyl-[1,3,2]-dioxaborolan-2-yl)hexanoic acid, tert-butylamide (1.07 g) in 6 N HCl (20 mL) was stirred at 90° C. for 1 day. After cooling to room temperature, the reaction mixture was transferred to a separatory funnel, diluted with deionized water (10 mL) and washed with dichloromethane (3×). The aqueous layer was frozen in liquid nitrogen and lyophilized to give title compound as a white solid (590 mg, 82%); $^1$H NMR (D$_2$O, 300 MHz) δ 8.00 (d, J=2.5 Hz, 1H), 7.47 (dd, J$_1$=9.0 Hz, J$_2$=2.5 Hz, 1H), 6.79 (d, J=9 Hz, 1H), 4.42 (d, J=13.5 Hz, 1H), 4.32 (d, J=13 Hz, 1H), 2.79 (t, J=12 Hz, 2H), 2.06 (m, 1H), 1.78-1.94 (m, 3H), 1.55-1.70 (m, 2H), 1.43 (m, 4H), 1.30 (m, 1H) and 0.82 (t, J=7 Hz, 2H); MS (+CI): m/z for C$_{16}$H$_{25}$BClN$_3$O$_4$: expected 369.2. found 370.2 (M+H)$^+$, 352.23 (M+H–H$_2$O)$^+$.

Example 86-A

Preparation of 2-amino-6-borono-2-(4-(4-chlorophenyl)cyclohexyl) hexanoic acid hydrochloride Step 1: 4-(4-Chlorophenyl)-cyclohexanecarboxylic acid, methoxy-methyl amide

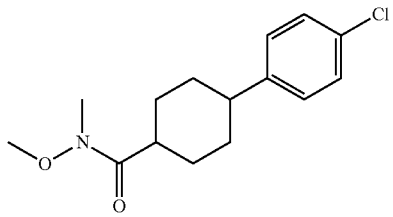 [SMILES: CON(C)C(=O)C1CCC(c2ccc(Cl)cc2)CC1]

EDC (3.21 g, 16.8 mmol) was added portionwise to a stirred solution of 4-(4-chlorophenyl)-cyclohexanecarboxylic acid (2.0 g, 8.4 mmol), DMAP (5 mg), HOBt (5 mg) and N,O-dimethylhydroxylamine hydrochloride (1.63 g, 16.8 mmol) in dichloromethane (40 mL). Triethylamine (3.4 g, 4.7 mL, 33.5 mmol) was added dropwise, and the reaction mixture was stirred at room temperature. After stirring overnight the reaction mixture was poured into water and extracted with ethyl acetate (3×). The combined organic phase was washed with saturated aqueous sodium chloride, dried over anhydrous magnesium sulfate, filtered and concentrated in vacuo to give 4-(4-chlorophenyl)-cyclohexanecarboxylic acid, methoxy-methyl amide as a colorless oil (1.85 g. 78%); MS (+CI): m/z for C$_{15}$H$_{20}$ClNO$_2$: expected 281.1. found 282.2 (M+H)$^+$.

Step 2:
1-[4-(4-Chlorophenyl)-cyclohexyl]pent-4-en-1-one

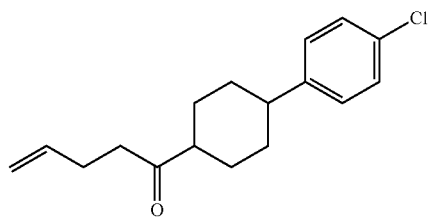 [SMILES: C=CCCC(=O)C1CCC(c2ccc(Cl)cc2)CC1]

While under a nitrogen atmosphere, a solution of 4-(4-chlorophenyl)-cyclohexanecarboxylic acid, methoxy-methyl amide (1.8 g, 6.39 mmol), in tetrahydrofuran (10 mL) was cooled to 0° C. and treated with 4-butenylmagnesiun bromide (0.5 M in THF, 31.95 mL, 15.98 mmol) dropwise. After stirring for 1 hour at 0° C. the reaction mixture was warmed to room temperature overnight, poured into water, acidified to pH 3-4 with 1 N hydrochloric acid and extracted with ethyl acetate (3×). The combined organic phase was washed with saturated aqueous sodium chloride, dried over anhydrous magnesium sulfate, filtered and concentrated in vacuo. Purification by flash column chromatography (silica gel, 0-20% ethyl acetate in heptane) gave 1-[4-(4-chlorophenyl)-cyclohexyl]pent-4-en-1-one as a colorless oil (1.62 g, 92%); $^1$H NMR (CDCl$_3$, 300 MHz) δ 7.26 (m, 2H), 7.12 (d, J=8 Hz, 2H), 5.81 (m, 1H), 5.02 (m, 2H), 2.58 (t, J=7 Hz, 2H), 2.44 (m, 2H), 2.34 (m, 2H), 1.99 (m, 4H) and 1.47 (m, 4H).

Step 3: 2-acetamido-N-tert-butyl-2-(4-(4-chlorophenyl)cyclohexyl)hex-5-enamide

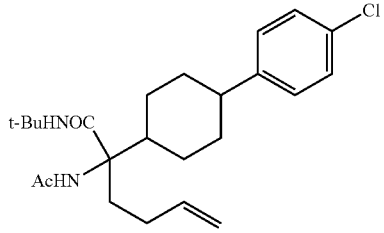

tert-Butyl isocyanide (301 mg, 0.41 mL, 3.6 mmol) was added to a stirred slurry of 1-[4-(4-chlorophenyl)-cyclohexyl]pent-4-en-1-one (800 mg, 2.9 mmol) and ammonium acetate (671 mg, 8.7 mmol) in 2,2,2-trifluoroethanol (0.4 mL). After stirring at room temperature for 8 days, the reaction mixture was poured into water and extracted with ethyl acetate (3×). The combined organic phase was washed with saturated aqueous sodium chloride, dried over anhydrous magnesium sulfate, filtered and concentrated in vacuo. Purification by flash column chromatography (silica gel, 10-50% ethyl acetate in heptane) gave 2-acetamido-N-tert-butyl-2-(4-(4-chlorophenyl)cyclohexyl)hex-5-enamide as a colorless oil (940 mg, 77%); $^1$H NMR (CDCl$_3$, 300 MHz) δ 7.24 (m, 2H), 7.15 (m, 2H), 7.04 (br s, NH, 1H), 5.80 (m, 1H), 5.544 (br s, NH, 1H), 4.97 (m, 2H), 3.04 (ddd, $J_1$=14 Hz, $J_2$=11.5 Hz, $J_3$=5.0 Hz, 1H), 2.38 (tt, $J_1$=12 Hz, $J_2$=2 Hz, 1H), 2.28 (tt, $J_1$=12 Hz, $J_2$=2 Hz, 1H), 2.03 (s, 3H), 1.68-1.95 (m, 5H), 1.42-1.61 (m, 4H), 1.41 (s, 9H), 1.26 (m, 1H) and 1.12 (m, 1H); MS (+CI): m/z for $C_{24}H_{35}ClN_2O_2$: expected 418.2. found 419.2 $(M+H)^+$.

Step 4. 2-acetamido-N-tert-butyl-2-(4-(4-chlorophenyl)cyclohexyl)-6-(4,4,5,5-tetramethyl-1,3,2-dioxaborolan-2-yl)hexanamide

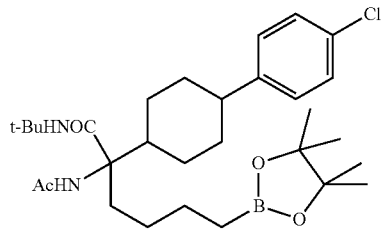

A solution of 2-acetylamino-2-[4-(4-chlorophenyl)-cyclohexyl]hex-5-enoic acid tert-butylamide (940 mg, 2.25 mmol) in dichloromethane (9 mL) was treated with chloro-1,5-cyclooctadiene iridium(I) dimer (45 mg, 3 mol %) and 1,2-bis(diphenylphosphino)ethane (54 mg, 6 mol %). After stirring for 30 minutes, 4,4,5,5-tetramethyl-[1,3,2]dioxaborolane (576 mg, 0.65 mL, 4.5 mmol) was added dropwise and the stirring was continued overnight. The reaction was poured into water and extracted with ethyl acetate (3×). The combined organic phase was washed with saturated aqueous sodium chloride, dried over anhydrous magnesium sulfate, filtered and concentrated in vacuo. Purification by flash column chromatography (silica gel, 10-40% ethyl acetate in heptane) gave 2-acetamido-N-tert-butyl-2-(4-(4-chlorophenyl)cyclohexyl)-6-(4,4,5,5-tetramethyl-1,3,2-dioxaborolan-2-yl)hexanamide as a colorless oil (985 mg, 80%); $^1$H NMR (CDCl$_3$, 300 MHz) δ 7.25 (d, J=7.5 Hz, 2H), 7.08 (d, J=7.5 Hz, 2H), 6.99 (br s, NH, 1H), 5.52 (br s, NH, 1H), 2.84 (td, $J_1$=13 Hz, $J_2$=3.0 Hz, 1H), 2.37 (t, J=12 Hz, 1H), 2.24 (t, J=12 Hz, 1H), 2.00 (s, 3H), 1.90 (m, 4H), 1.20-1.48 (m, 7H), 1.38 (s, 9H), 1.22 (s, 12H), 1.06 (m, 2H) and 0.75 (t, J=7.5 Hz, 2H); MS (+CI): m/z for $C_{30}H_{48}BClN_2O_4$: expected 546.3. found 547.3 $(M+H)^+$, 569.3 $(M+Na)^+$.

Step 5: 2-amino-6-borono-2-(4-(4-chlorophenyl)cyclohexyl)hexanoic acid

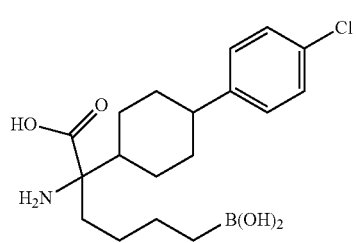

(86-A)

A solution of 2-acetylamino-2-[4-(4-chlorophenyl)-cyclohexyl]-6-(4,4,5,5-tetramethyl-[1,3,2]-dioxaborolan-2-yl) hexanoic acid tert-butylamide (980 mg) in 6 N HCl (15 mL) was stirred at 90° C. for 1 day. After cooling to room temperature, the reaction mixture was transferred to a separatory funnel, diluted with deionized water (10 mL) and washed with dichloromethane (3×). The aqueous layer was frozen in liquid nitrogen and lyophilized to give 2-amino-6-borono-2-(4-(4-chlorophenyl)cyclohexyl)hexanoic acid (535 mg, 81%). $^1$H NMR (D$^4$-MeOH, 300 MHz) δ 7.24 (d, J=8.5 Hz, 2H), 7.19 (dd, J=8.5 Hz, 2H), 2.50 (m, 1H), 1.78-2.06 (m, 7H), 1.38-1.56 (m, 7H), 1.21 (m, 1H) and 0.82 (t, J=6.5 Hz, 2H); MS (+CI): m/z for $C_{18}H_{27}BClNO_4$: expected 367.2. found 368.2 $(M+H)^+$, 350.2 $(M+H-H_2O)^+$.

Example 87-A

Preparation of 2-amino-2-(1-benzylpiperidin-4-yl)-6-boronohexanoic acid dihydrochloride Step 1: benzyl 4-(methoxy(methyl)carbamoyl)piperidine-1-carboxylate

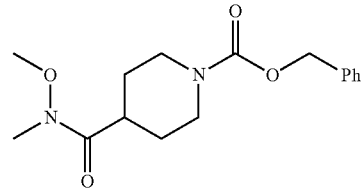 [SMILES: CON(C)C(=O)C1CCN(C(=O)OCc2ccccc2)CC1]

In a 1 L round-bottomed flask, a solution of 1-(benzyloxycarbonyl)piperidine-4-carboxylic acid (21.0 g, 80 mmol) in anhydrous dichloromethane (250 mL) was stirred at room temperature until completely dissolved. After becoming clear, the reaction mixture was cooled to 0° C. and sequentially treated with N,O-dimethylhydroxylamine hydrochloride (9.74 g, 100 mmol), EDC (19.2 g, 100 mmol), and triethylamine (30.4 g, 41.81 mL, 300 mmol). After the additions were complete, the reaction mixture was stirred at room temperature overnight. 1 N HCl (250 mL) was added and after 5 min of additional stirring, the organic phase was separated, washed with 1 N HCl (100 mL), saturated aqueous NaHCO$_3$ (150 mL), dried over MgSO$_4$, filtered and concentrated. Purification by MPLC (100 g column, 50-100% ethyl acetate in heptane) gave benzyl 4-(methoxy(methyl)carbamoyl)piperidine-1-carboxylate (22.23 g, 91%) as a colorless oil. $^1$H NMR (CDCl$_3$, 300 MHz) δ 7.42-7.29 (m, 5H), 5.21 (s, 2H), 4.32-4.16 (m, 2H), 3.70 (s, 3H), 3.18 (s, 3H), 2.96-2.78 (m, 3H), 1.80-1.64 (m, 4H). ESI MS found for $C_{16}H_{22}N_2O_4$ m/z [307.1 (M+1), 329.2 (M+23)].

Step 2: benzyl 4-pent-4-enoylpiperidine-1-carboxylate

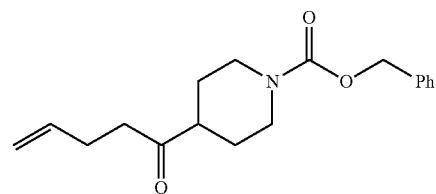 [SMILES: C=CCCC(=O)C1CCN(C(=O)OCc2ccccc2)CC1]

While under an argon atmosphere, a solution of benzyl 4-(methoxy(methyl) carbamoyl)piperidine-1-carboxylate (15.0 g, 49.0 mmol) in THF (100 mL) was cooled to −78° C.

(dry ice/acetone bath) and treated with 3-butenylmagnesium bromide (250 mL, 0.5 M sol. in THF, 125 mmol, Aldrich) via canula. After the addition was complete, the cooling bath was removed allowing the solution to slowly warm to room temperature. After stirring overnight (16 h), the reaction mixture was quenched with 0.1N HCl (200 mL) and diluted with ethyl acetate (300 mL). After stirring an additional 5 min, the organic phase was separated, washed with saturated sodium bicarbonate (200 mL), dried over MgSO$_4$, filtered and concentrated. Purification by MPLC (100 g column, 20-50% ethyl acetate in heptane) gave benzyl 4-pent-4-enoylpiperidine-1-carboxylate (14.5, 98%) as a colorless oil. $^1$H NMR (CDCl$_3$, 300 MHz) δ 7.38-7.32 (m, 5H), 5.79 (dddd, J$_1$=17.1 Hz, J$_2$=10.2 Hz, J$_3$=6.9 Hz, J$_4$=6.6 Hz, 1H), 5.12 (s, 2H), 5.02 (dd, J$_1$=17.1 Hz, J$_2$=1.5 Hz, 1H), 4.97 (dd, J$_1$=10.2 Hz, J$_2$=1.5 Hz, 1H), 4.28-4.10 (m, 2H), 2.86 (br t, J=12 Hz, 2H), 2.58-2.43 (m, 3H), 2.35-2.28 (m, 2H), 1.9-1.74 (m, 2H), 1.62-1.48 (m, 2H). ESI MS found for C$_{18}$H$_{23}$NO$_3$ m/z [302.3 (M+1), 324.1 (M+23)].

Step 3 benzyl 4-(2-acetamido-1-(tert-butylamino)-1-oxohex-5-en-2-yl)piperidine-1-carboxylate

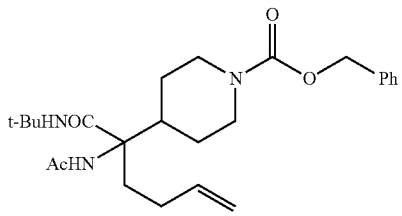

A solution of benzyl 4-pent-4-enoylpiperidine-1-carboxylate (10.0 g, 33.2 mmol) and ammonium acetate (6.16 g, 80 mmol) in 2,2,2-trifluoroethanol (10 mL) was treated with tert-butyl isocyanide (2.57 g, 3.50 mL, 31 mmol). After stirring at room temperature for 14 days, the reaction mixture was added to a separatory funnel, diluted with water (100 mL) and extracted with ethyl acetate (2×100 mL). The organic layer was washed with saturated aqueous sodium chloride, dried over MgSO$_4$, filtered and concentrated. MPLC purification (100 g column, 50-100% ethyl acetate in heptane) gave benzyl 4-(2-acetamido-1-(tert-butylamino)-1-oxohex-5-en-2-yl)piperidine-1-carboxylate as colorless oil (8.2 g, 56%). $^1$H NMR (CDCl$_3$, 300 MHz) δ 7.36-7.31 (m, 5H), 6.98 (bs, 1H), 5.85-5.71 (m, 1H), 5.49 (bs, 1H), 5.11 (s, 2H), 5.00 (dd, J$_1$=16.8 Hz, J$_2$=1.5 Hz, 1H), 4.95 (dd, J$_1$=9.9 Hz, J$_2$=1.5 Hz, 1H), 4.36-4.12 (m, 2H), 2.96 (ddd, J$_1$=14.1 Hz, J$_2$=11.7 Hz, J$_3$=5.4 Hz, 1H), 2.78-2.61 (m, 2H), 2.37 (ddd, J$_1$=12.0 Hz, J$_2$=11.7 Hz, J$_3$=0.9 Hz, 1H), 2.10-1.96 (m, 1H), 2.00 (s, 3H), 1.84-1.64 (m, 3H), 1.56-1.39 (m, 1H), 1.39-1.21 (m, 1H), 1.34 (s, 9H), 1.20-1.03 (m, 1H). ESI MS found for C$_{25}$H$_{37}$N$_3$O$_4$ m/z [444.3 (M+1), 466.1 (M+23)].

Step 4: benzyl 4-(2-acetamido-1-(tert-butylamino)-1-oxo-6-(4,4,5,5-tetramethyl-1,3,2-dioxaborolan-2-yl)hexan-2-yl)piperidine-1-carboxylate

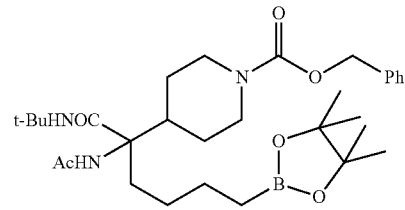

While under an argon atmosphere, a solution of 1,2-bis(diphenylphosphino)ethane (306 mg, 0.77 mmol) and chloro-1,5-cyclooctadiene iridium (I) dimer (258 mg, 0.39 mmol) in anhydrous THF (30 mL) was treated with 4,4,5,5-tetramethyl-1,3,2-dioxaborolane (1.48 g, 1.67 mL, 11.6 mmol) in one portion. After stirring for 15 minutes the solution was cooled to 5° C. (ice-water batch) and treated with benzyl 4-(2-acetamido-1-(tert-butylamino)-1-oxohex-5-en-2-yl)piperidine-1-carboxylate (3.42 g, 7.70 mmol) in one portion. After the addition was complete, the cooling bath was removed and the reaction mixture was allowed to warm up to room temperature. After 2 hours of stirring the reaction was quenched with saturated aqueous sodium bicarbonate (50 mL) and extracted using ethyl acetate (2×150 mL). The organic layer was dried over MgSO$_4$, filtered and concentrated. MPLC purification (100 g column, 40-80% ethyl acetate in heptane) gave benzyl 4-(2-acetamido-1-(tert-butylamino)-1-oxo-6-(4,4,5,5-tetramethyl-1,3,2-dioxaborolan-2-yl)hexan-2-yl)piperidine-1-carboxylate as a colorless oil (3.10 g, 71% yield). $^1$H NMR (CDCl$_3$, 300 MHz) δ 7.36-7.30 (m, 5H), 6.94 (bs, 1H), 5.46 (s, 1H), 5.10 (s, 2H), 4.36-4.10 (m, 2H), 2.86-2.60 (m, 3H), 2.40-2.28 (bt, J=12.3 Hz, 1H), 1.98 (s, 3H), 1.78-1.61 (m, 2H), 1.49-1.17 (m, 5H), 1.33 (s, 9H), 1.20 (s, 8H), 1.12-0.94 (m, 2H), 0.73 (t, J=7.8 Hz, 2H).

Step 5: 2-acetamido-N-tert-butyl-2-(piperidin-4-yl)-6-(4,4,5,5-tetramethyl-1,3,2-dioxaborolan-2-yl)hexanamide

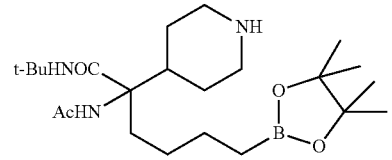

In a 100 mL round bottom flask while under an argon atmosphere, benzyl 4-(2-acetamido-1-(tert-butylamino)-1-oxo-6-(4,4,5,5-tetramethyl-1,3,2-dioxaborolan-2-yl)hexan-2-yl)piperidine-1-carboxylate (3.0 g, 5.25 mmol) in methanol (40 mL) was degassed with argon (bubbled through solution) and subsequently treated with palladium (25 mg, 10 wt % on active carbon, wet, Degussa type E101 NE/W). After continued bubbling for 10 min the argon was replaced with a slow stream of hydrogen. After 1.5 h the reaction was complete (reaction monitored by TLC for the disappearance of starting material (50% ethyl acetate in heptane, $R_f$ 0.3) and solution was purged with argon, filtered through the Celite 545 and the filter cake washed with methanol. The methanol solution was concentrated and collected solvents evaporated to give crude 2-acetamido-N-tert-butyl-2-(piperidin-4-yl)-6-(4,4,5,5-tetramethyl-1,3,2-dioxaborolan-2-yl)hexanamide (2.20 g 96%) which was used without further purification (contained approximately 10% product with loss of boronic acid protecting group). $^1$H NMR (CDCl$_3$, 300 MHz) δ 6.95 (s, 1H), 5.53 (s, 1H), 3.09 (bt, J=11.1 Hz, 2H), 2.80 (ddd, $J_1$=14.1 Hz, $J_2$=13.5 Hz, $J_3$=4.5 Hz, 1H), 2.65-2.48 (m, 2H), 2.26 (dddd, $J_1$=12.0 Hz, $J_2$=12.0 Hz, $J_3$=3.0 Hz, $J_4$=2.7 Hz, 1H), 2.00-1.90 (m, 1H), 1.98 (s, 3H), 1.78-1.63 (m, 2H), 1.45-1.00 (m, 5H), 1.36 (s, 9H), 1.21 (s, 8H), 0.73 (t, J=7.5 Hz, 2H).

Step 6: 2-acetamido-2-(1-benzylpiperidin-4-yl)-N-tert-butyl-6-(4,4,5,5-tetramethyl-1,3,2-dioxaborolan-2-yl)hexanamide

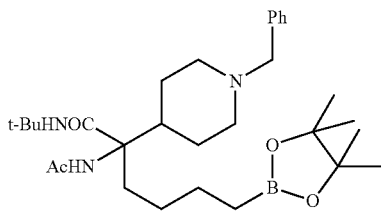

A solution of 2-acetamido-N-tert-butyl-2-(piperidin-4-yl)-6-(4,4,5,5-tetramethyl-1,3,2-dioxaborolan-2-yl)hexanamide (480 mg, 1.10 mmol) and benzaldehyde (138 mg, 131 jut, 1.30 mmol) in 1,2-dichloroethane (1 mL) was stirred for 20 minutes then treated with sodium triacetoxyborohydride (420 mg, 2.20 mmol). After 5 hours, the reaction mixture was quenched with saturated aqueous sodium bicarbonate (10 mL), diluted with saturated aqueous sodium chloride (50 mL) and extracted with dichloromethane (3×40 mL). Organic layers were collected, dried over MgSO$_4$, filtered and concentrated. MPLC purification (25 g column, 1-10% methanol in dichloromethane) gave 2-acetamido-2-(1-benzylpiperidin-4-yl)-N-tert-butyl-6-(4,4,5,5-tetramethyl-1,3,2-dioxaborolan-2-yl)hexanamide as a colorless oil (538 mg, 93%), which was used immediately in the subsequent step (approximately 10% of the product had the boronic acid deprotected).

Step 7: 2-amino-2-(1-benzylpiperidin-4-yl)-6-boronohexanoic acid

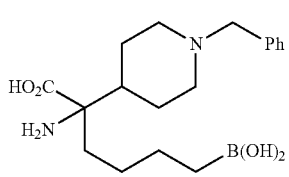

(87-A)

A solution of 2-acetamido-2-(1-benzylpiperidin-4-yl)-N-tert-butyl-6-(4,4,5,5-tetramethyl-1,3,2-dioxaborolan-2-yl) hexanamide (510 mg, 0.97 mmol) in 6 N HCl (15 mL) was heated to a gentle reflux for 16 h. After cooling to room temperature, the reaction mixture was transferred to a separatory funnel, diluted with deionized water (15 mL) and washed with dichloromethane (3×25 mL). The aqueous layer was concentrated to give an off-white solid that was purified by HPLC (5-95% acetonitrile in water). The fractions containing product were concentrated, redissolved in deionized water (15 mL), frozen in liquid nitrogen and lyophilized to give 2-amino-2-(1-benzylpiperidin-4-yl)-6-boronohexanoic acid (210 mg, 62%) as its dihydrochloride salt and trihydrate. $^1$H NMR (D$_2$O, 500 MHz) δ 7.37-7.43 (m, 5H), 4.21 (s, 2H), 3.51 (brt, J=10 Hz, 2H), 2.92-2.99 (m, 2H), 2.02-2.10 (m, 2H), 1.66-1.84 (m, 4H), 1.41 (dq, $J_1$=13.0 Hz, $J_1$=4.0 Hz, 1H), 1.29-1.35 (m, 2H), 1.23-1.28 (m, 1H), 1.08-1.12 (m, 1H), 0.68 (t; J=8.0 Hz, 2H). ESI MS found for C$_{18}$H$_{29}$BFN$_2$O$_4$ m/z [331.6 (M+1−18) 13%, 313.6 (M+1−2×18) 100%, 329.6 (M−1−18) 100%]. Anal. Calcd for C$_{18}$H$_{29}$BN$_2$O$_4$×2HCl× 3H$_2$O: C, 45.49; H, 7.85; N, 5.89. Found C, 45.60; H, 7.10; N, 5.55.

Example 88-A

Preparation of 2-amino-6-borono-2-(piperidin-4-yl)hexanoic acid dihydrochloride

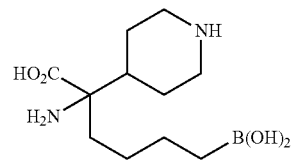

(88-A)

2-Amino-6-borono-2-(piperidin-4-yl)hexanoic acid dihydrochloride is prepared using the synthesis set forth in Example 87-A, except the intermediate from step 5 (2-acetamido-N-tert-butyl-2-(piperidin-4-yl)-6-(4,4,5,5-tetramethyl-1,3,2-dioxaborolan-2-yl)hexanamide) was directly deprotected as described in step 7. $^1$H NMR (D$_2$O, 300 MHz) δ 3.45 (brd, J=12.0 Hz, 2H), 2.92-2.98 (m, 2H), 2.15 (brt, J=12.0 Hz, 1H), 2.04 (brd, J=14.0 Hz, 1H), 1.79-1.86 (m, 3H), 1.71 (dq, $J_1$=13.0 Hz, $J_2$=3.0 Hz, 1H), 1.43 (dq, $J_1$=13.0 Hz, $J_2$=3.0 Hz, 1H), 1.27-1.38 (m, 3H), 1.09-1.17 (m, 1H), 0.71 (t, J=8.0 Hz, 2H). ESI MS found for C$_{11}$H$_{23}$BN$_2$O$_4$ m/z [281.5 (M+Na$^+$) 3%, 263.5 (M+Na$^+$-18) 5%, 241.5 (M+1−18) 15%, 223.4 (M+1−2×18) 100%].

Example 89-A

Preparation of 2-amino-6-borono-2-(1-(4-chlorobenzyl)piperidin-4-yl)hexanoic acid dihydrochloride

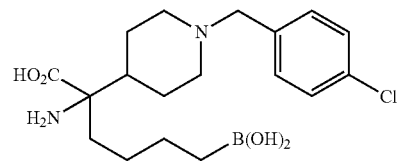

(120)

2-Amino-6-borono-2-(1-(4-chlorobenzyl)piperidin-4-yl) hexanoic acid dihydrochloride is prepared in a manner analogous to that set forth in Example 87-A, except 4-chlorobenzaldehyde is used as the aldehyde in step 6. $^1$H NMR (D$_2$O, 300 MHz) δ 7.31 (d$_{AB}$, J=8.4 Hz, 2H), 7.25 (d$_{AB}$, J=8.4 Hz, 2H), 4.11 (s, 2H), 3.47-3.35 (m, 2H), 2.93-2.80 (m, 2H), 2.09 (bt, J=12.3 Hz, 1H), 1.92 (d, J=13.8 Hz, 1H), 1.84-1.60 (m, 4H), 1.45-1.31 (m, 1H), 1.30-1.13 (m, 3H), 1.10-0.95 (m, 1H), 0.59 (t, J=7.2 Hz, 2H). ESI MS found for $C_{18}H_{28}BClN_2O_4$ m/z [383.2 (M+1)].

Example 90-A

Preparation of 2-amino-2-(1-(benzo[d][1,3]dioxol-5-ylmethyl)piperidin-4-yl)-6-boronohexanoic acid dihydrochloride

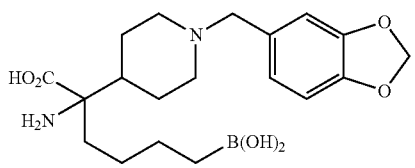

(90-A)

2-Amino-2-(1-(benzo[d][1,3]dioxol-5-ylmethyl)piperidin-4-yl)-6-boronohexanoic acid dihydrochloride is prepared in a manner analogous to that set forth in Example 87-A, except benzo[d][1,3]dioxole-5-carbaldehyde is used as the aldehyde in step 6. $^1$H NMR (D$_2$O, 300 MHz) δ 6.87-6.74 (m, 3H), 5.85 (s, 2H), 4.05 (s, 2H), 3.50-3.32 (m, 2H), 2.95-2.75 (m, 2H), 2.04-1.90 (m, 2H), 1.80-1.60 (m, 4H), 1.50-0.95 (m, 5H), 0.62 (t, J=7.2 Hz, 2H). ESI MS found for $C_{19}H_{29}BN_2O_6$ m/z [393.2 (M+1)].

Example 91-A

PREPARATION of 2-amino-6-borono-2-(1-((6-chlorobenzo[d][1,3]dioxol-5-yl)methyl)piperidin-4-yl)hexanoic acid dihydrochloride

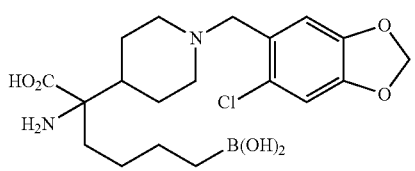

(91-A)

2-Amino-6-borono-2-(1-((6-chlorobenzo[d][1,3]dioxol-5-yl)methyl)piperidin-4-yl)hexanoic acid dihydrochloride is prepared in a manner analogous to that set forth in Example 87-A, except 6-chlorobenzo[d][1,3]dioxole-5-carbaldehyde is used as the aldehyde in step 6. $^1$H NMR (D$_2$O, 500 MHz) δ 6.98, (s, 1H), 6.94, (s, 1H), 5.97 (s, 2H), 4.29 (s, 2H), 3.58 (t, J=11.6 Hz, 2H), 3.11-3.05 (m, 2H), 2.15-2.04 (m, 2H), 1.50-1.42 (m, 1H), 1.36-1.25 (m, 3H), 1.14-1.07 (m, 1H), 0.69 (t, J=7.6 Hz, 2H). ESI MS found for $C_{19}H_{28}BClN_2O_6$ m/z [409.6/411.6 (M+1−18) 10%, 391.5/393.5 (M+1−2×18) 63%, 425.5/427.5 (M−1) 27%, 407.6/409.6 (M−1−18) 100%].

Example 92-A

Preparation of 2-amino-6-borono-2-(1-isopentylpiperidin-4-yl)hexanoic acid dihydrochloride

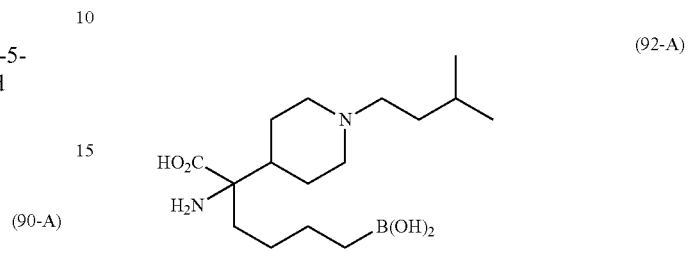

(92-A)

2-Amino-6-borono-2-(1-isopentylpiperidin-4-yl)hexanoic acid dihydrochloride is prepared in a manner analogous to that set forth in Example 87-A, except isopentanal (3-methylbutanal) is used as the aldehyde in step 6. $^1$H NMR (D$_2$O, 500 MHz) δ 3.55 (t, J=11.7 Hz, 2H), 3.00-2.97 (m, 2H), 2.88-2.82 (m, 2H), 2.11-2.01 (m, 2H), 1.84-1.70 (m, 4H), 1.52-1.38 (m, 4H), 1.33-1.21 (m, 3H), 1.10-1.03 (m, 1H), 0.77 (d, J=5.5 Hz, 6H), 0.66 (t, J=7.6 Hz, 2H). ESI MS found for $C_{16}H_{33}BN_2O_4$ m/z [329.7 (M+1) 2%, 311.6 (M+1−18) 20%, 293.6 (M+1−2×18) 100%, 327.7 (M−1) 10%, 309.6 (M−1−18) 100%].

Example 93-A

Preparation of 2-amino-6-borono-2-(1-(4-(trifluoromethyl)benzyl)piperidin-4-yl)hexanoic acid

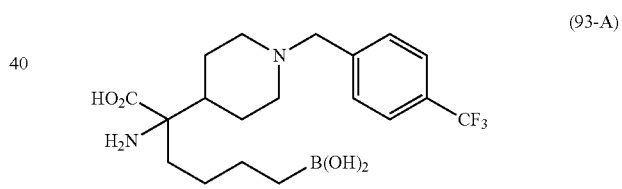

(93-A)

2-Amino-6-borono-2-(1-(4-(trifluoromethyl)benzyl)piperidin-4-yl)hexanoic acid is prepared in a manner analogous to that set forth in Example 87-A, except 4-(trifluoromethyl)benzaldehyde is used as the aldehyde in step 6. $^1$H NMR (D$_2$O, 400 MHz) δ 7.76-7.70 (m, 2H), 7.65-7.54 (m, 2H), 4.25 (s, 2H), 3.60-3.37 (m, 2H), 3.07-2.84 (m, 2H), 2.07-1.95 (m, 2H), 1.82 (s, 3H), 1.81-1.63 (m, 4H), 1.47-1.16 (m, 4H), 1.14-1.00 (m, 1H), 0.67 (t, J=8.29 Hz, 2H) MS found for $C_{19}H_{28}BF_3N_2O_4$ m/z[399.1, (M−18+1), 381.1 (M−36+1)].

Example 94-A

Preparation of 2-amino-6-borono-2-(1-(4-fluorobenzyl)piperidin-4-yl)hexanoic acid dihydrochloride

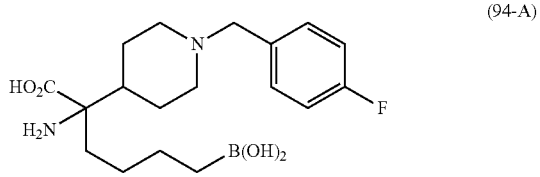 [SMILES: NC(CCCCB(O)O)(C(=O)O)C1CCN(Cc2ccc(F)cc2)CC1]

(94-A)

2-Amino-6-borono-2-(1-(4-fluorobenzyl)piperidin-4-yl)hexanoic acid dihydrochloride is prepared in a manner analogous to that set forth in Example 87-A, except 4-fluorobenzaldehyde is used as the aldehyde in step 6. $^1$H NMR (D$_2$O, 400 MHz) δ 7.42-7.35 (m, 2H), 7.16-7.07 (m, 2H), 4.19 (s, 2H), 3.60-3.35 (m, 2H), 3.06-2.81 (m, 2H), 2.07-1.94 (m, 2H), 1.86 (s, 3H), 1.84-1.60 (m, 4H), 1.45-1.16 (m, 4H), 1.14-0.99 (m, 1H), 0.68 (t, J=8.3 Hz, 2H). MS found for C$_{18}$H$_{28}$BFN$_2$O$_4$ m/z[349.1, (M−18+1), 331.1 (M−36+1)].

Example 95-A

Preparation of 2-amino-6-borono-2-(1-(3,4-dichlorobenzyl)piperidin-4-yl)hexanoic acid dihydrochloride

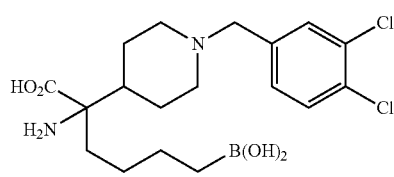

(95-A)

2-Amino-6-borono-2-(1-(3,4-dichlorobenzyl)piperidin-4-yl)hexanoic acid dihydrochloride is prepared in a manner analogous to that set forth in Example 118, except 3,4-dichlorobenzaldehyde is used as the aldehyde in step 6. $^1$H NMR (D$_2$O, 400 MHz) δ 7.56-7.50 (m, 2H), 7.29-7.24 (m, 1H), 4.16 (s, 2H), 3.57-3.32 (m, 2H), 3.01-2.76 (m, 2H), 2.05-1.95 (m, 2H), 1.80 (s, 3H), 1.79-1.63 (m, 4H), 1.45-1.15 (m, 4H), 1.14-0.99 (m, 1H), 0.68 (t, J=8.29 Hz, 2H) MS found for C$_{18}$H$_{27}$BCl$_2$N$_2$O$_4$ m/z[399.2, (M−18+1), 381.2 (M−36+1)].

Example 96-A

Preparation of 2-amino-6-borono-2-(1-(2-fluoro-4,5-dimethoxybenzyl)piperidin-4-yl)hexanoic acid dihydrochloride

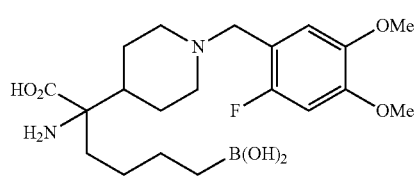

(96-A)

2-Amino-6-borono-2-(1-(2-fluoro-4,5-dimethoxybenzyl)piperidin-4-yl)hexanoic acid dihydrochloride is prepared in a manner analogous to that set forth in Example 87-A, except 2-fluoro-4,5-dimethoxybenzaldehyde is used as the aldehyde in step 6. $^1$H NMR (D$_2$O, 400 MHz) δ 6.97 (d, J=7.1 Hz, 1H), 6.89 (d, J=7.1 Hz, 1H), 4.02 (s, 2H), 3.82 (s, 3H), 3.79 (s, 3H), 3.47-3.34 (m, 2H), 2.85-2.69 (m, 2H), 2.05-1.90 (m, 2H), 1.85 (s, 3H), 1.81-1.61 (m, 4H), 1.45-1.22 (m, 4H), 1.20-1.08 (m, 1H), 0.72 (t, J=8.3 Hz, 2H). MS found for C$_{20}$H$_{32}$BFN$_2$O$_6$ m/z[409.2, (M−18+1), 391.2 (M−36+1)].

Example 97-A

Preparation of 2-amino-6-borono-2-(1-(2,4-dichlorobenzyl)piperidin-4-yl)hexanoic acid dihydrochloride

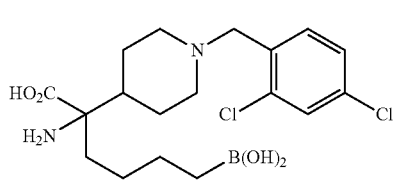

(97-A)

2-Amino-6-borono-2-(1-(2,4-dichlorobenzyl)piperidin-4-yl)hexanoic acid dihydrochloride is prepared in a manner analogous to that set forth in Example 87-A, except 2,4-dichlorobenzaldehyde is used as the aldehyde in step 6. $^1$H NMR (D$_2$O, 400 MHz) δ 7.66 (d, J=2.0 Hz, 1H), 7.53 (s, 1H), 7.47 (d, J=2.1 Hz, 1H), 4.46 (s, 2H), 3.71-3.61 (m, 2H), 3.26-3.12 (m, 2H), 2.18-2.07 (m, 2H), 1.90-1.76 (m, 3H), 1.61-1.47 (m, 1H), 1.46-1.19 (m, 3H), 1.25-1.11 (m, 1H), 0.77 (t, J=7.4 Hz, 2H). ESI$^+$/ESI$^-$ MS: obsd m/z 400.1 (M−18+H)$^+$, 381.1 (M−36+H)$^+$, 399.1 (M−18−1)$^-$, 381.1 (M−36−1)$^-$.

Example 98-A

Preparation of 2-amino-6-borono-2-(1-(naphthalen-1-ylmethyl)piperidin-4-yl)hexanoic acid dihydrochloride

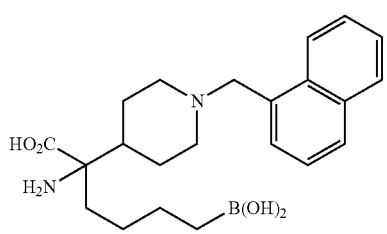

(98-A)

2-Amino-6-borono-2-(1-(naphthalen-1-ylmethyl)piperidin-4-yl)hexanoic acid dihydrochloride is prepared in a manner analogous to that set forth in Example 87-A, except 1-naphthaldehyde is used as the aldehyde in step 6. $^1$H NMR (D$_2$O, 400 MHz) δ 8.15 (d, J=8.4 Hz, 1H), 8.09 (d, J=8.4 Hz, 1H), 8.05 (d, J=8.4 Hz, 1H), 7.74-7.58 (m, 4H), 4.81 (s, 2H), 3.71-3.56 (m, 2H), 3.27-3.11 (m, 2H), 2.19-2.03 (m, 2H), 1.90-1.70 (m, 4H), 1.57-1.27 (m, 4H), 1.25-1.09 (m, 1H), 0.77 (t, J=7.6 Hz, 2H). ESI⁺/ESI⁻ MS: obsd m/z 381.1 (M−18+H)⁺, 363.1 (M−36+H)⁺, 379.1 (M−18−1)⁻.

Example 99-A

Preparation of 2-amino-6-borono-2-(1-(naphthalen-2-ylmethyl)piperidin-4-yl)hexanoic acid dihydrochloride

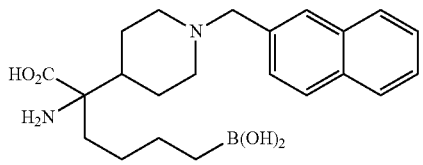

(99-A)

2-Amino-6-borono-2-(1-(naphthalen-2-ylmethyl)piperidin-4-yl)hexanoic acid dihydrochloride is prepared in a manner analogous to that set forth in Example 87-A, except 2-naphthaldehyde is used as the aldehyde in step 6. $^1$H NMR (D$_2$O, 400 MHz) δ 8.04-7.96 (m, 4H), 7.67-7.57 (m, 2H), 7.55 (d, J=8.4 Hz, 1H), 4.41 (s, 2H), 3.65-3.53 (m, 2H), 3.11-2.95 (m, 2H), 2.16-2.04 (m, 2H), 1.87-1.70 (m, 4H), 1.57-1.27 (m, 4H), 1.25-1.11 (m, 1H), 0.77 (t, J=7.6 Hz, 2H). ESI⁺/ESI⁻ MS: obsd m/z 381.1 (M−18+H)⁺, 363.1 (M−36+H)⁺, 379.1 (M−18−1)⁻.

Example 100-A

Preparation of 2-amino-6-borono-2-(1-(4-(trifluoromethoxy)benzyl)piperidin-4-yl)hexanoic acid dihydrochloride

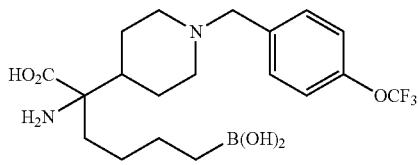

(100-A)

2-Amino-6-borono-2-(1-(4-(trifluoromethoxy)benzyl)piperidin-4-yl)hexanoic acid dihydrochloride is prepared in a manner analogous to that set forth in Example 87-A, except 4-(trifluoromethoxy)benzaldehyde is used as the aldehyde in step 6. $^1$H NMR (D$_2$O, 400 MHz) δ 7.55 (d, J=8.8 Hz, 2H), 7.41 (d, J=8.8 Hz, 2H), 4.28 (s, 2H), 3.60-3.50 (m, 2H), 3.06-2.92 (m, 2H), 2.14-2.04 (m, 2H), 1.88-1.73 (m, 4H), 1.56-1.28 (m, 4H), 1.25-1.11 (m, 1H), 0.77 (t, J=7.6 Hz, 2H). $^{19}$F NMR (D$_2$O, 400 MHz) δ−57.9 (s, 3F). ESI⁺/ESI⁻ MS: obsd m/z 415.2 (M−18+1)⁺, 397.2 (M−36+1)⁺, 413.2 (M−18−1)⁻.

Example 101-A

Preparation of 2-amino-6-borono-2-(1-propylpiperidin-4-yl)hexanoic acid dihydrochloride

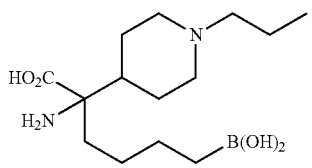

(101-A)

2-Amino-6-borono-2-(1-propylpiperidin-4-yl)hexanoic acid dihydrochloride is prepared in a manner analogous to that set forth in Example 87-A, except propionaldehyde is used as the aldehyde in step 6. $^1$H NMR (D$_2$O, 500 MHz) δ 3.51 (t, J=11.0 Hz, 2H), 2.91-2.88 (m, 2H), 2.86-2.81 (m, 2H), 2.10 (t, J=12.4 Hz, 1H), 2.00 (d, J=13.7 Hz, 1H), 1.83-1.67 (m, 4H), 1.59-1.52 (m, 2H), 1.46-1.37 (m, 1H), 1.30-1.20 (m, 3H), 1.07-1.00 (m, 1H), 0.77 (t, J=7.6 Hz, 3H), 0.62 (t, J=7.6 Hz, 2H). ESI MS found for C$_{14}$H$_{29}$BN$_2$O$_4$ m/z [301.5 (M+1) 1%, 283.5 (M+1−18) 17%, 265.5 (M+1−2×18) 100%, 581.9 (2M−1−18) 13%, 299.6 (M−1) 25%, 281.5 (M−1−18) 100%].

Example 102-A

Preparation of 2-amino-6-borono-2-(1-(3-phenylpropyl)piperidin-4-yl)hexanoic acid dihydrochloride

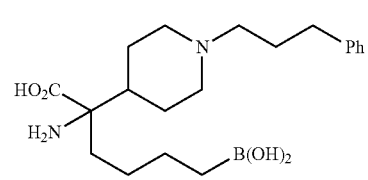

(102-A)

2-Amino-6-borono-2-(1-(3-phenylpropyl)piperidin-4-yl)hexanoic acid dihydrochloride is prepared in a manner analogous to that set forth in Example 87-A, except 3-phenylpropanal is used as the aldehyde in step 6. $^1$H NMR (D$_2$O, 500 MHz) δ 7.30 (d, J=7.6 Hz, 1H), 7.29 (d, J=7.6 Hz, 1H), 7.21-7.20 (m, 3H), 3.56 (t, J=11.6 Hz, 2H), 3.02-2.99 (m, 2H), 2.90-2.83 (m, 2H), 2.62 (t, J=7.6 Hz, 2H), 2.12-2.04 (m, 2H), 1.99-1.93 (m, 2H), 1.86-1.74 (m, 4H), 1.49-1.41 (m, 1H), 1.37-1.24 (m, 3H), 1.14-1.08 (m, 1H), 0.70 (t, J=7.6 Hz, 2H). ESI MS found for C$_{20}$H$_{33}$BN$_2$O$_4$ m/z [359.6 (M+1−18) 15%, 341.6 (M+1−2×18) 100%, 734.0 (2M−1−18) 15%, 375.6 (M−1) 11%, 357.6 (M−1−18) 100%]. Anal. Calcd for C$_{20}$H$_{33}$BN$_2$O$_4$×2HCl×2H$_2$O: C, 49.50; H, 8.10; N, 5.77. Found C, 49.50; H, 8.49; N, 5.86.

Example 103-A

Preparation of 2-amino-6-borono-2-(1-(3-(trifluoromethoxy)benzyl)piperidin-4-yl)hexanoic acid dihydrochloride

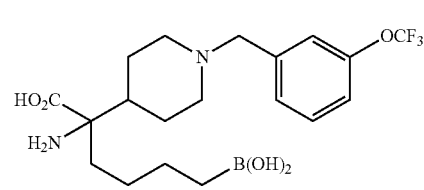

(103-A)

2-Amino-6-borono-2-(1-(3-(trifluoromethoxy)benzyl)piperidin-4-yl)hexanoic acid dihydrochloride is prepared in a manner analogous to that set forth in Example 87-A, except 3-(trifluoromethoxy)benzaldehyde is used as the aldehyde in step 6. $^1$H NMR (D$_2$O, 400 MHz) δ 7.54 (t, J=7.8 Hz, 1H), 7.45-7.38 (m, 3H), 4.14 (s, 2H), 3.51-3.37 (m, 2H), 2.92-2.76 (m, 2H), 2.11-1.98 (m, 2H), 1.86-1.65 (m, 4H), 1.50-1.28 (m, 4H), 1.24-1.10 (m, 1H), 0.77 (t, J=7.6 Hz, 2H). $^{19}$F NMR (D$_2$O, 400 MHz) δ−57.9 (s, 3F), ESI⁺/ESI⁻ MS: obsd m/z 415.1 (M−18+H)⁺, 397.1 (M−36+H)⁺, 413.1 (M−18)⁻.

Example 104-A

Preparation of 2-amino-2-(1-(benzo[b]thiophen-3-ylmethyl)piperidin-4-yl)-6-boronohexanoic acid dihydrochloride

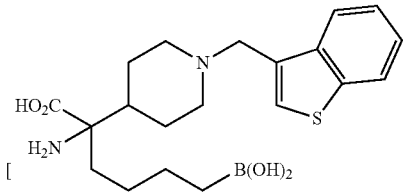

(104-A)

2-Amino-2-(1-(benzo[b]thiophen-3-ylmethyl)piperidin-4-yl)-6-boronohexanoic acid dihydrochloride is prepared in a manner analogous to that set forth in Example 87-A, except benzo[b]thiophene-3-carbaldehyde is used as the aldehyde in step 6. $^1$H NMR (D$_2$O, 400 MHz) δ 8.05 (d, J=7.7 Hz, 1H), 7.95-7.92 (m, 2H), 7.58-7.47 (m, 2H), 4.61 (s, 2H), 3.70-3.60 (m, 2H), 3.21-3.08 (m, 2H), 2.16-2.05 (m, 2H), 1.92-1.74 (m, 4H), 1.58-1.26 (m, 4H), 1.23-1.10 (m, 1H), 0.77 (t, J=7.6 Hz, 2H). ESI$^+$/ESI$^-$ MS: obsd m/z 387.1 (M−18+H)$^+$, 369.1 (M−36+H)$^+$, 385.1 (M−18−1)$^-$.

Example 105-A

Preparation of 3-((4-(1-amino-5-borono-1-carboxypentyl)piperidin-1-yl)methyl)benzoic acid dihydrochloride

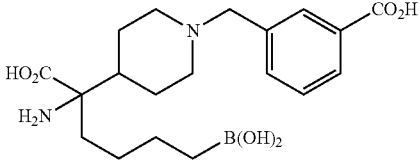

(105-A)

3-((4-(1-Amino-5-borono-1-carboxypentyl)piperidin-1-yl)methyl)benzoic acid dihydrochloride is prepared in a manner analogous to that set forth in Example 87-A, except tert-butyl 3-formylbenzoate is used as the aldehyde in step 6. $^1$H NMR (D$_2$O, 400 MHz) δ 7.84 (d, J=8.7 Hz, 1H), 7.79 (s, 1H), 7.52-7.42 (m, 2H), 4.25 (s, 2H), 3.55-3.43 (m, 2H), 3.05-2.89 (m, 2H), 2.09-1.79 (m, 2H), 1.83 (s, 3H), 1.80-1.65 (m, 6H), 1.49-1.35 (m, 1H), 1.35-1.71 (m, 1H), 1.14-0.99 (m, 1H), 0.67 (t, J=8.3 Hz, 2H). MS found for C$_{19}$H$_{29}$BN$_2$O$_6$ m/z [375.1, (M−18+1), 357.1 (M−36+1)].

Example 106-A

Preparation of 2-amino-6-borono-2-(1-(3-cyanobenzyl)piperidin-4-yl)hexanoic acid dihydrochloride

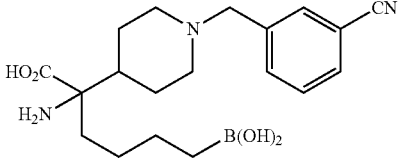

(106-A)

2-Amino-6-borono-2-(1-(3-cyanobenzyl)piperidin-4-yl)hexanoic acid dihydrochloride is prepared in a manner analogous to that set forth in Example 87-A, except 3-formylbenzonitrile is used as the aldehyde in step 6. $^1$H NMR (D$_2$O, 400 MHz) δ 7.82-7.76 (m, 2H), 7.69 (d, J=7.4 Hz, 1H), 7.56 (t, J=8.0 Hz, 1H), 4.19 (s, 2H), 3.49-3.36 (m, 2H), 2.91-2.78 (m, 2H), 2.06-1.94 (m, 2H), 1.81 (s, 3H), 1.80-1.62 (m, 4H), 1.46-1.19 (m, 4H), 1.16-1.03 (m, 1H), 0.69 (t, J=8.29 Hz, 2H). MS found for C$_{19}$H$_{28}$BN$_3$O$_4$ m/z[356.2 (M−18+1), 338.2 (M−36+1)].

Methods and Uses

Inventive Formula I and Formula II compounds are useful for inhibiting the expression or activity of arginase I, arginase II or a combination of these enzymes. The enzymes of the arginase family play an important role in regulating the physiological levels of the L-arginine, a precursor of the signaling molecule nitric oxide (nitric oxide (NO)), as well as in regulating levels of L-ornithine, a precursor of certain polyamines that are important physiological signal transducers.

More specifically, the invention provides methods and uses for inhibiting arginase I, arginase II, or a combination thereof in a cell, comprising contacting the cell with at least one compound according to Formula I or Formula II, or composition thereof as described herein. In some embodiments, the invention provides a method for the treatment or prevention of a disease or condition associated with expression or activity of arginase I, arginase II, or a combination thereof in a subject.

For instance, the disease or condition is selected from the group consisting of heart disease, hypertension, sexual disorders, gastric disorders, autoimmune disorders, parasitic infections, pulmonary disorders, smooth muscle relaxation disorders and hemolytic disorders.

More specifically, hypertension includes systemic hypertension, pulmonary arterial hypertension (PAH), and pulmonary arterial hypertension in high altitude.

Exemplary sexual disorders are disease or conditions selected from the group consisting of Peyronie's Disease and erectile dysfunction (ED).

In one embodiment an arginase inhibitor in accordance with the present invention is suitable for treating a pulmonary disorder selected from the group consisting of chemically-induced lung fibrosis, idiopathic pulmonary fibrosis, cystic fibrosis, chronic obstructive pulmonary disease (COPD.

Compounds in accordance with the present invention are also useful for treating gastrointestinal disorders, such as diseases or conditions selected from the group consisting of gastrointestinal motility disorders, gastric cancers, reduced hepatic blood flow disorders, inflammatory bowel disease, Crohn's disease, ulcerative colitis, and gastric ulcers.

The transport of organs increases the risk of ischemia reperfusion (IR) injury, such as liver IR, kidney IR, and myocardial IR. Formula I or Formula II compounds in accordance with the present invention are useful in protecting organs during organ transport.

In another embodiment, inhibitors of arginase in accordance with the present invention are used to treat hemolytic disorders selected from the group consisting of paroxysmal nocturnal hemoglobinuria (PNH), sickle-cell disease, thalassemias, hereditary spherocytosis and stomatocytosis, microangiopathic hemolytic anemias, pyruvate kinase deficiency, ABO mismatch transfusion reaction, paroxysmal cold hemoglobinuria, severe idiopathic autoimmune hemolytic anemia, infection-induced anemia, cardiopulmonary bypass, mechanical heart valve-induced anemia and chemical induced anemia. In addition, the compounds described herein are useful in the treatment of malaria.

The inventive compounds are useful in the treatment of autoimmune diseases selected from the group consisting of encephalomyelitis, multiple sclerosis, anti-phospholipid syndrome 1, autoimmune hemolytic anaemia, chronic inflammatory demyelinating polyradiculoneuropathy, dermatitis herpetiformis, dermatomyositis, myasthenia gravis, pemphigus, rheumatoid arthritis, stiff-person syndrome, type 1 diabetes and ankylosing spondylitis. In another embodiment, Formulae I or II compounds are useful for treating immune disorders selected from the group consisting of immune-response, T-cell dysfunction, such as myeloid-derived suppressor cell (MDSC) mediated T-cell dysfunction, human immunodeficiency virus (HIV) and autoimmune encephalomyelitis.

Other exemplary disease conditions for which compounds described herein are candidate therapeutics are African sleeping sickness, Chagas' disease, smooth muscle relaxation disorders, for example, disorders of smooth muscle selected from the group consisting of a gastrointestinal smooth muscle, anal sphincter smooth muscle, esophageal sphincter muscle, corpus cavernosum, sphincter of Oddi, arterial smooth muscle, heart smooth muscle, pulmonary smooth muscle, kidney smooth muscle, uterine smooth muscle, vaginal smooth muscle, cervical smooth muscle, placental smooth muscle, and ocular smooth muscle disorder.

The increased levels of arginase in certain cancer patients implicates a therapeutic role for the inventive arginase inhibitors in the treatment of certain cancers, for example, renal cell carcinoma, prostate cancer, colorectal cancer, breast cancer, skin cancer, lung cancer, ovarian cancer, gastric cancer.

Advantageously, the compounds of the invention are especially useful in treating conditions or disorders selected from the group consisting of arthritis, myocardial infarction and atherosclerosis, renal disease, asthma, inflammation, psoriasis, leishmaniasis, sickle cell disease (SCD), neurodegenerative diseases, wound healing, such as infected and uninfected wound healing, hepatitis B virus (HBV), H. pylori infections, fibrotic diseases such as cystic fibrosis, candidiasis, periodontal disease, keloids, adenotonsilar disease, cerebral vasospasm, and Goodpasture's syndrome.

In some embodiments, the subject receiving treatment is a mammal. For instance, the methods and uses described herein are suitable for medical use in humans. Alternatively, the methods and uses are also suitable in a veterinary context, wherein the subject includes but is not limited to a dog, cat, horse, cow, sheep, lamb and reptile.

More specific descriptions of diseases and conditions follow below.

Erectile Dysfunction

The observation that there are differences in the activity of arginase in the penis of young mice versus older mice led to the conclusion that arginase may play a role in erectile dysfunction (ED). In this context, Champion et. al., (Am. J. Physiol. Heart Circ. Physiol. 292:340-351, (2006) and Biochem. and Biophys. Research Communications, 283:923-27, (2001)), observed an increase of mRNA expression levels and arginase protein in aged mice along with a reduction in the activity of constitutively active NOS.

Nitric oxide is implicated in nonadrenergic, noncholinergic neurotransmission that leads to smooth-muscle relaxation in the corpus cavernosum enabling penile erection (New England Journal of Medicine, 326, (1992)), Hence, erectile dysfunction can often be treated by elevating penile tissue nitric oxide (NO) levels. Such an elevation in tissue nitric oxide (NO) levels can be achieved by inhibiting arginase activity in penile tissue of aged subjects. Stated differently, arginase has been postulated to deplete the pool of free L-arginine available to NOS in cells which results in lower levels of nitric oxide (NO) and erectile dysfunction. See, Christianson et. al., (Acc. Chem. Res., 38:191-201, (2005)), and (Nature Structural Biol., 6(11):1043-1047, (1999)) Inhibitors of arginase, therefore, can play a role in the treatment of erectile dysfunction.

Pulmonary Hypertension

It has been proposed that alterations in arginine metabolism are involved in the pathogenesis of pulmonary hypertension (Xu et al., FASEB J., 18:1746-48, 2004). The proposition is based in part on the finding that arginase II expression and arginase activity are significantly elevated in pulmonary artery endothelial cells derived from lung explants of patients with class I pulmonary hypertension.

Additionally, secondary pulmonary hypertension is emerging as one of the leading causes of mortality and morbidity in patients suffering from hemolytic anemias, such as thalassemia and sickle cell disease. The underlying cause for secondary pulmonary hypertension is impaired nitric oxide bioavailability due to release of arginase following hemolysis which decreases the pool of free arinine that is required for nitric oxide (NO) synthesis. Accordingly, inhibition of arginase activity can provide a potential therapeutic avenue for treating pulmonary hypertension.

Hypertension

Xu, W. et al., *FASEB* 2004, 14, 1746-8 proposed a fundamental role of arginase II in blood pressure regulation. In this context, high levels of vascular arginase are correlated to concomitant reduction of vascular nitric oxide (NO) in hypertensive animals. For instance, up-regulation of arginase activity precedes a rise in blood pressure in rats that were genetically predisposed to hypertension (i.e., spontaneously hypertensive rats), but administration of the anti-hypertensive agent hydralazine lowered blood pressure with a decrease in the expression levels of vascular arginase, thereby indicating a strong correlation between the arginase activity and blood pressure (Berthelot et al. Life Sciences, 80:1128-34, (2008). Similar administration of the known arginase inhibitor $N^{\omega}$-hydroxy-nor-L-arginine (nor-NOHA) lowered blood pressure and improved the vascular response of resistance vessels to blood flow and pressure in spontaneously hypertensive animals, thereby highlighting inhibitors of arginase as candidate therapeutics for treating hypertension (Demougeot et al., (J. Hypertension, 26:1110-18, (2008).

Arginase also plays a role in reflex cutaneous hypertension by lowering the cellular levels of nitric oxide (NO). Nitric oxide causes vasodilation and levels of nitric oxide (NO) are normally elevated or lowered to maintain blood pressure at physiologically acceptable levels. Kenny et al., (J. of Physiology 581 (2007) 863-872), hypothesized that reflex vasodilation in hypertensive subjects can attenuate arginase inhibition, thereby implicating a role for arginase inhibitors for the treatment of hypertension.

Asthma

Arginase activity is also associated with airway hyperresponsiveness in asthma. For example, arginase I is upregulated in human asthmatics and in mice suffering from acute and chronic asthma, whilst levels of arginase II and NOS isoforms remain unchanged (Scott et al., Am. J. Physiol. Lung Cell Mol. Physiol. 296:911-920 (2009)). Furthermore, methacholine induced responsiveness of the central airways in the murine chronic model attenuated upon the administration of the arginase inhibitor S-(2-boronoethyl)-L-cysteine. The similarity between expression profiles of ARG I in humans and in mice having chronic asthma indicates that compounds capable of inhibiting arginase activity are candidate therapeutics for treating asthma.

Other lines of evidence reveal further correlations between increased activity of arginase in asthmatic lung tissue and disease progression, such as an upregulation for genes related to the metabolism of cationic amino acids, including arginase I and II in mice having asthma (Rothenberg et al., (J. Clin. Invest., 111:1863-74 (2003), and Meurs et. al., (Expert Opin. Investig Drugs, 14 (10:12211231, (2005)).

Further, levels of all amino acids are lower in the plasma of asthmatics, but the levels of arginine are significantly lower in plasma compared to that of a normal subject (Morris et al., (Am. J. Respir. Crit. Care Med., 170:148-154, (2004)). Thus, arginase activity is significantly increased in the plasma from an asthmatic, in which elevated levels of arginase activity may contribute to the lower bioavailability of plasma arginine that creates an nitric oxide (NO) deficiency, which is responsible for promoting hyperreactive airways in asthmatics.

Inflammation

Arginase activity also is associated with autoimmune inflammation (Chen et al., Immunology, 110:141-148, (2003)). The authors identified upregulation in the expression levels of the ARG I gene in murine spinal cells from animals undergoing experimental autoimmune encephalomyelitis (EAE). Administration of the arginase inhibitor amino-6-boronohexanoic acid (ABH), however, resulted in the animals developing a much milder form of EAE than in control animals. These results implicate inhibitors of arginase in a therapeutic role for treating autoimmune encephalomyelitis.

Moreover, Horowitz et al., (American J. Physiol Gastrointestinal Liver Physiol., 292:G1323-36, (2007)), suggest a role for arginase enzymes in vascular pathophysiology. For example, these authors indicate a loss of nitric oxide (NO) production in chronically inflamed gut blood vessels in patients suffering from irritable bowel disease (IBD), Crohn's disease and ulcerative colitis. The loss in nitric oxide (NO) production correlated with an upregulation of arginase expression and activity that reduced levels of arginine preventing nitric oxide synthase (NOS), from synthesizing nitric oxide (NO) Inhibitors of arginase activity, therefore, may be candidate therapeutics for treating vascular pathophysiology.

Ischaemia Reperfusion

Arginase inhibition is also suggested to play a cardioprotective role during ischaemia reperfusion. More specifically, inhibition of arginase protects against myocardial infarction by a mechanism that may be dependent on NOS activity and the consequent bioavailability of nitric oxide (NO) (Pernow et al., (Cardiovascular Research, 85:147-154 (2010)).

Myocardial Infarction and Artherosclerosis

Arginase I polymorphism is associated with myocardial infarction along with an increased risk of developing carotid artery intima media thickness that is considered to be a reliable indicator of arthrosclerosis as well as of other coronary arterial diseases (Brousseau et al., (J. Med Genetics, 44:526-531, (2007)). Increased arginase activity elevates levels of ornithine that is biochemically involved in promoting the formation of the matrix and cellular components of artherosclerotic plaque. Id. Thus, arginase inhibitors may serve as candidate therapeutics for treating artherosclerosis. Berkowitz et al., (Circulation Res. 102, (2008)), implicated a role for ARGII in the formation of plaque and atherosclerosis. Oxidation of LDLP that accompanies plaque formation increases arginase activity and lower nitric oxide (NO) levels in endothelial cells. In particular, levels of ARGII are elevated in artherosclerotic mice, indicating a role for inhibitors of arginase as candidate therapeutics for treating artherosclerosis.

Additionally, studies by Ming et. al., (Current Hypertension Reports., 54:54-59, (2006)), indicate that an upregulation of arginase rather than endothelial nitric oxide (NO) dysfunction plays an important role in cardiovascular disorders, including artherosclerosis. That arginase is involved in cardiovascular diseases is further supported by the observation ARGI and ARGII activity is upregulated in cardiac myocytes which in turn negatively impacts NOS activity and myocardial contractility. (See, Margulies et. al., Am. J. Physiol. Heart Circ. Physiol., 290:1756-62, (2006)).

Immune Response

The arginine/nitric oxide (NO) pathway may also play a role in immune response, such as after organ transplants. For instance, it was postulated that reperfusion of an orthotopic liver transplant graft caused a significant increase in ornithine levels due to upregulation of arginase activity in the graft (Tsikas et al., (Nitric oxide, 20:61-67, (2009)). The elevated levels of hydrolytic and proteolytic enzymes in the graft may result in a less favorable outcome for the grafted organ. Thus, inhibiting the arginase enzymes may present an alternate therapeutic avenue for improving the outcome of a transplant.

Psoriasis

Arginase has been implicated to play a role in the pathogenesis of psoriasis. For example, ARG I is highly expressed in hyperproliferative psoriasis, and in fact, it is responsible for down regulation of nitric oxide (NO) an inhibitor of cell proliferation, by competing for the common substrate L-arginine as postulated by D. Bruch-Gerharz et al. *American Journal of Pathology* 162(1) (2003) 203-211. More recent work by Abeyakirthi et al. (British J. Dermatology, (2010)), and Berkowitz et al, (WO/2007/005620) support the finding of low nitric oxide (NO) levels in psoriatic keratinocytes. Abeyakirthi et al, found that psoriatic keratinocytes were poorly differentiated and hyperproliferative. The poor differentiation was postulated to result from low levels of nitric oxide (NO), not because of poor expression of NOS, but rather the over expression of arginase that competes with NOS for substrate L-arginine. Thus, inhibition of arginase may provide therapeutic relief from psoriasis.

Wound Healing

Under normal physiological conditions, nitric oxide (NO) plays an important role in promoting wound healing. For example, Hulst et al., (Nitric Oxide, 21:175-183, (2009)), studied the role of ARGI and ARG II in wound healing. Immediately following injury, it is desirable to elevate tissue levels of nitric oxide (NO) so as to promote angiogenesis and cell proliferation that are important for healing Inhibitors of arginase may therefore find use as therapeutics to treat wounds because such compounds would elevate tissue levels of nitric oxide (NO). Further support for the use of arginase inhibitors as candidate therapeutics for treating wounds was provided by South et al. (Experimental Dermatology, 29:664-668 (2004)), who found a 5-fold increase in arginase I in chronic wounds such as skin erosions and blisters.

Cystic Fibrosis

Cystic fibrosis (CF) is a multisystem disorder caused by mutations of the cystic fibrosis transmembrane conductance regulator (CFTR) gene. The common symptoms of CF are persistent pulmonary infection, difficulty in breathing, pancreatic insufficiency, and elevated sweat chloride levels. CF can be fatal if untreated, with pulmonary diseases, resulting from mucus build-up and decreased mucociliary clearance, being the leading cause of morbidity and mortality.

It has been asserted that patients with cystic fibrosis (CF) have increased plasma and sputum arginase activity, with an accompanying decrease in the levels of plasma 1-arginine (H. Grasemann et al., *Am. J. Respir. Crit. Care Med.* 172(12) (2005) 1523-1528. The increased arginase activity, however, results in lower physiological levels of nitric oxide (NO) that can cause airway obstruction decreased pulmonary function in patients suffering from cystic fibrosis (CF).

Impaired electrical field induced-stimulation of smooth muscle relaxation in the airway of a mouse model of CF and the administration of 1-arginine and NO reversed this effect as proposed by M. Mhanna et al. *Am. J. Respir. Cell Mol. Biol.* 24(5) (200) 1 621-626. Graesmann et al., found a positive correlation exists between pulmonary function and exhaled NO and NO metabolite concentrations in the sputum of CF patients (Grasemann, H; Michler, E; Wallot, M; Ratjen, F., *Pediatr Pulmonol.* 1997, 24, 173-7).

Taken together, theses results indicate that increased Arginase activity in CF contributes to the NO deficiency and pulmonary obstruction in CF by limiting the availability of 1-arginine to NOS. Thus, inhibitors of arginase activity are candidate therapeutics for treating cystic fibrosis (CF)

Organ Protection

Another therapeutic avenue for compounds in accordance with the present invention is protecting organs during transport from donor to a site where they will be transplanted into a recipient. Ischemic reperfusion injury (IR) due to exposure of the transplant organs to a period of warm ischemia (time from donor until flushed with preservation media), and cold ischemia (hypothermic preservation) is frequently observed in patients undergoing transplant surgery. Ischemic reperfusion injury (IR) and accompanying primary graft dysfunction and/or acute or chronic rejection results due to alteration in the cellular activity of the L-Arginine/NO pathway.

It was proposed that Arginase 1 and arginase 2 are released from apoptotic endothelial cells and kidney cells within the first 24 hours of organ removal from the body. To counteract the released arginase, L-Arginine is added to preservation media. Results with canine kidney transplants indicate that addition of L-arginine reduced the incidence and severity of ischemia, resulted in post-transplant with lower MDA levels at 1 hour, and lowered BUN & Serum creatinine levels during the first 72 hrs. See Erkasap, S; Ates, E., *Nephrol Dial Transplant.* 2000, 15, 1224-7.

Similar results were observed for canine lung grafts over a 24 hour period when lungs were preserved in the University of Wisconsin solution supplemented with L-Arginine. Yen et al., observed that the addition of L-arginine to the preservation medium increased pulmonary endothelial protection and lowered the incidence of ischemia when compared to a control that is preserved in medium that does not contain L-arginine (Chu, Y; Wu, Y. C.; Chou, Y. C.; Chueh, H. Y, Liu H P, Chu J J, Lin P J., *J Heart Lung Transplant.* 2004, 23, 592-8).

Koch et al. stated that improved myocardial contractility and relaxation in heart muscle of rats following transplantation when hearts were preserved in HTK solution having L-Arginine and N-alpha-acetyl-histidine (Koch A, Radovits T, Loganathan S, Sack F U, Karck M, Szabó G B., *Transplant Proc.* 2009, 41, 2592-4).

Addition of an arginase inhibitor, therefore, can be a candidate therapeutic for preventing and/or reducing the incidence and risk of ischemic reperfusion injury by a synergistically increasing the organ protective effect of the preservation media. Given the low number of available organs that are suitable for transplant and the loss and injury of organs due to the onset of ischemia, arginase inhibitors in accordance with the present invention can find use as therapeutics for preserving organs, increasing organ availability by reducing the amount of ischemic reperfusion injury during organ transport.

Leishmaniasis

Leishmaniasis is caused by a protozoan and manifests as cutaneous leishmaniasis (i.e., skin infection causing hypopigmented nodules) and visceral lieshmaniasis (more severe affecting internal organs). Arginase it postulated to play a role in disease progression since the parasite relies on arginase for the synthesis of cellular polyamines that are essential for pathogenesis Inhibition of arginase, therefore, would reduce cellular parasitic burden and promote increased nitric oxide (NO) levels enhancing parasitic clearance. See Liew F Y et al. *Eur J Immunol* 21 (1991) 2489, Iniesta V et al. *Parasite Immunol.* 24 (2002) 113-118, and Kane M M et al. *J. Immunol.* 166 (2001) 1141-1147. Compounds according to Formula I or Formula II, therefore can be used as therapeutics for treating liesmaniasis.

Myeloid Derived Suppressor Cells (MDSC)

MDSC's are potent immune modulators that limit immune responses through several pathways, such as, L-arginine depletion via arginase 1 release into the microenvironment (Rodriguez 2009 Cancer Res), MHC restricted suppression (Nagaraj S, Gupta K, Pisarev V, Kinarsky L, Sherman S, Kang L, Herber D L, Schneck J, Gabrilovich D I., *Nat. Med.* 2007, 13, 828-35), induction of T regulatory cells (Serafini P, Mgebroff S, Noonan K, Borrello I., *Cancer Res.* 2008, 68, 5439-49), and production of IL10 (Rodrigues J C, Gonzalez G C, Zhang L, Ibrahim G, Kelly J J, Gustafson M P, Lin Y, Dietz A B, Forsyth P A, Yong V W, Parney I F., *Neuro Oncol.* 2010, 12, 351-65) (Sinha P, Clements V K, Bunt S K, Albelda S M, Ostrand-Rosenberg S., *J Immunol.* 2007, 179, 977-83), for instance.

It is postulated that tumor development is accompanied by an increase in the number of MDSC's both peripherally and infiltrated within tumors. See Almand B, Clark J I, Nikitina E, van Beynen J, English N R, Knight S C, Carbone D P, Gabrilovich D I., *J Immunol.* 2001, 166, 678-89 and Gabrilovich D., *Nat Rev Immunol.* 2004, 4, 941-52. Treatment of tumor bearing mice with established chemotherapeutics such as gemcitabine and 5-Fluorouracil eliminates MDSC immunesuppression and results in delayed tumor growth. See Le H K, Graham L, Cha E, Morales J K, Manjili M H, Bear H D., *Int Immunopharmacol.* 2009, 9, 900-9 and Vincent J, Mignot G, Chalmin F, Ladoire S, Bruchard M, Chevriaux A, Martin F, Apetoh L, Rébé C, Ghiringhelli F., *Cancer Res.* 2010, 70, 3052-61, respectively. Moreover, inhibition of arginase 1 enhanced antitumor immunity by reducing MDSC function. Thus, inhibitors of arginase, such as compounds in accordance with the present invention reduce or delay tumor growth and can be used in combination with established anti-cancer agents in the treatment of cancer.

Helicobacter pylori (*H. pylori*)

Helicobacter pylori (*H. pylori*) is a Gram-negative bacterium that colonizes the human gastric mucosa. Bacterial colonization can lead to acute or chronic gastritis and is highly associated with peptic ulcer disease and stomach cancer. The observation that the addition of L-arginine to co-culture of *H. pylori* and macrophages increased nitric oxide (NO) mediated killing of the *H. pylori* (Chaturvedi R, Asim M, Lewis N D, Algood H M, Cover T L, Kim P Y, Wilson K T., *Infect Immun.* 2007, 75, 4305-15), supports the hypothesis that bacterial arginase competes with macrophage arginase for free arginine that is required for nitric oxide (NO) synthesis. See Gobert A P, McGee D J, Akhtar M, Mendz G L, Newton J C, Cheng Y, Mobley H L, Wilson K T., *Proc Natl Acad Sci USA.* 2001, 98, 13844-9. L-arginine is required for T-cell activation and for the rapid clearance of bacteria from infected cells. By depleting the pools of free L-arginine in vivo, *H. pyroli* reduces arginine-induced CD3zeta expression on T-cells and prevents T-cell activation and proliferation. See Zabaleta J, McGee D J, Zea A H, Hernandez C P, Rodriguez P C, Sierra R A, Correa P, Ochoa A C., *J. Immunol.* 2004, 173, 586-93.

The inhibition of bacterial arginase using the known inhibitor NOHA, however, reestablished CD3 expression on T-cells and (Zabaleta J 2004), and enhanced production of NO by macrophages, thus, promoting macrophage mediated clearance of bacteria from infected cells. See Chaturvedi R, Asim M, Lewis N D, Algood H M, Cover T L, Kim P Y, Wilson K T., *Infect Immun.* 2007, 75, 4305-15.

Furthermore, Lewis et al., have suggested a role for arginase II in *H. pyroli* infection. For example, these authors indicate that argII−/− primary macrophages incubated with *H. pylori* extracts showed enhanced NO production and correspondingly an increased (~15%) NO-mediated killing of bacterial cells (Lewis N D, Asim M, Barry D P, Singh K, de Sablet T, Boucher J L, Gobert A P, Chaturvedi R, Wilson K T., *J Immunol.* 2010, 184, 2572-82) Inhibitors of arginase activity, therefore, may be candidate therapeutics for treating vascular pathophysiology Inhibitors of arginase activity, therefore, may be candidate therapeutics for treating *H. pyroli* infections and for treating gastric ulcers, peptic ulcers and cancer.

Sickle Cell Disease (SCD)

Sickle-cell disease (SCD), or sickle-cell anaemia, or drepanocytosis, is a genetic blood disorder, characterized by red blood cells that assume an abnormal, rigid, sickle shape. Sickling decreases the cells' flexibility and increases the risk of complications. An increase in the concentration of reactive oxygen species (ROS) in circulation causes adherence of blood cells and consumption of NO that results in poor vasodilation or the inability of blood vessels to vasodilate. The inability to vasodilate along with the increased adherence of blood cells in SCD results in vaso occlusive crisis and pain.

Low levels of plasma L-arginine are normally detected in patients with SCD (Morris C R, Kato G J, Poljakovic M, Wang X, Blackwelder W C, Sachdev V, Hazen S L, Vichinsky E P, Morris S M Jr, Gladwin M T., *JAMA.* 2005, 294, 81-90) According to these authors, lysis of red blood cells (RBC's) in patients suffering from SCD causes the release of arginase and a subsequent lowering of physiological L-Arginine levels. This sequence of biological events lowers physiological concentrations of nitric oxide (NO), a signaling molecule that plays a role in vasodilation. Other biological events also limit NO bioavailabilty. These include, for example, the uncoupling of nitric oxide synthase (NOS), and the subsequent decrease in physiological NO levels, as well as the reaction of superoxide ($O^{-2}$) reactive oxygen species with NO to sequester the latter as $ONOO^-$.

Based on theses observations, inhibitors of arginase, especially arginase I inhibitors are being proposed by the present inventors as candidate therapeutics for patients with sickle cell disease. As stated above, SCD causes the uncoupling of eNOS due to low physiological levels L-arginine Inhibition of arginase present in the blood circulation, however, may address this problem by increasing the physiological levels L-arginine, the substrate of endothelial nitric oxide synthase (eNOS). This sequence of events, importantly, are proposed by the present inventors to enhance endothelial function and relieve vasoconstriction associated with SCD.

Human Immunodeficiency Virus (HIV)

HIV is caused by virus that infects CD4+ helper T cells and causes severe lymphopaenia that predisposes the infected individuals to opportunistic infection. Although, anti-retroviral therapy (ART) is extensively used to combat HIV infection, the wide spread use of anti-retroviral drugs has resulted in the generation of resistant strains of HIV.

A correlation exists between the activity of arginase in patients suffering from HIV and the severity of HIV disease. That is increased arginase activity has been correlated to increased viral titres in HIV patients. These patients also show decrease serum arginine levels as well as decreased levels of CD4+/CD8+ cells.

Taken together, these observations suggest a role for arginase inhibitors, such as compounds according to Formulae I or II as candidate therapeutics in the treatment of HIV infection.

Chronic Hepatitis B Virus (HBV)

Chronic hepatitis B infection is a viral disease that is transmitted by contact with infected body fluids. Chronic HBV infections are characterized by inflammation of the liver and jaundice and if left untreated can cause cirrhosis of the liver that can progresses to form hepatocellular carcinomas. Antiviral drugs currently used, however, have low efficacy against chronic HBV infections. Serum and liver homogenates of patients with chronic HBV infections show reduced levels of arginine and increased arginase activity. For infected patients moreover, the increased arginase activity is correlated to an impaired cytotoxic T-lymphocytes (CTL) response with reduced IL-2 production and CD3z expression.

Replenishing serum arginine to physiologically acceptable levels, however, reconstituted CD3z and IL-2 expression, implicating a role for arginase inhibitors as potential therapeutics in the treatment of chronic HBV infections.

Routes of Administration and Dosing Regimen

Despite ample evidence associating arginase inhibition with therapies of various diseases and conditions, only a limited number of compounds are known that are capable of inhibiting arginase activity. The present invention therefore provides compounds and their pharmaceutical compositions that are useful in treating a subject suffering from such a disease or condition, as more generally set forth above.

The compound or composition of the invention can be formulated as described hereinabove and is suitable for administration in a therapeutically effective amount to the subject in any number of ways. The therapeutically effective amount of a Formula I or Formula II compound can depend upon the amounts and types of excipients used, the amounts and specific types of active ingredients in a dosage form, and the route by which the compound is to be administered to patients. However, typical dosage forms of the invention comprise a compound, or a pharmaceutically acceptable salt, solvate, hydrate, isomer, or prodrug thereof.

Typical dosage levels for Formula I or Formula II compounds generally range from about 0.001 to about 100 mg per kg of the patient's body weight per day which can be administered in single or multiple doses. An exemplary dosage is about 0.01 to about 25 mg/kg per day or about 0.05 to about 10 mg/kg per day. In other embodiments, the dosage level is from about 0.01 to about 25 mg/kg per day, about 0.05 to about 10 mg/kg per day, or about 0.1 to about 5 mg/kg per day.

A dose typically ranges from about 0.1 mg to about 2000 mg per day, given as a single once-a-day dose or, alternatively, as divided doses throughout the day, optionally taken with food. In one embodiment, the daily dose is administered twice daily in equally divided doses. A daily dose range can be from about 5 mg to about 500 mg per day, such as, for example, between about 10 mg and about 300 mg per day. In managing the patient, the therapy can be initiated at a lower dose, perhaps from about 1 mg to about 25 mg, and increased if necessary up to from about 200 mg to about 2000 mg per day as either a single dose or divided doses, depending on the patient's global response.

Depending on the disease to be treated and the subject's condition, the compounds according to Formula I or Formula II may be administered by oral, parenteral (e.g., intramuscular, intraperitoneal, intravenous, ICV, intracisternal injection or infusion, subcutaneous injection or implant), inhalation, nasal, vaginal, rectal, sublingual, or topical (e.g., transdermal, local) routes of administration. The compounds can be formulated, alone or together, in suitable dosage unit formulations containing conventional non-toxic pharmaceutically acceptable carriers, adjuvants and vehicles, as described above, that are appropriate for each route of administration. The invention also contemplates administration of the compounds of the invention in a depot formulation, in which the active ingredient is released over a defined time period.

Inhibition of Arginase

The inventive compounds inhibit human arginase I (ARG I) and arginase II (ARG II) as evidenced by an ex vivo assay set forth by a published protocol (Baggio et al. *J. Pharmacol. Exp. Ther.* 1999, 290, 1409-1416). The assay established the concentration of inhibitor that is required to reduce arginase activity by 50% ($IC_{50}$).

Assay Protocol

Inhibition of arginase I (ARG I) and arginase II (ARG II) by Formula I and Formula II compounds is followed spectrophotometrically at 530 nm. The compound to be tested is dissolved in DMSO at an initial concentration 50-fold greater than its final concentration in the cuvette. 10 µl of the stock solution is diluted in 90 µl of the assay buffer that comprises 0.1M sodium phosphate buffer containing 130 mM NaCl, pH 7.4, to which is added ovalbumin (OVA) at a concentration of 1 mg/ml. Solutions of arginase I and II are prepared in 100 mM sodium phosphate buffer, pH 7.4 containing 1 mg/ml of OVA to give an arginase stock solution at a final concentration of 100 ng/ml.

To each well of a 96-well microtiter plate is add 40 µl of enzyme, 10 µl of an inventive compound and 10 µl of enzyme substrate (L-arginine+manganese sulfate). For wells that are used as positive controls, only the enzyme and its substrate are added, while wells used as negative controls contain only manganese sulfate.

After incubating the microtiter plate at 37° C. for 60 minutes, 150 µl of a urea reagent obtained by combining equal proportions (1:1) of reagents A and B is added to each well of the microtiter plate to stop the reaction. The urea reagent is made just before use by combining Reagent A (10 mM o-phthaldialdehyde, and 0.4% polyoxyethylene (23) lauryl ether (w/v) in 1.8 M sulfuric acid) with Reagent B (1.3 mM primaquine diphosphate, 0.4% polyoxyethylene (23) lauryl ether (w/v), 130 mM boric acid in 3.6 M sulfuric acid). After quenching the reaction mixture, the microtiter plate is allowed to stand for an additional 10 minutes at room temperature to allow color development. The inhibition of arginase is computed by measuring the optical density (OD) of the reaction mixture at 530 nm and normalizing the OD value to percent inhibition observed in the control. The normalized OD is then used to generate a dose-response curve by plotting the normalized OD values against log [concentration] and using regression analysis to compute the $IC_{50}$ values.

Table 2 below ranks the potency of Formula I compounds on a scale from 1 through 5, that is, the most potent compounds are designated as 1 and the least potent compounds being designated as 5. A similar potency analysis for Formula II compounds is illustrated in Table 2-A. Thus, a potency value of 1 refers to inventive compounds with $IC_{50}$ values in the range from 0.1 nM to 250 nM; a potency value of 2 refers to inventive compounds with $IC_{50}$ values in the range from 251 nM to 1000 nM; compounds having a potency value of 3 exhibit $IC_{50}$ values in the range from 1001 nM to 2000 nM; inventive compounds with $IC_{50}$ values in the range from 2001 nM to 5000 nM are assigned a potency value of 4, and compounds with $IC_{50}$ values above 5001 nM are assigned a potency value of 5.

TABLE 2

| Ex. # | Structure | Potency (ARG I)[a] | Potency (ARG II)[a] |
|---|---|---|---|
| 1 | 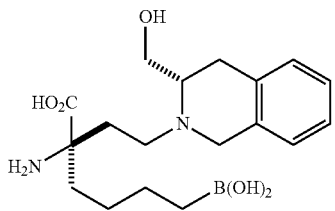 | 2 | 2 |
| 2 | 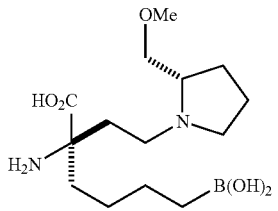 | 2 | 2 |
| 3 | 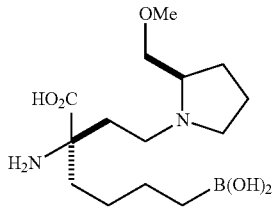 | 3 | 3 |

TABLE 2-continued

| Ex. # | Structure | Potency (ARG I)<sup>a</sup> | Potency (ARG II)<sup>a</sup> |
|---|---|---|---|
| 4 | (structure) | 2 | 2 |
| 5 | (structure) | 3 | 4 |
| 6 | (structure) | 2 | 3 |
| 7 | (structure) | 1 | 2 |
| 8 | (structure) | 3 | 4 |
| 9 | (structure) | 1 | 2 |
| 10 | (structure) | 1 | 2 |
| 11 | (structure) | 1 | 1 |

TABLE 2-continued
| Ex. # | Structure | Potency (ARG I)[a] | Potency (ARG II)[a] |
|---|---|---|---|
| 12 | 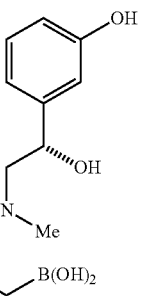 | 1 | 1 |
| 13 | 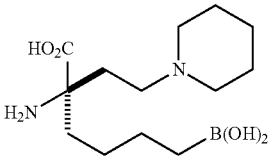 | 1 | 2 |
| 14 | 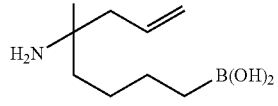 | 43 | 5 |
| 15 | 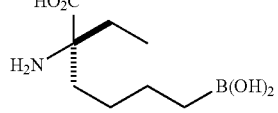 | 4 | 4 |
| 16 | 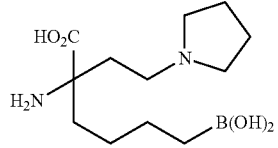 | 2 | 3 |
| 17 | 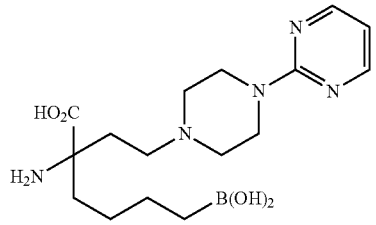 | 4 | 4 |
| 18 | 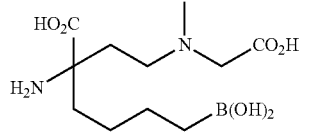 | 4 | 4 |
| 19 | 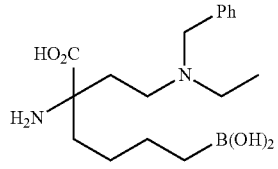 | 4 | 3 |

TABLE 2-continued

| Ex. # | Structure | Potency (ARG I)[a] | Potency (ARG II)[a] |
|---|---|---|---|
| 20 | (structure) | 4 | 4 |
| 21 | (structure) | 3 | 3 |
| 22 | (structure) | 2 | 2 |
| 23 | (structure) | 2 | 2 |
| 24 | (structure) | — | 4 |
| 25 | (structure) | 2 | 2 |
| 26 | (structure) | 2 | 2 |
| 27 | (structure) | 3 | 3 |

TABLE 2-continued

| Ex. # | Structure | Potency (ARG I)[a] | Potency (ARG II)[a] |
|---|---|---|---|
| 28 | 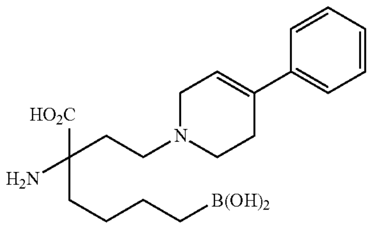 [SMILES: NC(CCCCB(O)O)(CCN1CC=C(c2ccccc2)CC1)C(=O)O] | 2 | 3 |
| 29 | 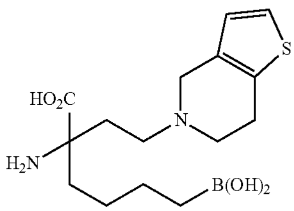 [SMILES: NC(CCCCB(O)O)(CCN1CCc2sccc2C1)C(=O)O] | 2 | 3 |
| 30 | 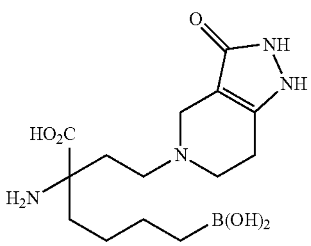 [SMILES: NC(CCCCB(O)O)(CCN1CCc2[nH][nH]c(=O)c2C1)C(=O)O] | 2 | 3 |
| 31 | 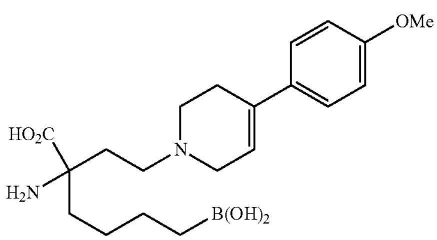 [SMILES: COc1ccc(C2=CCN(CCC(N)(CCCCB(O)O)C(=O)O)CC2)cc1] | 2 | 2 |
| 32 | 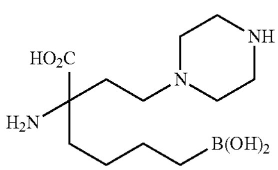 [SMILES: NC(CCCCB(O)O)(CCN1CCNCC1)C(=O)O] | — | 4 |
| 33 | 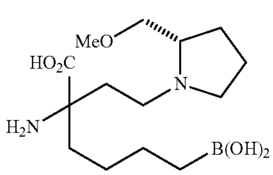 [SMILES: COC[C@@H]1CCCN1CCC(N)(CCCCB(O)O)C(=O)O] | 2 | 2 |
| 34 | 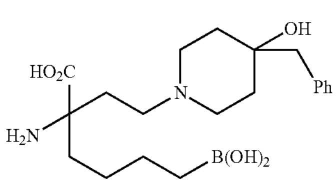 [SMILES: NC(CCCCB(O)O)(CCN1CCC(O)(Cc2ccccc2)CC1)C(=O)O] | 2 | 3 |

TABLE 2-continued

| Ex. # | Structure | Potency (ARG I)[a] | Potency (ARG II)[a] |
|---|---|---|---|
| 35 | 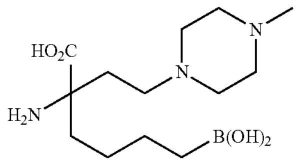 [SMILES: CN1CCN(CCC(N)(CCCCB(O)O)C(=O)O)CC1] | | 4 |
| 36 | 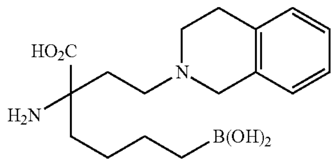 [SMILES: NC(CCCCB(O)O)(CCN1CCc2ccccc2C1)C(=O)O] | 2 | 3 |
| 37 | 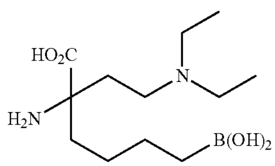 [SMILES: CCN(CC)CCC(N)(CCCCB(O)O)C(=O)O] | 2 | 3 |
| 38 | 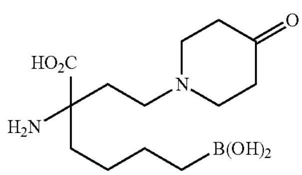 [SMILES: NC(CCCCB(O)O)(CCN1CCC(=O)CC1)C(=O)O] | 4 | 4 |
| 39 | 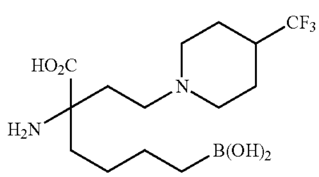 [SMILES: NC(CCCCB(O)O)(CCN1CCC(C(F)(F)F)CC1)C(=O)O] | 3 | 4 |
| 40 | 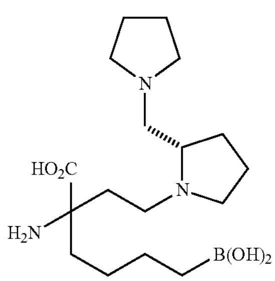 [SMILES: NC(CCCCB(O)O)(CCN1CCC[C@H]1CN1CCCC1)C(=O)O] | 3 | 4 |
| 41 | 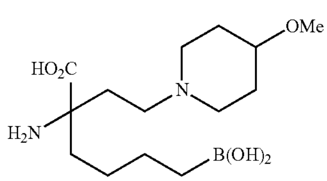 [SMILES: COC1CCN(CCC(N)(CCCCB(O)O)C(=O)O)CC1] | 3 | 4 |
| 42 | 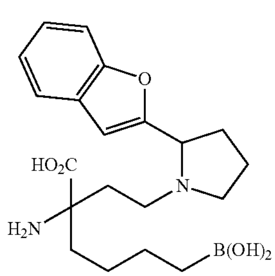 [SMILES: NC(CCCCB(O)O)(CCN1CCCC1c1cc2ccccc2o1)C(=O)O] | 4 | 4 |

TABLE 2-continued

| Ex. # | Structure | Potency (ARG I)[a] | Potency (ARG II)[a] |
|---|---|---|---|
| 43 | 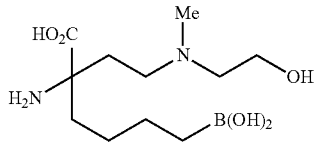 [SMILES: CN(CCO)CCC(N)(CCCCB(O)O)C(=O)O] | 3 | 4 |
| 44 | 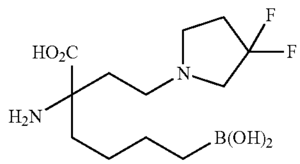 [SMILES: NC(CCCCB(O)O)(CCN1CCC(F)(F)C1)C(=O)O] | 5 | 5 |
| 45 | 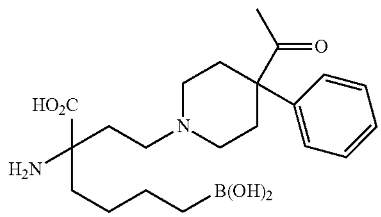 [SMILES: CC(=O)C1(c2ccccc2)CCN(CCC(N)(CCCCB(O)O)C(=O)O)CC1] | 3 | 4 |
| 46 | 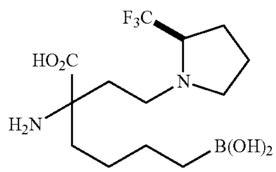 [SMILES: NC(CCCCB(O)O)(CCN1CCC[C@@H]1C(F)(F)F)C(=O)O] | 5 | 5 |
| 47 | 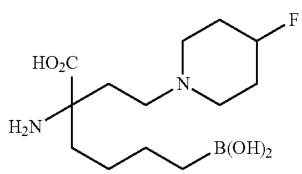 [SMILES: NC(CCCCB(O)O)(CCN1CCC(F)CC1)C(=O)O] | 3 | 4 |
| 48 | 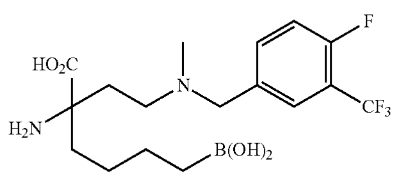 [SMILES: CN(CCC(N)(CCCCB(O)O)C(=O)O)Cc1ccc(F)c(C(F)(F)F)c1] | 4 | 5 |
| 49 | 3 HCl | 4 | 4 |
| 50 | 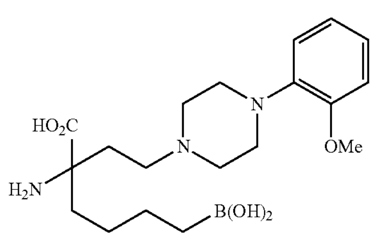 [SMILES: COc1ccccc1N1CCN(CCC(N)(CCCCB(O)O)C(=O)O)CC1] | 5 | 5 |

TABLE 2-continued

| Ex. # | Structure | Potency (ARG I)$^a$ | Potency (ARG II)$^a$ |
|---|---|---|---|
| 51 | [Structure with HO₂C, H₂N, N(CH₂CH₂NH₂)₂, B(OH)₂] | 3 | 4 |
| 52 | [Structure with HO₂C, H₂N, piperidine-2-CO₂H, B(OH)₂] | 4 | 4 |
| 53 | [Structure with HO₂C, H₂N, piperidine-3-CO₂H, B(OH)₂] | 4 | 4 |
| 54 | [Structure with HO₂C, H₂N, prolyl-N(Me)₂, B(OH)₂] | 5 | 5 |
| 55 | [Structure with HO₂C, H₂N, NH-iPr, B(OH)₂] | 1 | 2 |
| 56 | [Structure with HO₂C, H₂N, piperidine-3-CO₂H, B(OH)₂] | 3 | 4 |
| 57 | [Structure with HO₂C, H₂N, 4-Me-4-CO₂H-piperidine, B(OH)₂] | 3 | 3 |

TABLE 2-continued

| Ex. # | Structure | Potency (ARG I)[a] | Potency (ARG II)[a] |
|---|---|---|---|
| 58 | 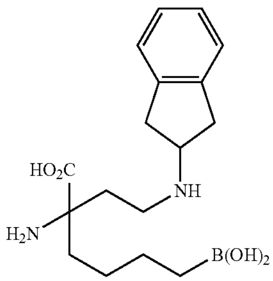 [SMILES: NC(CCCCB(O)O)(CCNC1Cc2ccccc2C1)C(=O)O] | 1 | 1 |
| 59 | 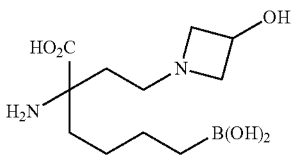 [SMILES: NC(CCCCB(O)O)(CCN1CC(O)C1)C(=O)O] | 3 | 4 |
| 60 | 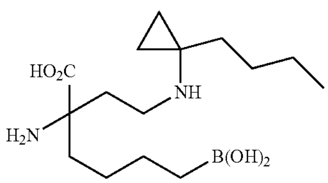 [SMILES: CCCCC1(NCCC(N)(CCCCB(O)O)C(=O)O)CC1] | 1 | 2 |
| 61 | 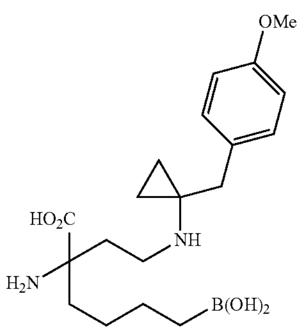 [SMILES: COc1ccc(CC2(NCCC(N)(CCCCB(O)O)C(=O)O)CC2)cc1] | 2 | 3 |
| 62 | 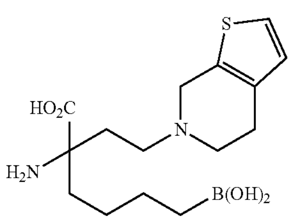 [SMILES: NC(CCCCB(O)O)(CCN1CCc2ccsc2C1)C(=O)O] | 2 | 3 |
| 63 | 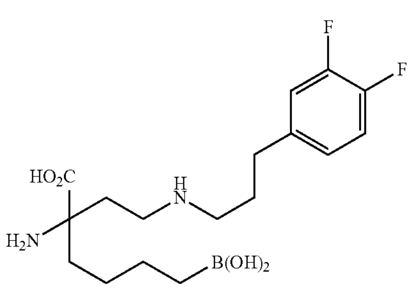 [SMILES: NC(CCCCB(O)O)(CCNCCCc1ccc(F)c(F)c1)C(=O)O] | 1 | 1 |

TABLE 2-continued

| Ex. # | Structure | Potency (ARG I)ᵃ | Potency (ARG II)ᵃ |
|---|---|---|---|
| 64 | [structure: 2-Cl-5-CF₃-phenylpropyl amine derivative with HO₂C, H₂N, B(OH)₂] | 1 | 1 |
| 65 | [structure: 3-OMe-phenylpropyl amine derivative with HO₂C, H₂N, B(OH)₂] | 1 | 1 |
| 66 | [structure: 2,4-diCl-phenylpropyl amine derivative with HO₂C, H₂N, B(OH)₂] | 1 | 1 |
| 67 | [structure: t-Bu NH derivative with HO₂C, H₂N, B(OH)₂] | 2 | 2 |
| 68 | [structure: cyclopropyl NH derivative with HO₂C, H₂N, B(OH)₂] | 2 | 2 |
| 69 | [structure: 4-OMe-benzyl amine derivative with HO₂C, H₂N, B(OH)₂] | 1 | 1 |
| 70 | [structure: benzyl (CH₂Ph) amine derivative with HO₂C, H₂N, B(OH)₂] | 1 | 2 |
| 71 | [structure: Me₂N-CH₂CH₂-N(Me)- derivative with HO₂C, H₂N, B(OH)₂] | 4 | 4 |

TABLE 2-continued

| Ex. # | Structure | Potency (ARG I)[a] | Potency (ARG II)[a] |
|---|---|---|---|
| 72 | (cyclopentyl-NH substituent) | 2 | 2 |
| 73 | (N-benzyl, N-aminoethyl substituent) | 1 | 2 |
| 74 | (N-methyl, N-(4-isopropoxybenzyl) substituent) | 4 | 5 |
| 75 | (azetidinyl substituent) | 2 | 3 |
| 76 | (4-phenylpiperazinyl substituent) | 5 | 5 |
| 77 | (4-(2-methoxyethyl)piperazinyl substituent) | 4 | 5 |
| 78 | (N-Me, N-(2-hydroxy-2-phenylethyl) substituent) | 4 | 4 |
| 79 | (piperidinyl substituent) | 4 | 5 |

TABLE 2-continued

| Ex. # | Structure | Potency (ARG I)[a] | Potency (ARG II)[a] |
|---|---|---|---|
| 80 | 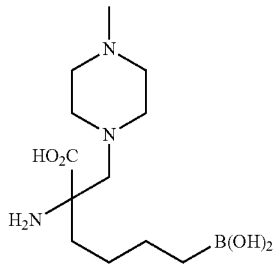 [SMILES: CN1CCN(CC(N)(CCCCB(O)O)C(=O)O)CC1] | 4 | 5 |
| 81 | 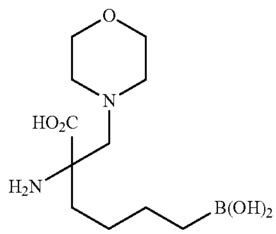 [SMILES: NC(CCCCB(O)O)(CN1CCOCC1)C(=O)O] | — | 5 |
| 82 | 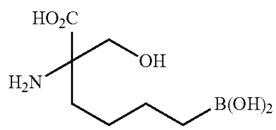 [SMILES: NC(CO)(CCCCB(O)O)C(=O)O] | — | 4 |
| 83 | 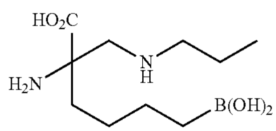 [SMILES: CCCNCC(N)(CCCCB(O)O)C(=O)O] | 4 | 4 |
| 84 | 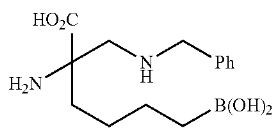 [SMILES: NC(CCCCB(O)O)(CNCc1ccccc1)C(=O)O] | 4 | 5 |
| 85 | 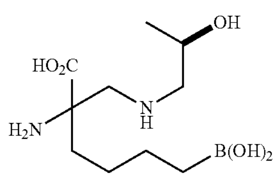 [SMILES: C[C@@H](O)CNCC(N)(CCCCB(O)O)C(=O)O] | 4 | 4 |
| 86 | 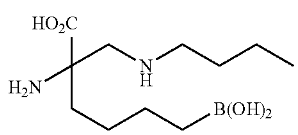 [SMILES: CCCCNCC(N)(CCCCB(O)O)C(=O)O] | 4 | 4 |
| 87 | 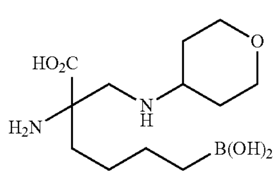 [SMILES: NC(CCCCB(O)O)(CNC1CCOCC1)C(=O)O] | 3 | 3 |
| 88 | 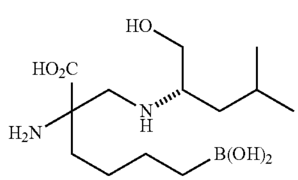 | 4 | 3 |

TABLE 2-continued

| Ex. # | Structure | Potency (ARG I)$^a$ | Potency (ARG II)$^a$ |
|---|---|---|---|
| 89 | 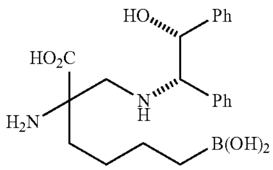 | 5 | 5 |
| 90 | 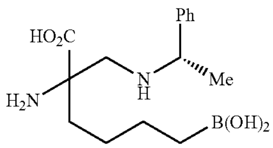 [SMILES: C[C@H](NCC(N)(CCCCB(O)O)C(=O)O)c1ccccc1] | 4 | 4 |
| 91 | 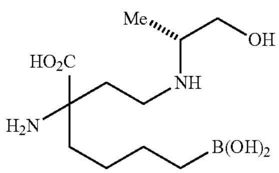 [SMILES: C[C@H](CO)NCCC(N)(CCCCB(O)O)C(=O)O] | 4 | 4 |
| 92 | 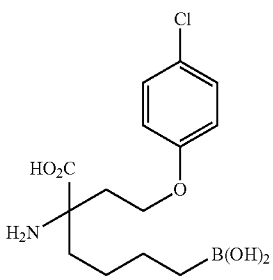 [SMILES: NC(CCCCB(O)O)(CCOc1ccc(Cl)cc1)C(=O)O] | 5 | 5 |
| 93 | 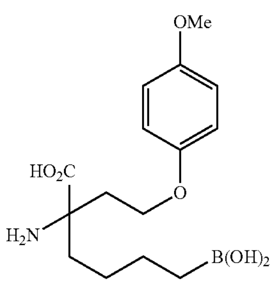 [SMILES: COc1ccc(OCCC(N)(CCCCB(O)O)C(=O)O)cc1] | 5 | 5 |
| 94 | 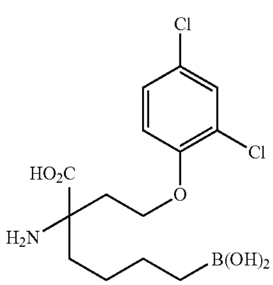 [SMILES: NC(CCCCB(O)O)(CCOc1ccc(Cl)cc1Cl)C(=O)O] | 5 | 5 |
| 95 | 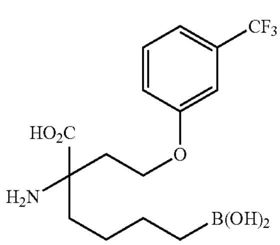 [SMILES: NC(CCCCB(O)O)(CCOc1cccc(C(F)(F)F)c1)C(=O)O] | 4 | 4 |

TABLE 2-continued

| Ex. # | Structure | Potency (ARG I)[a] | Potency (ARG II)[a] |
|---|---|---|---|
| 96 | [structure: 2-amino-2-carboxy with (CH2)3-O-(4-chlorophenyl) and (CH2)4-B(OH)2] | 3 | 3 |
| 97 | [structure: 2-amino-2-carboxy-2-methyl with (CH2)4-B(OH)2] | 4 | 5 |
| 98 | [structure: 2-amino-2-carboxy with CH2-(3-fluorophenyl) and (CH2)4-B(OH)2] | — | 5 |
| 99 | [structure: 2-amino-2-carboxy with CH2-phenyl and (CH2)4-B(OH)2] | — | 5 |
| 100 | [structure: 2-amino-2-carboxy with (CH2)3-OMe and (CH2)4-B(OH)2] | — | 5 |
| 101 | [structure: 2-amino-2-carboxy with (CH2)3-OH and (CH2)4-B(OH)2] | 4 | — |
| 102 | [structure: 2-amino-2-carboxy with CH2-imidazolyl and (CH2)4-B(OH)2] | 4 | 4 |
| 103 | [structure: pyrrolidine-2-carboxylic acid with (CH2)3-B(OH)2 at 2-position] | — | 5 |

TABLE 2-continued

| Ex. # | Structure | Potency (ARG I)[a] | Potency (ARG II)[a] |
|---|---|---|---|
| 104 | (structure) | — | 5 |
| 105 | (structure) | — | 5 |
| 106 | (structure) | 5 | 5 |
| 107 | (structure) | 5 | 5 |
| 108 | (structure) | 3 | 4 |
| 109 | (structure) | 4 | 5 |
| 110 | (structure) | 3 | 4 |
| 111 | (structure) | 4 | 4 |

TABLE 2-continued

| Ex. # | Structure | Potency (ARG I)$^a$ | Potency (ARG II)$^a$ |
|---|---|---|---|
| 112 | 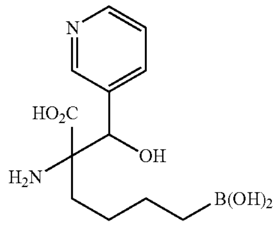 [SMILES: NC(CCCCB(O)O)(C(=O)O)C(O)c1cccnc1] | 4 | 4 |
| 113 | 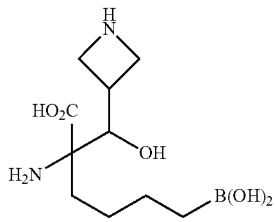 [SMILES: NC(CCCCB(O)O)(C(=O)O)C(O)C1CNC1] | 1 | 2 |
| 114 | 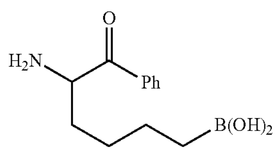 [SMILES: NC(CCCCB(O)O)C(=O)c1ccccc1] | 5 | 5 |
| 115 | 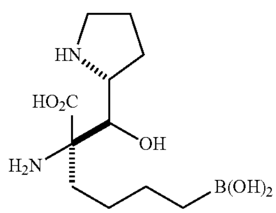 | 1 | 1 |
| 116 | 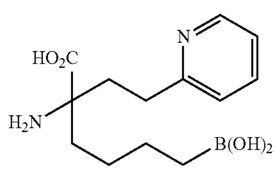 [SMILES: NC(CCCCB(O)O)(CCc1ccccn1)C(=O)O] | 4 | 4 |
| 117 | 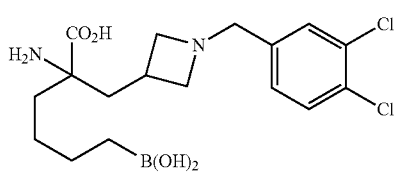 [SMILES: NC(CCCCB(O)O)(CC1CN(Cc2ccc(Cl)c(Cl)c2)C1)C(=O)O] | 2 | 4 |
| 118 | 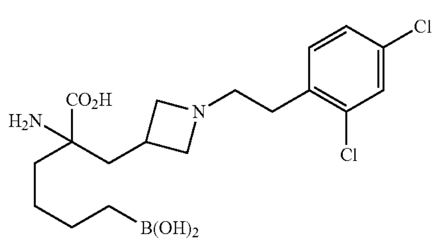 [SMILES: NC(CCCCB(O)O)(CC1CN(CCc2ccc(Cl)cc2Cl)C1)C(=O)O] | 2 | 2 |
| 119 | 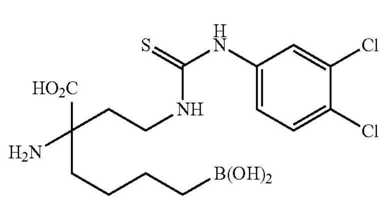 [SMILES: NC(CCCCB(O)O)(CCNC(=S)Nc1ccc(Cl)c(Cl)c1)C(=O)O] | 2 | 3 |

TABLE 2-continued

| Ex. # | Structure | Potency (ARG I)[a] | Potency (ARG II)[a] |
|---|---|---|---|
| 120 | 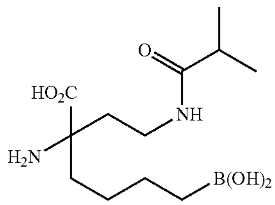 [SMILES: CC(C)C(=O)NCCC(N)(CCCCB(O)O)C(=O)O] | 3 | 4 |
| 121 | 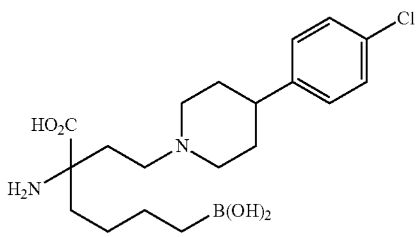 [SMILES: NC(CCCCB(O)O)(CCN1CCC(c2ccc(Cl)cc2)CC1)C(=O)O] | 2 | 2 |
| 122 | 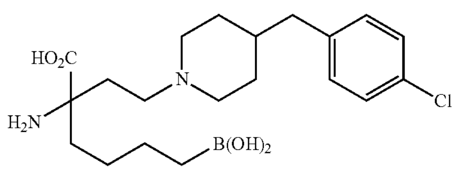 [SMILES: NC(CCCCB(O)O)(CCN1CCC(Cc2ccc(Cl)cc2)CC1)C(=O)O] | 2 | 2 |
| 123 | 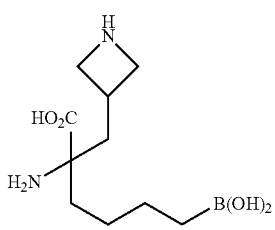 [SMILES: NC(CCCCB(O)O)(CC1CNC1)C(=O)O] | 4 | 5 |
| 124 | 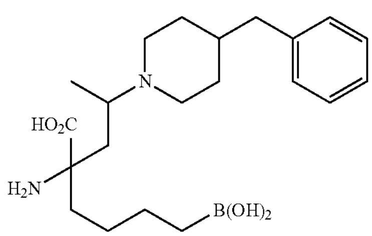 [SMILES: CC(CC(N)(CCCCB(O)O)C(=O)O)N1CCC(Cc2ccccc2)CC1] | 2 | 4 |
| 125 | 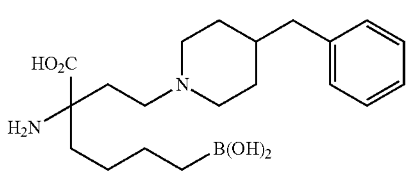 [SMILES: NC(CCCCB(O)O)(CCN1CCC(Cc2ccccc2)CC1)C(=O)O] | 2 | 2 |
| 126 | 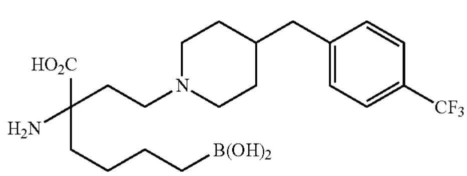 [SMILES: NC(CCCCB(O)O)(CCN1CCC(Cc2ccc(C(F)(F)F)cc2)CC1)C(=O)O] | 2 | 2 |

TABLE 2-continued

| Ex. # | Structure | Potency (ARG I)[a] | Potency (ARG II)[a] |
|---|---|---|---|
| 127 | 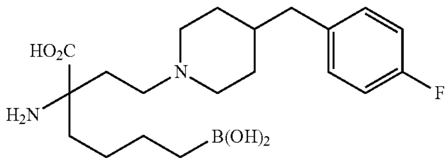 [SMILES: NC(CCCCB(O)O)(CCN1CCC(Cc2ccc(F)cc2)CC1)C(=O)O] | 2 | 2 |
| 128 | 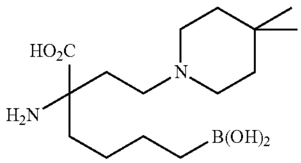 [SMILES: CC1(C)CCN(CCC(N)(CCCCB(O)O)C(=O)O)CC1] | 2 | 3 |
| 129 | 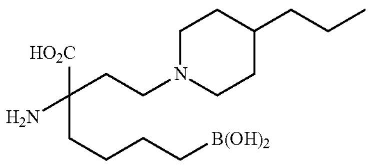 [SMILES: CCCC1CCN(CCC(N)(CCCCB(O)O)C(=O)O)CC1] | 2 | 3 |
| 130 | 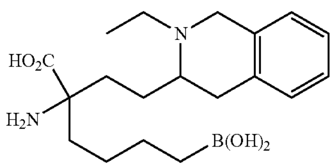 [SMILES: CCN1Cc2ccccc2CC1CCC(N)(CCCCB(O)O)C(=O)O] | 1 | 2 |
| 131 | 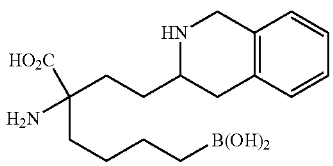 [SMILES: NC(CCCCB(O)O)(CCC1Cc2ccccc2CN1)C(=O)O] | 2 | — |
| 132 | 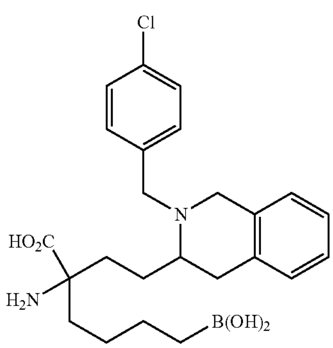 [SMILES: NC(CCCCB(O)O)(CCC1Cc2ccccc2CN1Cc1ccc(Cl)cc1)C(=O)O] | 1 | 2 |
| 133 | 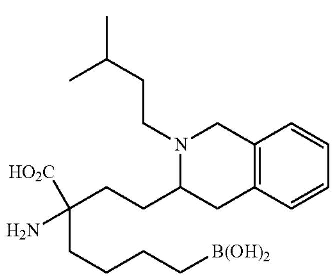 [SMILES: CC(C)CCN1Cc2ccccc2CC1CCC(N)(CCCCB(O)O)C(=O)O] | 1 | 1 |

TABLE 2-continued

| Ex. # | Structure | Potency (ARG I)[a] | Potency (ARG II)[a] |
|---|---|---|---|
| 134 | 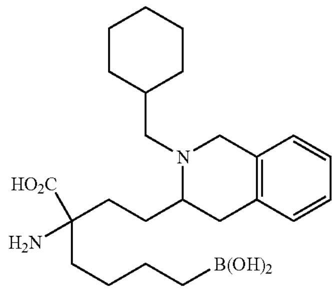 [SMILES: NC(CCCCB(O)O)(CCC1Cc2ccccc2CN1CC1CCCCC1)C(=O)O] | 1 | 2 |
| 135 | 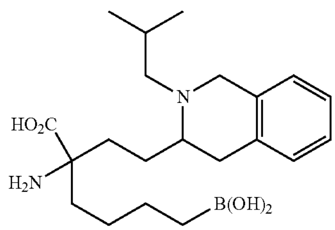 [SMILES: CC(C)CN1Cc2ccccc2CC1CCC(N)(CCCCB(O)O)C(=O)O] | 1 | 2 |
| 136 | 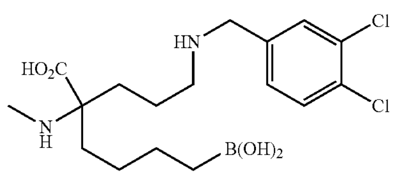 [SMILES: CNC(CCCCB(O)O)(CCCNCc1ccc(Cl)c(Cl)c1)C(=O)O] | 1 | 1 |
| 137 | 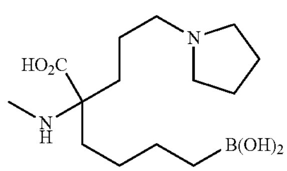 [SMILES: CNC(CCCCB(O)O)(CCCN1CCCC1)C(=O)O] | 1 | 1 |
| 138 | 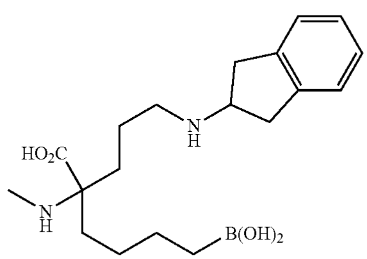 [SMILES: CNC(CCCCB(O)O)(CCCNC1Cc2ccccc2C1)C(=O)O] | 1 | 1 |
| 139 | 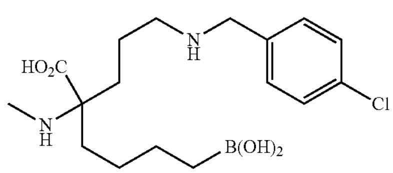 [SMILES: CNC(CCCCB(O)O)(CCCNCc1ccc(Cl)cc1)C(=O)O] | 1 | 1 |
| 140 | 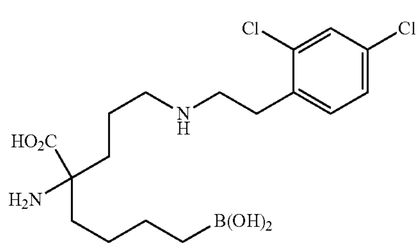 [SMILES: NC(CCCCB(O)O)(CCCNCCc1ccc(Cl)cc1Cl)C(=O)O] | 1 | 1 |

TABLE 2-continued

| Ex. # | Structure | Potency (ARG I)[a] | Potency (ARG II)[a] |
|---|---|---|---|
| 141 | [structure: 2-amino-2-carboxy compound with (3,4-dichlorobenzyl)aminopropyl and 4-boronobutyl substituents] | 1 | 1 |
| 142 | [structure: 2-amino-2-carboxy compound with 4-(4-chlorobenzyl)piperidin-1-yl-propyl and 4-boronobutyl substituents] | 2 | 2 |
| 143 | [structure: 2-amino-2-carboxy compound with pyrrolidin-2-yl-ethyl and 4-boronobutyl substituents] | 1 | 1 |
| 144 | [structure: 2-methylamino-2-carboxy compound with pyrrolidin-2-yl-propyl and 4-boronobutyl substituents] | 1 | 1 |
| 145 | [structure: 2-((4-chlorobenzyl)amino)-6-boronohexanoic acid] | 3 | 3 |
| 146 | [structure: 2-(methylamino)-6-boronohexanoic acid] | 3 | 4 |
| 147 | [structure: 2-amino-2-carboxy compound with 3-(piperidin-1-yl)propyl and 4-boronobutyl substituents] | 1 | 2 |
| 148 | [structure: 2-(methylamino)-2-carboxy compound with 3-(piperidin-1-yl)propyl and 4-boronobutyl substituents] | 1 | 1 |
| 149 | [structure: 2-(methylamino)-2-carboxy compound with 2-(piperidin-1-yl)ethyl and 4-boronobutyl substituents] | 1 | 1 |

[a]Order of Potency (highest-lowest): 1 = 0.1 nM → 250 nM; 2 = 251 nM → 1000 nM; 3 = 1001 nM → 2000 nM; 4 = 2001 nM → 5000 nM; and 5 = 5001 nM → greater.

Table 2-A below ranks the inhibition potency of exemplary Formula II compounds for arginase I (ARG I) and arginase II (ARG II).

TABLE 2-A

| Ex # | Structure | Potency (ARG I)[a] | Potency (ARG)[a] |
|---|---|---|---|
| 1-A | 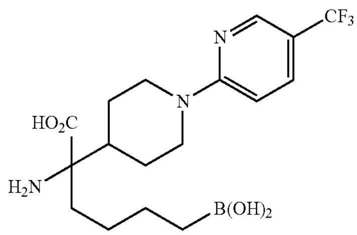 [SMILES: NC(CCCCB(O)O)(C(=O)O)C1CCN(c2ccc(C(F)(F)F)cn2)CC1] | 2 | 3 |
| 2-A | 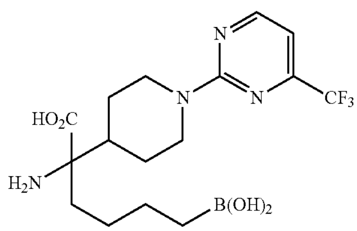 [SMILES: NC(CCCCB(O)O)(C(=O)O)C1CCN(c2nccc(C(F)(F)F)n2)CC1] | 3 | 4 |
| 3-A | 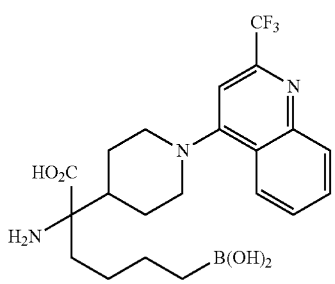 [SMILES: NC(CCCCB(O)O)(C(=O)O)C1CCN(c2cc(C(F)(F)F)nc3ccccc23)CC1] | 3 | 3 |
| 4-A | 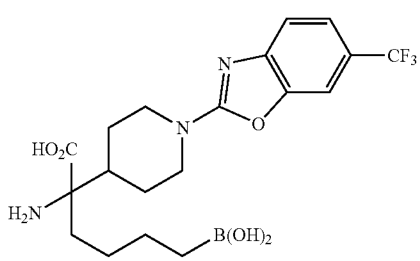 [SMILES: NC(CCCCB(O)O)(C(=O)O)C1CCN(c2nc3ccc(C(F)(F)F)cc3o2)CC1] | 2 | 3 |
| 5-A | 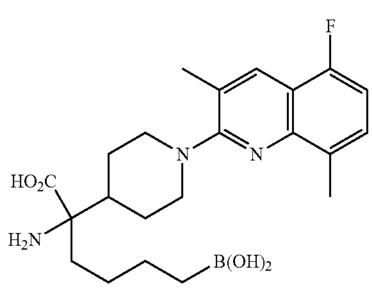 [SMILES: Cc1cc2c(F)ccc(C)c2nc1N1CCC(C(N)(CCCCB(O)O)C(=O)O)CC1] | 3 | 2 |

TABLE 2-A-continued

| Ex # | Structure | Potency (ARG I)[a] | Potency (ARG)[a] |
|---|---|---|---|
| 6-A | 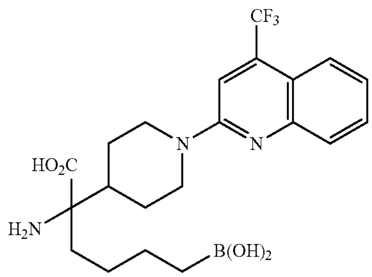 [SMILES: NC(CCCCB(O)O)(C(=O)O)C1CCN(c2cc(C(F)(F)F)c3ccccc3n2)CC1] | 2 | 3 |
| 7-A | 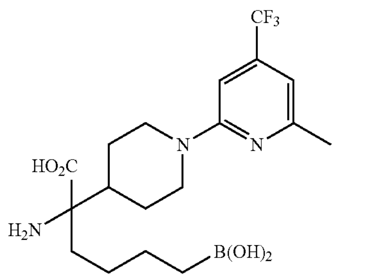 [SMILES: Cc1cc(C(F)(F)F)cc(N2CCC(C(N)(CCCCB(O)O)C(=O)O)CC2)n1] | 3 | 4 |
| 8-A | 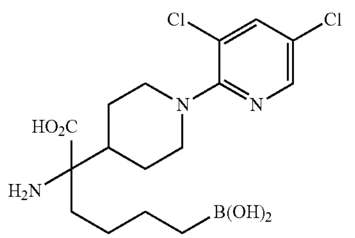 [SMILES: NC(CCCCB(O)O)(C(=O)O)C1CCN(c2ncc(Cl)cc2Cl)CC1] | 4 | 4 |
| 9-A | 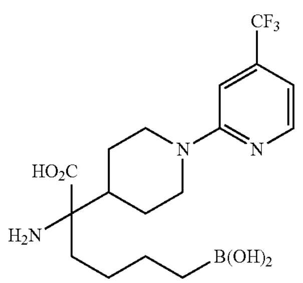 [SMILES: NC(CCCCB(O)O)(C(=O)O)C1CCN(c2cc(C(F)(F)F)ccn2)CC1] | 3 | 4 |
| 10-A | 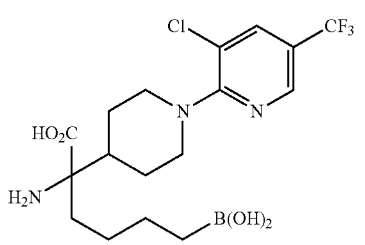 [SMILES: NC(CCCCB(O)O)(C(=O)O)C1CCN(c2ncc(C(F)(F)F)cc2Cl)CC1] | 4 | 4 |
| 11-A | 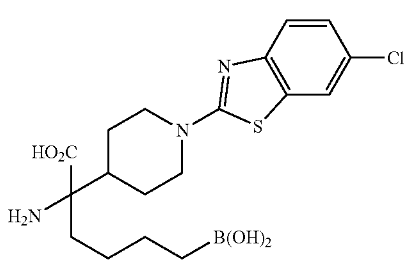 | 2 | 2 |

TABLE 2-A-continued
| Ex # | Structure | Potency (ARG I)[a] | Potency (ARG)[a] |
|---|---|---|---|
| 12-A | 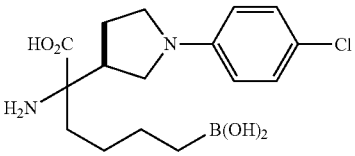 | 4 | 4 |
| 13-A | 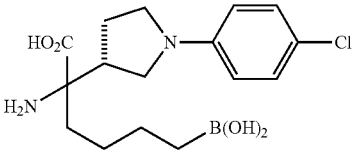 | 4 | 4 |
| 14-A | 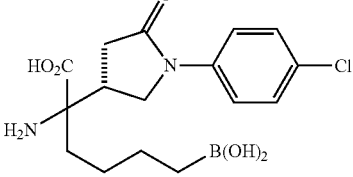 | 4 | 4 |
| 15-A | 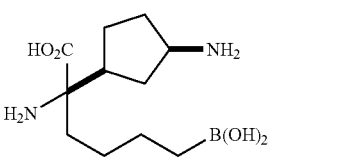 | 1 | 1 |
| 16-A | 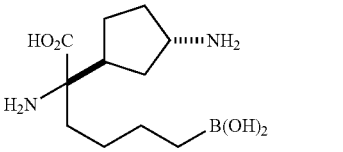 | 1 | 1 |
| 17-A | 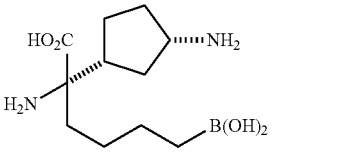 | 1 | 1 |
| 18-A | 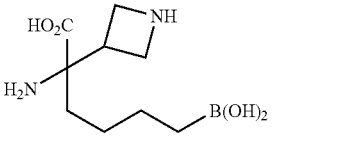 | 4 | 4 |
| 19-A | 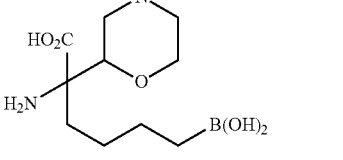 | 4 | 4 |
| 20-A | 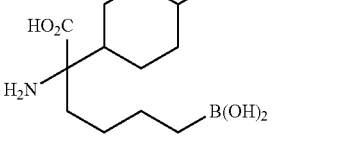 | 2 | 2 |

TABLE 2-A-continued

| Ex # | Structure | Potency (ARG I)[a] | Potency (ARG)[a] |
|---|---|---|---|
| 21-A | 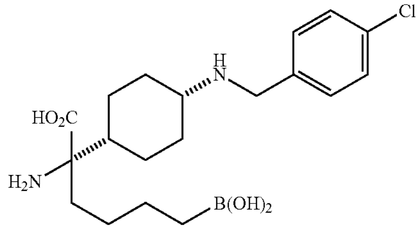 | 2 | 3 |
| 22-A | 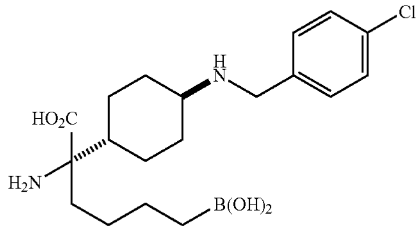 | 2 | 2 |
| 23-A | 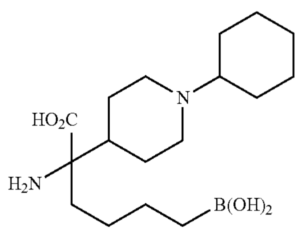 [SMILES: NC(CCCCB(O)O)(C(=O)O)C1CCN(C2CCCCC2)CC1] | 2 | 2 |
| 24-A | 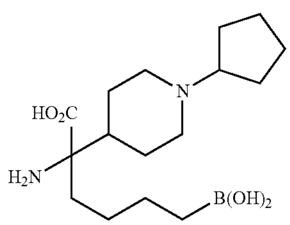 [SMILES: NC(CCCCB(O)O)(C(=O)O)C1CCN(C2CCCC2)CC1] | 2 | 2 |
| 25-A | 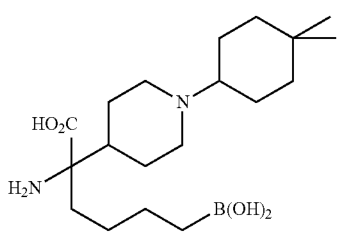 [SMILES: CC1(C)CCC(N2CCC(C(N)(CCCCB(O)O)C(=O)O)CC2)CC1] | 1 | 2 |
| 26-A | 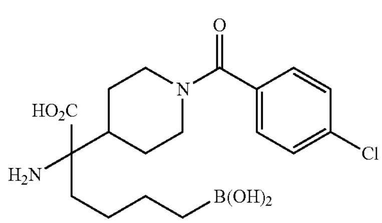 [SMILES: NC(CCCCB(O)O)(C(=O)O)C1CCN(C(=O)c2ccc(Cl)cc2)CC1] | 4 | 4 |
| 27-A | 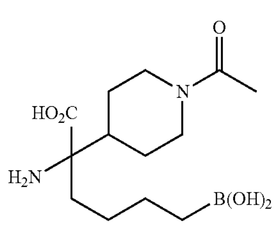 [SMILES: CC(=O)N1CCC(C(N)(CCCCB(O)O)C(=O)O)CC1] | 4 | 4 |

TABLE 2-A-continued

| Ex # | Structure | Potency (ARG I)[a] | Potency (ARG)[a] |
|---|---|---|---|
| 28-A | 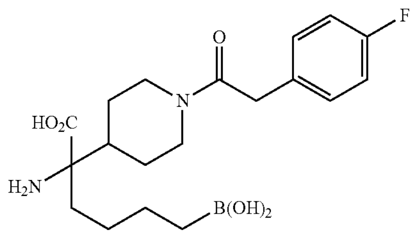 [SMILES: NC(CCCCB(O)O)(C(=O)O)C1CCN(C(=O)Cc2ccc(F)cc2)CC1] | 4 | 4 |
| 29-A | 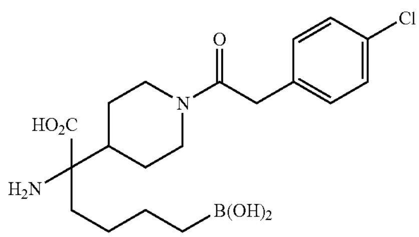 | 3 | 5 |
| 30-A | 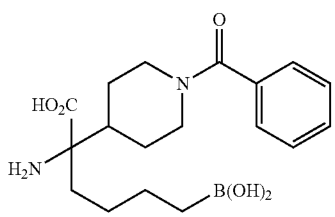 [SMILES: NC(CCCCB(O)O)(C(=O)O)C1CCN(C(=O)c2ccccc2)CC1] | 4 | 4 |
| 31-A | 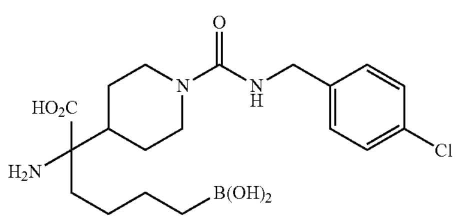 | 3 | 4 |
| 32-A | 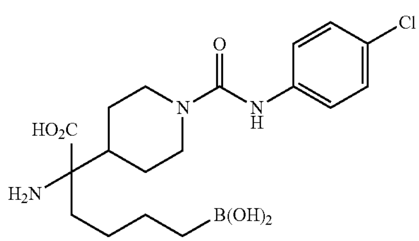 | 2 | 2 |
| 33-A | 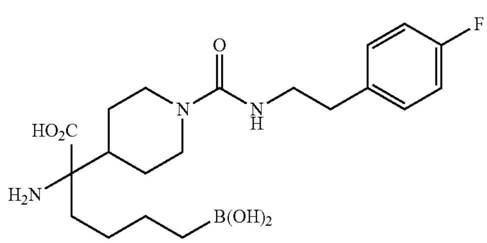 [SMILES: NC(CCCCB(O)O)(C(=O)O)C1CCN(C(=O)NCCc2ccc(F)cc2)CC1] | 3 | 3 |

TABLE 2-A-continued
| Ex # | Structure | Potency (ARG I)[a] | Potency (ARG)[a] |
|---|---|---|---|
| 34-A | 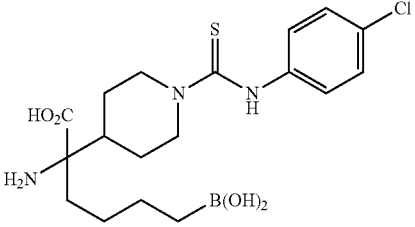 [SMILES: NC(CCCCB(O)O)(C(=O)O)C1CCN(C(=S)Nc2ccc(Cl)cc2)CC1] | 2 | 2 |
| 35-A | 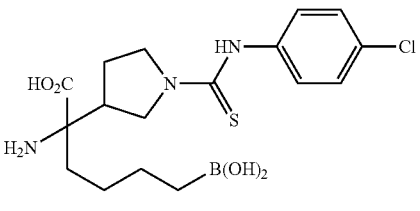 [SMILES: NC(CCCCB(O)O)(C(=O)O)C1CCN(C(=S)Nc2ccc(Cl)cc2)C1] | 2 | 2 |
| 36-A | 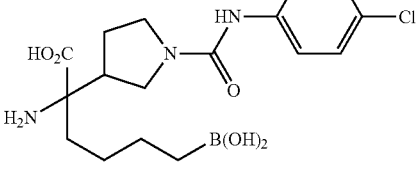 | 2 | 4 |
| 37-A | 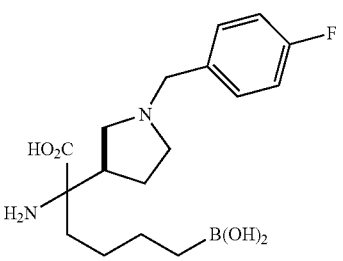 | 2 | 3 |
| 38-A | 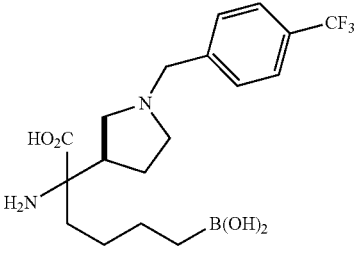 | 2 | 2 |
| 39-A | 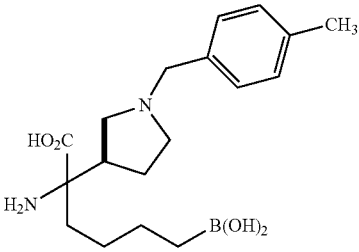 | 2 | 2 |

TABLE 2-A-continued

| Ex # | Structure | Potency (ARG I)[a] | Potency (ARG)[a] |
|---|---|---|---|
| 40-A | 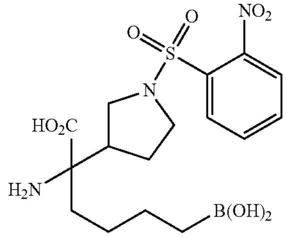 [SMILES: NC(CCCCB(O)O)(C(=O)O)C1CCN(S(=O)(=O)c2ccccc2[N+](=O)[O-])C1] | 2 | 2 |
| 41-A | 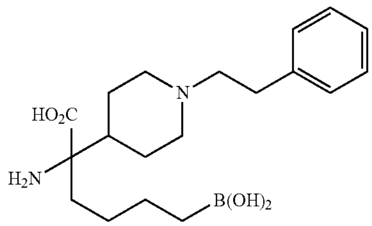 [SMILES: NC(CCCCB(O)O)(C(=O)O)C1CCN(CCc2ccccc2)CC1] | 2 | 1 |
| 42-A | 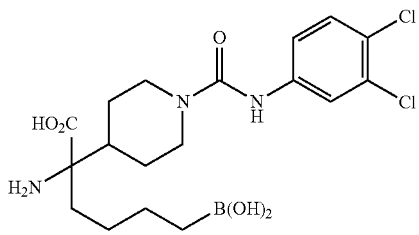 [SMILES: NC(CCCCB(O)O)(C(=O)O)C1CCN(C(=O)Nc2ccc(Cl)c(Cl)c2)CC1] | 2 | 3 |
| 43-A | 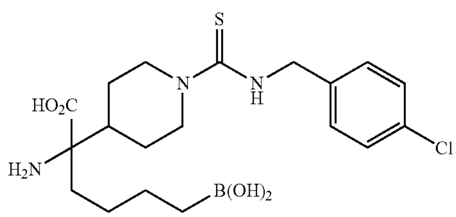 [SMILES: NC(CCCCB(O)O)(C(=O)O)C1CCN(C(=S)NCc2ccc(Cl)cc2)CC1] | 2 | 3 |
| 44-A | 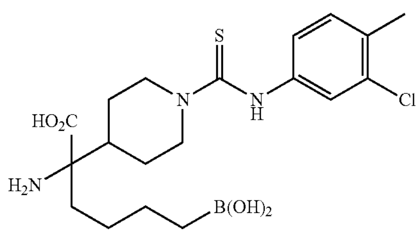 [SMILES: Cc1ccc(NC(=S)N2CCC(C(N)(CCCCB(O)O)C(=O)O)CC2)cc1Cl] | 2 | 3 |
| 45-A | 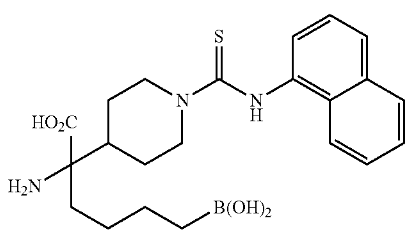 [SMILES: NC(CCCCB(O)O)(C(=O)O)C1CCN(C(=S)Nc2cccc3ccccc23)CC1] | 2 | 3 |
| 46-A | 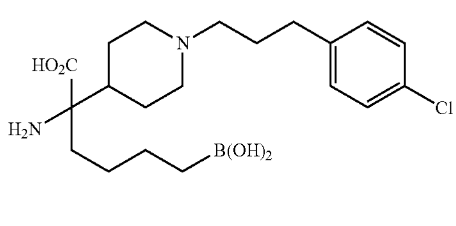 [SMILES: NC(CCCCB(O)O)(C(=O)O)C1CCN(CCCc2ccc(Cl)cc2)CC1] | 1 | 1 |

TABLE 2-A-continued

| Ex # | Structure | Potency (ARG I)[a] | Potency (ARG)[a] |
|---|---|---|---|
| 47-A | 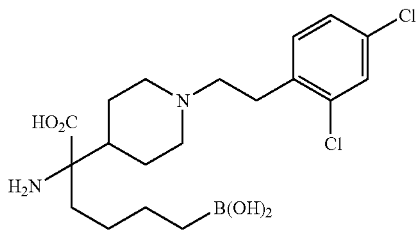 [SMILES: NC(CCCCB(O)O)(C(=O)O)C1CCN(CCc2ccc(Cl)cc2Cl)CC1] | 1 | 2 |
| 48-A | 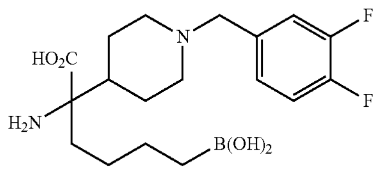 [SMILES: NC(CCCCB(O)O)(C(=O)O)C1CCN(Cc2ccc(F)c(F)c2)CC1] | 1 | 2 |
| 49-A | 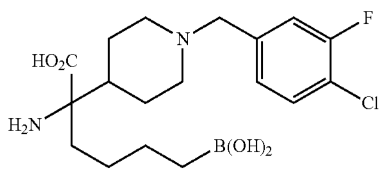 [SMILES: NC(CCCCB(O)O)(C(=O)O)C1CCN(Cc2ccc(Cl)c(F)c2)CC1] | 2 | 2 |
| 50-A | 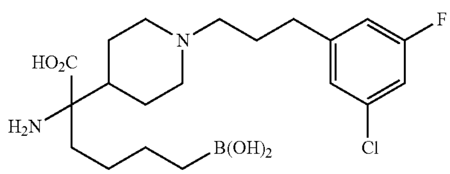 [SMILES: NC(CCCCB(O)O)(C(=O)O)C1CCN(CCCc2cc(F)cc(Cl)c2)CC1] | 1 | 1 |
| 51-A | 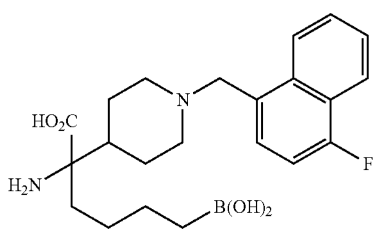 [SMILES: NC(CCCCB(O)O)(C(=O)O)C1CCN(Cc2ccc(F)c3ccccc23)CC1] | 1 | 2 |
| 52-A | 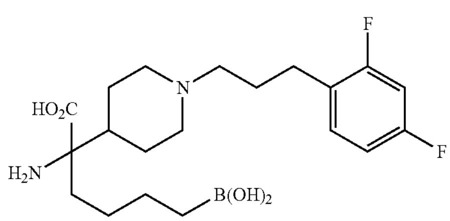 [SMILES: NC(CCCCB(O)O)(C(=O)O)C1CCN(CCCc2ccc(F)cc2F)CC1] | 1 | 1 |
| 53-A | 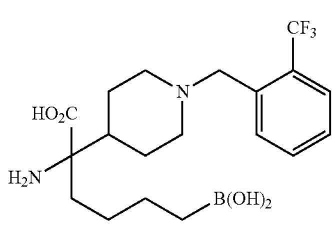 [SMILES: NC(CCCCB(O)O)(C(=O)O)C1CCN(Cc2ccccc2C(F)(F)F)CC1] | 2 | 2 |

TABLE 2-A-continued
| Ex # | Structure | Potency (ARG I)<sup>a</sup> | Potency (ARG)<sup>a</sup> |
|---|---|---|---|
| 54-A | 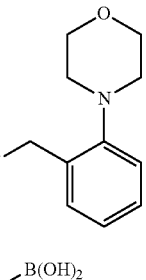 | 1 | 2 |
| 55-A | 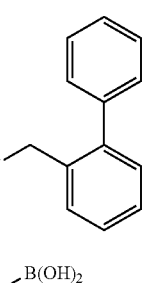 | 1 | 1 |
| 56-A | 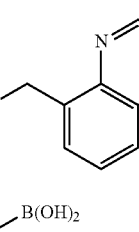 | 1 | 2 |
| 57-A | 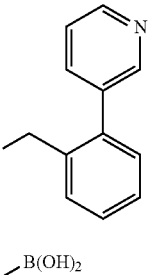 | 1 | 2 |
| 58-A | 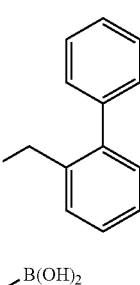 | 1 | 2 |

TABLE 2-A-continued

| Ex # | Structure | Potency (ARG I)[a] | Potency (ARG)[a] |
|---|---|---|---|
| 59-A | (piperidine with HO₂C, H₂N, B(OH)₂ chain; N-CH₂CH₂-(3,4-difluorophenyl)) | 1 | 1 |
| 60-A | (piperidine with HO₂C, H₂N, B(OH)₂ chain; N-CH₂-chroman-8-yl) | 1 | 1 |
| 61-A | (piperidine with HO₂C, H₂N, B(OH)₂ chain; N-CH₂-(1H-indol-7-yl)) | 1 | 1 |
| 62-A | (piperidine with HO₂C, H₂N, B(OH)₂ chain; N-CH₂-(1,3-dimethyl-1H-pyrazol-5-yl)) | 2 | 2 |
| 63-A | (piperidine with HO₂C, H₂N, B(OH)₂ chain; N-CH₂CH₂CH₂-(4-CF₃-phenyl)) | 1 | 1 |
| 64-A | (piperidine with HO₂C, H₂N, B(OH)₂ chain; N-CH₂-(4-(3,4-dichlorophenoxy)phenyl)) | 1 | 1 |
| 65-A | (piperidine with HO₂C, H₂N, B(OH)₂ chain; N-CH₂-(3-((1H-pyrazol-1-yl)methyl)phenyl)) | 1 | 1 |
| 66-A | (piperidine with HO₂C, H₂N, B(OH)₂ chain; N-CH₂CH₂CH₂-(2,4-dichlorophenyl)) | 1 | 1 |

TABLE 2-A-continued
| Ex # | Structure | Potency (ARG I)[a] | Potency (ARG)[a] |
|---|---|---|---|
| 67-A | 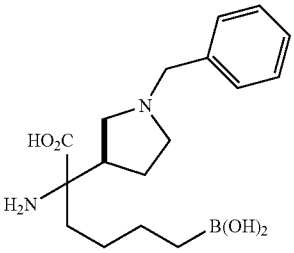 | 2 | 2 |
| 68-A | 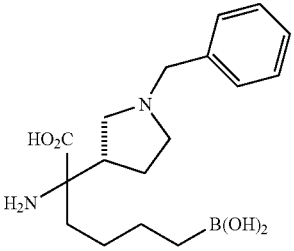 | 2 | 2 |
| 69-A | 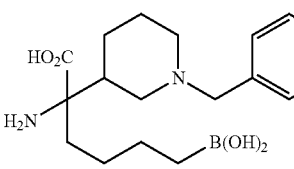 | 2 | 3 |
| 70-A | 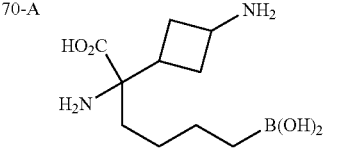 | — | — |
| 71-A | 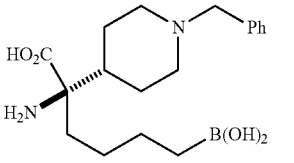 |  |  |
| 72-A | 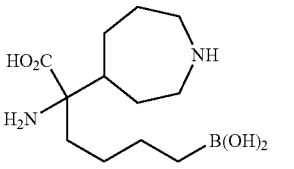 [SMILES: NC(CCCCB(O)O)(C(=O)O)C1CCCNCC1] | 1 | 2 |
| 73-A | 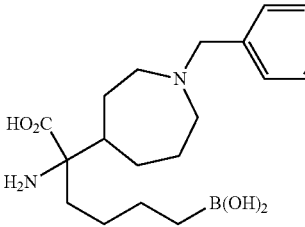 | 1 | 2 |

TABLE 2-A-continued

| Ex # | Structure | Potency (ARG I)[a] | Potency (ARG)[a] |
|---|---|---|---|
| 74-A | 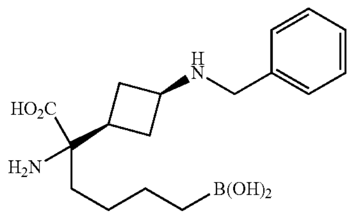 [SMILES: NC(CCCCB(O)O)(C(=O)O)[C@H]1C[C@@H](NCc2ccccc2)C1] | 1 | 1 |
| 75-A | 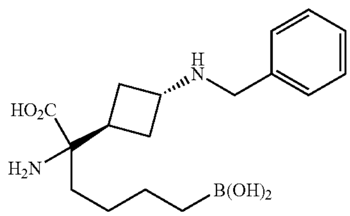 [SMILES: NC(CCCCB(O)O)(C(=O)O)[C@H]1C[C@H](NCc2ccccc2)C1] | 1 | 2 |
| 76-A | 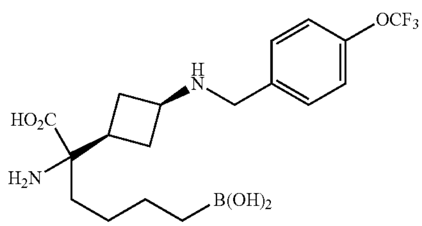 [SMILES: NC(CCCCB(O)O)(C(=O)O)[C@H]1C[C@@H](NCc2ccc(OC(F)(F)F)cc2)C1] | 1 | 1 |
| 77-A | 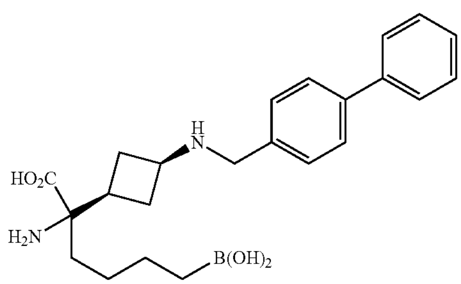 [SMILES: NC(CCCCB(O)O)(C(=O)O)[C@H]1C[C@@H](NCc2ccc(-c3ccccc3)cc2)C1] | 1 | 1 |
| 78-A | 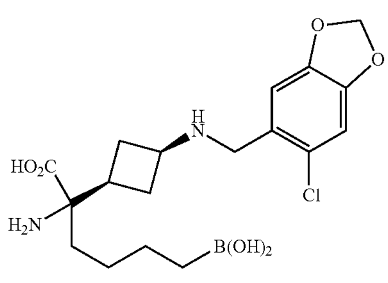 [SMILES: NC(CCCCB(O)O)(C(=O)O)[C@H]1C[C@@H](NCc2cc3c(cc2Cl)OCO3)C1] | 1 | 1 |
| 79-A | 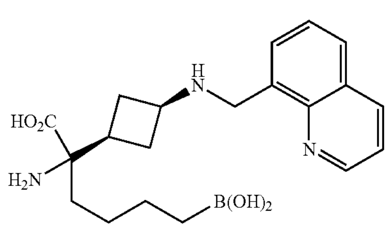 | 1 | 1 |

TABLE 2-A-continued

| Ex # | Structure | Potency (ARG I)[a] | Potency (ARG)[a] |
|---|---|---|---|
| 80-A | 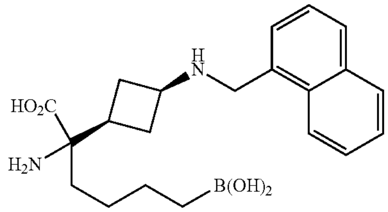 | 1 | 1 |
| 81-A | 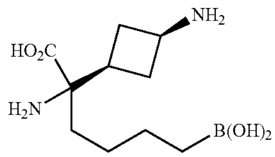 [SMILES: NC(CCCCB(O)O)(C(=O)O)[C@H]1C[C@@H](N)C1] | 1 | 1 |
| 82-A | 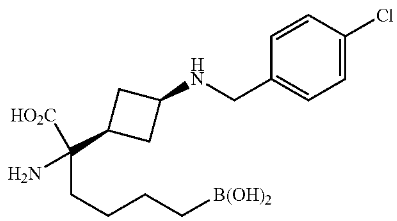 [SMILES: NC(CCCCB(O)O)(C(=O)O)[C@H]1C[C@@H](NCc2ccc(Cl)cc2)C1] | 1 | 1 |
| 83-A | 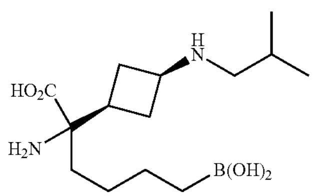 [SMILES: CC(C)CN[C@H]1C[C@@H](C(N)(CCCCB(O)O)C(=O)O)C1] | 1 | 1 |
| 84-A | 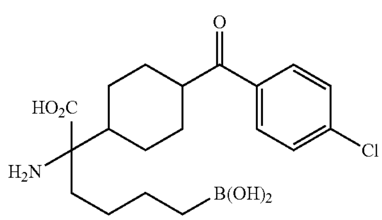 | 5 | 5 |
| 85-A | 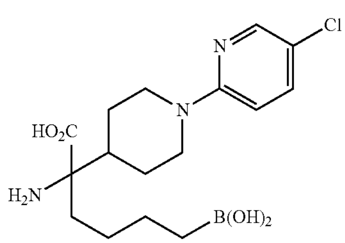 | 3 | 2 |
| 86-A | 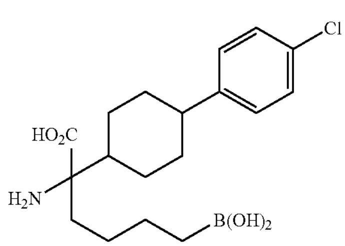 [SMILES: NC(CCCCB(O)O)(C(=O)O)C1CCC(c2ccc(Cl)cc2)CC1] | 5 | 5 |

TABLE 2-A-continued
| Ex # | Structure | Potency (ARG I)[a] | Potency (ARG)[a] |
|---|---|---|---|
| 87-A | 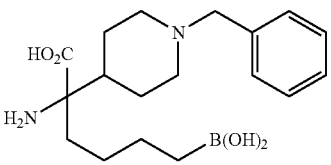 [SMILES: NC(CCCCB(O)O)(C(=O)O)C1CCN(Cc2ccccc2)CC1] | 1 | 1 |
| 88-A | 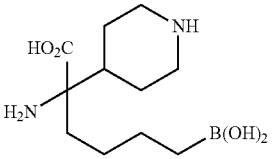 [SMILES: NC(CCCCB(O)O)(C(=O)O)C1CCNCC1] | 2 | 2 |
| 89-A | 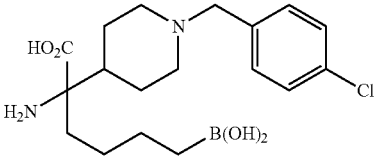 [SMILES: NC(CCCCB(O)O)(C(=O)O)C1CCN(Cc2ccc(Cl)cc2)CC1] | 1 | 1 |
| 90-A | 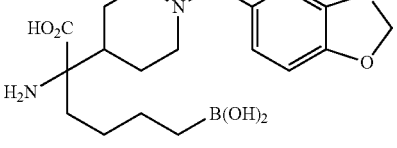 | 1 | 1 |
| 91-A | 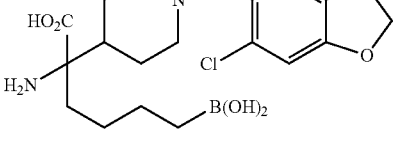 | 1 | 2 |
| 92-A | 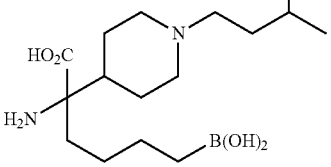 | 1 | 1 |
| 93-A | 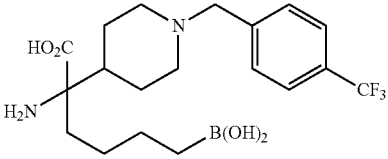 [SMILES: NC(CCCCB(O)O)(C(=O)O)C1CCN(Cc2ccc(C(F)(F)F)cc2)CC1] | 2 | 2 |
| 94-A | 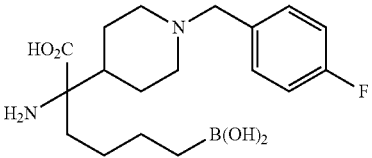 [SMILES: NC(CCCCB(O)O)(C(=O)O)C1CCN(Cc2ccc(F)cc2)CC1] | 1 | 2 |
| 95-A | 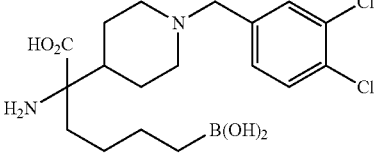 | 1 | 2 |

TABLE 2-A-continued

| Ex # | Structure | Potency (ARG I)[a] | Potency (ARG)[a] |
|---|---|---|---|
| 96-A | (piperidine N-CH2-aryl with 2-F, 4,5-diOMe; quaternary C bearing HO2C, H2N, and (CH2)3B(OH)2) | 1 | 2 |
| 97-A | (piperidine N-CH2-aryl with 2,4-diCl; quaternary C bearing HO2C, H2N, and (CH2)3B(OH)2) | 2 | 2 |
| 98-A | (piperidine N-CH2-(1-naphthyl); quaternary C bearing HO2C, H2N, and (CH2)4B(OH)2) | 1 | 1 |
| 99-A | (piperidine N-CH2-(2-naphthyl); quaternary C bearing HO2C, H2N, and (CH2)3B(OH)2) | 1 | 1 |
| 100-A | (piperidine N-CH2-aryl-4-OCF3; quaternary C bearing HO2C, H2N, and (CH2)3B(OH)2) | 1 | 1 |
| 101-A | (piperidine N-propyl; quaternary C bearing HO2C, H2N, and (CH2)3B(OH)2) | 2 | 1 |
| 102-A | (piperidine N-(3-phenylpropyl); quaternary C bearing HO2C, H2N, and (CH2)3B(OH)2) | 1 | 1 |

TABLE 2-A-continued

| Ex # | Structure | Potency (ARG I)[a] | Potency (ARG)[a] |
|---|---|---|---|
| 103-A | piperidine with HO2C, H2N, B(OH)2 substituents; N-CH2-phenyl-OCF3 | 1 | 1 |
| 104-A | piperidine with HO2C, H2N, B(OH)2 substituents; N-CH2-benzothiophene | 1 | 1 |
| 105-A | piperidine with HO2C, H2N, B(OH)2 substituents; N-CH2-phenyl-CO2H | 2 | 2 |
| 106-A | piperidine with HO2C, H2N, B(OH)2 substituents; N-CH2-phenyl-CN | 2 | 2 |

[a]Order of Potency: 1 = 0.1 nM-250 nM; 2 = 251 nM-1000 nM; 3 = 1001 nM-2000 nM; 4 = 2001 nM-5000 nM; and 5 = 5001 nM or greater.

Efficacy Model

As described hereinabove, the compounds according to the invention are useful in the treatment and prevention of a variety of disorders and conditions that are affected by levels of nitric oxide (NO) regulated, in part, by arginase enzymes. The compounds are assessed for efficacy in such treatment and prevention by their performances in standardized in vivo tests. In vivo models to assess efficacy are developed for this purpose as described below.

Erectile Dysfunction (ED)

The inventive compounds are candidate therapeutics for treating ED, as assessed by measurements of penile erectile response according to a protocol described by Wingard C, Fulton J, and Husain S, *J Sex Med* 4: 348-363, 2007. Table 3 below presents the erectile responses:

TABLE 3

| Treatment | Structure | Effect* |
|---|---|---|
| Baseline | — | — |
| 0.9% NaCl | — | 0 |
| Ex. 13 | (S)-2-amino-2-(carboxy)-piperidinyl-butyl-B(OH)2 structure | +++ |
| Enantiomer of Ex. 13 | (R)-enantiomer structure | 0 |

*increased response relative to baseline @ 2.5 V stimulation;
0 <10%;
+ 11-50%;
++ 51-100%;
+++ >100%

This example demonstrates that Example 13 is effective in eliciting erectile responses in vivo, whereas the enantiomer of Example 13 is not.

The foregoing examples are intended illustrate certain embodiments of the invention, which is defined in full below by the claims. In addition, all publications cited herein are incorporated by reference as if fully set forth herein.

We claim:
1. The compound according to the following structure:
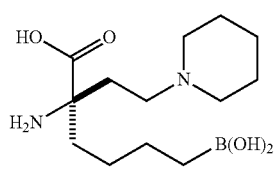
or a pharmaceutically acceptable salt, tautomer, or prodrug thereof.
2. A pharmaceutical composition comprising a therapeutically effective amount of the compound according to claim 1, or a pharmaceutically acceptable salt, tautomer, or prodrug thereof; and a pharmaceutically acceptable carrier.
* * * * *